US012692435B2

(12) United States Patent
Tasaki et al.

(10) Patent No.: US 12,692,435 B2
(45) Date of Patent: Jul. 28, 2026

(54) ORGANIC ELECTROLUMINESCENT ELEMENT, COMPOUND, AND ELECTRONIC EQUIPMENT

(71) Applicant: IDEMITSU KOSAN CO., LTD., Tokyo (JP)

(72) Inventors: Satomi Tasaki, Tokyo (JP); Kazuki Nishimura, Tokyo (JP); Ryota Takahashi, Tokyo (JP); Yuki Nakano, Tokyo (JP); Maiko Iida, Tokyo (JP); Hiroaki Itoi, Tokyo (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 929 days.

(21) Appl. No.: 17/914,590

(22) PCT Filed: Mar. 31, 2021

(86) PCT No.: PCT/JP2021/014045
§ 371 (c)(1),
(2) Date: Sep. 26, 2022

(87) PCT Pub. No.: WO2021/201176
PCT Pub. Date: Oct. 7, 2021

(65) Prior Publication Data

US 2024/0284786 A1 Aug. 22, 2024

(30) Foreign Application Priority Data

Apr. 1, 2020 (JP) ................................ 2020-065976
Apr. 1, 2020 (JP) ................................ 2020-066072

(51) Int. Cl.

| | |
|---|---|
| ***H10K 85/60*** | (2023.01) |
| ***C07C 15/38*** | (2006.01) |
| ***C07D 307/91*** | (2006.01) |
| ***C07D 311/78*** | (2006.01) |
| ***C09K 11/06*** | (2006.01) |
| *H10K 50/11* | (2023.01) |

(52) U.S. Cl.
CPC .............. *C09K 11/06* (2013.01); *C07C 15/38* (2013.01); *C07D 307/91* (2013.01); *C07D 311/78* (2013.01); *H10K 85/622* (2023.02); *H10K 85/623* (2023.02); *H10K 85/626* (2023.02); *H10K 85/6574* (2023.02); *C07C 2603/50* (2017.05); *C07C 2603/52* (2017.05); *C09K 2211/1003* (2013.01); *C09K 2211/1018* (2013.01); *H10K 50/11* (2023.02)

(58) Field of Classification Search
None
See application file for complete search history.

(56) References Cited

U.S. PATENT DOCUMENTS 8,072,136 B2 * 12/2011 Igawa .................... C09K 11/06 313/504
8,283,053 B2 * 10/2012 Hashimoto ............. C07C 25/22 585/27
2008/0007160 A1 * 1/2008 Sado .................... H10K 85/624 313/504
2008/0286610 A1 11/2008 Deaton et al.
2009/0102371 A1 * 4/2009 Hashimoto ............. C07C 13/66 585/27
2009/0110957 A1 * 4/2009 Begley .................. H05B 33/20 428/690
2009/0149649 A1 * 6/2009 Shin ..................... C07D 513/04 445/24
2010/0295444 A1 11/2010 Kuma et al.
2011/0295017 A1 * 12/2011 Ebisawa ............... C07C 211/54 585/27

(Continued)

FOREIGN PATENT DOCUMENTS

JP 2011-236135 A 11/2011
JP 2019-503041 A 1/2019

(Continued)

OTHER PUBLICATIONS

International Searching Authority, "Written Opinion," issued in connection with International Patent Application No. PCT/JP2021/014045, dated Jun. 22, 2021 (English translation).
Karunakaran et al., "Synthesis of Benzo[ k ]fluoranthene Derivatives through Diels-Alder Reaction of 1,3-Diarylbenzo[ c ]furans," European Journal of Organic Chemistry, vol. 2017, No. 45, 2017, pp. 6747-6762.

(Continued)

*Primary Examiner* — Robert S Loewe
(74) *Attorney, Agent, or Firm* — Foley & Lardner LLP

(57) ABSTRACT

An organic electroluminescence device includes a first emitting layer and a second emitting layer provided between an anode and a cathode, in which the first emitting layer contains, as a first host material, a first compound represented by a formula (1) below and having at least one group represented by a formula (11) below, and the second emitting layer contains a second host material.

(1)

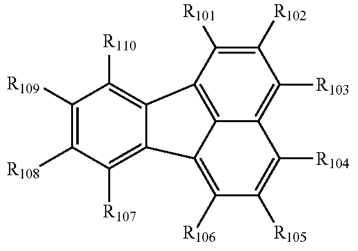

(11)

$$*\!-\!(L_{101})_{mx}\!-\!Ar_{101}.$$

19 Claims, 1 Drawing Sheet

(56) References Cited

U.S. PATENT DOCUMENTS

| | | | | |
|---|---|---|---|---|
| 2011/0315965 | A1* | 12/2011 | Takashima | H10K 85/615 585/27 |
| 2013/0126832 | A1* | 5/2013 | Yamamoto | H10K 85/626 257/40 |
| 2014/0183500 | A1 | 7/2014 | Ikeda et al. | |
| 2017/0324043 | A1 | 11/2017 | Ikeda et al. | |
| 2019/0123279 | A1* | 4/2019 | Kajimoto | H10K 50/18 |
| 2019/0165279 | A1 | 5/2019 | Fujita | |
| 2019/0333968 | A1* | 10/2019 | Yamada | H10K 85/633 |
| 2020/0044175 | A1* | 2/2020 | Kotake | H10K 50/171 |
| 2020/0212312 | A1 | 7/2020 | Kang et al. | |

FOREIGN PATENT DOCUMENTS

| | | | | |
|---|---|---|---|---|
| JP | 2019-096823 | A | 6/2019 | |
| JP | 2019-161218 | A | 9/2019 | |
| JP | 2019-192557 | A | 10/2019 | |
| JP | 2020-021862 | A | 2/2020 | |
| WO | WO-2007/100010 | A1 | 9/2007 | |
| WO | WO-2008/059713 | A1 | 5/2008 | |
| WO | WO-2010134350 | A1 * | 11/2010 | C09B 3/78 |
| WO | WO-2014/104144 | A1 | 7/2014 | |
| WO | WO-2017071791 | A1 * | 5/2017 | C07D 405/04 |

OTHER PUBLICATIONS

International Searching Authority, "International Search Report," issued in connection with International Patent Application No. PCT/JP2021/014045, dated Jun. 22, 2021.

International Searching Authority, "Written Opinion," issued in connection with International Patent Application No. PCT/JP2021/014045, dated Jun. 22, 2021.

* cited by examiner

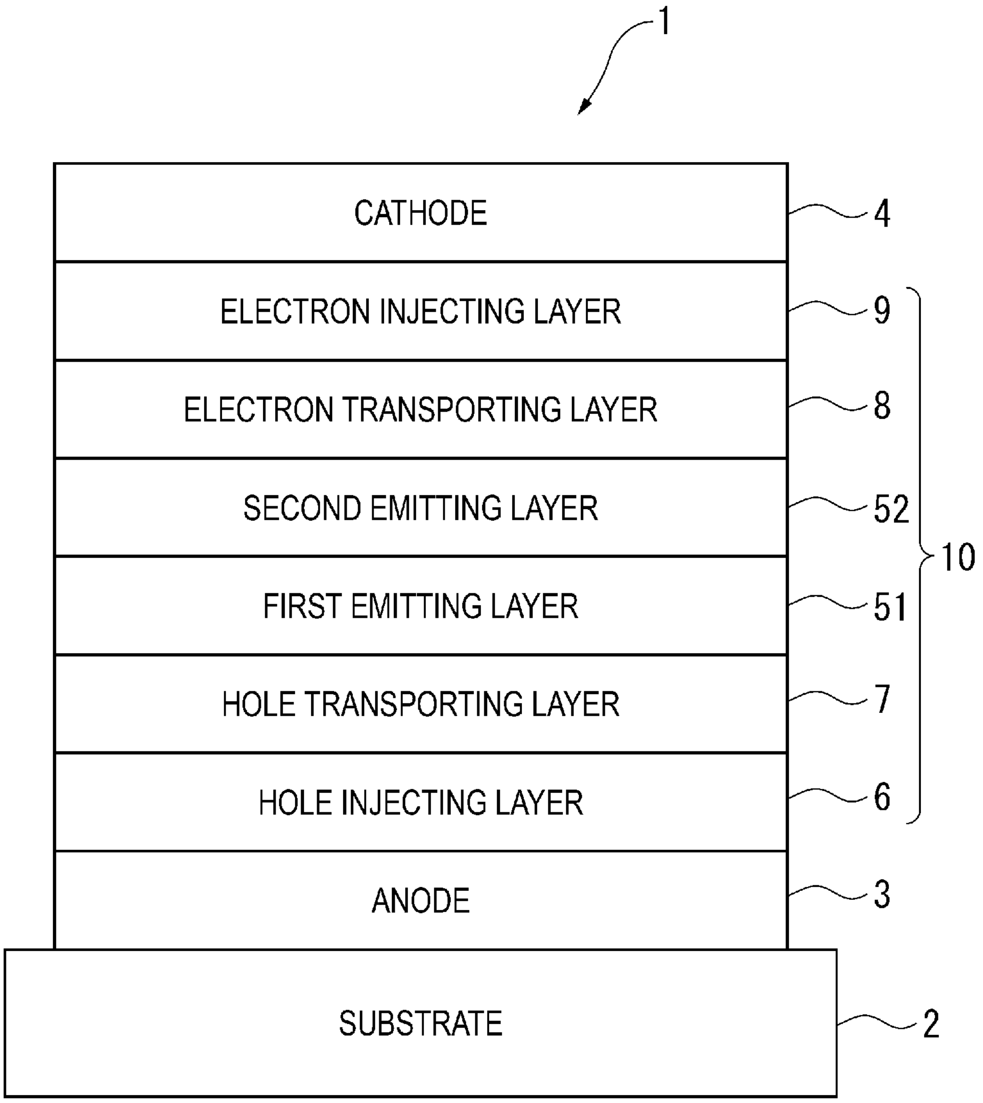
1
CATHODE
4
ELECTRON INJECTING LAYER
9
ELECTRON TRANSPORTING LAYER
8
SECOND EMITTING LAYER
52
10
FIRST EMITTING LAYER
51
HOLE TRANSPORTING LAYER
7
HOLE INJECTING LAYER
6
ANODE
3
SUBSTRATE
2

ORGANIC ELECTROLUMINESCENT ELEMENT, COMPOUND, AND ELECTRONIC EQUIPMENT

CROSS-REFERENCE TO RELATED APPLICATIONS

The present application claims priority under 37 U.S.C. § 371 to International Patent Application No. PCT/JP2021/014045, filed Mar. 31, 2021, which claims priority to and the benefit of Japanese Patent Application Nos. 2020-065976 and 2020-066072, filed on Apr. 1, 2020. The contents of these applications are hereby incorporated by reference in their entireties.

TECHNICAL FIELD

The present invention relates to an organic electroluminescence device, a compound and an electronic device.

BACKGROUND ART

An organic electroluminescence device (hereinafter, occasionally referred to as "organic EL device") has found its application in a full-color display for mobile phones, televisions and the like. When a voltage is applied to an organic EL device, holes and electrons are injected from an anode and a cathode, respectively, into an emitting layer. The injected holes and electrons are recombined in the emitting layer to form excitons. Specifically, according to the electron spin statistics theory, singlet excitons and triplet excitons are generated at a ratio of 25%:75%.

Various studies have been made for compounds to be used for the organic EL device in order to enhance the performance of the organic EL device (e.g., see Patent Literatures 1 and 2). The performance of the organic EL device is evaluable in terms of, for instance, luminance, emission wavelength, chromaticity, emission efficiency, drive voltage, and lifetime.

CITATION LIST

Patent Literature(s)

Patent Literature 1: JP 2019-161218 A
Patent Literature 2: JP 2019-96823 A

SUMMARY OF THE INVENTION

Problems to be Solved by the Invention

An object of the invention is to provide an organic electroluminescence device with enhanced performance. Another object of the invention is to provide an organic electroluminescence device with improved luminous efficiency. Still another object of the invention is to provide an organic electroluminescence device emitting light with a long lifetime. A further object of the invention is to provide a compound capable of enhancing performance of an organic electroluminescence device. A still further object of the invention is to provide an electronic device including the organic electroluminescence device.

Means for Solving the Problem(s)

According to an aspect of the invention, there is provided an organic electroluminescence device including: an anode; a cathode; a first emitting layer provided between the anode and the cathode; and a second emitting layer provided between the anode and the cathode, in which the first emitting layer contains, as a first host material, a first compound represented by a formula (1) below and having at least one group represented by a formula (11) below, the second emitting layer contains a second host material, and the first host material and the second host material are mutually different.

[Formula 1]

(1)

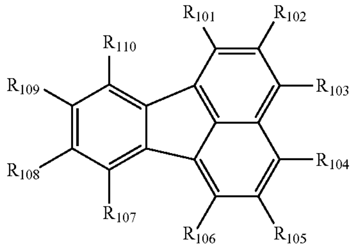

(11)

$$*-(L_{101})_{mx}-Ar_{101}$$

In the formula (1):

at least one combination of adjacent two or more of $R_{101}$ to $R_{110}$ are mutually bonded to form a substituted or unsubstituted monocyclic ring, mutually bonded to form a substituted or unsubstituted fused ring, or not mutually bonded;

$R_{101}$ to $R_{110}$ not forming the substituted or unsubstituted monocyclic ring and not forming the substituted or unsubstituted fused ring are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $-Si(R_{901})(R_{902})(R_{903})$, a group represented by $-O-(R_{904})$, a group represented by $-S-(R_{905})$, a substituted or unsubstituted aralkyl group having 7 to 50 carbon atoms, a group represented by $-C(=O)R_{801}$, a group represented by $-COOR_{802}$, a halogen atom, a cyano group, a nitro group, a substituted or unsubstituted aryl group having 6 to 50 ring carbon atoms, a substituted or unsubstituted heterocyclic group having 5 to 50 ring atoms, or a group represented by the formula (11);

at least one of a substituent, if present, for the substituted or unsubstituted monocyclic ring, a substituent, if present, for the substituted or unsubstituted fused ring or $R_{101}$ to $R_{110}$ is a group represented by the formula (11);

when a plurality of groups represented by the formula (11) are present, the plurality of groups represented by the formula (11) are mutually the same or different; $L_{101}$ is a single bond, a substituted or unsubstituted arylene group having 6 to 50 ring carbon atoms, or a substituted or unsubstituted divalent heterocyclic group having 5 to 50 ring atoms;

$Ar_{101}$ is a substituted or unsubstituted aryl group having 6 to 50 ring carbon atoms, or a substituted or unsubstituted heterocyclic group having 5 to 50 ring atoms;

mx is 0, 1, 2, 3, 4, or 5;

when two or more $L_{101}$ are present, the two or more $L_{101}$ are mutually the same or different;

when two or more $Ar_{101}$ are present, the two or more $Ar_{101}$ are mutually the same or different; and

* in the formula (11) represents a bonding position to a ring represented by the formula (1).

According to another aspect of the invention, there is provided an organic electroluminescence device including: an anode; a cathode; a first emitting layer provided between the anode and the cathode; and a second emitting layer provided between the first emitting layer and the cathode, in which the first emitting layer contains, as the first host material, the first compound represented by the formula (1) and having at least one group represented by the formula (11), at least one combination of adjacent two or more of $R_{101}$ to $R_{110}$ in the formula (1) are mutually bonded to form a substituted or unsubstituted monocyclic ring or mutually bonded to form a substituted or unsubstituted fused ring, the second emitting layer contains a second compound represented by a formula (2) below as the second host material, and the first emitting layer and the second emitting layer are in direct contact with each other.

According to still another aspect of the invention, there is provided an organic electroluminescence device including: an anode; a cathode; a first emitting layer provided between the anode and the cathode; and a second emitting layer provided between the first emitting layer and the cathode, in which the first emitting layer contains, as the first host material, the first compound represented by the formula (1) and having at least one group represented by the formula (11), none of combinations of adjacent two or more of $R_{101}$ to $R_{110}$ are mutually bonded, the second emitting layer contains the second compound represented by the formula (2) as the second host material, and the first emitting layer and the second emitting layer are in direct contact with each other.

[Formula 2]

(2)

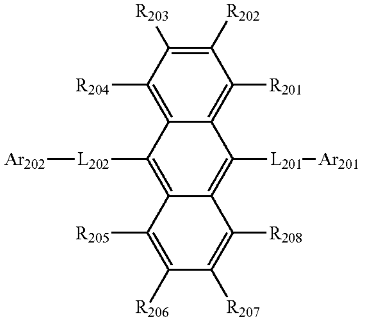

In the formula (2):

$R_{201}$ to $R_{208}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $—Si(R_{901})(R_{902})(R_{903})$, a group represented by $—O—(R_{904})$, a group represented by $—S—(R_{905})$, a group represented by $—N(R_{906})(R_{907})$, a substituted or unsubstituted aralkyl group having 7 to 50 carbon atoms, a group represented by $—C(=O)R_{801}$, a group represented by $—COOR_{802}$, a halogen atom, a cyano group, a nitro group, a substituted or unsubstituted aryl group having 6 to 50 ring carbon atoms, or a substituted or unsubstituted heterocyclic group having 5 to 50 ring atoms;

$L_{201}$ and $L_{202}$ are each independently a single bond, a substituted or unsubstituted arylene group having 6 to 50 ring carbon atoms, or a substituted or unsubstituted divalent heterocyclic group having 5 to 50 ring atoms; and $Ar_{201}$ and $Ar_{202}$ are each independently a substituted or unsubstituted aryl group having 6 to 50 ring carbon atoms, or a substituted or unsubstituted heterocyclic group having 5 to 50 ring atoms.

In the first compound represented by the formula (1) and the second compound represented by the formula (2), $R_{901}$, $R_{902}$, $R_{903}$, $R_{904}$, $R_{905}$, $R_{906}$, $R_{907}$, $R_{801}$ and $R_{802}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

when a plurality of $R_{901}$ are present, the plurality of $R_{901}$ are mutually the same or different;

when a plurality of $R_{902}$ are present, the plurality of $R_{902}$ are mutually the same or different;

when a plurality of $R_{903}$ are present, the plurality of $R_{903}$ are mutually the same or different;

when a plurality of $R_{904}$ are present, the plurality of $R_{904}$ are mutually the same or different;

when a plurality of $R_{905}$ are present, the plurality of $R_{905}$ are mutually the same or different;

when a plurality of $R_{906}$ are present, the plurality of $R_{906}$ are mutually the same or different;

when a plurality of $R_{907}$ are present, the plurality of $R_{907}$ are mutually the same or different;

when a plurality of $R_{801}$ are present, the plurality of $R_{801}$ are mutually the same or different; and when a plurality of $R_{802}$ are present, the plurality of $R_{802}$ are mutually the same or different.

According to a further aspect of the invention, a compound represented by a formula (151) below and having at least one group represented by a formula (152) below is provided.

[Formula 3]

(151)

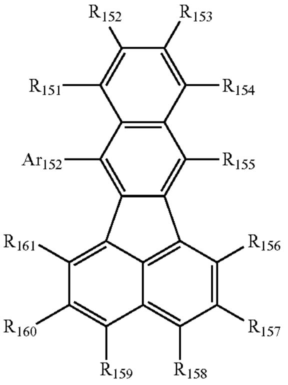

(152)

$$*—L_{151}—Ar_{151}$$

In the formula (151):

at least one of $R_{151}$ to $R_{155}$ is a group represented by the formula (152);

$R_{151}$ to $R_{154}$ not being the group represented by the formula (152) are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a substituted or unsubstituted aralkyl group having 7 to 50 carbon atoms, a group represented by —C(═O)$R_{801}$, a group represented by —COOR$_{802}$, a halogen atom, a cyano group, a nitro group, a substituted or unsubstituted aryl group having 6 to 50 ring carbon atoms, or a substituted or unsubstituted heterocyclic group having 5 to 50 ring atoms;

$R_{155}$ not being the group represented by the formula (152) is a substituted or unsubstituted aryl group having 6 to 50 ring carbon atoms, or a substituted or unsubstituted heterocyclic group having 5 to 50 ring atoms;

$R_{156}$ to $R_{161}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a substituted or unsubstituted aralkyl group having 7 to 50 carbon atoms, a group represented by —C(═O)$R_{801}$, a group represented by —COOR$_{802}$, a halogen atom, a cyano group, or a nitro group; $Ar_{152}$ is an unsubstituted aryl group having 6 to 50 ring carbon atoms;

when $R_{155}$ is a group represented by the formula (152), $Ar_{152}$ is a group different from $R_{155}$;

in the formula (152):

$Ar_{151}$ is an aryl group including four or more six-membered rings, or a heterocyclic group including one or more oxygen atoms and having 5 to 50 ring atoms;

$L_{151}$ is a single bond, a substituted or unsubstituted arylene group having 6 to 50 ring carbon atoms, or a substituted or unsubstituted divalent heterocyclic group having 5 to 50 ring atoms;

when two or more $L_{151}$ are present, the two or more $L_{151}$ are mutually the same or different;

when two or more $Ar_{151}$ are present, the two or more $Ar_{151}$ are mutually the same or different; and

* in the formula (152) represents a bonding position to a ring represented by the formula (151).

In the compound represented by the formula (151), $R_{901}$, $R_{902}$, $R_{903}$, $R_{904}$, $R_{905}$, $R_{801}$ and $R_{802}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

when a plurality of $R_{901}$ are present, the plurality of $R_{901}$ are mutually the same or different;

when a plurality of $R_{902}$ are present, the plurality of $R_{902}$ are mutually the same or different;

when a plurality of $R_{903}$ are present, the plurality of $R_{903}$ are mutually the same or different;

when a plurality of $R_{904}$ are present, the plurality of $R_{904}$ are mutually the same or different;

when a plurality of $R_{905}$ are present, the plurality of $R_{905}$ are mutually the same or different;

when a plurality of $R_{801}$ are present, the plurality of $R_{801}$ are mutually the same or different; and when a plurality of $R_{802}$ are present, the plurality of $R_{802}$ are mutually the same or different.

According to a still further aspect of the invention, an electronic device including the organic electroluminescence device according to the above aspect of the invention is provided.

According to the above aspects of the invention, an organic electroluminescence device with enhanced performance can be provided. According to the above aspects of the invention, an organic electroluminescence device with improved luminous efficiency can be provided. According to the above aspects of the invention, an organic electroluminescence device emitting light with a long lifetime can be provided. According to the above aspect of the invention, a compound capable of enhancing performance of an organic electroluminescence device can be provided. According to the above aspect of the invention, an electronic device including the organic electroluminescence device can be provided.

BRIEF DESCRIPTION OF DRAWINGS

The FIGURE schematically shows an exemplary arrangement of an organic electroluminescence device according to an exemplary embodiment of the invention.

DESCRIPTION OF EMBODIMENT(S)

Definitions

Herein, a hydrogen atom includes isotopes having different numbers of neutrons, specifically, protium, deuterium and tritium.

In chemical formulae herein, it is assumed that a hydrogen atom (i.e. protium, deuterium and tritium) is bonded to each of bondable positions that are not annexed with signs "R" or the like or "D" representing a deuterium.

Herein, the ring carbon atoms refer to the number of carbon atoms among atoms forming a ring of a compound (e.g., a monocyclic compound, fused-ring compound, cross-linking compound, carbon ring compound, and heterocyclic compound) in which the atoms are bonded to each other to form the ring. When the ring is substituted by a substituent (s), carbon atom(s) contained in the substituent(s) is not counted in the ring carbon atoms. Unless otherwise specified, the same applies to the "ring carbon atoms" described later. For instance, a benzene ring has 6 ring carbon atoms, a naphthalene ring has 10 ring carbon atoms, a pyridine ring has 5 ring carbon atoms, and a furan ring has 4 ring carbon atoms. Further, for instance, 9,9-diphenylfluorenyl group has 13 ring carbon atoms and 9,9'-spirobifluorenyl group has 25 ring carbon atoms.

When a benzene ring is substituted by a substituent in a form of, for instance, an alkyl group, the number of carbon atoms of the alkyl group is not counted in the number of the ring carbon atoms of the benzene ring. Accordingly, the benzene ring substituted by an alkyl group has 6 ring carbon atoms. When a naphthalene ring is substituted by a substituent in a form of, for instance, an alkyl group, the number of carbon atoms of the alkyl group is not counted in the number of the ring carbon atoms of the naphthalene ring. Accordingly, the naphthalene ring substituted by an alkyl group has 10 ring carbon atoms.

Herein, the ring atoms refer to the number of atoms forming a ring of a compound (e.g., a monocyclic compound, fused-ring compound, cross-linking compound, carbon ring compound, and heterocyclic compound) in which the atoms are bonded to each other to form the ring (e.g., monocyclic ring, fused ring, and ring assembly). Atom(s) not forming the ring (e.g., hydrogen atom(s) for saturating the valence of the atom which forms the ring) and atom(s) in a substituent by which the ring is substituted are not counted as the ring atoms. Unless otherwise specified, the same applies to the "ring atoms" described later. For instance, a pyridine ring has 6 ring atoms, a quinazoline ring has 10 ring atoms, and a furan ring has 5 ring atoms. For instance, the number of hydrogen atom(s) bonded to a pyridine ring or the number of atoms forming a substituent are not counted as the pyridine ring atoms. Accordingly, a pyridine ring bonded to a hydrogen atom(s) or a substituent (s) has 6 ring atoms. For instance, the hydrogen atom(s) bonded to carbon atom(s) of a quinazoline ring or the atoms forming a substituent are not counted as the quinazoline ring atoms. Accordingly, a quinazoline ring bonded to hydrogen atom(s) or a substituent(s) has 10 ring atoms.

Herein, "XX to YY carbon atoms" in the description of "substituted or unsubstituted ZZ group having XX to YY carbon atoms" represent carbon atoms of an unsubstituted ZZ group and do not include carbon atoms of a substituent(s) of the substituted ZZ group. Herein, "YY" is larger than "XX," "XX" representing an integer of 1 or more and "YY" representing an integer of 2 or more.

Herein, "XX to YY atoms" in the description of "substituted or unsubstituted ZZ group having XX to YY atoms" represent atoms of an unsubstituted ZZ group and do not include atoms of a substituent(s) of the substituted ZZ group. Herein, "YY" is larger than "XX," "XX" representing an integer of 1 or more and "YY" representing an integer of 2 or more.

Herein, an unsubstituted ZZ group refers to an "unsubstituted ZZ group" in a "substituted or unsubstituted ZZ group," and a substituted ZZ group refers to a "substituted ZZ group" in a "substituted or unsubstituted ZZ group."

Herein, the term "unsubstituted" used in a "substituted or unsubstituted ZZ group" means that a hydrogen atom(s) in the ZZ group is not substituted with a substituent(s). The hydrogen atom(s) in the "unsubstituted ZZ group" is protium, deuterium, or tritium.

Herein, the term "substituted" used in a "substituted or unsubstituted ZZ group" means that at least one hydrogen atom in the ZZ group is substituted with a substituent. Similarly, the term "substituted" used in a "BB group substituted by AA group" means that at least one hydrogen atom in the BB group is substituted with the AA group.

Substituents Mentioned Herein

Substituents mentioned herein will be described below.

An "unsubstituted aryl group" mentioned herein has, unless otherwise specified herein, 6 to 50, preferably 6 to 30, more preferably 6 to 18 ring carbon atoms.

An "unsubstituted heterocyclic group" mentioned herein has, unless otherwise specified herein, 5 to 50, preferably 5 to 30, more preferably 5 to 18 ring atoms.

An "unsubstituted alkyl group" mentioned herein has, unless otherwise specified herein, 1 to 50, preferably 1 to 20, more preferably 1 to 6 carbon atoms.

An "unsubstituted alkenyl group" mentioned herein has, unless otherwise specified herein, 2 to 50, preferably 2 to 20, more preferably 2 to 6 carbon atoms.

An "unsubstituted alkynyl group" mentioned herein has, unless otherwise specified herein, 2 to 50, preferably 2 to 20, more preferably 2 to 6 carbon atoms.

An "unsubstituted cycloalkyl group" mentioned herein has, unless otherwise specified herein, 3 to 50, preferably 3 to 20, more preferably 3 to 6 ring carbon atoms.

An "unsubstituted arylene group" mentioned herein has, unless otherwise specified herein, 6 to 50, preferably 6 to 30, more preferably 6 to 18 ring carbon atoms.

An "unsubstituted divalent heterocyclic group" mentioned herein has, unless otherwise specified herein, 5 to 50, preferably 5 to 30, more preferably 5 to 18 ring atoms.

An "unsubstituted alkylene group" mentioned herein has, unless otherwise specified herein, 1 to 50, preferably 1 to 20, more preferably 1 to 6 carbon atoms.

Substituted or Unsubstituted Aryl Group

Specific examples (specific example group G1) of the "substituted or unsubstituted aryl group" mentioned herein include unsubstituted aryl groups (specific example group G1A) below and substituted aryl groups (specific example group G1B) below. (Herein, an unsubstituted aryl group refers to an "unsubstituted aryl group" in a "substituted or unsubstituted aryl group", and a substituted aryl group refers to a "substituted aryl group" in a "substituted or unsubstituted aryl group.") A simply termed "aryl group" herein includes both of an "unsubstituted aryl group" and a "substituted aryl group."

The "substituted aryl group" refers to a group derived by substituting at least one hydrogen atom in an "unsubstituted aryl group" with a substituent. Examples of the "substituted aryl group" include a group derived by substituting at least one hydrogen atom in the "unsubstituted aryl group" in the specific example group G1A below with a substituent, and examples of the substituted aryl group in the specific example group G1B below. It should be noted that the examples of the "unsubstituted aryl group" and the "substituted aryl group" mentioned herein are merely exemplary, and the "substituted aryl group" mentioned herein includes a group derived by further substituting a hydrogen atom bonded to a carbon atom of a skeleton of a "substituted aryl group" in the specific example group G1B below, and a group derived by further substituting a hydrogen atom of a substituent of the "substituted aryl group" in the specific example group G1B below.

Unsubstituted Aryl Group (Specific Example Group G1A):

a phenyl group, p-biphenyl group, m-biphenyl group, o-biphenyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-terphenyl-4-yl group, o-terphenyl-3-yl group, o-terphenyl-2-yl group, 1-naphthyl group, 2-naphthyl group, anthryl group, benzanthryl group, phenanthryl group, benzophenanthryl group, phenalenyl group, pyrenyl group, chrysenyl group, benzochrysenyl group, triphenylenyl group, benzotriphenylenyl group, tetracenyl group, pentacenyl group, fluorenyl group, 9,9'-spirobifluorenyl group, benzofluorenyl group, dibenzofluorenyl group, fluoranthenyl group, benzofluoranthenyl group, perylenyl group, and a monovalent aryl group derived by removing one hydrogen atom from cyclic structures represented by formulae (TEMP-1) to (TEMP-15) below.

[Formula 4]
(TEMP-1)
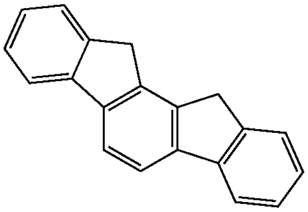
(TEMP-2)
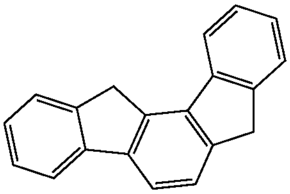
(TEMP-3)
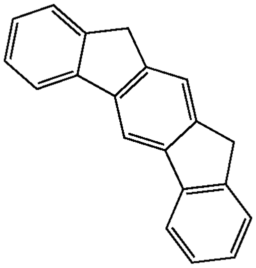
(TEMP-4)
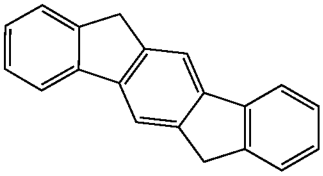
(TEMP-5)
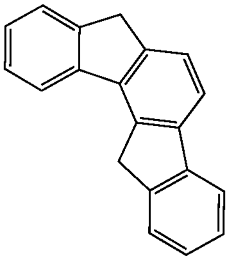
(TEMP-6)
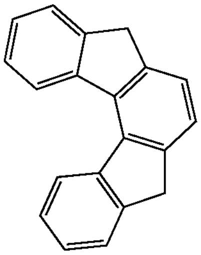
(TEMP-7)
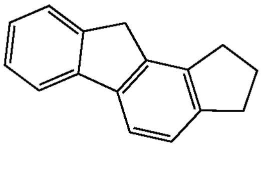
-continued
(TEMP-8)
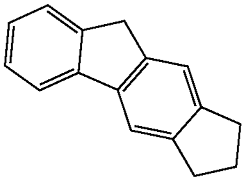
(TEMP-9)
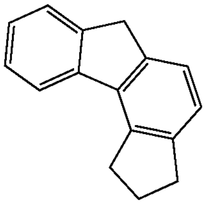
[Formula 5]
(TEMP-10)
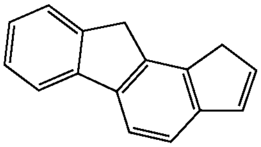
(TEMP-11)
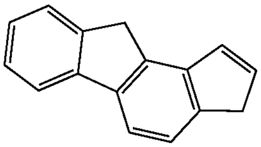
(TEMP-12)
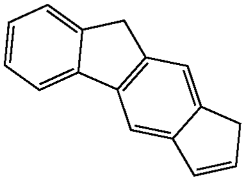
(TEMP-13)
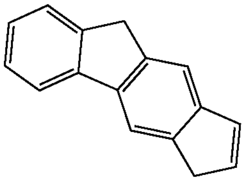
(TEMP-14)
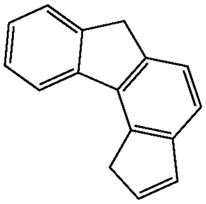
(TEMP-15)
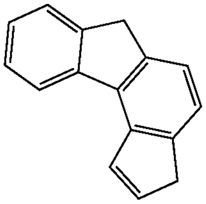

Substituted Aryl Group (Specific Example Group G1B):

o-tolyl group, m-tolyl group, p-tolyl group, para-xylyl group, meta-xylyl group, ortho-xylyl group, para-isopropylphenyl group, meta-isopropylphenyl group, ortho-isopropylphenyl group, para-t-butylphenyl group, meta-t-butylphenyl group, ortho-t-butylphenyl group, 3,4,5-trimethylphenyl group, 9,9-dimethylfluorenyl group, 9,9-diphenylfluorenyl group, 9,9-bis(4-methylphenyl)fluorenyl group, 9,9-bis(4-isopropylphenyl)fluorenyl group, 9,9-bis(4-t-butylphenyl)fluorenyl group, cyanophenyl group, triphenylsilylphenyl group, trimethylsilylphenyl group, phenylnaphthyl group, naphthylphenyl group, and a group derived by substituting at least one hydrogen atom of a monovalent group derived from one of the cyclic structures represented by the formulae (TEMP-1) to (TEMP-15) with a substituent.

Substituted or Unsubstituted Heterocyclic Group

The "heterocyclic group" mentioned herein refers to a cyclic group having at least one hetero atom in the ring atoms. Specific examples of the hetero atom include a nitrogen atom, oxygen atom, sulfur atom, silicon atom, phosphorus atom, and boron atom.

The "heterocyclic group" mentioned herein is a monocyclic group or a fused-ring group.

The "heterocyclic group" mentioned herein is an aromatic heterocyclic group or a non-aromatic heterocyclic group.

Specific examples (specific example group G2) of the "substituted or unsubstituted heterocyclic group" mentioned herein include unsubstituted heterocyclic groups (specific example group G2A) and substituted heterocyclic groups (specific example group G2B). (Herein, an unsubstituted heterocyclic group refers to an "unsubstituted heterocyclic group" in a "substituted or unsubstituted heterocyclic group," and a substituted heterocyclic group refers to a "substituted heterocyclic group" in a "substituted or unsubstituted heterocyclic group.") A simply termed "heterocyclic group" herein includes both of "unsubstituted heterocyclic group" and "substituted heterocyclic group."

The "substituted heterocyclic group" refers to a group derived by substituting at least one hydrogen atom in an "unsubstituted heterocyclic group" with a substituent. Specific examples of the "substituted heterocyclic group" include a group derived by substituting at least one hydrogen atom in the "unsubstituted heterocyclic group" in the specific example group G2A below with a substituent, and examples of the substituted heterocyclic group in the specific example group G2B below. It should be noted that the examples of the "unsubstituted heterocyclic group" and the "substituted heterocyclic group" mentioned herein are merely exemplary, and the "substituted heterocyclic group" mentioned herein includes a group derived by further substituting a hydrogen atom bonded to a ring atom of a skeleton of a "substituted heterocyclic group" in the specific example group G2B below, and a group derived by further substituting a hydrogen atom of a substituent of the "substituted heterocyclic group" in the specific example group G2B below.

The specific example group G2A includes, for instance, unsubstituted heterocyclic groups including a nitrogen atom (specific example group G2A1) below, unsubstituted heterocyclic groups including an oxygen atom (specific example group G2A2) below, unsubstituted heterocyclic groups including a sulfur atom (specific example group G2A3) below, and monovalent heterocyclic groups (specific example group G2A4) derived by removing a hydrogen atom from cyclic structures represented by formulae (TEMP-16) to (TEMP-33) below.

The specific example group G2B includes, for instance, substituted heterocyclic groups including a nitrogen atom (specific example group G2B1) below, substituted heterocyclic groups including an oxygen atom (specific example group G2B2) below, substituted heterocyclic groups including a sulfur atom (specific example group G2B3) below, and groups derived by substituting at least one hydrogen atom of the monovalent heterocyclic groups (specific example group G2B4) derived from the cyclic structures represented by formulae (TEMP-16) to (TEMP-33) below.

Unsubstituted Heterocyclic Groups Including Nitrogen Atom (Specific Example Group G2A1):

pyrrolyl group, imidazolyl group, pyrazolyl group, triazolyl group, tetrazolyl group, oxazolyl group, isoxazolyl group, oxadiazolyl group, thiazolyl group, isothiazolyl group, thiadiazolyl group, pyridyl group, pyridazynyl group, pyrimidinyl group, pyrazinyl group, triazinyl group, indolyl group, isoindolyl group, indolizinyl group, quinolizinyl group, quinolyl group, isoquinolyl group, cinnolyl group, phthalazinyl group, quinazolinyl group, quinoxalinyl group, benzimidazolyl group, indazolyl group, phenanthrolinyl group, phenanthridinyl group, acridinyl group, phenazinyl group, carbazolyl group, benzocarbazolyl group, morpholino group, phenoxazinyl group, phenothiazinyl group, azacarbazolyl group, and diazacarbazolyl group.

Unsubstituted Heterocyclic Groups Including Oxygen Atom (Specific Example Group G2A2):

furyl group, oxazolyl group, isoxazolyl group, oxadiazolyl group, xanthenyl group, benzofuranyl group, isobenzofuranyl group, dibenzofuranyl group, naphthobenzofuranyl group, benzoxazolyl group, benzisoxazolyl group, phenoxazinyl group, morpholino group, dinaphthofuranyl group, azadibenzofuranyl group, diazadibenzofuranyl group, azanaphthobenzofuranyl group, and diazanaphthobenzofuranyl group.

Unsubstituted Heterocyclic Groups Including Sulfur Atom (Specific Example Group G2A3):

thienyl group, thiazolyl group, isothiazolyl group, thiadiazolyl group, benzothiophenyl group (benzothienyl group), isobenzothiophenyl group (isobenzothienyl group), dibenzothiophenyl group (dibenzothienyl group), naphthobenzothiophenyl group (nahthobenzothienyl group), benzothiazolyl group, benzisothiazolyl group, phenothiazinyl group, dinaphthothiophenyl group (dinaphthothienyl group), azadibenzothiophenyl group (azadibenzothienyl group), diazadibenzothiophenyl group (diazadibenzothienyl group), azanaphthobenzothiophenyl group (azanaphthobenzothienyl group), and diazanaphthobenzothiophenyl group (diazanaphthobenzothienyl group).

Monovalent Heterocyclic Groups Derived by Removing One Hydrogen Atom from Cyclic Structures Represented by Formulae (TEMP-16) to (TEMP-33) (Specific Example Group G2A4):

[Formula 6]

(TEMP-16)

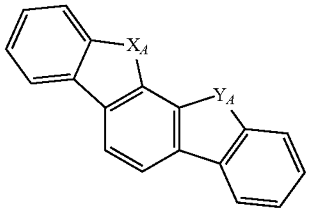

-continued
(TEMP-17)
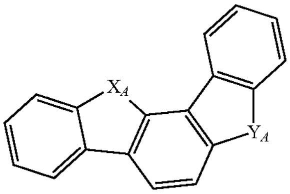
(TEMP-18)
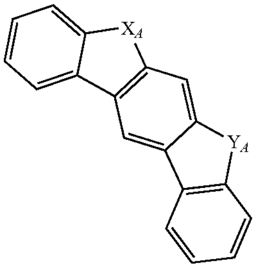
(TEMP-19)
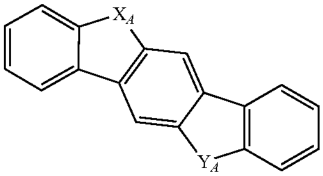
(TEMP-20)
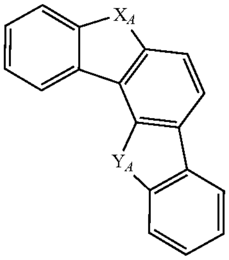
(TEMP-21)
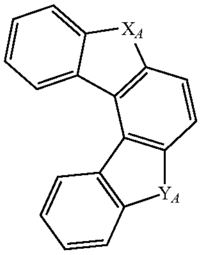
(TEMP-22)
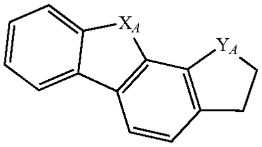
(TEMP-23)
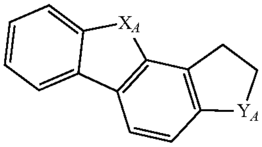
-continued
(TEMP-24)
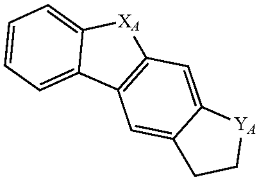
[Formula 7]
(TEMP-25)
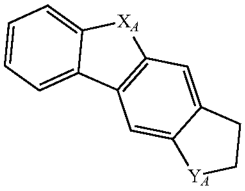
(TEMP-26)
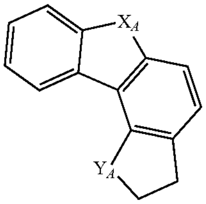
(TEMP-27)
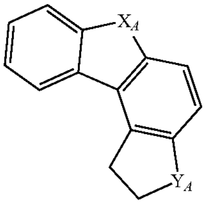
(TEMP-28)
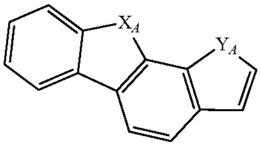
(TEMP-29)
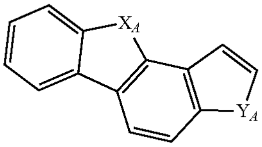
(TEMP-30)
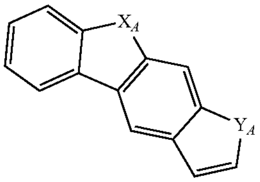
(TEMP-31)
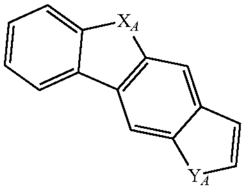

-continued (TEMP-32)

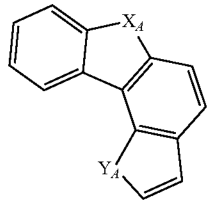

(TEMP-33)

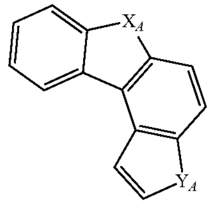

In the formulae (TEMP-16) to (TEMP-33), $X_A$ and $Y_A$ are each independently an oxygen atom, a sulfur atom, NH, or $CH_2$, with a proviso that at least one of $X_A$ or $Y_A$ is an oxygen atom, a sulfur atom, or NH.

When at least one of $X_A$ or $Y_A$ in the formulae (TEMP-16) to (TEMP-33) is NH or $CH_2$, the monovalent heterocyclic groups derived from the cyclic structures represented by the formulae (TEMP-16) to (TEMP-33) include a monovalent group derived by removing one hydrogen atom from NH or $CH_2$.

Substituted Heterocyclic Groups Including Nitrogen Atom (Specific Example Group G2B1):

(9-phenyl)carbazolyl group, (9-biphenylyl)carbazolyl group, (9-phenyl)phenylcarbazolyl group, (9-naphthyl)carbazolyl group, diphenylcarbazole-9-yl group, phenylcarbazole-9-yl group, methylbenzimidazolyl group, ethylbenzimidazolyl group, phenyltriazinyl group, biphenylyltriazinyl group, diphenyltriazinyl group, phenylquinazolinyl group, and biphenylquinazolinyl group.

Substituted Heterocyclic Groups Including Oxygen Atom (Specific Example Group G2B2):

phenyldibenzofuranyl group, methyldibenzofuranyl group, t-butyldibenzofuranyl group, and monovalent residue of spiro[9H-xanthene-9,9'-[9H]fluorene].

Substituted Heterocyclic Groups Including Sulfur Atom (Specific Example Group G2B3):

phenyldibenzothiophenyl group, methyldibenzothiophenyl group, t-butyldibenzothiophenyl group, and monovalent residue of spiro[9H-thioxanthene-9,9'-[9H]fluorene].

Groups Obtained by Substituting at Least One Hydrogen Atom of Monovalent Heterocyclic Group Derived from Cyclic Structures Represented by Formulae (TEMP-16) to (TEMP-33) with Substituent (Specific Example Group G2B4):

The "at least one hydrogen atom of a monovalent heterocyclic group" means at least one hydrogen atom selected from a hydrogen atom bonded to a ring carbon atom of the monovalent heterocyclic group, a hydrogen atom bonded to a nitrogen atom of at least one of $X_A$ or $Y_A$ in a form of NH, and a hydrogen atom of one of $X_A$ and $Y_A$ in a form of a methylene group ($CH_2$).

Substituted or Unsubstituted Alkyl Group

Specific examples (specific example group G3) of the "substituted or unsubstituted alkyl group" mentioned herein include unsubstituted alkyl groups (specific example group G3A) and substituted alkyl groups (specific example group G3B) below. (Herein, an unsubstituted alkyl group refers to an "unsubstituted alkyl group" in a "substituted or unsubstituted alkyl group," and a substituted alkyl group refers to a "substituted alkyl group" in a "substituted or unsubstituted alkyl group.") A simply termed "alkyl group" herein includes both of "unsubstituted alkyl group" and "substituted alkyl group."

The "substituted alkyl group" refers to a group derived by substituting at least one hydrogen atom in an "unsubstituted alkyl group" with a substituent. Specific examples of the "substituted alkyl group" include a group derived by substituting at least one hydrogen atom of an "unsubstituted alkyl group" (specific example group G3A) below with a substituent, and examples of the substituted alkyl group (specific example group G3B) below. Herein, the alkyl group for the "unsubstituted alkyl group" refers to a chain alkyl group. Accordingly, the "unsubstituted alkyl group" include linear "unsubstituted alkyl group" and branched "unsubstituted alkyl group." It should be noted that the examples of the "unsubstituted alkyl group" and the "substituted alkyl group" mentioned herein are merely exemplary, and the "substituted alkyl group" mentioned herein includes a group derived by further substituting a hydrogen atom of a skeleton of the "substituted alkyl group" in the specific example group G3B, and a group derived by further substituting a hydrogen atom of a substituent of the "substituted alkyl group" in the specific example group G3B.

Unsubstituted Alkyl Group (Specific Example Group G3A):

methyl group, ethyl group, n-propyl group, isopropyl group, n-butyl group, isobutyl group, s-butyl group, and t-butyl group.

Substituted Alkyl Group (Specific Example Group G3B):

heptafluoropropyl group (including isomer thereof), pentafluoroethyl group, 2,2,2-trifluoroethyl group, and trifluoromethyl group.

Substituted or Unsubstituted Alkenyl Group

Specific examples (specific example group G4) of the "substituted or unsubstituted alkenyl group" mentioned herein include unsubstituted alkenyl groups (specific example group G4A) and substituted alkenyl groups (specific example group G4B). (Herein, an unsubstituted alkenyl group refers to an "unsubstituted alkenyl group" in a "substituted or unsubstituted alkenyl group," and a substituted alkenyl group refers to a "substituted alkenyl group" in a "substituted or unsubstituted alkenyl group.") A simply termed "alkenyl group" herein includes both of "unsubstituted alkenyl group" and "substituted alkenyl group."

The "substituted alkenyl group" refers to a group derived by substituting at least one hydrogen atom in an "unsubstituted alkenyl group" with a substituent. Specific examples of the "substituted alkenyl group" include an "unsubstituted alkenyl group" (specific example group G4A) substituted by a substituent, and examples of the substituted alkenyl group (specific example group G4B) below. It should be noted that the examples of the "unsubstituted alkenyl group" and the "substituted alkenyl group" mentioned herein are merely exemplary, and the "substituted alkenyl group" mentioned herein includes a group derived by further substituting a hydrogen atom of a skeleton of the "substituted alkenyl group" in the specific example group G4B with a substituent, and a group derived by further substituting a hydrogen atom of a substituent of the "substituted alkenyl group" in the specific example group G4B with a substituent.

Unsubstituted Alkenyl Group (Specific Example Group G4A):

vinyl group, allyl group, 1-butenyl group, 2-butenyl group, and 3-butenyl group.

Substituted Alkenyl Group (Specific Example Group G4B):

1,3-butanedienyl group, 1-methylvinyl group, 1-methylallyl group, 1,1-dimethylallyl group, 2-methylallyl group, and 1,2-dimethylallyl group.

Substituted or Unsubstituted Alkynyl Group

Specific examples (specific example group G5) of the "substituted or unsubstituted alkynyl group" mentioned herein include unsubstituted alkynyl groups (specific example group G5A) below. (Herein, an unsubstituted alkynyl group refers to an "unsubstituted alkynyl group" in a "substituted or unsubstituted alkynyl group.") A simply termed "alkynyl group" herein includes both of "unsubstituted alkynyl group" and "substituted alkynyl group."

The "substituted alkynyl group" refers to a group derived by substituting at least one hydrogen atom in an "unsubstituted alkynyl group" with a substituent. Specific examples of the "substituted alkynyl group" include a group derived by substituting at least one hydrogen atom of the "unsubstituted alkynyl group" (specific example group G5A) below with a substituent.

Unsubstituted Alkynyl Group (Specific Example Group G5A):

ethynyl group.

Substituted or Unsubstituted Cycloalkyl Group

Specific examples (specific example group G6) of the "substituted or unsubstituted cycloalkyl group" mentioned herein include unsubstituted cycloalkyl groups (specific example group G6A) and substituted cycloalkyl groups (specific example group G6B). (Herein, an unsubstituted cycloalkyl group refers to an "unsubstituted cycloalkyl group" in a "substituted or unsubstituted cycloalkyl group," and a substituted cycloalkyl group refers to a "substituted cycloalkyl group" in a "substituted or unsubstituted cycloalkyl group.") A simply termed "cycloalkyl group" herein includes both of "unsubstituted cycloalkyl group" and "substituted cycloalkyl group."

The "substituted cycloalkyl group" refers to a group derived by substituting at least one hydrogen atom of an "unsubstituted cycloalkyl group" with a substituent. Specific examples of the "substituted cycloalkyl group" include a group derived by substituting at least one hydrogen atom of the "unsubstituted cycloalkyl group" (specific example group G6A) below with a substituent, and examples of the substituted cycloalkyl group (specific example group G6B) below. It should be noted that the examples of the "unsubstituted cycloalkyl group" and the "substituted cycloalkyl group" mentioned herein are merely exemplary, and the "substituted cycloalkyl group" mentioned herein includes a group derived by substituting at least one hydrogen atom bonded to a carbon atom of a skeleton of the "substituted cycloalkyl group" in the specific example group G6B with a substituent, and a group derived by further substituting a hydrogen atom of a substituent of the "substituted cycloalkyl group" in the specific example group G6B with a substituent.

Unsubstituted Cycloalkyl Group (Specific Example Group G6A):

cyclopropyl group, cyclobutyl group, cyclopentyl group, cyclohexyl group, 1-adamantyl group, 2-adamantyl group, 1-norbornyl group, and 2-norbornyl group.

Substituted Cycloalkyl Group (Specific Example Group G6B):

4-methylcyclohexyl group.

Group Represented by —Si($R_{901}$)($R_{902}$)($R_{903}$)

Specific examples (specific example group G7) of the group represented herein by —Si($R_{901}$)($R_{902}$)($R_{903}$) include: —Si(G1)(G1)(G1); —Si(G1)(G2)(G2); —Si(G1)(G1)(G2); —Si(G2)(G2)(G2); —Si(G3)(G3)(G3); and —Si(G6)(G6)(G6), where:

G1 represents a "substituted or unsubstituted aryl group" in the specific example group G1;

G2 represents a "substituted or unsubstituted heterocyclic group" in the specific example group G2;

G3 represents a "substituted or unsubstituted alkyl group" in the specific example group G3;

G6 represents a "substituted or unsubstituted cycloalkyl group" in the specific example group G6;

a plurality of G1 in —Si(G1)(G1)(G1) are mutually the same or different;

a plurality of G2 in —Si(G1)(G2)(G2) are mutually the same or different;

a plurality of G1 in —Si(G1)(G1)(G2) are mutually the same or different;

a plurality of G2 in —Si(G2)(G2)(G2) are mutually the same or different;

a plurality of G3 in —Si(G3)(G3)(G3) are mutually the same or different; and a plurality of G6 in —Si(G6)(G6)(G6) are mutually the same or different.

Group Represented by —O—($R_{904}$)

Specific examples (specific example group G8) of a group represented by —O—($R_{904}$) herein include: —O(G1); —O(G2); —O(G3); and —O(G6), where:

G1 represents a "substituted or unsubstituted aryl group" in the specific example group G1;

G2 represents a "substituted or unsubstituted heterocyclic group" in the specific example group G2;

G3 represents a "substituted or unsubstituted alkyl group" in the specific example group G3; and G6 represents a "substituted or unsubstituted cycloalkyl group" in the specific example group G6.

Group Represented by —S—($R_{905}$)

Specific examples (specific example group G9) of a group represented herein by —S—($R_{905}$) include: —S(G1); —S(G2); —S(G3); and —S(G6), where:

G1 represents a "substituted or unsubstituted aryl group" in the specific example group G1;

G2 represents a "substituted or unsubstituted heterocyclic group" in the specific example group G2;

G3 represents a "substituted or unsubstituted alkyl group" in the specific example group G3; and G6 represents a "substituted or unsubstituted cycloalkyl group" in the specific example group G6.

Group Represented by —N($R_{906}$)($R_{907}$)

Specific examples (specific example group G10) of a group represented herein by —N($R_{906}$)($R_{907}$) include: —N(G1)(G1); —N(G2)(G2); —N(G1)(G2); —N(G3)(G3); and —N(G6)(G6), where:

G1 represents a "substituted or unsubstituted aryl group" in the specific example group G1;

G2 represents a "substituted or unsubstituted heterocyclic group" in the specific example group G2;

G3 represents a "substituted or unsubstituted alkyl group" in the specific example group G3;

G6 represents a "substituted or unsubstituted cycloalkyl group" in the specific example group G6;

a plurality of G1 in —N(G1)(G1) are mutually the same or different;

a plurality of G2 in —N(G2)(G2) are mutually the same or different;

a plurality of G3 in —N(G3)(G3) are mutually the same or different; and a plurality of G6 in —N(G6)(G6) are mutually the same or different.

Halogen Atom

Specific examples (specific example group G11) of "halogen atom" mentioned herein include a fluorine atom, chlorine atom, bromine atom, and iodine atom.

Substituted or Unsubstituted Fluoroalkyl Group

The "substituted or unsubstituted fluoroalkyl group" mentioned herein refers to a group derived by substituting at least one hydrogen atom bonded to at least one of carbon atoms forming an alkyl group in the "substituted or unsubstituted alkyl group" with a fluorine atom, and also includes a group (perfluoro group) derived by substituting all of hydrogen atoms bonded to carbon atoms forming the alkyl group in the "substituted or unsubstituted alkyl group" with fluorine atoms. An "unsubstituted fluoroalkyl group" has, unless otherwise specified herein, 1 to 50, preferably 1 to 30, more preferably 1 to 18 carbon atoms. The "substituted fluoroalkyl group" refers to a group derived by substituting at least one hydrogen atom in a "fluoroalkyl group" with a substituent. It should be noted that the examples of the "substituted fluoroalkyl group" mentioned herein include a group derived by further substituting at least one hydrogen atom bonded to a carbon atom of an alkyl chain of a "substituted fluoroalkyl group" with a substituent, and a group derived by further substituting at least one hydrogen atom of a substituent of the "substituted fluoroalkyl group" with a substituent. Specific examples of the "substituted fluoroalkyl group" include a group derived by substituting at least one hydrogen atom of the "alkyl group" (specific example group G3) with a fluorine atom.

Substituted or Unsubstituted Haloalkyl Group

The "substituted or unsubstituted haloalkyl group" mentioned herein refers to a group derived by substituting at least one hydrogen atom bonded to carbon atoms forming the alkyl group in the "substituted or unsubstituted alkyl group" with a halogen atom, and also includes a group derived by substituting all hydrogen atoms bonded to carbon atoms forming the alkyl group in the "substituted or unsubstituted alkyl group" with halogen atoms. An "unsubstituted haloalkyl group" has, unless otherwise specified herein, 1 to 50, preferably 1 to 30, more preferably 1 to 18 carbon atoms. The "substituted haloalkyl group" refers to a group derived by substituting at least one hydrogen atom in a "haloalkyl group" with a substituent. It should be noted that the examples of the "substituted haloalkyl group" mentioned herein include a group derived by further substituting at least one hydrogen atom bonded to a carbon atom of an alkyl chain of a "substituted haloalkyl group" with a substituent, and a group derived by further substituting at least one hydrogen atom of a substituent of the "substituted haloalkyl group" with a substituent. Specific examples of the "unsubstituted haloalkyl group" include a group derived by substituting at least one hydrogen atom of the "alkyl group" (specific example group G3) with a halogen atom. The haloalkyl group is sometimes referred to as a halogenated alkyl group.

Substituted or Unsubstituted Alkoxy Group

Specific examples of a "substituted or unsubstituted alkoxy group" mentioned herein include a group represented by —O(G3), G3 being the "substituted or unsubstituted alkyl group" in the specific example group G3. An "unsubstituted alkoxy group" has, unless otherwise specified herein, 1 to 50, preferably 1 to 30, more preferably 1 to 18 carbon atoms.

Substituted or Unsubstituted Alkylthio Group

Specific examples of a "substituted or unsubstituted alkylthio group" mentioned herein include a group represented by —S(G3), G3 being the "substituted or unsubstituted alkyl group" in the specific example group G3. An "unsubstituted alkylthio group" has, unless otherwise specified herein, 1 to 50, preferably 1 to 30, more preferably 1 to 18 carbon atoms.

Substituted or Unsubstituted Aryloxy Group

Specific examples of a "substituted or unsubstituted aryloxy group" mentioned herein include a group represented by —O(G1), G1 being the "substituted or unsubstituted aryl group" in the specific example group G1. An "unsubstituted aryloxy group" has, unless otherwise specified herein, 6 to 50, preferably 6 to 30, more preferably 6 to 18 ring carbon atoms.

Substituted or Unsubstituted Arylthio Group

Specific examples of a "substituted or unsubstituted arylthio group" mentioned herein include a group represented by —S(G1), G1 being the "substituted or unsubstituted aryl group" in the specific example group G1. An "unsubstituted arylthio group" has, unless otherwise specified herein, 6 to 50, preferably 6 to 30, more preferably 6 to 18 ring carbon atoms.

Substituted or Unsubstituted Trialkylsilyl Group

Specific examples of a "trialkylsilyl group" mentioned herein include a group represented by —Si(G3)(G3)(G3), G3 being the "substituted or unsubstituted alkyl group" in the specific example group G3. The plurality of G3 in —Si(G3)(G3)(G3) are mutually the same or different. Each of the alkyl groups in the "trialkylsilyl group" has, unless otherwise specified herein, 1 to 50, preferably 1 to 20, more preferably 1 to 6 carbon atoms.

Substituted or Unsubstituted Aralkyl Group

Specific examples of a "substituted or unsubstituted aralkyl group" mentioned herein include a group represented by (G3)-(G1), G3 being the "substituted or unsubstituted alkyl group" in the specific example group G3, G1 being the "substituted or unsubstituted aryl group" in the specific example group G1. Accordingly, the "aralkyl group" is a group derived by substituting a hydrogen atom of the "alkyl group" with a substituent in a form of the "aryl group," which is an example of the "substituted alkyl group." An "unsubstituted aralkyl group," which is an "unsubstituted alkyl group" substituted by an "unsubstituted aryl group," has, unless otherwise specified herein, 7 to 50 carbon atoms, preferably 7 to 30 carbon atoms, more preferably 7 to 18 carbon atoms.

Specific examples of the "substituted or unsubstituted aralkyl group" include a benzyl group, 1-phenylethyl group, 2-phenylethyl group, 1-phenylisopropyl group, 2-phenylisopropyl group, phenyl-t-butyl group, α-naphthylmethyl group, 1-α-naphthylethyl group, 2-α-naphthylethyl group, 1-α-naphthylisopropyl group, 2-α-naphthylisopropyl group, β-naphthylmethyl group, 1-β-naphthylethyl group, 2-β-naphthylethyl group, 1-β-naphthylisopropyl group, and 2-β-naphthylisopropyl group.

Preferable examples of the substituted or unsubstituted aryl group mentioned herein include, unless otherwise specified herein, a phenyl group, p-biphenyl group, m-biphenyl group, o-biphenyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-terphenyl-4-yl group, o-terphenyl-3-yl group, o-terphenyl-2-yl group, 1-naphthyl group, 2-naphthyl group, anthryl group, phenanthryl group, pyrenyl group, chrysenyl group, triphenylenyl group, fluorenyl group, 9,9'-spirobifluorenyl group, 9,9-dimethylfluorenyl group, and 9,9-diphenylfluorenyl group.

Preferable examples of the substituted or unsubstituted heterocyclic group mentioned herein include, unless otherwise specified herein, a pyridyl group, pyrimidinyl group, triazinyl group, quinolyl group, isoquinolyl group, quinazolinyl group, benzimidazolyl group, phenanthrolinyl group, carbazolyl group (1-carbazolyl group, 2-carbazolyl group, 3-carbazolyl group, 4-carbazolyl group, or 9-carbazolyl group), benzocarbazolyl group, azacarbazolyl group, diazacarbazolyl group, dibenzofuranyl group, naphthobenzofuranyl group, azadibenzofuranyl group, diazadibenzofuranyl group, dibenzothiophenyl group, naphthobenzothiophenyl group, azadibenzothiophenyl group, diazadibenzothiophenyl group, (9-phenyl)carbazolyl group ((9-phenyl)carbazole-1-yl group, (9-phenyl)carbazole-2-yl group, (9-phenyl)carbazole-3-yl group, or (9-phenyl)carbazole-4-yl group), (9-biphenylyl)carbazolyl group, (9-phenyl)phenylcarbazolyl group, diphenylcarbazole-9-yl group, phenylcarbazole-9-yl group, phenyltriazinyl group, biphenylyltriazinyl group, diphenyltriazinyl group, phenyldibenzofuranyl group, and phenyldibenzothiophenyl group.

The carbazolyl group mentioned herein is, unless otherwise specified herein, specifically a group represented by one of formulae below.

[Formula 8]

(TEMP-Cz1)

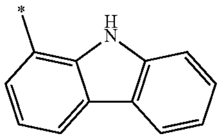

(TEMP-Cz2)

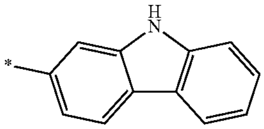

(TEMP-Cz3)

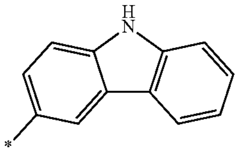

(TEMP-Cz4)

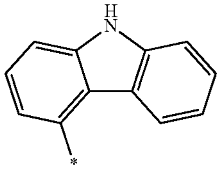

(TEMP-Cz5)

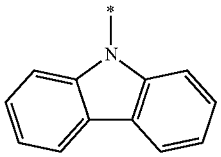

The (9-phenyl)carbazolyl group mentioned herein is, unless otherwise specified herein, specifically a group represented by one of formulae below.

[Formula 9]

(TEMP-Cz6)

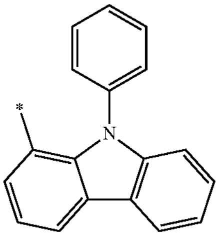

(TEMP-Cz7)

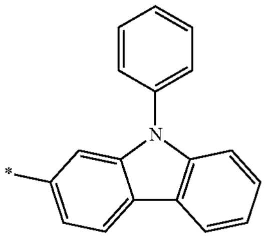

(TEMP-Cz8)

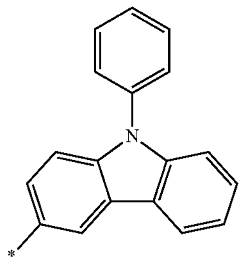

(TEMP-Cz9)

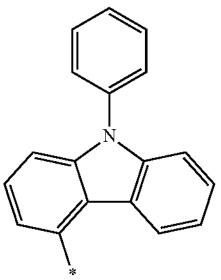

In the formulae (TEMP-Cz1) to (TEMP-Cz9), * represents a bonding position.

The dibenzofuranyl group and dibenzothiophenyl group mentioned herein are, unless otherwise specified herein, each specifically represented by one of formulae below.

[Formula 10]

(TEMP-34)

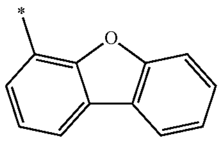

(TEMP-35)

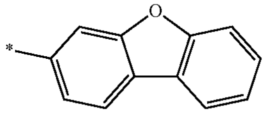

-continued (TEMP-36)

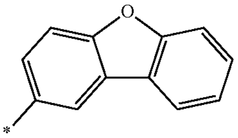

(TEMP-37)

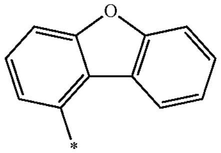

(TEMP-38)

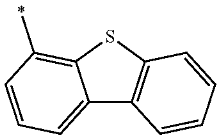

(TEMP-39)

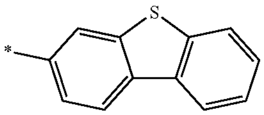

(TEMP-40)

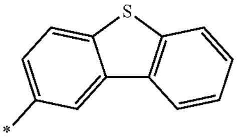

(TEMP-41)

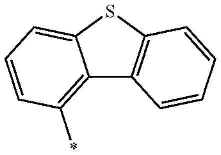

In the formulae (TEMP-34) to (TEMP-41), * represents a bonding position.

Preferable examples of the substituted or unsubstituted alkyl group mentioned herein include, unless otherwise specified herein, a methyl group, ethyl group, propyl group, isopropyl group, n-butyl group, isobutyl group, and t-butyl group.

Substituted or Unsubstituted Arylene Group

The "substituted or unsubstituted arylene group" mentioned herein is, unless otherwise specified herein, a divalent group derived by removing one hydrogen atom on an aryl ring of the "substituted or unsubstituted aryl group." Specific examples of the "substituted or unsubstituted arylene group" (specific example group G12) include a divalent group derived by removing one hydrogen atom on an aryl ring of the "substituted or unsubstituted aryl group" in the specific example group G1.

Substituted or Unsubstituted Divalent Heterocyclic Group

The "substituted or unsubstituted divalent heterocyclic group" mentioned herein is, unless otherwise specified herein, a divalent group derived by removing one hydrogen atom on a heterocycle of the "substituted or unsubstituted heterocyclic group." Specific examples of the "substituted or unsubstituted divalent heterocyclic group" (specific example group G13) include a divalent group derived by removing one hydrogen atom on a heterocyclic ring of the "substituted or unsubstituted heterocyclic group" in the specific example group G2.

Substituted or Unsubstituted Alkylene Group

The "substituted or unsubstituted alkylene group" mentioned herein is, unless otherwise specified herein, a divalent group derived by removing one hydrogen atom on an alkyl chain of the "substituted or unsubstituted alkyl group." Specific examples of the "substituted or unsubstituted alkylene group" (specific example group G14) include a divalent group derived by removing one hydrogen atom on an alkyl chain of the "substituted or unsubstituted alkyl group" in the specific example group G3.

The substituted or unsubstituted arylene group mentioned herein is, unless otherwise specified herein, preferably any one of groups represented by formulae (TEMP-42) to (TEMP-68) below.

[Formula 11]

(TEMP-42)

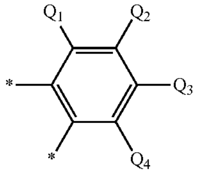

(TEMP-43)

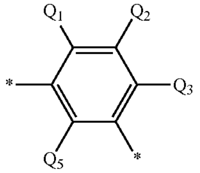

(TEMP-44)

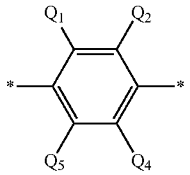

(TEMP-45)

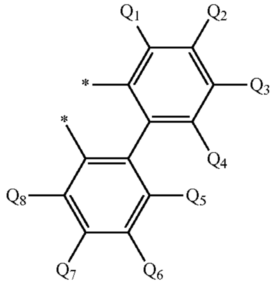

(TEMP-46)

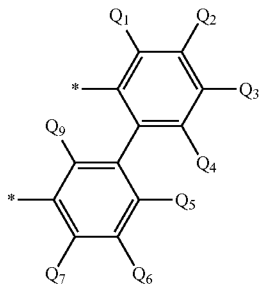

-continued
(TEMP-47)
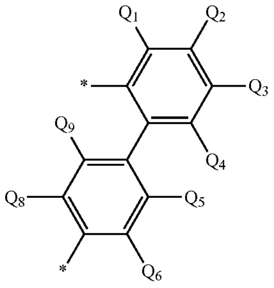
[Formula 12]
(TEMP-48)
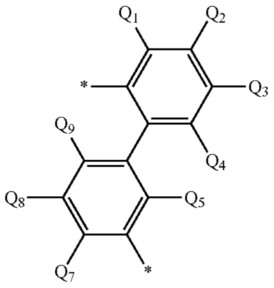
(TEMP-49)
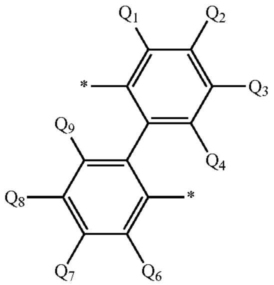
(TEMP-50)
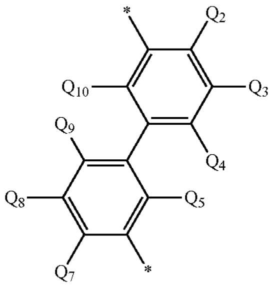
(TEMP-51)
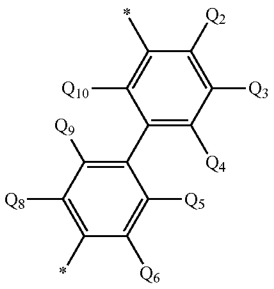
-continued
(TEMP-52)
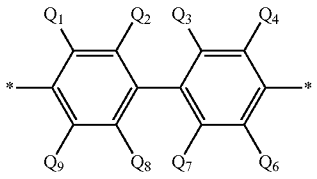
In the formulae (TEMP-42) to (TEMP-52), $Q_1$ to $Q_{10}$ are each independently a hydrogen atom or a substituent.
In the formulae (TEMP-42) to (TEMP-52), * represents a bonding position.
[Formula 13]
(TEMP-53)
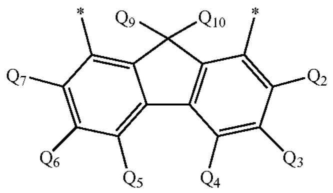
(TEMP-54)
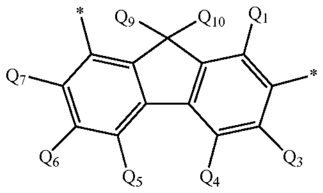
(TEMP-55)
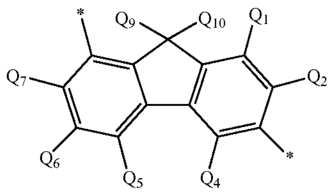
(TEMP-56)
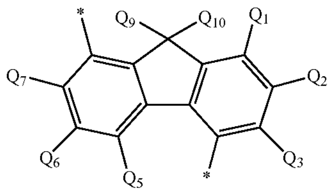
(TEMP-57)
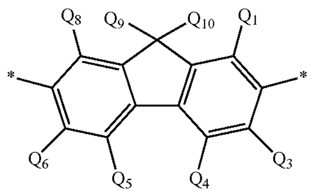
(TEMP-58)
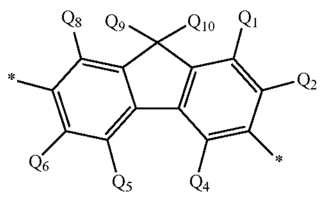

-continued (TEMP-59)

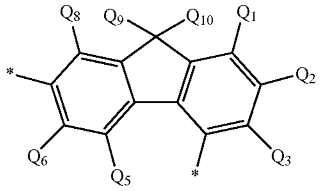

(TEMP-60)

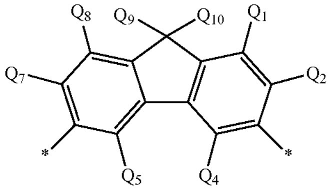

(TEMP-61)

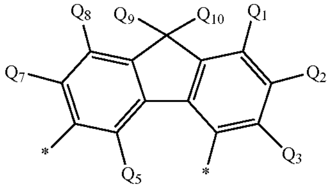

(TEMP-62)

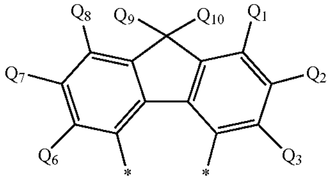

In the formulae (TEMP-53) to (TEMP-62), $Q_1$ to $Q_{10}$ are each independently a hydrogen atom or a substituent.

In the formulae, $Q_9$ and $Q_{10}$ may be mutually bonded through a single bond to form a ring.

In the formulae (TEMP-53) to (TEMP-62), * represents a bonding position.

[Formula 14]

(TEMP-63)

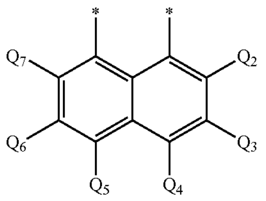

(TEMP-64)

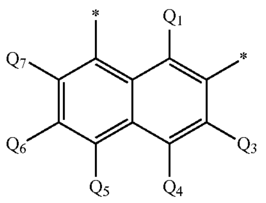

-continued (TEMP-65)

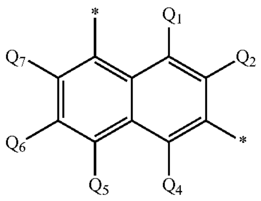

(TEMP-66)

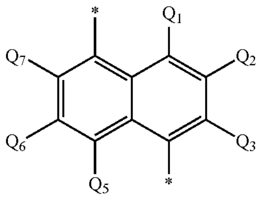

(TEMP-67)

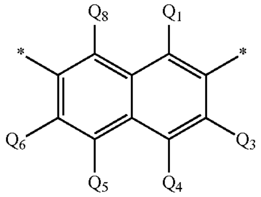

(TEMP-68)

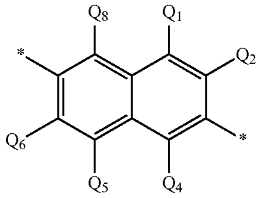

In the formulae (TEMP-63) to (TEMP-68), $Q_1$ to Qs are each independently a hydrogen atom or a substituent.

In the formulae (TEMP-63) to (TEMP-68), * represents a bonding position.

The substituted or unsubstituted divalent heterocyclic group mentioned herein is, unless otherwise specified herein, preferably a group represented by any one of formulae (TEMP-69) to (TEMP-102) below.

[Formula 15]

(TEMP-69)

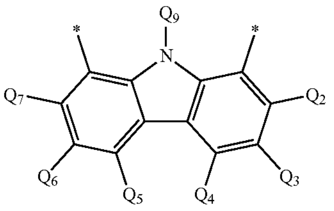

(TEMP-70)

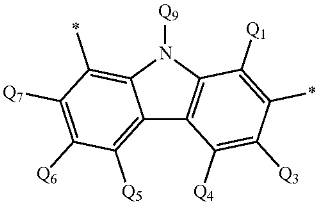

-continued
(TEMP-71)
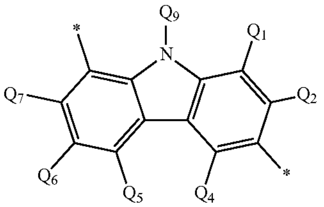
(TEMP-72)
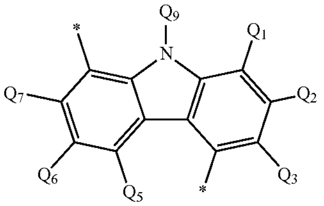
(TEMP-73)
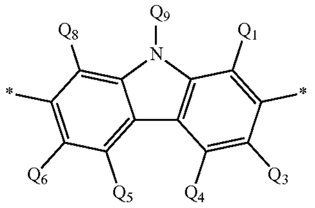
(TEMP-74)
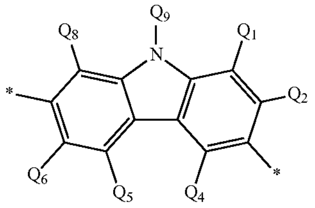
[Formula 16]
(TEMP-75)
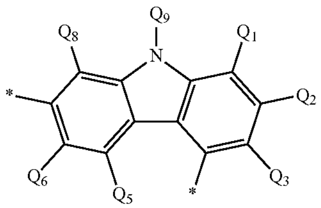
(TEMP-76)
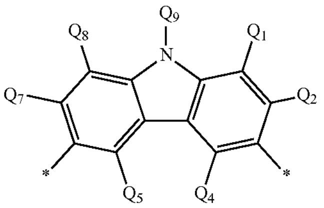
(TEMP-77)
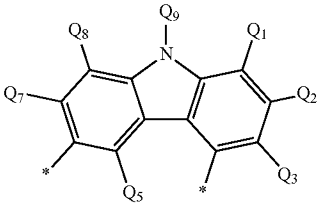
-continued
(TEMP-78)
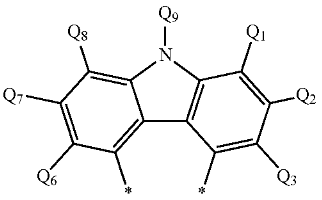
(TEMP-79)
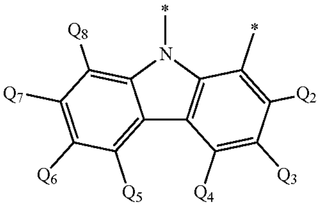
(TEMP-80)
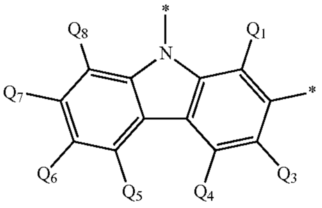
[Formula 17]
(TEMP-81)
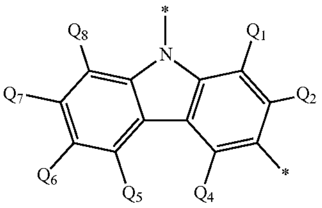
(TEMP-82)
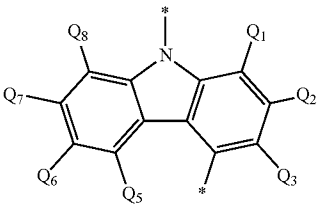
In the formulae (TEMP-69) to (TEMP-82), $Q_1$ to $Q_9$ are each independently a hydrogen atom or a substituent.
[Formula 18]
(TEMP-83)
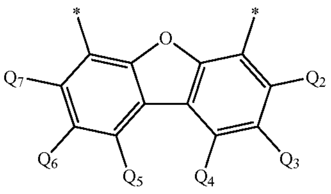

-continued
(TEMP-84)
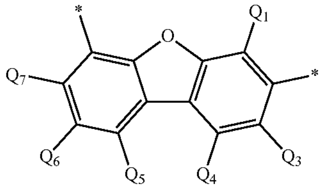
(TEMP-85)
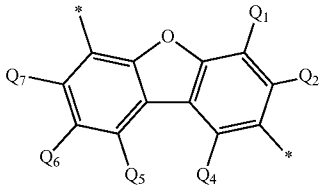
(TEMP-86)
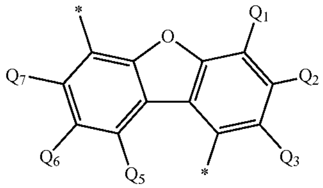
(TEMP-87)
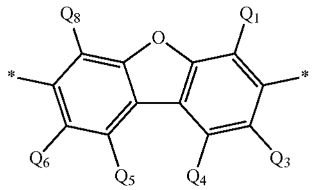
(TEMP-88)
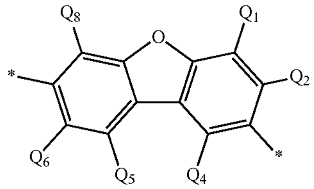
[Formula 19]
(TEMP-89)
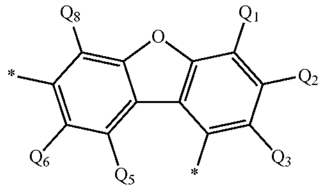
(TEMP-90)
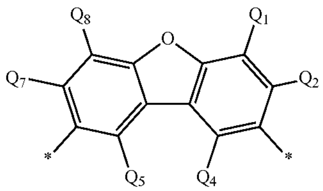
(TEMP-91)
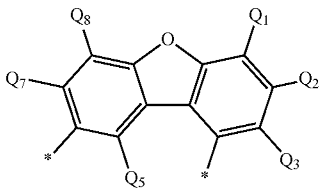
-continued
(TEMP-92)
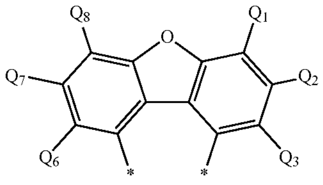
[Formula 20]
(TEMP-93)
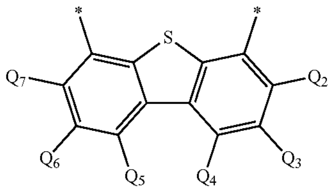
(TEMP-94)
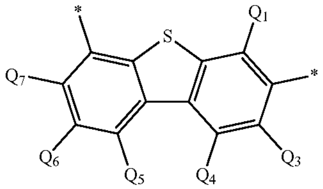
(TEMP-95)
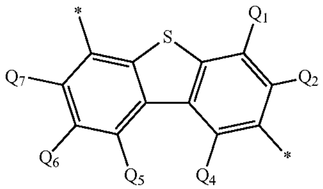
(TEMP-96)
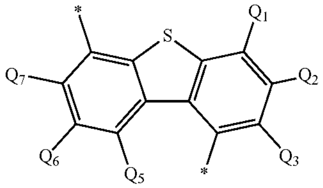
(TEMP-97)
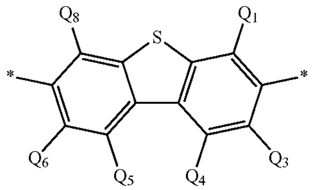
(TEMP-98)
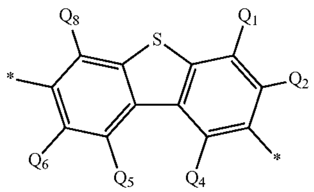

-continued

[Formula 21]

(TEMP-99)

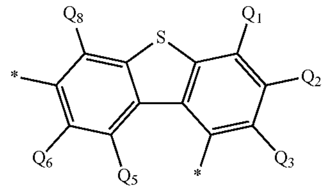

(TEMP-100)

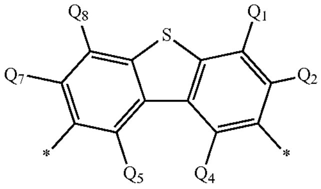

(TEMP-101)

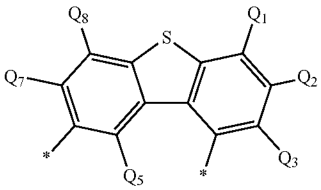

(TEMP-102)

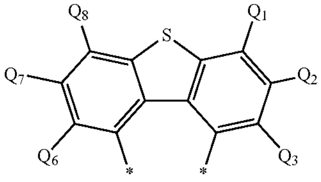

In the formulae (TEMP-83) to (TEMP-102), $Q_1$ to $Q_8$ are each independently a hydrogen atom or a substituent.

The substituent mentioned herein has been described above.

Instance of "Bonded to Form Ring"

Instances where "at least one combination of adjacent two or more (of . . . ) are mutually bonded to form a substituted or unsubstituted monocyclic ring, mutually bonded to form a substituted or unsubstituted fused ring, or not mutually bonded" mentioned herein refer to instances where "at least one combination of adjacent two or more (of . . . ) are mutually bonded to form a substituted or unsubstituted monocyclic ring, "at least one combination of adjacent two or more (of . . . ) are mutually bonded to form a substituted or unsubstituted fused ring," and "at least one combination of adjacent two or more (of . . . ) are not mutually bonded."

Instances where "at least one combination of adjacent two or more (of . . . ) are mutually bonded to form a substituted or unsubstituted monocyclic ring" and "at least one combination of adjacent two or more (of . . . ) are mutually bonded to form a substituted or unsubstituted fused ring" mentioned herein (these instances will be sometimes collectively referred to as an instance of "bonded to form a ring" hereinafter) will be described below. An anthracene compound having a basic skeleton in a form of an anthracene ring and represented by a formula (TEMP-103) below will be used as an example for the description.

[Formula 22]

(TEMP-103)

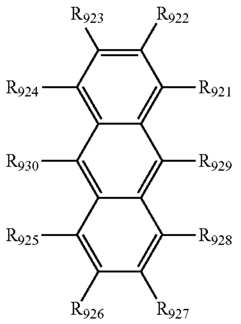

For instance, when "at least one combination of adjacent two or more of $R_{921}$ to $R_{930}$ are mutually bonded to form a ring," the combination of adjacent ones of $R_{921}$ to $R_{930}$ (i.e. the combination at issue) is a combination of $R_{921}$ and $R_{922}$, a combination of $R_{922}$ and $R_{923}$, a combination of $R_{923}$ and $R_{924}$, a combination of $R_{924}$ and $R_{930}$, a combination of $R_{930}$ and $R_{925}$, a combination of $R_{925}$ and $R_{926}$, a combination of $R_{926}$ and $R_{927}$, a combination of $R_{927}$ and $R_{928}$, a combination of $R_{928}$ and $R_{929}$, or a combination of $R_{929}$ and $R_{921}$.

The term "at least one combination" means that two or more of the above combinations of adjacent two or more of $R_{921}$ to $R_{930}$ may simultaneously form rings. For instance, when $R_{921}$ and $R_{922}$ are mutually bonded to form a ring $Q_A$ and $R_{925}$ and $R_{926}$ are simultaneously mutually bonded to form a ring $Q_B$, the anthracene compound represented by the formula (TEMP-103) is represented by a formula (TEMP-104) below.

[Formula 23]

(TEMP-104)

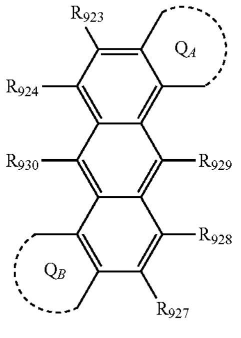

The instance where the "combination of adjacent two or more" form a ring means not only an instance where the "two" adjacent components are bonded but also an instance where adjacent "three or more" are bonded. For instance, $R_{921}$ and $R_{922}$ are mutually bonded to form a ring $Q_A$ and $R_{922}$ and $R_{923}$ are mutually bonded to form a ring Qc, and mutually adjacent three components ($R_{921}$, $R_{922}$ and $R_{923}$) are mutually bonded to form a ring fused to the anthracene basic skeleton. In this case, the anthracene compound represented by the formula (TEMP-103) is represented by a formula (TEMP-105) below. In the formula (TEMP-105) below, the ring $Q_A$ and the ring Qc share $R_{922}$.

[Formula 24]

(TEMP-105)

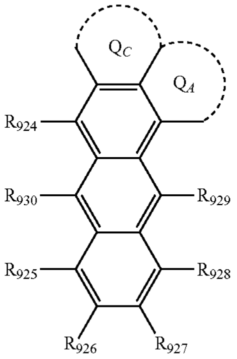

The formed "monocyclic ring" or "fused ring" may be, in terms of the formed ring in itself, a saturated ring or an unsaturated ring. When the "combination of adjacent two" form a "monocyclic ring" or a "fused ring," the "monocyclic ring" or "fused ring" may be a saturated ring or an unsaturated ring. For instance, the ring $Q_A$ and the ring $Q_B$ formed in the formula (TEMP-104) are each independently a "monocyclic ring" or a "fused ring." Further, the ring $Q_A$ and the ring Qc formed in the formula (TEMP-105) are each a "fused ring." The ring $Q_A$ and the ring Qc in the formula (TEMP-105) are fused to form a fused ring. When the ring $Q_A$ in the formula (TMEP-104) is a benzene ring, the ring $Q_A$ is a monocyclic ring. When the ring $Q_A$ in the formula (TMEP-104) is a naphthalene ring, the ring $Q_A$ is a fused ring.

The "unsaturated ring" represents an aromatic hydrocarbon ring or an aromatic heterocycle. The "saturated ring" represents an aliphatic hydrocarbon ring or a non-aromatic heterocycle.

Specific examples of the aromatic hydrocarbon ring include a ring formed by terminating a bond of a group in the specific example of the specific example group G1 with a hydrogen atom.

Specific examples of the aromatic heterocycle include a ring formed by terminating a bond of an aromatic heterocyclic group in the specific example of the specific example group G2 with a hydrogen atom.

Specific examples of the aliphatic hydrocarbon ring include a ring formed by terminating a bond of a group in the specific example of the specific example group G6 with a hydrogen atom.

The phrase "to form a ring" herein means that a ring is formed only by a plurality of atoms of a basic skeleton, or by a combination of a plurality of atoms of the basic skeleton and one or more optional atoms. For instance, the ring $Q_A$ formed by mutually bonding $R_{921}$ and $R_{922}$ shown in the formula (TEMP-104) is a ring formed by a carbon atom of the anthracene skeleton bonded to $R_{921}$, a carbon atom of the anthracene skeleton bonded to $R_{922}$, and one or more optional atoms. Specifically, when the ring $Q_A$ is a monocyclic unsaturated ring formed by $R_{921}$ and $R_{922}$, the ring formed by a carbon atom of the anthracene skeleton bonded to $R_{921}$, a carbon atom of the anthracene skeleton bonded to $R_{922}$, and four carbon atoms is a benzene ring.

The "optional atom" is, unless otherwise specified herein, preferably at least one atom selected from the group consisting of a carbon atom, nitrogen atom, oxygen atom, and sulfur atom. A bond of the optional atom (e.g. a carbon atom and a nitrogen atom) not forming a ring may be terminated by a hydrogen atom or the like or may be substituted by an "optional substituent" described later. When the ring includes an optional element other than carbon atom, the resultant ring is a heterocycle.

The number of "one or more optional atoms" forming the monocyclic ring or fused ring is, unless otherwise specified herein, preferably in a range from 2 to 15, more preferably in a range from 3 to 12, further preferably in a range from 3 to 5.

Unless otherwise specified herein, the ring, which may be a "monocyclic ring" or "fused ring," is preferably a "monocyclic ring."

Unless otherwise specified herein, the ring, which may be a "saturated ring" or "unsaturated ring," is preferably an "unsaturated ring."

Unless otherwise specified herein, the "monocyclic ring" is preferably a benzene ring.

Unless otherwise specified herein, the "unsaturated ring" is preferably a benzene ring.

When "at least one combination of adjacent two or more" (of . . . ) are "mutually bonded to form a substituted or unsubstituted monocyclic ring" or "mutually bonded to form a substituted or unsubstituted fused ring," unless otherwise specified herein, at least one combination of adjacent two or more of components are preferably mutually bonded to form a substituted or unsubstituted "unsaturated ring" formed of a plurality of atoms of the basic skeleton, and 1 to 15 atoms of at least one element selected from the group consisting of carbon, nitrogen, oxygen and sulfur.

When the "monocyclic ring" or the "fused ring" has a substituent, the substituent is the substituent described in later-described "optional substituent." When the "monocyclic ring" or the "fused ring" has a substituent, specific examples of the substituent are the substituents described in the above under the subtitle "Substituent Mentioned Herein."

When the "saturated ring" or the "unsaturated ring" has a substituent, the substituent is the substituent described in later-described "optional substituent." When the "monocyclic ring" or the "fused ring" has a substituent, specific examples of the substituent are the substituents described in the above under the subtitle "Substituent Mentioned Herein."

The above is the description for the instances where "at least one combination of adjacent two or more (of . . . ) are mutually bonded to form a substituted or unsubstituted monocyclic ring" and "at least one combination of adjacent two or more (of . . . ) are mutually bonded to form a substituted or unsubstituted fused ring" mentioned herein (sometimes referred to as an instance of "bonded to form a ring").

Substituent for Substituted or Unsubstituted Group

In an exemplary embodiment herein, a substituent for the substituted or unsubstituted group (sometimes referred to as an "optional substituent" hereinafter) is, for instance, a group selected from the group consisting of an unsubstituted alkyl group having 1 to 50 carbon atoms, an unsubstituted alkenyl group having 2 to 50 carbon atoms, an unsubstituted alkynyl group having 2 to 50 carbon atoms, an unsubstituted cycloalkyl group having 3 to 50 ring carbon atoms, $-Si(R_{901})(R_{902})(R_{903})$, $-O-(R_{904})$, $-S-(R_{905})$, $-N(R_{906})(R_{907})$, a halogen atom, a cyano group, a nitro group, an unsubstituted aryl group having 6 to 50 ring carbon atoms, and an unsubstituted heterocyclic group having 5 to 50 ring atoms.

$R_{901}$ to $R_{907}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

when two or more $R_{901}$ are present, the two or more $R_{901}$ are mutually the same or different;

when two or more $R_{902}$ are present, the two or more $R_{902}$ are mutually the same or different;

when two or more $R_{903}$ are present, the two or more $R_{903}$ are mutually the same or different;

when two or more $R_{904}$ are present, the two or more $R_{904}$ are mutually the same or different;

when two or more $R_{905}$ are present, the two or more $R_{905}$ are mutually the same or different;

when two or more $R_{906}$ are present, the two or more $R_{906}$ are mutually the same or different; and when two or more $R_{907}$ are present, the two or more $R_{907}$ are mutually the same or different.

In an exemplary embodiment, a substituent for the substituted or unsubstituted group is selected from the group consisting of an alkyl group having 1 to 50 carbon atoms, an aryl group having 6 to 50 ring carbon atoms, and a heterocyclic group having 5 to 50 ring atoms.

In an exemplary embodiment, a substituent for the substituted or unsubstituted group is selected from the group consisting of an alkyl group having 1 to 18 carbon atoms, an aryl group having 6 to 18 ring carbon atoms, and a heterocyclic group having 5 to 18 ring atoms.

Specific examples of the above optional substituent are the same as the specific examples of the substituent described in the above under the subtitle "Substituent Mentioned Herein."

Unless otherwise specified herein, adjacent ones of the optional substituents may form a "saturated ring" or an "unsaturated ring," preferably a substituted or unsubstituted saturated five-membered ring, a substituted or unsubstituted saturated six-membered ring, a substituted or unsubstituted unsaturated five-membered ring, or a substituted or unsubstituted unsaturated six-membered ring, more preferably a benzene ring.

Unless otherwise specified herein, the optional substituent may further include a substituent. Examples of the substituent for the optional substituent are the same as the examples of the optional substituent.

Herein, numerical ranges represented by "AA to BB" represent a range whose lower limit is the value (AA) recited before "to" and whose upper limit is the value (BB) recited after "to."

First Exemplary Embodiment

Organic Electroluminescence Device

An organic electroluminescence device according to a first exemplary embodiment includes: an anode; a cathode; a first emitting layer provided between the anode and the cathode; and a second emitting layer provided between the anode and the cathode, in which the first emitting layer contains, as a first host material, a first compound represented by a formula (1) below and having at least one group represented by a formula (11) below, the second emitting layer contains a second host material, and the first host material and the second host material are mutually different.

Herein, the "host material" refers to, for instance, a material that accounts for "50 mass % or more of the layer." Accordingly, for instance, the first emitting layer contains 50 mass % or more of the first compound represented by the formula (1) below with respect to a total mass of the first emitting layer. The second emitting layer contains 50 mass % or more of the second compound represented by the formula (2) below with respect to a total mass of the second emitting layer.

Emission Wavelength of Organic EL Device

The organic electroluminescence device according to the exemplary embodiment preferably emits light having a maximum peak wavelength in a range from 430 nm to 480 nm when being driven.

The maximum peak wavelength of the light emitted from the organic EL device when being driven is measured as follows. Voltage is applied on the organic EL device so that a current density becomes 10 $mA/cm^2$, where spectral radiance spectrum is measured by a spectroradiometer CS-2000 (manufactured by Konica Minolta, Inc.). A peak wavelength of an emission spectrum, at which the luminous intensity of the obtained spectral radiance spectrum is at the maximum, is measured and defined as a maximum peak wavelength (unit: nm).

The organic EL device according to the exemplary embodiment may include one or more organic layer(s) in addition to the first emitting layer and the second emitting layer. Examples of the organic layer include, for instance, at least one layer selected from the group consisting of a hole injecting layer, a hole transporting layer, an emitting layer, an electron injecting layer, an electron transporting layer, a hole blocking layer, and an electron blocking layer.

In the organic EL device according to the exemplary embodiment, the organic layer may consist of the first emitting layer and the second emitting layer. Alternatively, the organic layer may further include, for instance, at least one layer selected from the group consisting of the hole injecting layer, the hole transporting layer, the electron injecting layer, the electron transporting layer, the hole blocking layer, and the electron blocking layer.

In the organic EL device according to the exemplary embodiment, the first emitting layer is also preferably disposed between the anode and the second emitting layer.

In the organic EL device according to the exemplary embodiment, the second emitting layer is also preferably disposed between the anode and the first emitting layer.

The organic EL device according to the exemplary embodiment may include the anode, the first emitting layer, the second emitting layer, and the cathode in this order, or the order of the first emitting layer and the second emitting layer may be reversed. That is, the organic EL device according to the exemplary embodiment may include the anode, the second emitting layer, the first emitting layer and the cathode in this order.

It is preferable that the organic EL device according to the exemplary embodiment includes a hole transporting layer between the anode, and the first emitting layer or the second emitting layer that is provided closer to the anode.

It is preferable that the organic EL device according to the exemplary embodiment includes an electron transporting layer between the cathode, and the first emitting layer or the second emitting layer that is provided closer to the cathode.

The FIGURE schematically shows an exemplary arrangement of the organic EL device according to the exemplary embodiment.

An organic EL device 1 includes a light-transmissive substrate 2, an anode 3, a cathode 4, and an organic layer 10 provided between the anode 3 and the cathode 4. The organic layer 10 includes a hole injecting layer 6, a hole transporting layer 7, a first emitting layer 51, a second emitting layer 52, an electron transporting layer 8, and an electron injecting layer 9, which are sequentially layered on the anode 3. It should be noted that the invention is not limited to the arrangement of the organic EL device shown in the FIGURE. For instance, in the organic layer of the organic EL device, the hole injecting layer, the hole transporting layer, the second emitting layer, the first emitting layer, the electron transporting layer and the electron injecting layer may be layered in this order on the anode.

First Compound

In the organic EL device according to the exemplary embodiment, the first compound is a compound represented by the formula (1) below.

[Formula 25]

(1)

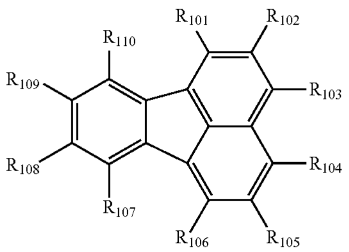

(11)

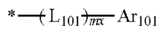

In the formula (1):

at least one combination of adjacent two or more of $R_{101}$ to $R_{110}$ are mutually bonded to form a substituted or unsubstituted monocyclic ring, mutually bonded to form a substituted or unsubstituted fused ring, or not mutually bonded;

$R_{101}$ to $R_{110}$ not forming the substituted or unsubstituted monocyclic ring and not forming the substituted or unsubstituted fused ring are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $-Si(R_{901})(R_{902})(R_{903})$, a group represented by $-O-(R_{904})$, a group represented by $-S-(R_{905})$, a substituted or unsubstituted aralkyl group having 7 to 50 carbon atoms, a group represented by $-C(=O)R_{801}$, a group represented by $-COOR_{802}$, a halogen atom, a cyano group, a nitro group, a substituted or unsubstituted aryl group having 6 to 50 ring carbon atoms, a substituted or unsubstituted heterocyclic group having 5 to 50 ring atoms, or a group represented by the formula (11);

at least one of a substituent, if present, for the substituted or unsubstituted monocyclic ring, a substituent, if present, for the substituted or unsubstituted fused ring or $R_{101}$ to $R_{110}$ is a group represented by the formula (11);

when a plurality of groups represented by the formula (11) are present, the plurality of groups represented by the formula (11) are mutually the same or different;

$L_{101}$ is a single bond, a substituted or unsubstituted arylene group having 6 to 50 ring carbon atoms, or a substituted or unsubstituted divalent heterocyclic group having 5 to 50 ring atoms;

$Ar_{101}$ is a substituted or unsubstituted aryl group having 6 to 50 ring carbon atoms, or a substituted or unsubstituted heterocyclic group having 5 to 50 ring atoms;

mx is 0, 1, 2, 3, 4, or 5; and when two or more $L_{101}$ are present, the two or more $L_{101}$ are mutually the same or different;

when two or more $Ar_{101}$ are present, the two or more $Ar_{101}$ are mutually the same or different; and

* in the formula (11) represents a bonding position to a ring represented by the formula (1).

In the first compound according to the exemplary embodiment, $R_{901}$, $R_{902}$, $R_{903}$, $R_{904}$, $R_{905}$, $R_{801}$ and $R_{802}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

when a plurality of $R_{901}$ are present, the plurality of $R_{901}$ are mutually the same or different;

when a plurality of $R_{902}$ are present, the plurality of $R_{902}$ are mutually the same or different;

when a plurality of $R_{903}$ are present, the plurality of $R_{903}$ are mutually the same or different;

when a plurality of $R_{904}$ are present, the plurality of $R_{904}$ are mutually the same or different;

when a plurality of $R_{905}$ are present, the plurality of $R_{905}$ are mutually the same or different;

when a plurality of $R_{801}$ are present, the plurality of $R_{801}$ are mutually the same or different; and when a plurality of $R_{802}$ are present, the plurality of $R_{802}$ are mutually the same or different.

In the formula (1), combinations of adjacent two of $R_{101}$ to $R_{110}$ refer to a combination of $R_{101}$ and $R_{102}$, a combination of $R_{102}$ and $R_{103}$, a combination of $R_{103}$ and $R_{104}$, a combination of $R_{104}$ and $R_{105}$, a combination of $R_{105}$ and $R_{106}$, a combination of $R_{107}$ and $R_{108}$, a combination of $R_{108}$ and $R_{109}$, and a combination of $R_{109}$ and $R_{110}$.

In the first compound, it is also preferable that at least one combination of adjacent two or more of $R_{101}$ to $R_{110}$ are mutually bonded to form a substituted or unsubstituted monocyclic ring, or mutually bonded to form a substituted or unsubstituted fused ring.

In the organic EL device according to the exemplary embodiment, the number of substituted or unsubstituted monocyclic rings or substituted or unsubstituted fused rings that are each formed by mutually bonding at least one combination of adjacent two or more of $R_{101}$ to $R_{110}$ is preferably in a range from 1 to 5, more preferably in a range from 1 to 3, further preferably 1 or 2, still further preferably 1.

In the organic EL device according to the exemplary embodiment, it is preferable that at least one combination of adjacent two or more of $R_{101}$ to $R_{110}$ are mutually bonded to form a substituted or unsubstituted monocyclic ring. The substituted or unsubstituted monocyclic ring is preferably a substituted or unsubstituted five-membered ring or a substituted or unsubstituted six-membered ring, more preferably a substituted or unsubstituted six-membered ring.

In the organic EL device according to the exemplary embodiment, the first compound represented by the formula (1) is preferably a compound represented by one of formulae (101) to (104) below and having at least one group represented by the formula (11).

[Formula 26]

(101)

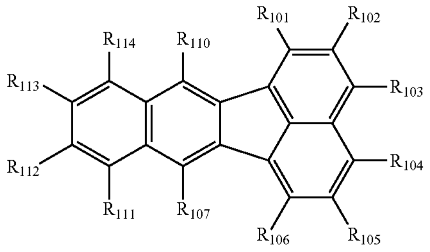

(102)

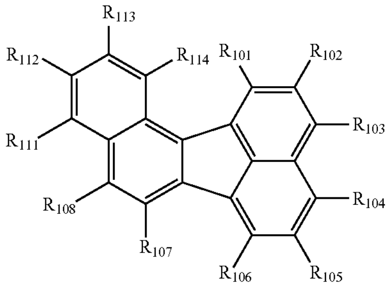

[Formula 27]

(103)

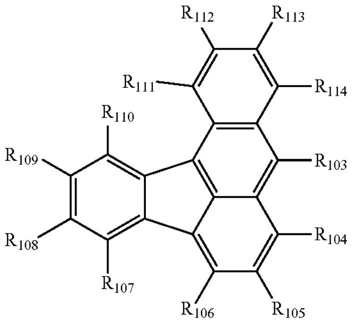

(104)

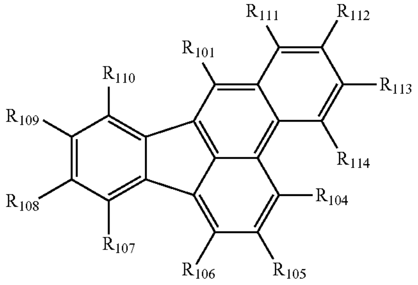

In the formulae (101) to (104):

$R_{101}$ to $R_{114}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —$Si(R_{901})(R_{902})(R_{903})$, a group represented by —O—($R_{904}$), a group represented by —S—($R_{905}$), a substituted or unsubstituted aralkyl group having 7 to 50 carbon atoms, a group represented by —C(═O)$R_{801}$, a group represented by —$COOR_{802}$, a halogen atom, a cyano group, a nitro group, a substituted or unsubstituted aryl group having 6 to 50 ring carbon atoms, a substituted or unsubstituted heterocyclic group having 5 to 50 ring atoms, or a group represented by the formula (11);

at least one of $R_{101}$ to $R_{114}$ is a group represented by the formula (11);

when a plurality of groups represented by the formula (11) are present, the plurality of groups represented by the formula (11) are mutually the same or different; and $R_{901}$, $R_{902}$, $R_{903}$, $R_{904}$, $R_{905}$, $R_{801}$ and $R_{802}$ in the formulae (101) to (104) each independently represent the same in the formula (1).

The first compound in which a combination of $R_{101}$ and $R_{102}$ are mutually bonded to form a substituted or unsubstituted six-membered ring is exemplified by a compound represented by the formula (101).

In the organic EL device according to the exemplary embodiment, the first compound is preferably a compound represented by the formula (101).

In the organic EL device according to the exemplary embodiment, the first compound preferably has one group represented by the formula (11).

In the organic EL device according to the exemplary embodiment, one of $R_{101}$ to $R_{110}$ is also preferably a group represented by the formula (11).

In the organic EL device according to the exemplary embodiment, the first compound also preferably has two or more groups represented by the formula (11).

In the organic EL device according to the exemplary embodiment, two or more of $R_{101}$ to $R_{110}$ are also preferably each a group represented by the formula (11).

In the organic EL device according to the exemplary embodiment, at least one of $R_{107}$ to $R_{110}$ is also preferably a group represented by the formula (11).

In the organic EL device according to the exemplary embodiment, the first compound is also preferably represented by a formula (1011) below.

[Formula 28]

(1011)

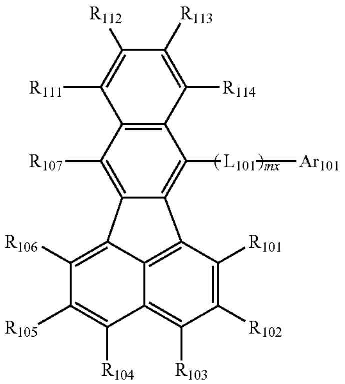

In the formula (1011):

$L_{101}$, mx and $Ar_{101}$ respectively represent the same as $L_{101}$, mx and $Ar_{101}$ in the formula (11);

$R_{101}$ to $R_{107}$ and $R_{111}$ to $R_{114}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a substituted or unsubstituted aralkyl group having 7 to 50 carbon atoms, a group represented by —C(═O)$R_{801}$, a group represented by —COOR$_{802}$, a halogen atom, a cyano group, a nitro group, a substituted or unsubstituted aryl group having 6 to 50 ring carbon atoms, a substituted or unsubstituted heterocyclic group having 5 to 50 ring atoms, or a group represented by the formula (11);

when a plurality of groups represented by the formula (11) are present, the plurality of groups represented by the formula (11) are mutually the same or different; and $R_{901}$, $R_{902}$, $R_{903}$, $R_{904}$, $R_{905}$, $R_{801}$ and $R_{802}$ in the formula (1011) each independently represent the same in the formula (1).

In the organic EL device according to the exemplary embodiment, at least one of $R_{102}$ or $R_{105}$ is also preferably a group represented by the formula (11).

In the organic EL device according to the exemplary embodiment, the first compound is also preferably represented by a formula (1012) below.

[Formula 29]

(1012)

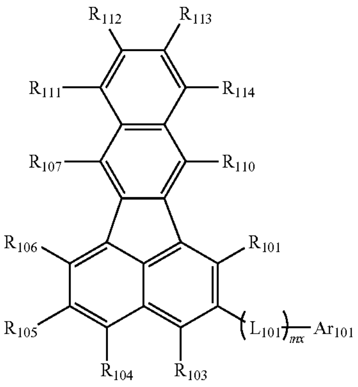

In the formula (1012):

$L_{101}$, mx and $Ar_{101}$ respectively represent the same as $L_{101}$, mx and $Ar_{101}$ in the formula (11);

$R_{101}$, $R_{103}$ to $R_{107}$ and $R_{110}$ to $R_{114}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a substituted or unsubstituted aralkyl group having 7 to 50 carbon atoms, a group represented by —C(═O)$R_{801}$, a group represented by —COOR$_{802}$, a halogen atom, a cyano group, a nitro group, a substituted or unsubstituted aryl group having 6 to 50 ring carbon atoms, a substituted or unsubstituted heterocyclic group having 5 to 50 ring atoms, or a group represented by the formula (11);

when a plurality of groups represented by the formula (11) are present, the plurality of groups represented by the formula (11) are mutually the same or different; and $R_{901}$, $R_{902}$, $R_{903}$, $R_{904}$, $R_{905}$, $R_{801}$ and $R_{802}$ in the formula (1012) each independently represent the same in the formula (1).

In the organic EL device according to the exemplary embodiment, at least one of $R_{112}$ or $R_{113}$ is also preferably a group represented by the formula (11).

In the organic EL device according to the exemplary embodiment, the first compound is also preferably represented by a formula (1013) below.

[Formula 30]

(1013)

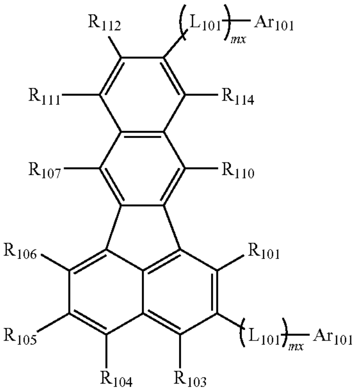

In the formula (1013):

$L_{101}$, mx and $Ar_{101}$ respectively represent the same as $L_{101}$, mx and $Ar_{101}$ in the formula (11);

$R_{101}$ to $R_{107}$, $R_{110}$ to $R_{112}$ and $R_{114}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a substituted or unsubstituted aralkyl group having 7 to 50 carbon atoms, a group represented by —C(═O)$R_{801}$, a group represented by —COOR$_{802}$, a halogen atom, a cyano group, a nitro group, a substituted or unsubstituted aryl group having 6 to 50 ring carbon atoms, a substituted or unsubstituted heterocyclic group having 5 to 50 ring atoms, or a group represented by the formula (11);

when a plurality of groups represented by the formula (11) are present, the plurality of groups represented by the formula (11) are mutually the same or different; and $R_{901}$, $R_{902}$, $R_{903}$, $R_{904}$, $R_{905}$, $R_{801}$ and $R_{802}$ in the formula (1013) each independently represent the same in the formula (1).

In the organic EL device according to the exemplary embodiment, it is also preferable that none of combinations of adjacent two or more of $R_{101}$ to $R_{110}$ are mutually bonded.

In the organic EL device according to the exemplary embodiment, an example of the first compound is a compound having a fused fluoranthene ring, such as benzofluoranthene, in which a fluoranthene ring is fused with a substituted or unsubstituted monocyclic ring or a substituted or unsubstituted fused ring. The first compound in this example is preferably a benzofluoranthene compound in which a benzene ring is fused.

Another example of the first compound is a compound having no fused fluoranthene ring but having a non-fused fluoranthene ring.

When none of combinations of adjacent two or more of $R_{101}$ to $R_{110}$ are mutually bonded, * in the formula (11) represents a bonding position to a fluoranthene ring in the formula (1).

In the organic EL device according to the exemplary embodiment, the first compound is also preferably represented by a formula (121) below.

[Formula 31]

(121)

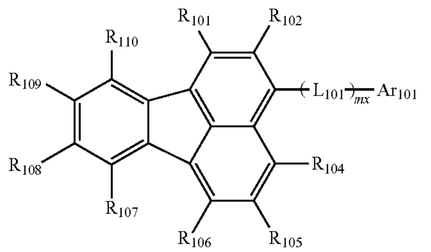

In the formula (121): $R_{101}$, $R_{102}$ and $R_{104}$ to $R_{110}$ each independently represent the same as $R_{101}$, $R_{102}$ and $R_{104}$ to $R_{110}$ in the formula (1); and $L_{101}$, mx and $Ar_{101}$ respectively represent the same as $L_{101}$, mx and $Ar_{101}$ in the formula (11).

In the organic EL device according to the exemplary embodiment, the first compound is also preferably represented by a formula (122) below.

[Formula 32]

(122)

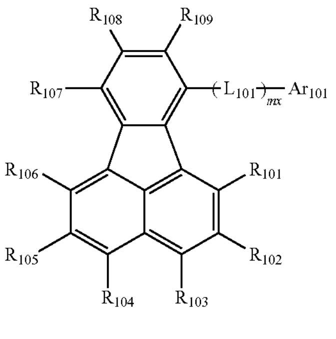

In the formula (122): $R_{101}$ to $R_{109}$ each independently represent the same as $R_{101}$ to $R_{109}$ in the formula (1); and $L_{101}$, mx and $Ar_{101}$ respectively represent the same as $L_{101}$, mx and $Ar_{101}$ in the formula (11).

In the formulae (121) and (122), it is preferable that none of combinations of adjacent two or more of $R_{101}$ to $R_{110}$ not being the group represented by the formula (11) are mutually bonded.

In the organic EL device according to the exemplary embodiment, it is also preferable that $Ar_{101}$ is not a substituted or unsubstituted fluoranthenyl group, $L_{101}$ is not a substituted or unsubstituted fluoranthene-diyl group, and the substituted or unsubstituted aryl group having 6 to 50 ring carbon atoms as $R_{101}$ to $R_{110}$ not being the group represented by the formula (11) is not a substituted or unsubstituted fluoranthenyl group.

In the organic EL device according to the exemplary embodiment, $Ar_{101}$ is also preferably a substituted or unsubstituted heterocyclic group having 5 to 50 ring atoms.

In the organic EL device according to the exemplary embodiment, $Ar_{101}$ in the formula (11) is also preferably a group represented by a formula (111) below.

[Formula 33]

(111)

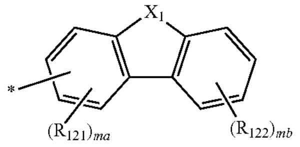

In the formula (111):

ma is 3, and three $R_{121}$ are mutually the same or different;

at least one combination of adjacent two or more of the three $R_{121}$ are mutually bonded to form a substituted or unsubstituted monocyclic ring, mutually bonded to form a substituted or unsubstituted fused ring, or not mutually bonded;

mb is 4, and four $R_{122}$ are mutually the same or different;

at least one combination of adjacent two or more of the four $R_{122}$ are mutually bonded to form a substituted or unsubstituted monocyclic ring, mutually bonded to form a substituted or unsubstituted fused ring, or not mutually bonded;

$X_1$ is $CR_{123}R_{124}$, an oxygen atom, a sulfur atom, or $NR_{125}$;

a combination of $R_{123}$ and $R_{124}$ are mutually bonded to form a substituted or unsubstituted monocyclic ring, mutually bonded to form a substituted or unsubstituted fused ring, or not mutually bonded;

$R_{121}$, $R_{122}$, $R_{123}$ and $R_{124}$ not forming the substituted or unsubstituted monocyclic ring and not forming the substituted or unsubstituted fused ring and $R_{125}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $-Si(R_{901})(R_{902})(R_{903})$, a group represented by $-O-(R_{904})$, a group represented by $-S-(R_{905})$, a substituted or unsubstituted aralkyl group having 7 to 50 carbon atoms, a group represented by $-C(=O)R_{801}$, a group represented by $-COOR_{802}$, a halogen atom, a cyano group, a nitro group, a substituted or unsubstituted aryl group having 6 to 50 ring carbon atoms, or a substituted or unsubstituted heterocyclic group having 5 to 50 ring atoms;

$R_{901}$, $R_{902}$, $R_{903}$, $R_{904}$, $R_{905}$, $R_{801}$ and $R_{802}$ respectively represent the same as $R_{901}$, $R_{902}$, $R_{903}$, $R_{904}$, $R_{905}$, $R_{801}$ and $R_{802}$ in the formula (1); and

* in the formula (111) represents a bonding position.

In the organic EL device according to the exemplary embodiment, it is preferable that the combination of $R_{123}$ and $R_{124}$ do not form the substituted or unsubstituted monocyclic ring and do not form the substituted or unsubstituted fused ring.

In the organic EL device according to the exemplary embodiment, it is preferable that the three $R_{121}$ do not form the substituted or unsubstituted monocyclic ring and do not form the substituted or unsubstituted fused ring.

In the organic EL device according to the exemplary embodiment, it is preferable that three $R_{122}$ do not form the substituted or unsubstituted monocyclic ring and do not form the substituted or unsubstituted fused ring.

In the organic EL device according to the exemplary embodiment, $Ar_{101}$ in the formula (11) is preferably a group represented by a formula (111A), (111B), (111C) or (111D) below.

[Formula 34]

(111A)

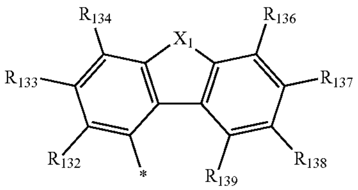

(111B)

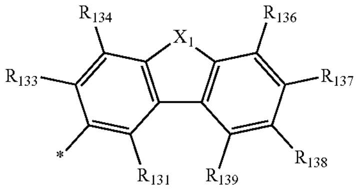

(111C)

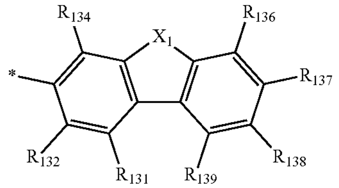

(111D)

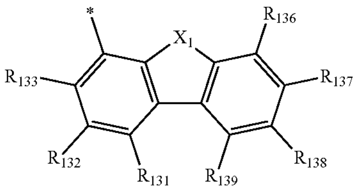

In the formulae (111A), (111B), (111C) and (111D):

$X_1$ represents the same as $X_1$ in the formula (111);

$R_{131}$ to $R_{139}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $-Si(R_{901})(R_{902})(R_{903})$, a group represented by $-O-(R_{904})$, a group represented by $-S-(R_{905})$, a substituted or unsubstituted aralkyl group having 7 to 50 carbon atoms, a group represented by $-C(=O)R_{801}$, a group represented by $-COOR_{802}$, a halogen atom, a cyano group, a nitro group, a substituted or unsubstituted aryl group having 6 to 50 ring carbon atoms, or a substituted or unsubstituted heterocyclic group having 5 to 50 ring atoms;

$R_{901}$, $R_{902}$, $R_{903}$, $R_{904}$, $R_{905}$, $R_{801}$ and $R_{802}$ respectively represent the same as $R_{901}$, $R_{902}$, $R_{903}$, $R_{904}$, $R_{905}$, $R_{801}$ and $R_{802}$ in the formula (1); and

* in the formulae (111A), (111B), (111C) and (111D) represents a bonding position.

In the organic EL device according to the exemplary embodiment, $X_1$ is preferably $C(R_{123})(R_{124})$ or an oxygen atom.

In the organic EL device according to the exemplary embodiment, $Ar_{101}$ is also preferably a substituted or unsubstituted aryl group having 6 to 50 ring carbon atoms.

In the organic EL device according to the exemplary embodiment, $Ar_{101}$ is also preferably a substituted or unsubstituted aryl group having 10 to 50 ring carbon atoms.

In the organic EL device according to the exemplary embodiment, it is preferable that the substituted or unsubstituted aryl group having 6 to 50 ring carbon atoms as $Ar_{101}$ is not a substituted or unsubstituted anthryl group.

In the organic EL device according to the exemplary embodiment, $Ar_{101}$ is also preferably a substituted or unsubstituted phenyl group, a substituted or unsubstituted naphthyl group, a substituted or unsubstituted biphenyl group, a substituted or unsubstituted terphenyl group, a substituted or unsubstituted pyrenyl group, a substituted or unsubstituted phenanthryl group, or a substituted or unsubstituted fluorenyl group.

In the organic EL device according to the exemplary embodiment, mx is preferably 0, 1 or 2.

In the organic EL device according to the exemplary embodiment, $L_{101}$ is preferably a single bond or a substituted or unsubstituted arylene group having 6 to 50 ring carbon atoms.

In the organic EL device according to the exemplary embodiment, mx is preferably 1 or 2.

In the organic EL device according to the exemplary embodiment, it is preferable that mx is 1 or 2 and $L_{101}$ is a single bond or a substituted or unsubstituted arylene group having 6 to 50 ring carbon atoms.

In the organic EL device according to the exemplary embodiment, it is preferable that mx is 1 or 2 and $L_{101}$ is a substituted or unsubstituted arylene group having 6 to 50 ring carbon atoms.

In the organic EL device according to the exemplary embodiment, it is also preferable that $L_{101}$ includes at least one divalent group selected from the group consisting of divalent groups represented by formulae (11a) and (11b) below.

[Formula 35]

(11a)

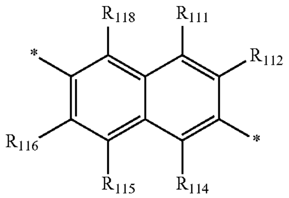

-continued (11b)

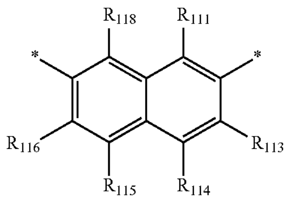

In the formulae (11a) and (11b):

$R_{111}$ to $R_{116}$ and $R_{118}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a substituted or unsubstituted aralkyl group having 7 to 50 carbon atoms, a group represented by —C(═O)$R_{801}$, a group represented by —COOR$_{802}$, a halogen atom, a cyano group, a nitro group, a substituted or unsubstituted aryl group having 6 to 50 ring carbon atoms, or a substituted or unsubstituted heterocyclic group having 5 to 50 ring atoms;

$R_{901}$, $R_{902}$, $R_{903}$, $R_{904}$, $R_{905}$, $R_{801}$ and $R_{802}$ in the formulae (11a) and (11b) each independently represent the same in the formula (1); and

* in the formulae (11a) and (11b) represents a bonding position.

It is preferable that one of two * in the formula (11a) or (11b) is a bonding position to $Ar_{101}$.

In the organic EL device according to the exemplary embodiment, it is also preferable that $R_{111}$ to $R_{116}$ and $R_{118}$ are each a hydrogen atom.

In the organic EL device according to the exemplary embodiment, it is preferable that $Ar_{101}$ is not a substituted or unsubstituted benzofluoranthenyl group, $L_{101}$ is not a substituted or unsubstituted benzofluoranthene-diyl group, and the substituted or unsubstituted aryl group having 6 to 50 ring carbon atoms not being the group represented by the formula (11) in the first compound is not a substituted or unsubstituted benzofluoranthenyl group.

In the organic EL device according to the exemplary embodiment, it is preferable that $R_{101}$ to $R_{110}$ not being the group represented by the formula (11) are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms.

In the organic EL device according to the exemplary embodiment, it is preferable that $R_{101}$ to $R_{110}$ not being the group represented by the formula (11) are each independently a hydrogen atom, a substituted or unsubstituted alkyl group having 1 to 50 carbon atoms, a substituted or unsubstituted cycloalkyl group having 3 to 50 ring carbon atoms, or a substituted or unsubstituted aryl group having 6 to 50 ring carbon atoms.

In the organic EL device according to the exemplary embodiment, it is preferable that $R_{101}$ to $R_{110}$ not being the group represented by the formula (11) are each a hydrogen atom or a substituted or unsubstituted aryl group having 6 to 50 ring carbon atoms.

In the organic EL device according to the exemplary embodiment, it is also preferable that $R_{101}$ to $R_{110}$ not being the group represented by the formula (11) are each independently a hydrogen atom, a substituted or unsubstituted alkyl group having 1 to 50 carbon atoms, or a substituted or unsubstituted cycloalkyl group having 3 to 50 ring carbon atoms.

In the organic EL device according to the exemplary embodiment, $R_{101}$ to $R_{110}$ not being the group represented by the formula (11) are each preferably a hydrogen atom.

In the first host material, all groups described as "substituted or unsubstituted" groups are preferably "unsubstituted" groups.

In the first compound according to the exemplary embodiment, all groups described as "substituted or unsubstituted" groups are preferably "unsubstituted" groups.

Manufacturing Method of First Compound

The first compound can be manufactured by a known method. The first compound can also be manufactured based on a known method through a known alternative reaction using a known material(s) tailored for the target compound.

Specific Examples of First Compound

Specific examples of the first compound include the following compounds. It should however be noted that the invention is not limited to the specific examples of the first compound.

[Formula 36]

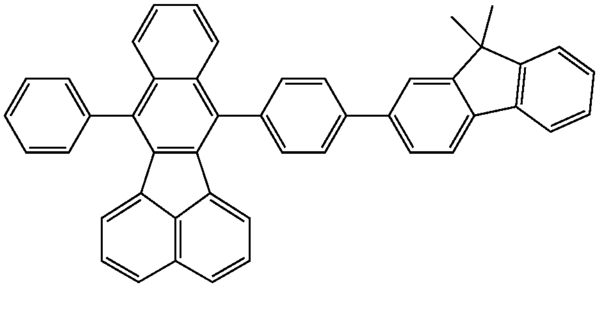

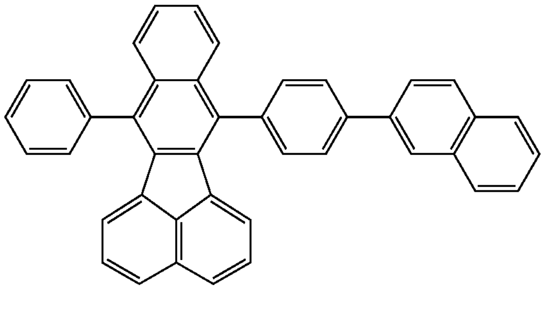

-continued
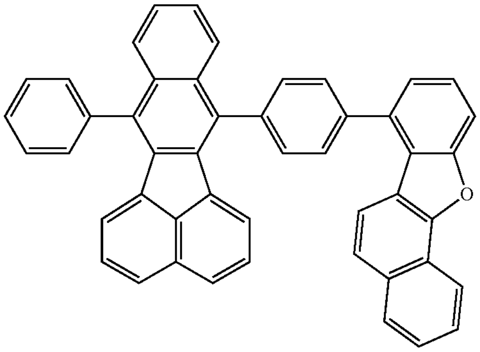
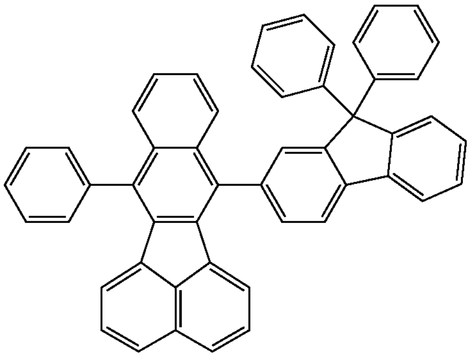
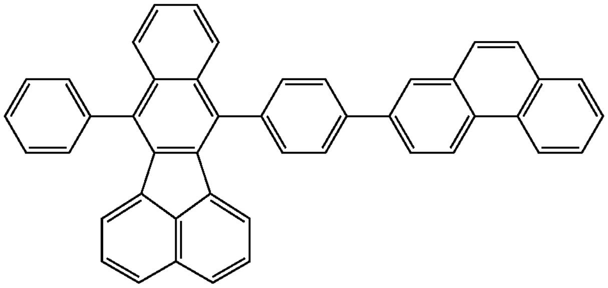
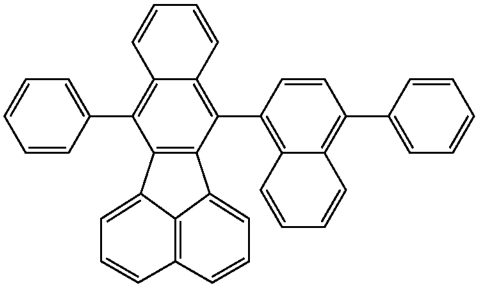
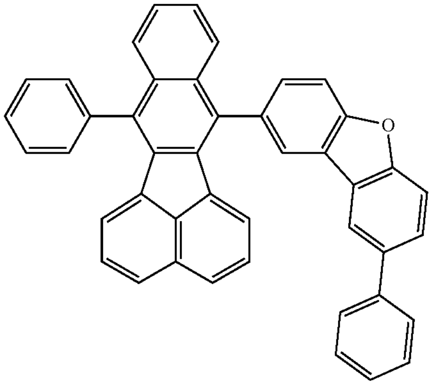
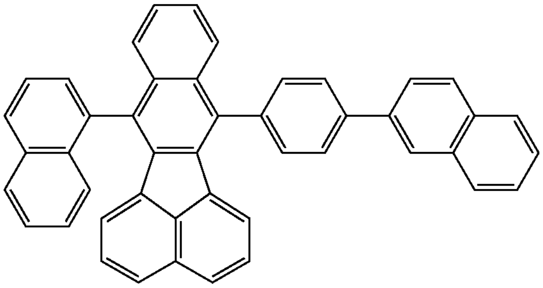
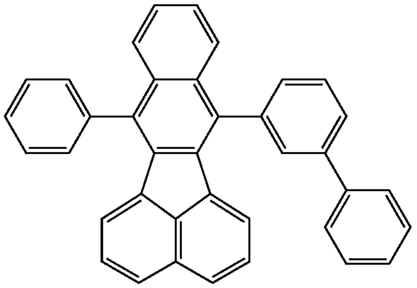
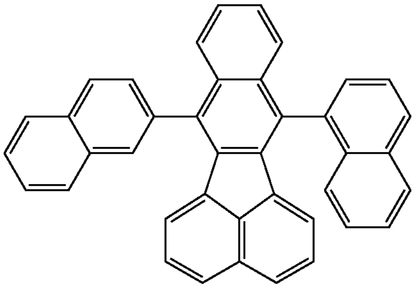
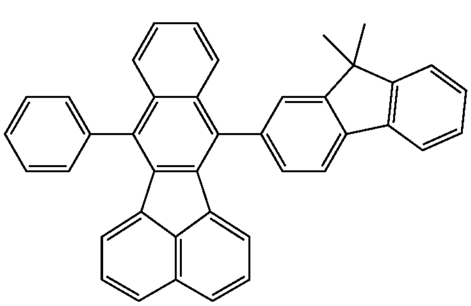
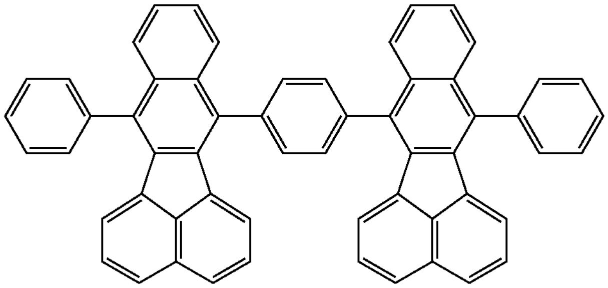

-continued
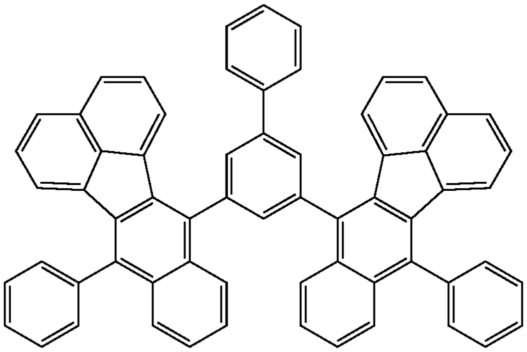
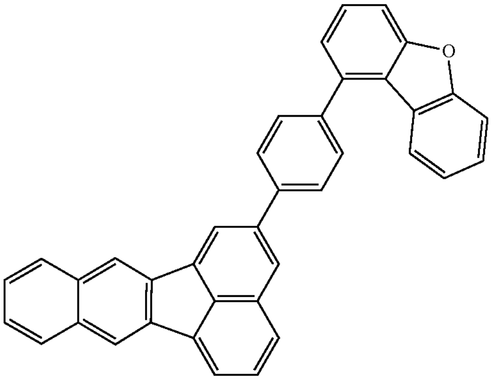
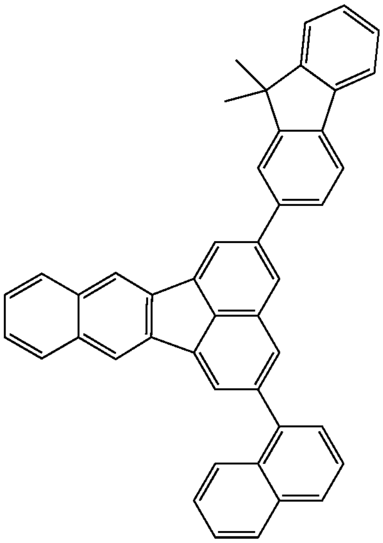
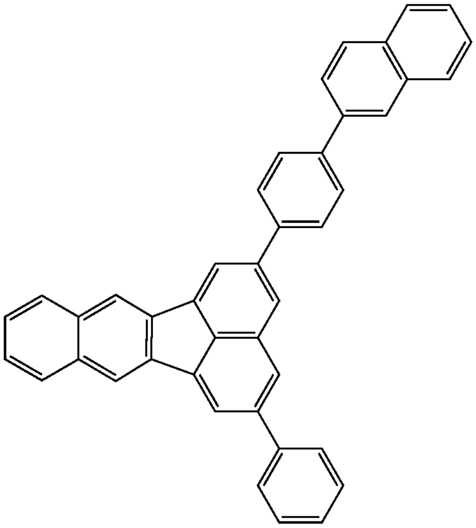
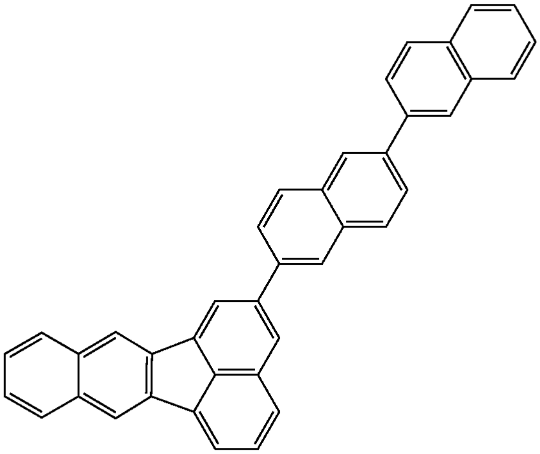
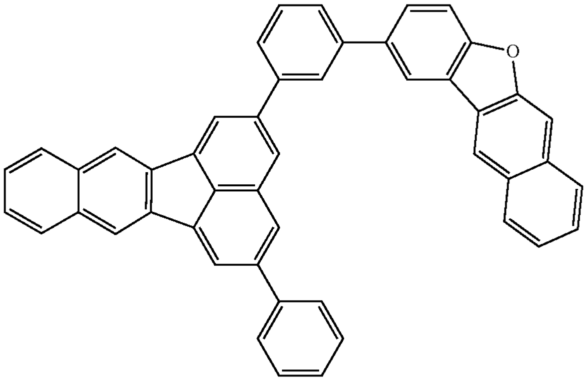

-continued
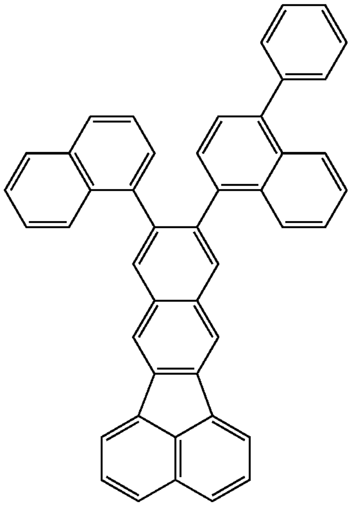
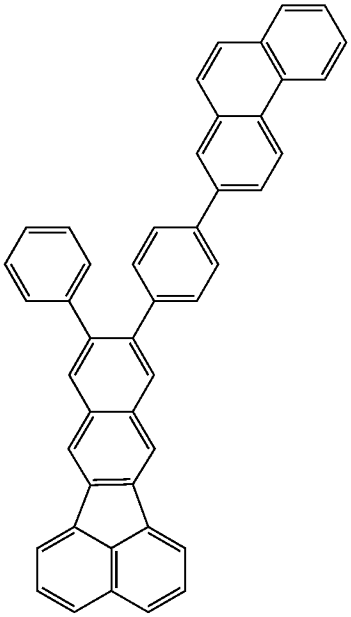
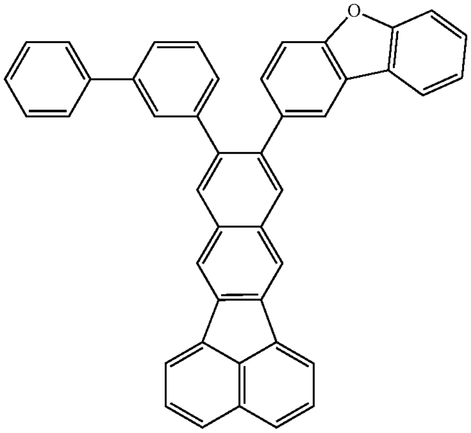
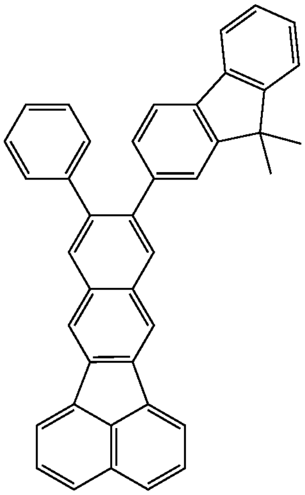
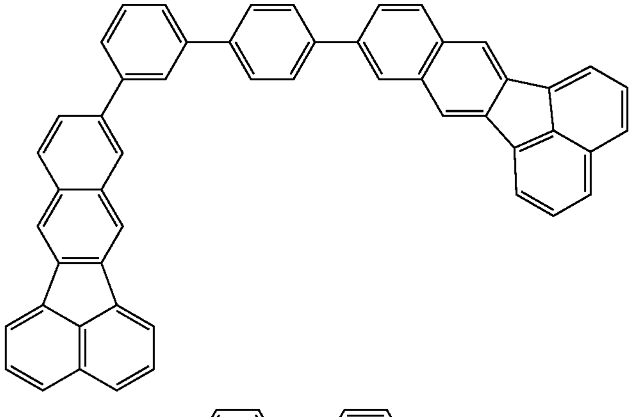
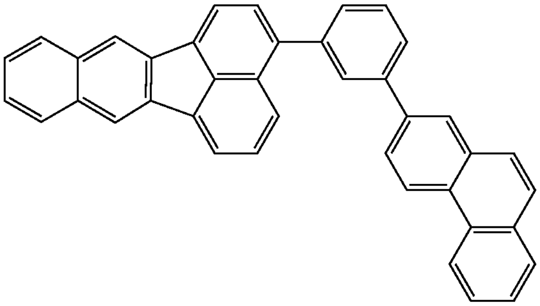
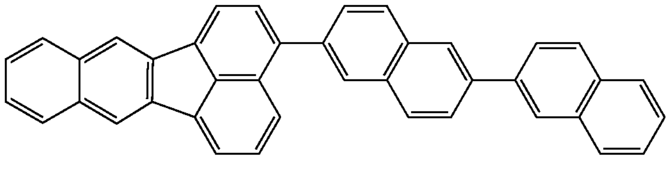

-continued
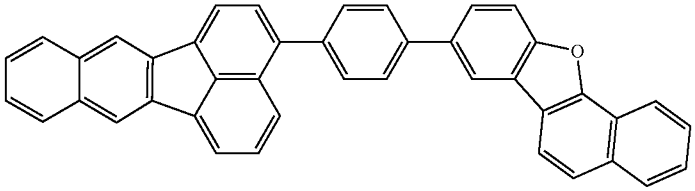
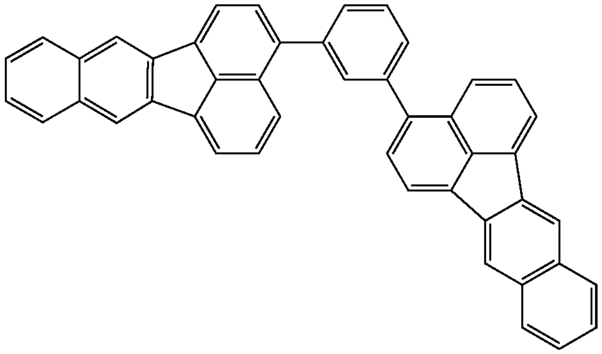
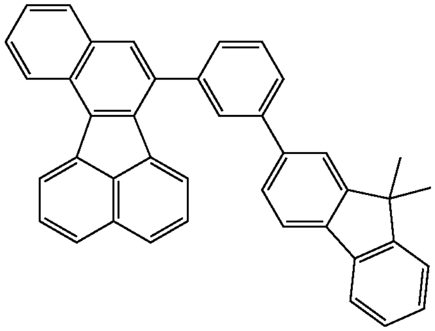
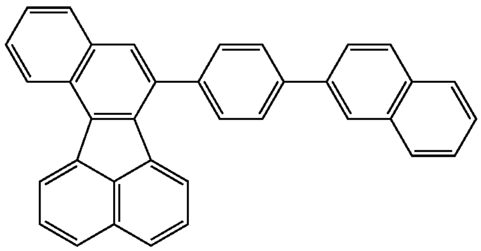
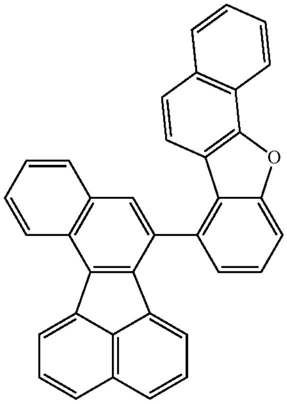
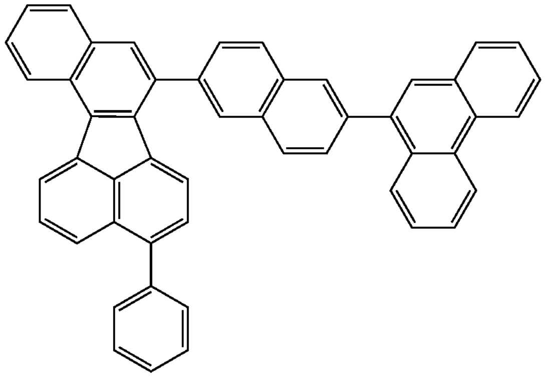
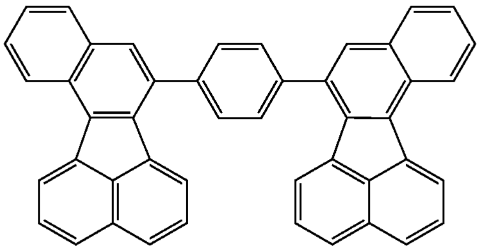
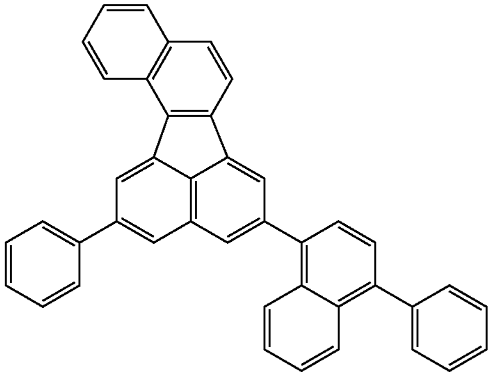
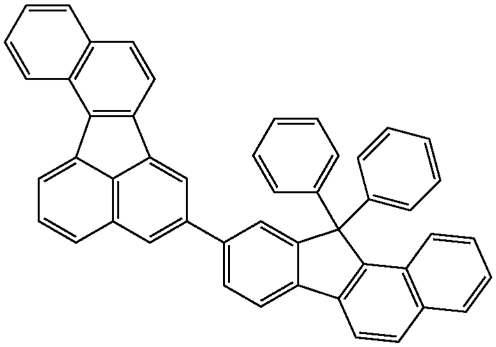

-continued
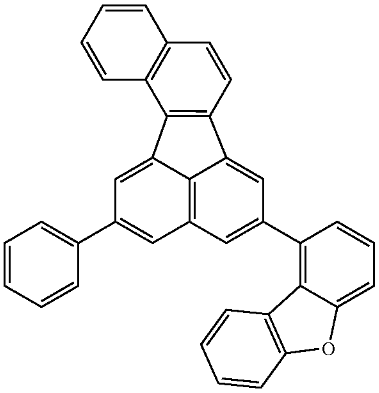
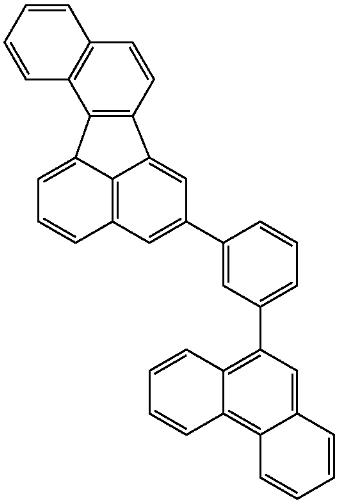
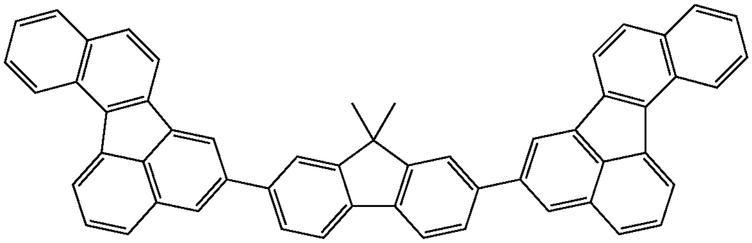
[Formula 37]
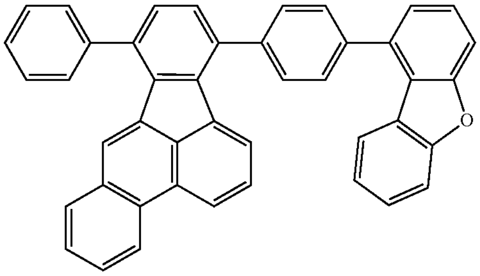
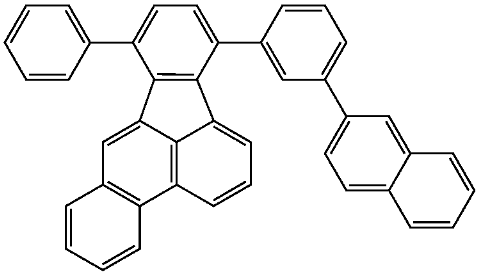
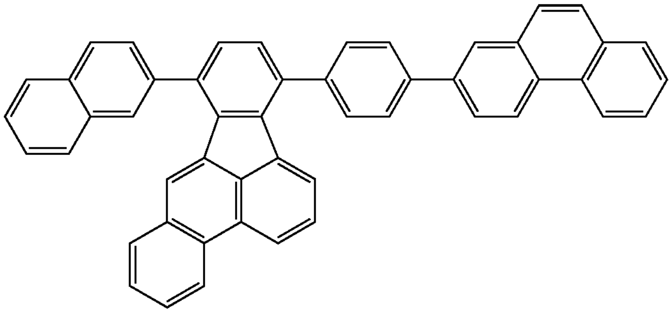
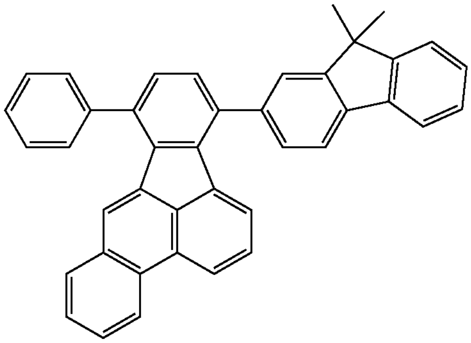

-continued
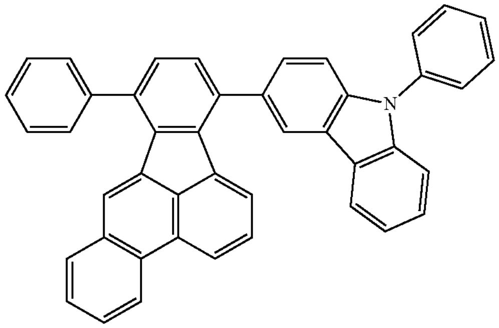
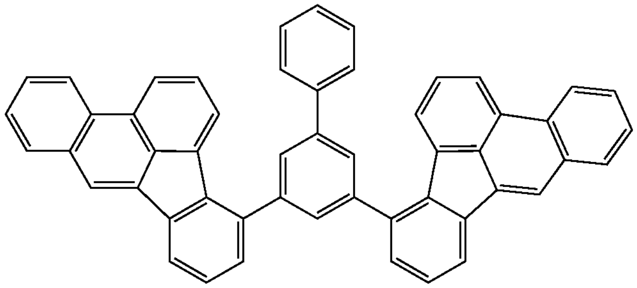
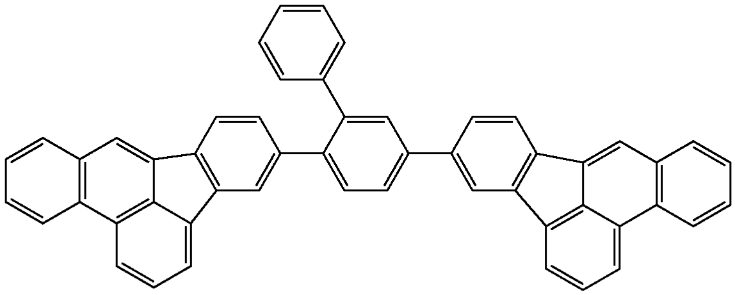
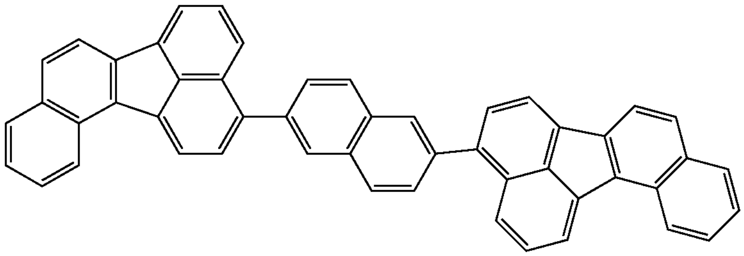
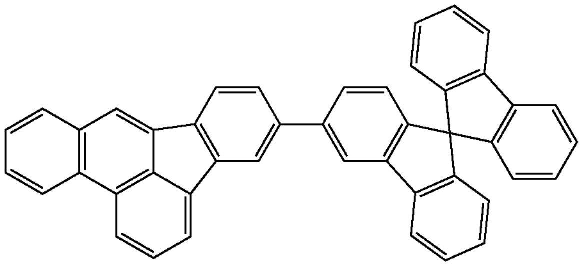
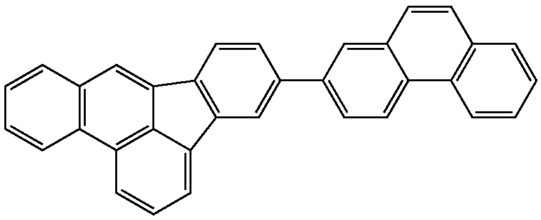
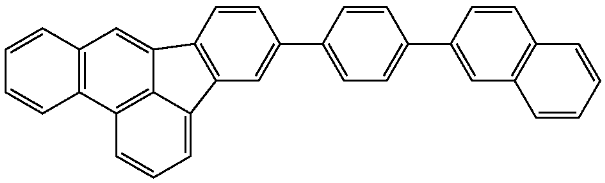
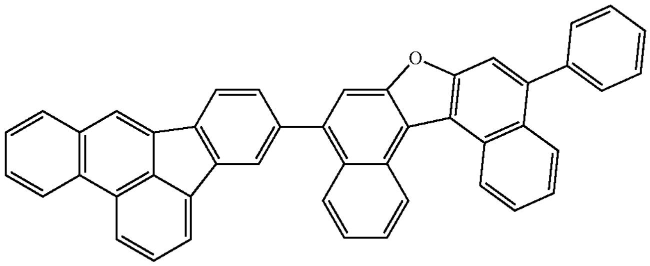

-continued
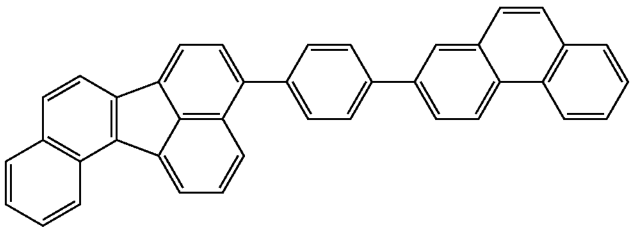
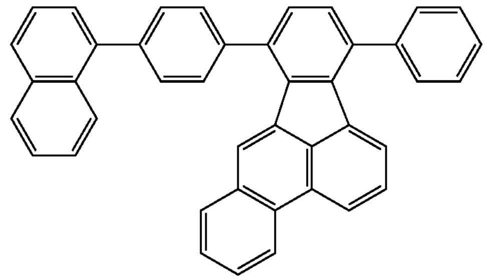
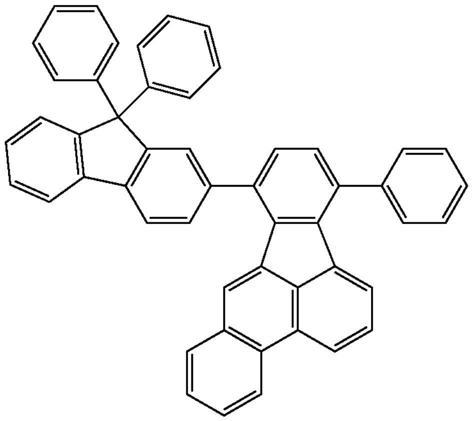
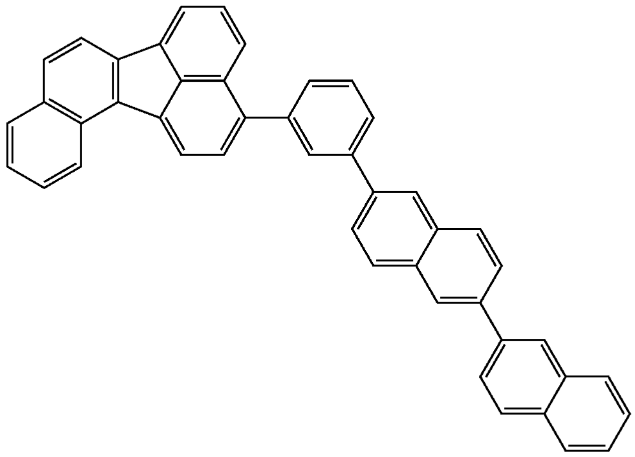
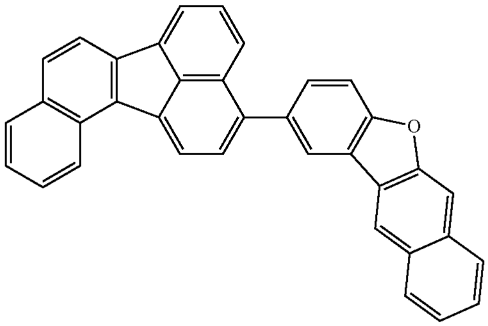
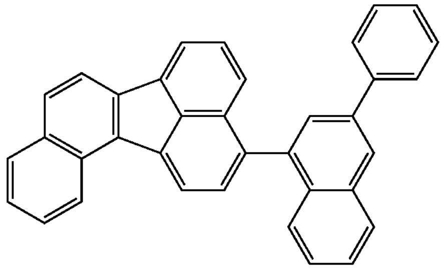
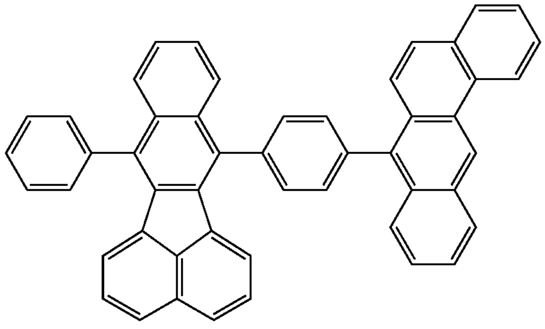
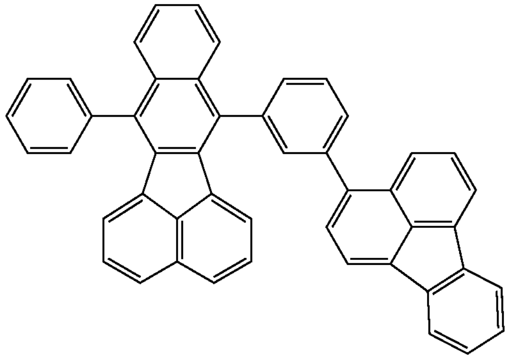

-continued
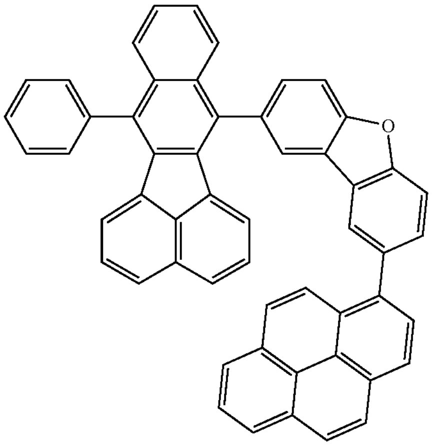
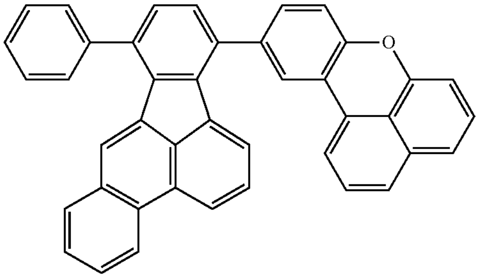
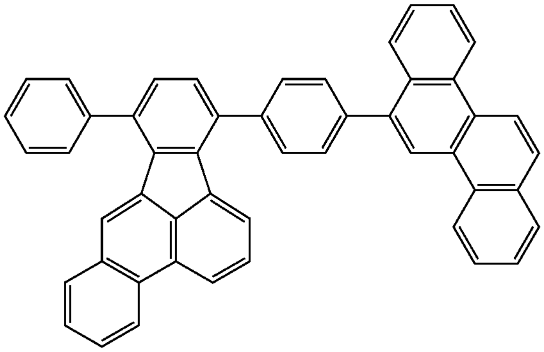
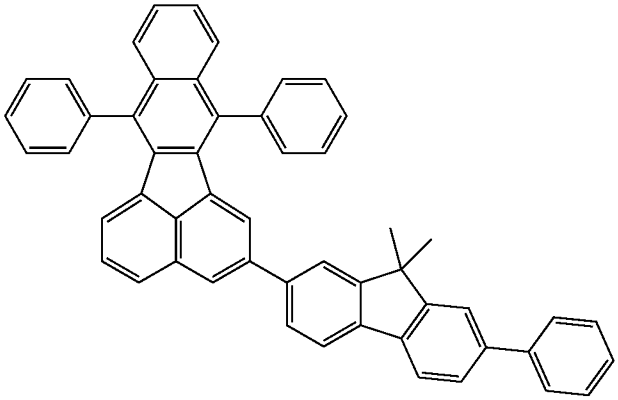
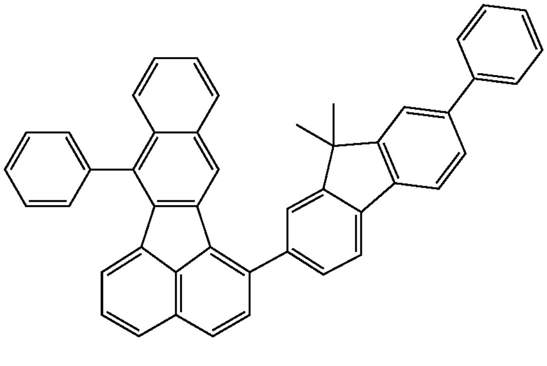
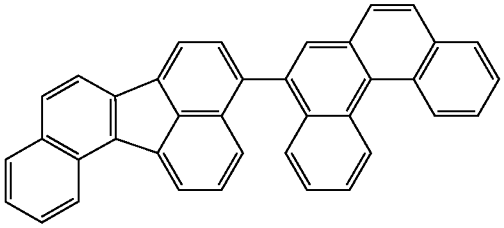
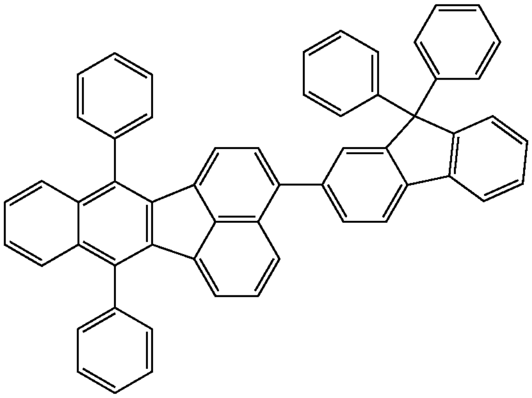
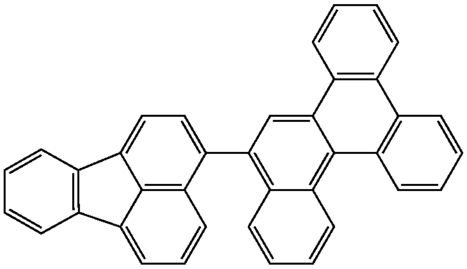

-continued
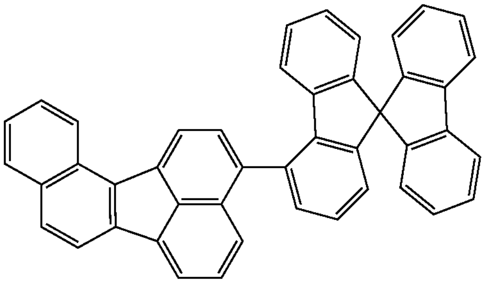
[Formula 38]
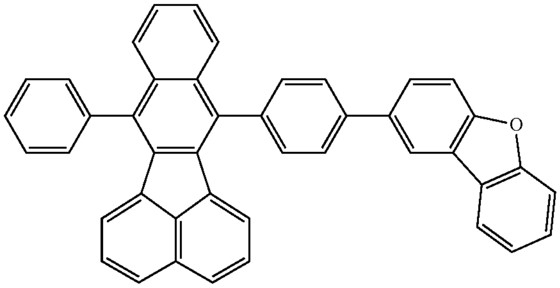
[Formula 39]
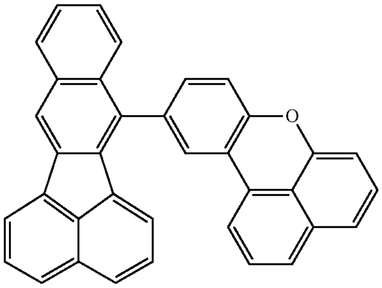
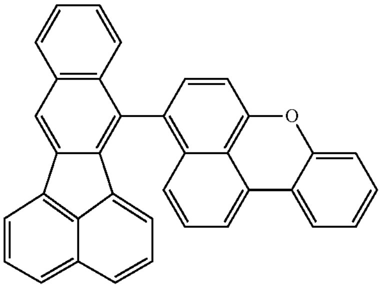
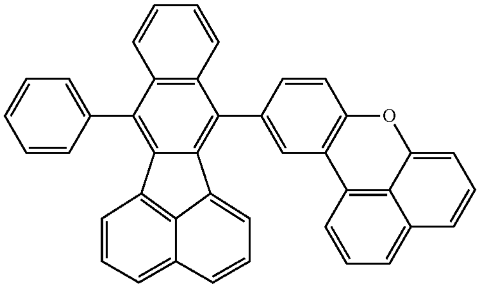
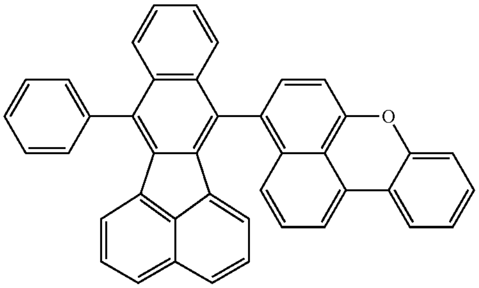
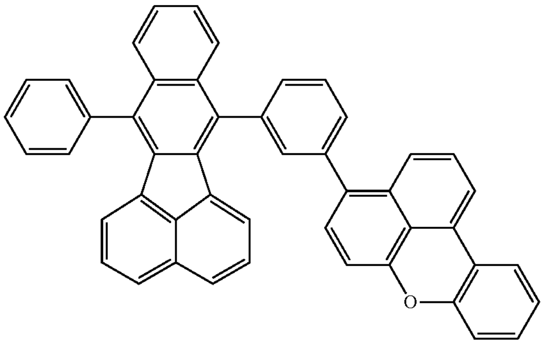
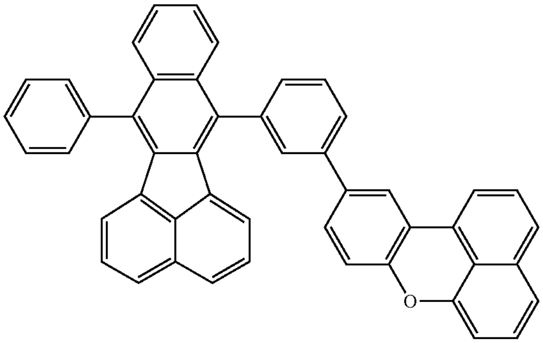

-continued
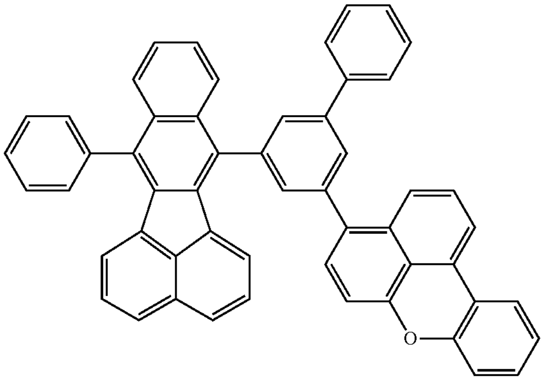
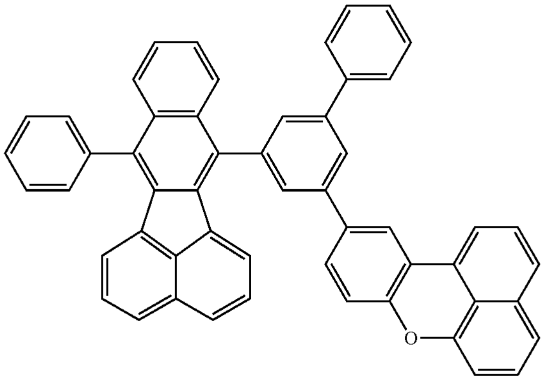
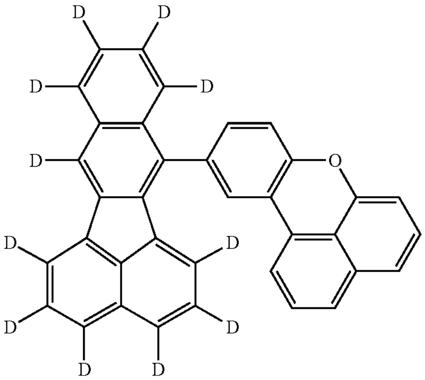
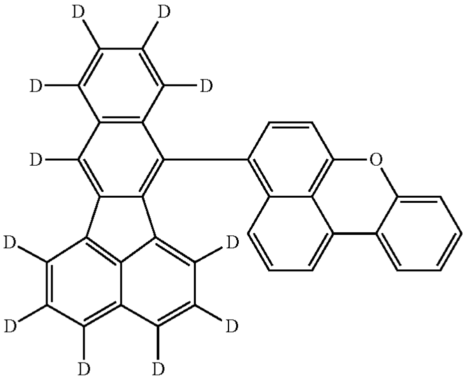
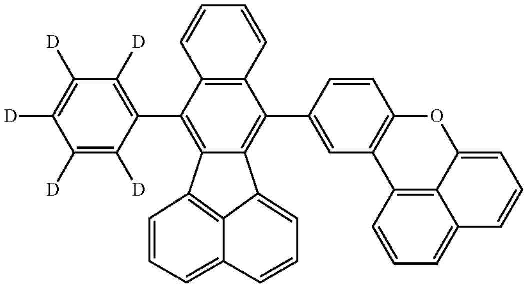
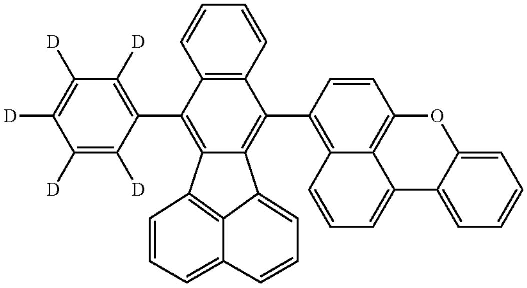
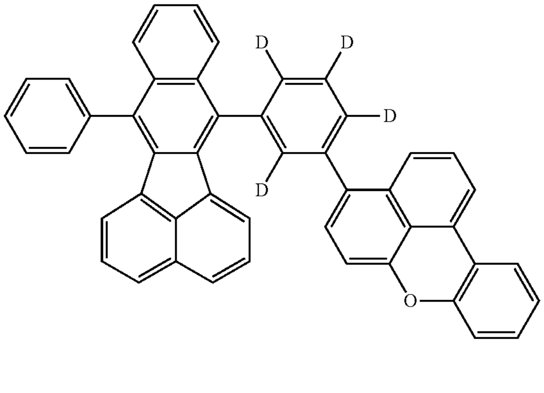
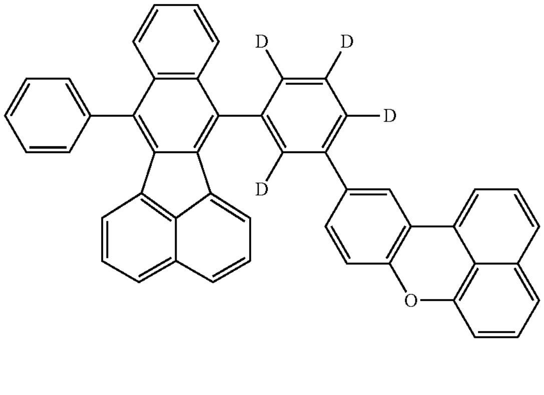

-continued
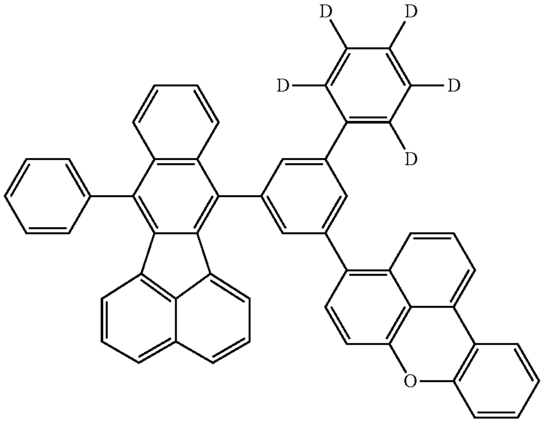
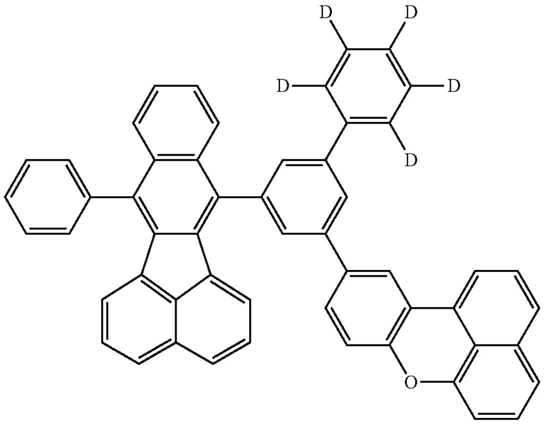
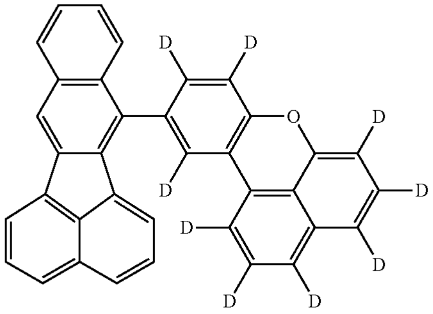
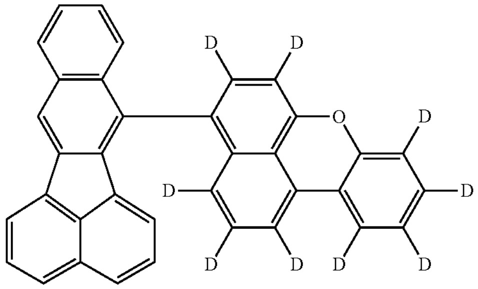
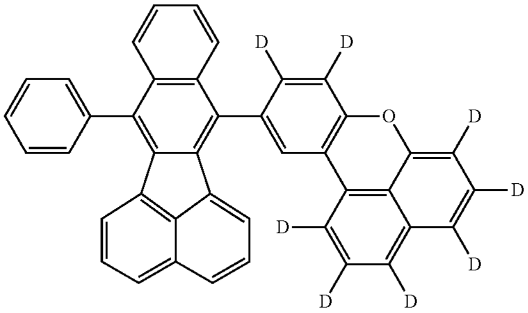
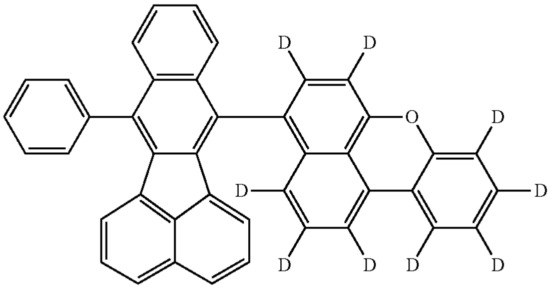
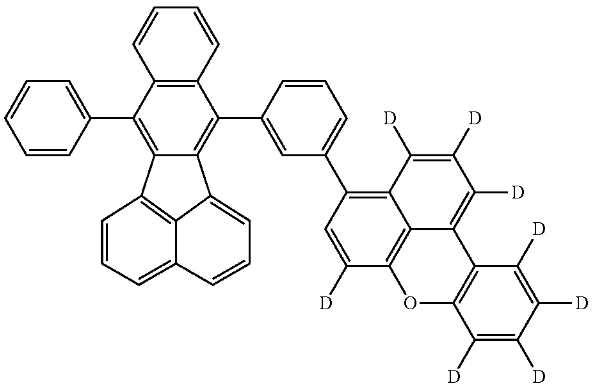
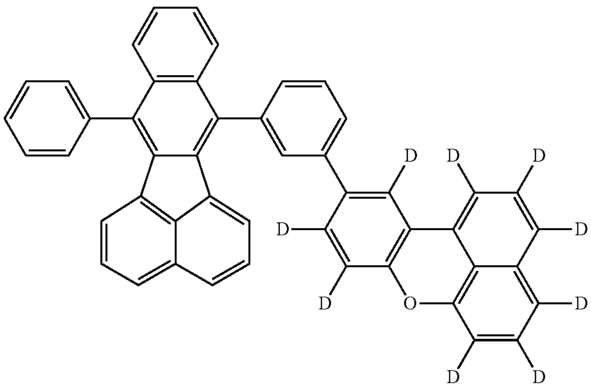

-continued
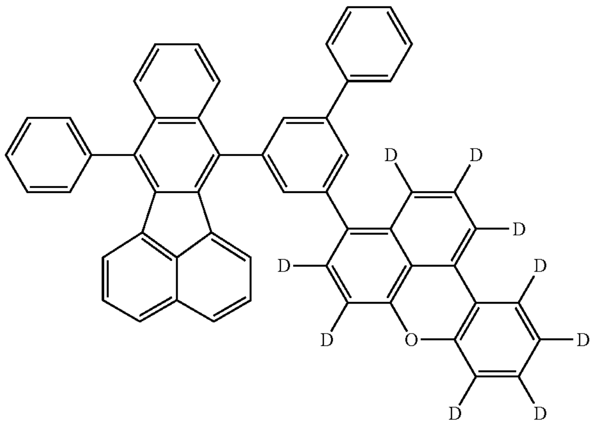
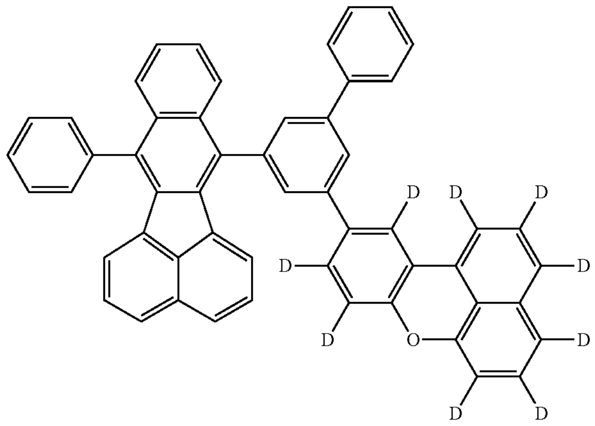
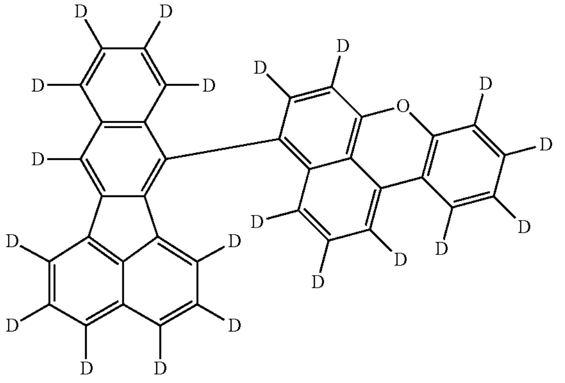
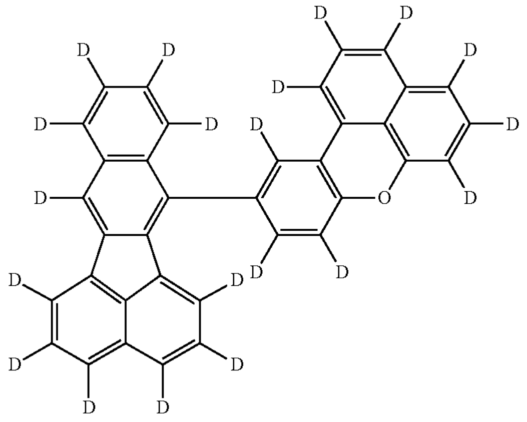
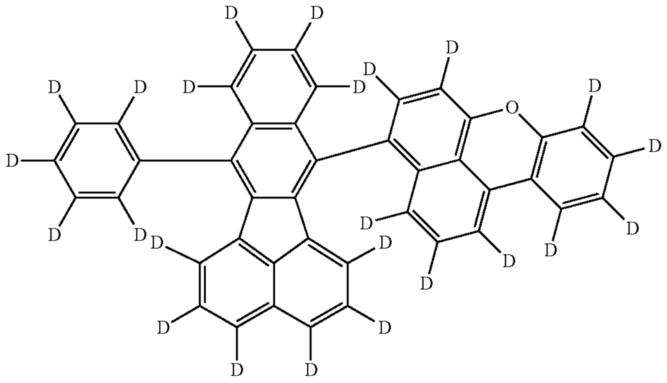
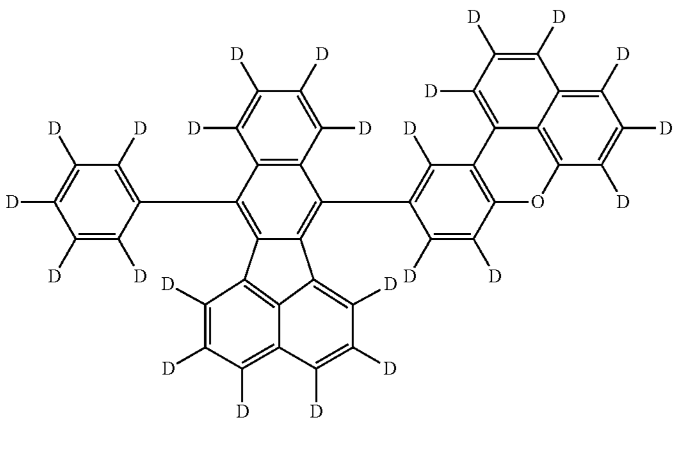

-continued
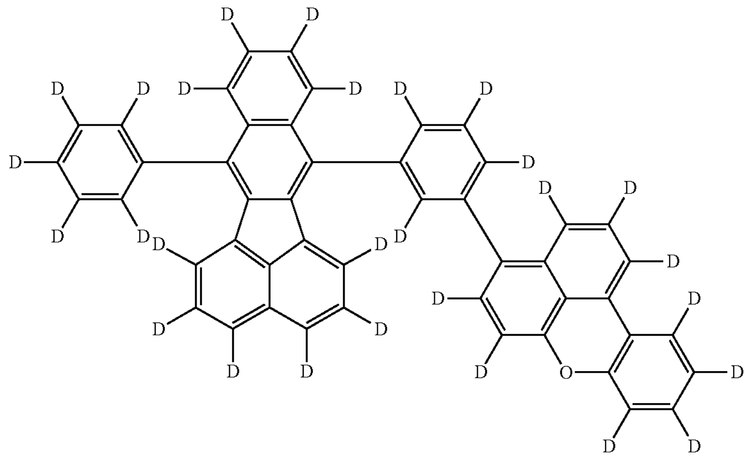
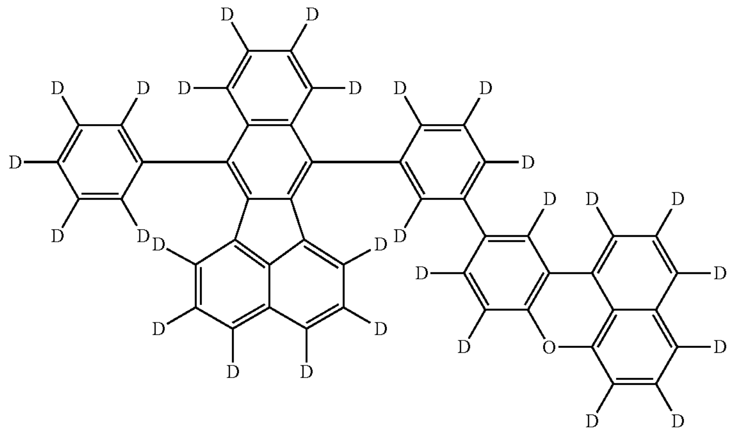
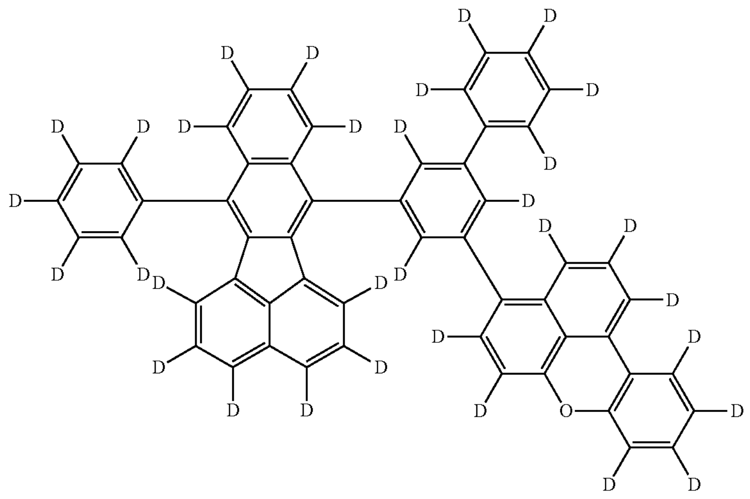

-continued
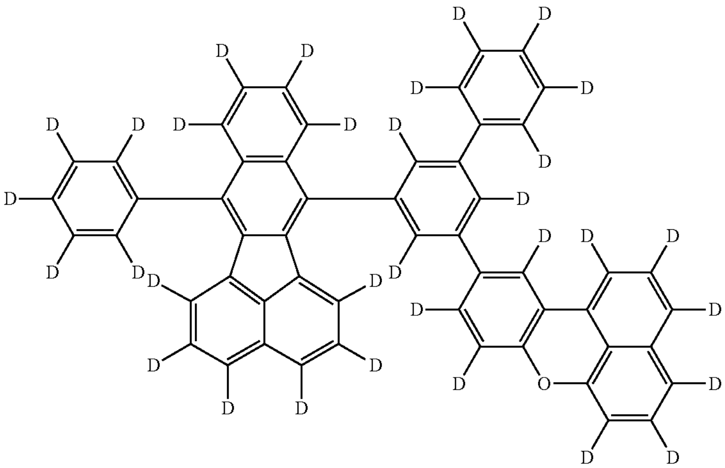
[Formula 40]
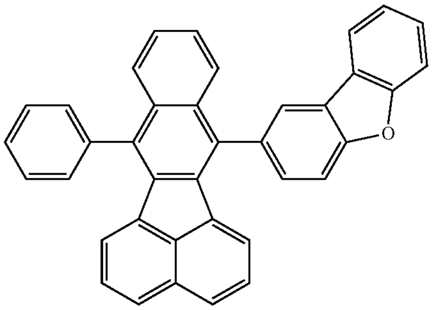
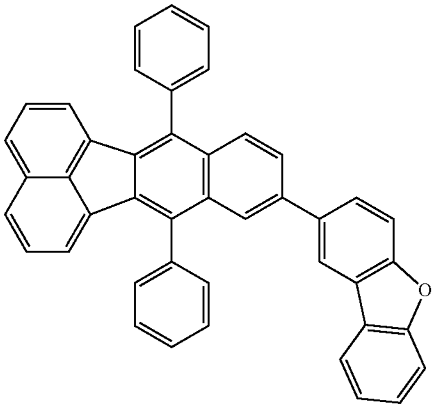
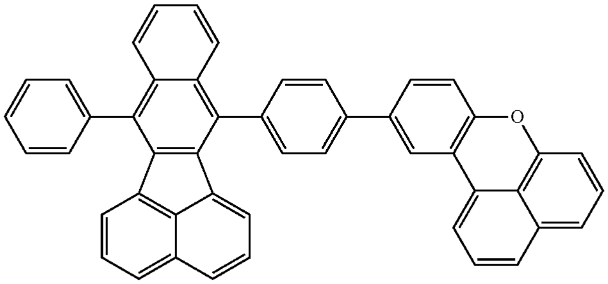
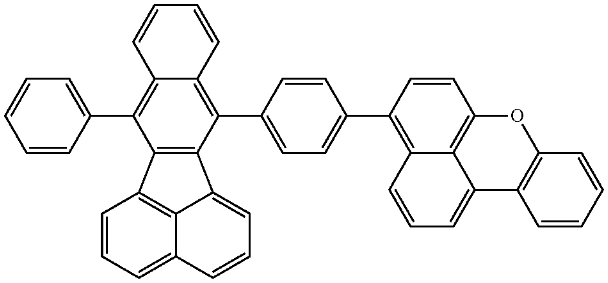

-continued
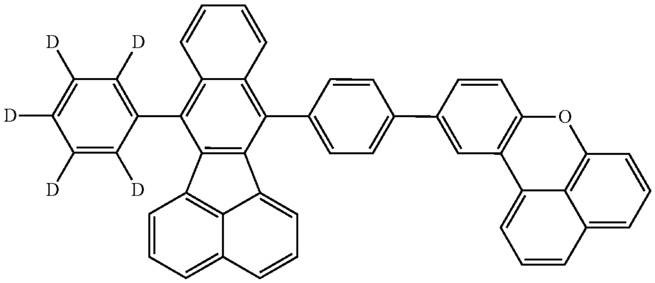
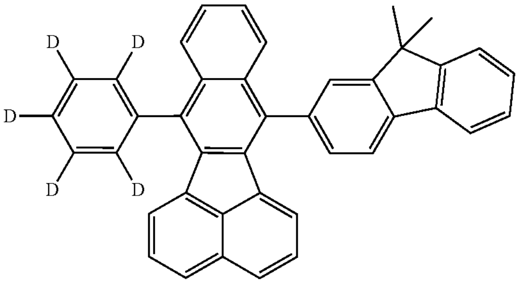
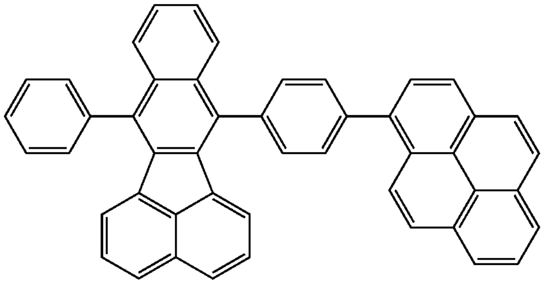
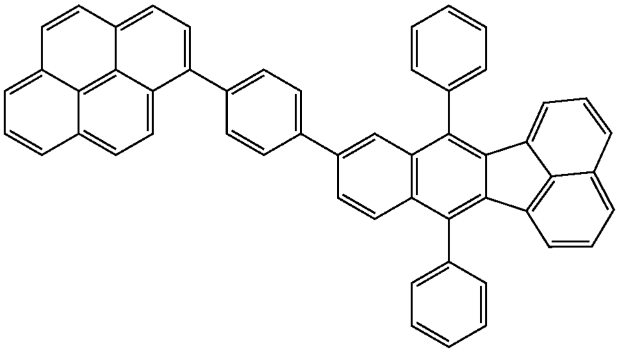
[Formula 41]
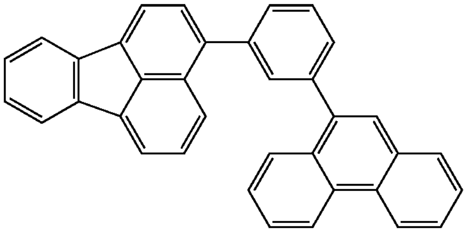
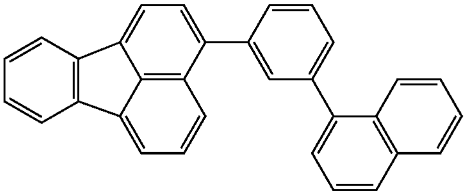
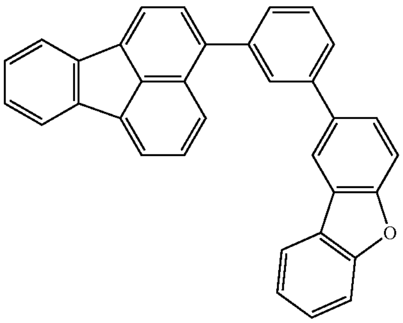
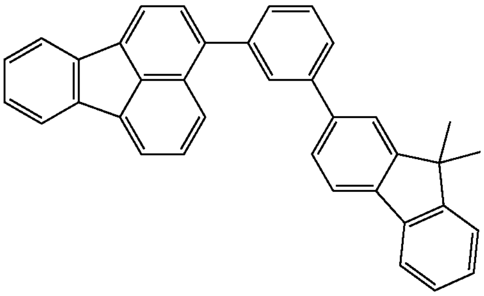

-continued
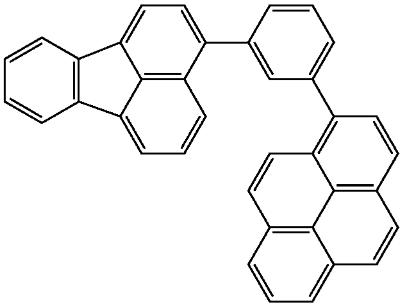
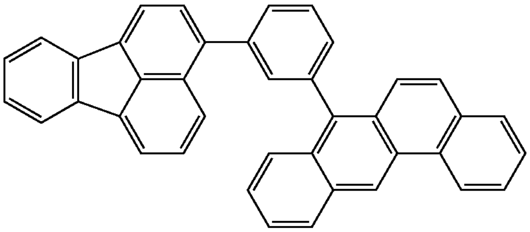
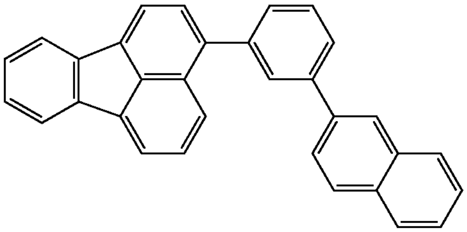
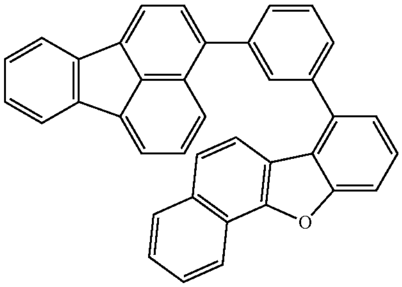
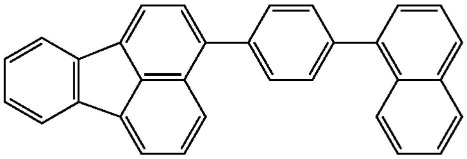
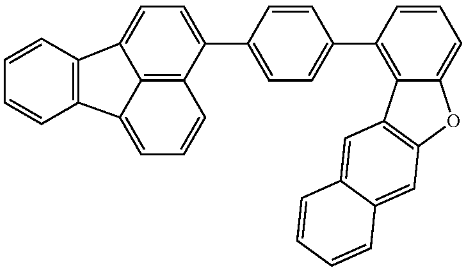
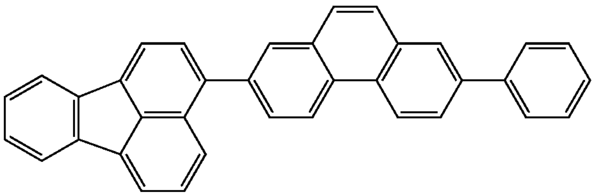
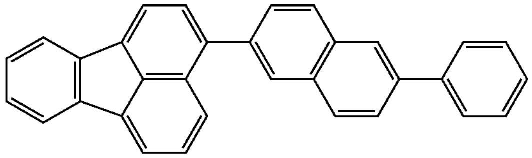
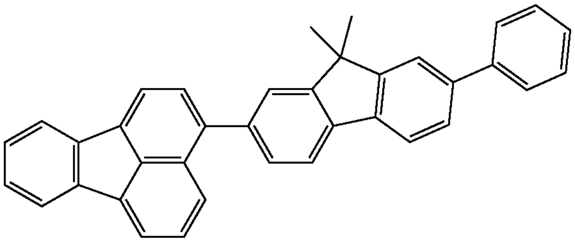
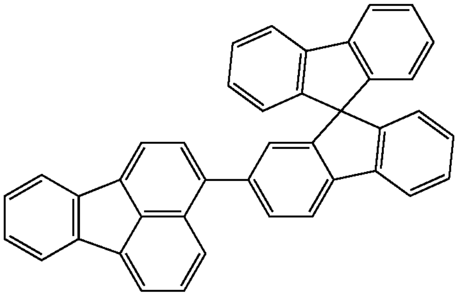

-continued
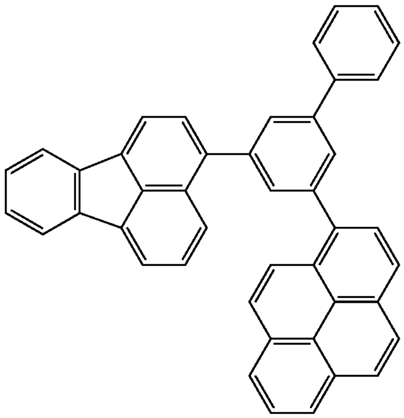
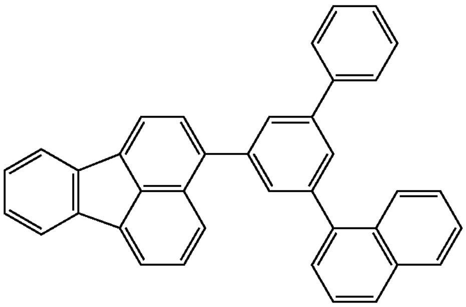
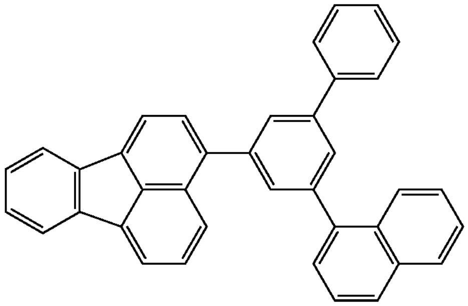
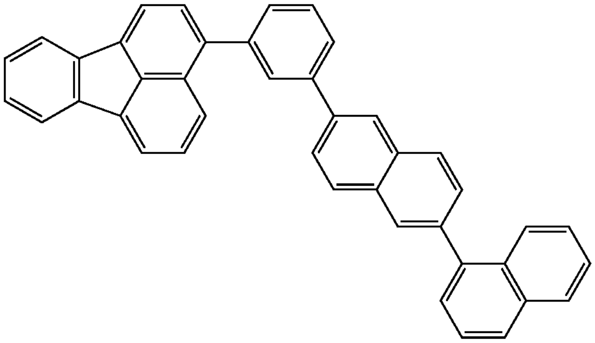
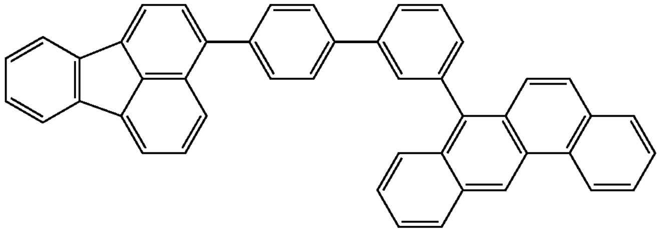
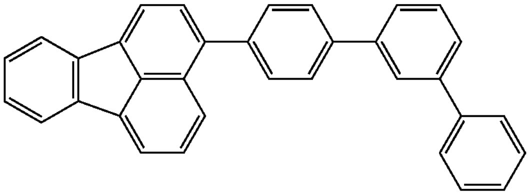
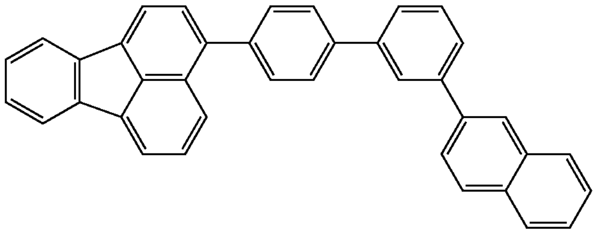
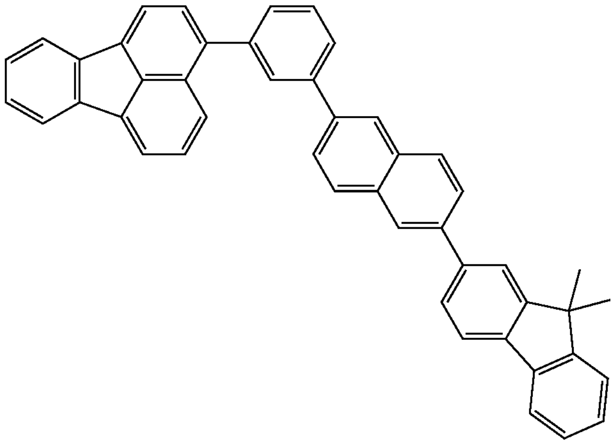

-continued
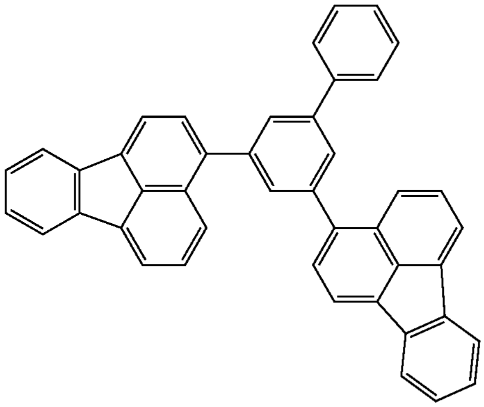
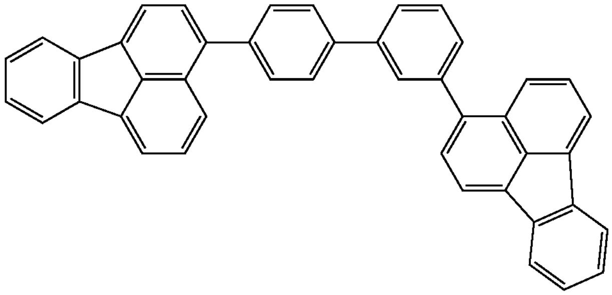
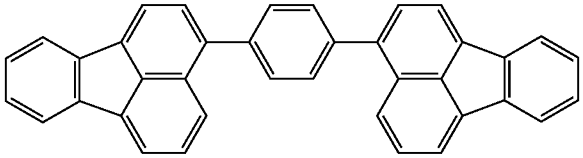
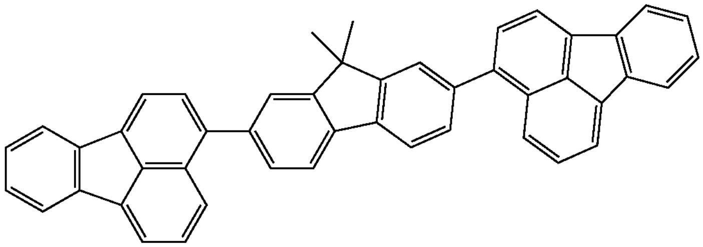
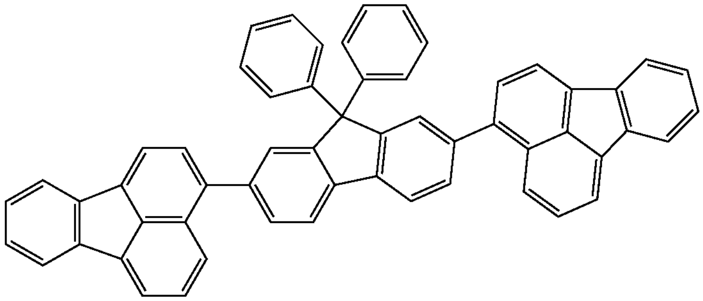
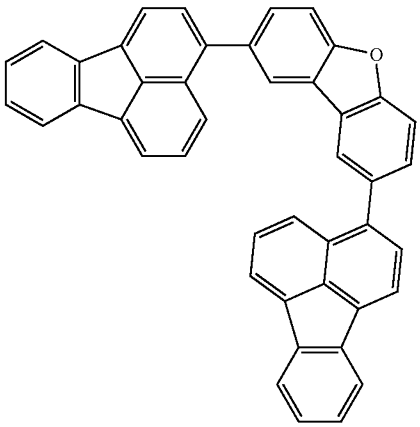
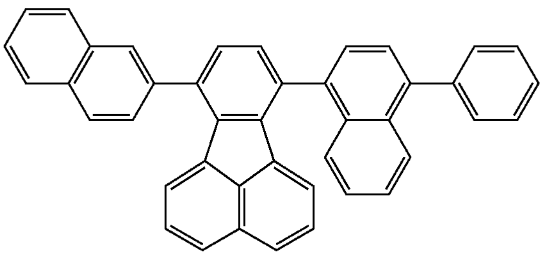

-continued
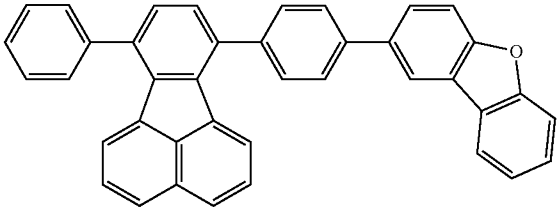
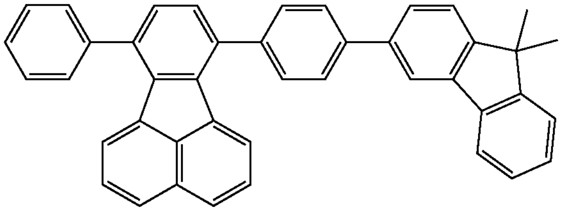
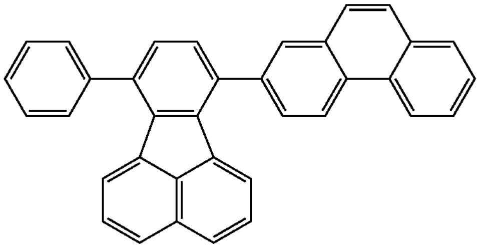
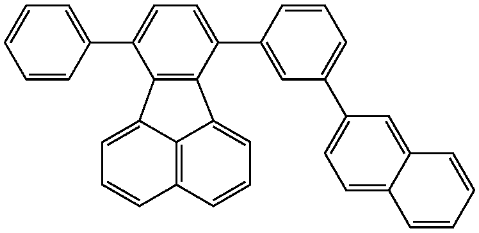
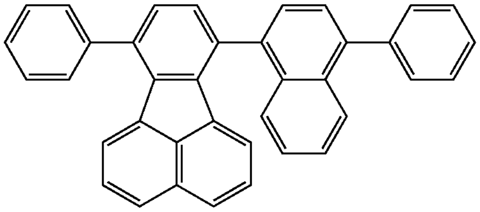
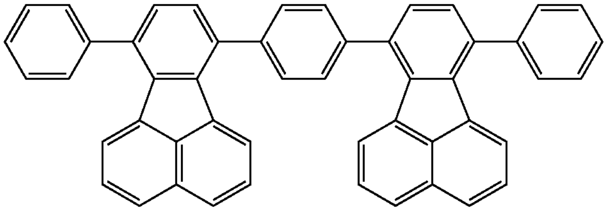
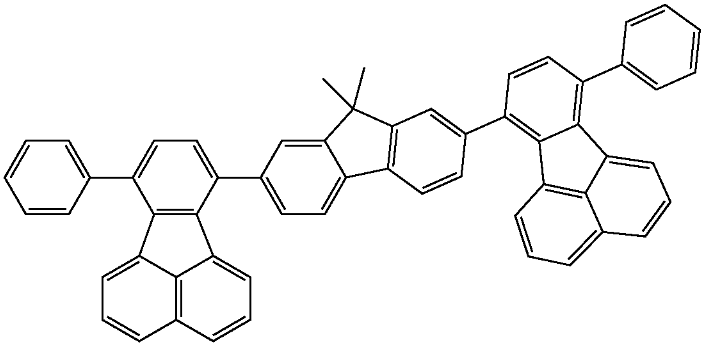
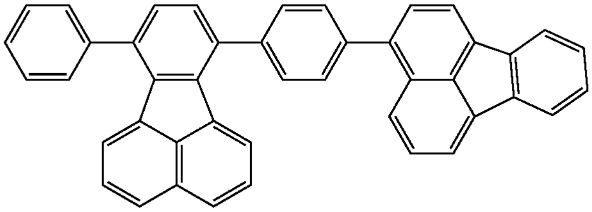
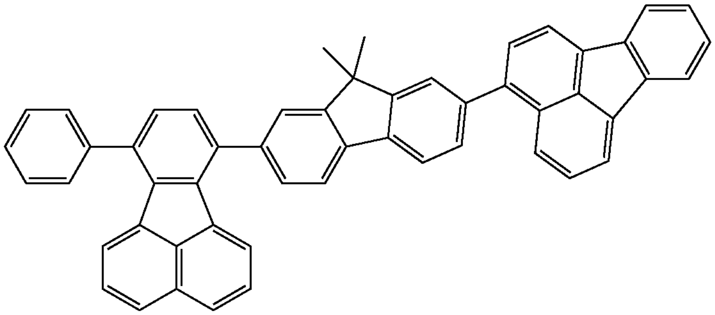

-continued
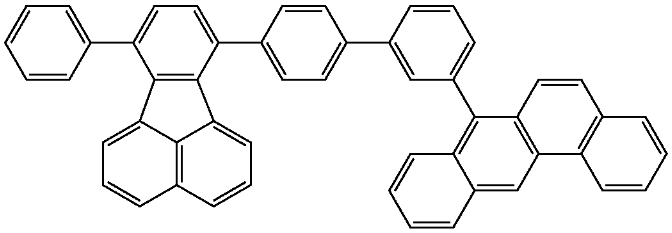
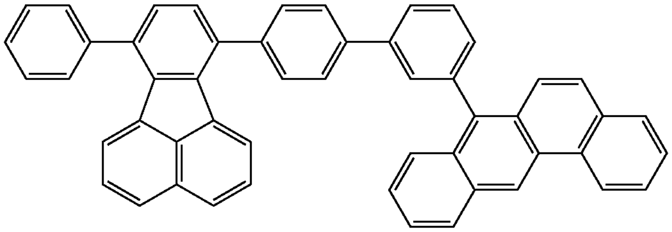
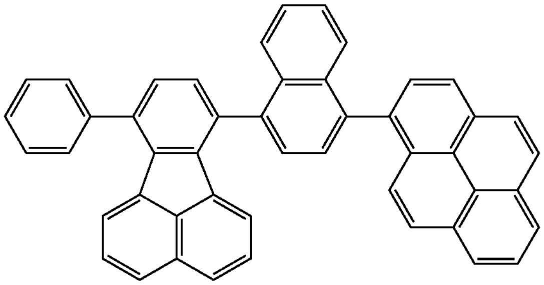
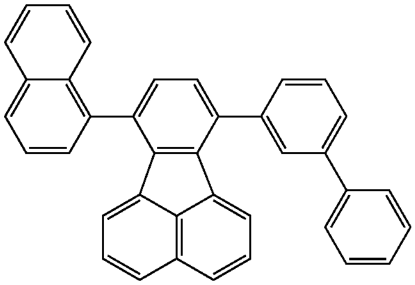
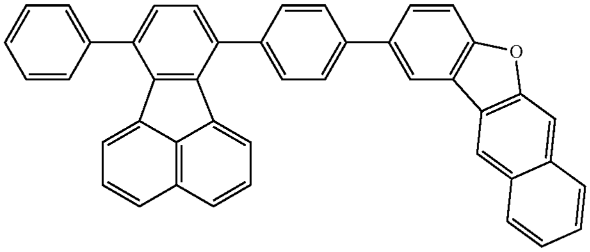
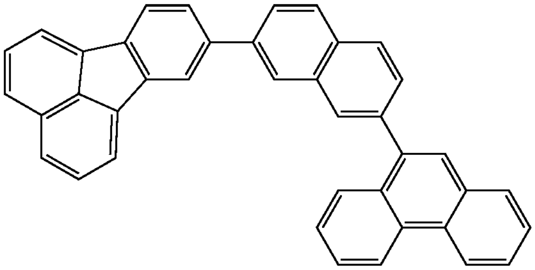
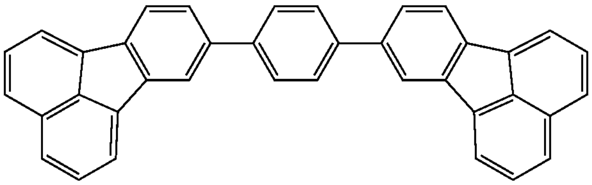
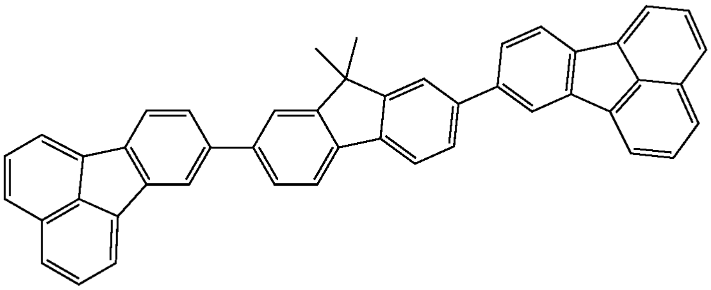

-continued
[Formula 42]
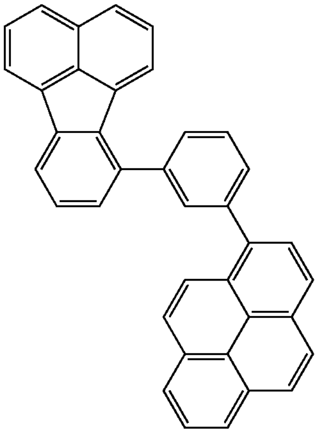
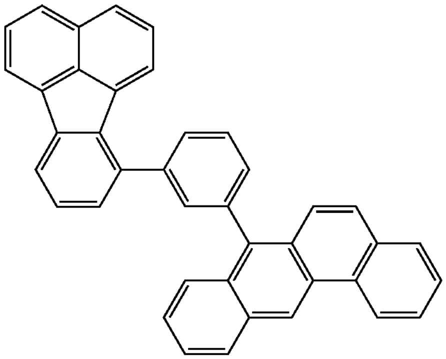
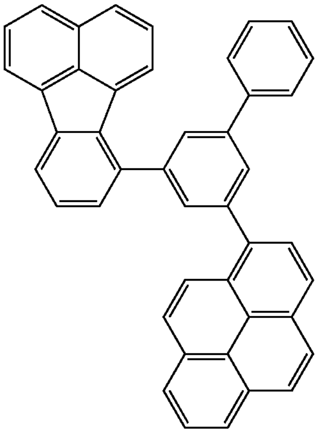
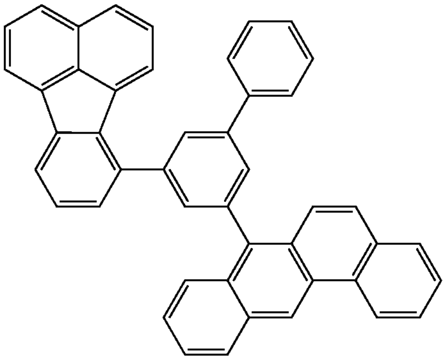
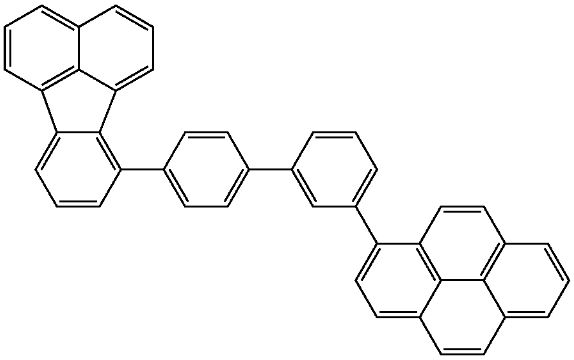
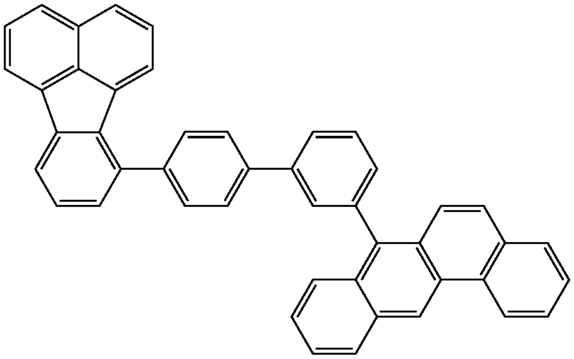
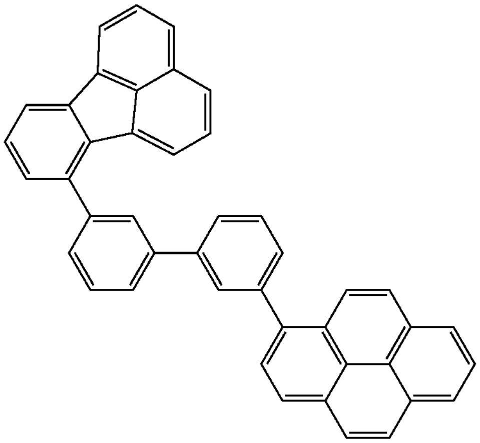
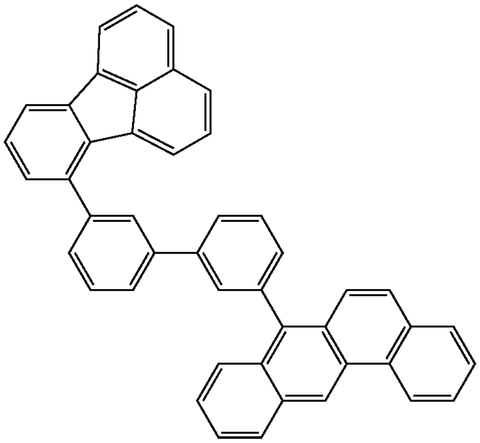

-continued
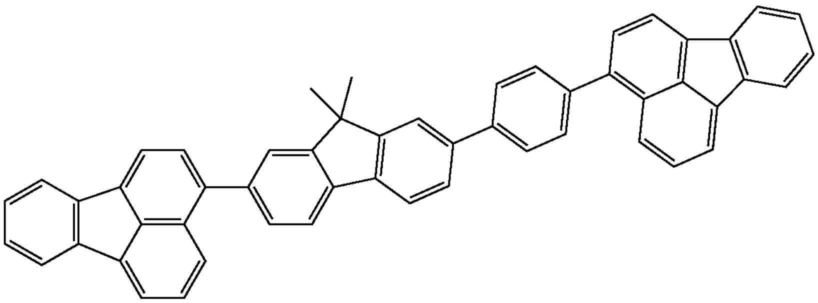
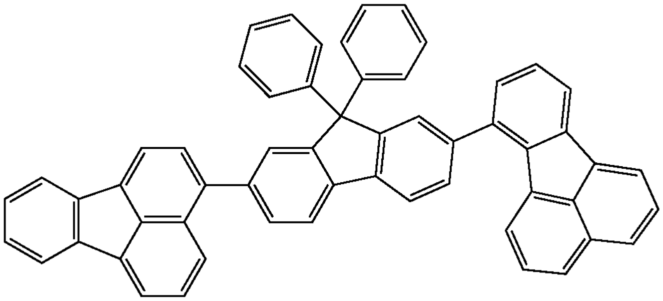
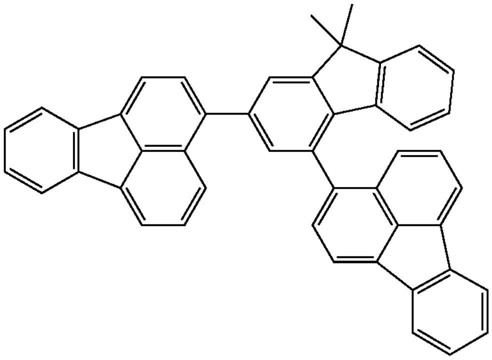
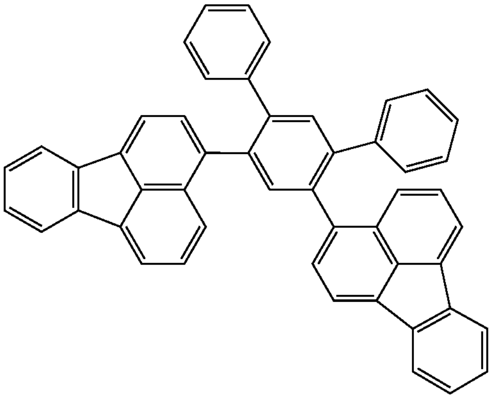
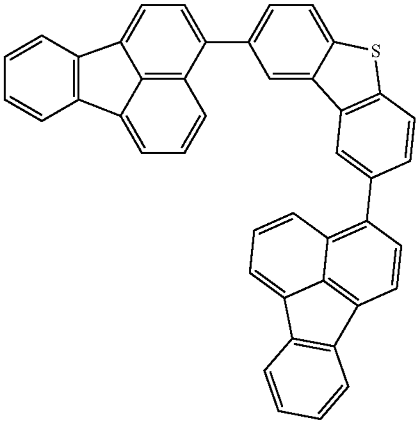
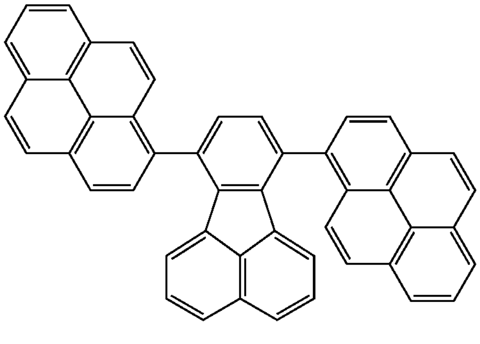

-continued
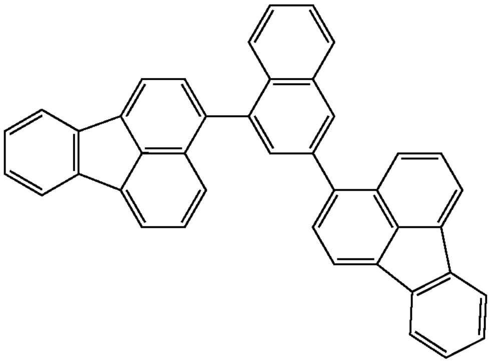
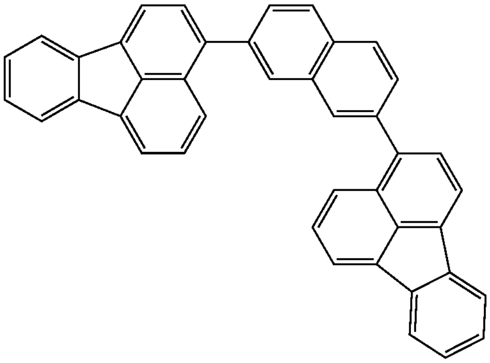
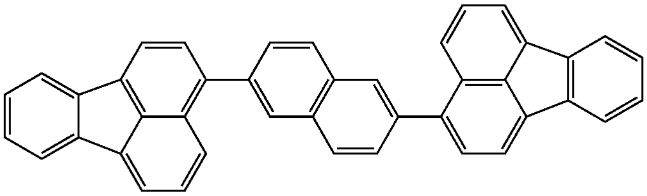
[Formula 43]
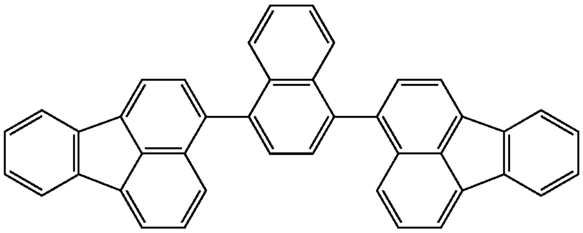
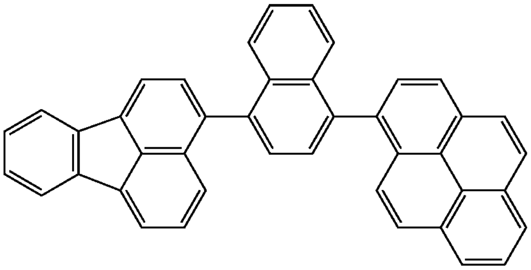
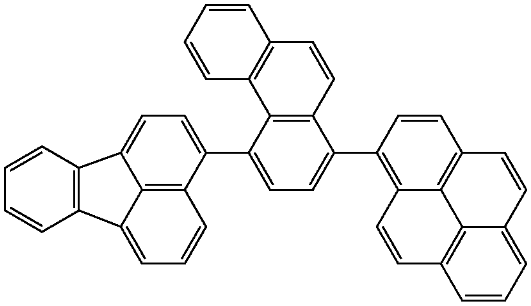
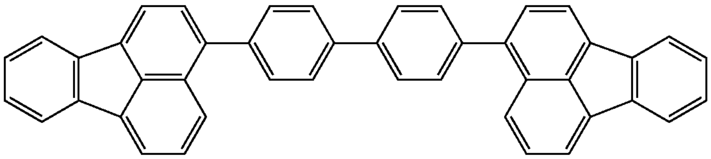
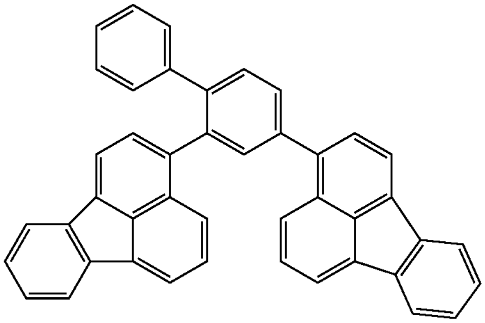
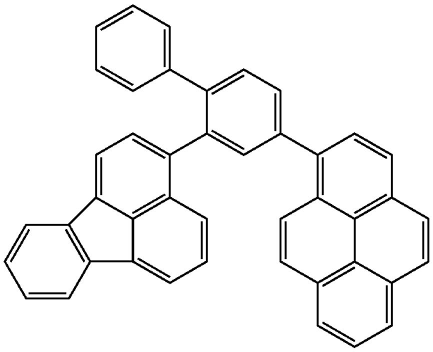

-continued
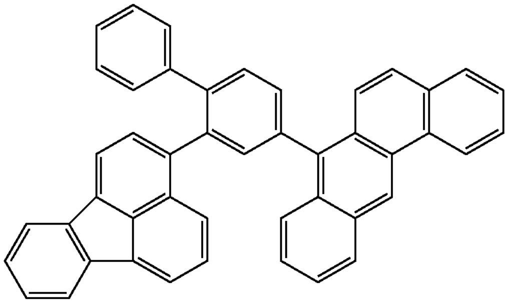
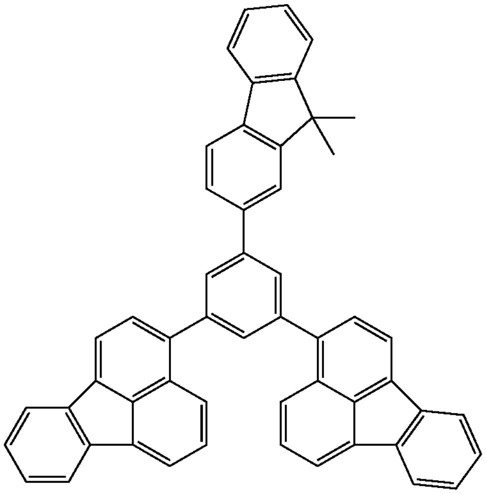
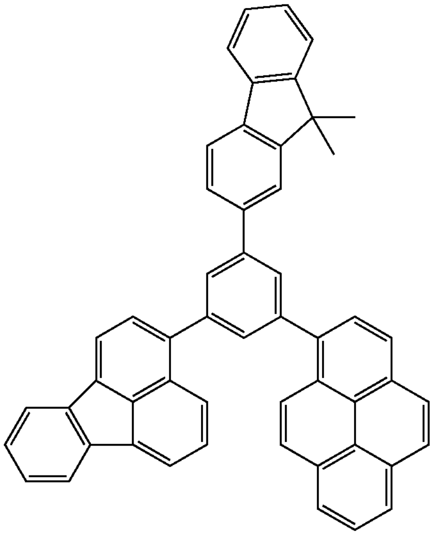
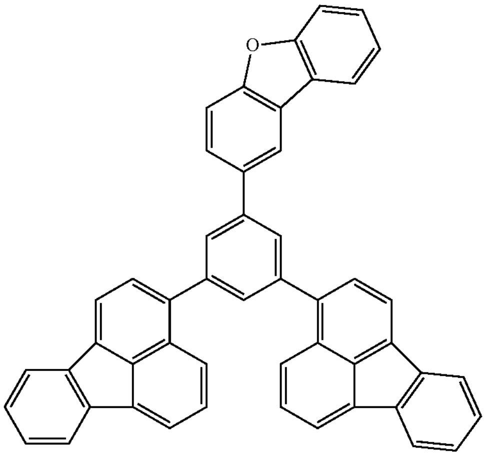
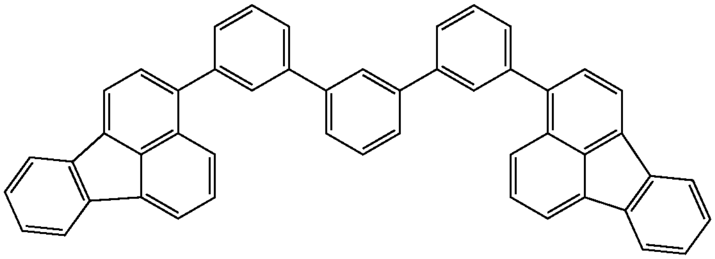
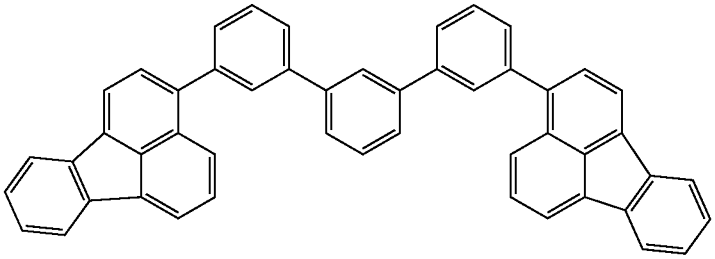

-continued
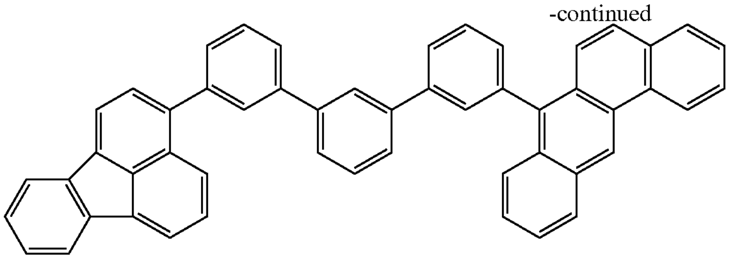
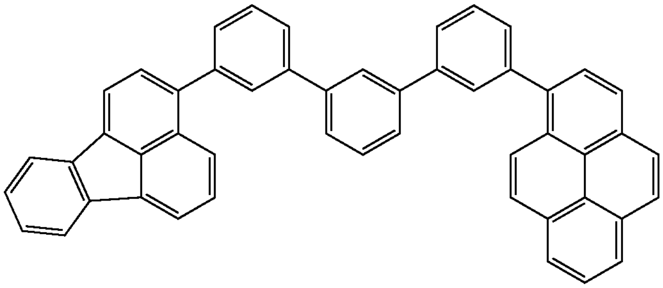
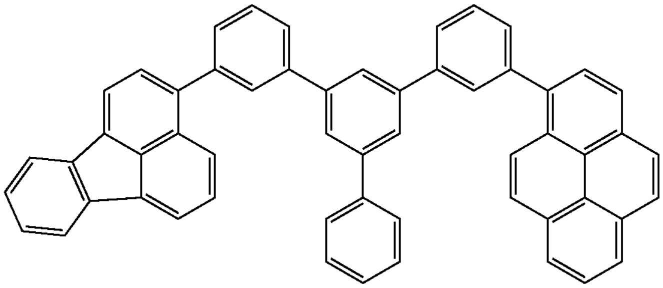
[Formula 44]
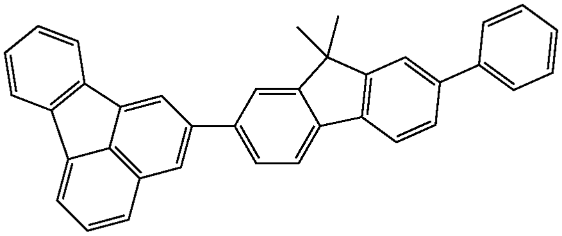
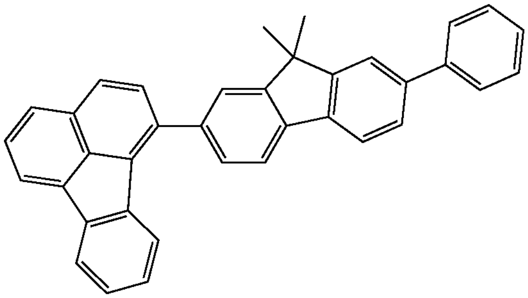
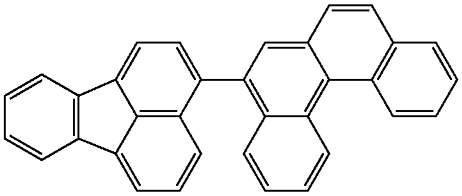
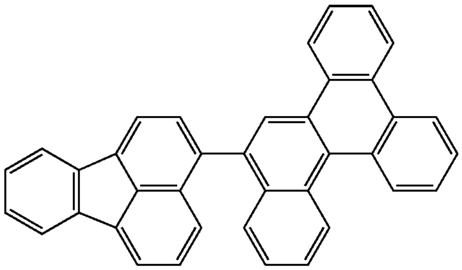
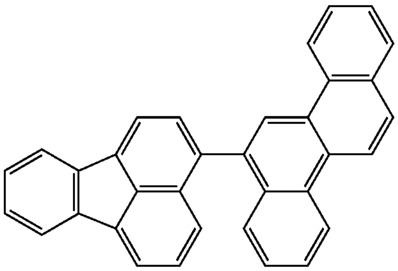
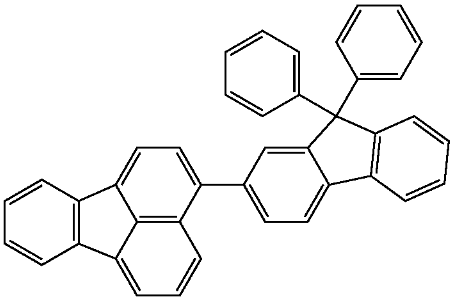

-continued

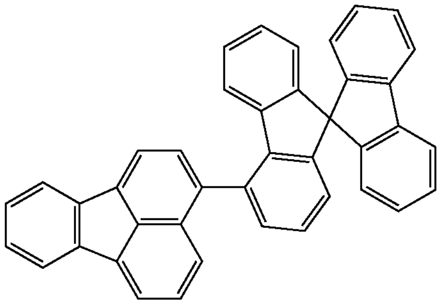

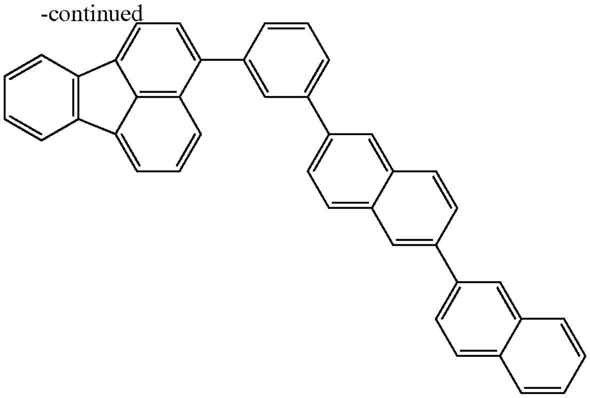

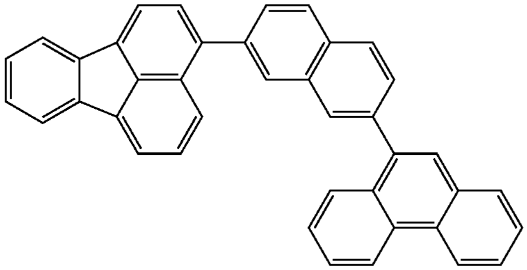 [SMILES: c1ccc2c(c1)-c1cccc3c(-c4ccc5ccc(-c6cc7ccccc7c7ccccc67)cc5c4)ccc-2c13]

Second Host Material

In the organic EL device according to the exemplary embodiment, the second host material is a compound different from the first host material.

In the organic EL device according to the exemplary embodiment, the second host material is not particularly limited. However, it is preferable that the second emitting layer contains the second compound represented by the formula (2) as the second host material.

Second Compound

In the organic EL device according to the exemplary embodiment, the second compound is a compound represented by the formula (2).

[Formula 45]

(2)

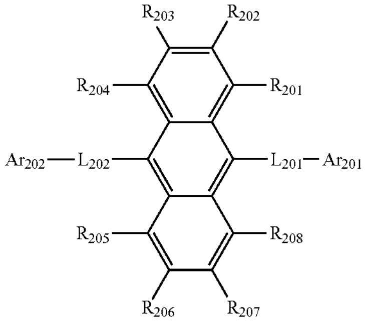

In the formula (2):

$R_{201}$ to $R_{208}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $-Si(R_{901})(R_{902})(R_{903})$, a group represented by $-O-(R_{904})$, a group represented by $-S-(R_{905})$, a group represented by $-N(R_{906})(R_{907})$, a substituted or unsubstituted aralkyl group having 7 to 50 carbon atoms, a group represented by $-C(=O)R_{801}$, a group represented by $-COOR_{802}$, a halogen atom, a cyano group, a nitro group, a substituted or unsubstituted aryl group having 6 to 50 ring carbon atoms, or a substituted or unsubstituted heterocyclic group having 5 to 50 ring atoms;

$L_{201}$ and $L_{202}$ are each independently a single bond, a substituted or unsubstituted arylene group having 6 to 50 ring carbon atoms, or a substituted or unsubstituted divalent heterocyclic group having 5 to 50 ring atoms; and $Ar_{201}$ and $Ar_{202}$ are each independently a substituted or unsubstituted aryl group having 6 to 50 ring carbon atoms, or a substituted or unsubstituted heterocyclic group having 5 to 50 ring atoms.

In the second compound according to the exemplary embodiment, $R_{901}$, $R_{902}$, $R_{903}$, $R_{904}$, $R_{905}$, $R_{906}$, $R_{907}$, $R_{801}$ and $R_{802}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

when a plurality of $R_{901}$ are present, the plurality of $R_{901}$ are mutually the same or different;

when a plurality of $R_{902}$ are present, the plurality of $R_{902}$ are mutually the same or different;

when a plurality of $R_{903}$ are present, the plurality of $R_{903}$ are mutually the same or different;

when a plurality of $R_{904}$ are present, the plurality of $R_{904}$ are mutually the same or different;

when a plurality of $R_{905}$ are present, the plurality of $R_{905}$ are mutually the same or different;

when a plurality of $R_{906}$ are present, the plurality of $R_{906}$ are mutually the same or different;

when a plurality of $R_{907}$ are present, the plurality of $R_{907}$ are mutually the same or different;

when a plurality of $R_{801}$ are present, the plurality of $R_{801}$ are mutually the same or different; and when a plurality of $R_{802}$ are present, the plurality of $R_{802}$ are mutually the same or different.

In the organic EL device according to the exemplary embodiment, it is preferable that $R_{201}$ to $R_{208}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $-Si(R_{901})(R_{902})(R_{903})$, a group represented by $-O-(R_{904})$, a group represented by $-S-(R_{905})$, a group represented by $-N(R_{906})(R_{907})$, a substituted or unsubstituted aralkyl group having 7 to 50 carbon atoms, a group represented by $-C(=O)R_{801}$, a group represented by $-COOR_{802}$, a halogen atom, a cyano group, or a nitro group; $L_{201}$ and $L_{202}$ are each independently a single bond, a substituted or unsubstituted arylene group having 6 to 50 ring carbon atoms, or a substituted or unsubstituted divalent heterocyclic group having 5 to 50 ring atoms; and $Ar_{201}$ and $Ar_{202}$ are each independently a substituted or unsubstituted aryl group having 6 to 50 ring carbon atoms, or a substituted or unsubstituted heterocyclic group having 5 to 50 ring atoms.

In the organic EL device according to the exemplary embodiment, it is preferable that $L_{201}$ and $L_{202}$ are each independently a single bond, or a substituted or unsubstituted arylene group having 6 to 50 ring carbon atoms; and $Ar_{201}$ and $Ar_{202}$ are each independently a substituted or unsubstituted aryl group having 6 to 50 ring carbon atoms.

In the organic EL device according to the exemplary embodiment, it is preferable that $Ar_{201}$ and $Ar_{202}$ are each independently a phenyl group, a naphthyl group, a phenanthryl group, a biphenyl group, a terphenyl group, a diphenylfluorenyl group, a dimethylfluorenyl group, a benzodiphenylfluorenyl group, a benzodimethylfluorenyl group, a dibenzofuranyl group, a dibenzothienyl group, a naphthobenzofuranyl group, or a naphthobenzothienyl group.

In the organic EL device according to the exemplary embodiment, the second compound represented by the formula (2) is preferably a compound represented by a formula (201), (202), (203), (204), (205), (206), (207), (208) or (209) below.

[Formula 46]

(201)

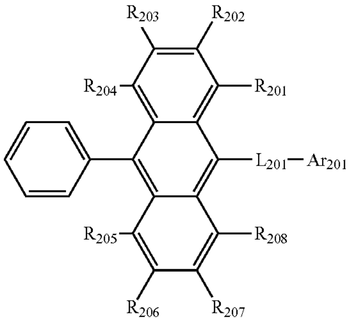

-continued

[Formula 47]

(202)

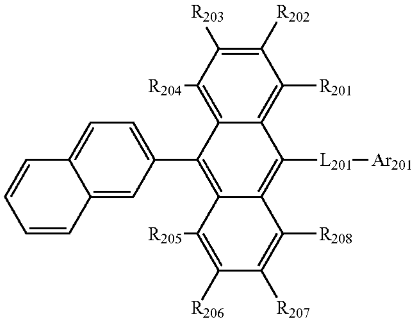

[Formula 48]

(203)

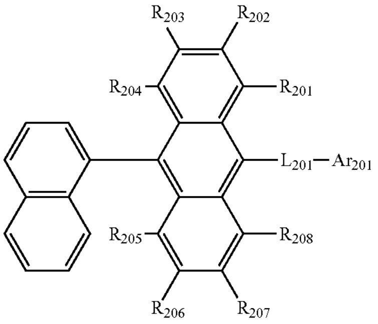

[Formula 49]

(204)

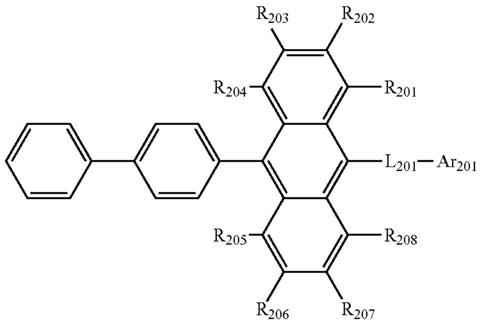

[Formula 50]

(205)

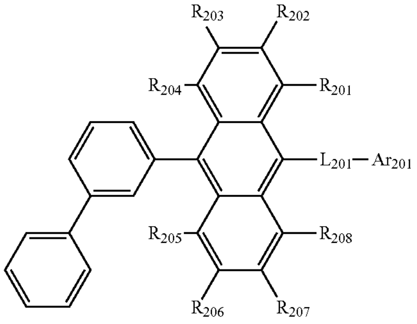

-continued
[Formula 51]
(206)
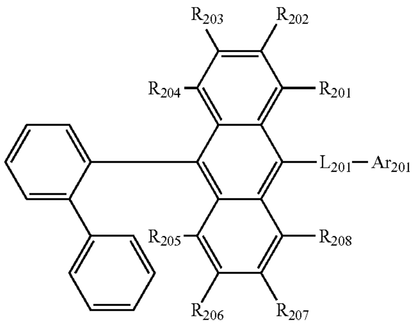
[Formula 52]
(207)
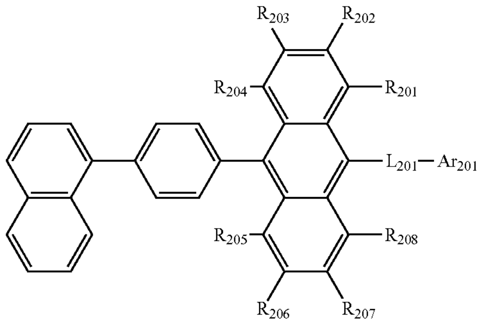
[Formula 53]
(208)
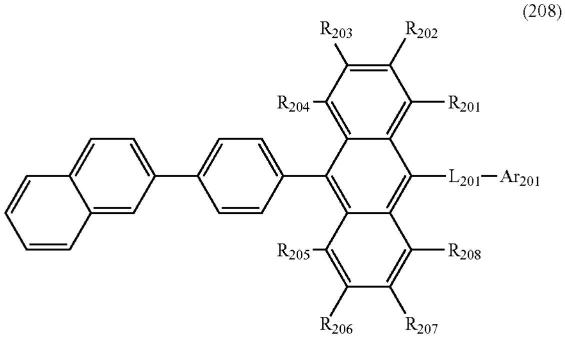
[Formula 54]
(209)
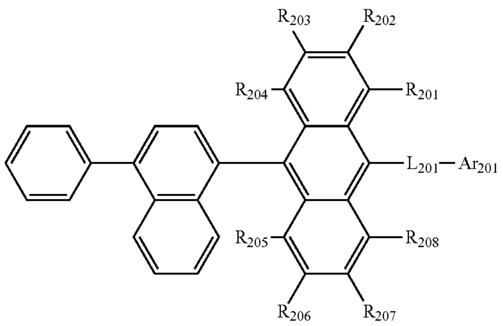
In the formulae (201) to (209):
$L_{201}$ and $Ar_{201}$ represent the same as $L_{201}$ and $Ar_{201}$ in the formula (2); and
$R_{201}$ to $R_{208}$ each independently represent the same as $R_{201}$ to $R_{208}$ in the formula (2).
The second compound represented by the formula (2) is also preferably a compound represented by a formula (221), (222), (223), (224), (225), (226), (227), (228) or (229) below.
[Formula 55]
(221)
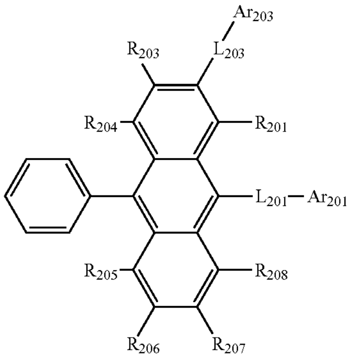
[Formula 56]
(222)
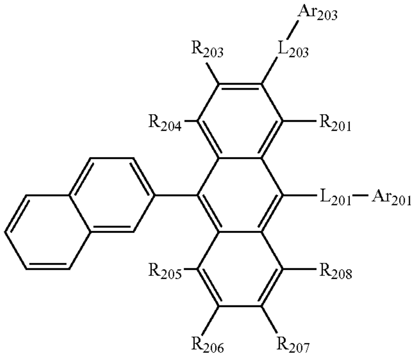
[Formula 57]
(223)
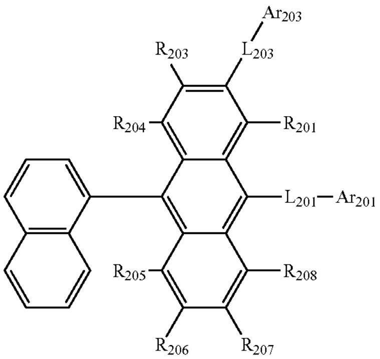

-continued

[Formula 58]

(224)

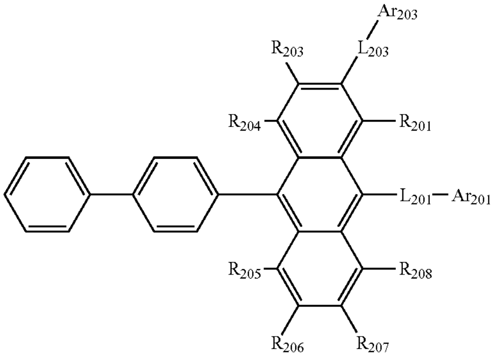

[Formula 59]

(225)

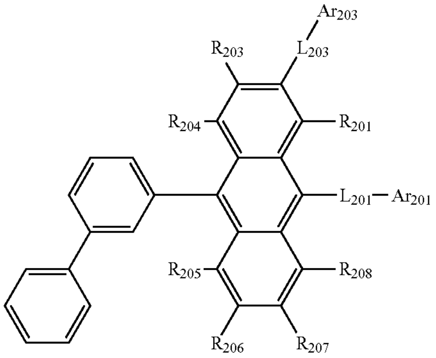

[Formula 60]

(226)

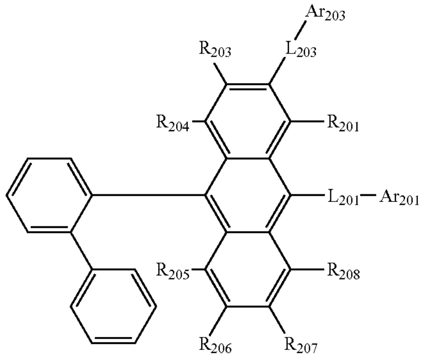

[Formula 61]

(227)

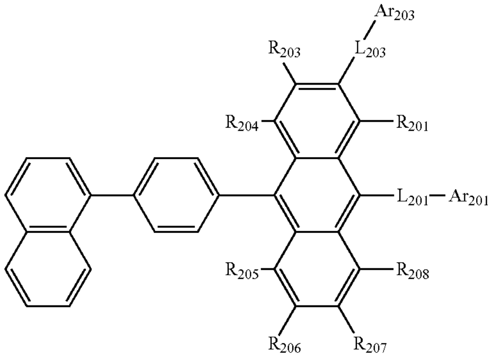

-continued

[Formula 62]

(228)

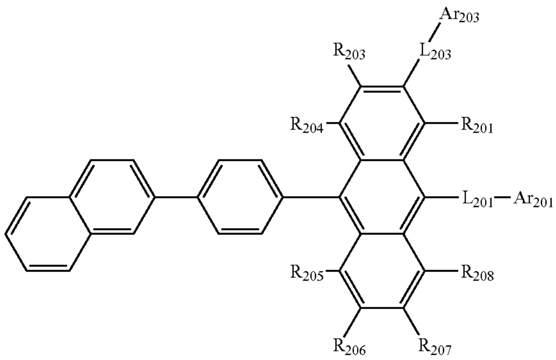

[Formula 63]

(229)

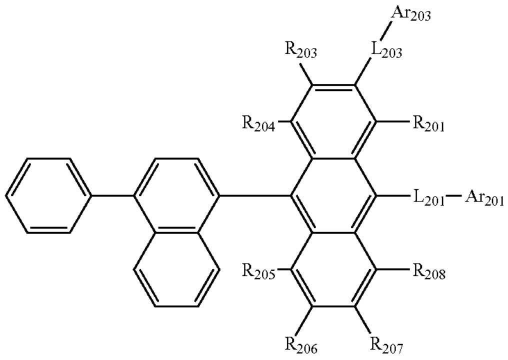

In the formulae (221), (222), (223), (224), (225), (226), (227), (228) and (229):

$R_{201}$ and $R_{203}$ to $R_{208}$ each independently represent the same as $R_{201}$ and $R_{203}$ to $R_{208}$ in the formula (2);

$L_{201}$ and $Ar_{201}$ respectively represent the same as $L_{201}$ and $Ar_{201}$ in the formula (2);

$L_{203}$ represents the same as $L_{201}$ in the formula (2);

$L_{203}$ and $L_{201}$ are mutually the same or different;

$Ar_{203}$ represents the same as $Ar_{201}$ in the formula (2); and $Ar_{203}$ and $Ar_{201}$ are mutually the same or different.

The second compound represented by the formula (2) is also preferably a compound represented by a formula (241), (242), (243), (244), (245), (246), (247), (248) or (249) below.

[Formula 64]

(241)

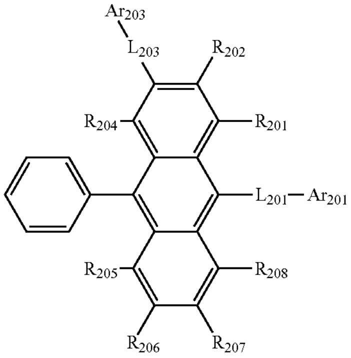

-continued
[Formula 65]
(242)
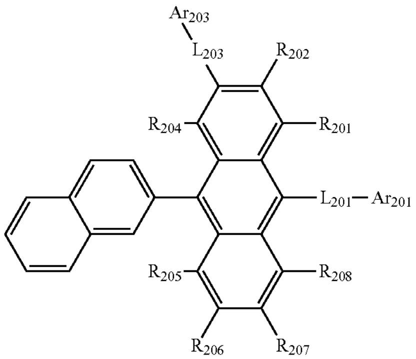
[Formula 66]
(243)
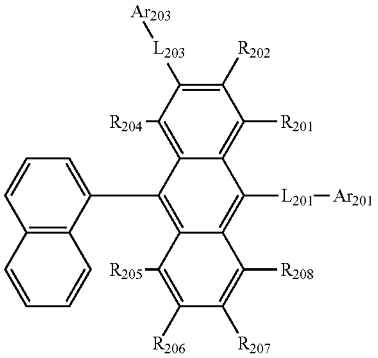
[Formula 67]
(244)
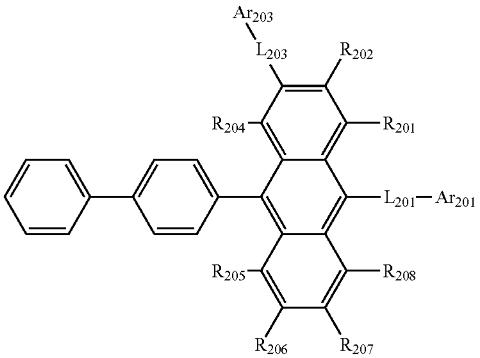
[Formula 68]
(245)
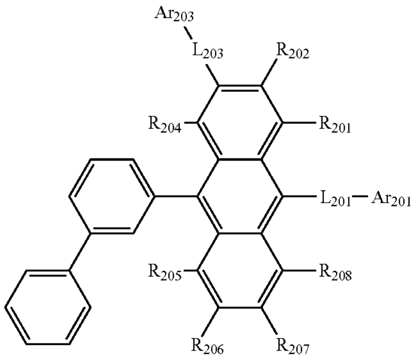
-continued
[Formula 69]
(246)
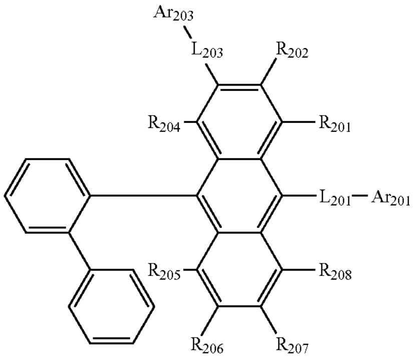
[Formula 70]
(247)
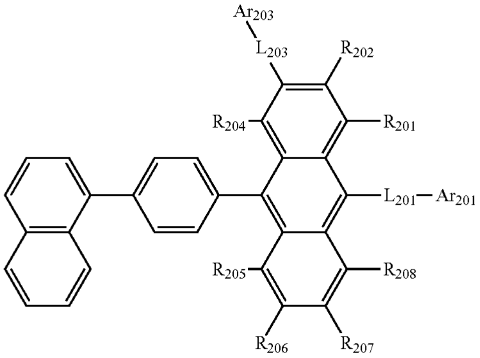
[Formula 71]
(248)
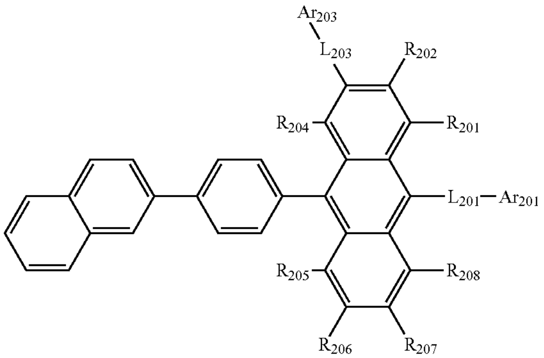
[Formula 72]
(249)
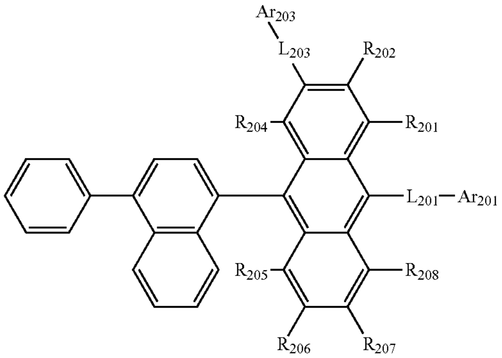

In the formulae (241), (242), (243), (244), (245), (246), (247), (248) and (249):

$R_{201}$, $R_{202}$ and $R_{204}$ to $R_{208}$ each independently represent the same as $R_{201}$, $R_{202}$ and $R_{204}$ to $R_{208}$ in the formula (2);

$L_{203}$ represents the same as $L_{201}$ in the formula (2);

$L_{203}$ and $L_{201}$ are mutually the same or different;

$Ar_{203}$ represents the same as $Ar_{201}$ in the formula (2); and $Ar_{203}$ and $Ar_{201}$ are mutually the same or different.

In the second compound represented by the formula (2), it is preferable that $R_{201}$ to $R_{208}$ not being the group represented by a formula (21) are each independently a hydrogen atom, a substituted or unsubstituted alkyl group having 1 to 50 carbon atoms, a substituted or unsubstituted cycloalkyl group having 3 to 50 ring carbon atoms, or a group represented by —$Si(R_{901})(R_{902})(R_{903})$.

It is preferable that $L_{101}$ is a single bond, or an unsubstituted arylene group having 6 to 22 ring carbon atoms; and $Ar_{101}$ is a substituted or unsubstituted aryl group having 6 to 22 ring carbon atoms.

In the organic EL device according to the exemplary embodiment, it is preferable that $R_{201}$ to $R_{208}$ in the second compound represented by the formula (2) are each independently a hydrogen atom, a substituted or unsubstituted alkyl group having 1 to 50 carbon atoms, a substituted or unsubstituted cycloalkyl group having 3 to 50 ring carbon atoms, or a group represented by —$Si(R_{901})(R_{902})(R_{903})$.

In the organic EL device according to the exemplary embodiment, it is preferable that $R_{201}$ to $R_{208}$ in the second compound represented by the formula (2) are each preferably a hydrogen atom.

In the second host material, all groups described as "substituted or unsubstituted" groups are preferably "unsubstituted" groups.

In the second compound, all groups described as "substituted or unsubstituted" groups are preferably "unsubstituted" groups.

In the organic EL device according to the exemplary embodiment, for instance, $Ar_{201}$ in the second compound represented by the formula (2) is a substituted or unsubstituted dibenzofuranyl group.

In the organic EL device according to the exemplary embodiment, for instance, $Ar_{201}$ in the second compound represented by the formula (2) is an unsubstituted dibenzofuranyl group.

In the organic EL device according to the exemplary embodiment, for instance, the second compound represented by the formula (2) has at least one hydrogen atom, the hydrogen atom including at least one deuterium atom.

In the organic EL device according to the exemplary embodiment, for instance, $L_{201}$ in the second compound represented by the formula (2) is one of TEMP-63 to TEMP-68.

[Formula 73]

(TEMP-63)

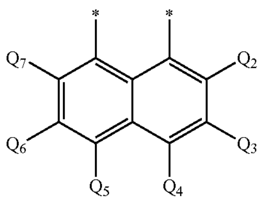

-continued (TEMP-64)

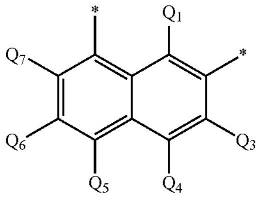

(TEMP-65)

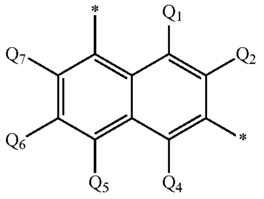

(TEMP-66)

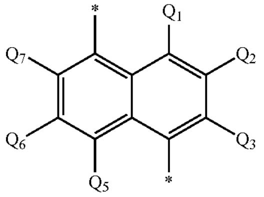

(TEMP-67)

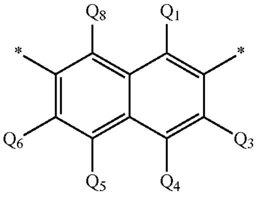

(TEMP-68)

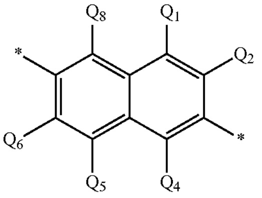

In the organic EL device according to the exemplary embodiment, for instance, $Ar_{201}$ in the second compound represented by the formula (2) is at least one group selected from the group consisting of substituted or unsubstituted anthryl group, benzanthryl group, phenanthryl group, benzophenanthryl group, phenalenyl group, pyrenyl group, chrysenyl group, benzochrysenyl group, triphenylenyl group, benzotriphenylenyl group, tetracenyl group, pentacenyl group, fluoranthenyl group, benzofluoranthenyl group, and perylenyl group.

In the organic EL device according to the exemplary embodiment, for instance, $Ar_{201}$ in the second compound represented by the formula (2) is a substituted or unsubstituted fluorenyl group.

In the organic EL device according to the exemplary embodiment, for instance, $Ar_{201}$ in the second compound represented by the formula (2) is a substituted or unsubstituted xanthenyl group.

In the organic EL device according to the exemplary embodiment, for instance, $Ar_{201}$ in the second compound represented by the formula (2) is a benzoxanthenyl group.

Manufacturing Method of Second Compound

The second compound can be manufactured by a known method. The second compound can also be manufactured based on a known method through a known alternative reaction using a known material(s) tailored for the target compound.

Specific Examples of Second Compound

Specific examples of the second compound include the following compounds. It should however be noted that the invention is not limited to the specific examples of the second compound.

[Formula 74]

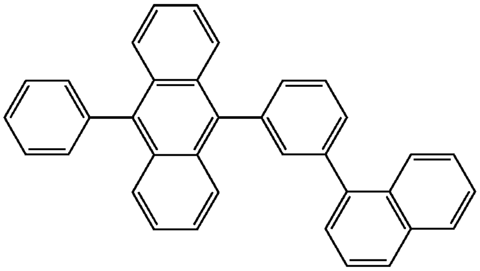

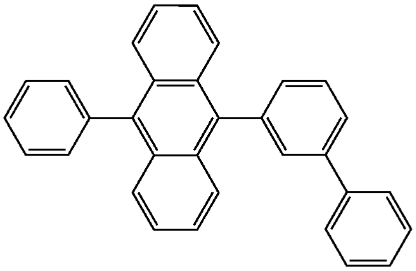

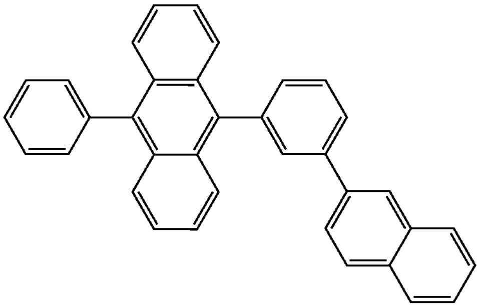

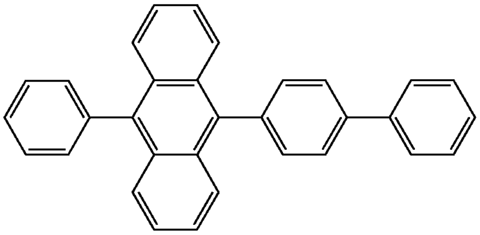

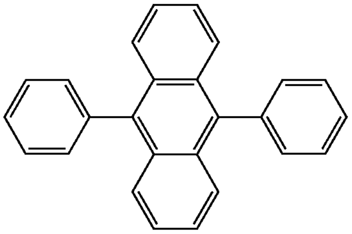

-continued

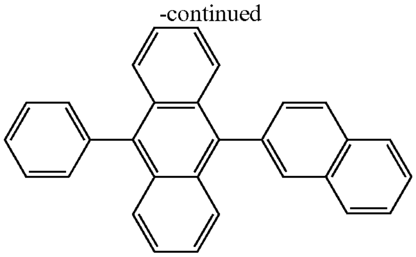

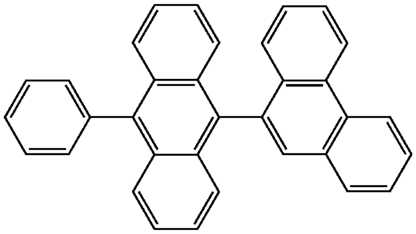

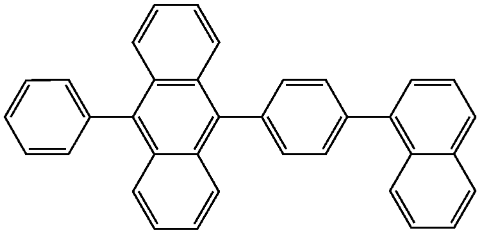

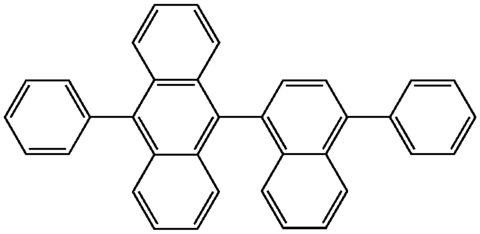

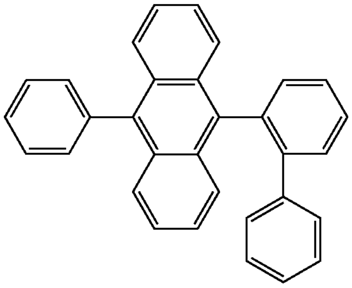

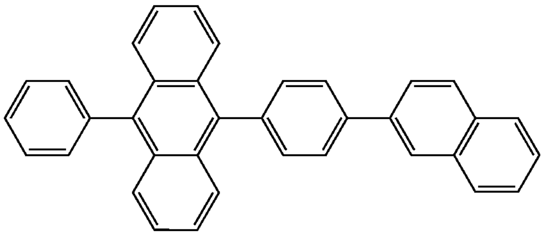

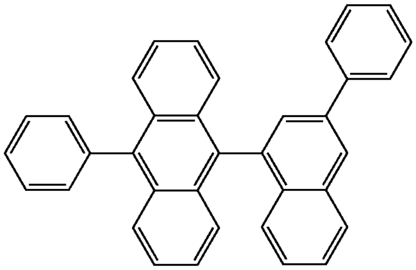

-continued
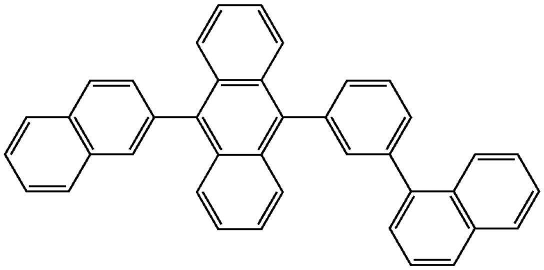
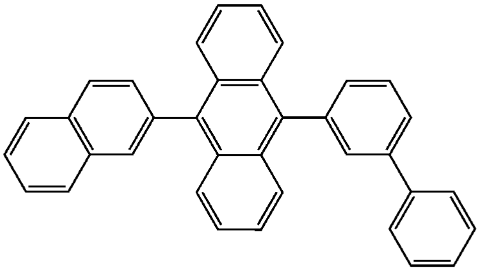
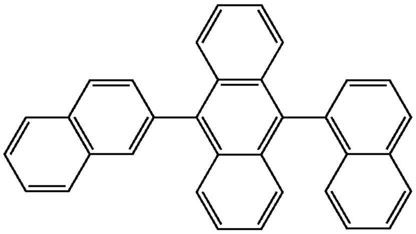
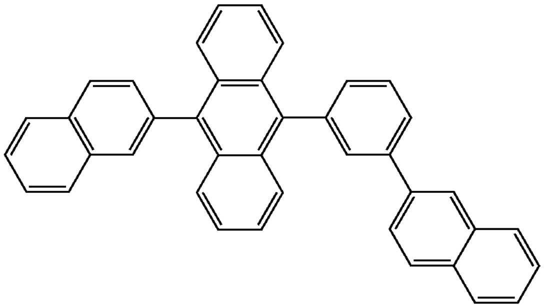
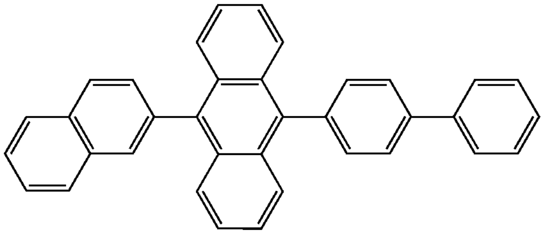
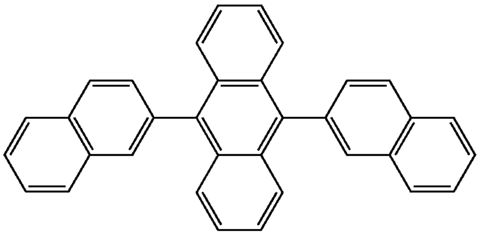
-continued
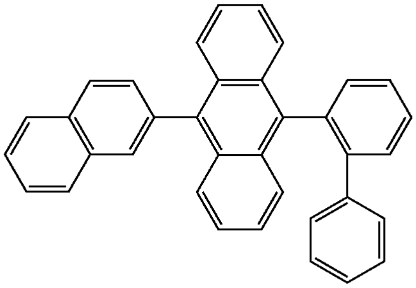
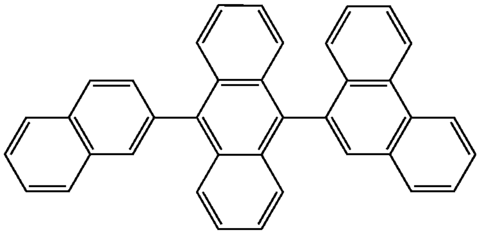
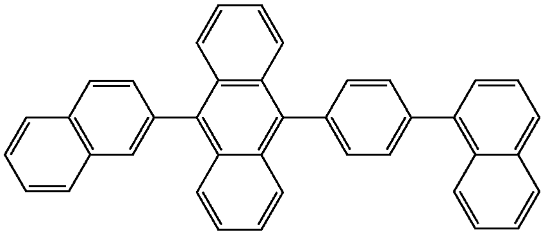
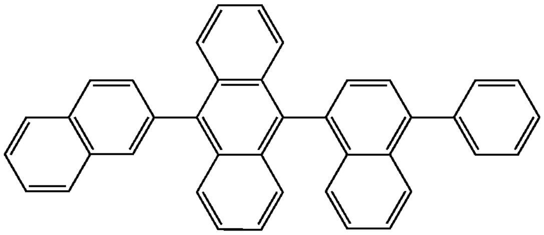
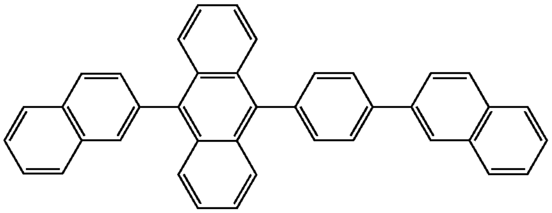
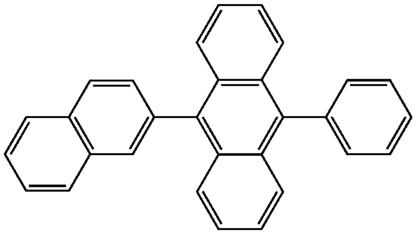
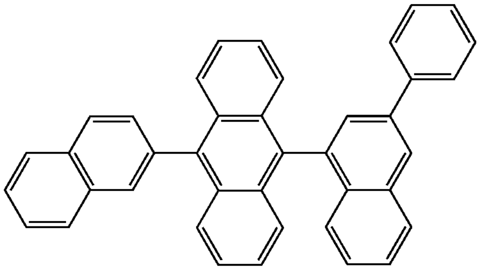

-continued
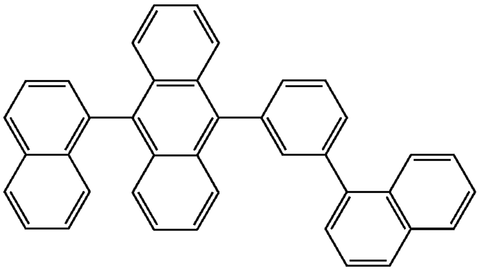
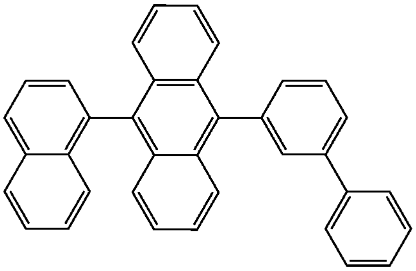
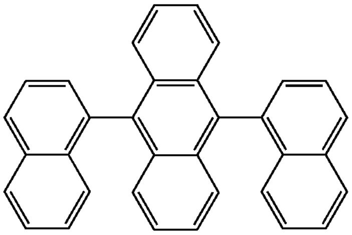
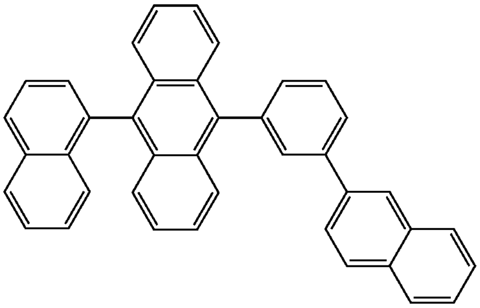
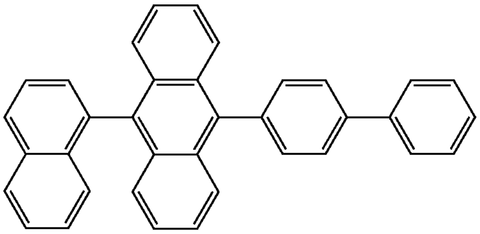
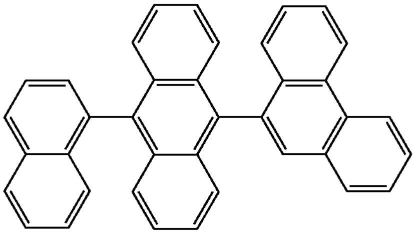
-continued
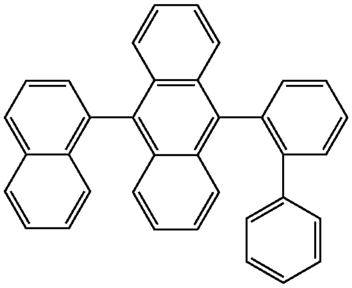
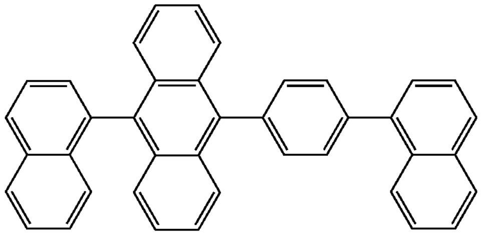
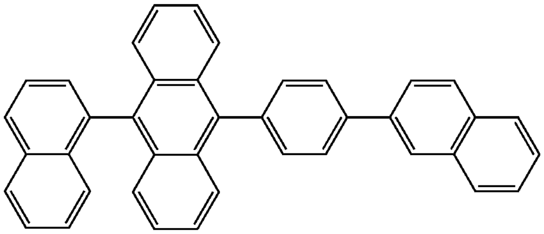
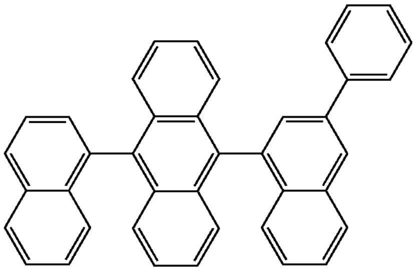
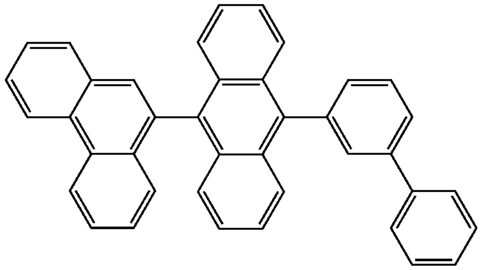
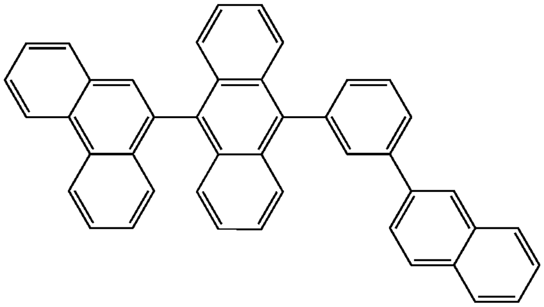

-continued
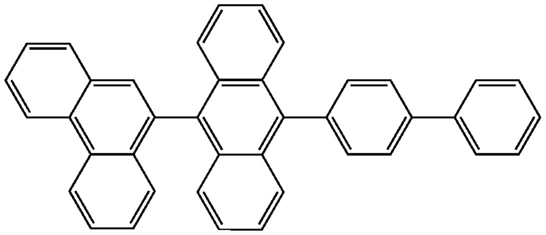
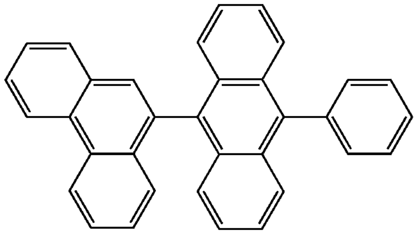
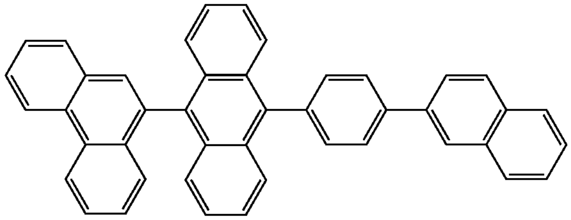
[Formula 75]
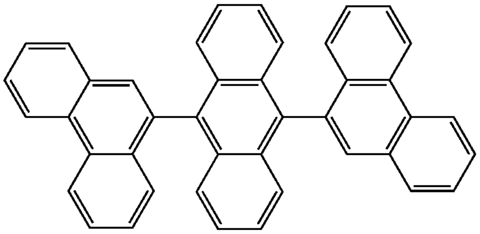
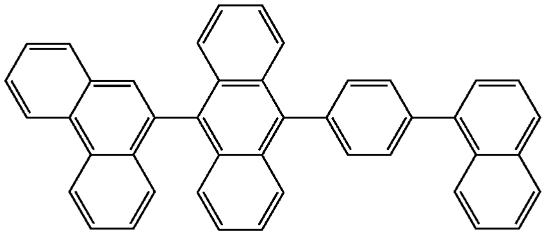
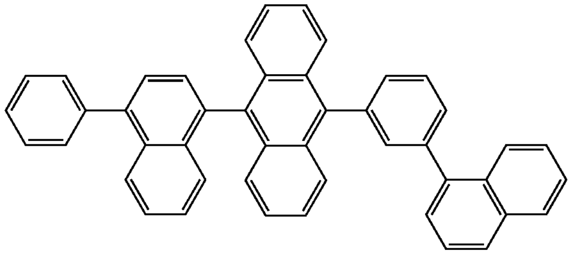
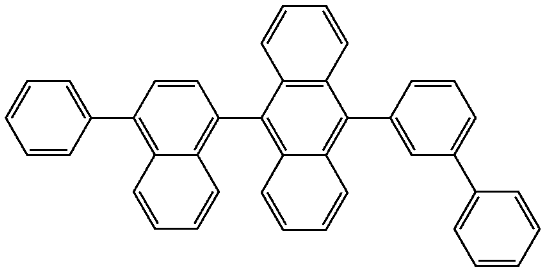
-continued
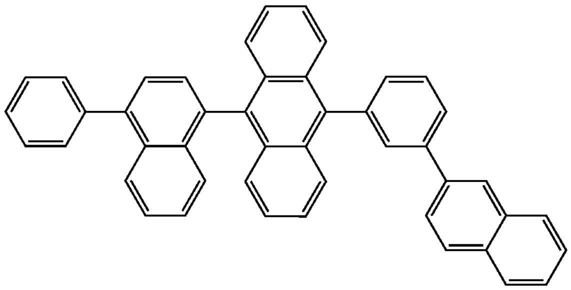
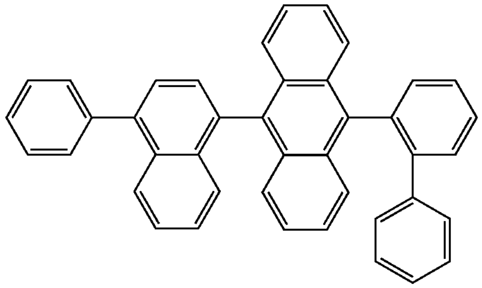
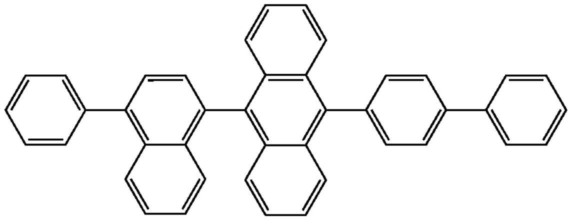
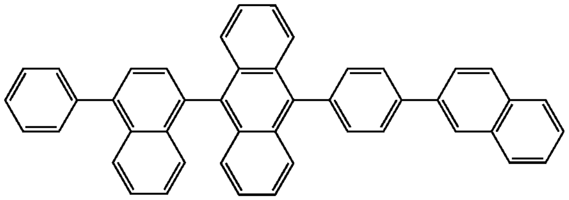
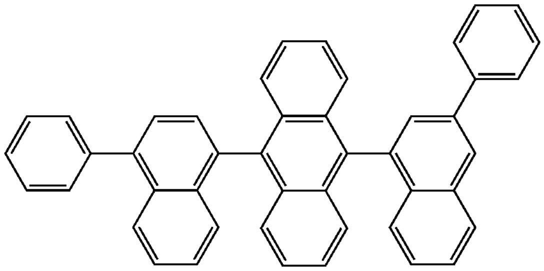
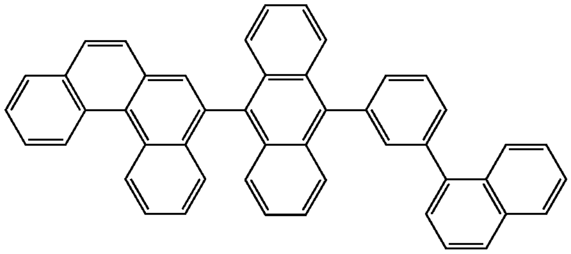

-continued
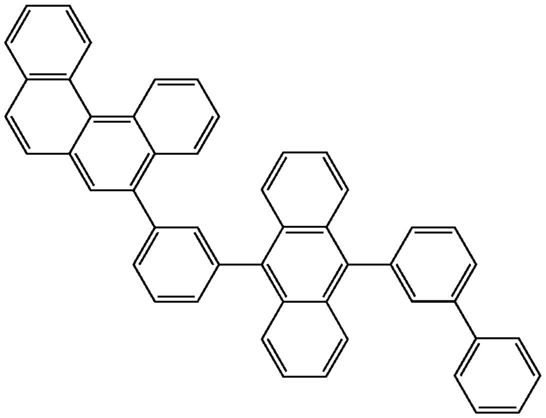
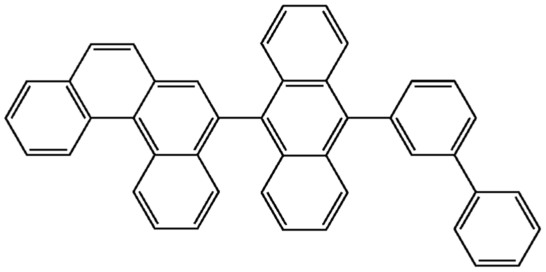
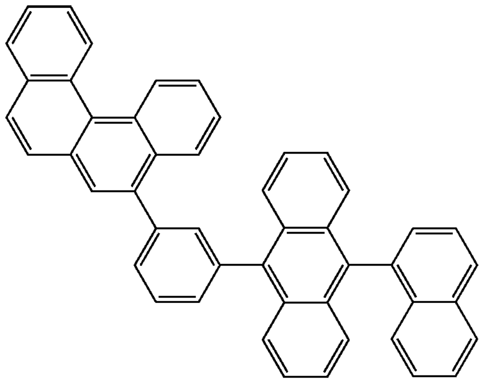
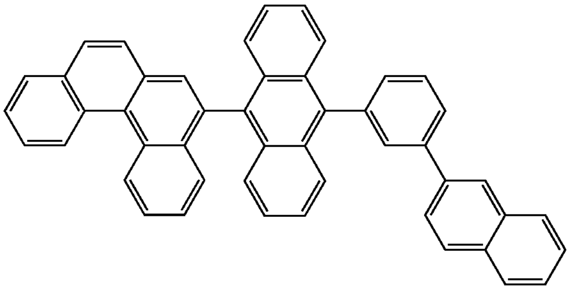
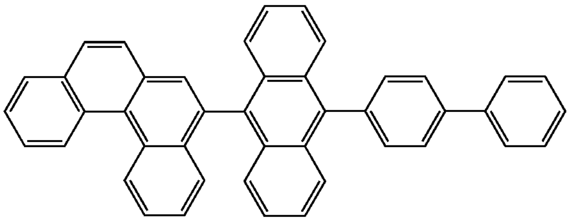
-continued
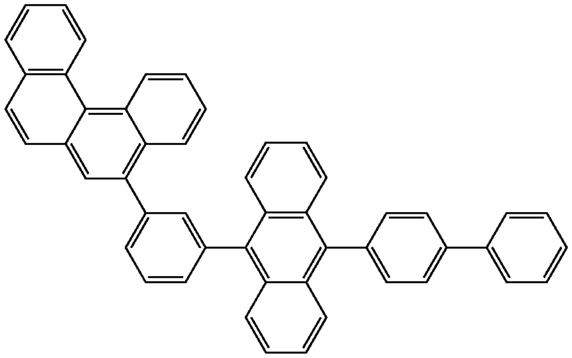
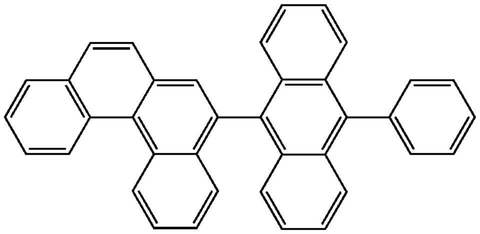
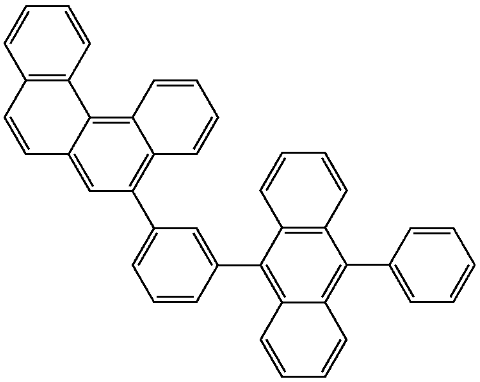
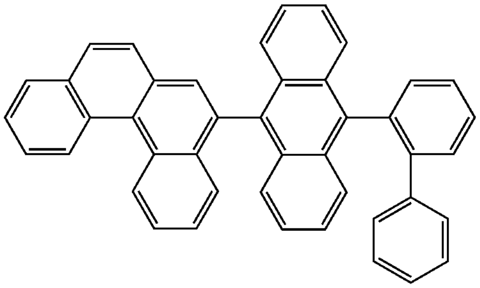
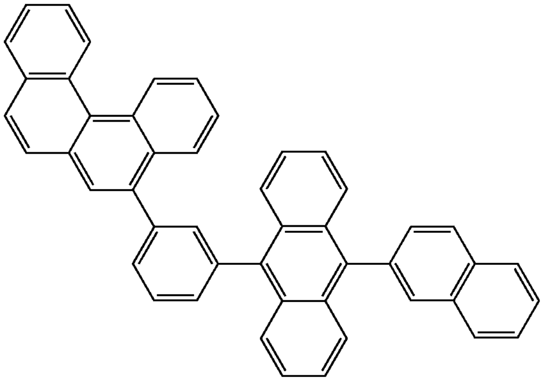

-continued
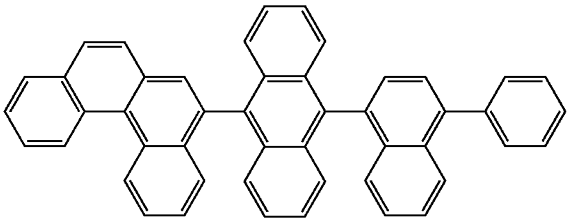
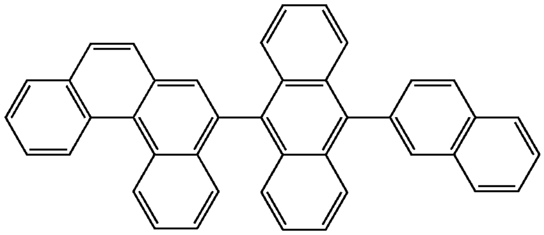
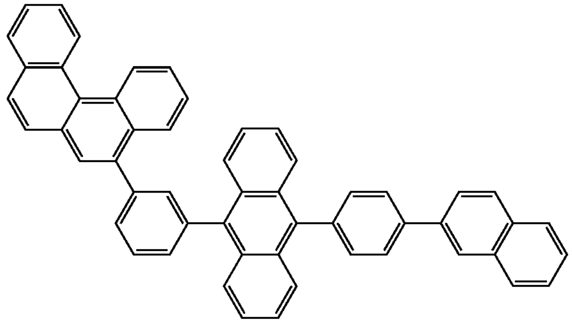
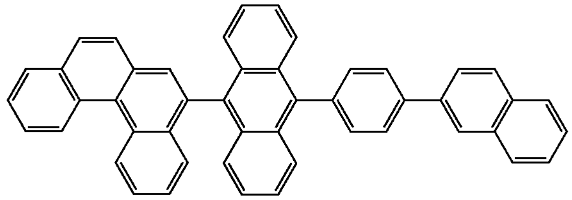
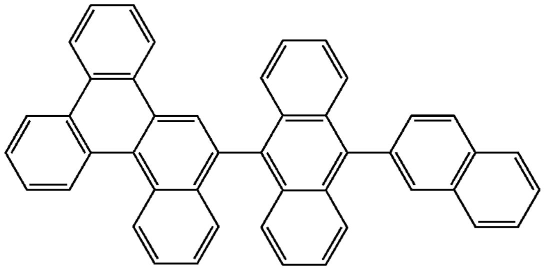
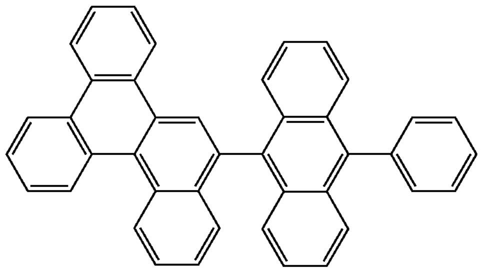
-continued
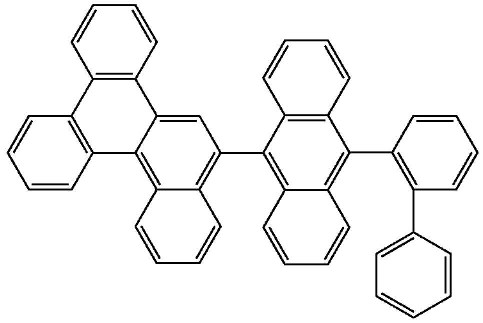
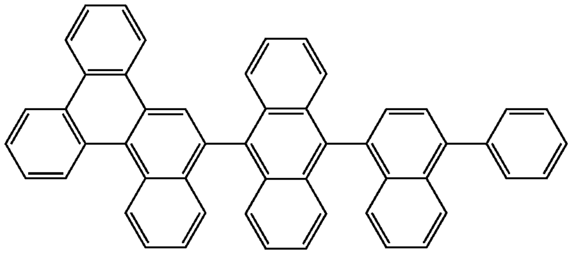
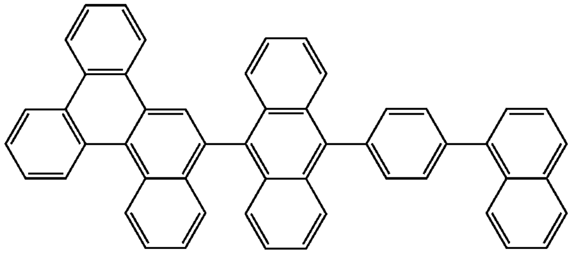
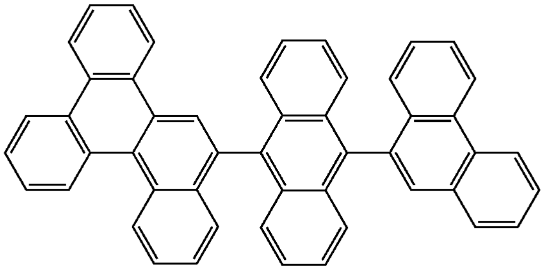
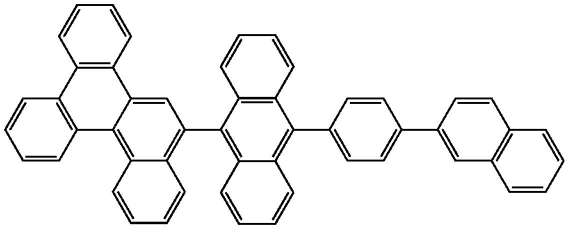
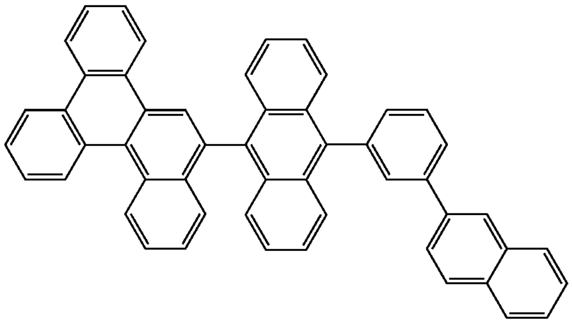

-continued
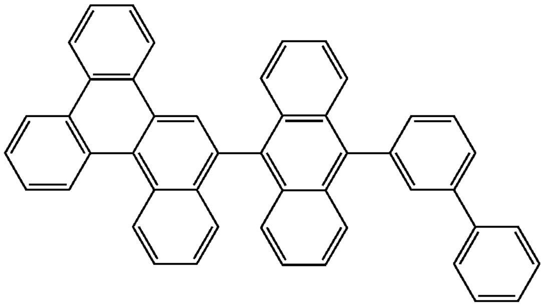
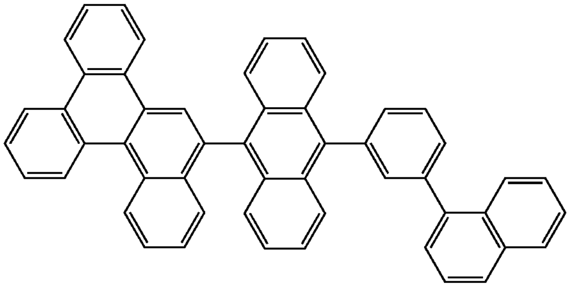
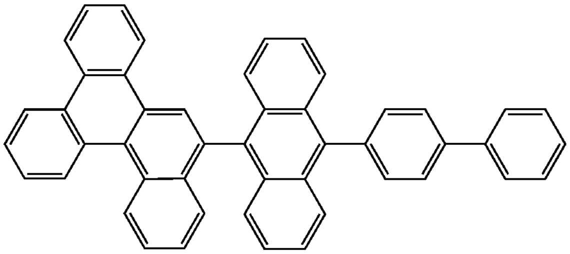
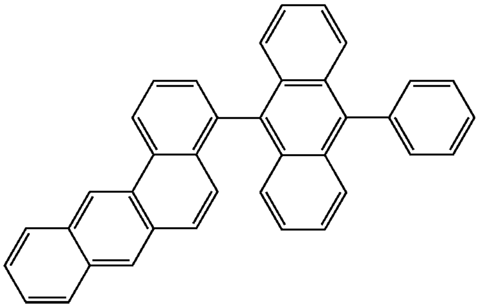
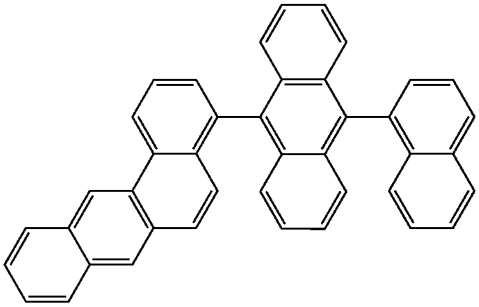
-continued
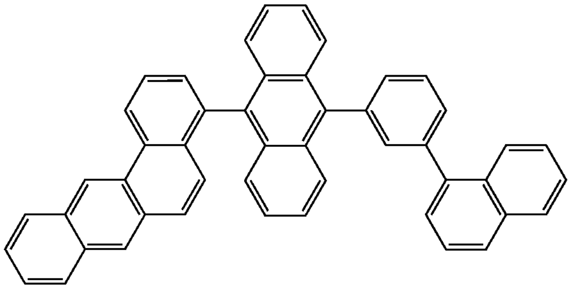
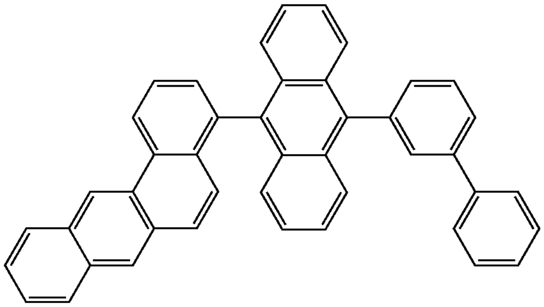
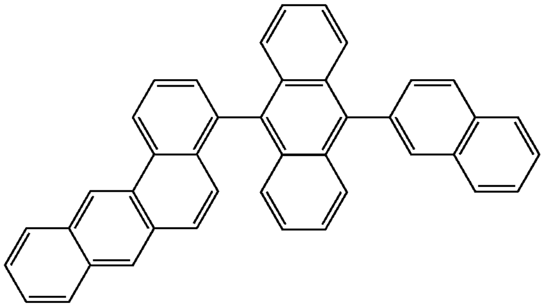
[Formula 76]
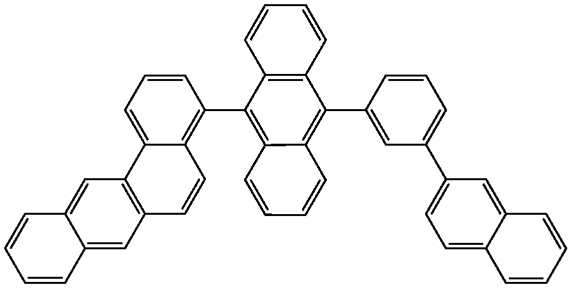
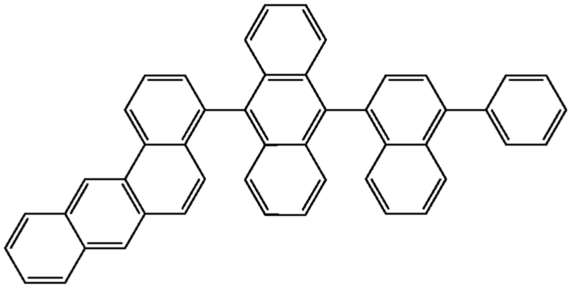

-continued
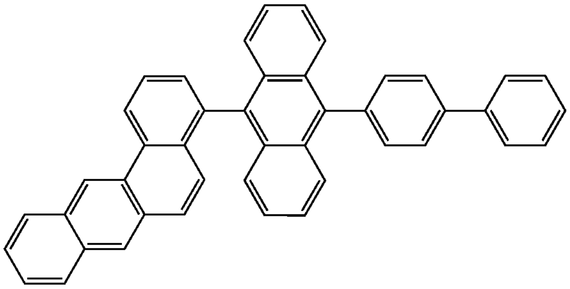
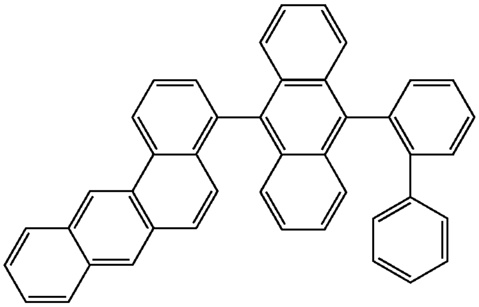
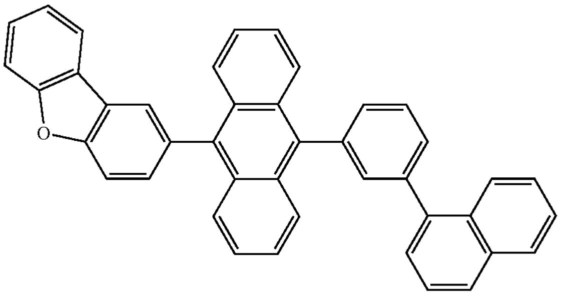
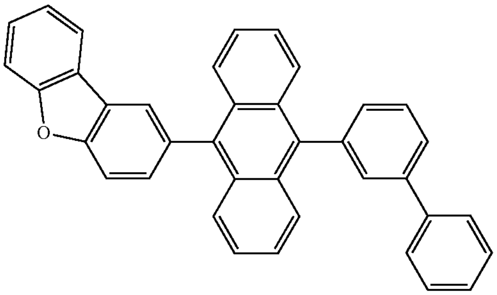
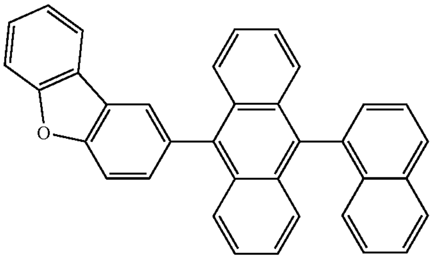
-continued
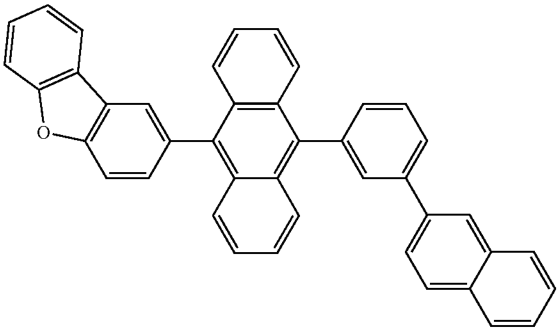
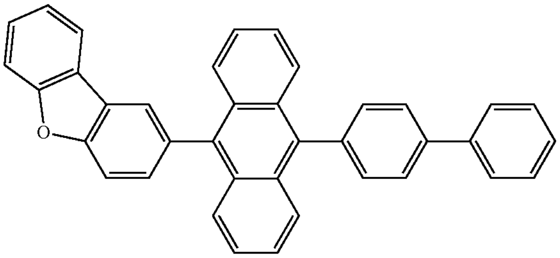
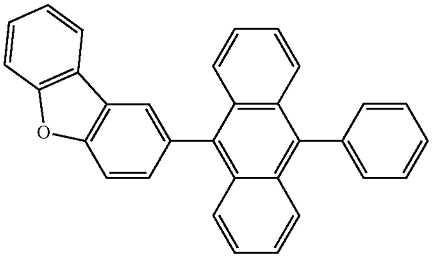
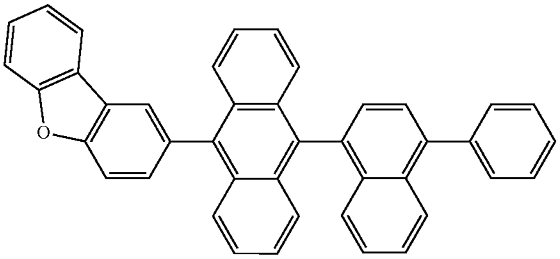
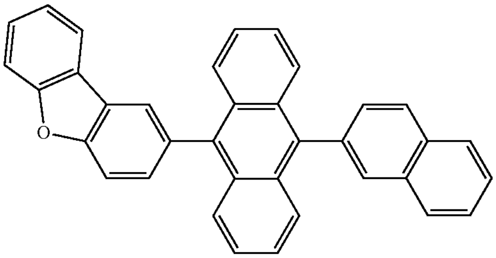
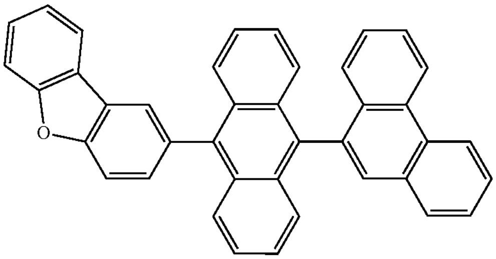

-continued
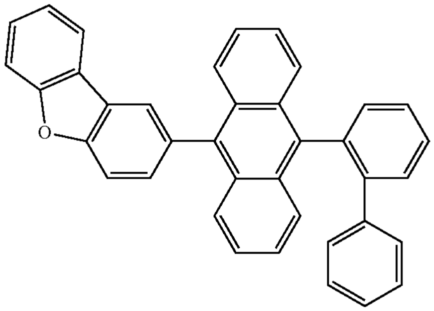
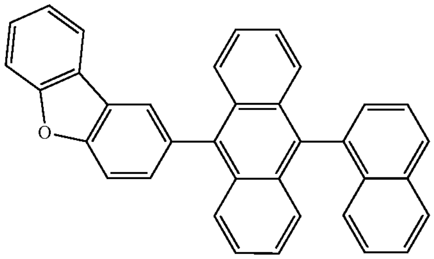
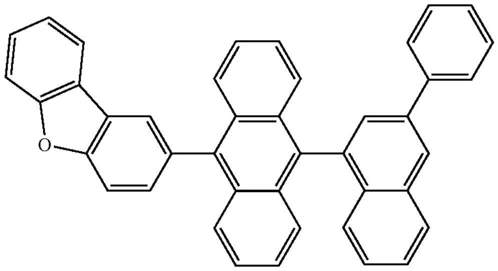
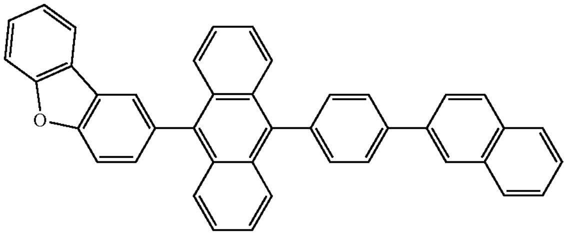
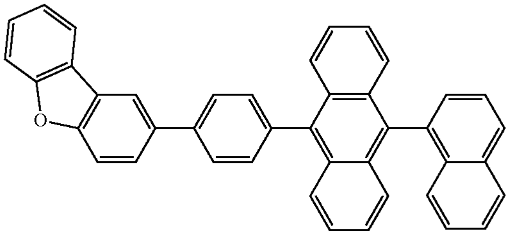
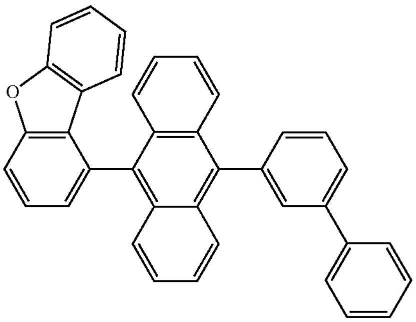
-continued
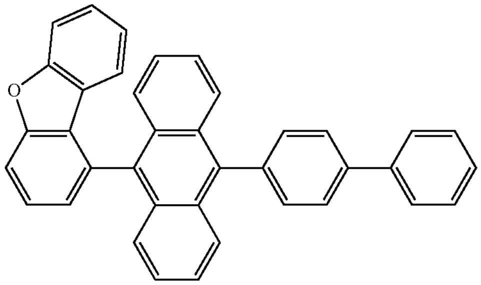
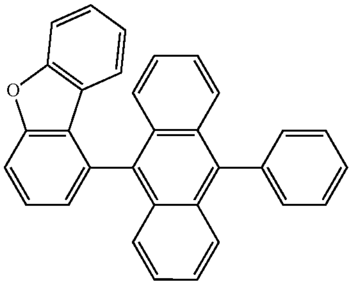
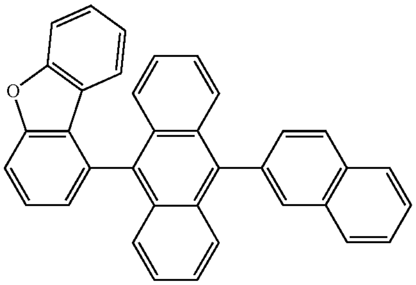
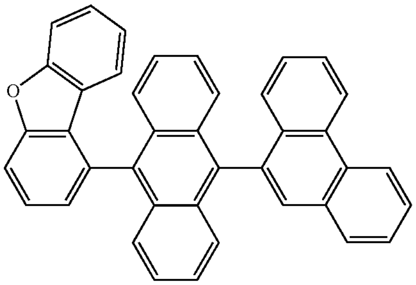
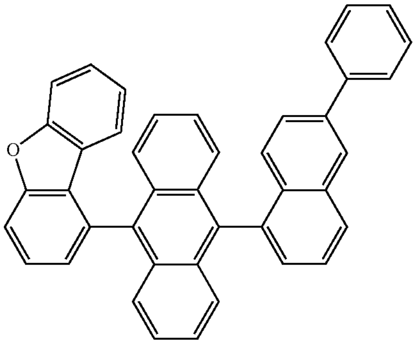

-continued
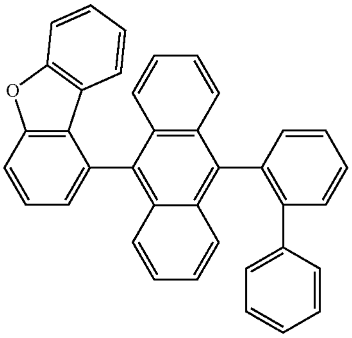
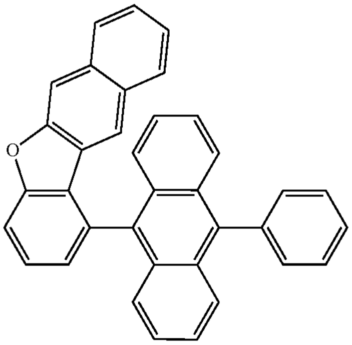
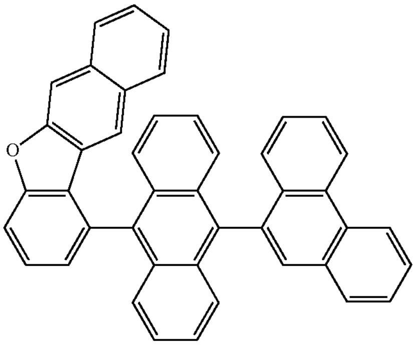
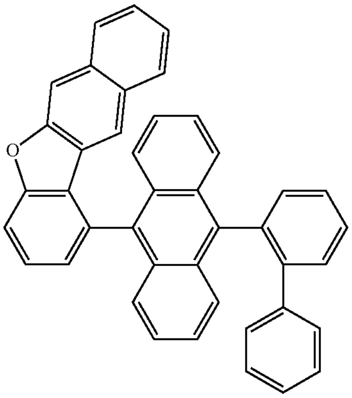
-continued
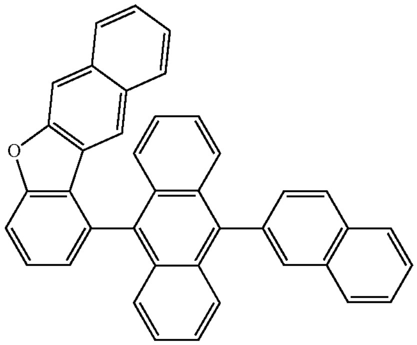
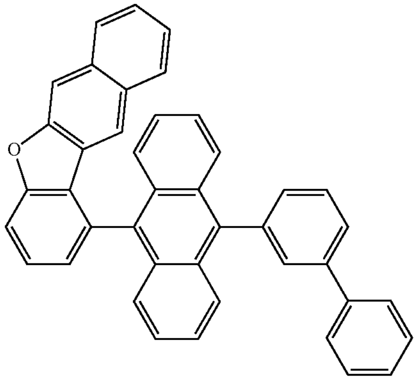
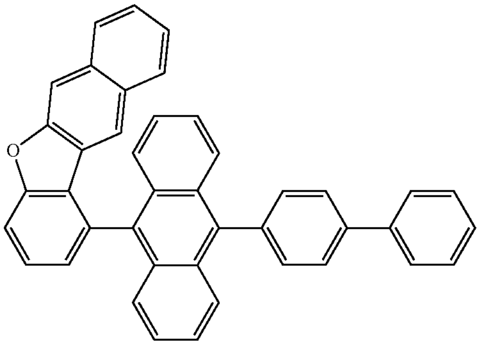
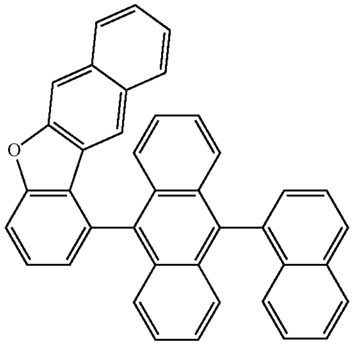

-continued
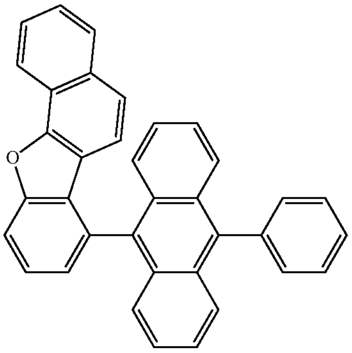
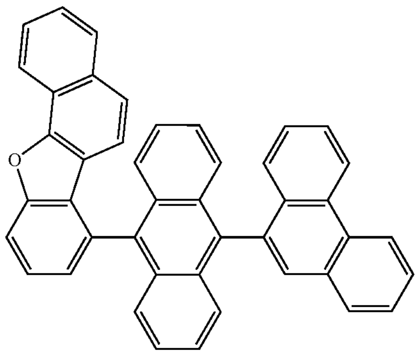
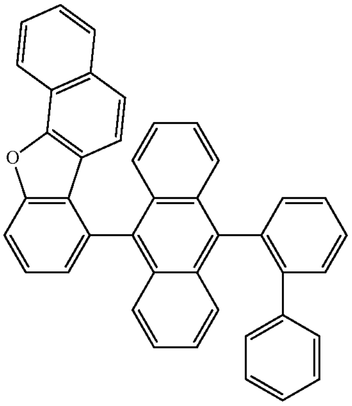
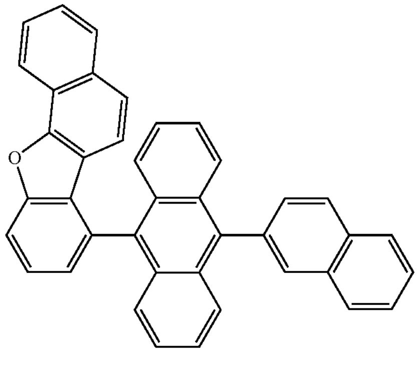
-continued
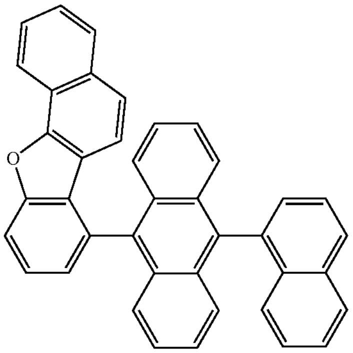
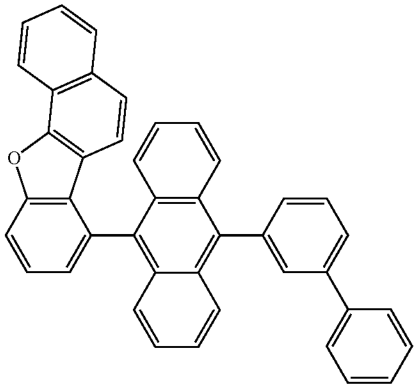
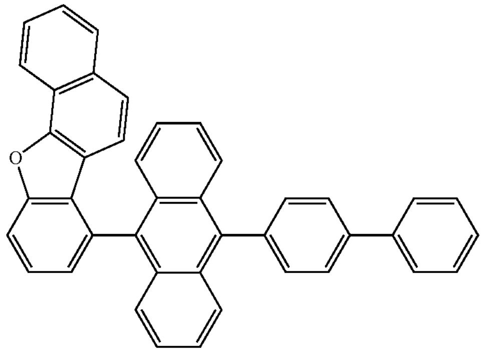
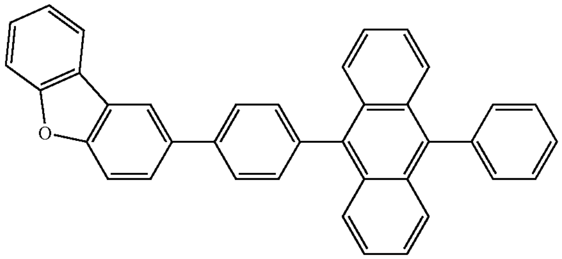
[Formula 77]
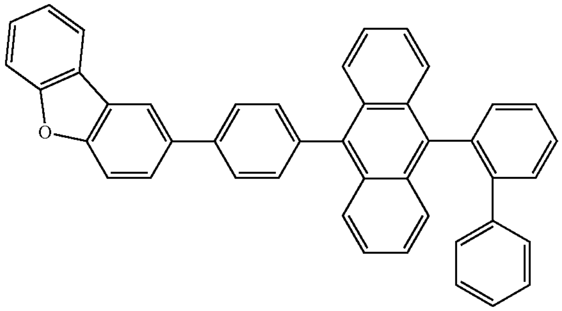

-continued
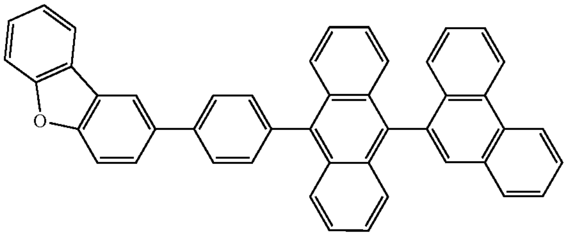
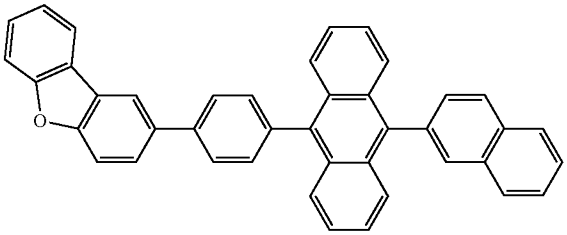
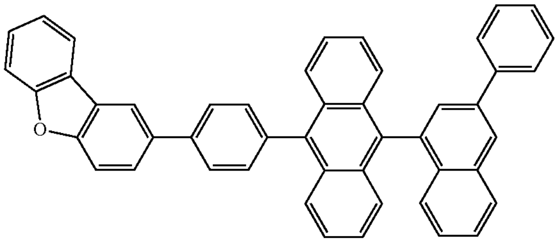
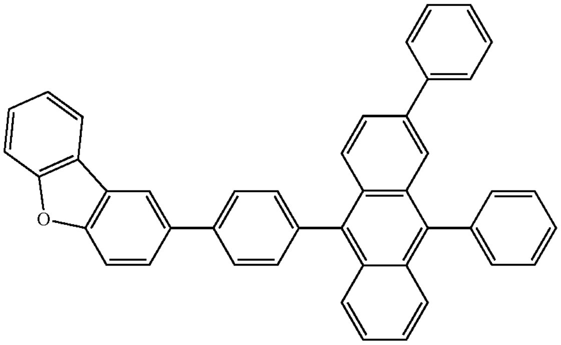
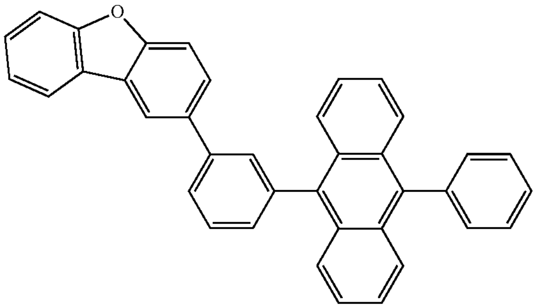
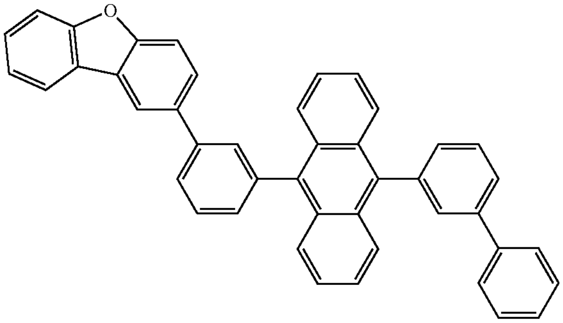
-continued
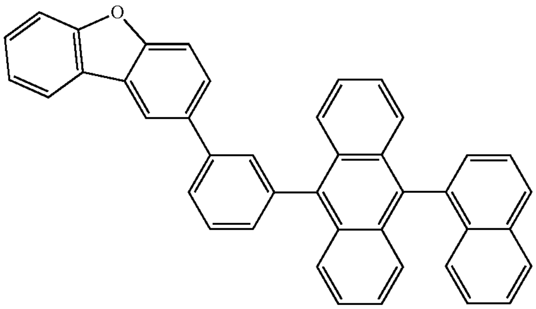
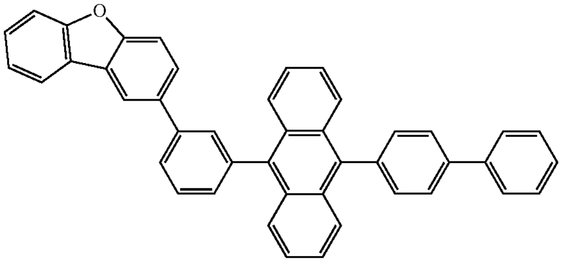
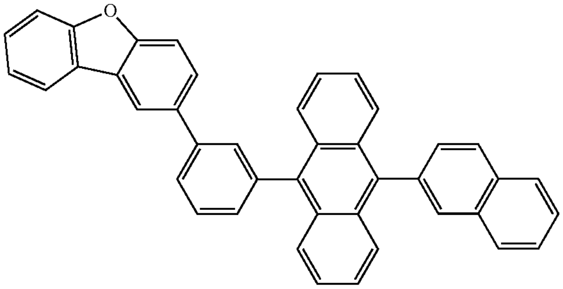
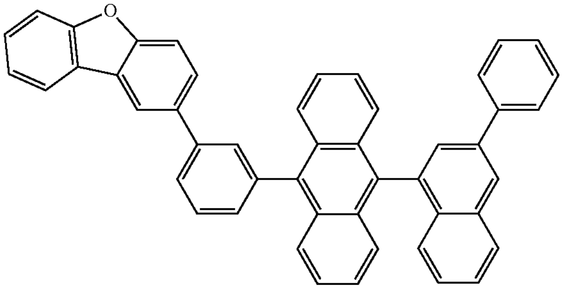
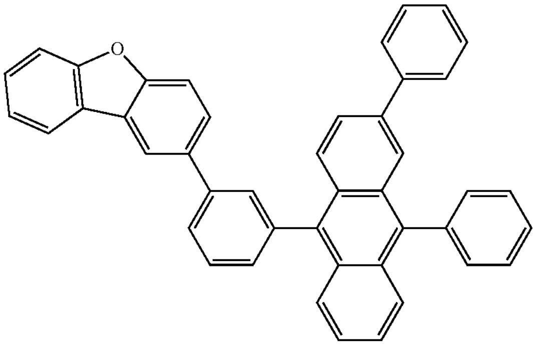

-continued
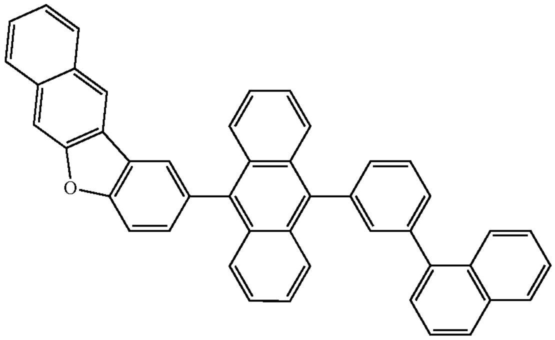
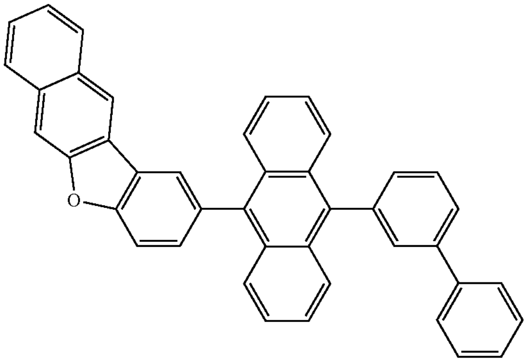
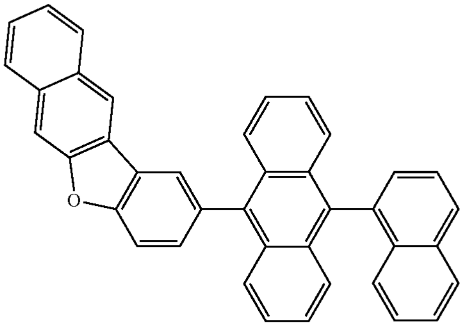
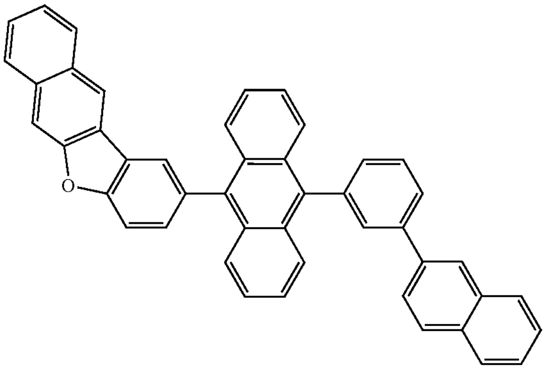
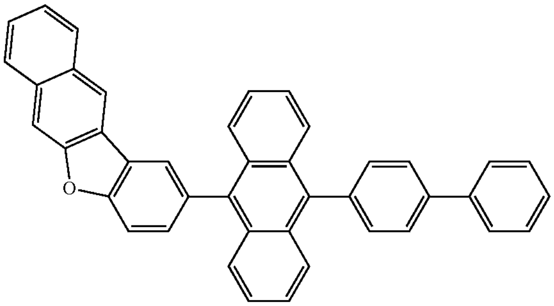
-continued
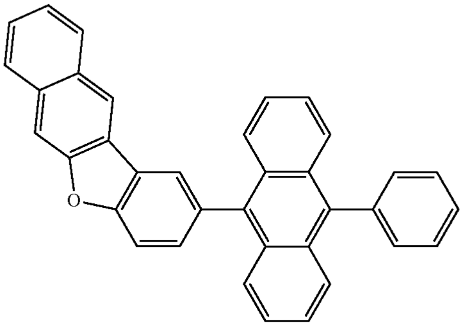
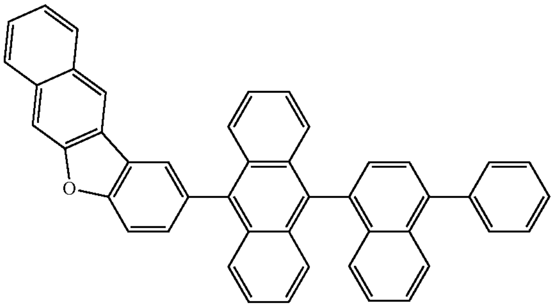
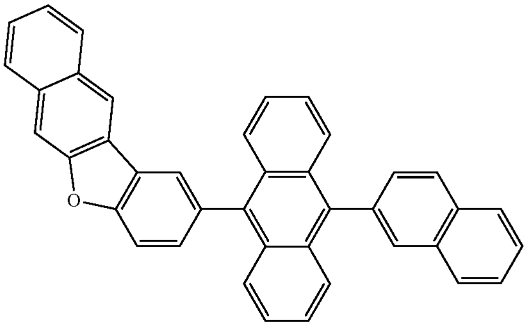
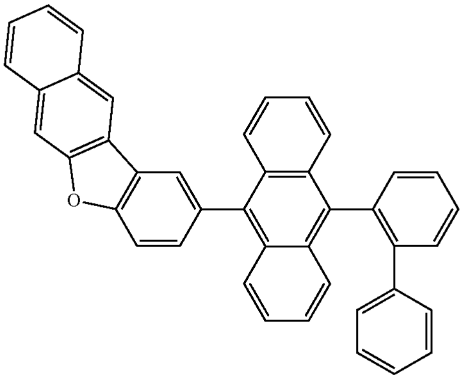
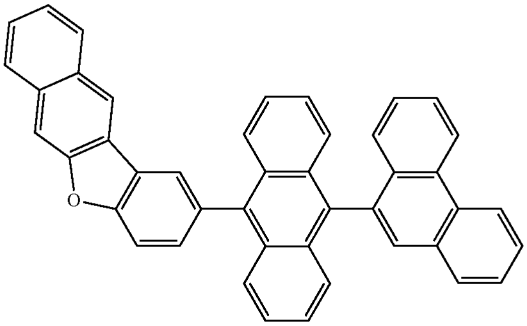

-continued
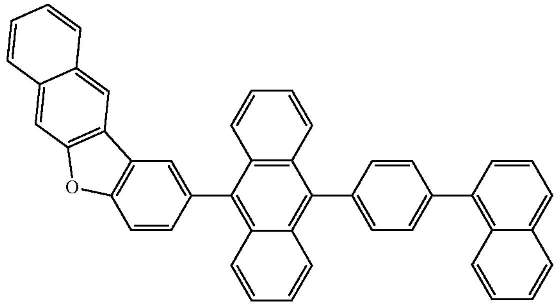
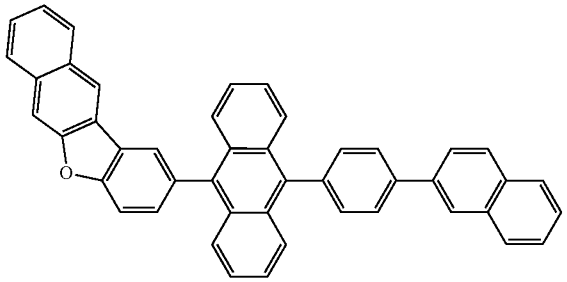
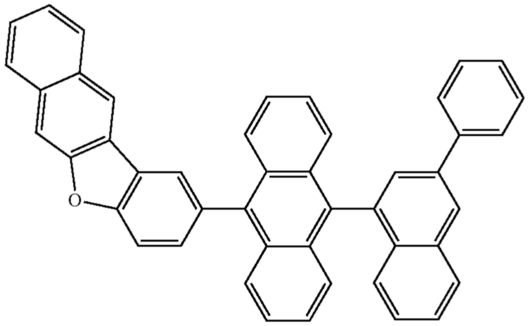
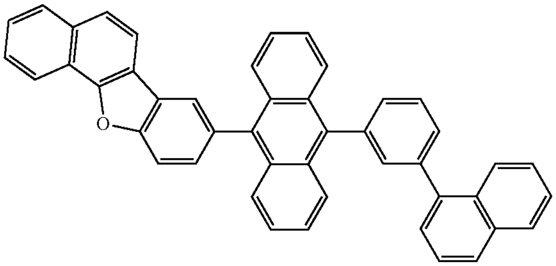
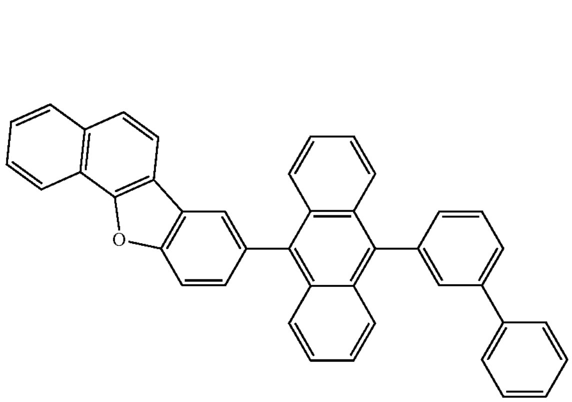
-continued
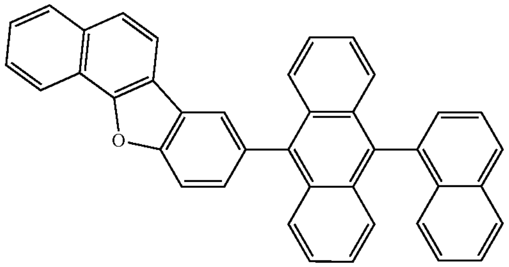
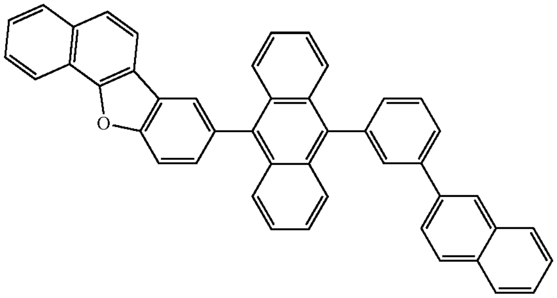
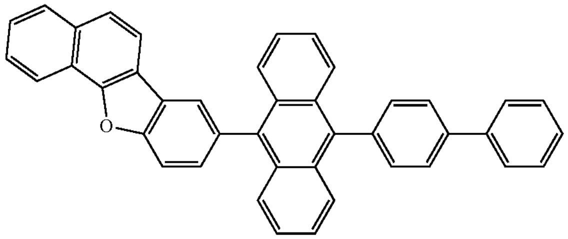
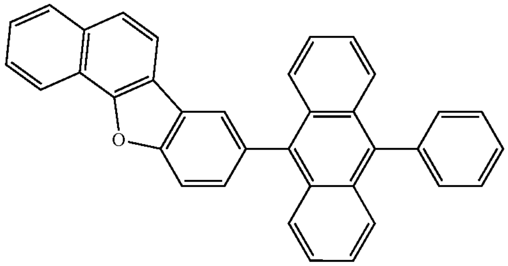
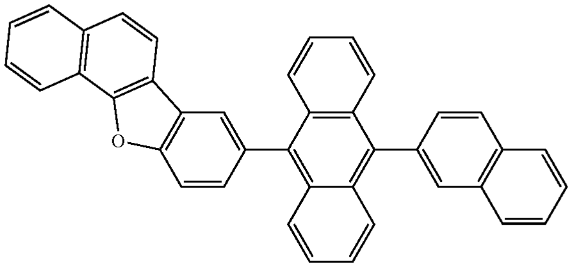
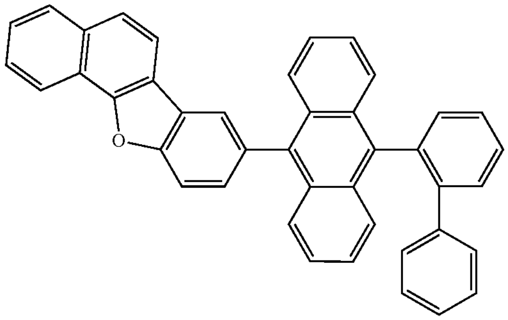

-continued
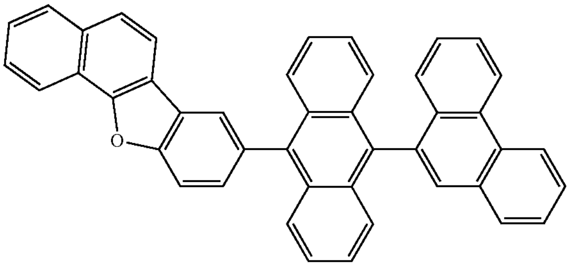
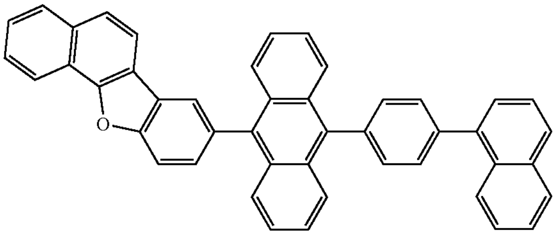
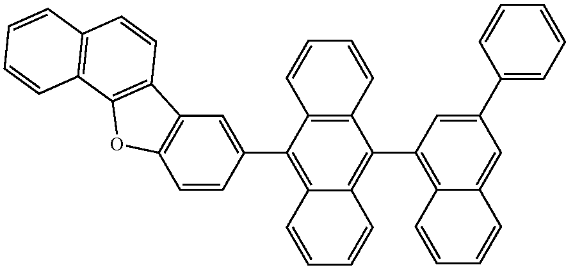
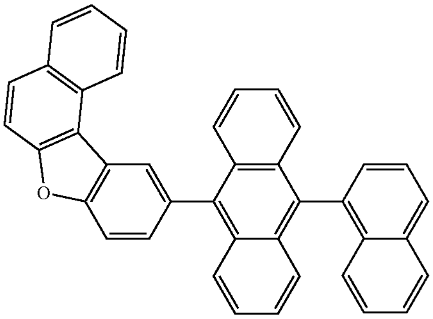
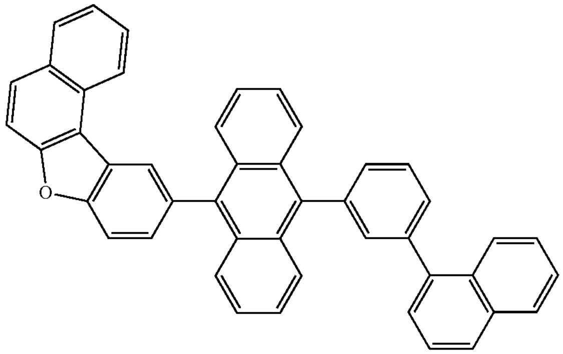
-continued
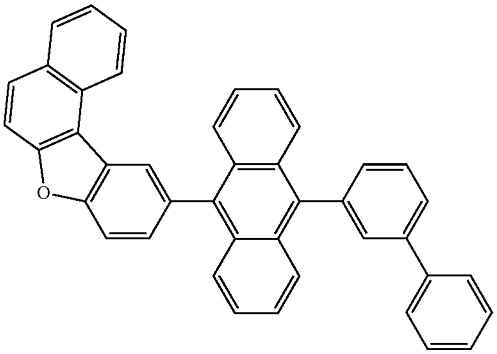
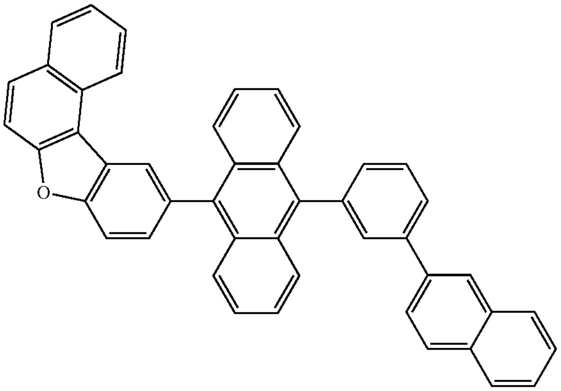
[Formula 78]
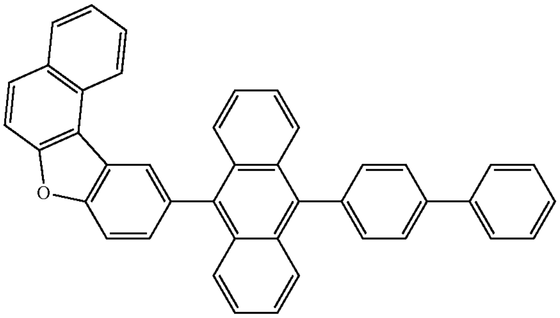
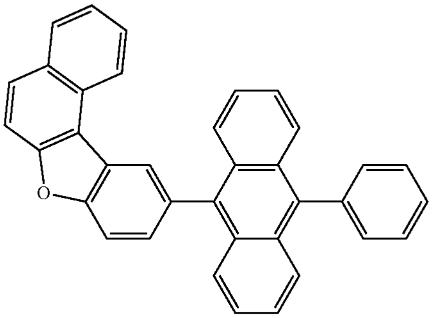

-continued
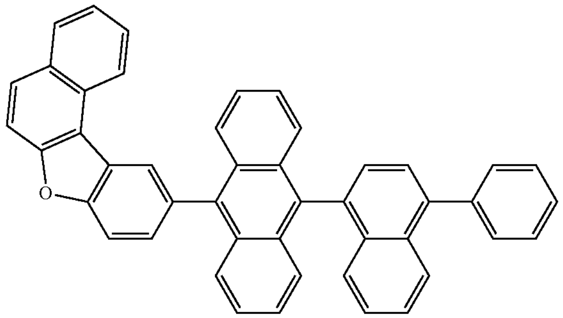
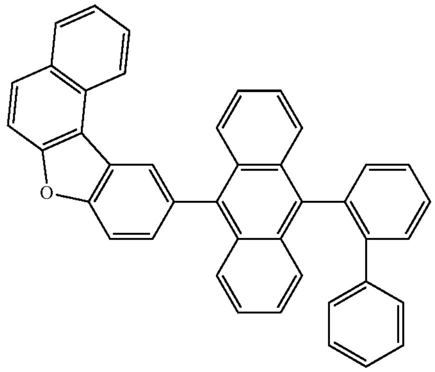
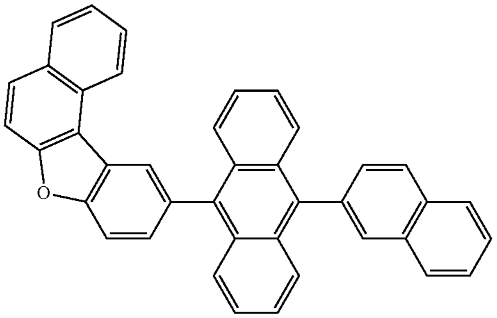
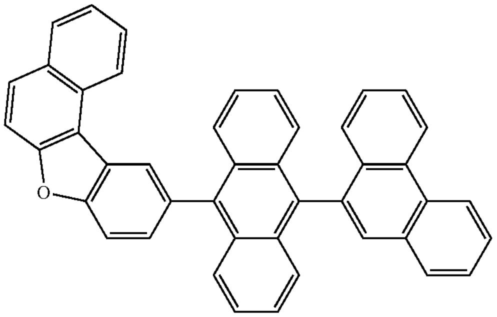
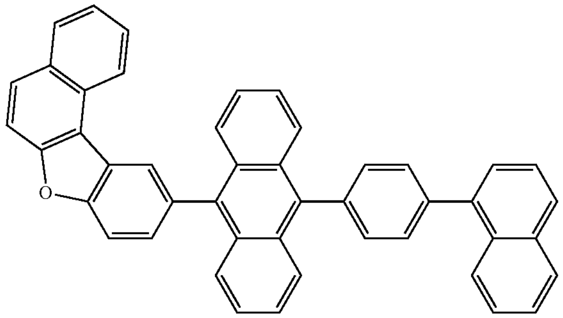
-continued
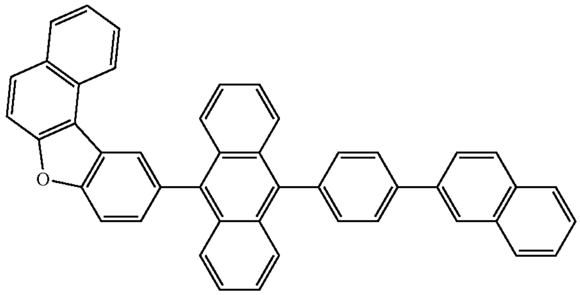
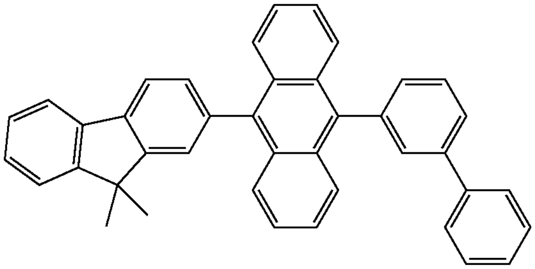
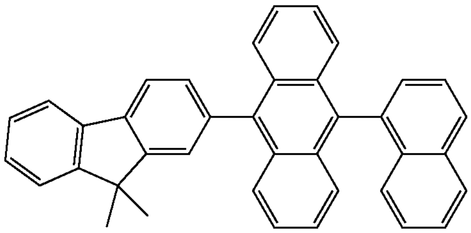
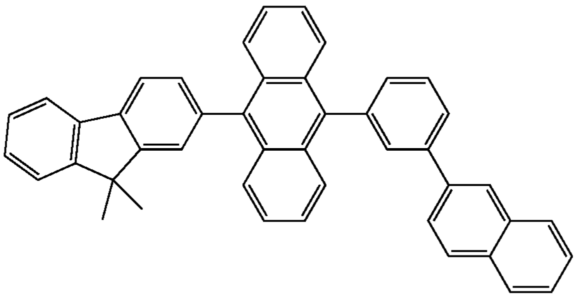
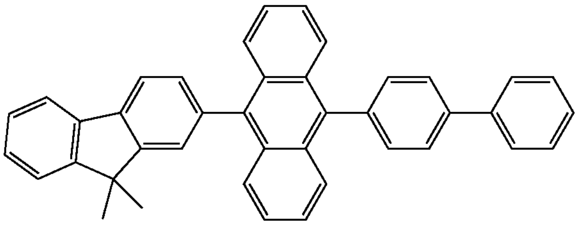
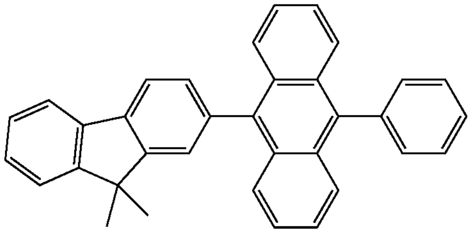

-continued
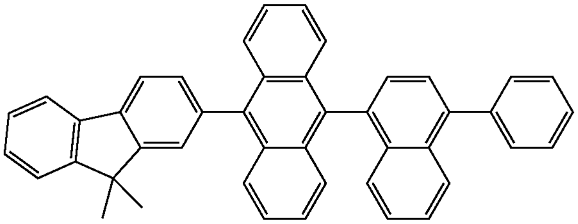
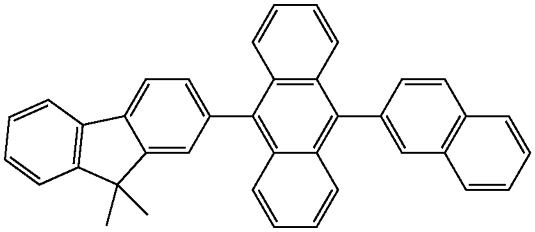
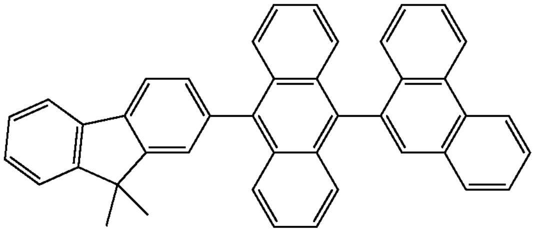
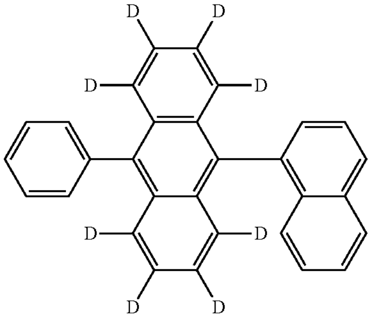
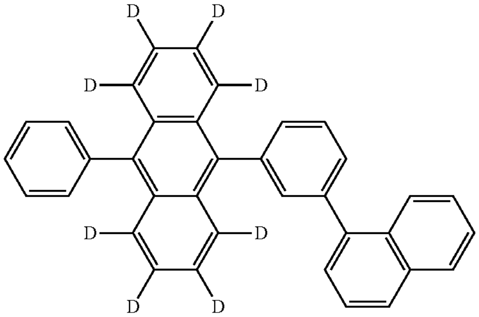
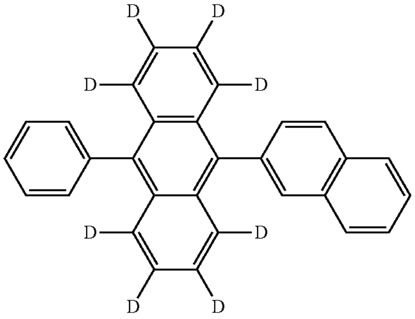
-continued
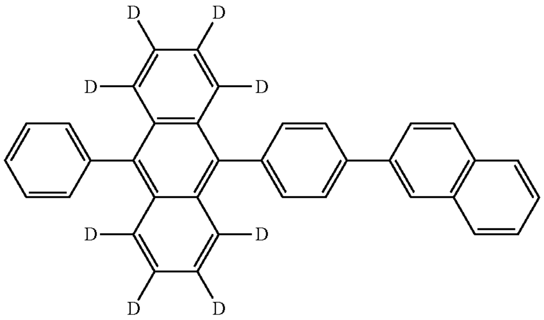
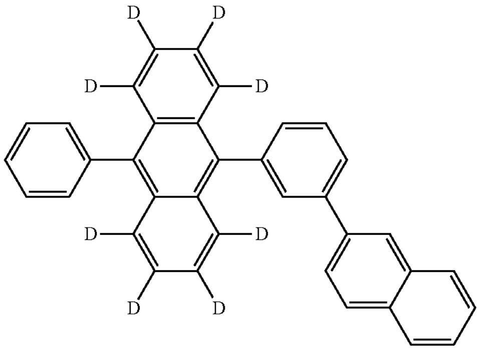
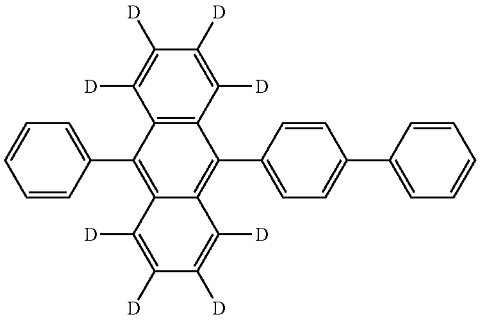
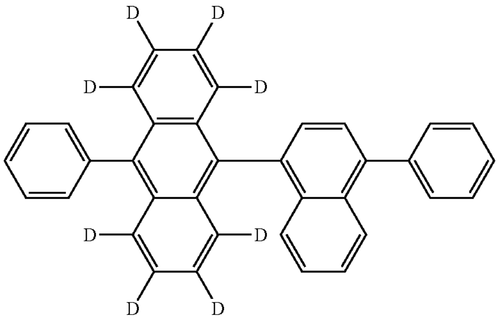
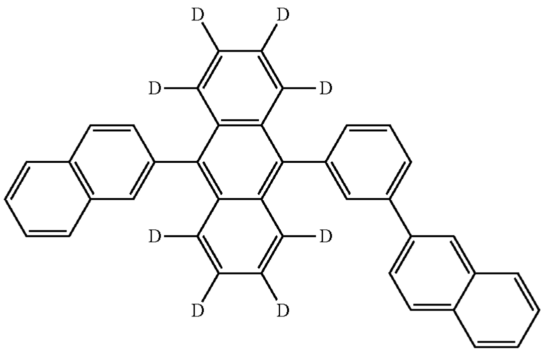

-continued
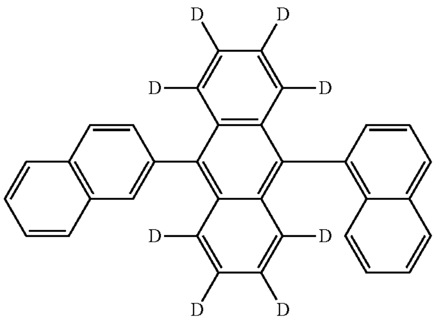
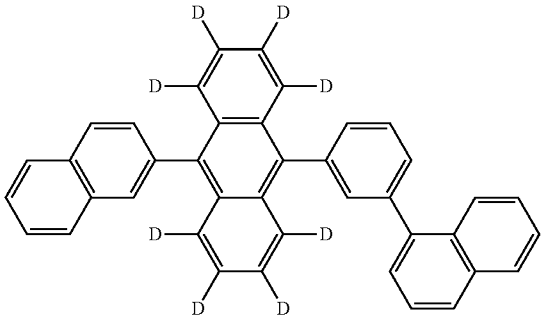
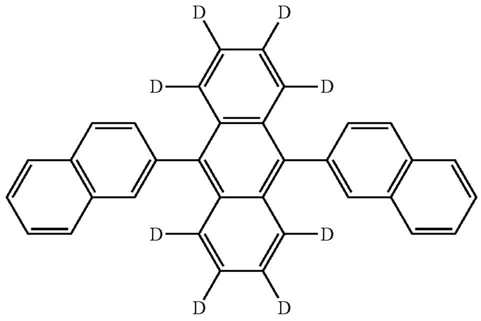
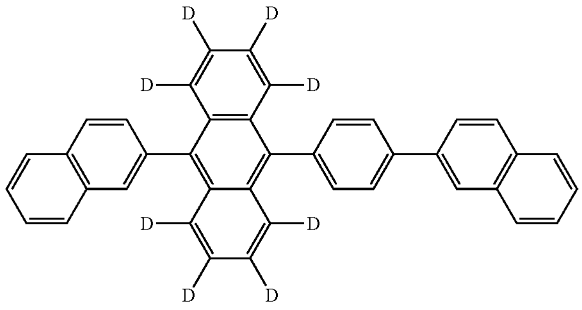
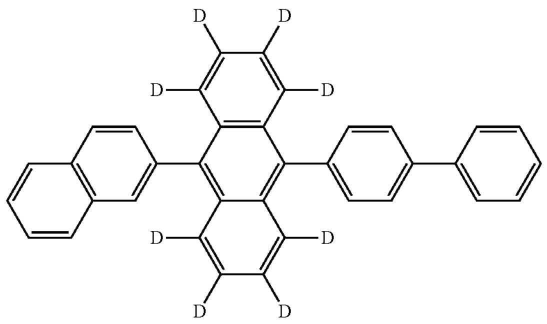
-continued
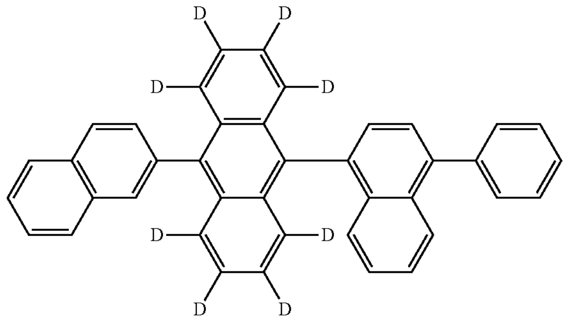
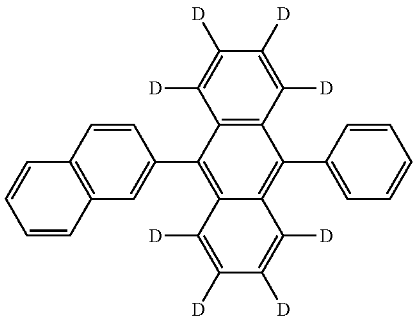
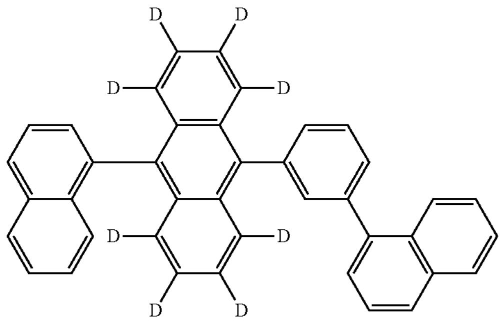
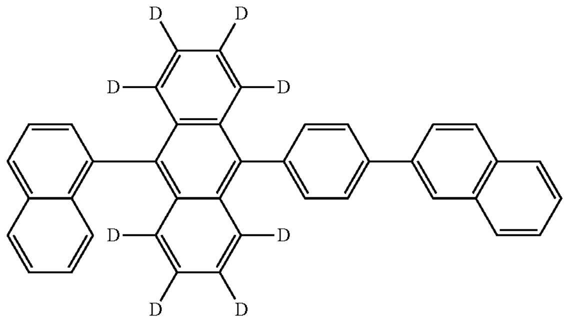
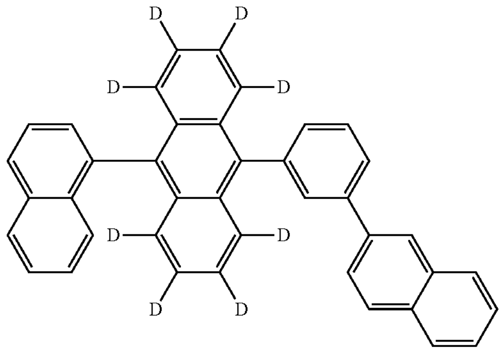

-continued
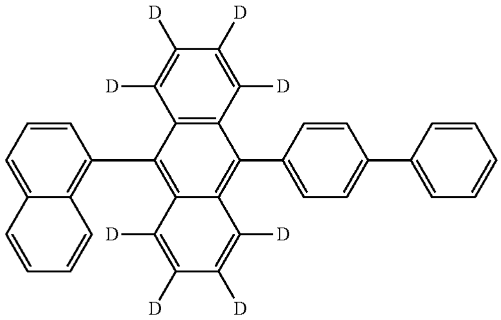
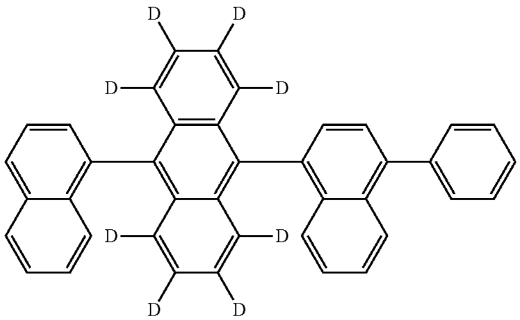
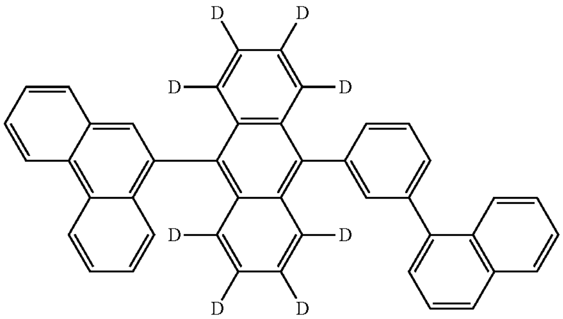
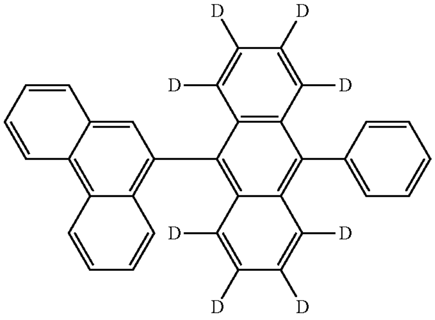
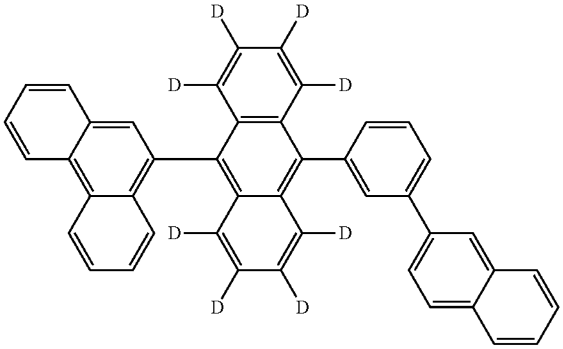
-continued
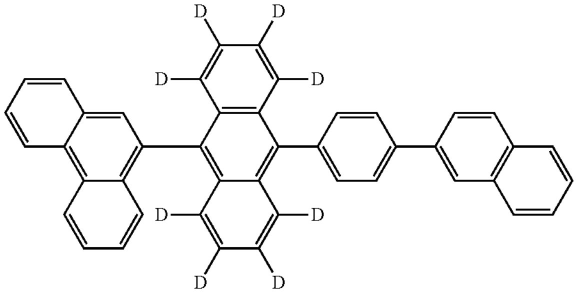
[Formula 79]
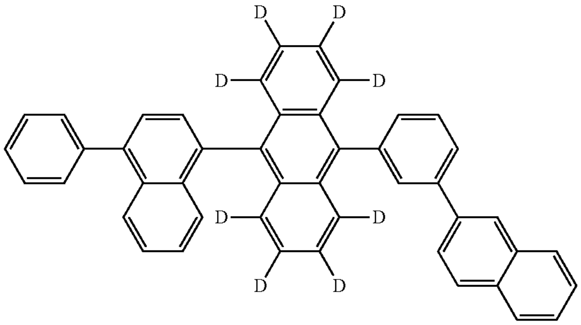
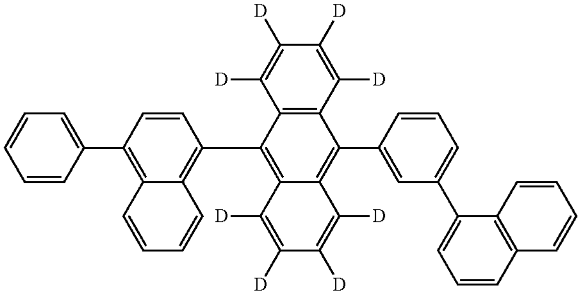
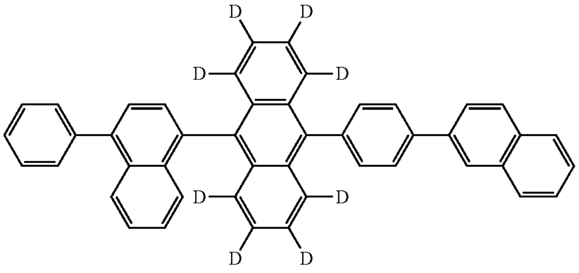
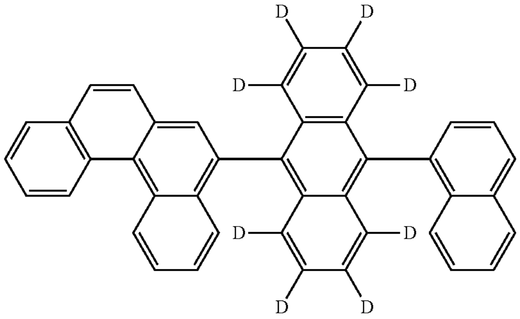

-continued
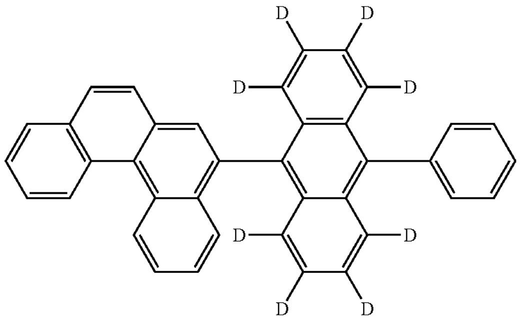
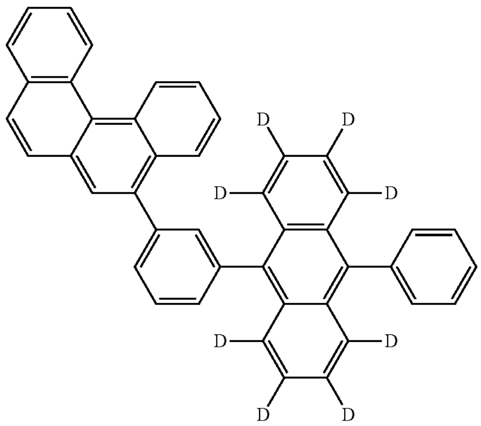
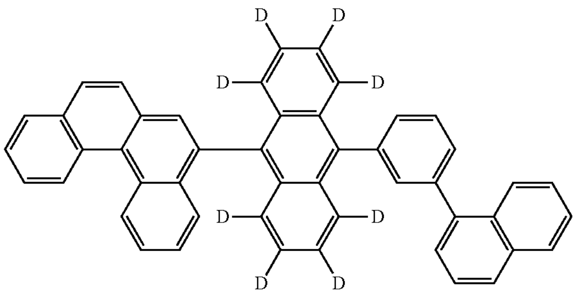
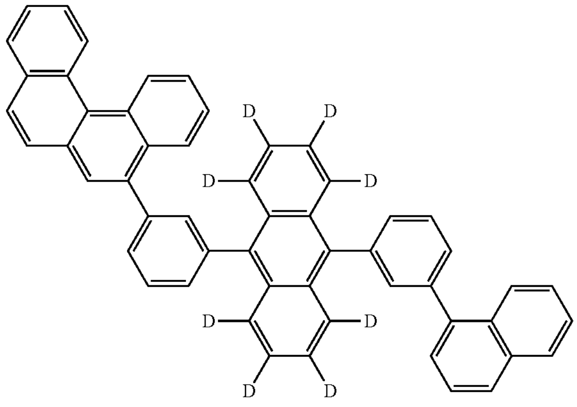
-continued
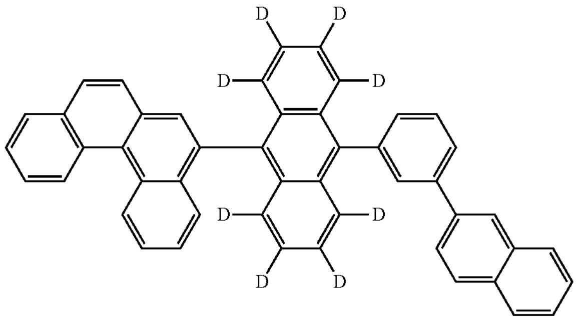
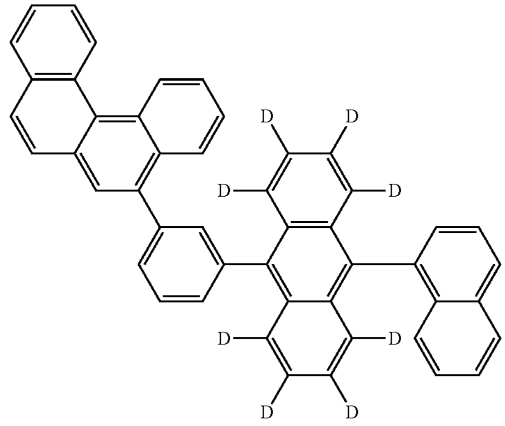
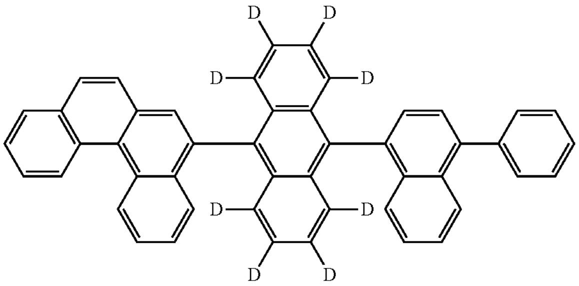
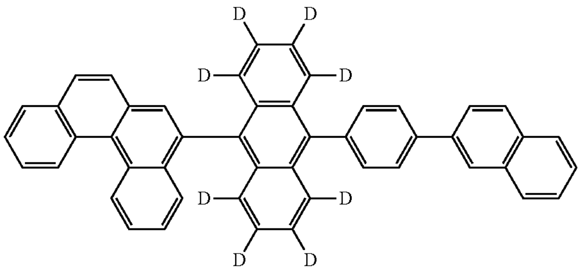
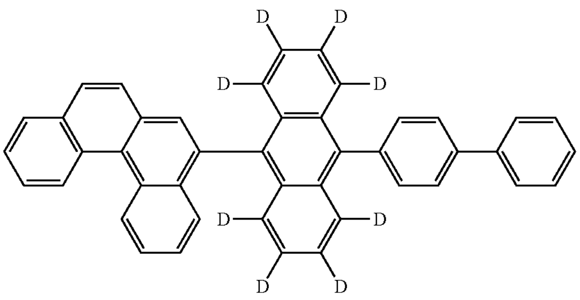

-continued
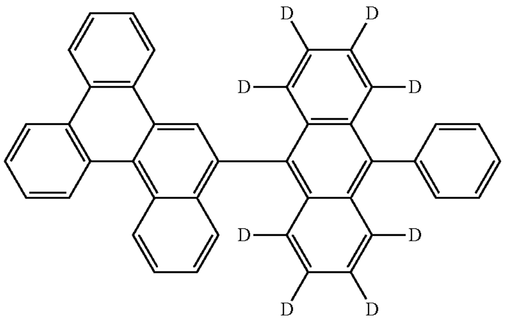
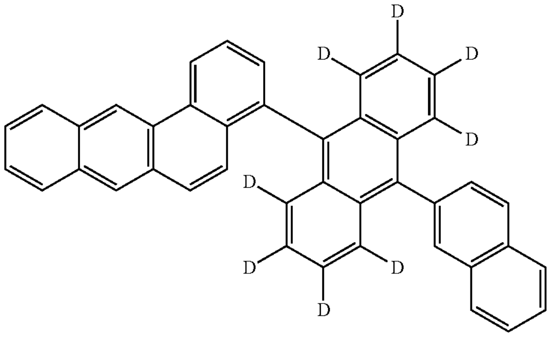
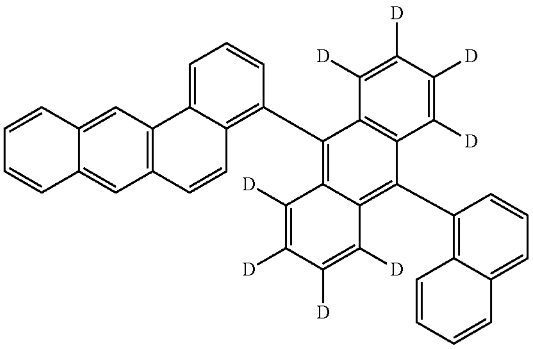
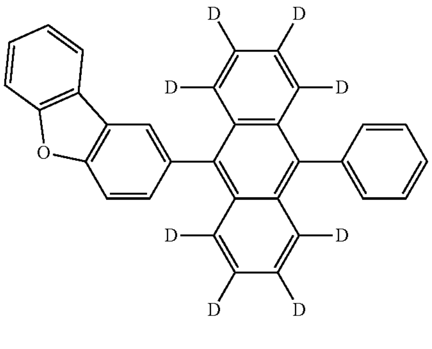
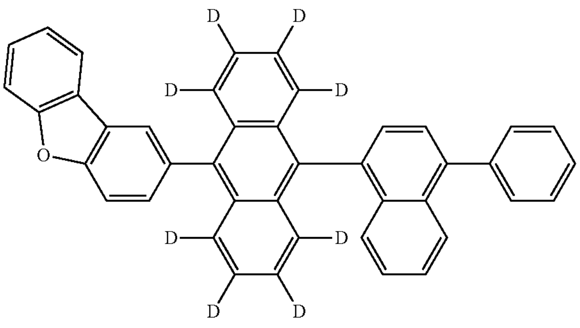
-continued
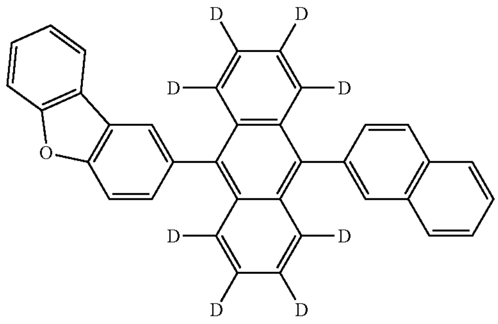
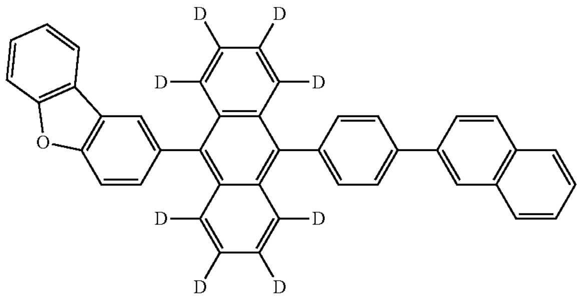
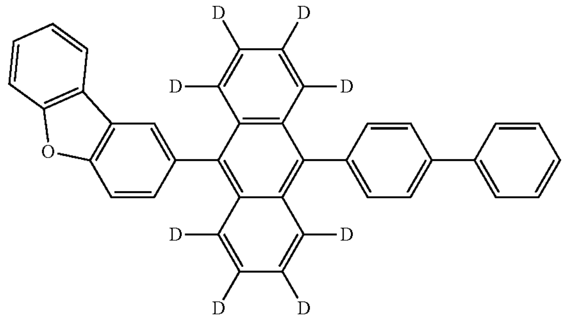
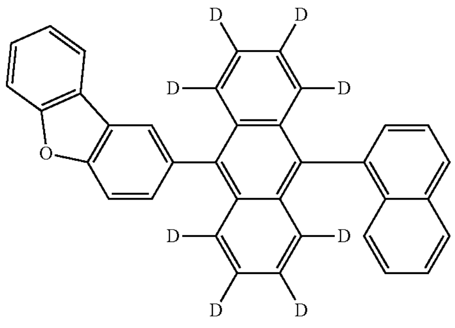
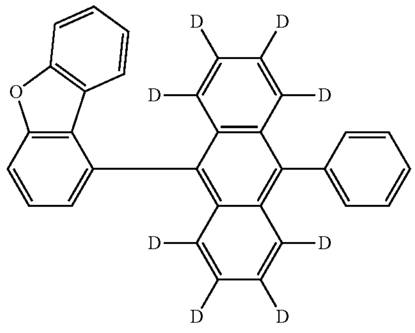

-continued
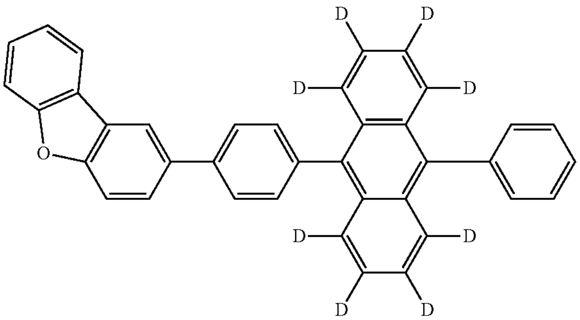
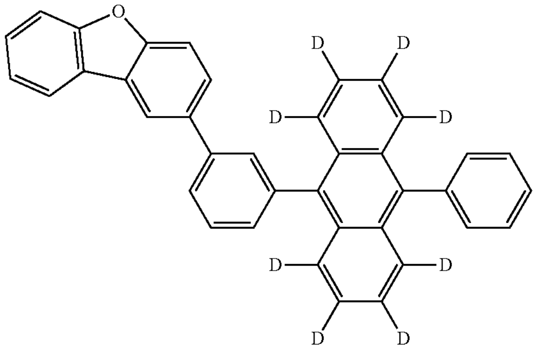
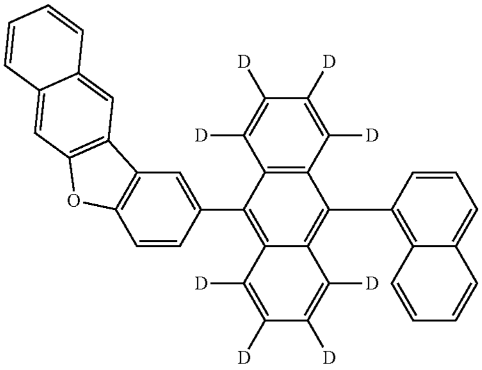
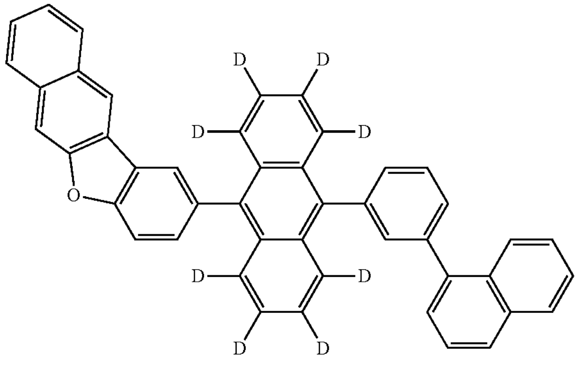
-continued
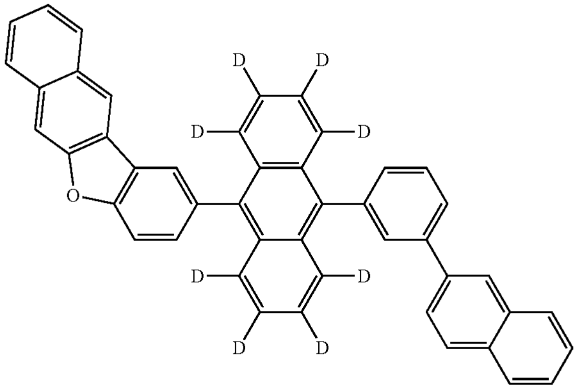
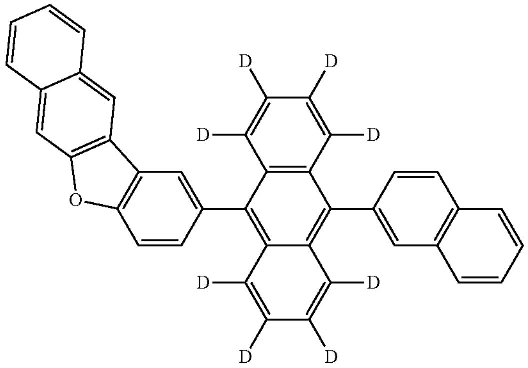
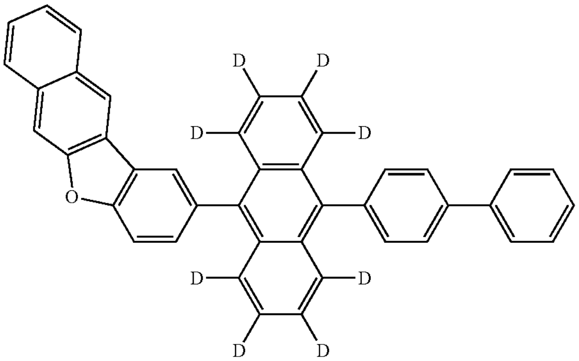
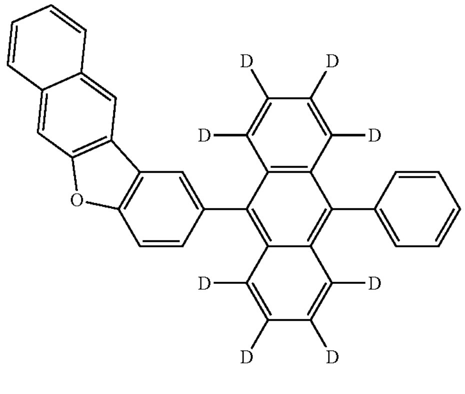

-continued
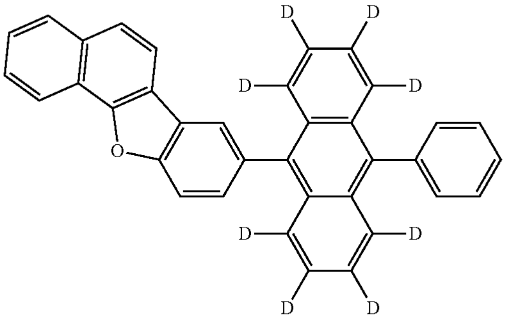
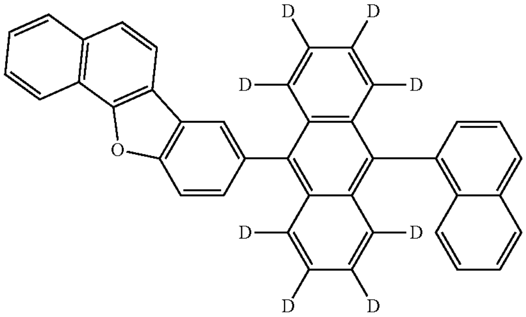
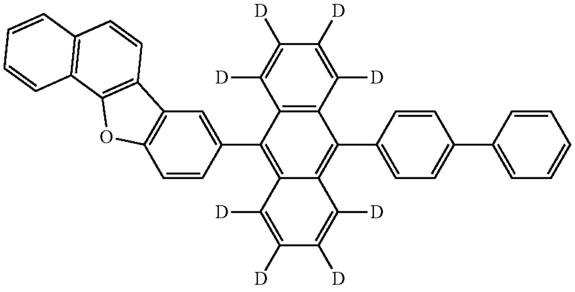
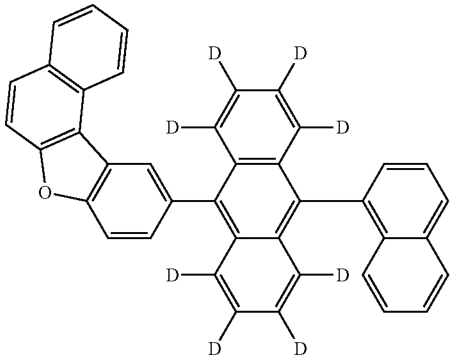
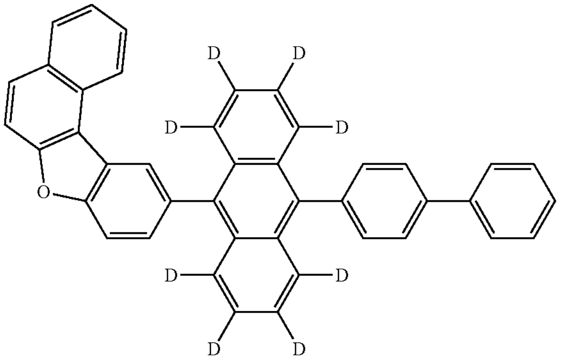
-continued
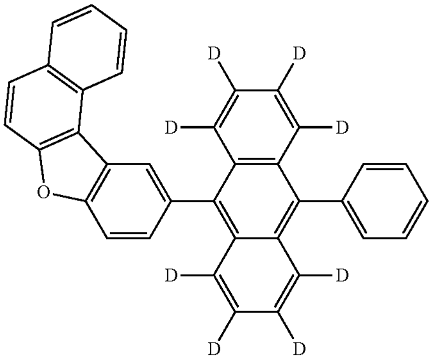
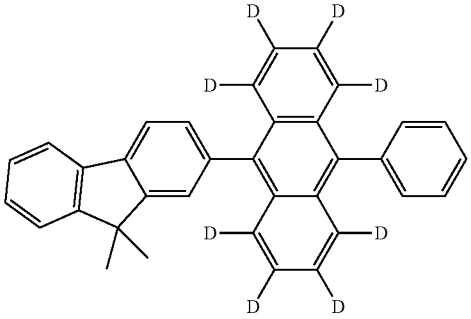
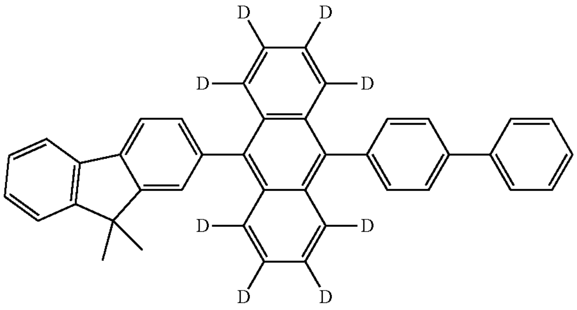
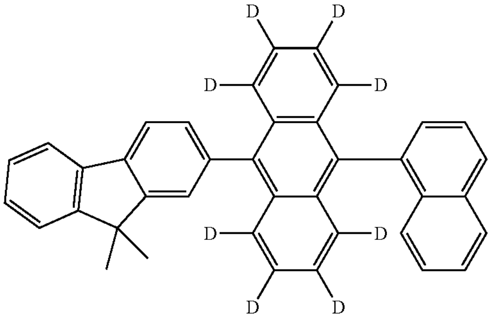
[Formula 80]
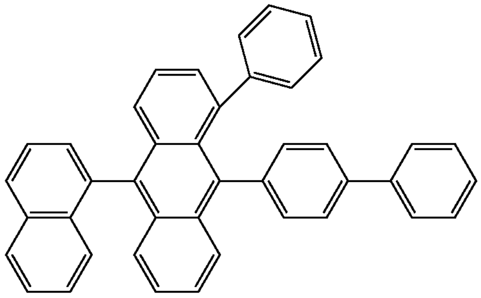

-continued
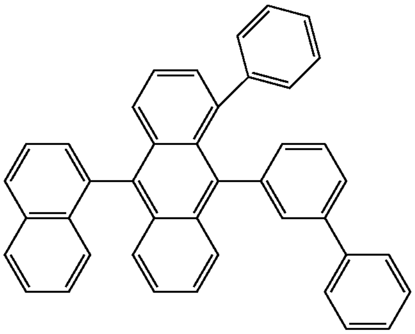
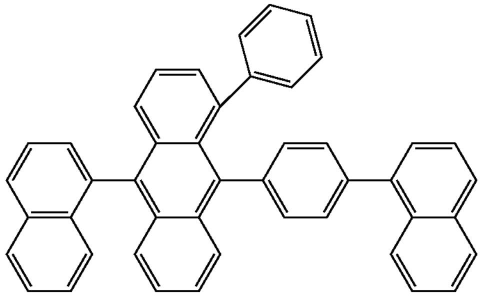
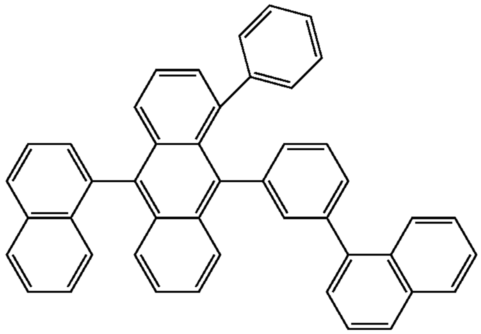
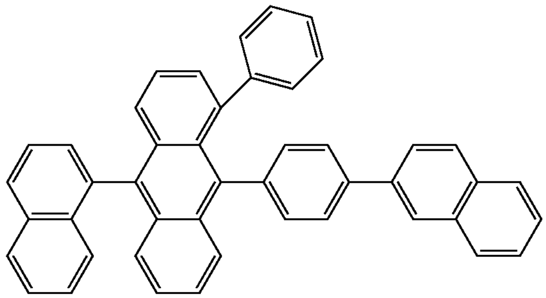
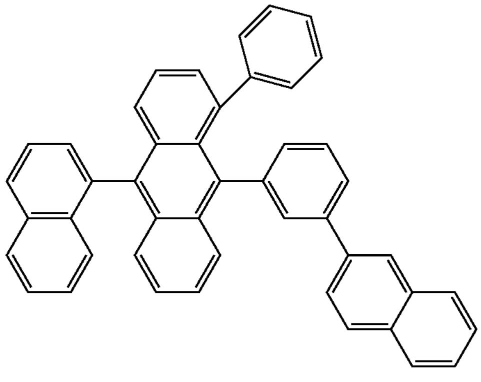
-continued
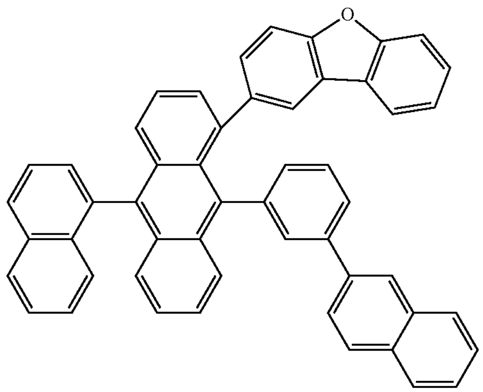
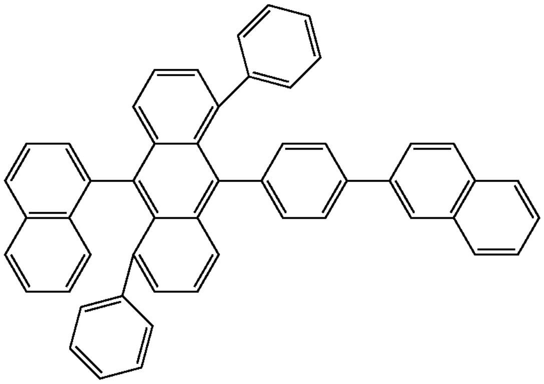
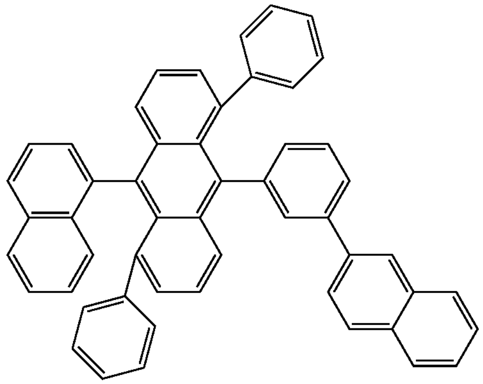
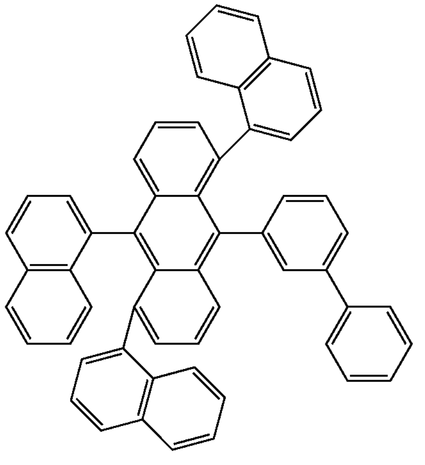

-continued
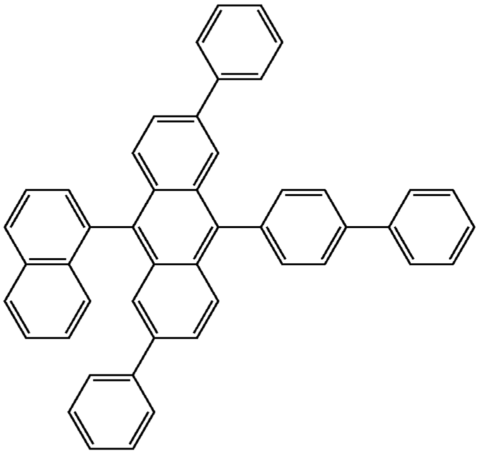
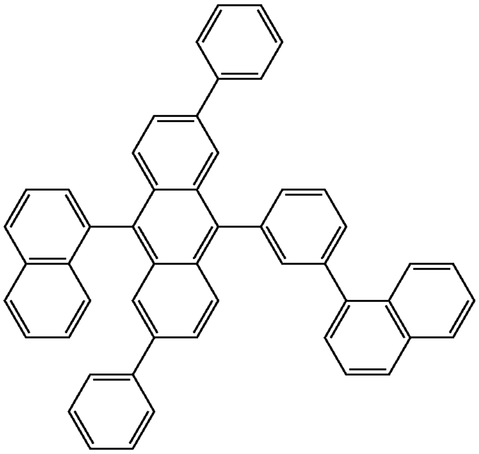
[Formula 81]
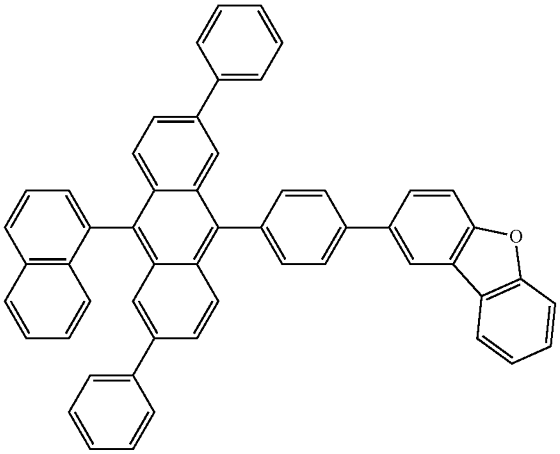
-continued
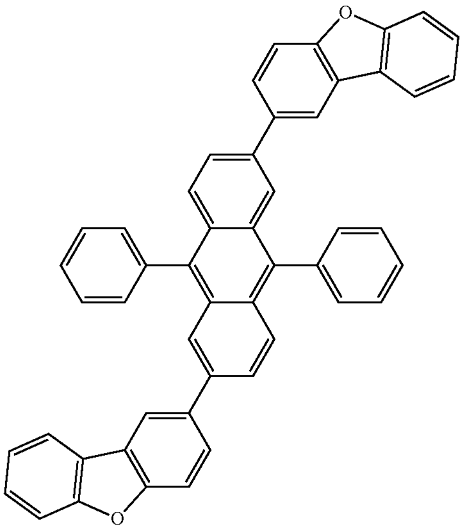
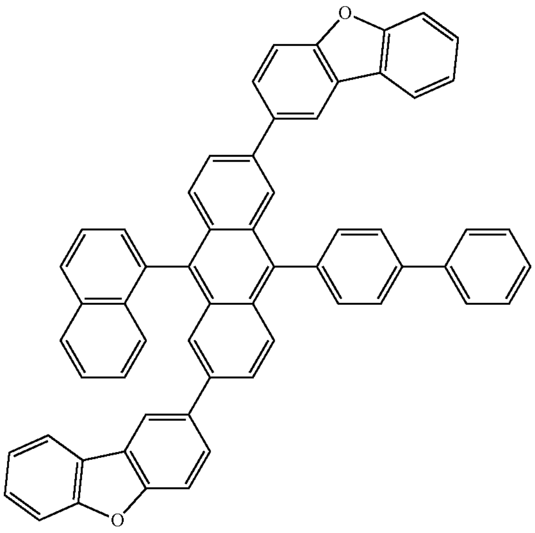
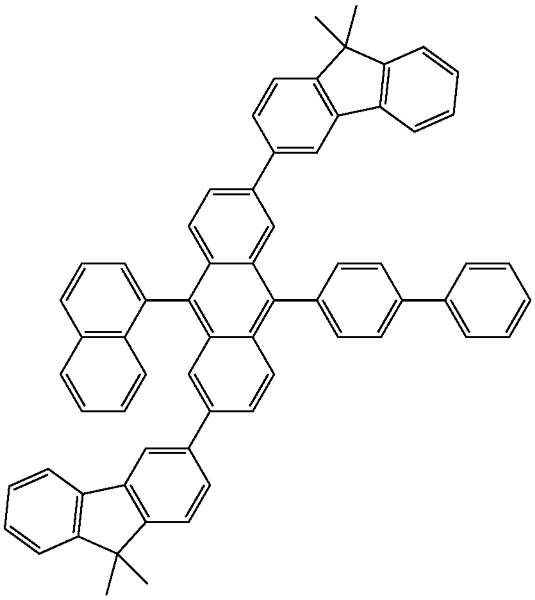

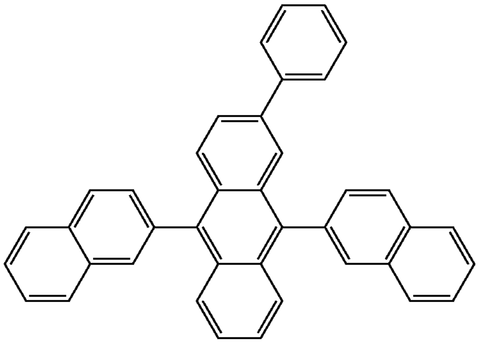
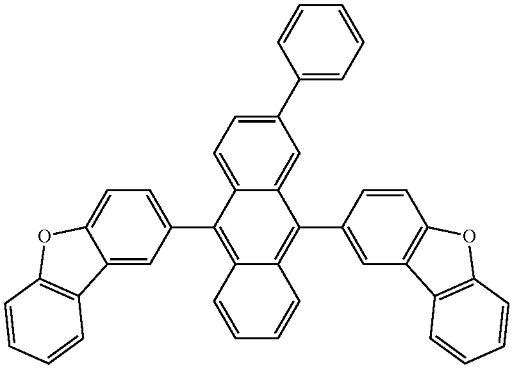
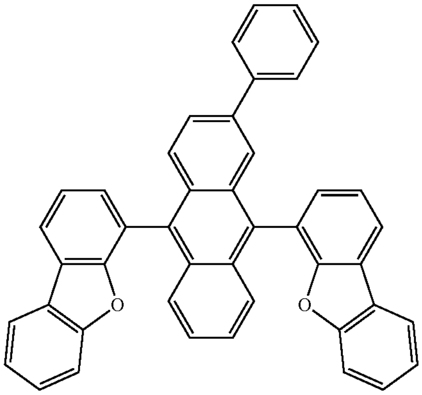
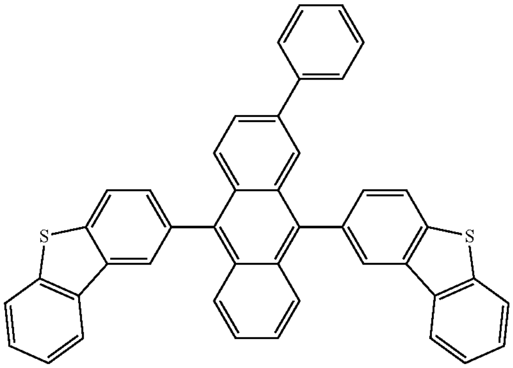
[Formula 82]
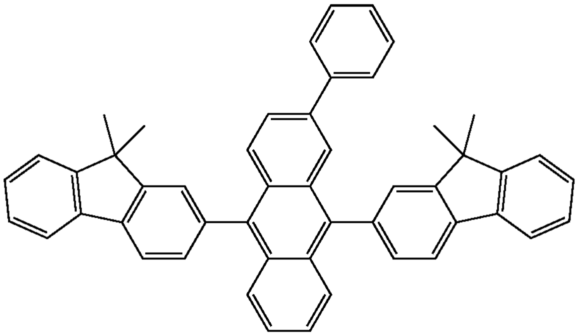
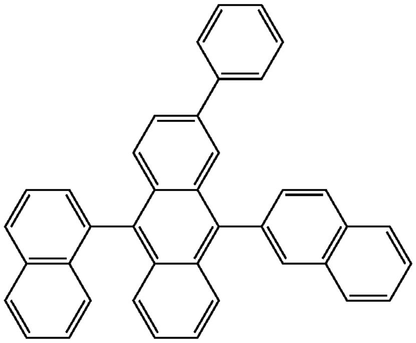
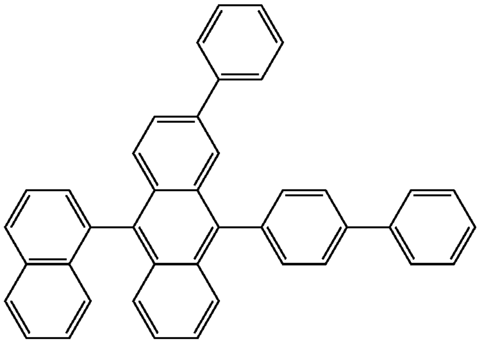
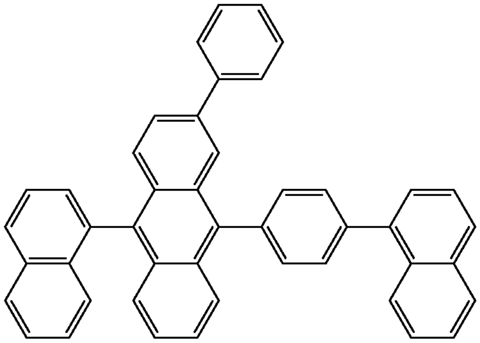

-continued
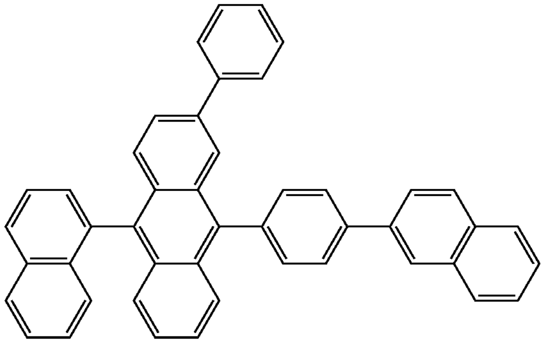
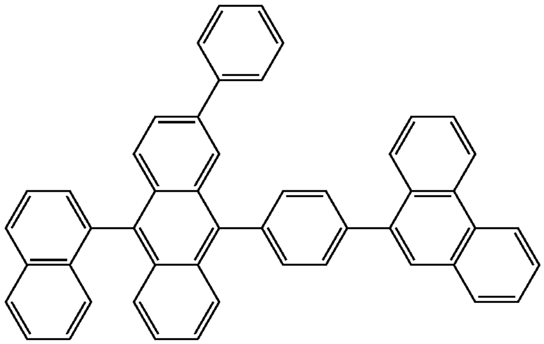
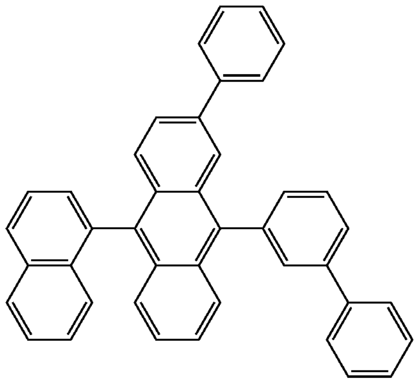
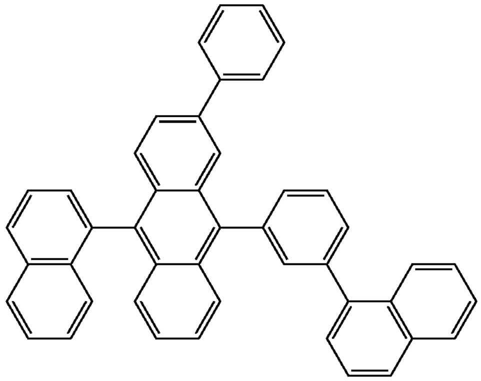
-continued
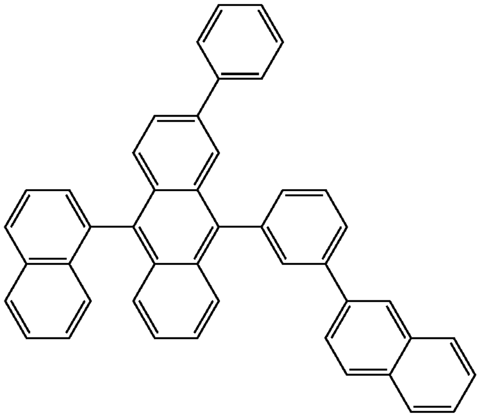
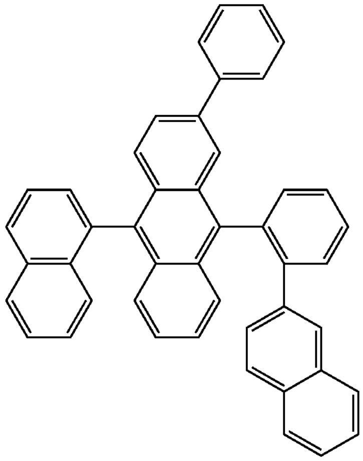
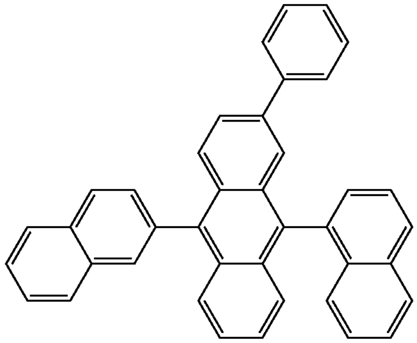
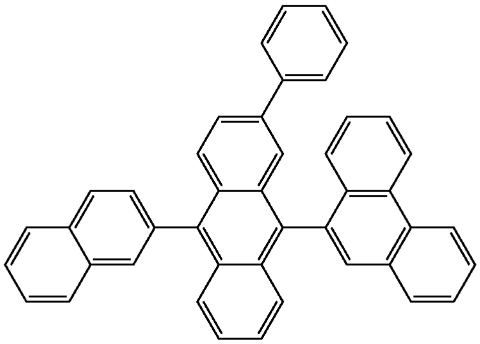

-continued
[Formula 83]
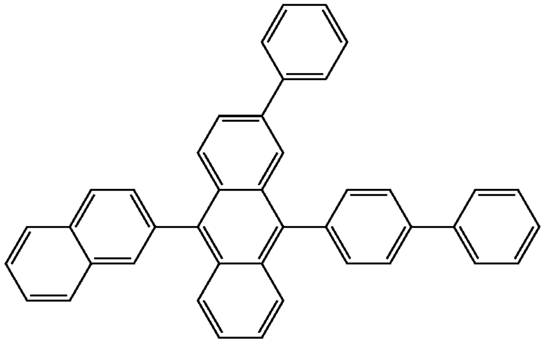
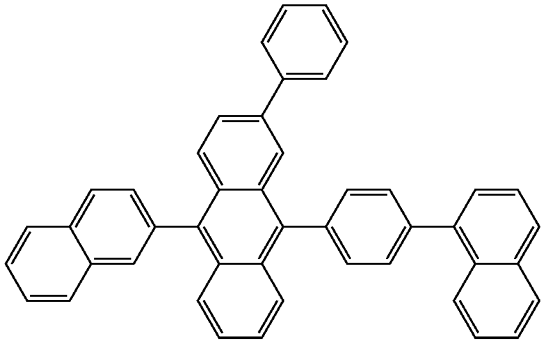
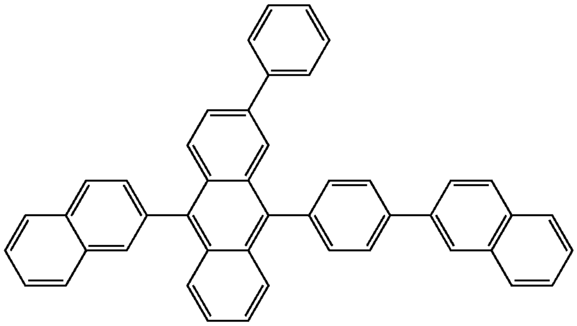
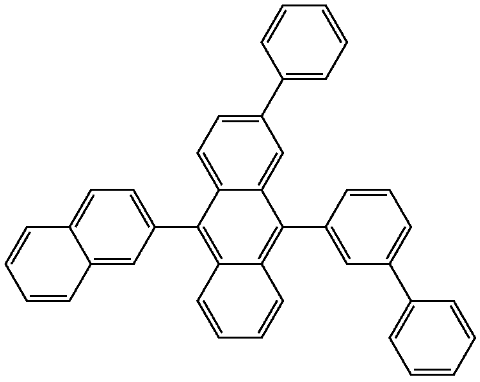
-continued
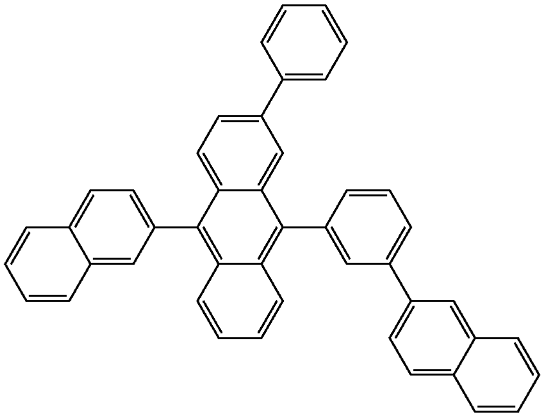
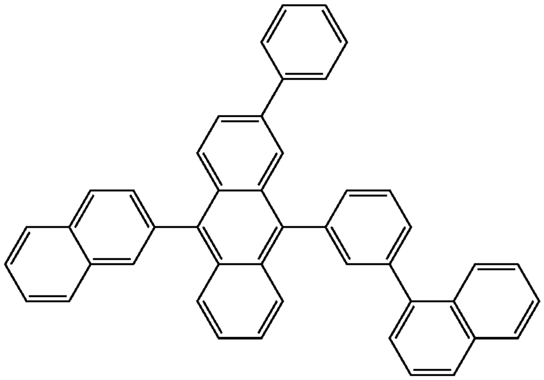
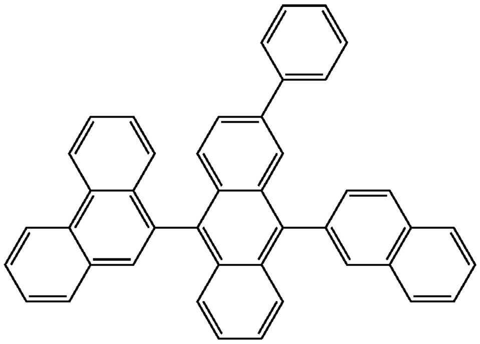
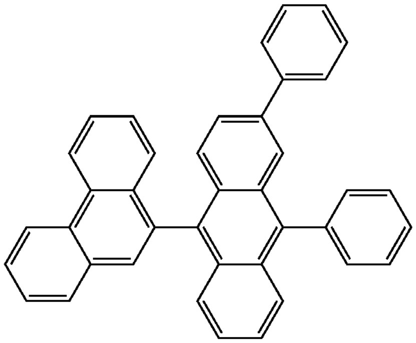

-continued
[Formula 84]
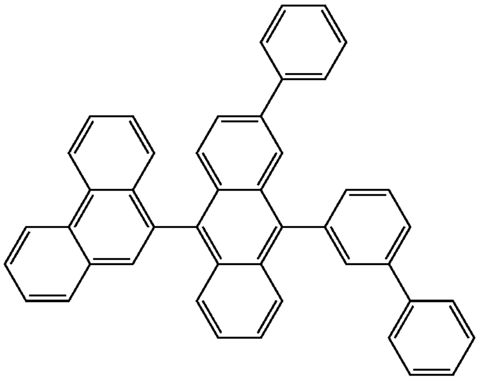
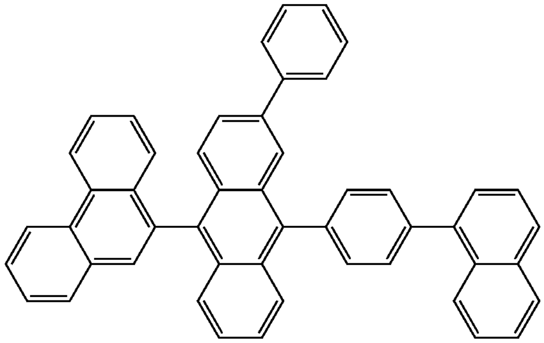
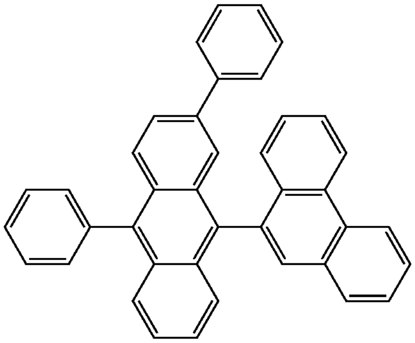
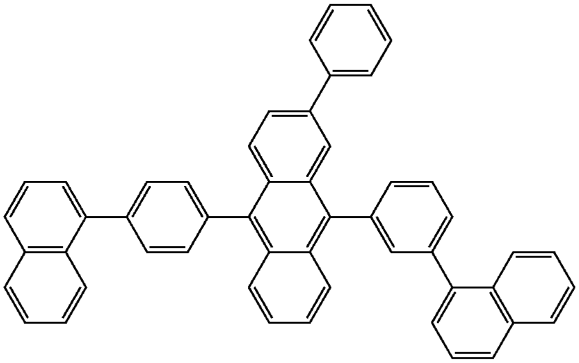
-continued
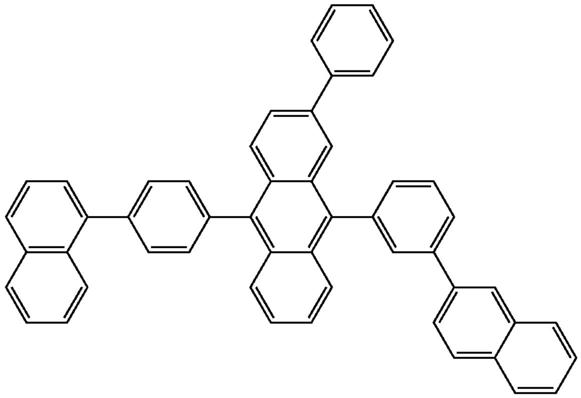
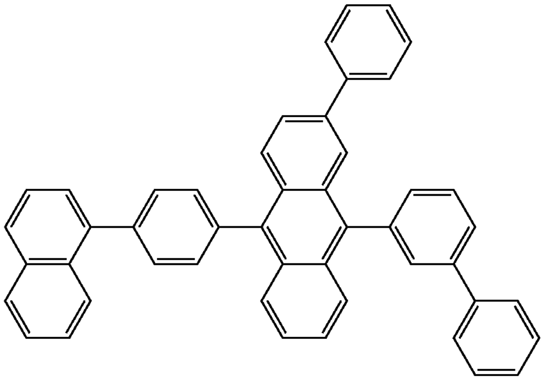
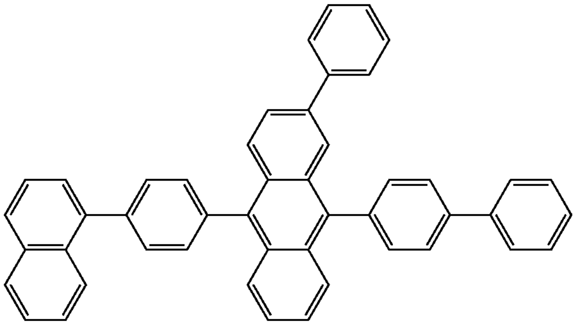
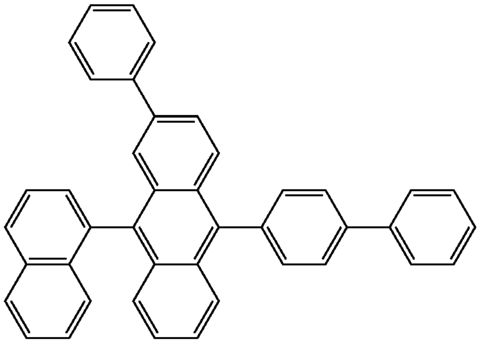

-continued
[Formula 85]
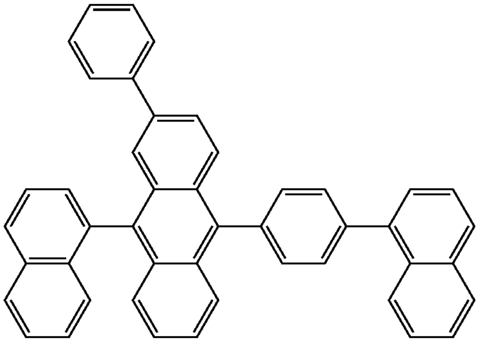
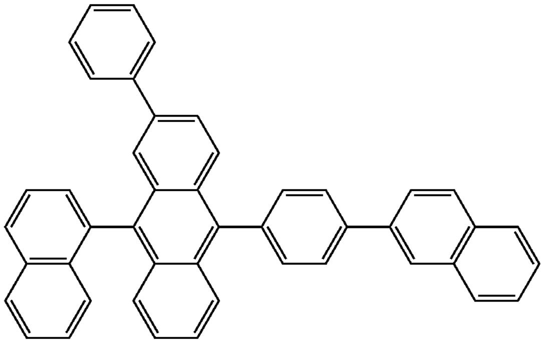
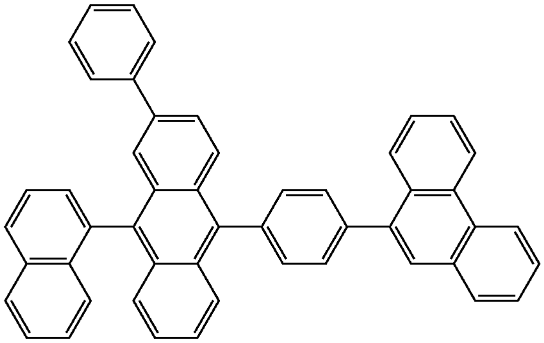
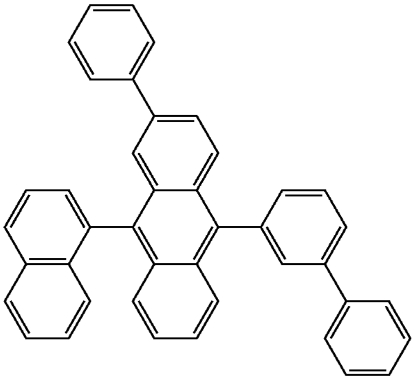
-continued
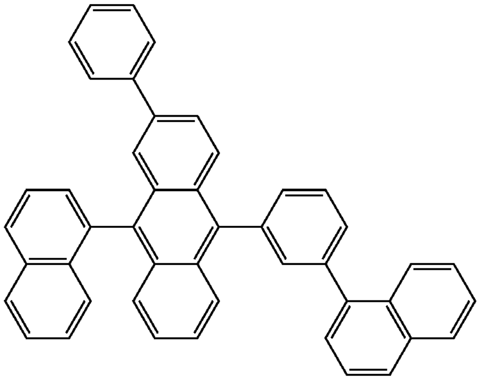
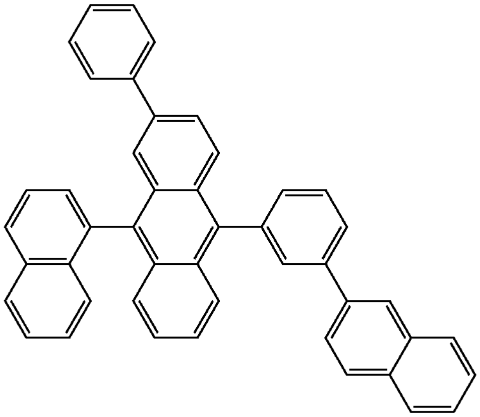
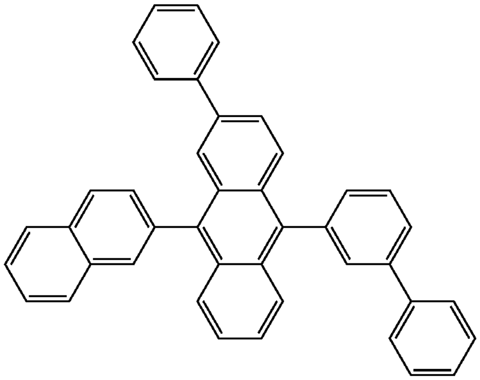
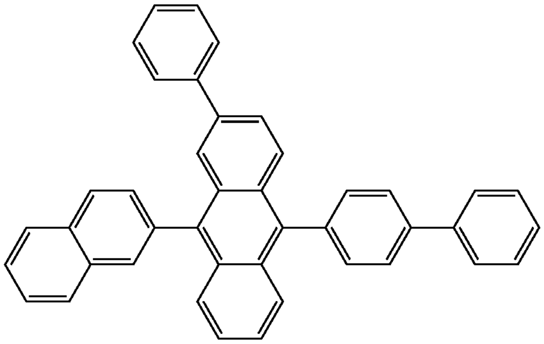

-continued
[Formula 86]
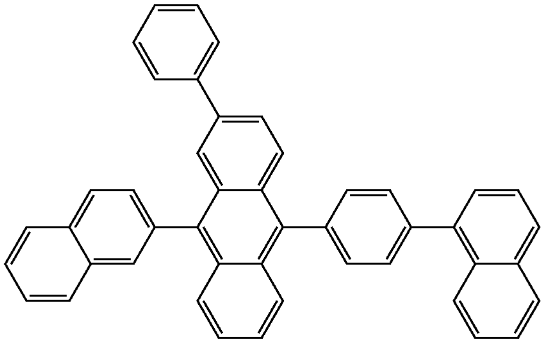
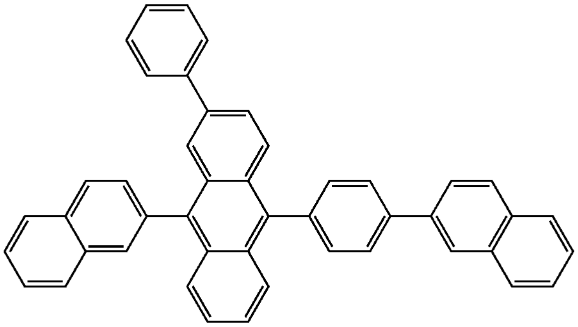
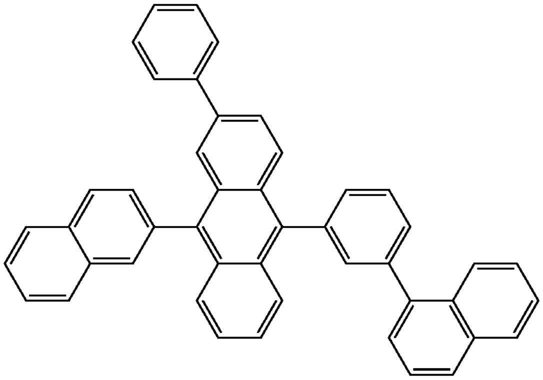
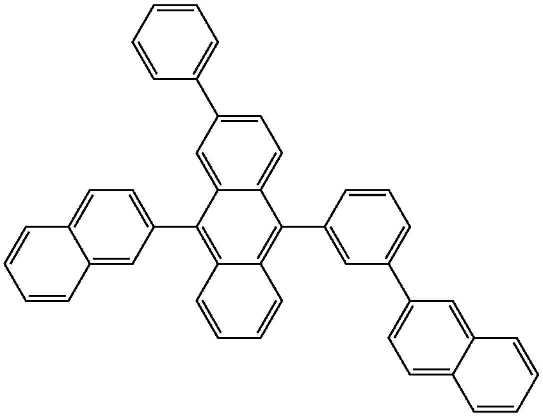
-continued
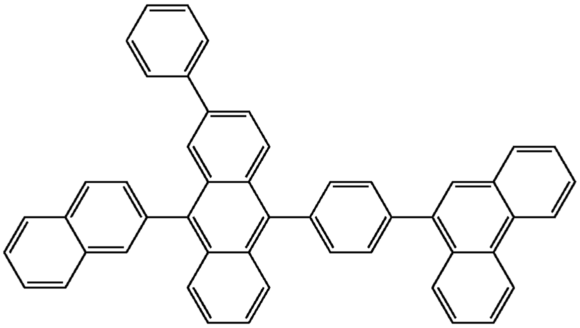
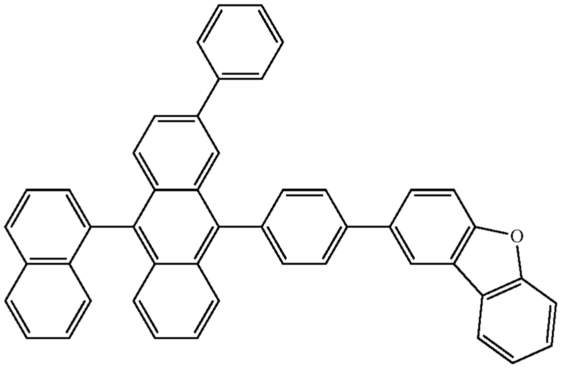
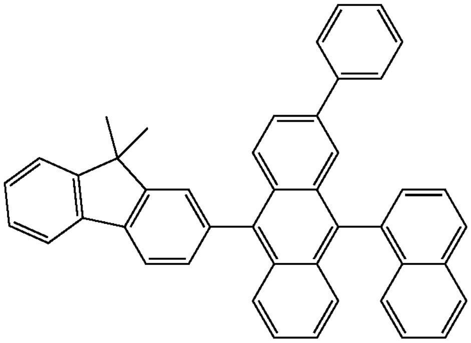
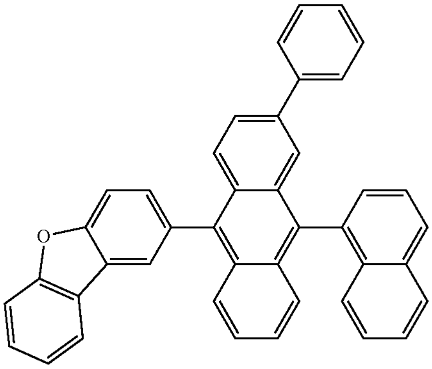

[Formula 87]
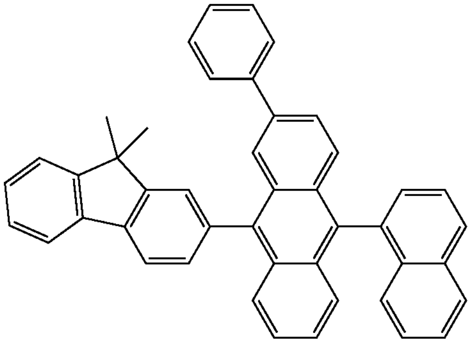
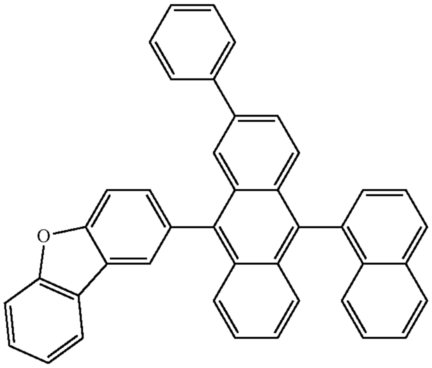
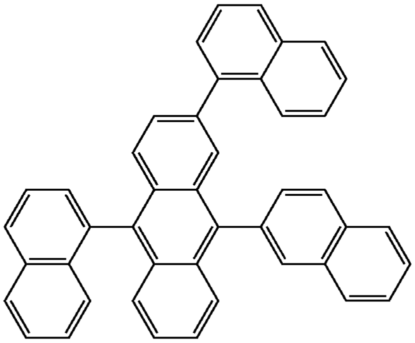
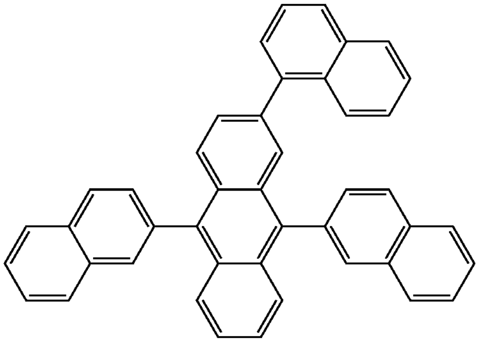
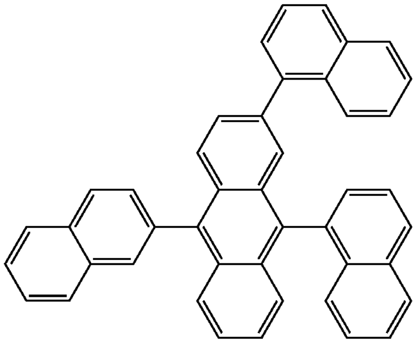
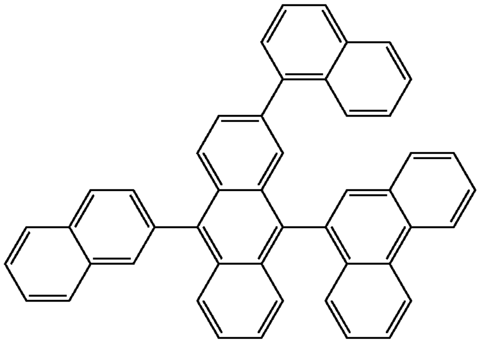
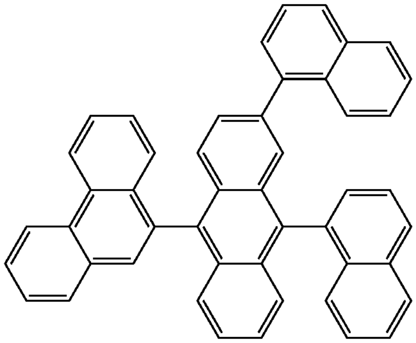
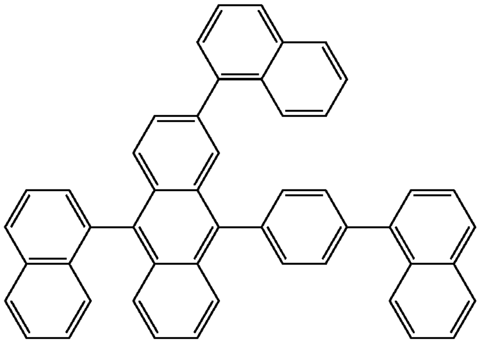

-continued
[Formula 88]
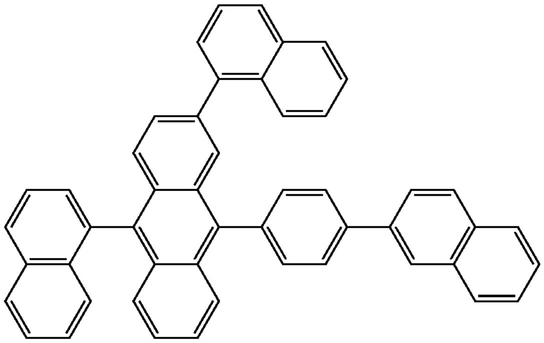
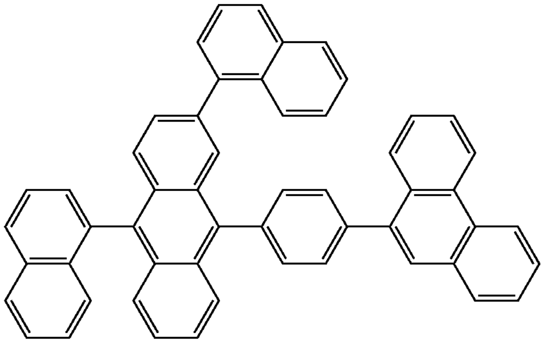
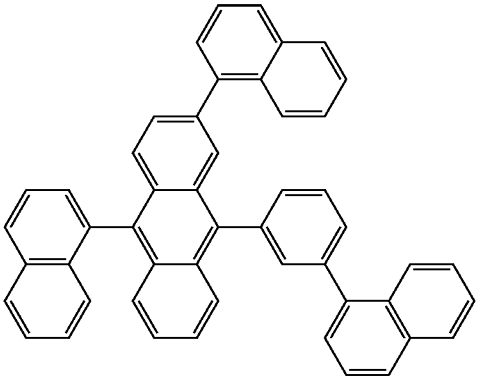
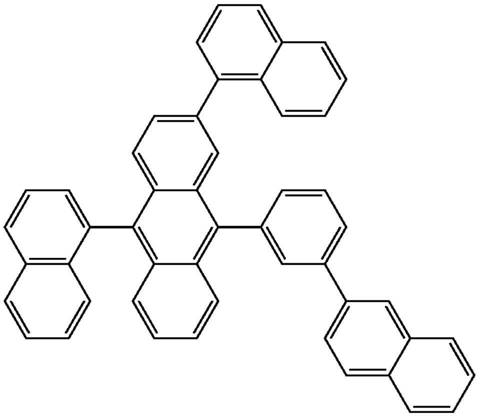
-continued
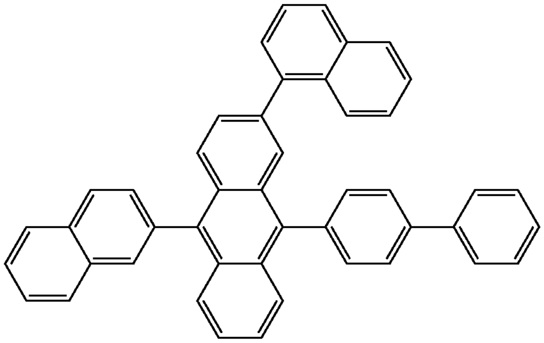
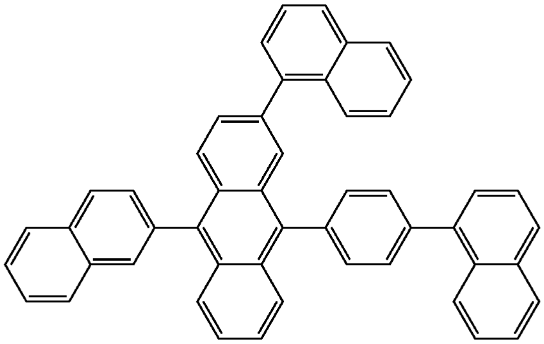
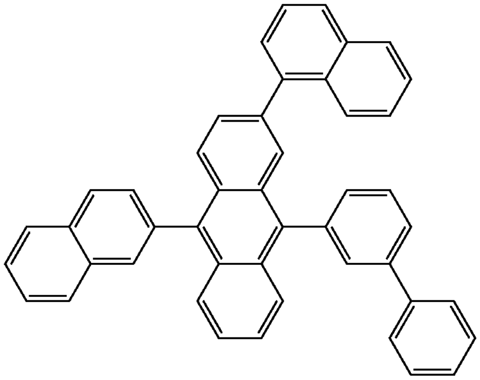
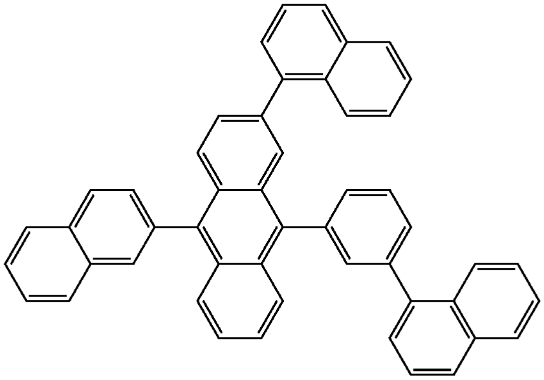

[Formula 89]
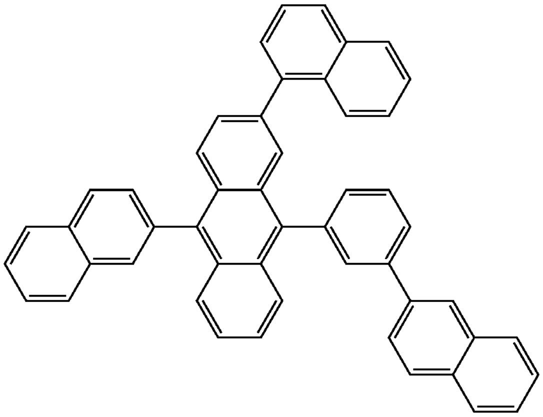
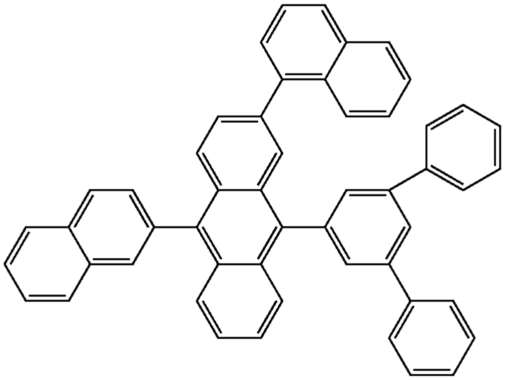
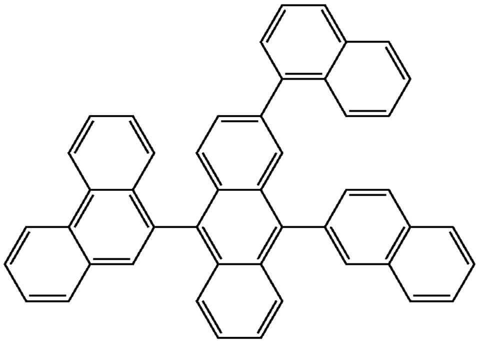
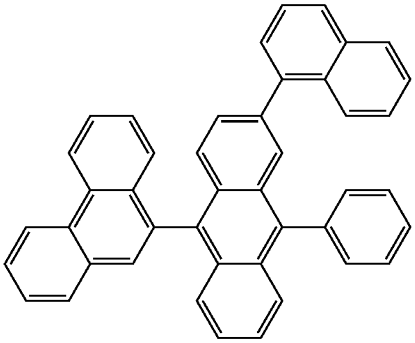
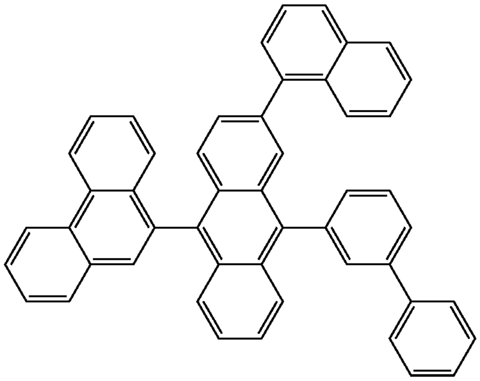
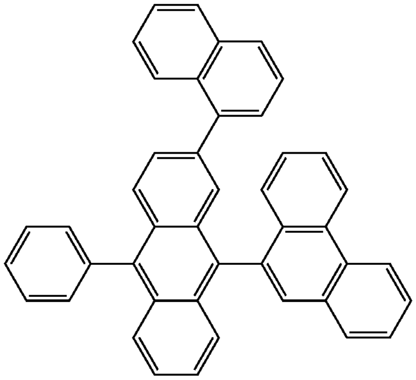
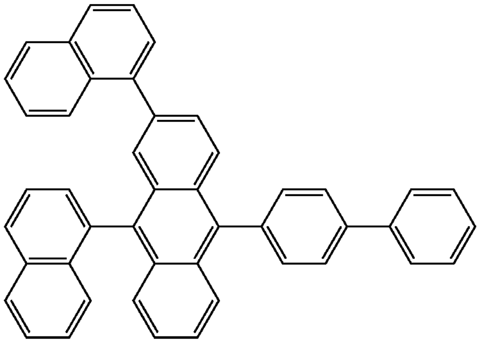
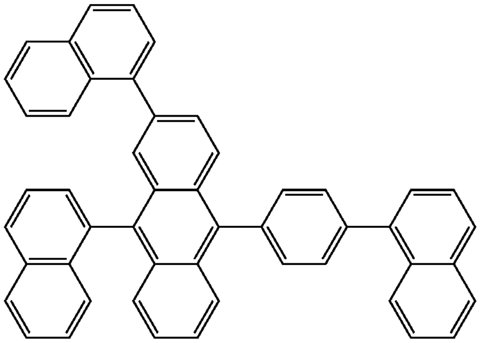

-continued
[Formula 90]
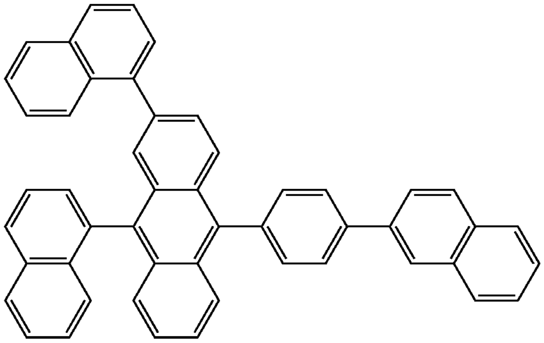
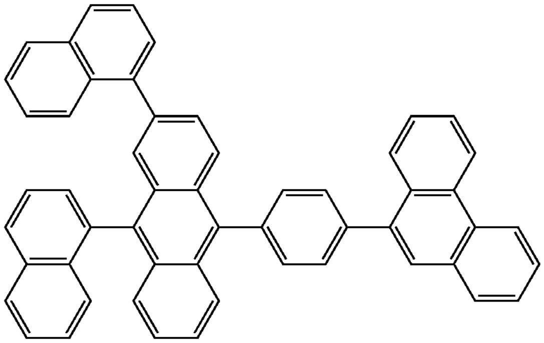
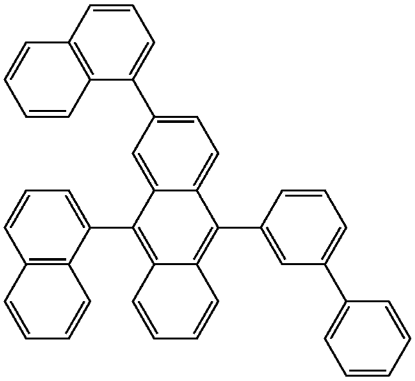
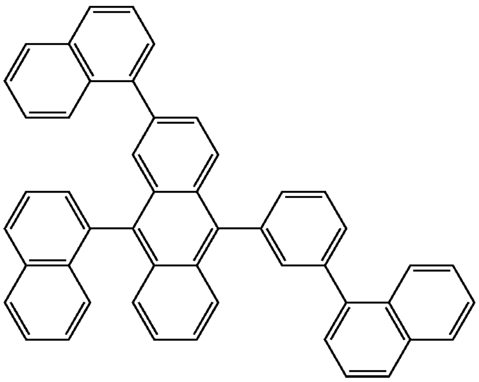
-continued
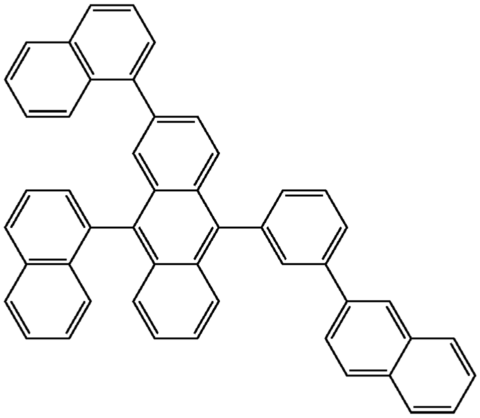
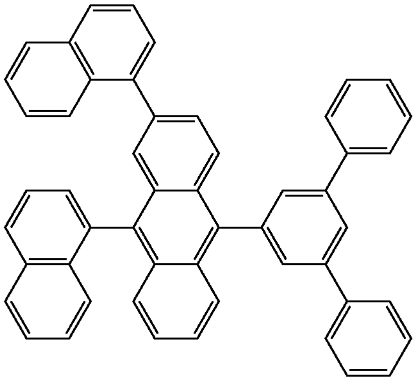
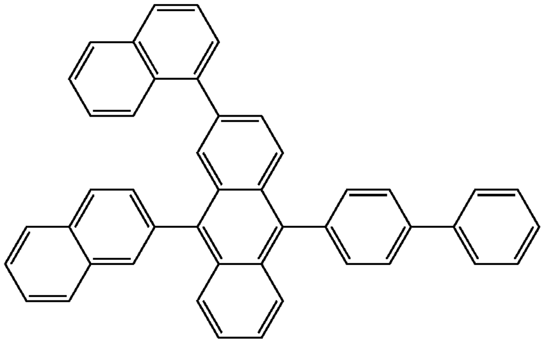
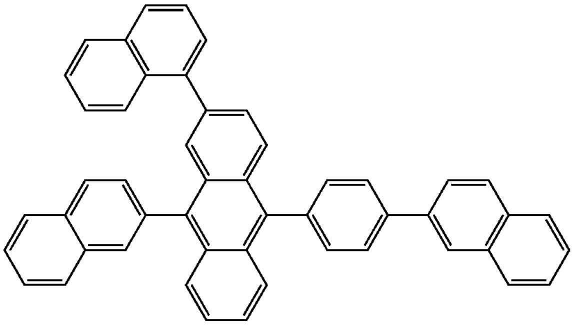

-continued
[Formula 91]
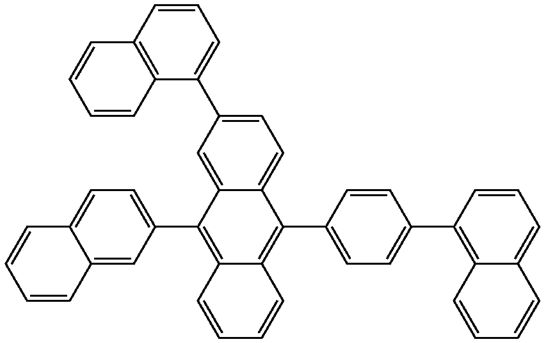
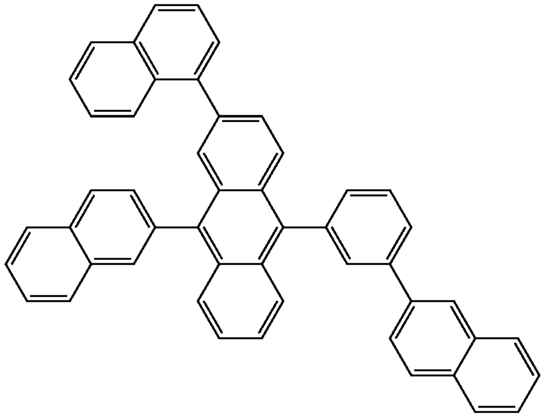
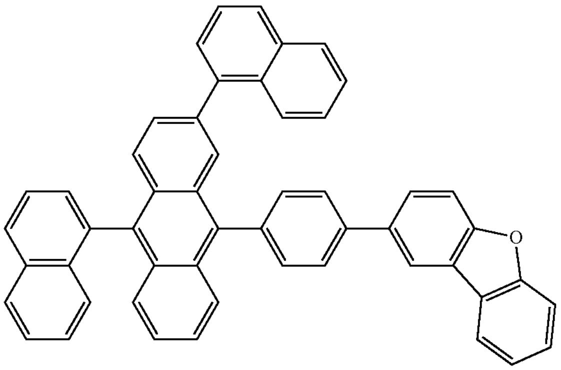
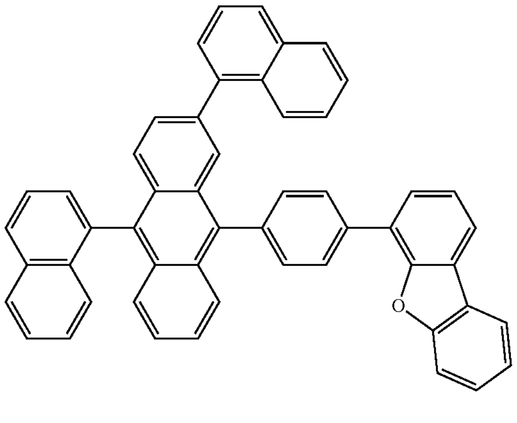
-continued
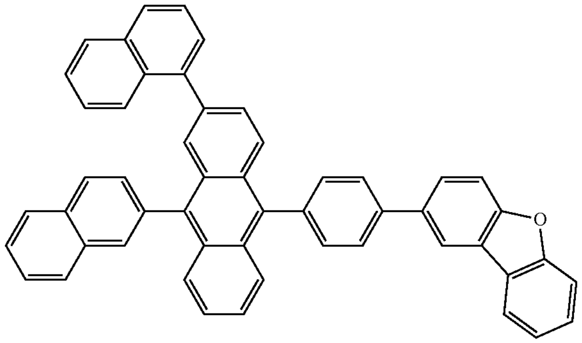
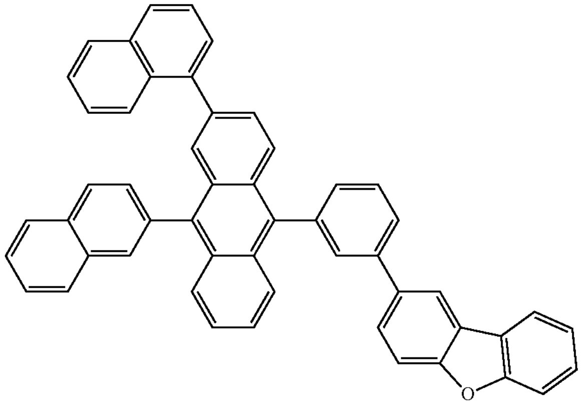
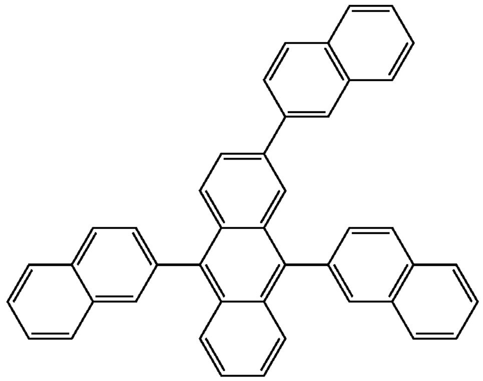
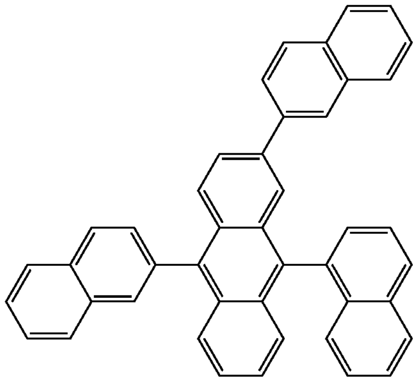

-continued
[Formula 92]
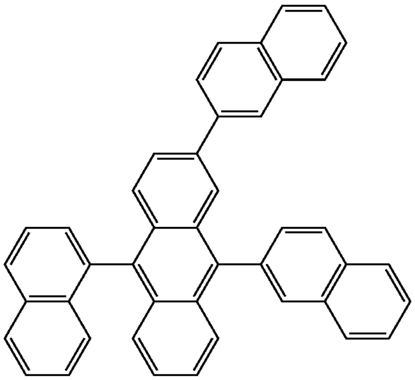
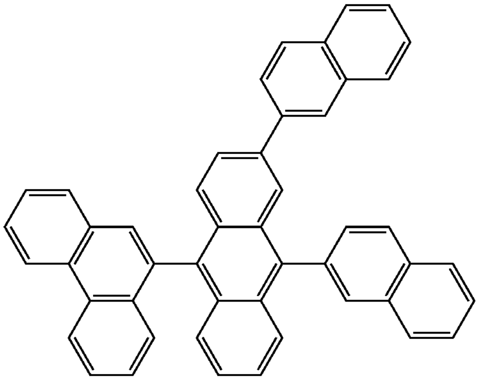
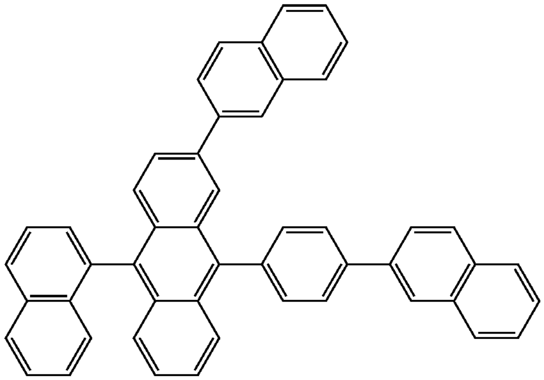
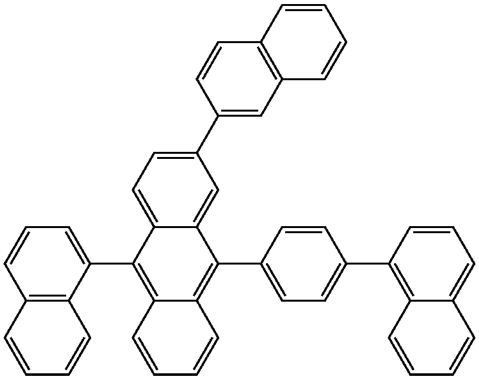
-continued
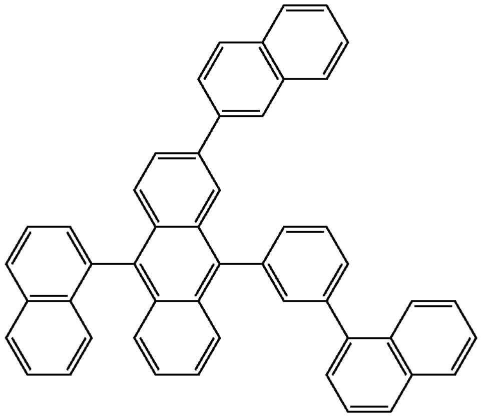
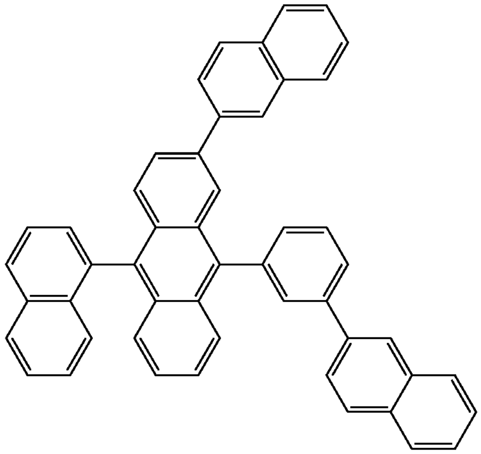
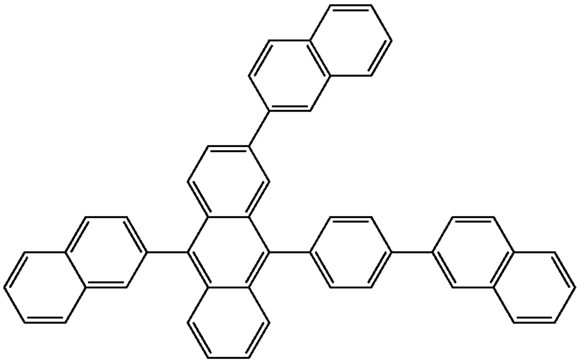
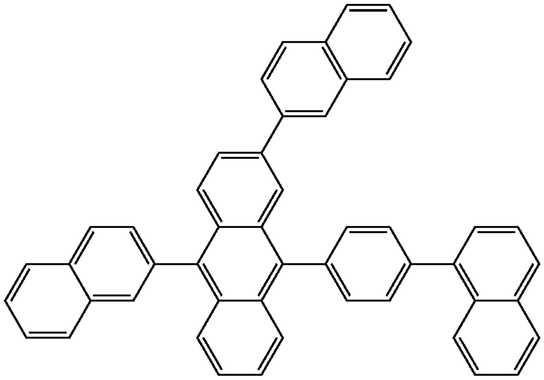

-continued
[Formula 93]
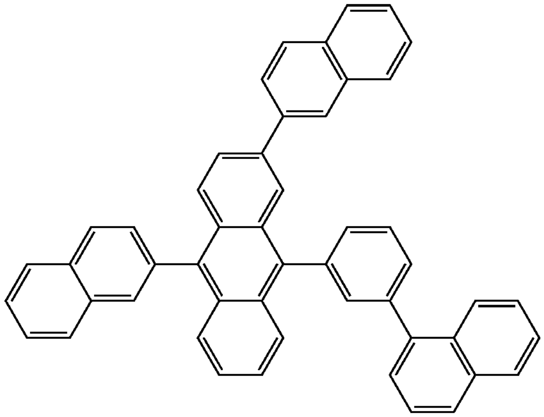
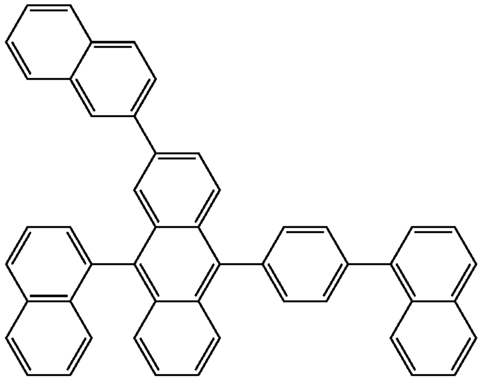
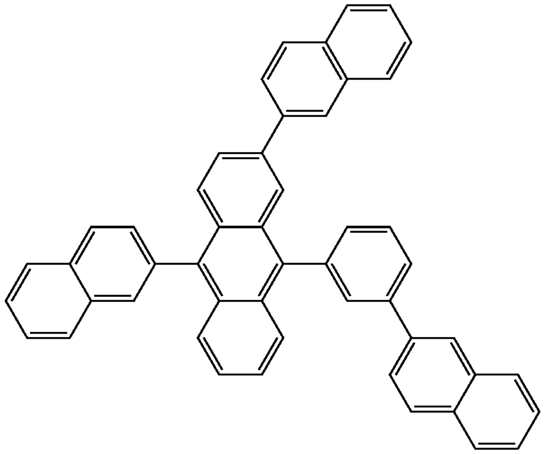
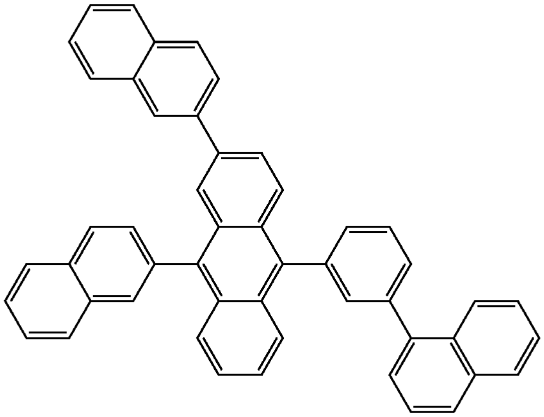
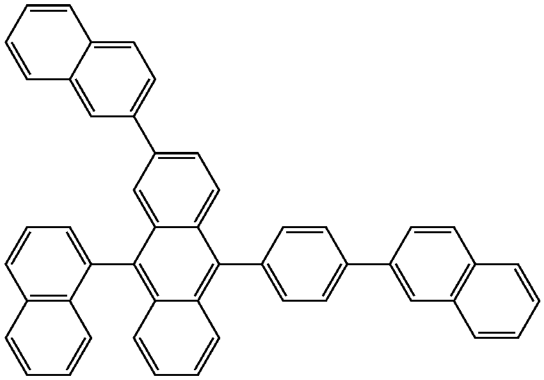
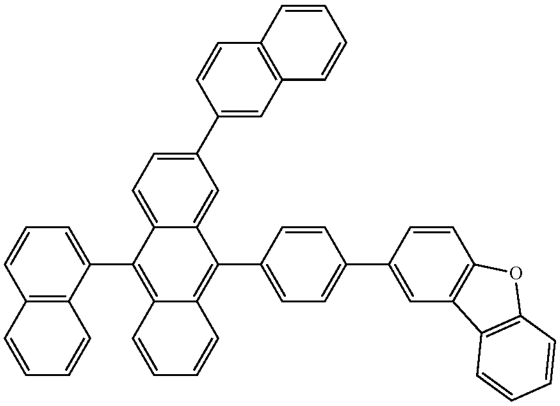
-continued -continued
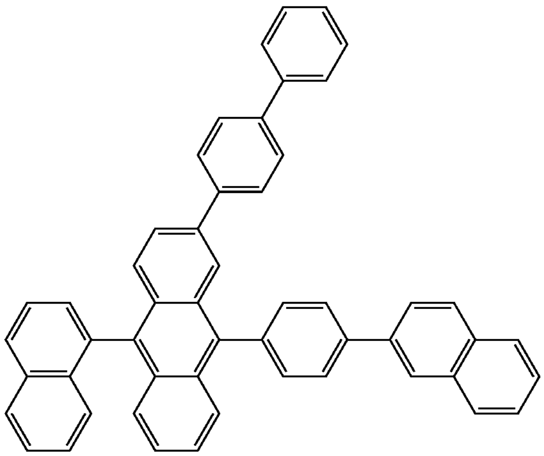
-continued
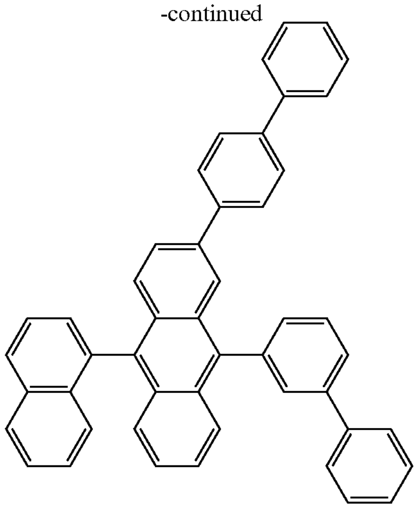
[Formula 94]
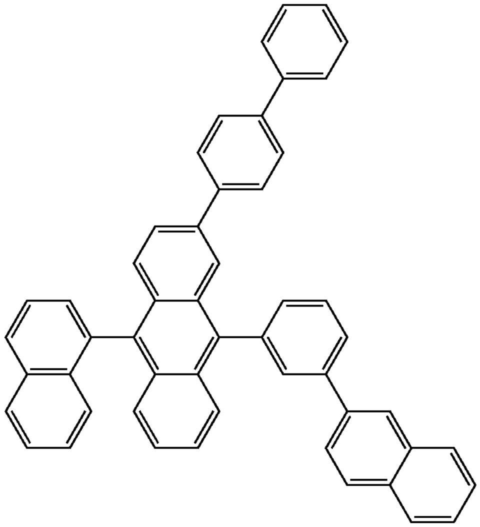
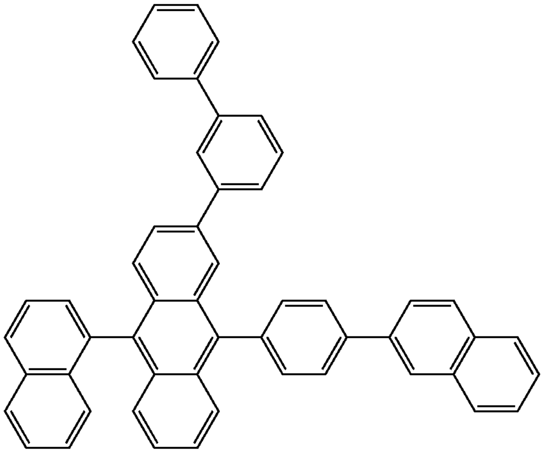
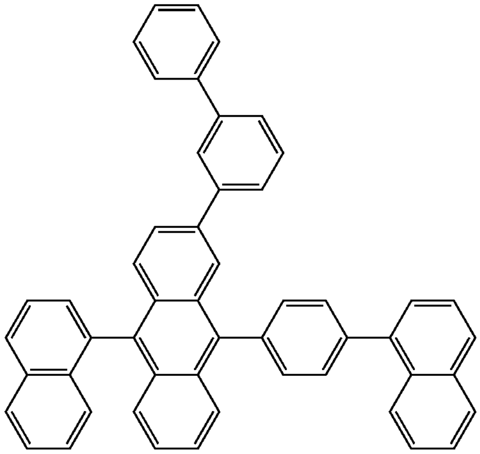
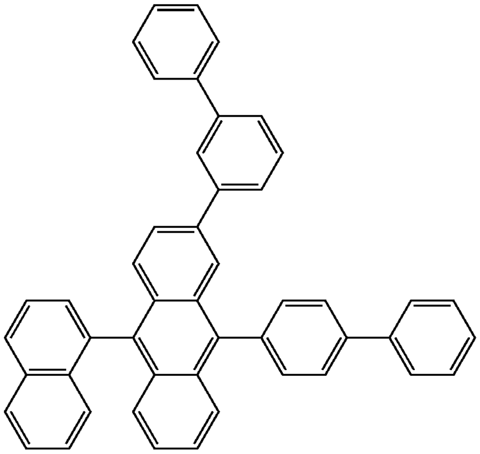

-continued
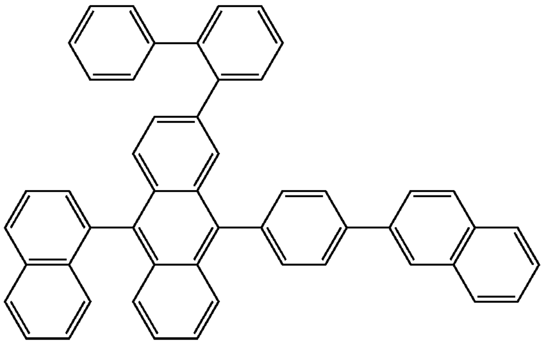
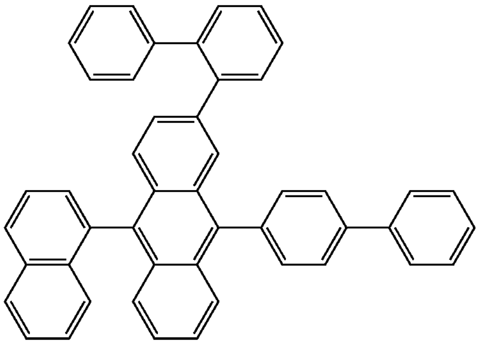
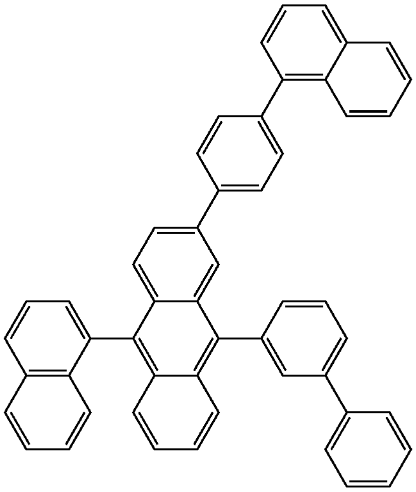
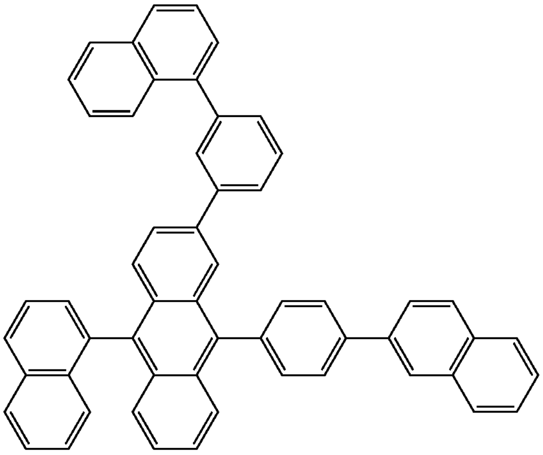
[Formula 95]
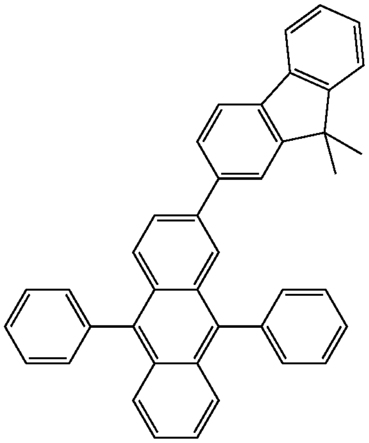
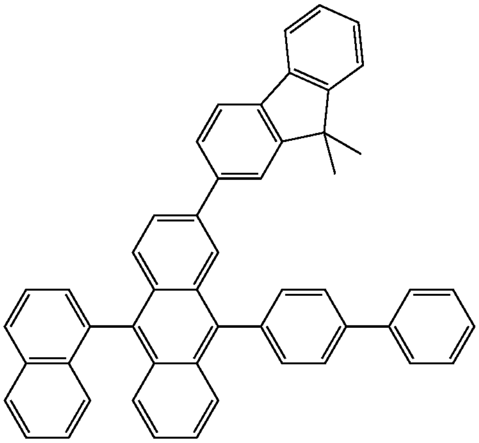

-continued
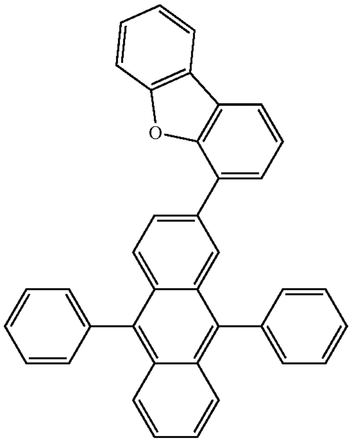
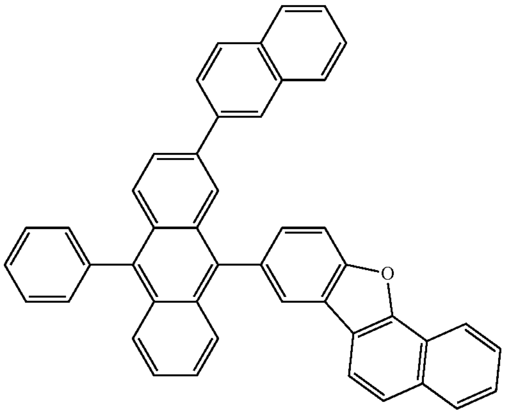
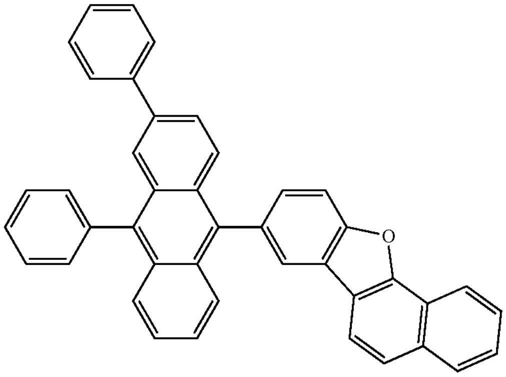
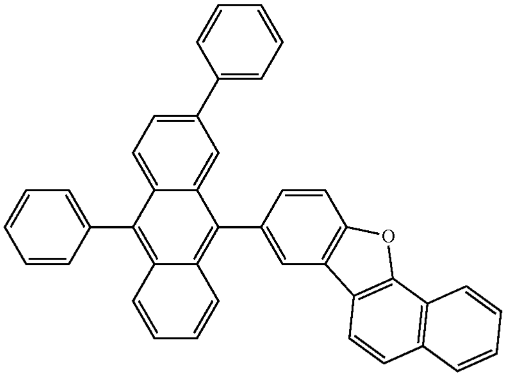
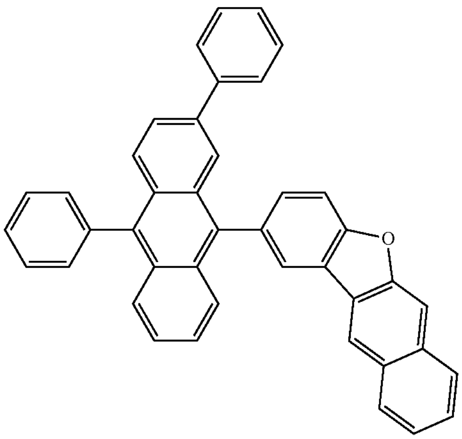
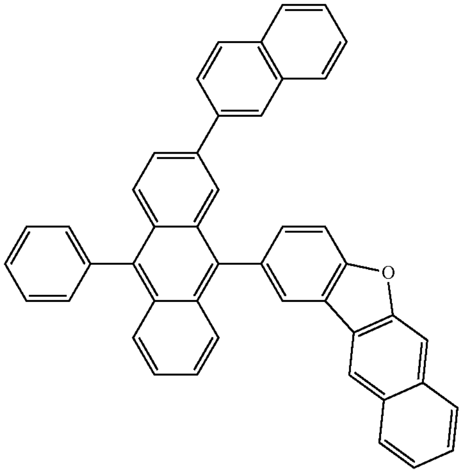

-continued
[Formula 96]
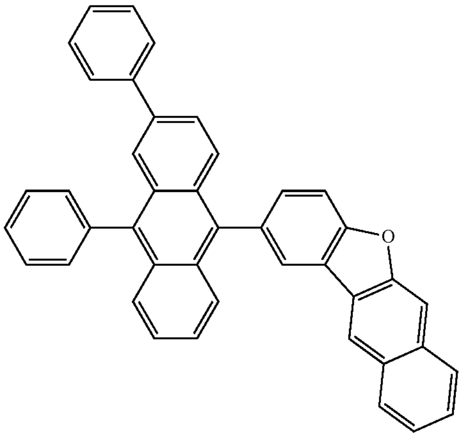
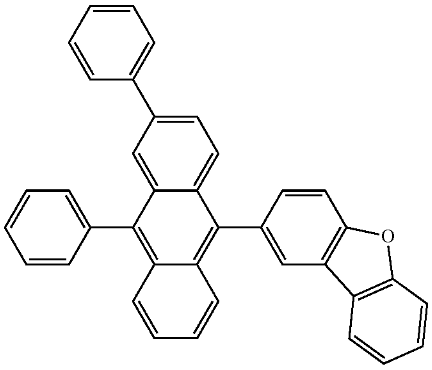
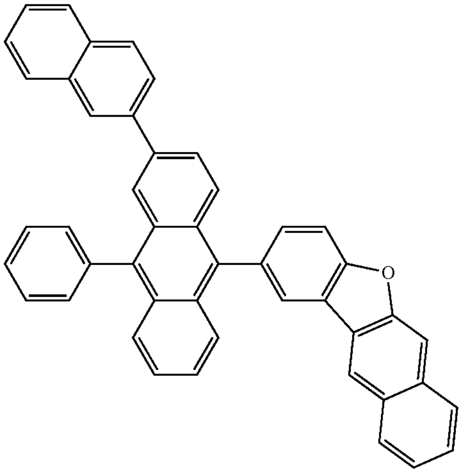
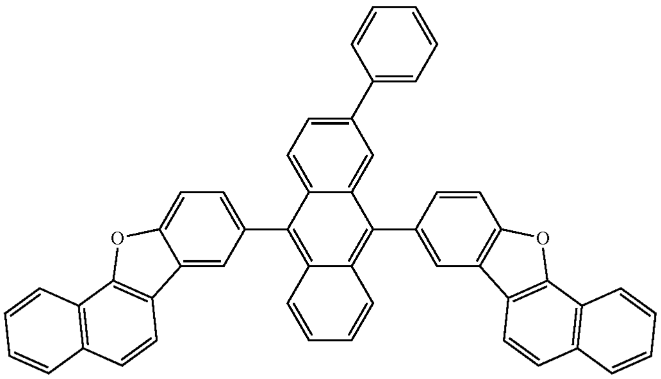
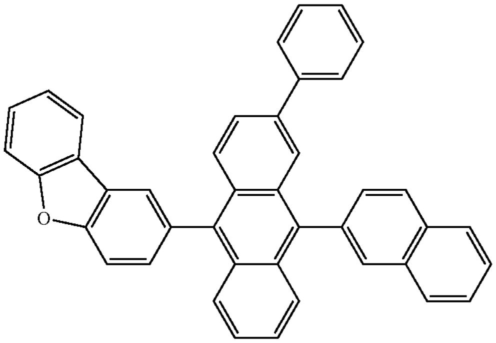
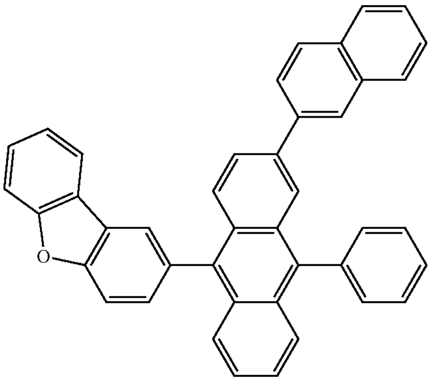
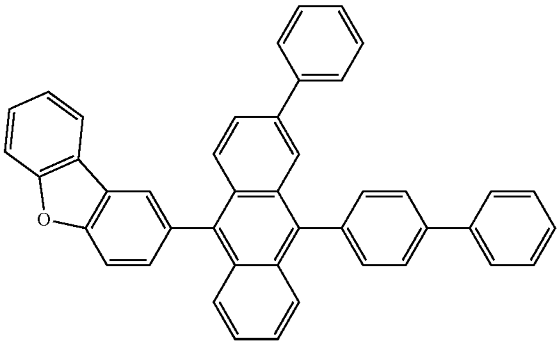
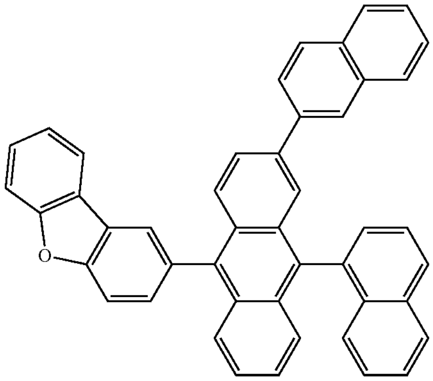

-continued
[Formula 97]
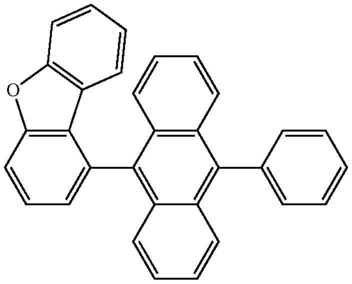
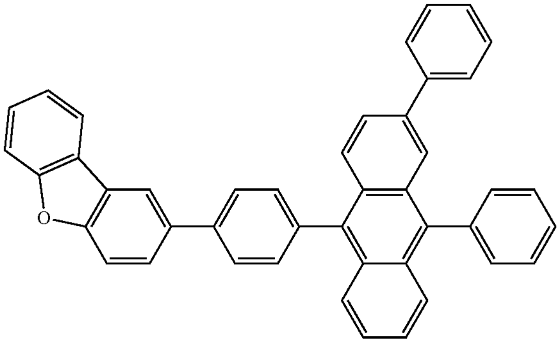
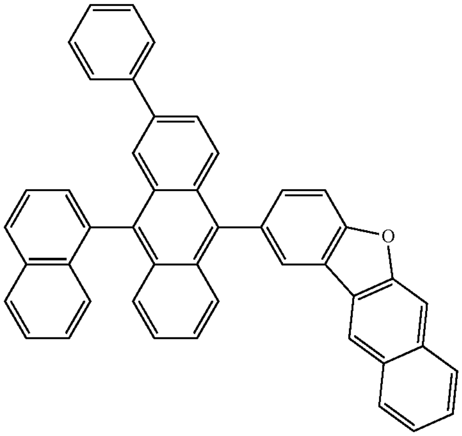
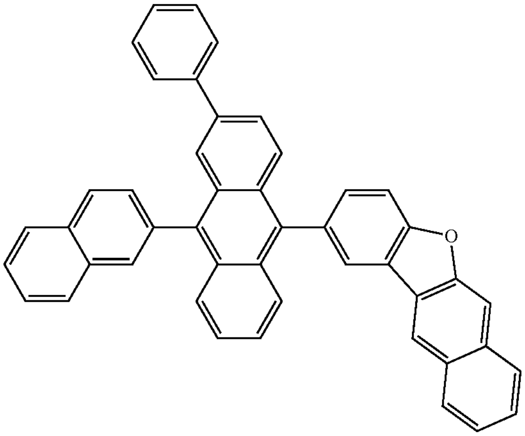
[Formula 98]
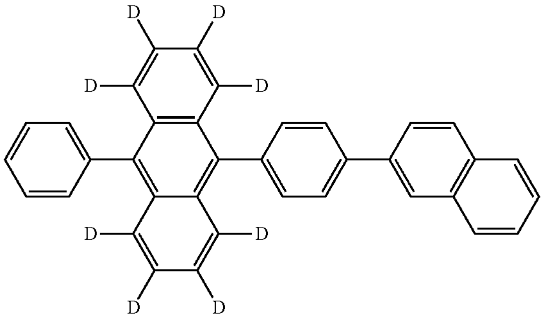
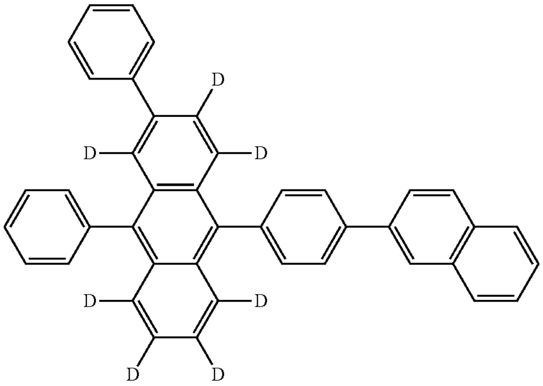
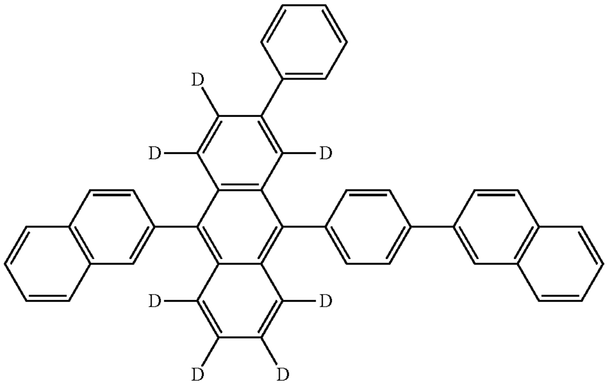
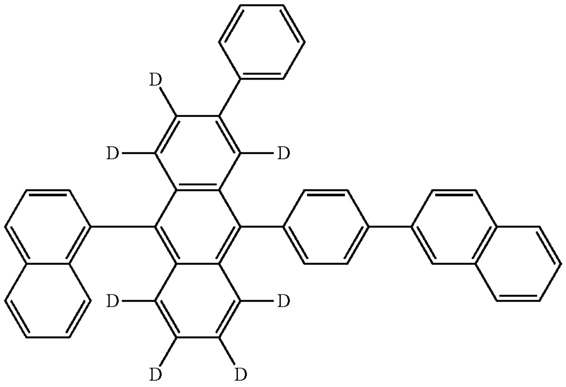

-continued
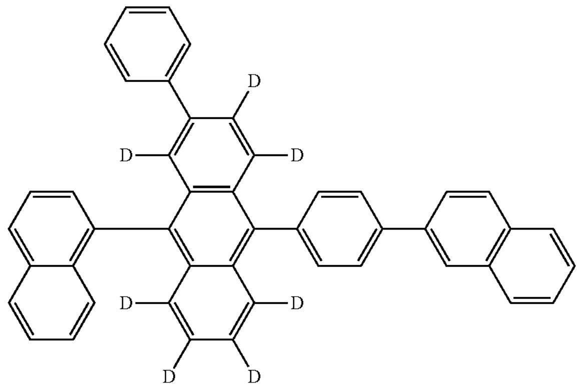
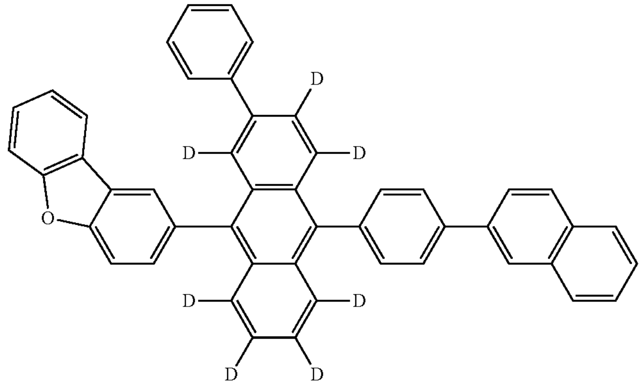
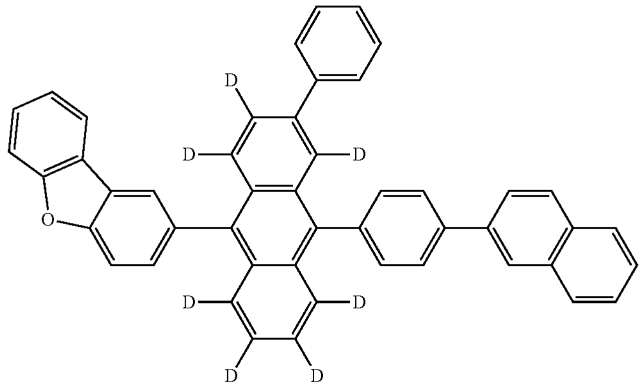
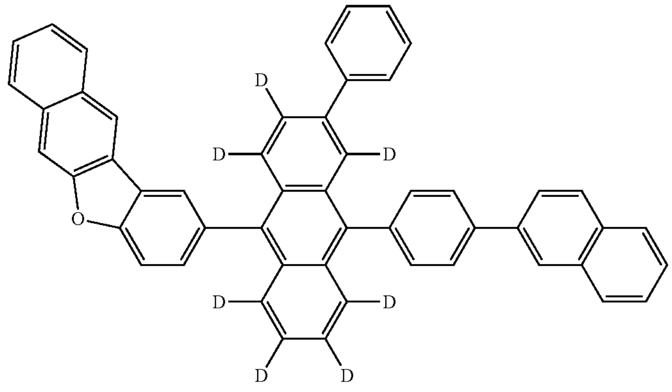

-continued
[Formula 99]
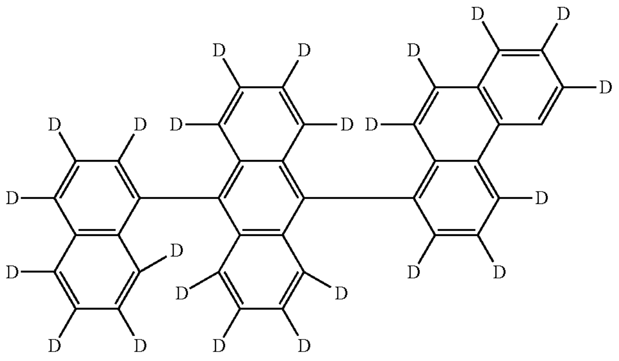
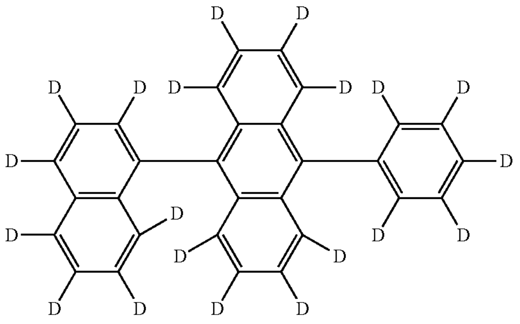
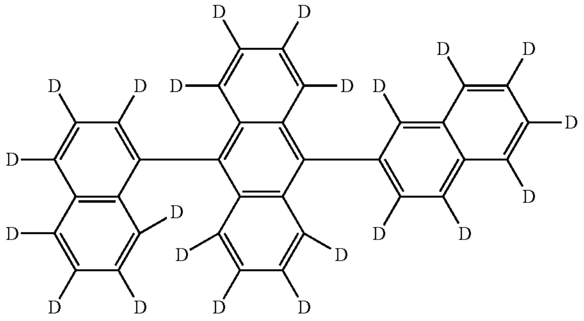
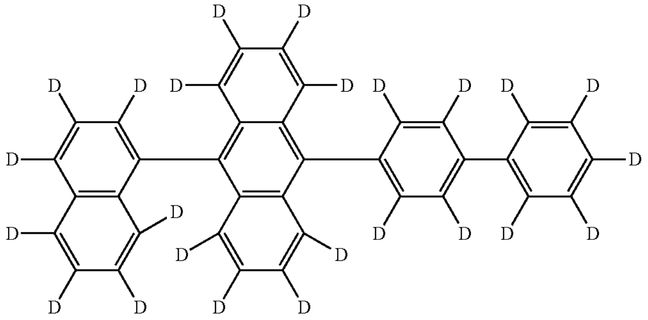
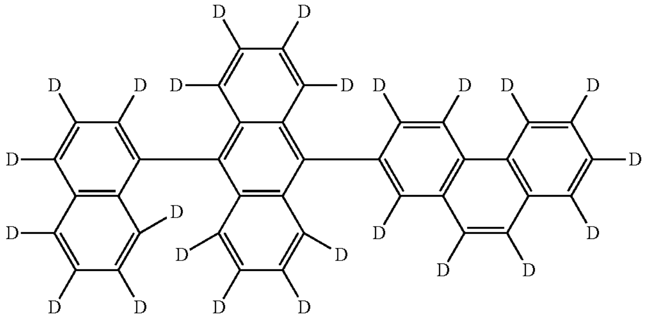
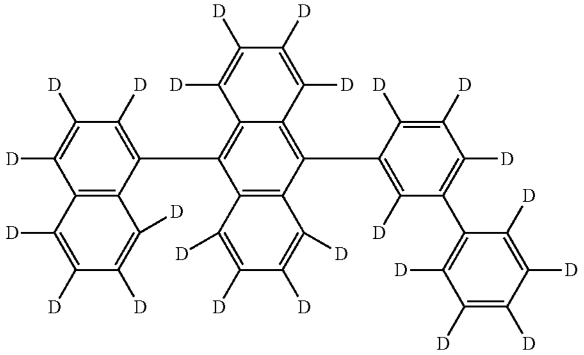
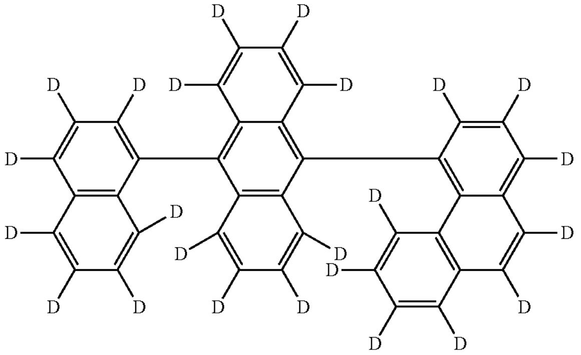

-continued
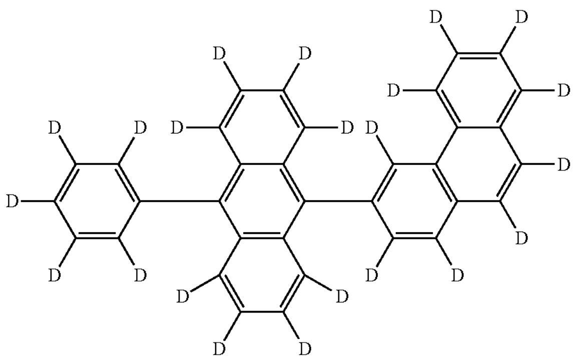
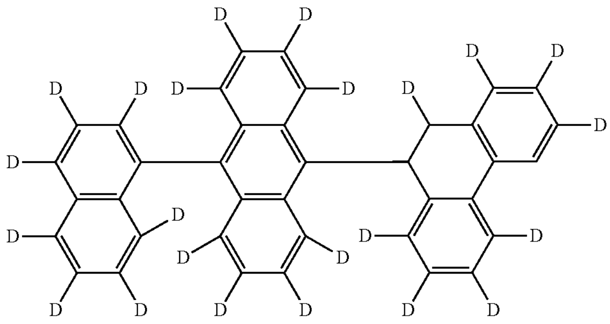
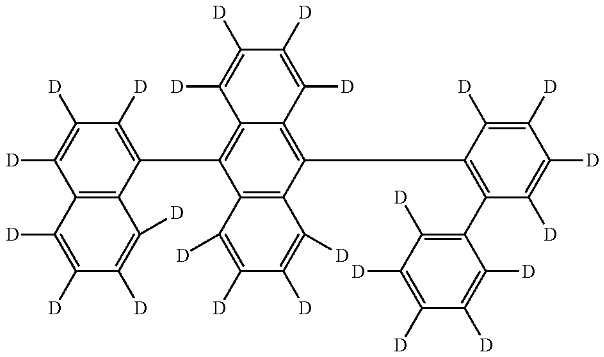
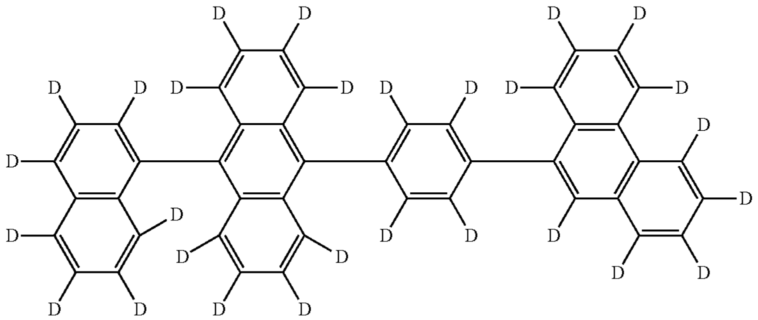
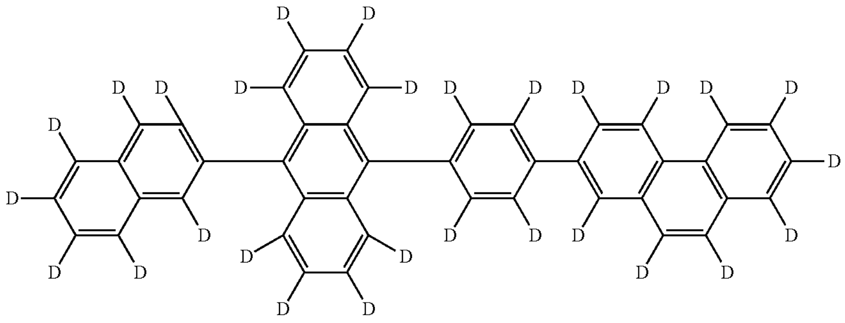
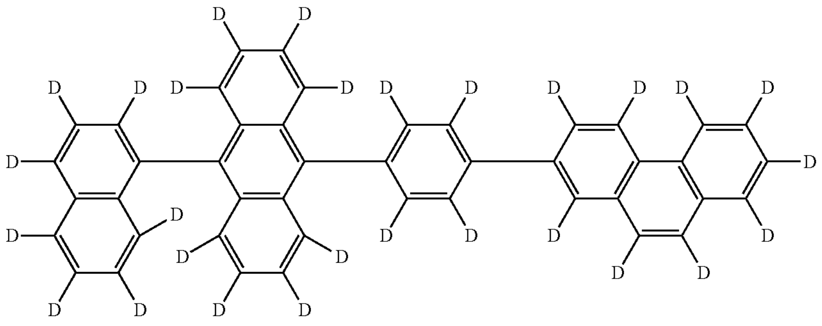

-continued
[Formula 100]
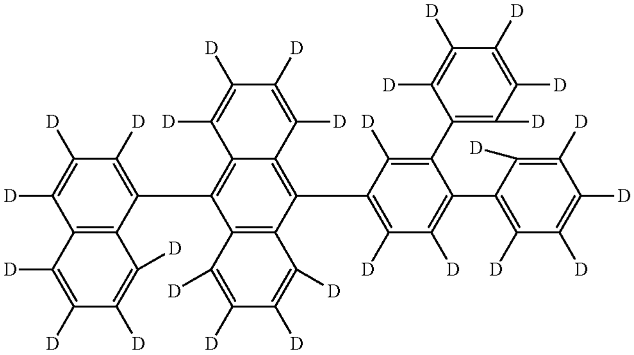
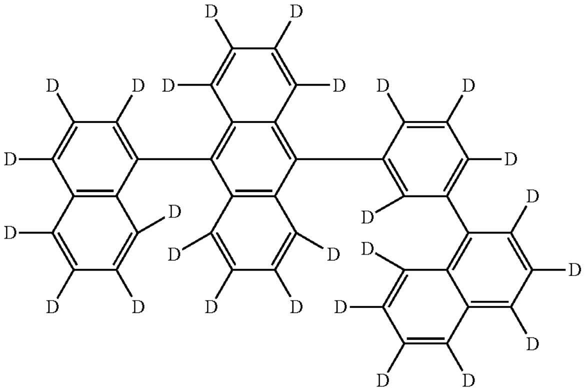
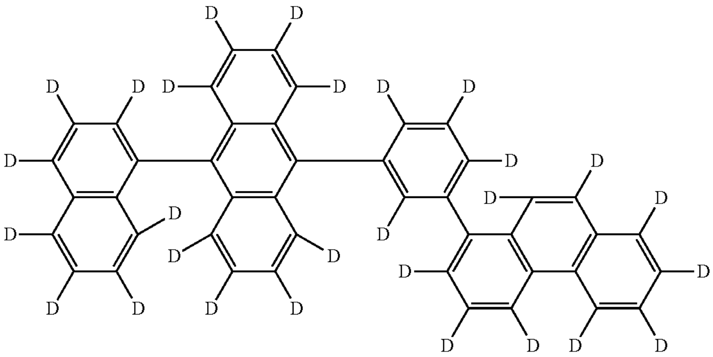
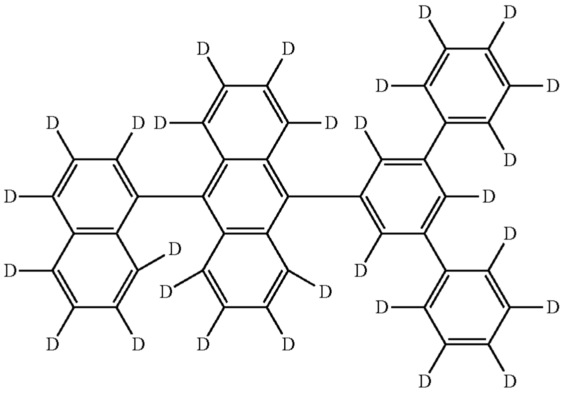

-continued
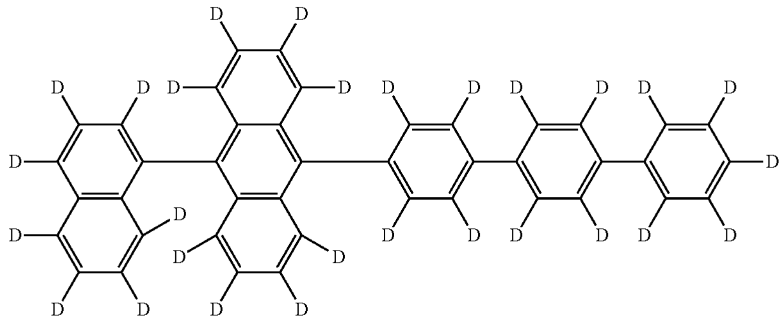
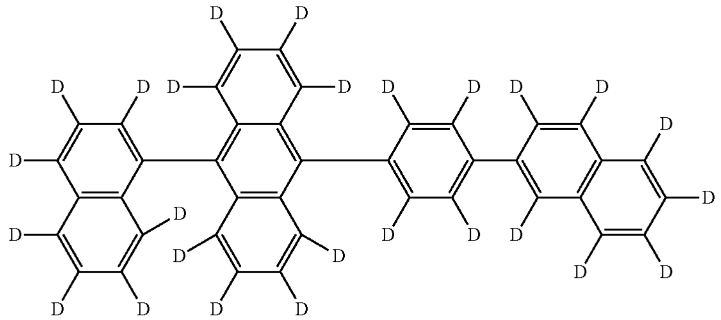
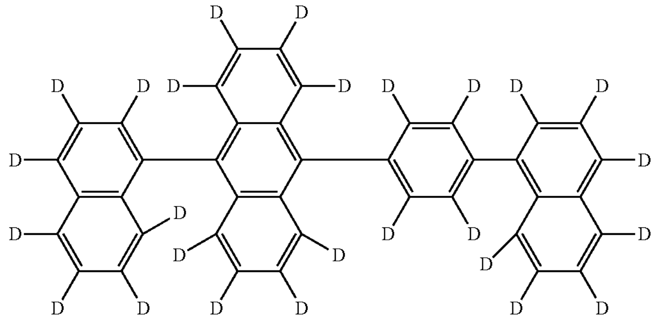
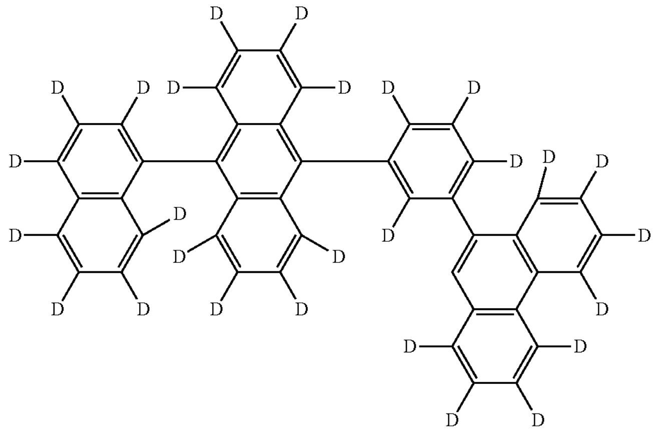

-continued
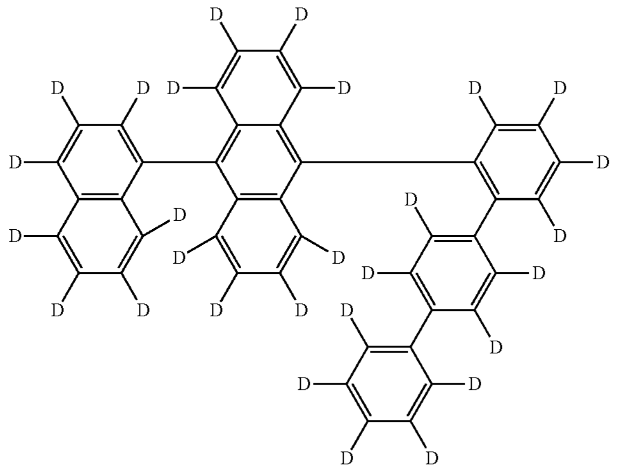
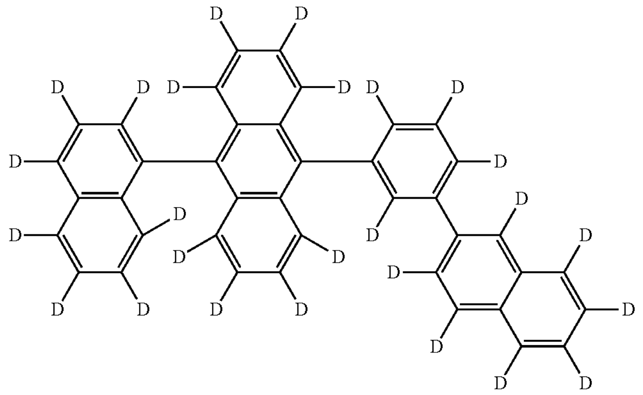
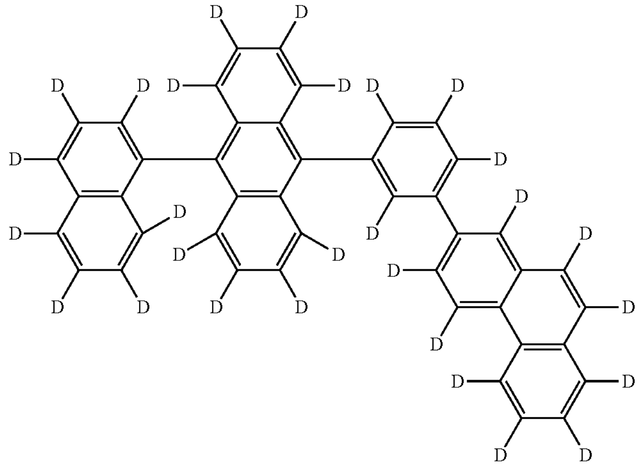
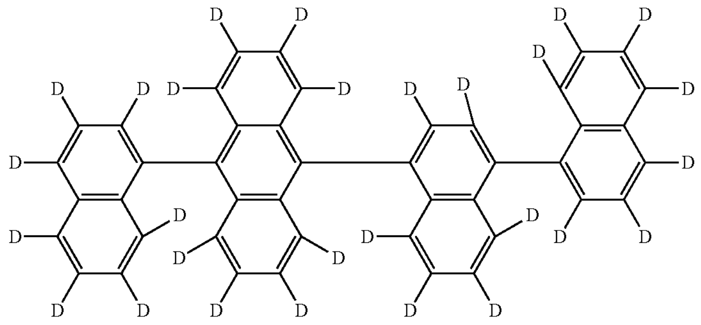

-continued
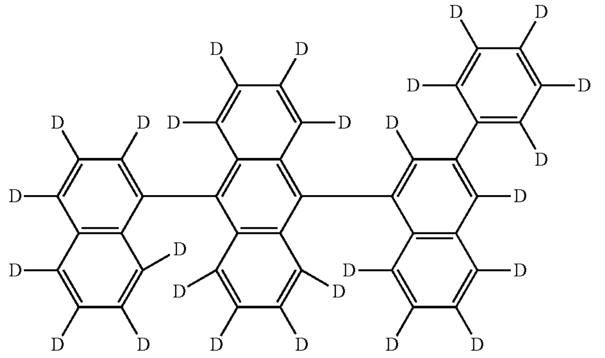
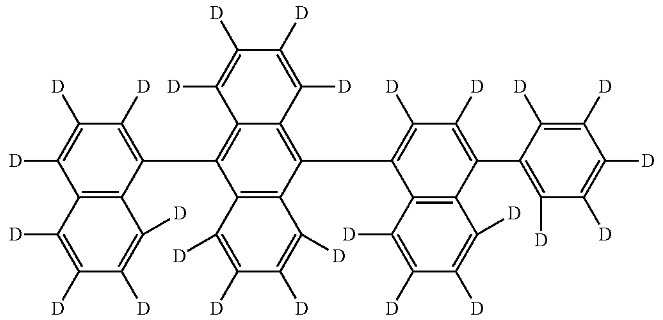
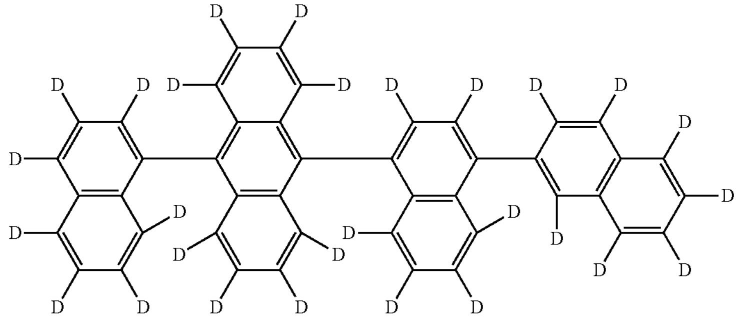
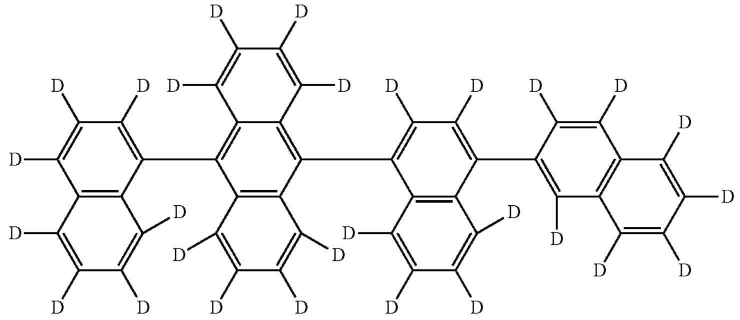
[Formula 101]
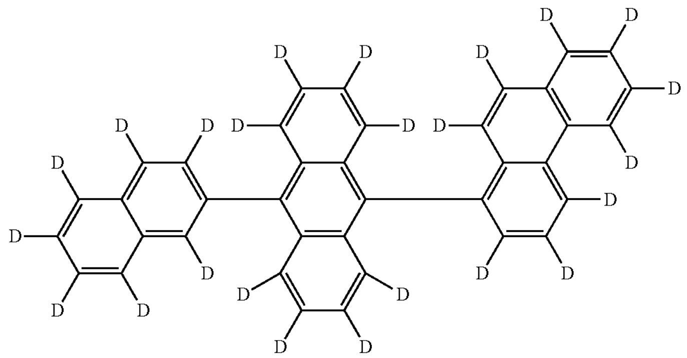

-continued
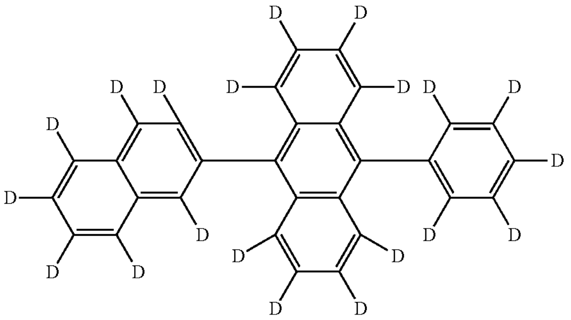
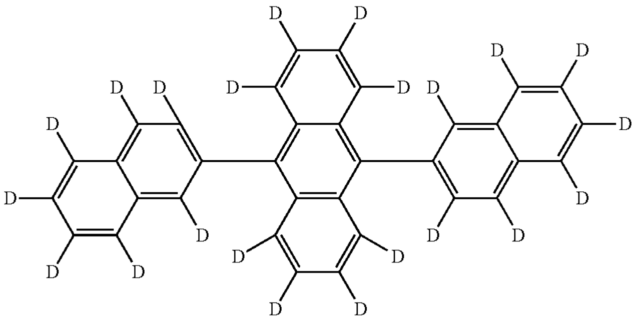
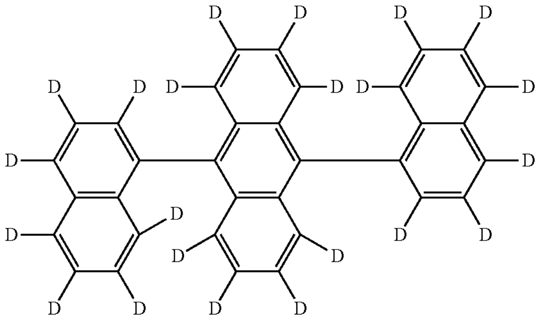
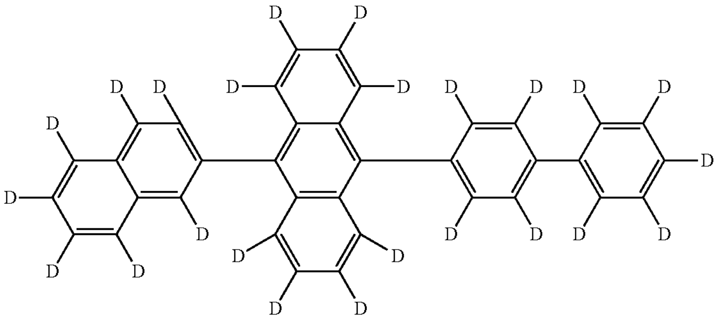
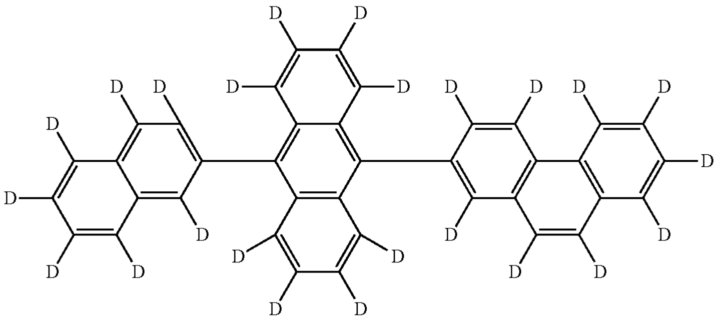
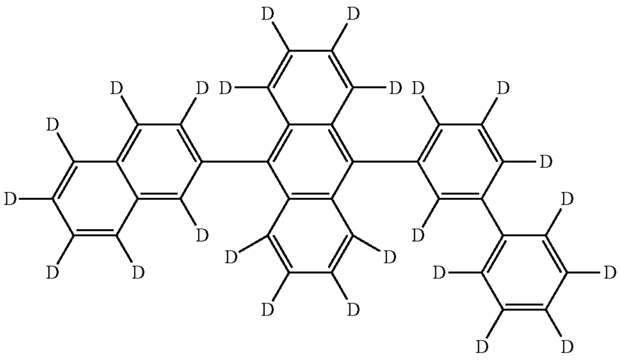

-continued
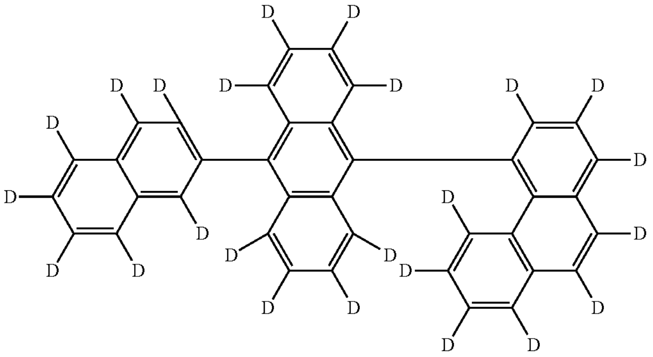
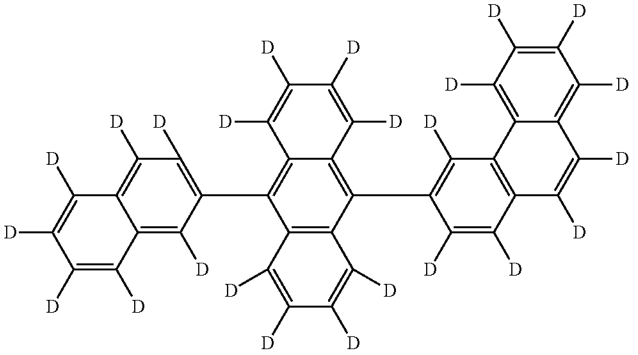
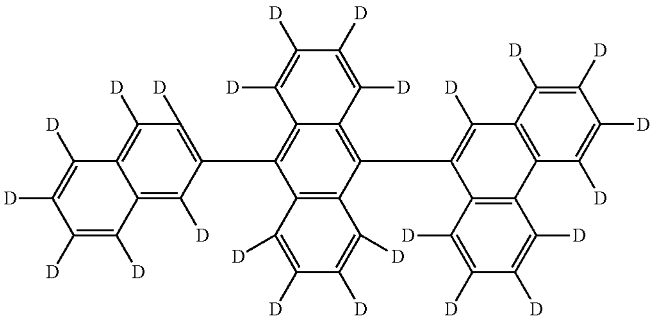
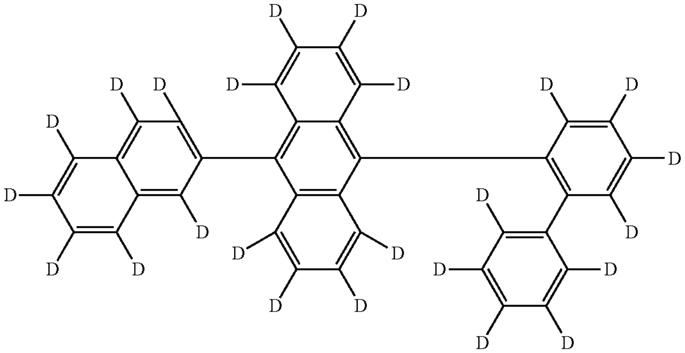
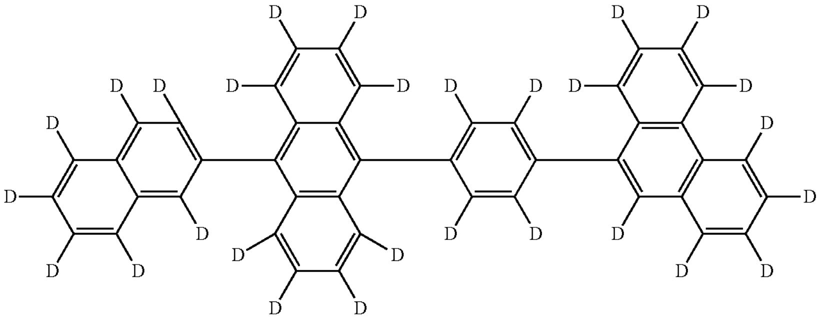

-continued
[Formula 102]
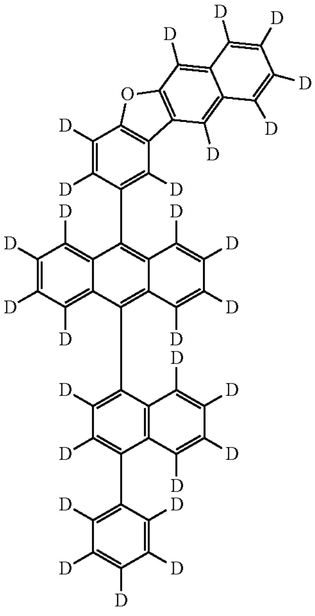
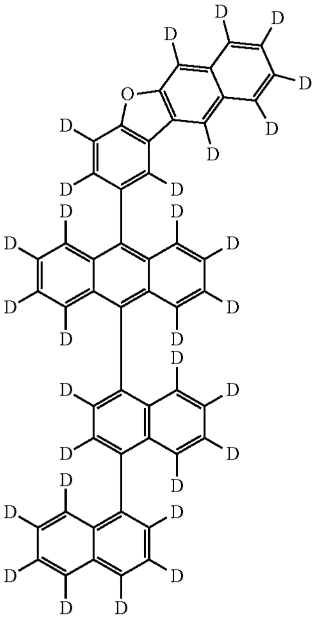
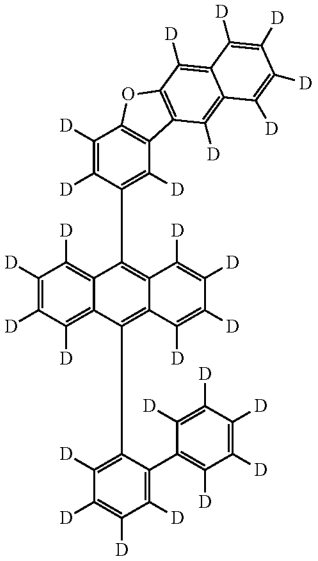
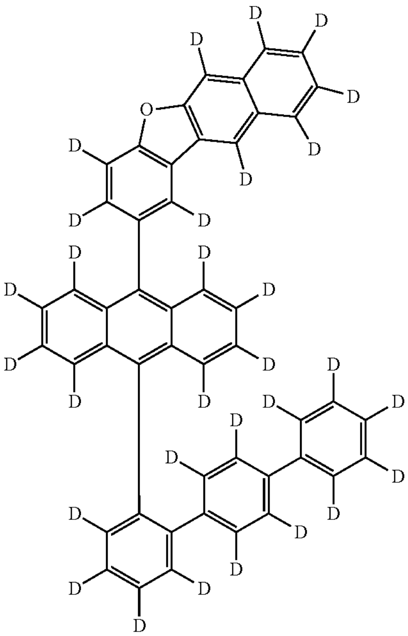
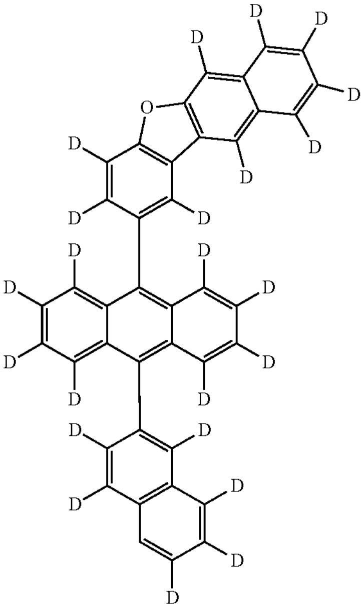
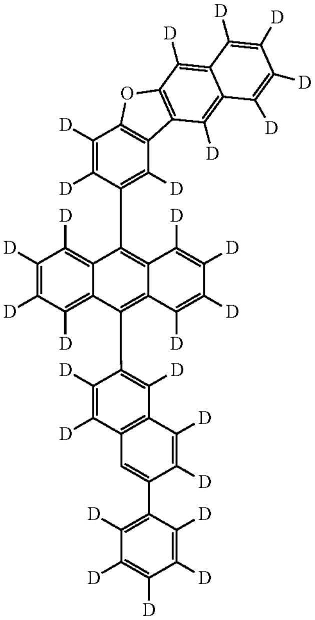

-continued
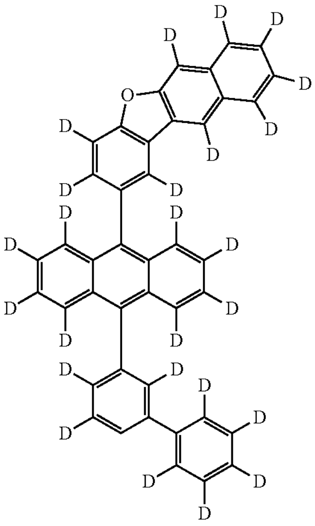
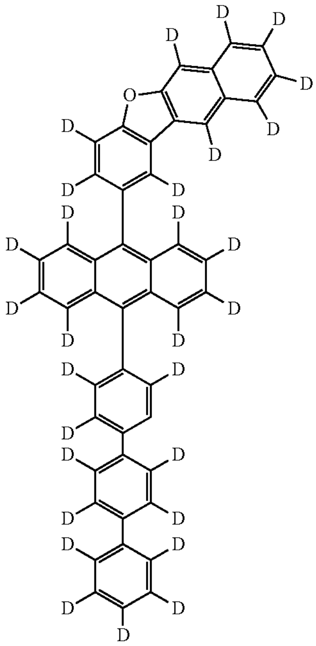
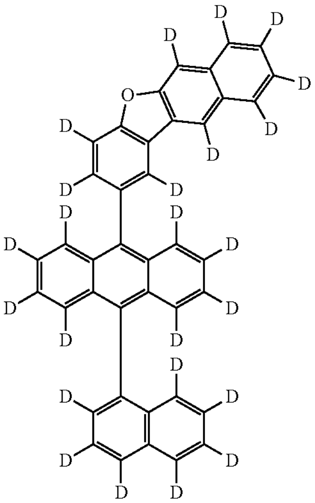
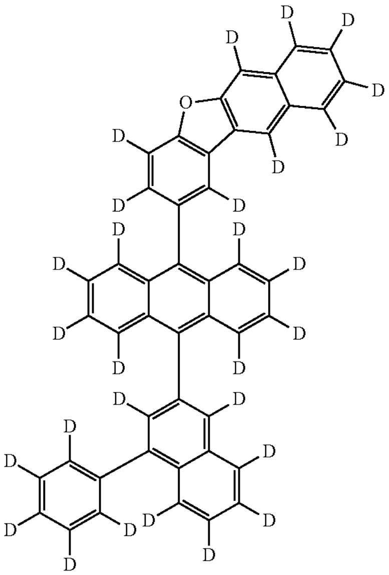
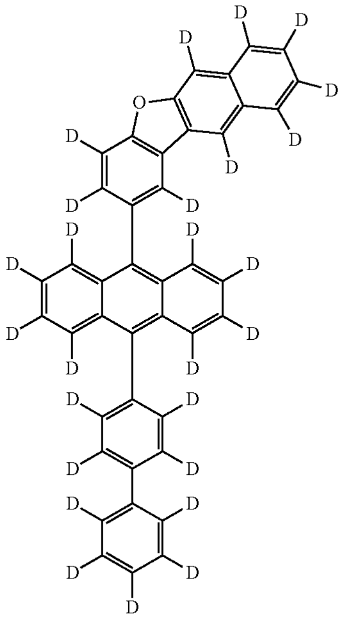
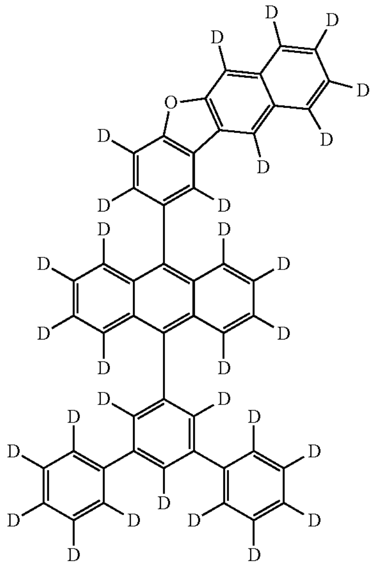

-continued
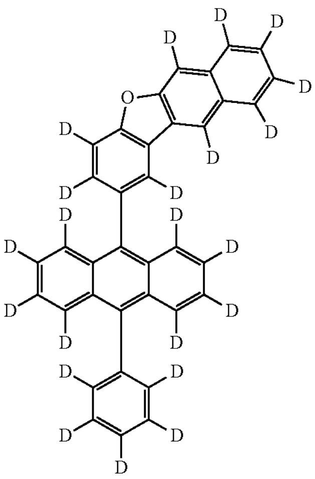
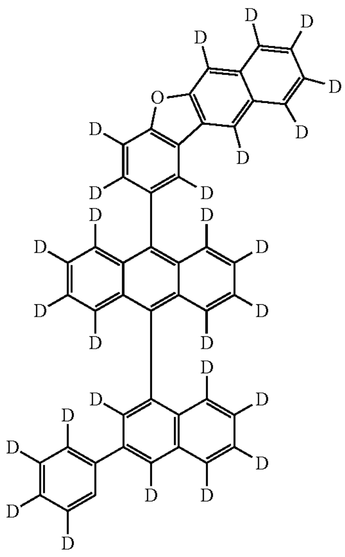
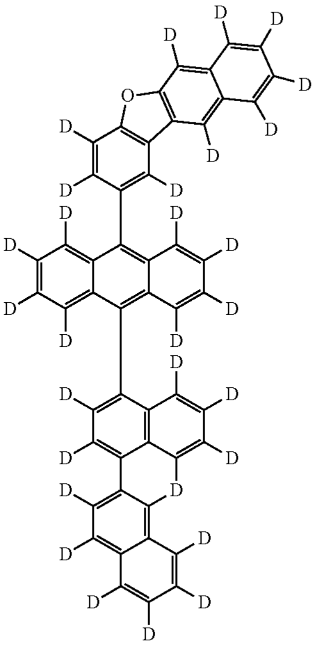
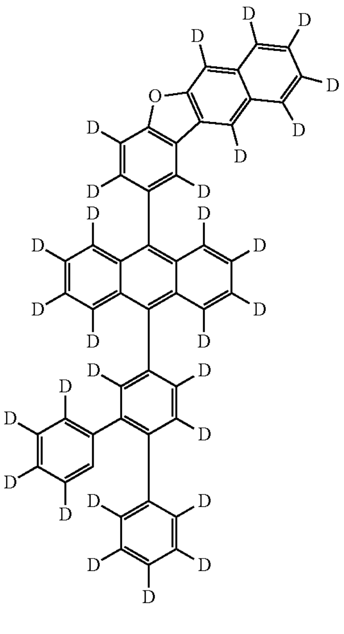

-continued
[Formula 103]
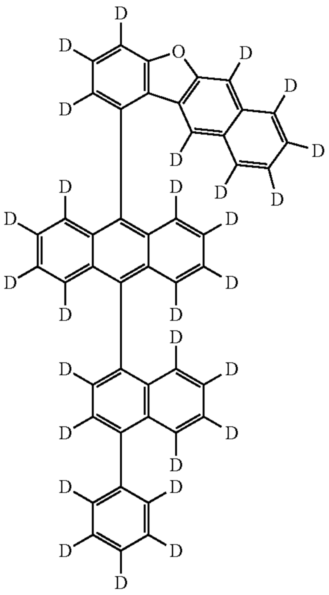
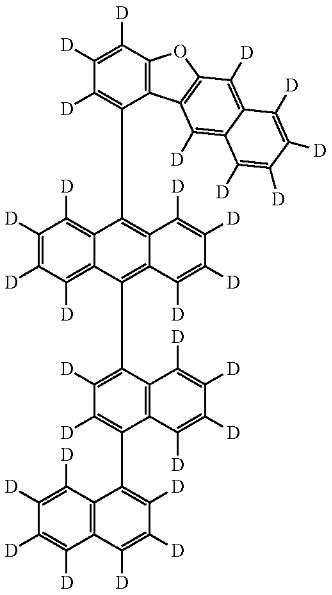
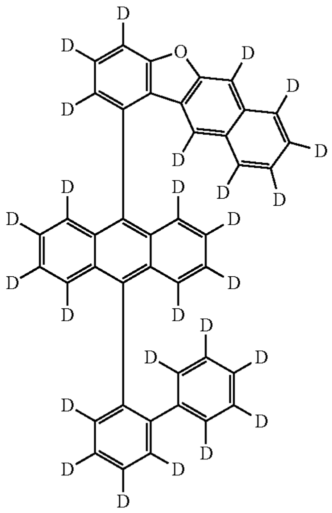
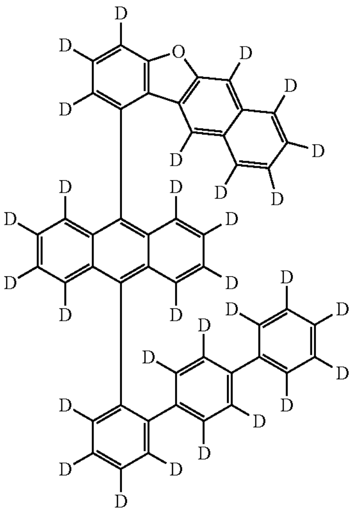
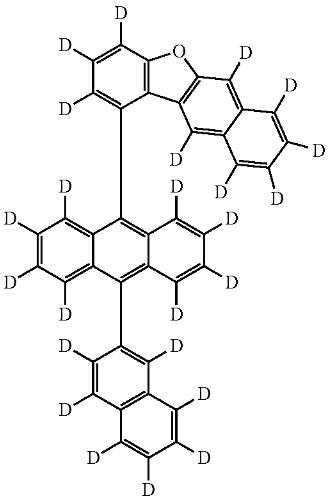
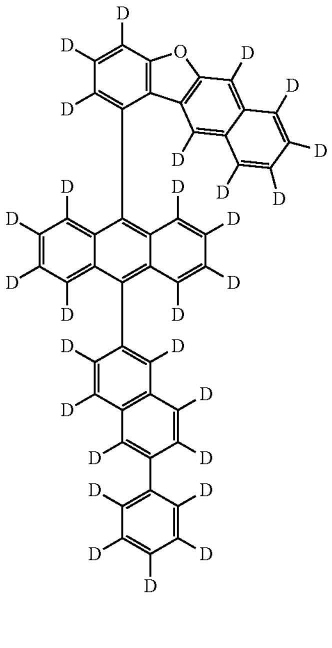

-continued
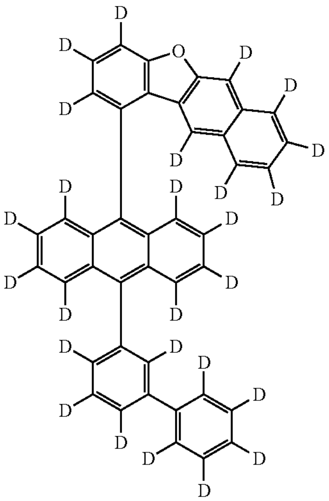
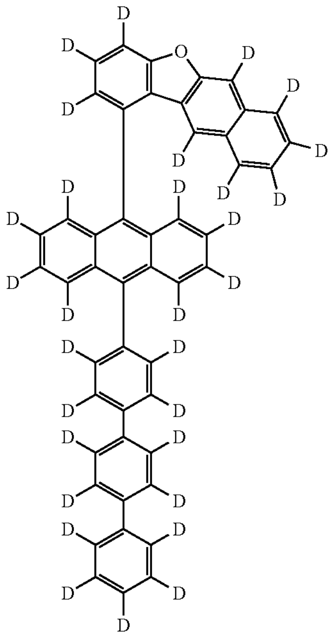
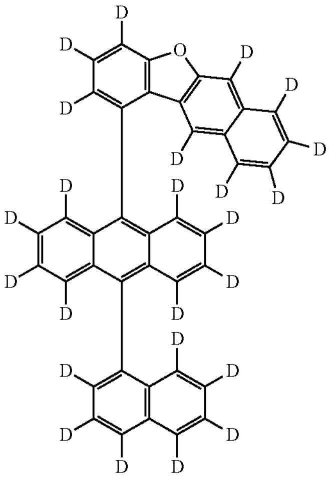
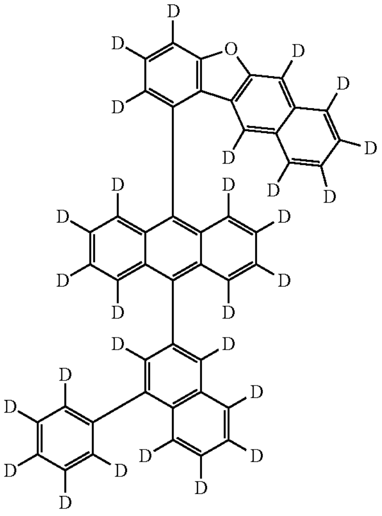
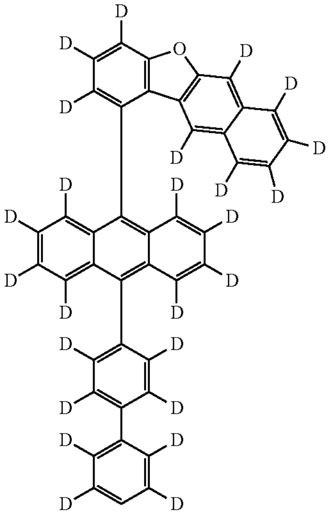
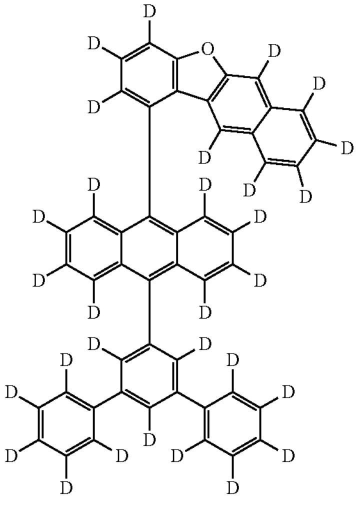

-continued
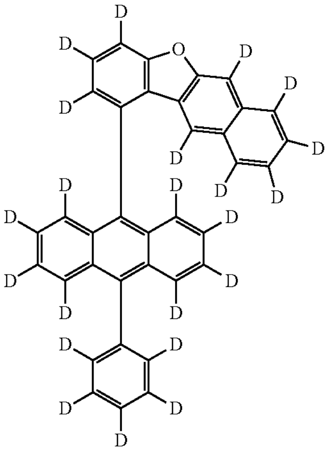
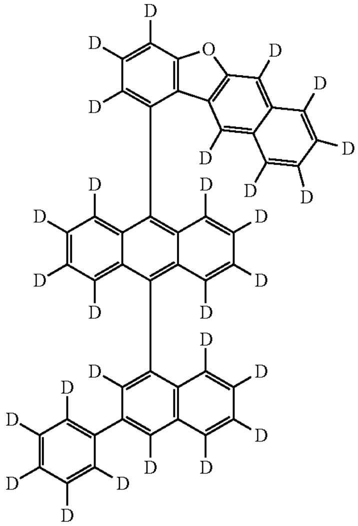
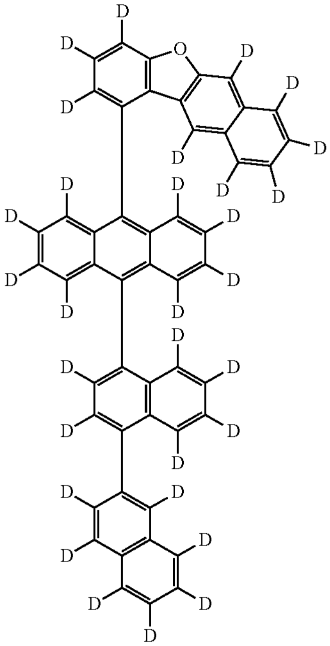
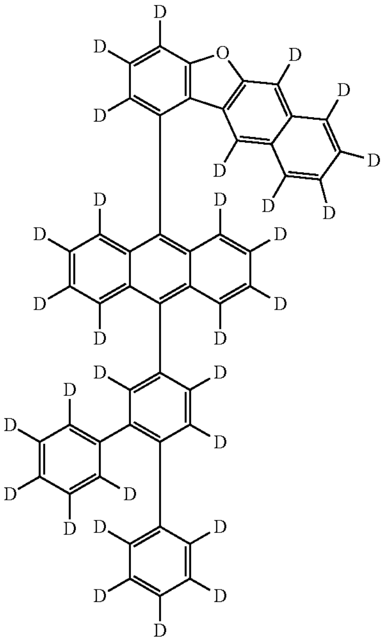

-continued
[Formula 104]
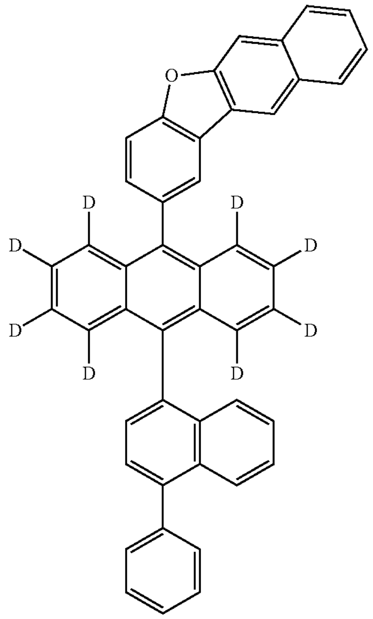
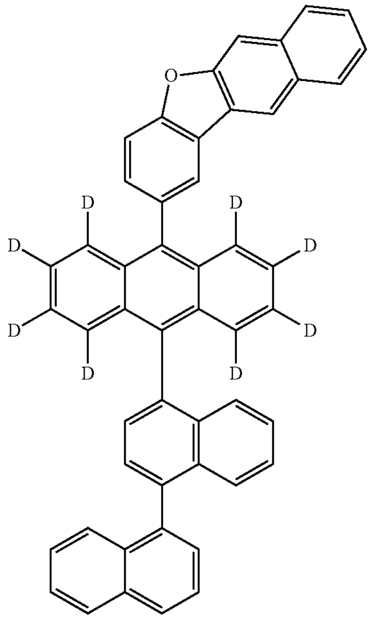
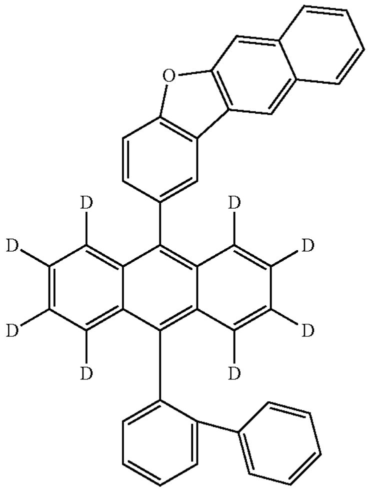
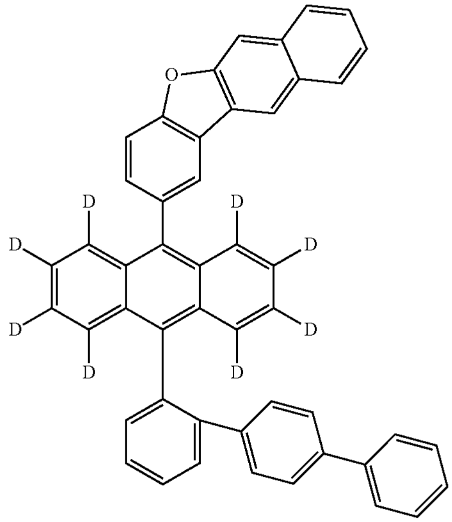
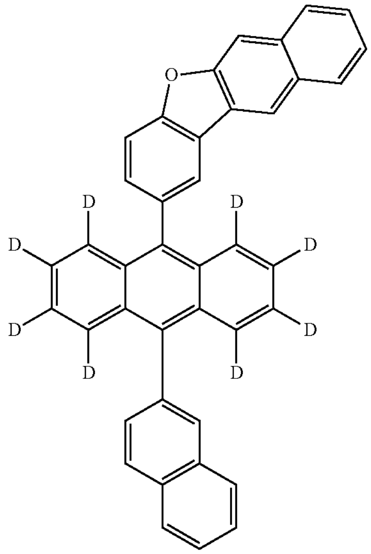
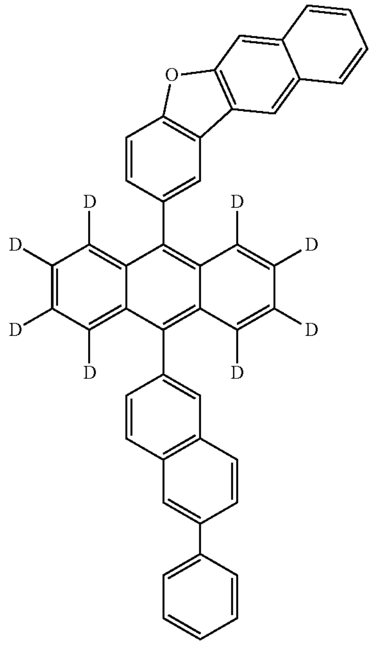

-continued
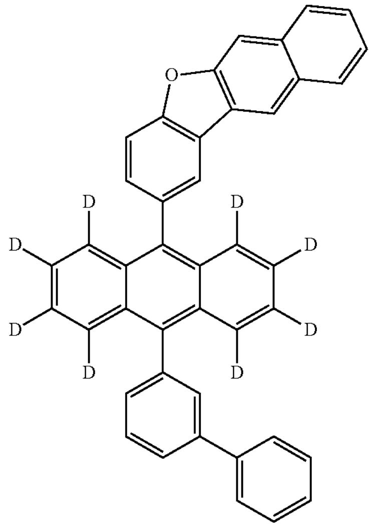
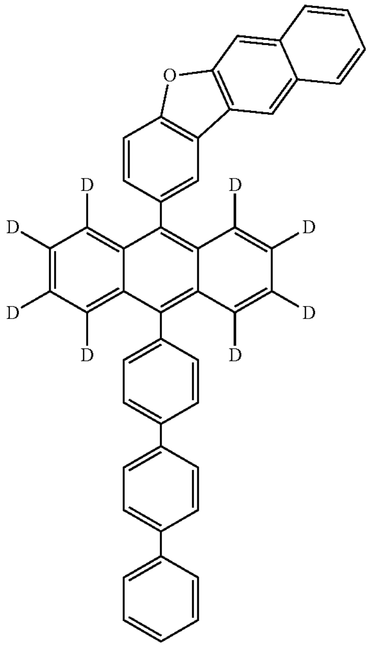
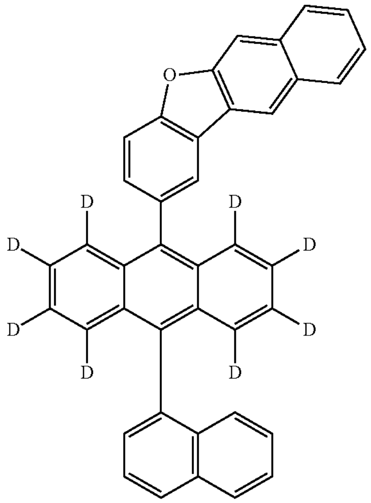
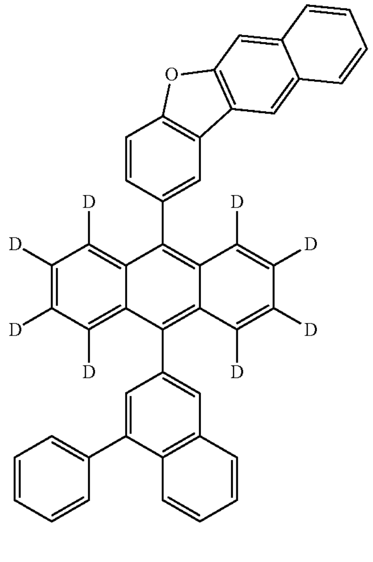
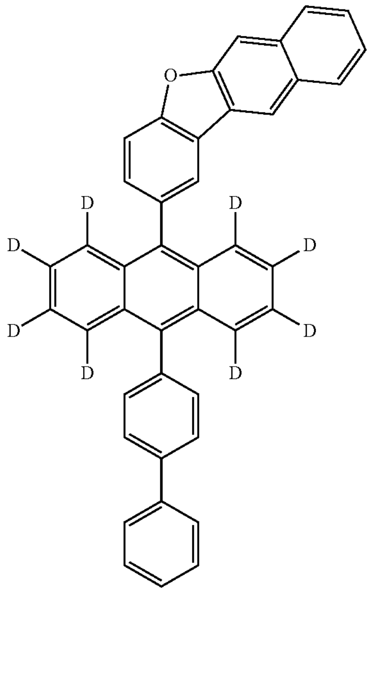
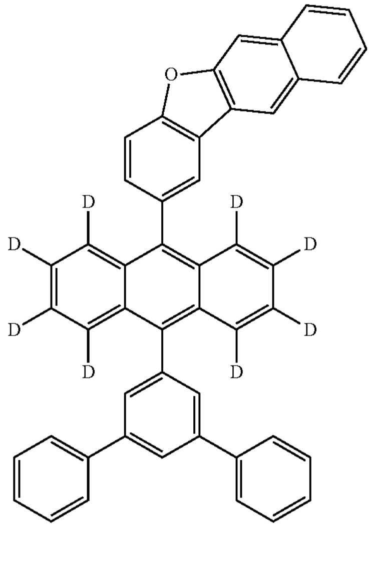

-continued
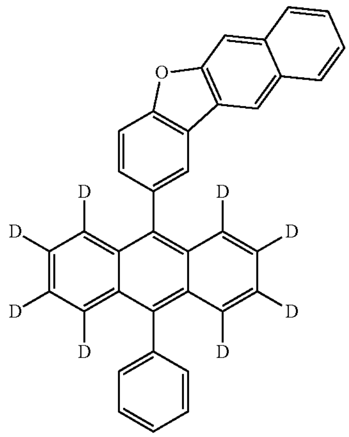
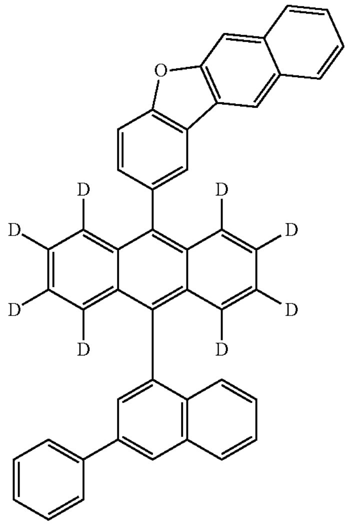
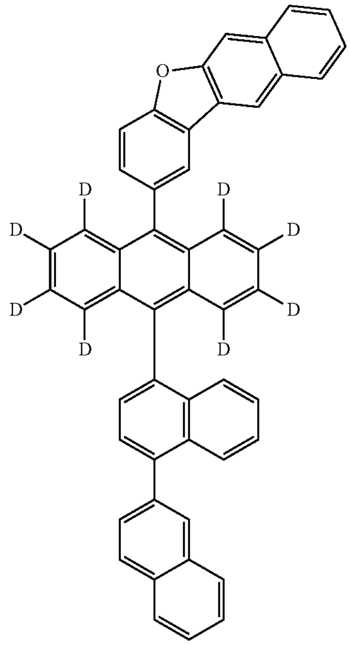
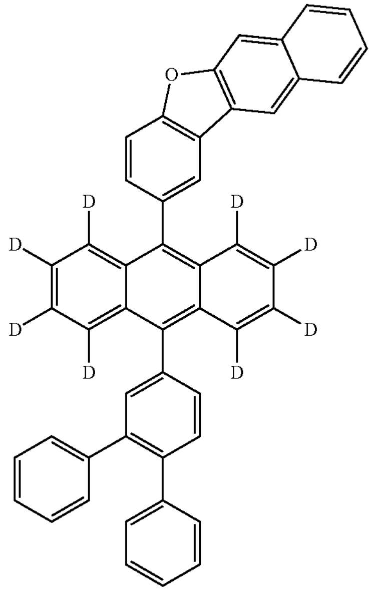

-continued
[Formula 105]
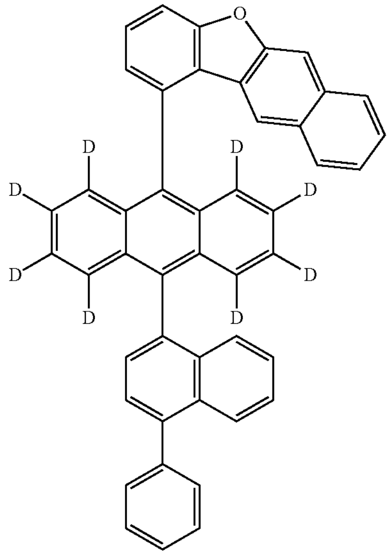
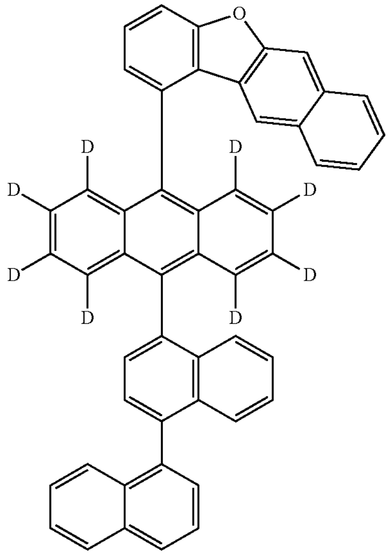
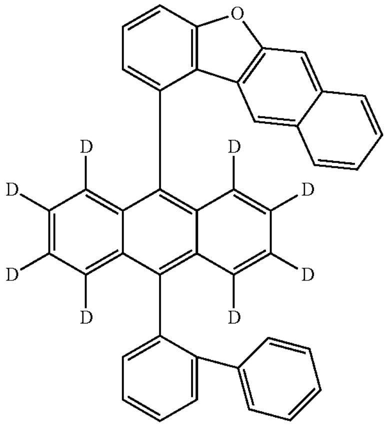
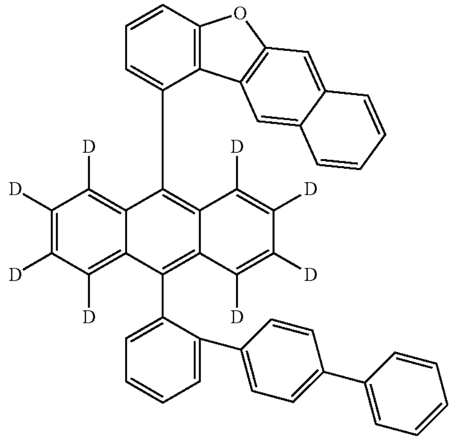
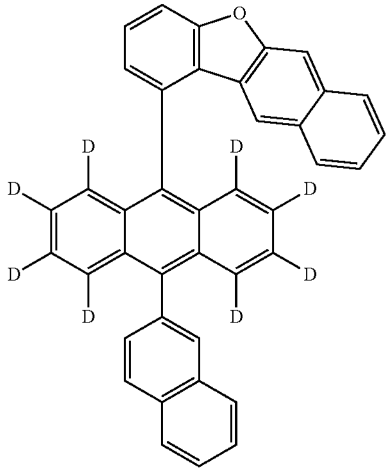
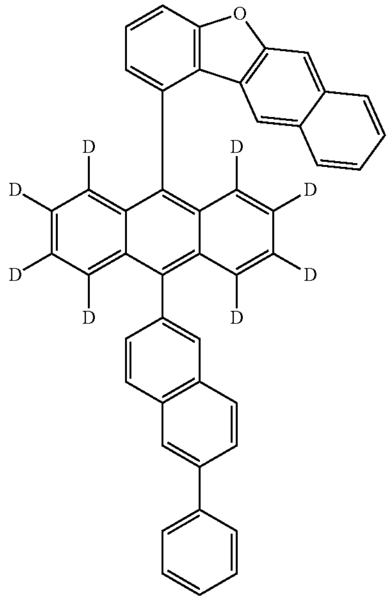
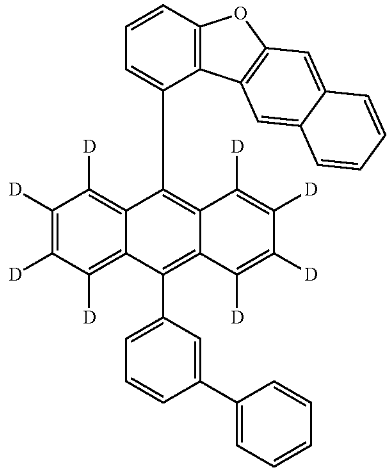
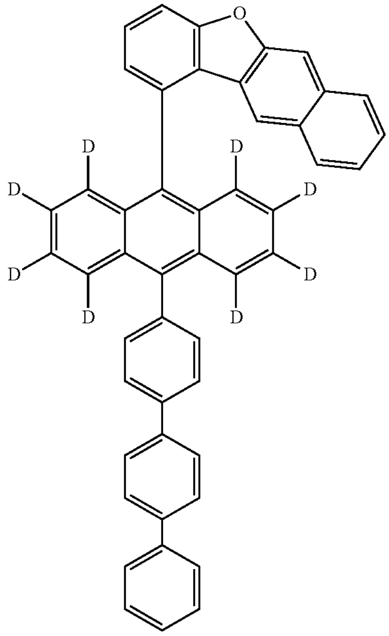

-continued
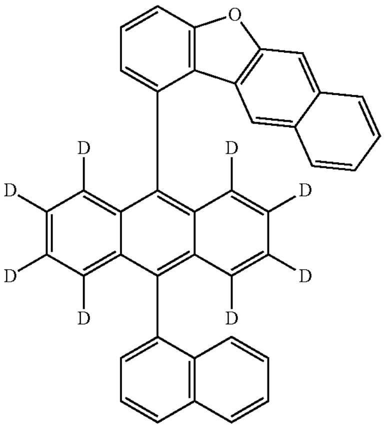
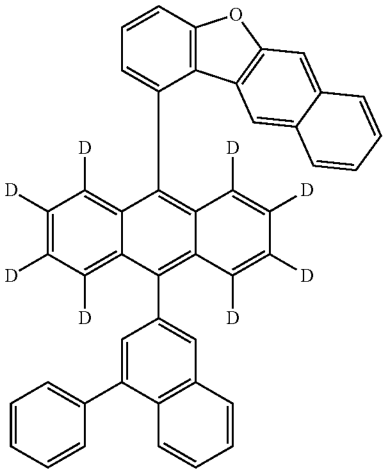
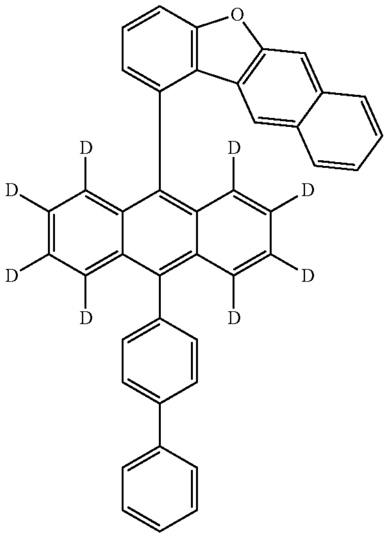
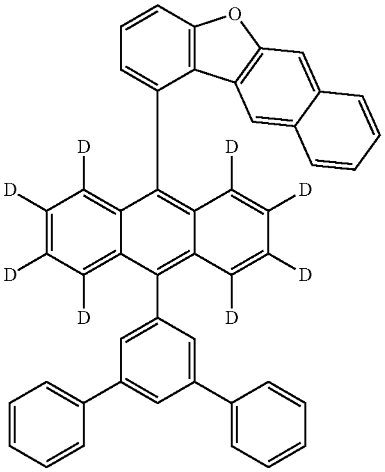
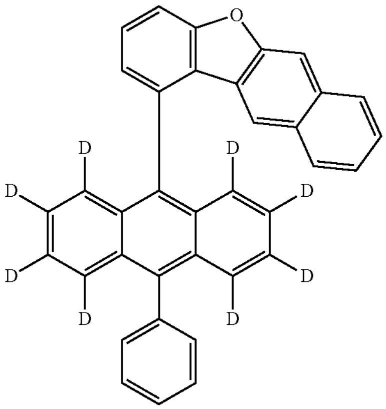
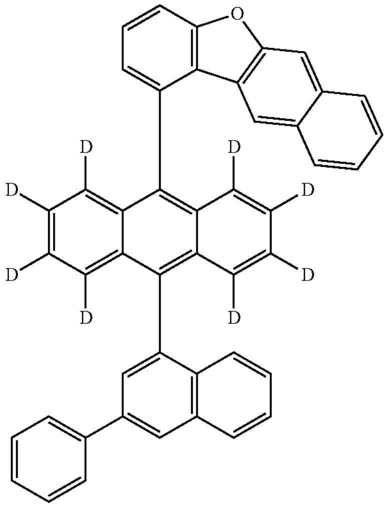
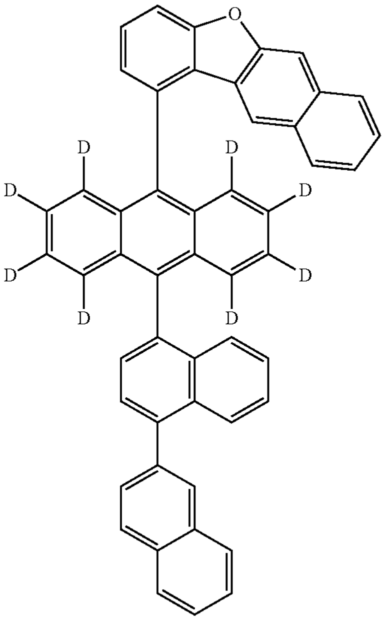
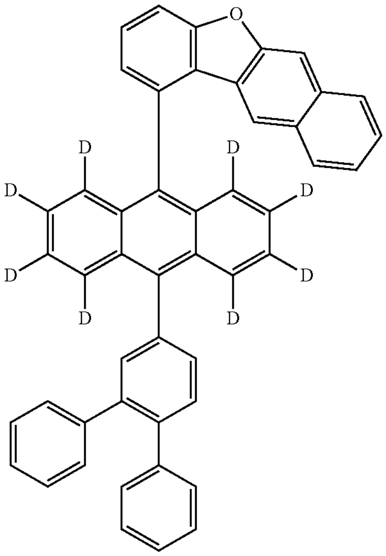

-continued
[Formula 106]
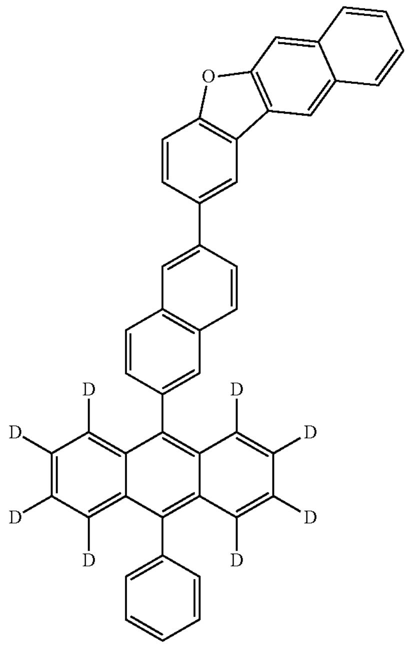
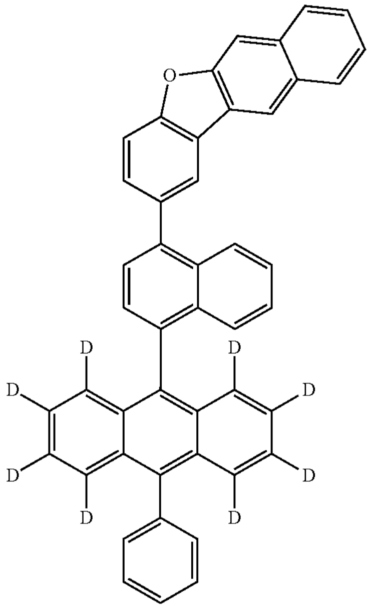
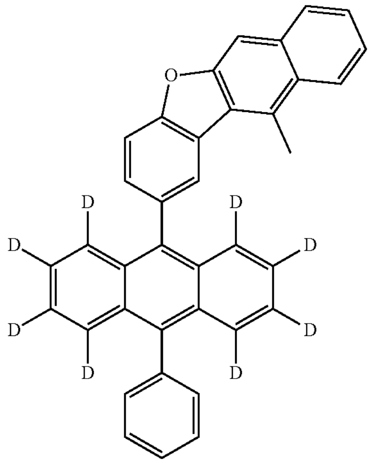
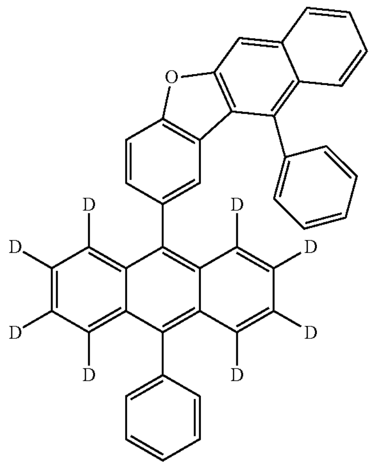
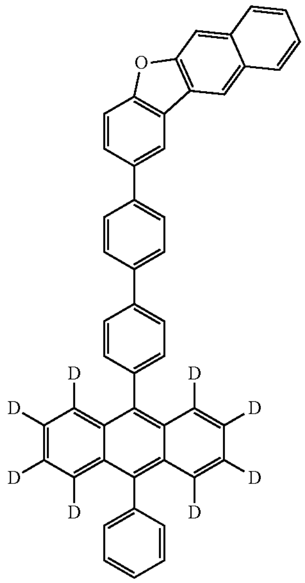
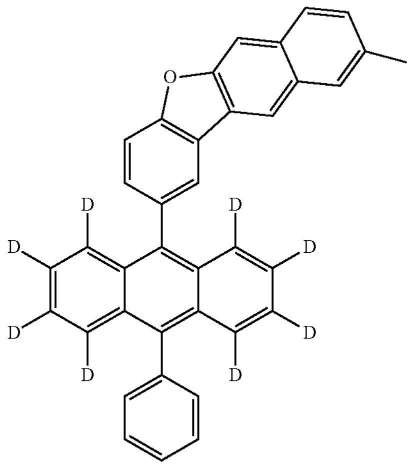
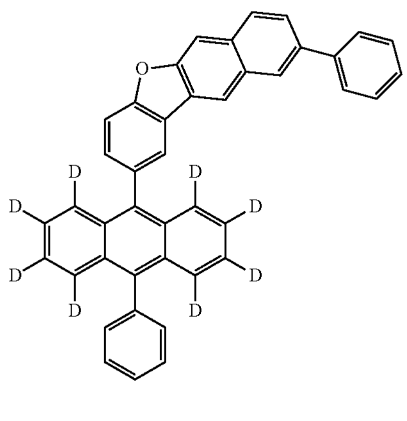
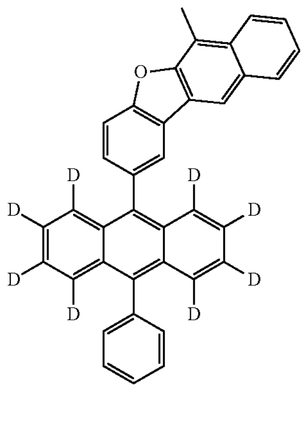
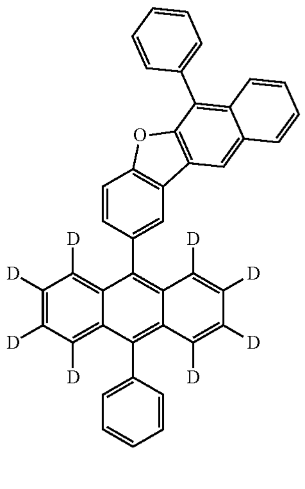

-continued
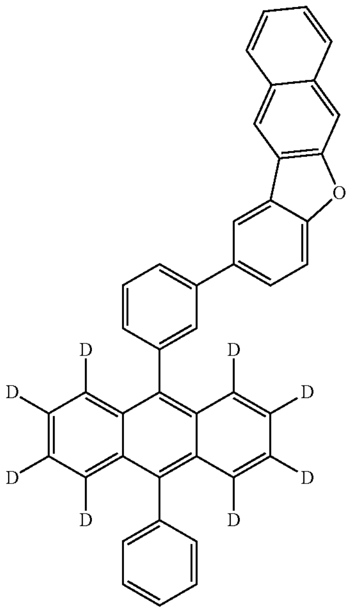
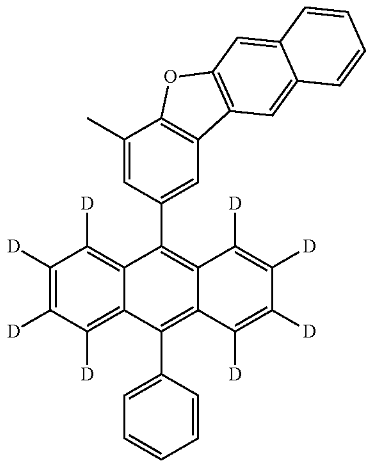
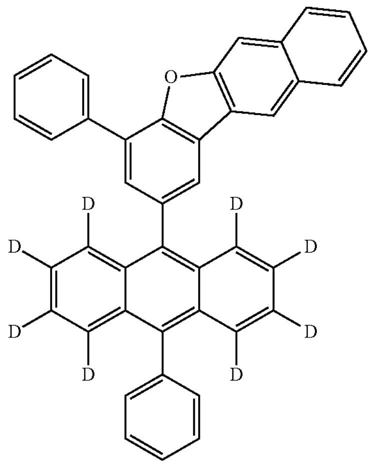
[Formula 107]
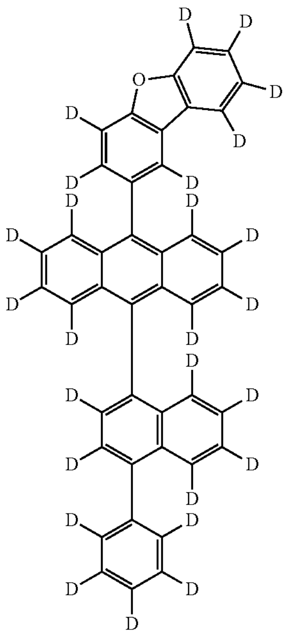
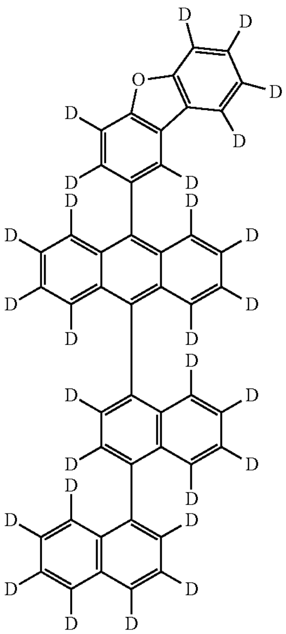
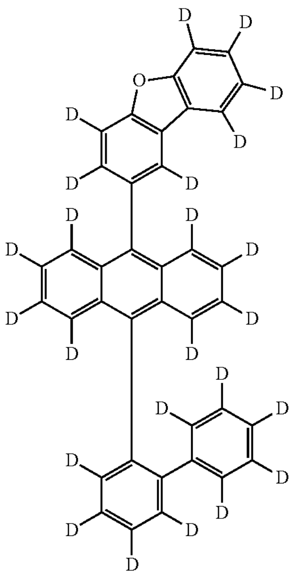

-continued
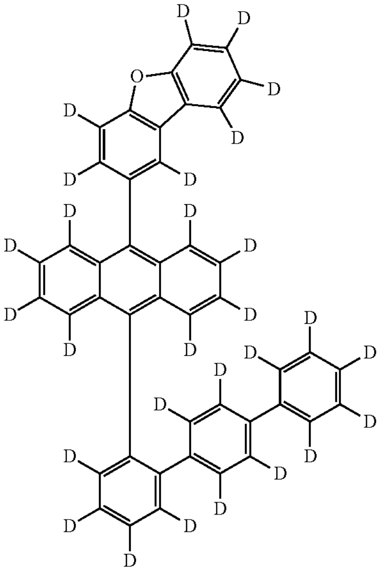
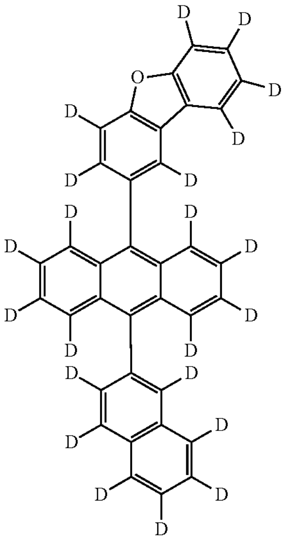
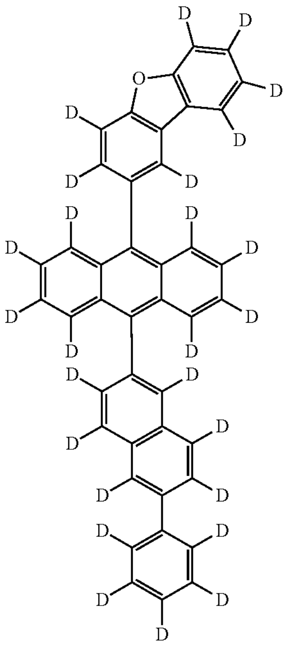
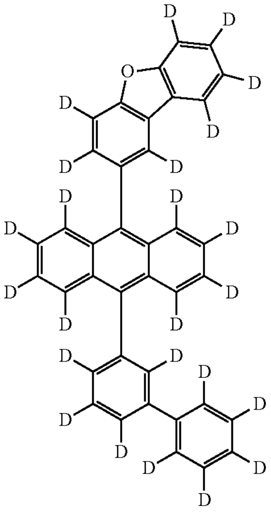
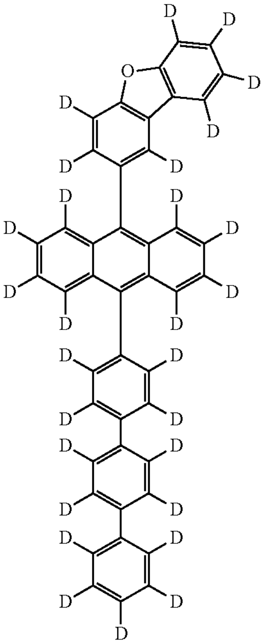
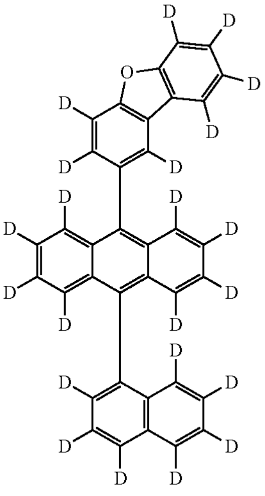

-continued
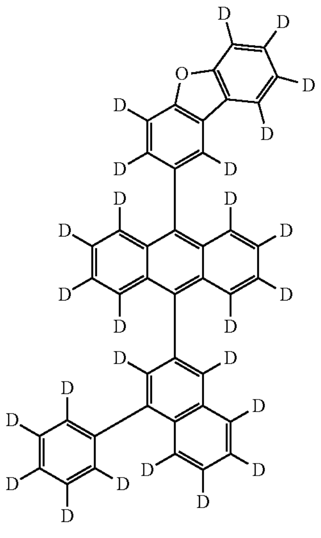
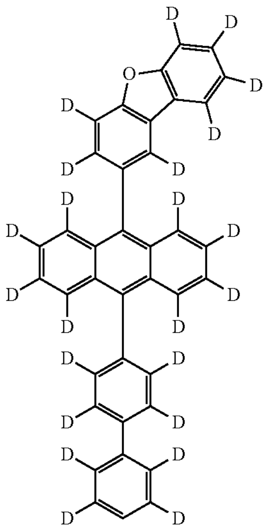
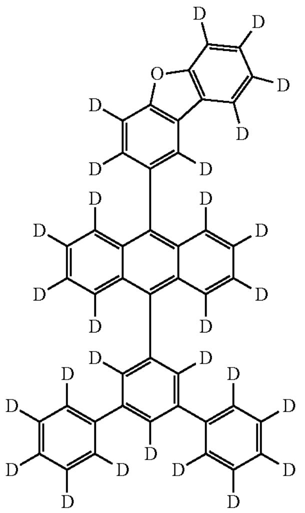
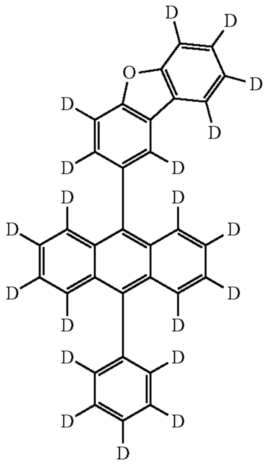
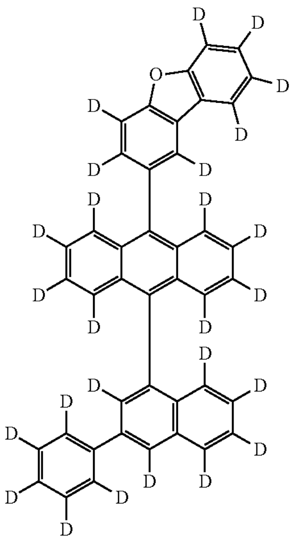
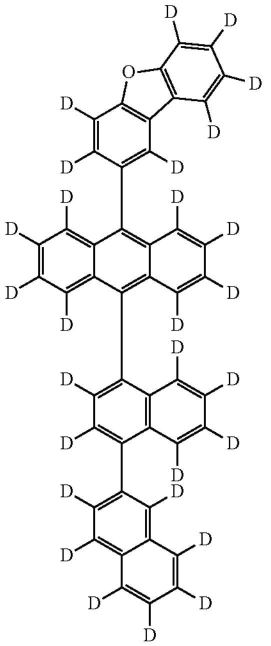
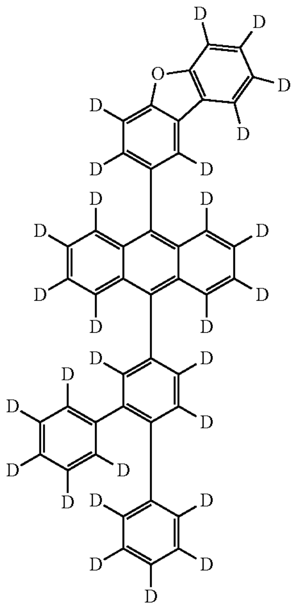

-continued
[Formula 108]
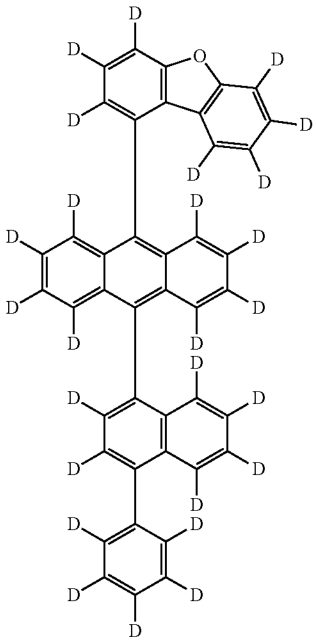
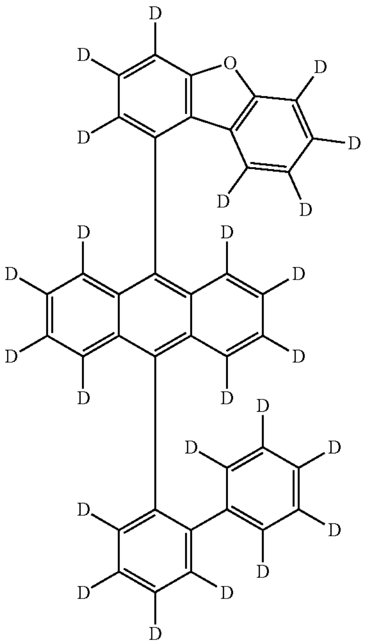
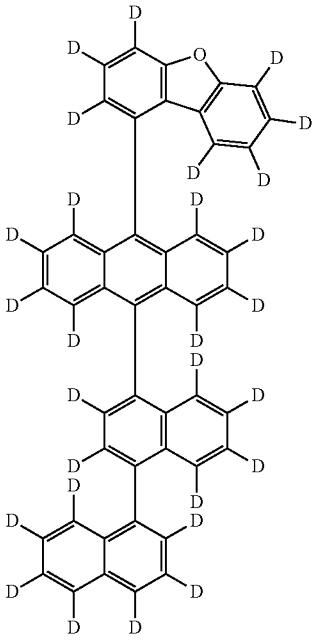
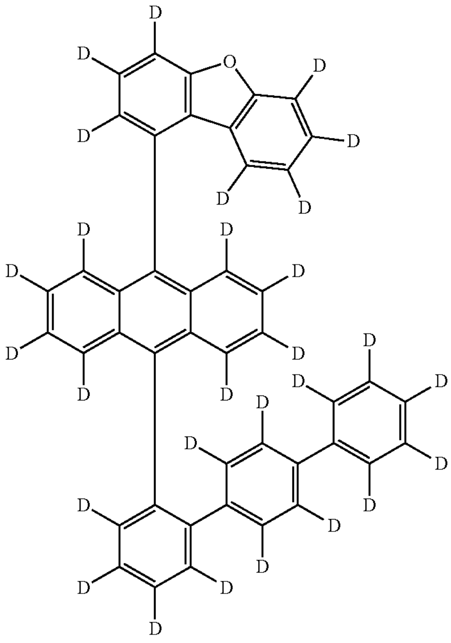

-continued
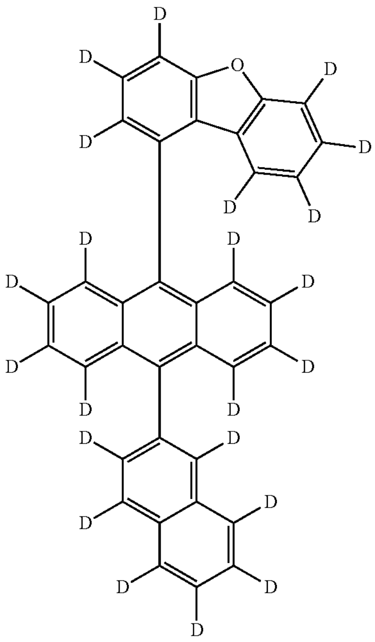
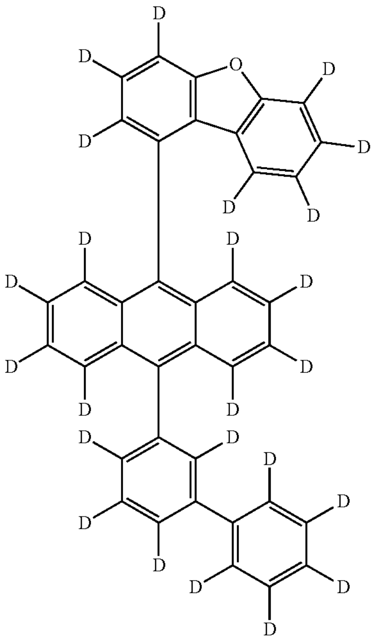
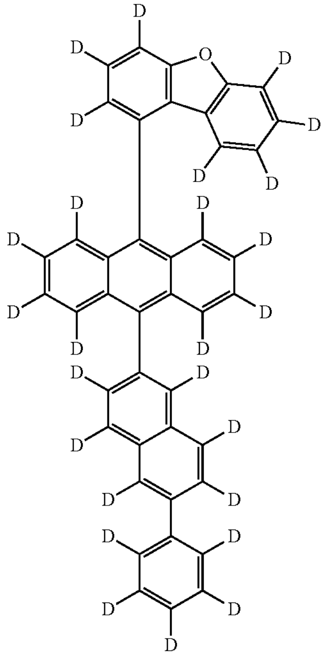
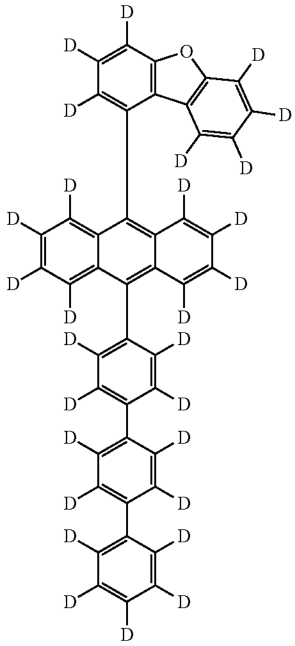

-continued
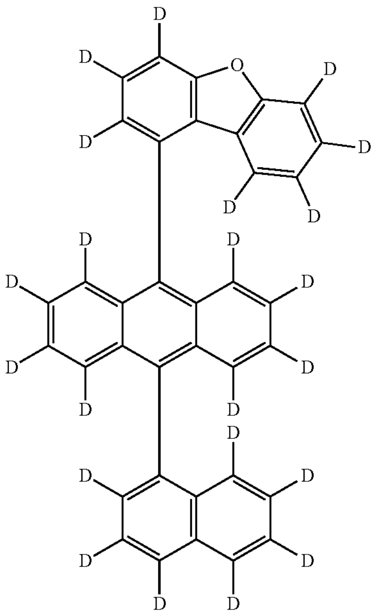
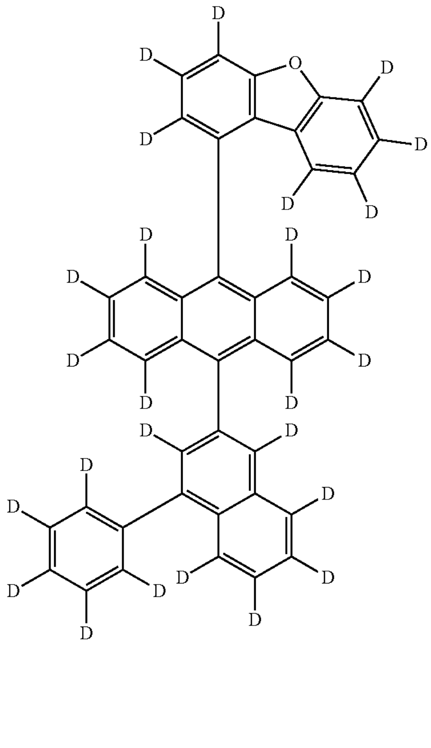
-continued
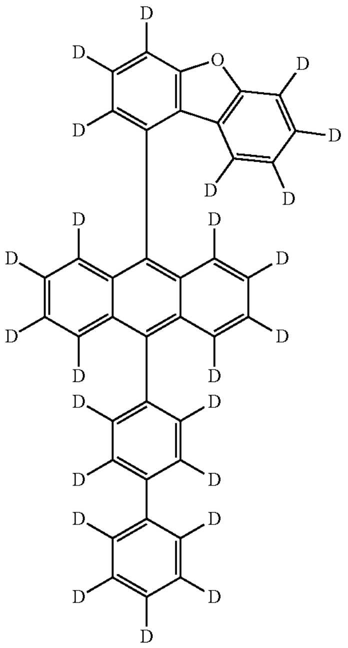
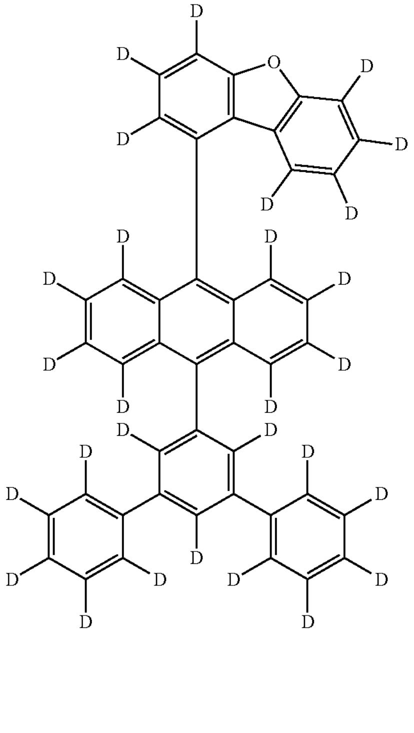

-continued
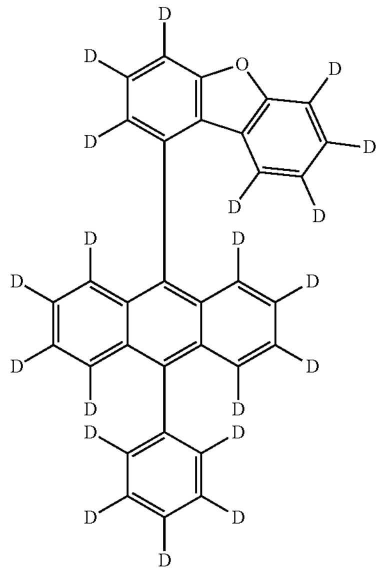
-continued
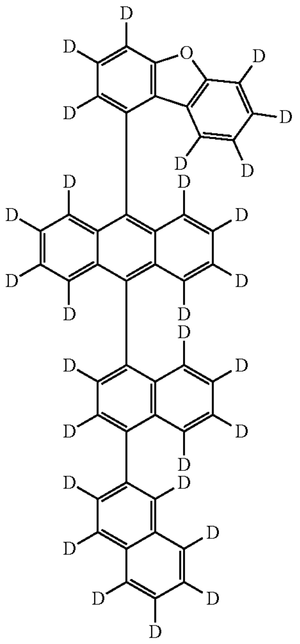
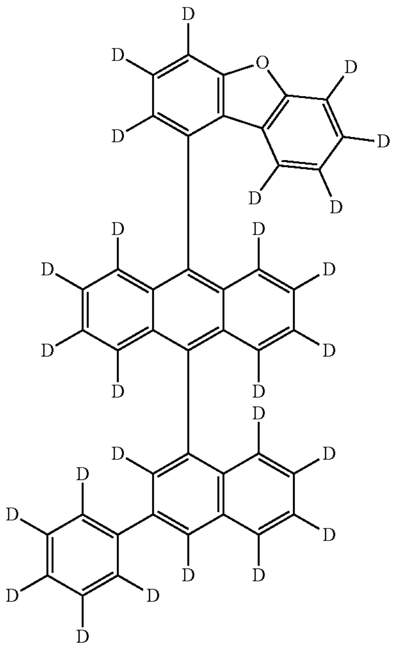
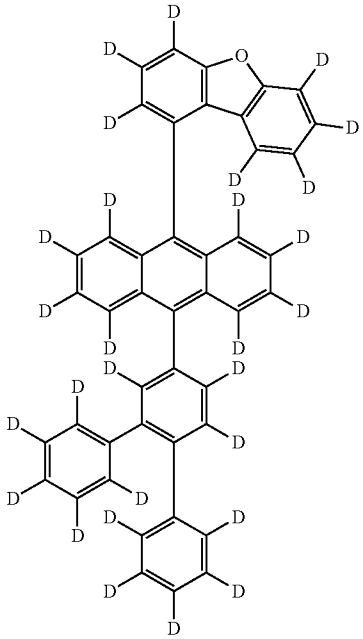

-continued
[Formula 109]
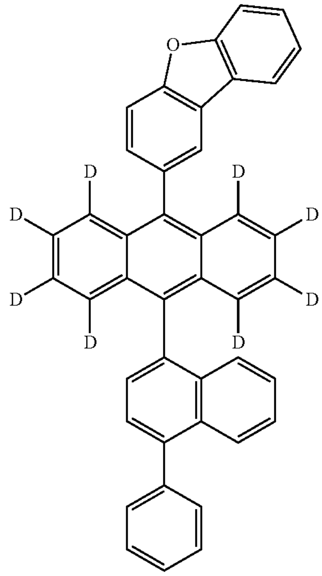
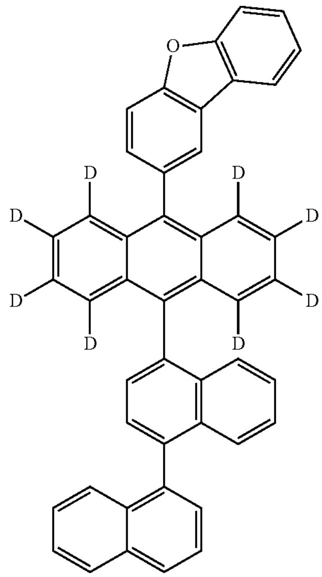
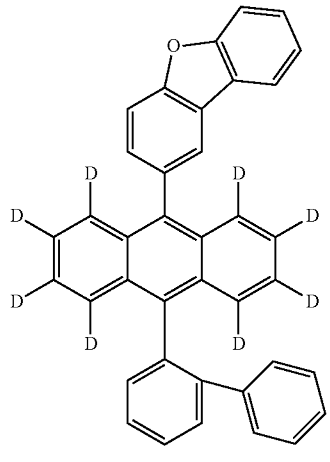
-continued
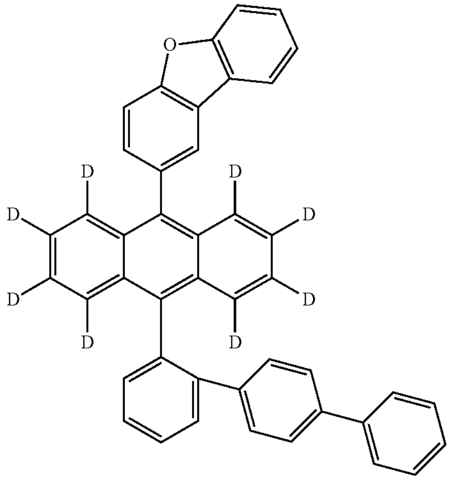
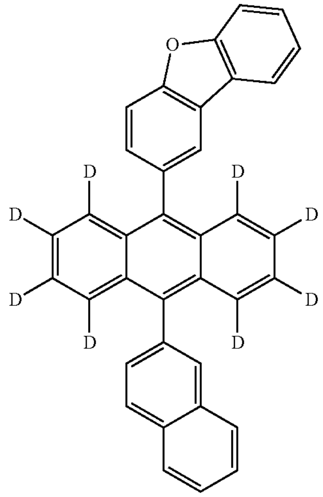
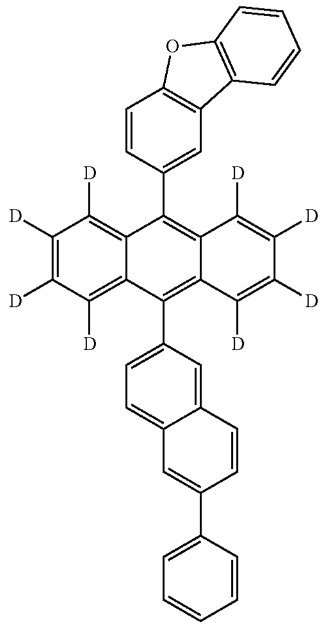

-continued
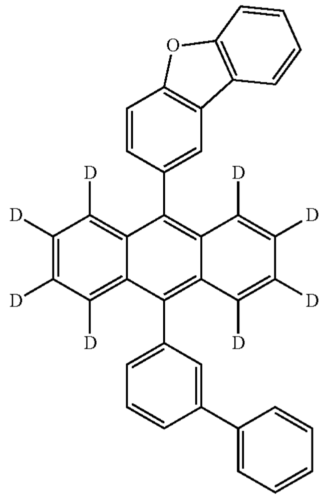
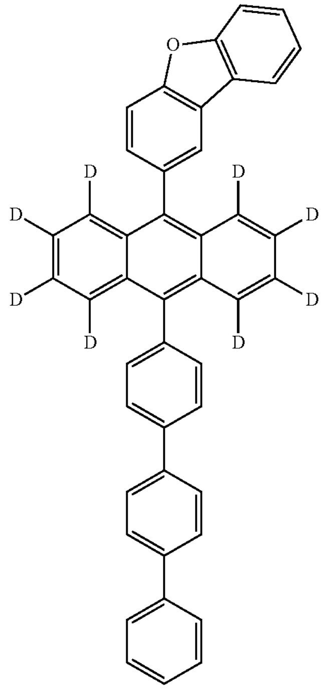
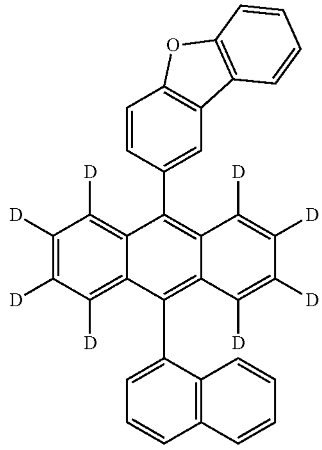
-continued
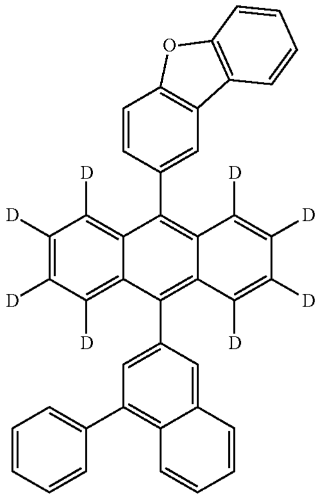
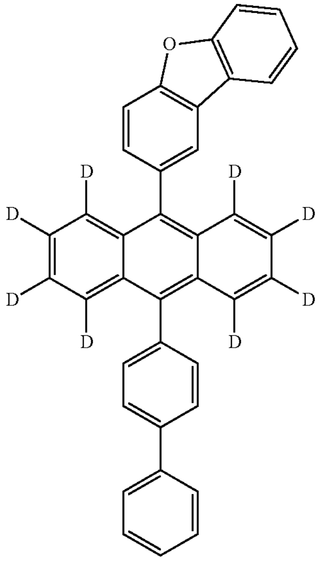
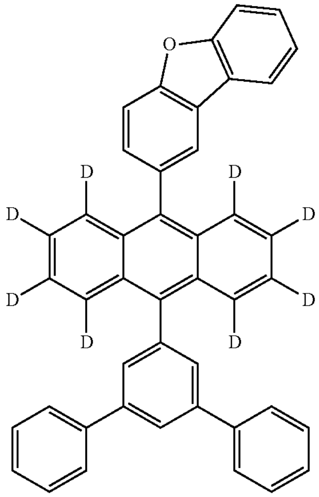

-continued
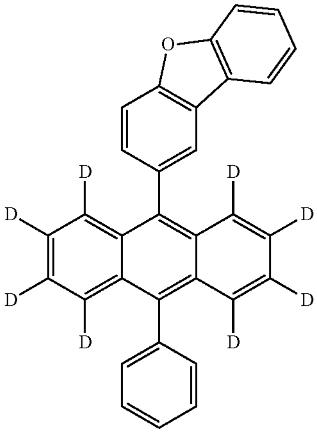
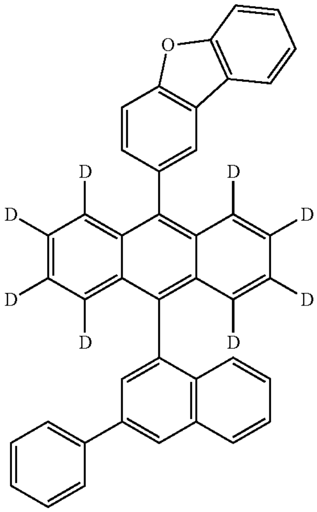
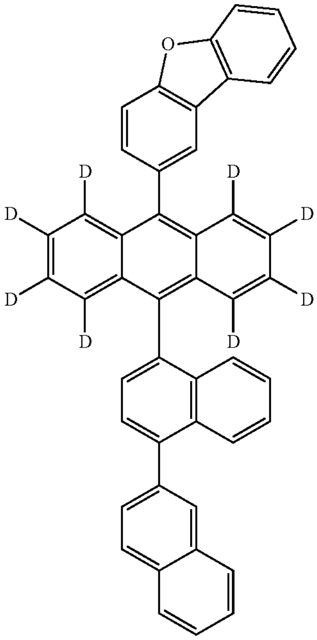
-continued
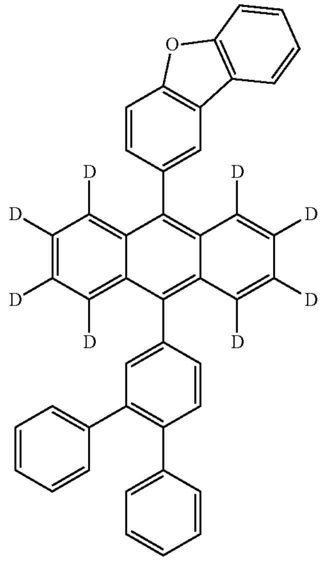 [SMILES: [2H]c1c([2H])c([2H])c2c(-c3ccc4oc5ccccc5c4c3)c3c([2H])c([2H])c([2H])c([2H])c3c(-c3ccc(-c4ccccc4)c(-c4ccccc4)c3)c2c1[2H]]
[Formula 110]
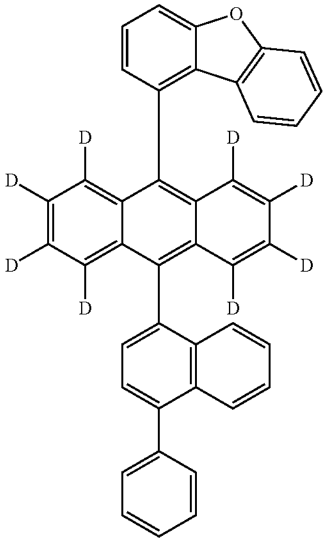
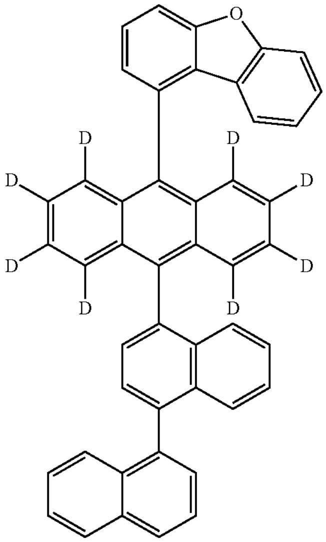

-continued
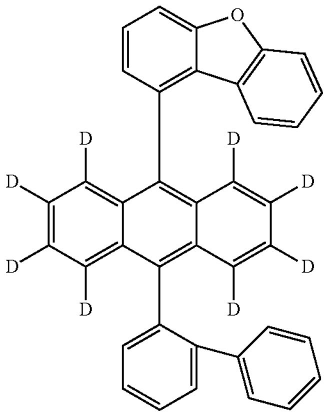
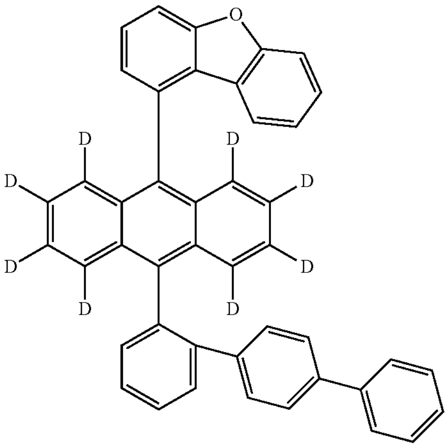
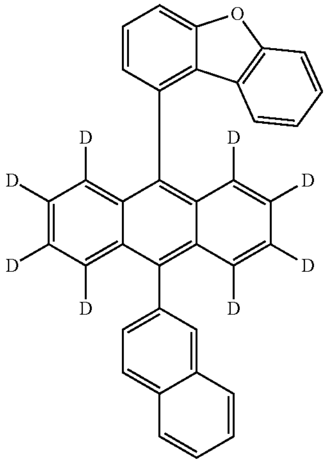
-continued
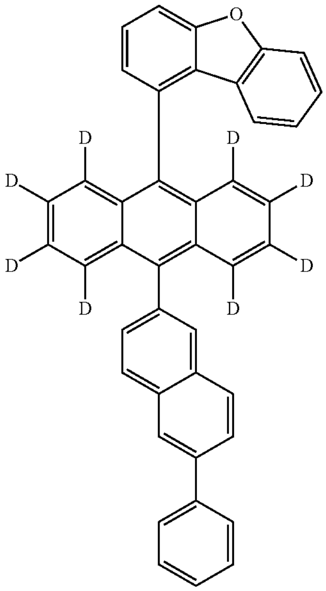
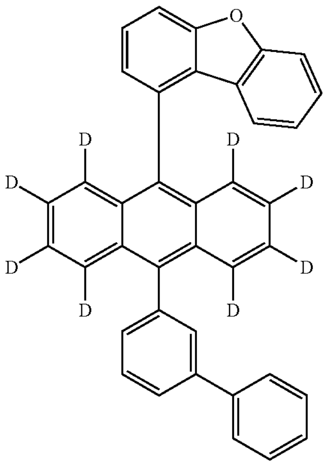
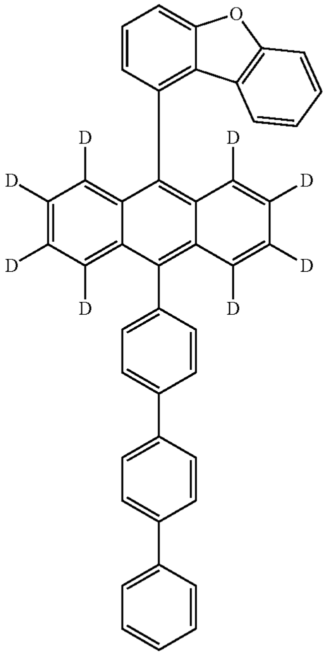

-continued
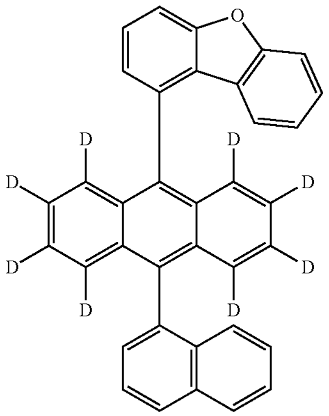
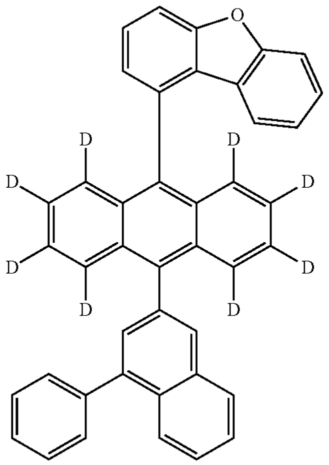
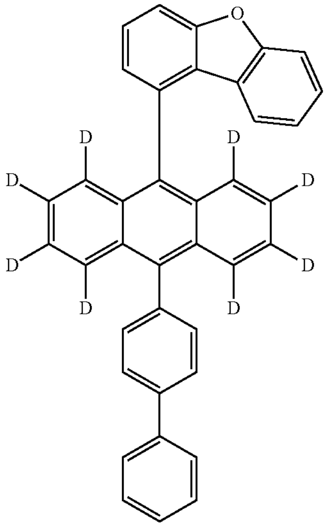
-continued
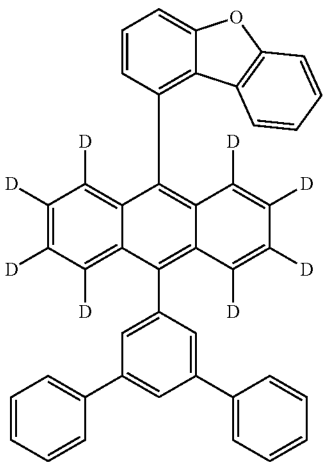
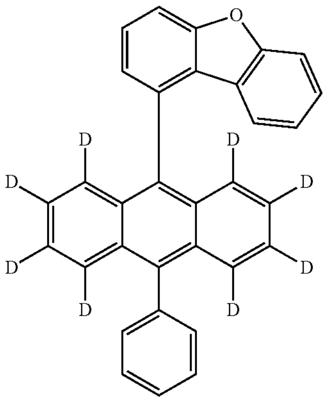
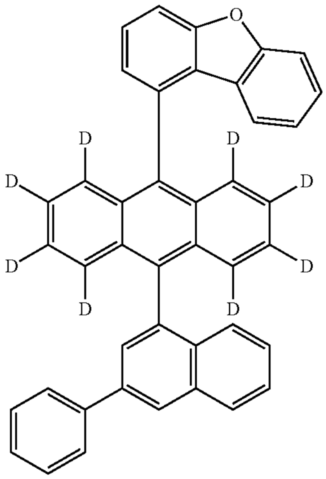

-continued
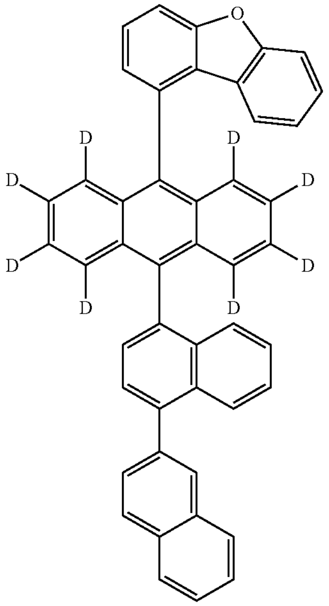
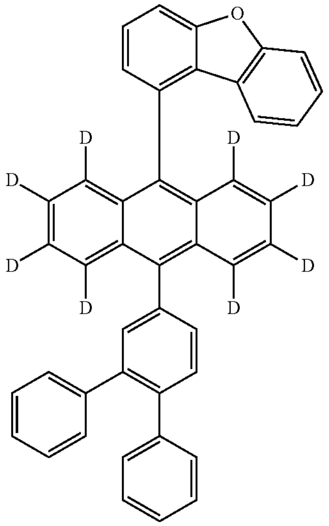 [SMILES: [2H]c1c([2H])c([2H])c2c(-c3cccc4oc5ccccc5c34)c3c([2H])c([2H])c([2H])c([2H])c3c(-c3ccc(-c4ccccc4)c(-c4ccccc4)c3)c2c1[2H]]
[Formula 111]
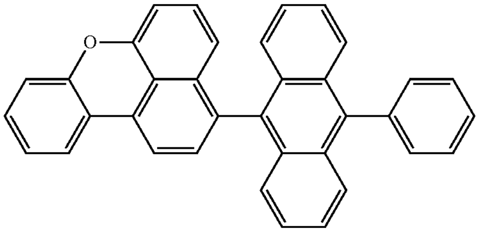
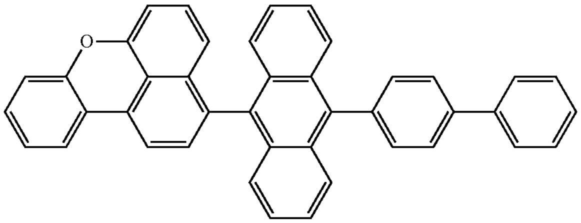
-continued
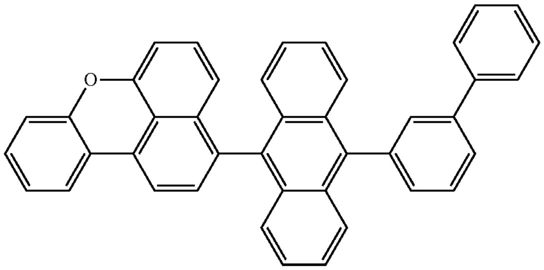
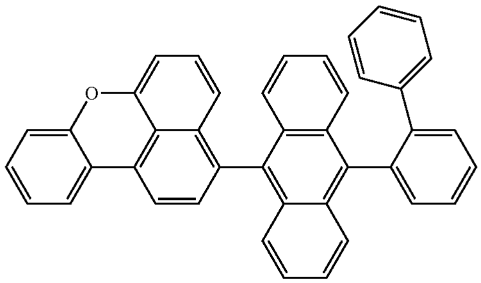
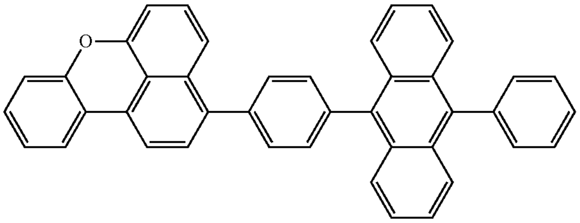
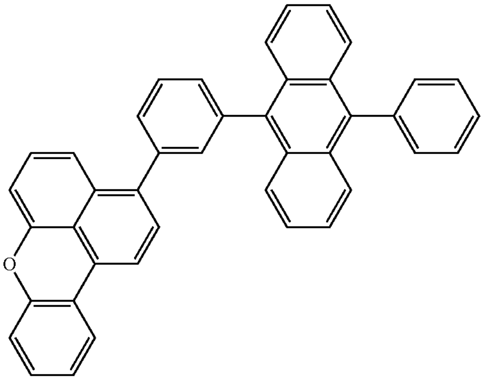
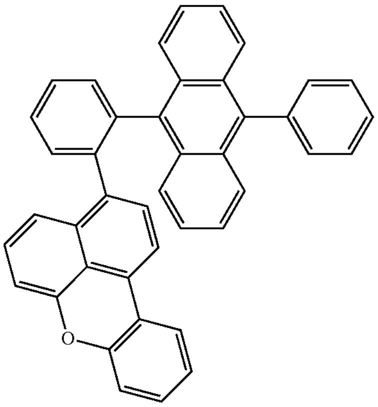

-continued
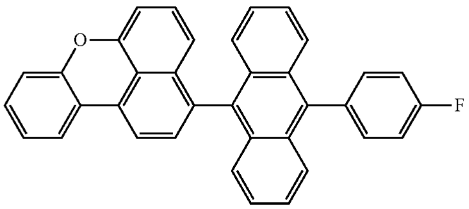
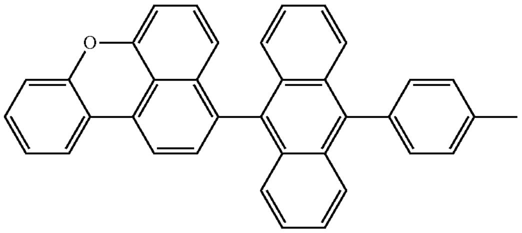
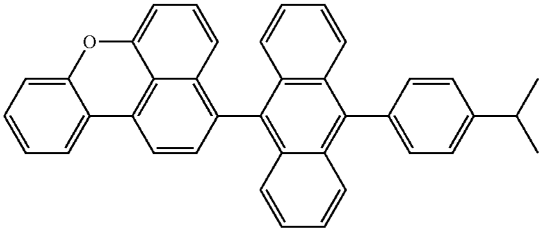
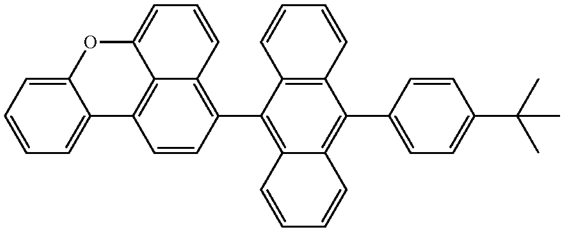
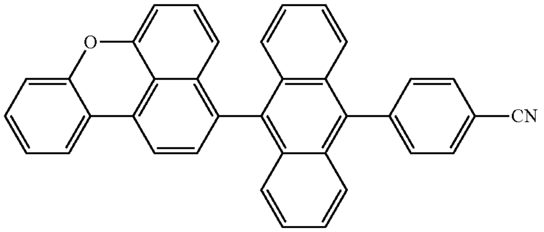
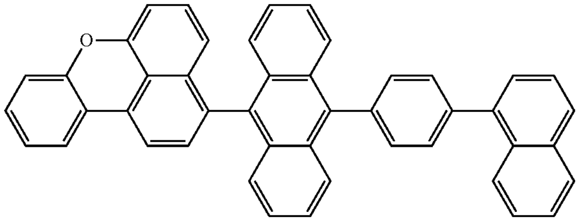
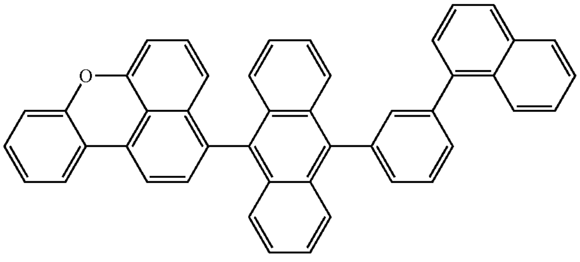
-continued
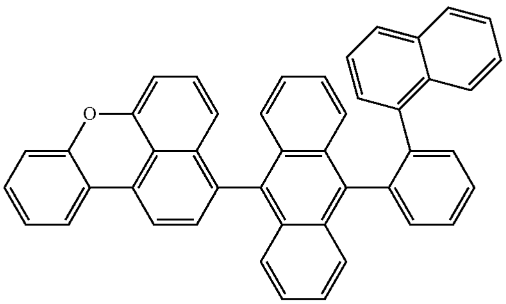
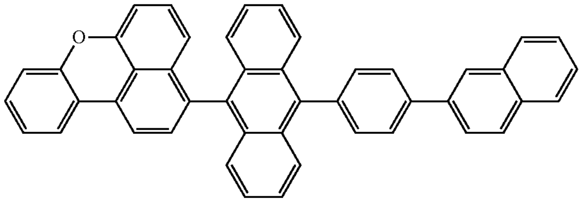
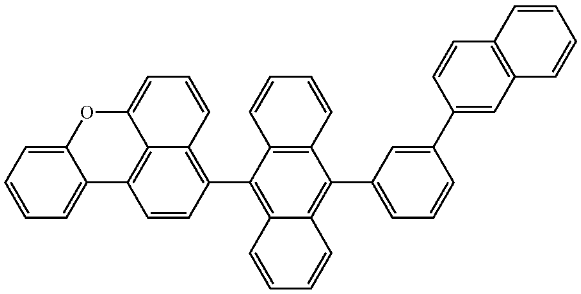
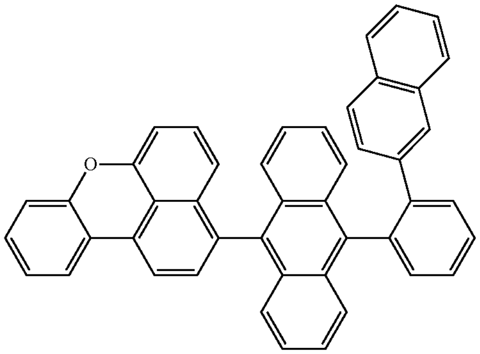
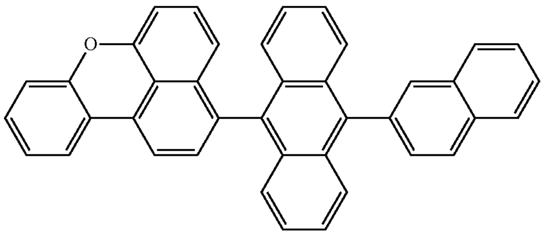
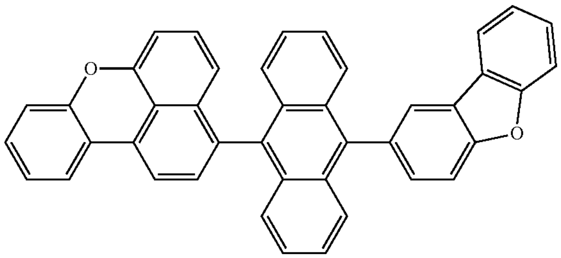

-continued
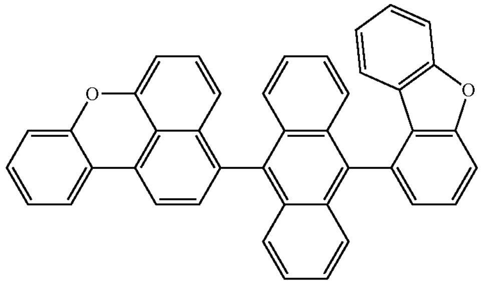
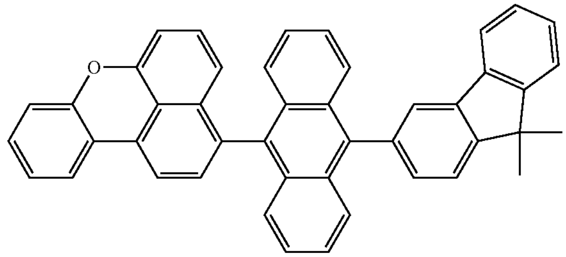
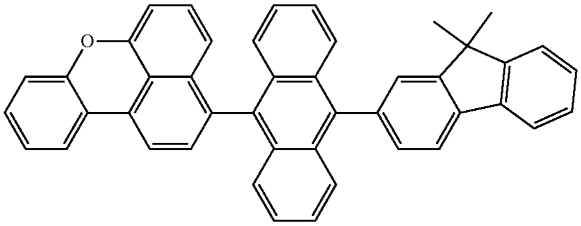
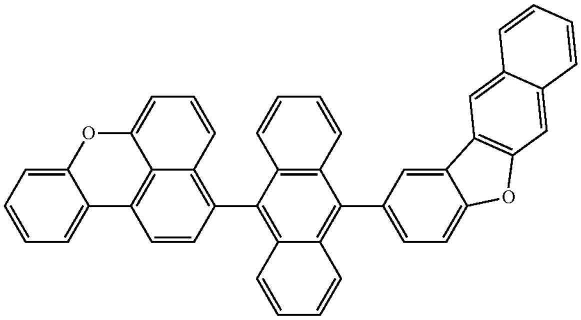
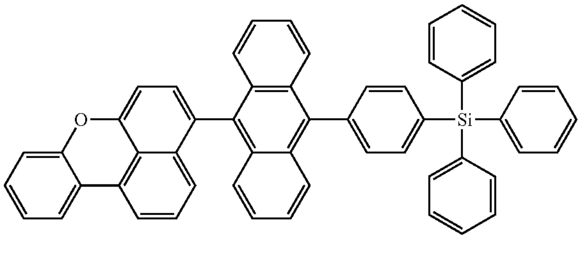
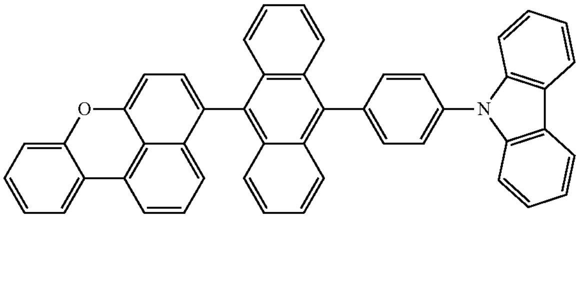
-continued
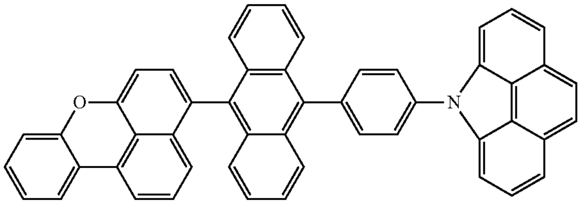
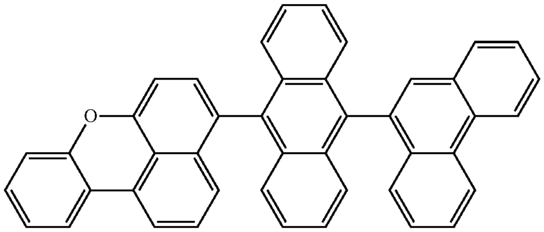
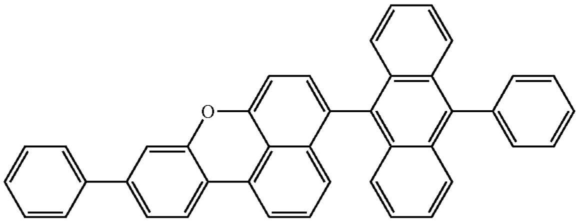
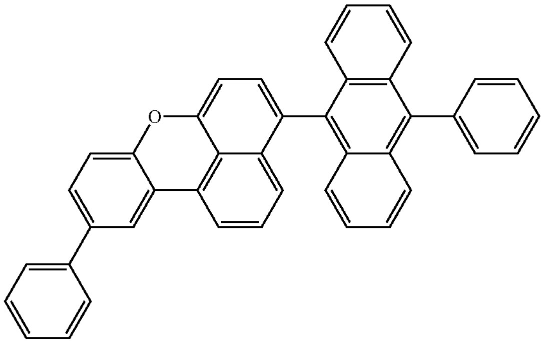
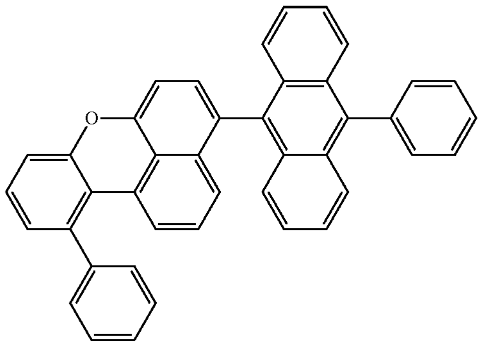
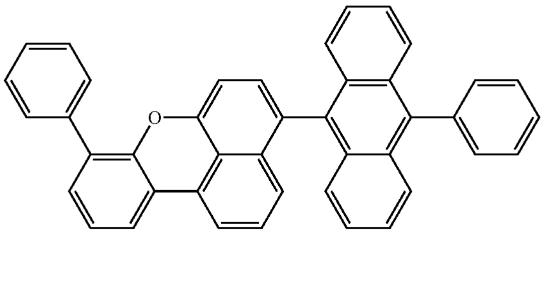

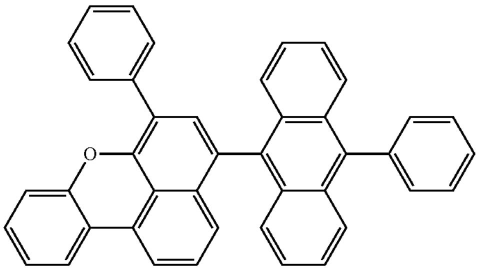
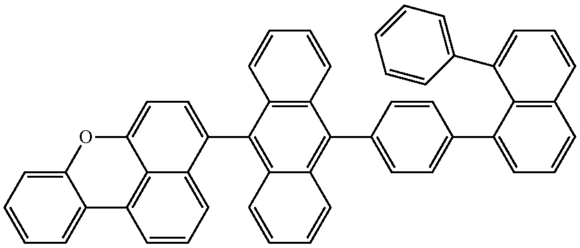
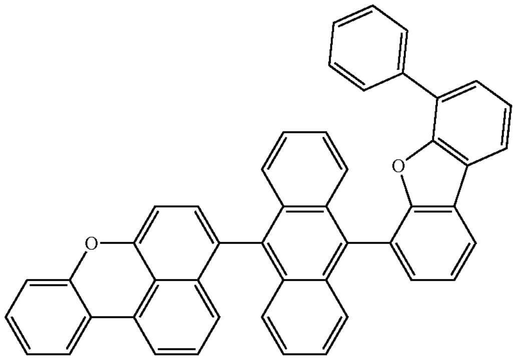
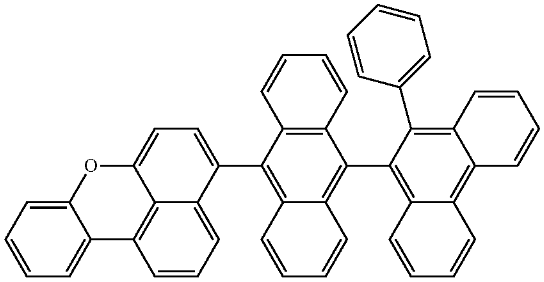
[Formula 112]
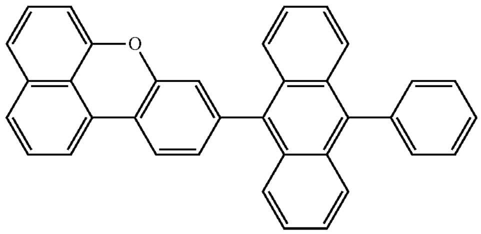
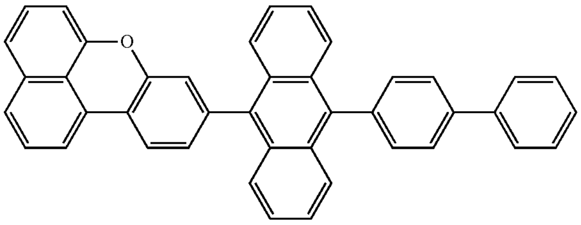
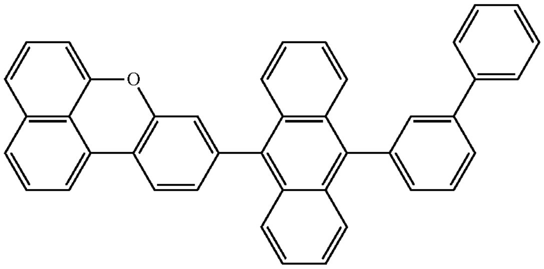
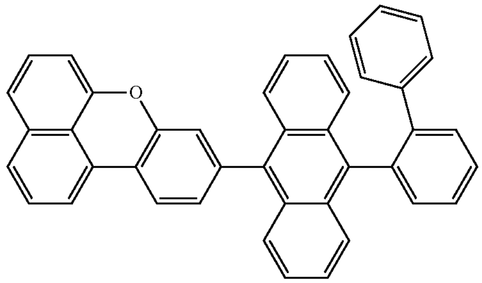
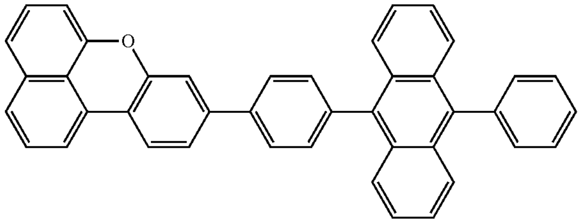
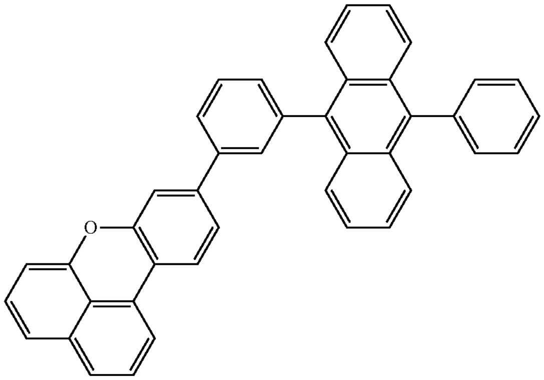
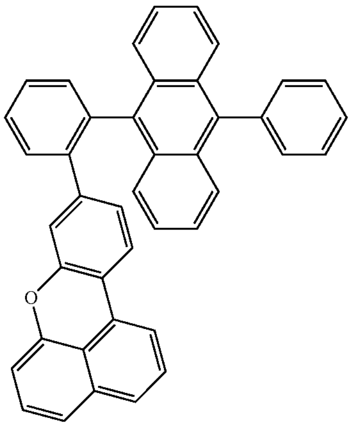

-continued
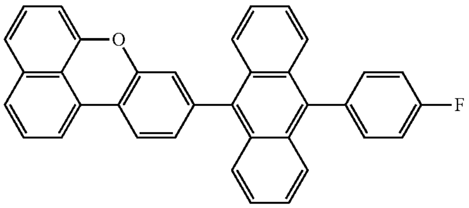
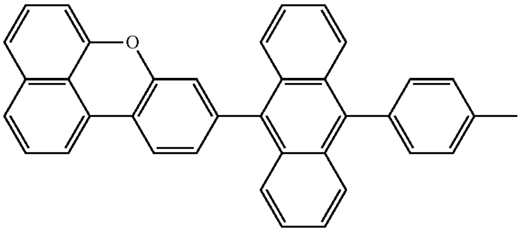
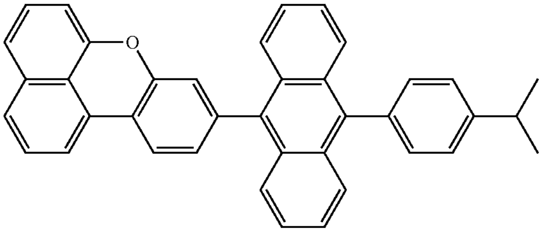
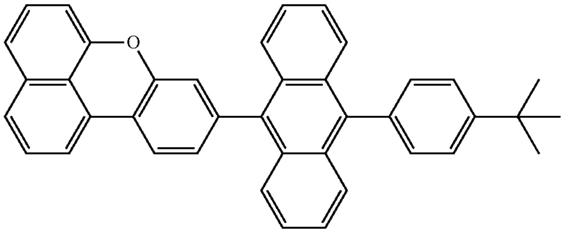
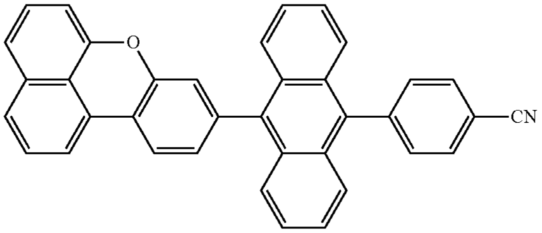
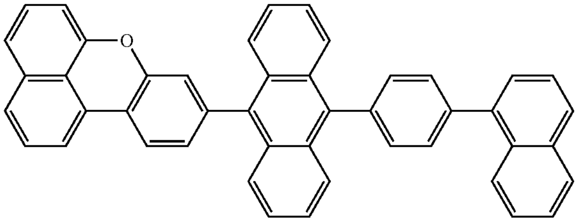
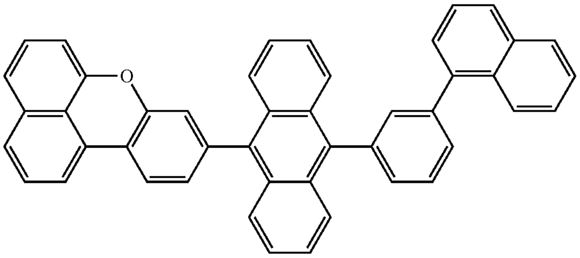
-continued
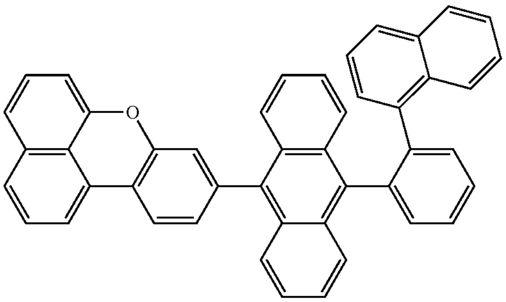
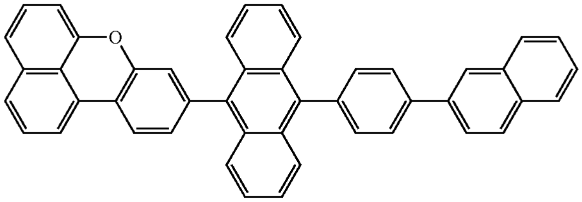
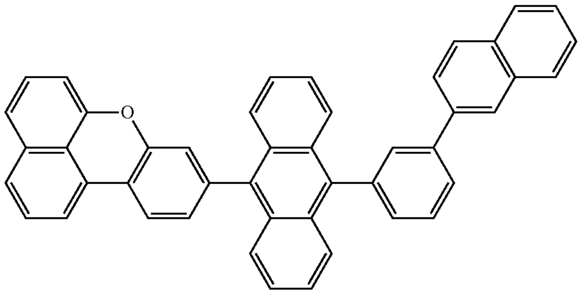
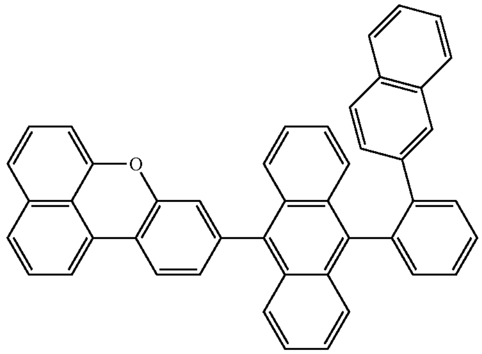
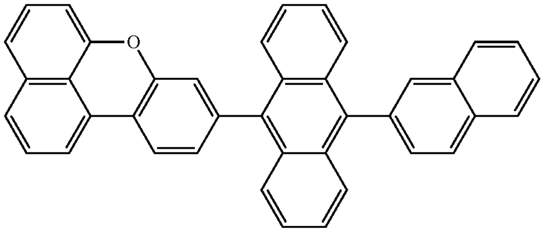
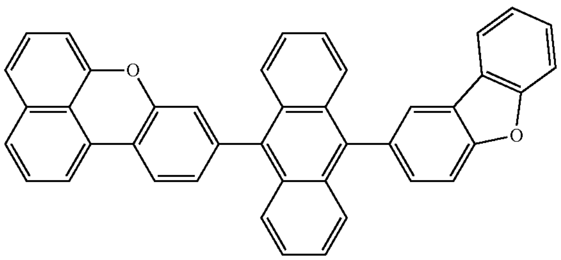

-continued
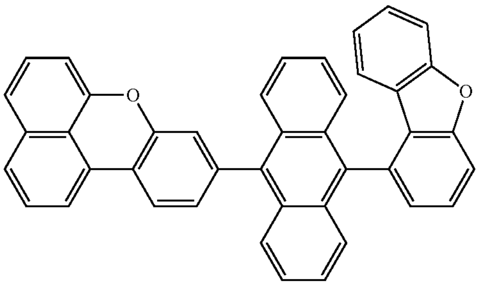
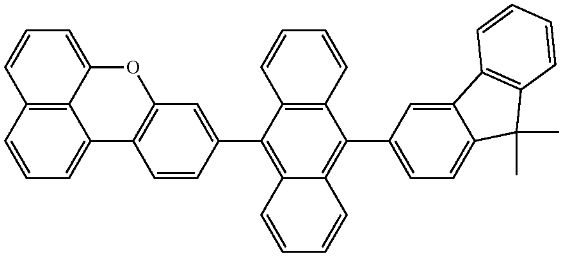
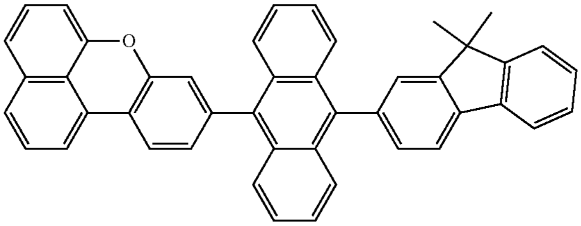
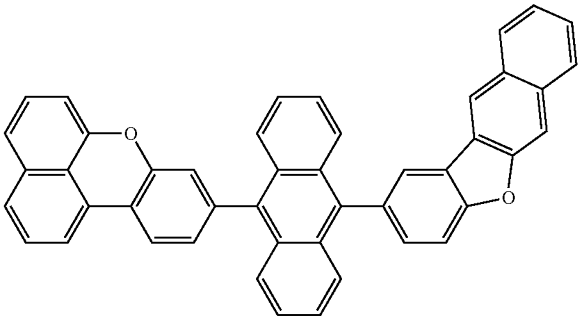
[Formula 113]
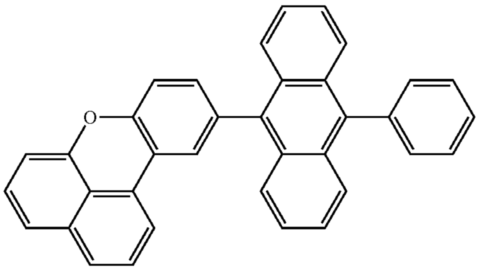
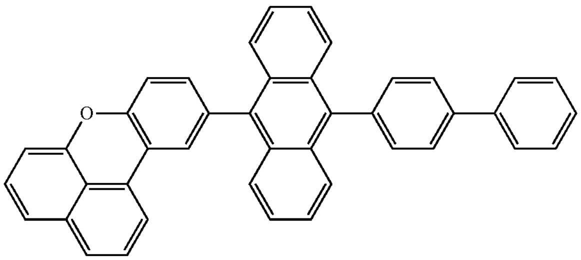
-continued
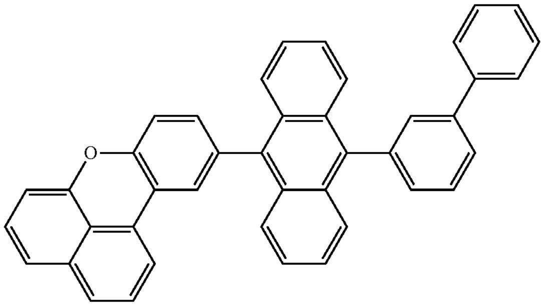
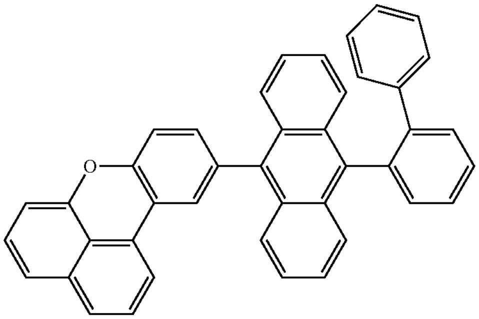
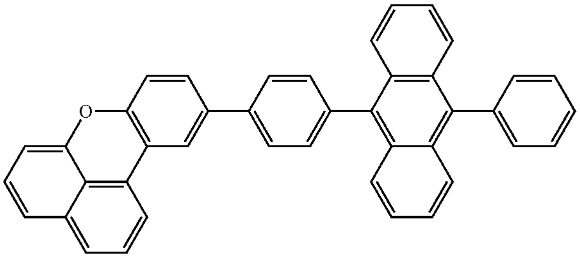
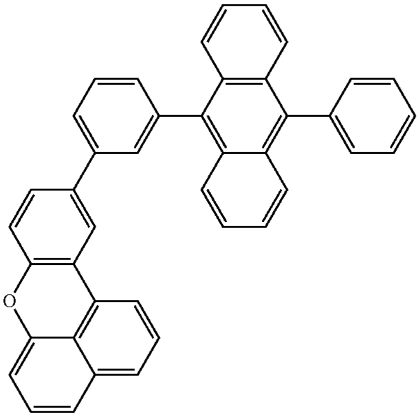
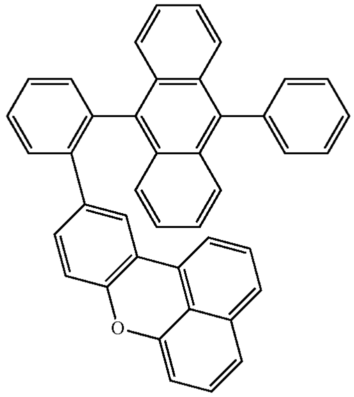

-continued
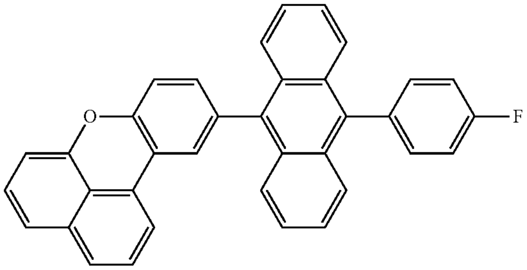
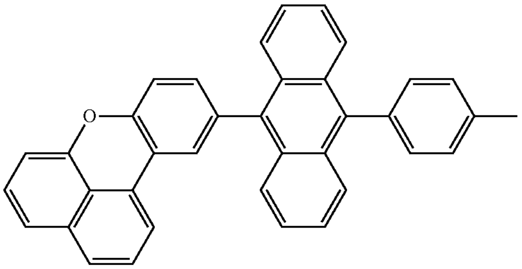
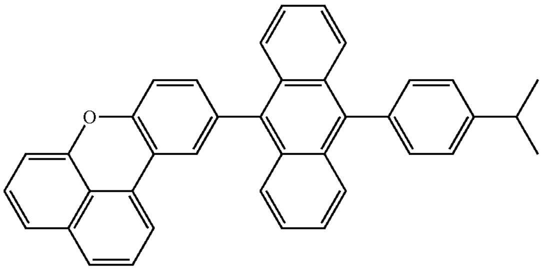
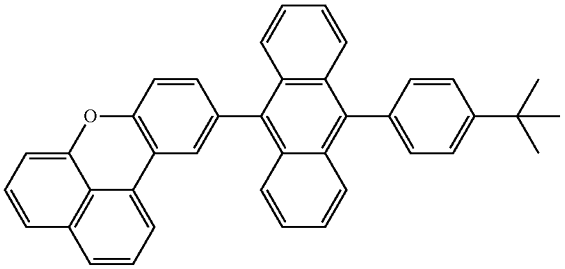
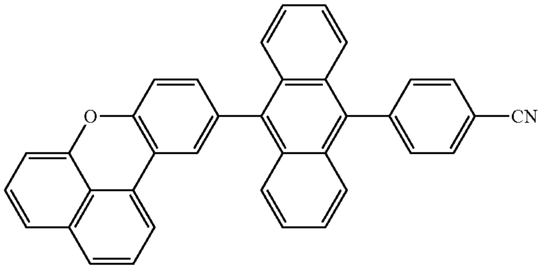
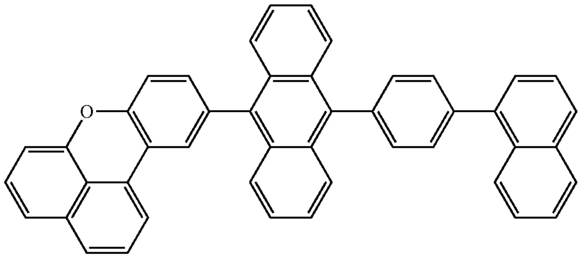
-continued
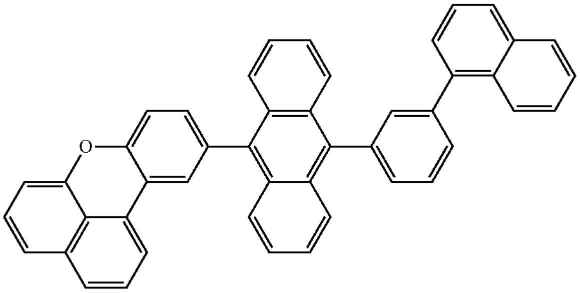
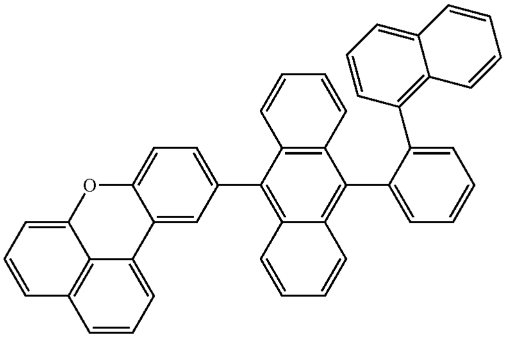
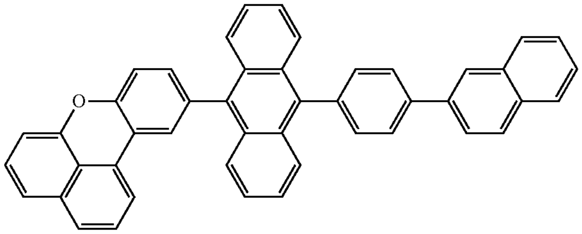
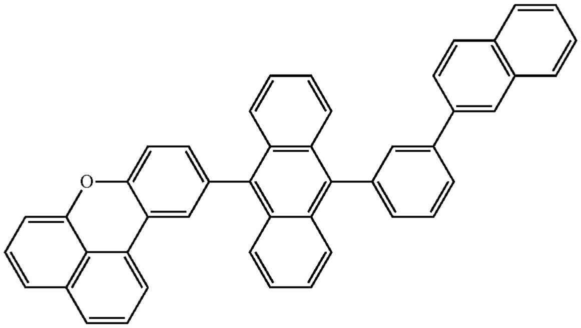
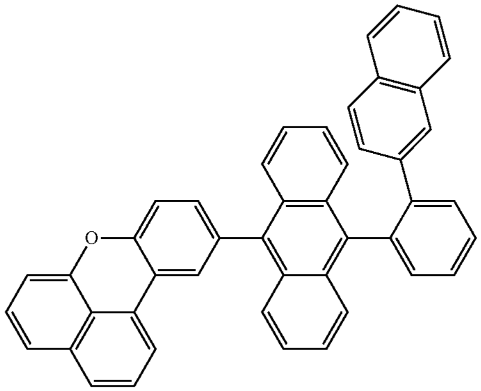

-continued
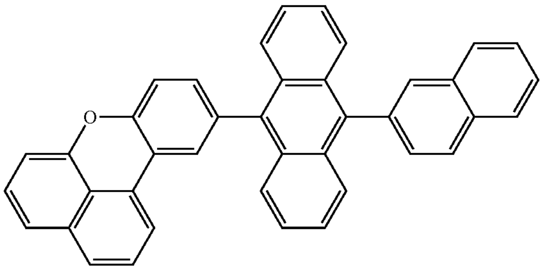
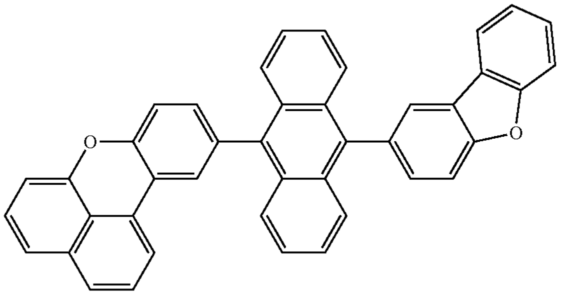
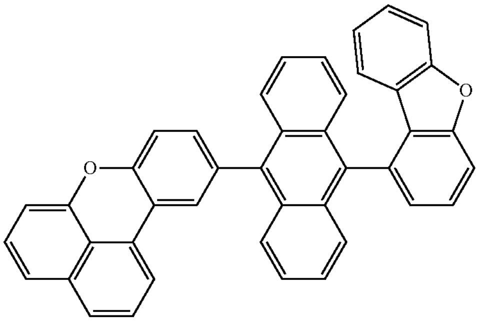
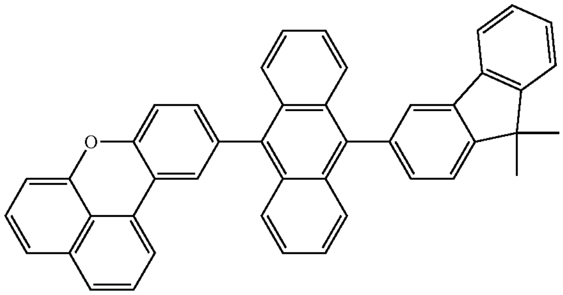
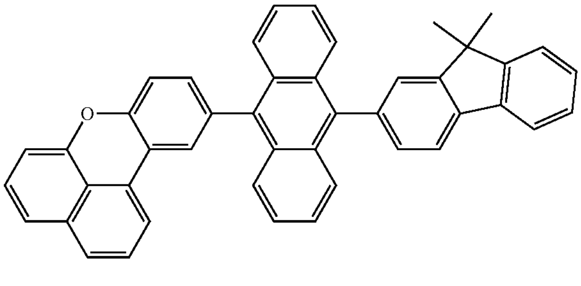
-continued
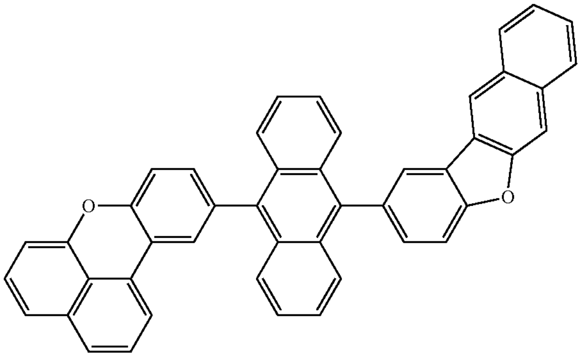
[Formula 114]
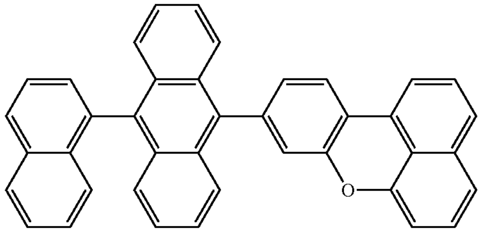
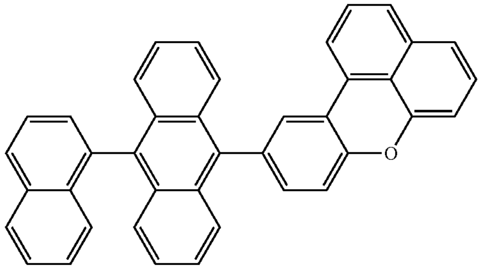
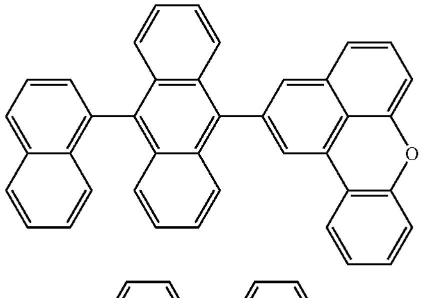
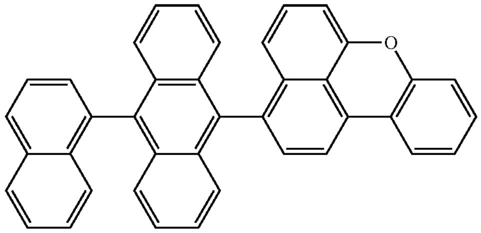
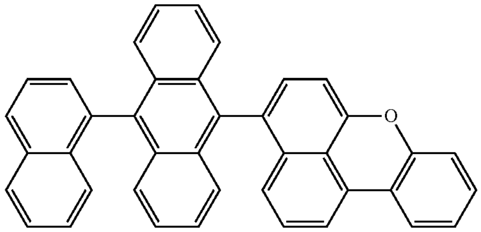

-continued
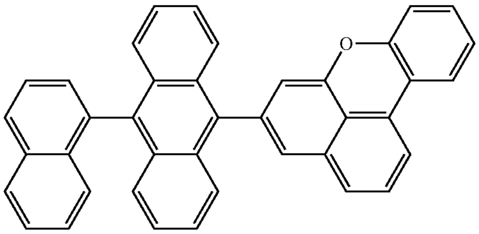
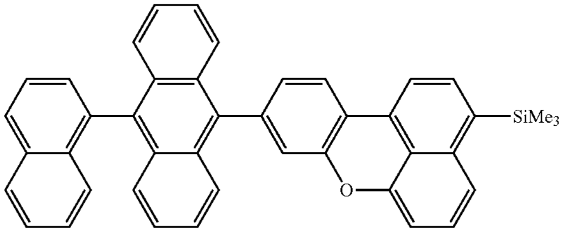
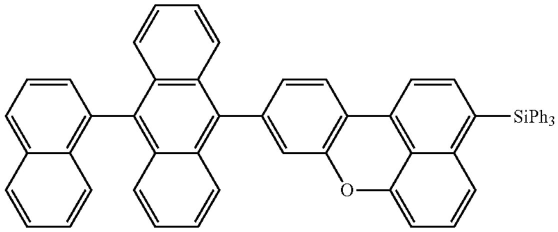
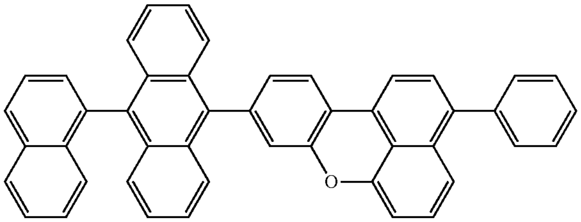
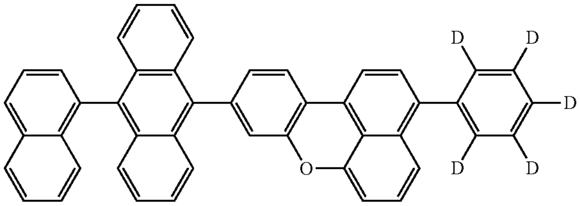
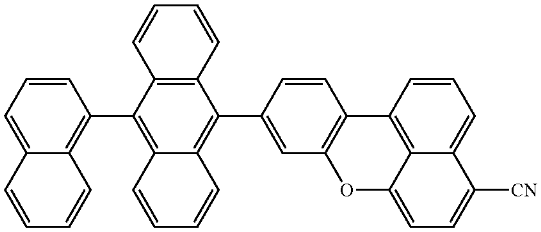
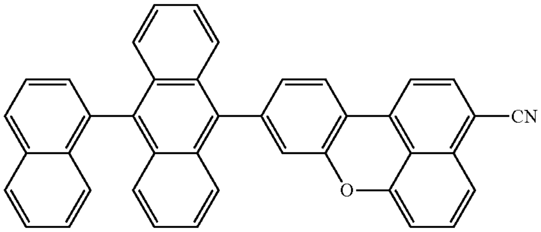
-continued
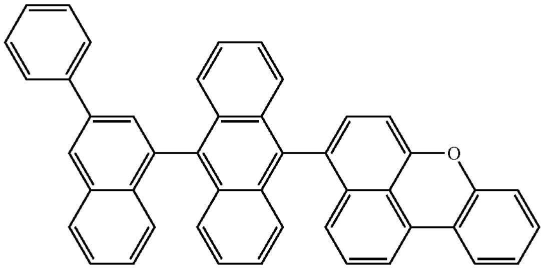
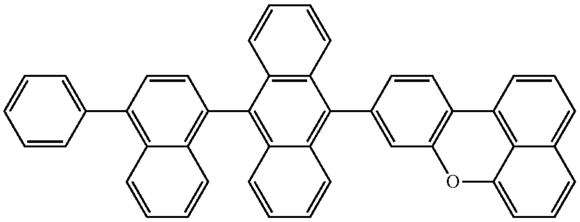
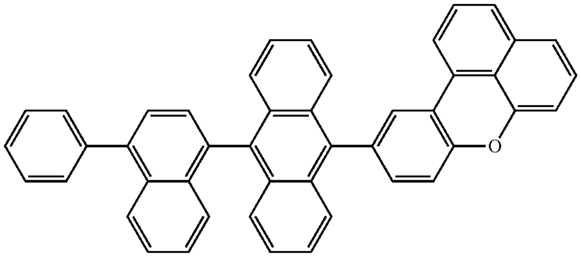
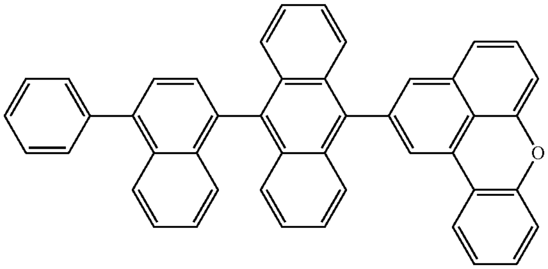
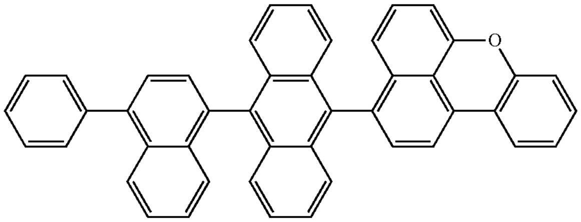
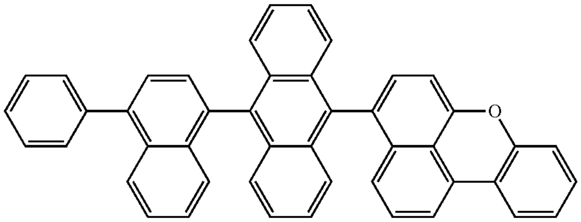
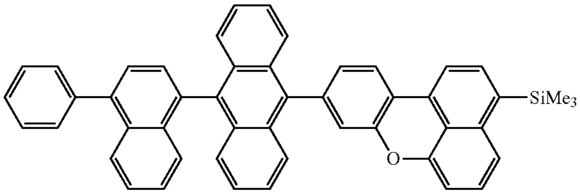

-continued
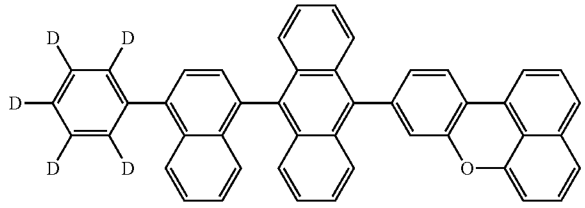
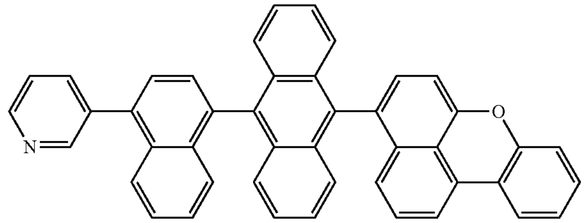
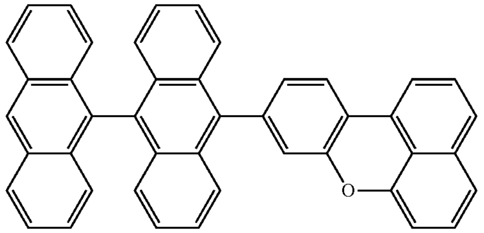
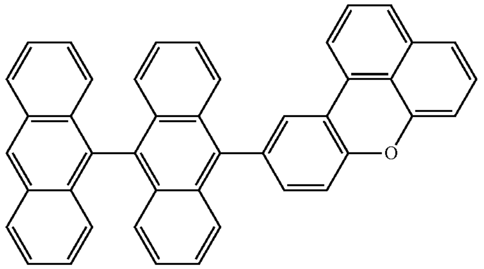
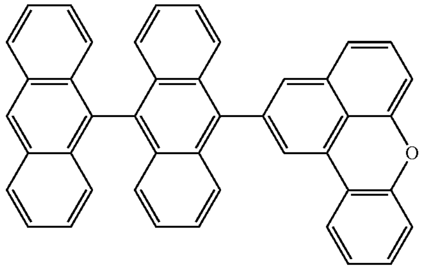
[Formula 115]
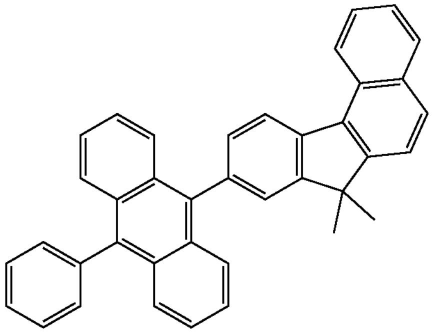
-continued
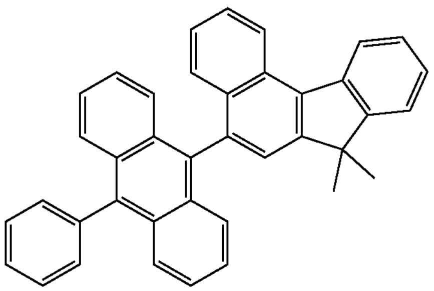
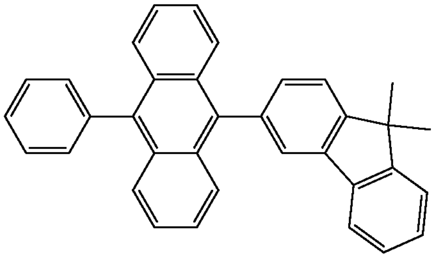
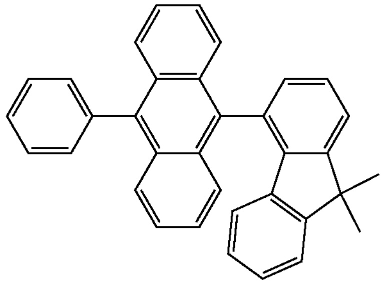
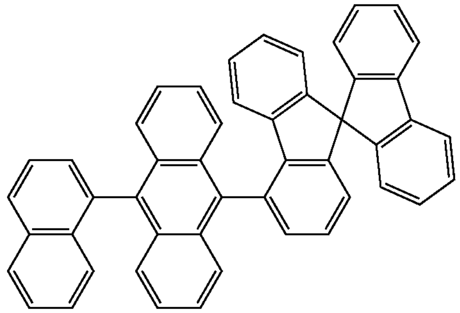
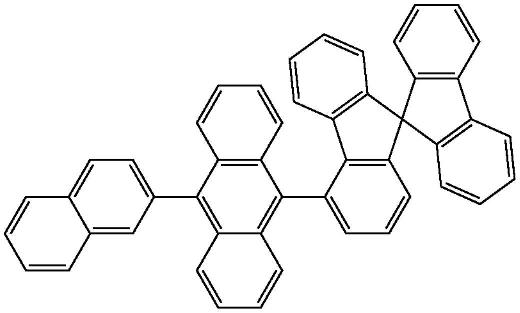
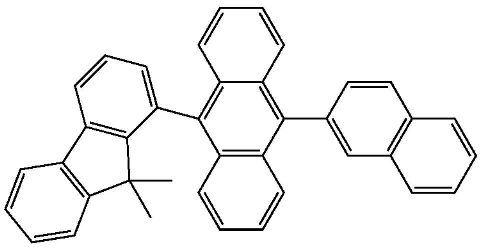 [SMILES: CC1(C)c2ccccc2-c2cccc(-c3c4ccccc4c(-c4ccc5ccccc5c4)c4ccccc34)c21]

-continued

[Formula 116]

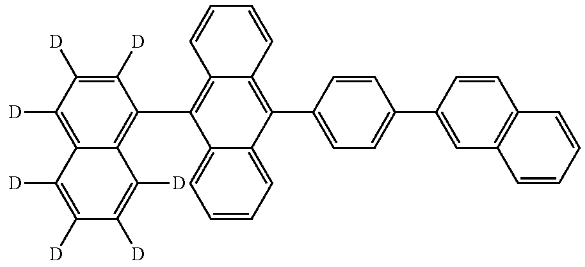

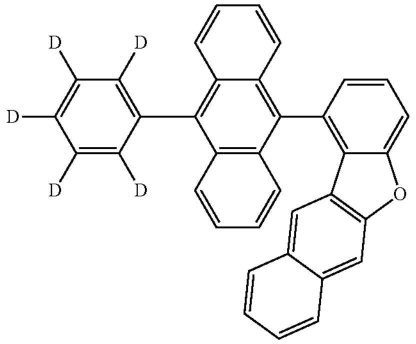

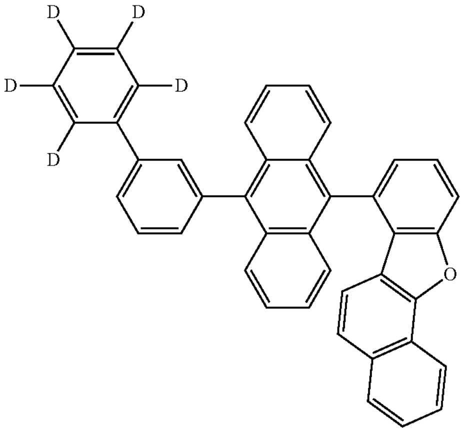

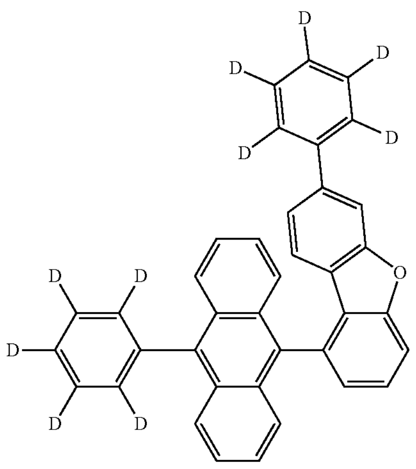

-continued

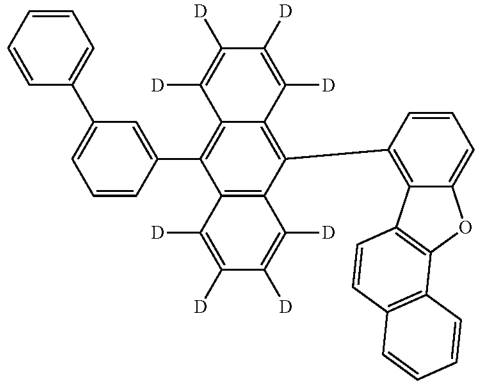 [SMILES: [2H]c1c([2H])c([2H])c2c(-c3cccc4oc5c6ccccc6ccc5c34)c3c([2H])c([2H])c([2H])c([2H])c3c(-c3cccc(-c4ccccc4)c3)c2c1[2H]]

Third Compound and Fourth Compound

In the organic EL device according to the exemplary embodiment, it is also preferable that the first emitting layer further contains a third compound that luminesces.

In the organic EL device according to the exemplary embodiment, it is also preferable that the second emitting layer further contains a fourth compound that luminesces.

When the first emitting layer contains the third compound and the second emitting layer contains the fourth compound, the third compound and the fourth compound are mutually the same or different.

It is preferable that the third compound and the fourth compound are each independently at least one compound selected from the group consisting of a compound represented by a formula (3) below, a compound represented by a formula (4) below, a compound represented by a formula (5) below, a compound represented by a formula (6) below, a compound represented by a formula (7) below, a compound represented by a formula (8) below, a compound represented by a formula (9) below and a compound represented by a formula (10) below.

Compound Represented by Formula (3)

The compound represented by the formula (3) will be described.

[Formula 117]

(3)

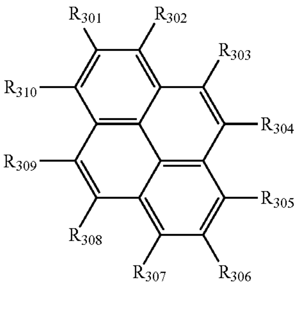

In the formula (3):

at least one combination of adjacent two or more of $R_{301}$ to $R_{310}$ are mutually bonded to form a substituted or unsubstituted monocyclic ring, mutually bonded to form a substituted or unsubstituted fused ring, or not mutually bonded;

at least one of $R_{301}$ to $R_{310}$ is a monovalent group represented by a formula (31) below; and $R_{301}$ to $R_{310}$ forming neither the monocyclic ring nor the fused ring and not being the monovalent group represented by the formula (31) are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms.

[Formula 118]

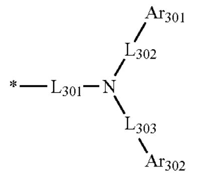

(31)

In the formula (31):

$Ar_{301}$ and $Ar_{302}$ are each independently a substituted or unsubstituted aryl group having 6 to 50 ring carbon atoms, or a substituted or unsubstituted heterocyclic group having 5 to 50 ring atoms;

$L_{301}$ to $L_{303}$ are each independently a single bond, a substituted or unsubstituted arylene group having 6 to 30 ring carbon atoms, or a substituted or unsubstituted divalent heterocyclic group having 5 to 30 ring atoms; and

* represents a bonding position to a pyrene ring in the formula (3).

In the third and fourth compounds, $R_{901}$, $R_{902}$, $R_{903}$, $R_{904}$, $R_{905}$, $R_{906}$, and $R_{907}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

a substituted or unsubstituted alkyl group having 1 to 50 carbon atoms, or a substituted or unsubstituted aryl group having 6 to 50 ring carbon atoms;

when a plurality of $R_{901}$ are present, the plurality of $R_{901}$ are mutually the same or different;

when a plurality of $R_{902}$ are present, the plurality of $R_{902}$ are mutually the same or different;

when a plurality of $R_{903}$ are present, the plurality of $R_{903}$ are mutually the same or different;

when a plurality of $R_{904}$ are present, the plurality of $R_{904}$ are mutually the same or different;

when a plurality of $R_{905}$ are present, the plurality of $R_{905}$ are mutually the same or different;

when a plurality of $R_{906}$ are present, the plurality of $R_{906}$ are mutually the same or different; and when a plurality of $R_{907}$ are present, the plurality of $R_{907}$ are mutually the same or different.

In the formula (3), it is preferable that two of $R_{301}$ to $R_{310}$ are each a group represented by the formula (31).

In an exemplary embodiment, the compound represented by the formula (3) is a compound represented by a formula (33) below.

[Formula 119]

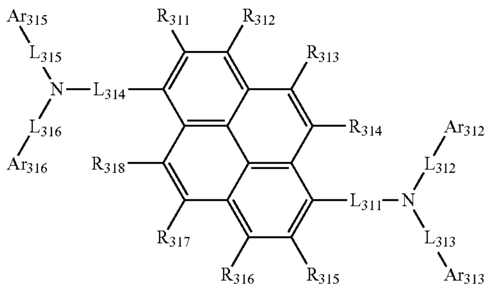

(33)

In the formula (33):

$R_{311}$ to $R_{318}$ each independently represent the same as $R_{301}$ to $R_{310}$ in the formula (3) that are not the monovalent group represented by the formula (31);

$L_{311}$ to $L_{316}$ are each independently a single bond, a substituted or unsubstituted arylene group having 6 to 30 ring carbon atoms, or a substituted or unsubstituted divalent heterocyclic group having 5 to 30 ring atoms; and $Ar_{312}$, $Ar_{313}$, $Ar_{315}$, and $Ar_{316}$ are each independently a substituted or unsubstituted aryl group having 6 to 50 ring carbon atoms, or a substituted or unsubstituted heterocyclic group having 5 to 50 ring atoms.

In the formula (31), $L_{301}$ is preferably a single bond, and $L_{302}$ and $L_{303}$ are each preferably a single bond.

In an exemplary embodiment, the compound represented by the formula (3) is represented by a formula (34) or a formula (35) below.

[Formula 120]

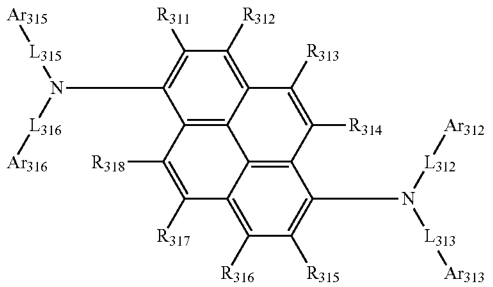

(34)

In the formula (34):

$R_{311}$ to $R_{318}$ each independently represent the same as $R_{301}$ to $R_{310}$ in the formula (3) that are not the monovalent group represented by the formula (31);

$L_{312}$, $L_{313}$, $L_{315}$ and $L_{316}$ each independently represent the same as $L_{312}$, $L_{313}$, $L_{315}$ and $L_{316}$ in the formula (33); and $Ar_{312}$, $Ar_{313}$, $Ar_{315}$ and $Ar_{316}$ each independently represent the same as $Ar_{312}$, $Ar_{313}$, $Ar_{315}$ and $Ar_{316}$ in the formula (33).

[Formula 121]

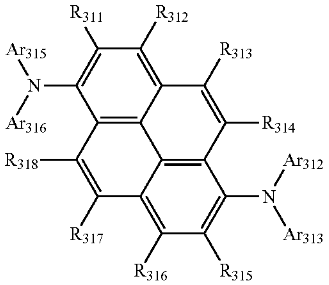

(35)

In the formula (35):

$R_{311}$ to $R_{318}$ each independently represent the same as $R_{301}$ to $R_{310}$ in the formula (3) that are not the monovalent group represented by the formula (31); and $Ar_{312}$, $Ar_{313}$, $Ar_{315}$ and $Ar_{316}$ each independently represent the same as $Ar_{312}$, $Ar_{313}$, $Ar_{315}$ and $Ar_{316}$ in the formula (33).

In the formula (31), at least one of $Ar_{301}$ or $Ar_{302}$ is preferably a group represented by a formula (36) below.

In the formulae (33) to (35), at least one of $Ar_{312}$ or $Ar_{313}$ is preferably a group represented by the formula (36) below.

In the formulae (33) to (35), at least one of $Ar_{315}$ or $Ar_{316}$ is preferably a group represented by the formula (36) below.

[Formula 122]

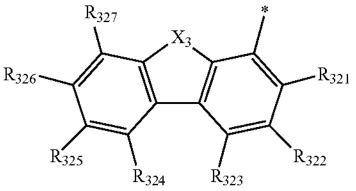

(36)

In the formula (36):

$X_3$ represents an oxygen atom or a sulfur atom;

at least one combination of adjacent two or more of $R_{321}$ to $R_{327}$ are mutually bonded to form a substituted or unsubstituted monocyclic ring, mutually bonded to form a substituted or unsubstituted fused ring, or not mutually bonded;

$R_{321}$ to $R_{327}$ forming neither the monocyclic ring nor the fused ring are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $-Si(R_{901})(R_{902})(R_{903})$, a group represented by $-O-(R_{904})$, a group represented by $-S-(R_{905})$, a group represented by $-N(R_{906})(R_{907})$, a halogen atom, a cyano group, a nitro group, a substituted or unsubstituted aryl group having 6 to 50 ring carbon atoms, or a substituted or unsubstituted heterocyclic group having 5 to 50 ring atoms; and

* represents a bonding position to $L_{302}$, $L_{303}$, $L_{312}$, $L_{313}$, $L_{315}$, Or $L_{316}$.

$X_3$ is preferably an oxygen atom.

At least one of $R_{321}$ to $R_{327}$ is preferably a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms.

In the formula (31), it is preferable that $Ar_{301}$ is a group represented by the formula (36) and $Ar_{302}$ is a substituted or unsubstituted aryl group having 6 to 50 ring carbon atoms.

In the formulae (33) to (35), it is preferable that $Ar_{312}$ is a group represented by the formula (36) and $Ar_{313}$ is a substituted or unsubstituted aryl group having 6 to 50 ring carbon atoms.

In the formulae (33) to (35), it is preferable that $Ar_{315}$ is a group represented by the formula (36) and $Ar_{316}$ is a substituted or unsubstituted aryl group having 6 to 50 ring carbon atoms.

In an exemplary embodiment, the compound represented by the formula (3) is represented by a formula (37) below.

[Formula 123]

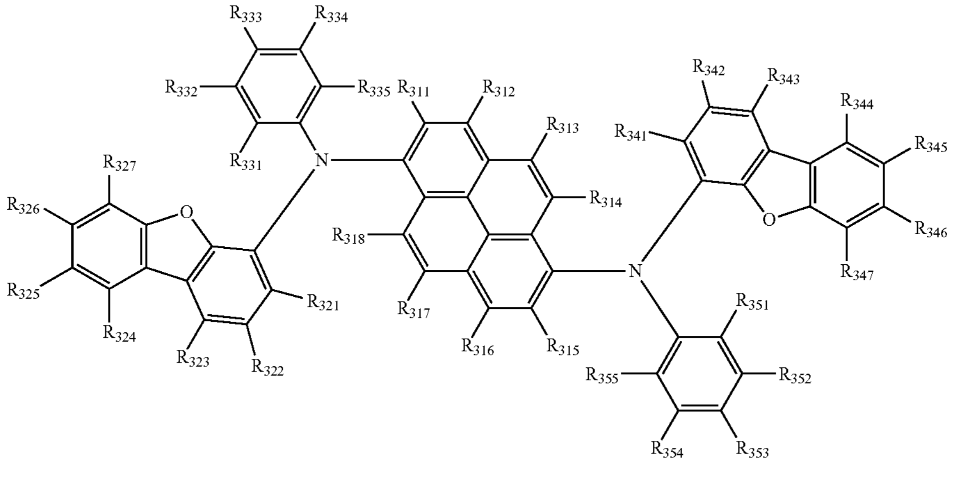

(37)

In the formula (37):

$R_{311}$ to $R_{318}$ each independently represent the same as $R_{301}$ to $R_{310}$ in the formula (3) that are not the monovalent group represented by the formula (31);

at least one combination of adjacent two or more of $R_{321}$ to $R_{327}$ are mutually bonded to form a substituted or unsubstituted monocyclic ring, mutually bonded to form a substituted or unsubstituted fused ring, or not mutually bonded;

at least one combination of adjacent two or more of $R_{341}$ to $R_{347}$ are mutually bonded to form a substituted or unsubstituted monocyclic ring, mutually bonded to form a substituted or unsubstituted fused ring, or not mutually bonded;

$R_{321}$ to $R_{327}$ and $R_{341}$ to $R_{347}$ forming neither the monocyclic ring nor the fused ring are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms; and $R_{331}$ to $R_{335}$ and $R_{351}$ to $R_{355}$ are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms.

Specific examples of the compound represented by the formula (3) include compounds shown below.

[Formula 124]

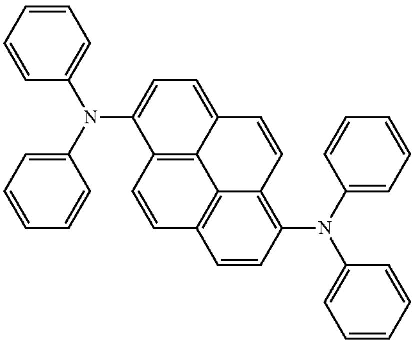

-continued

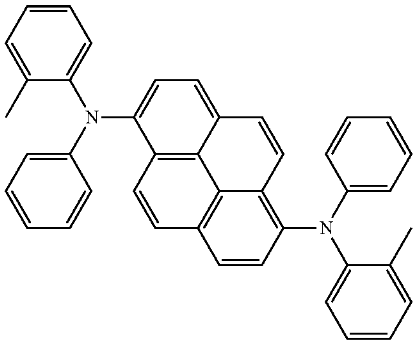

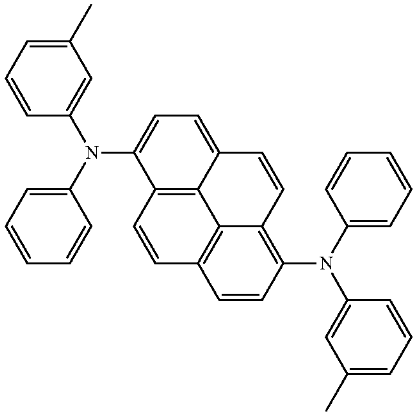

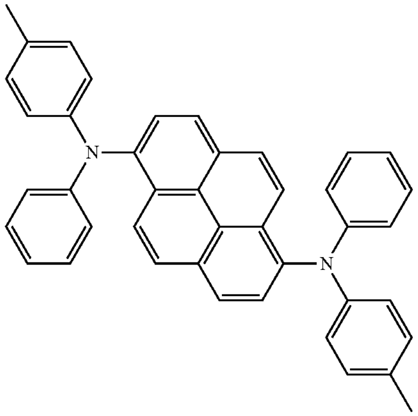

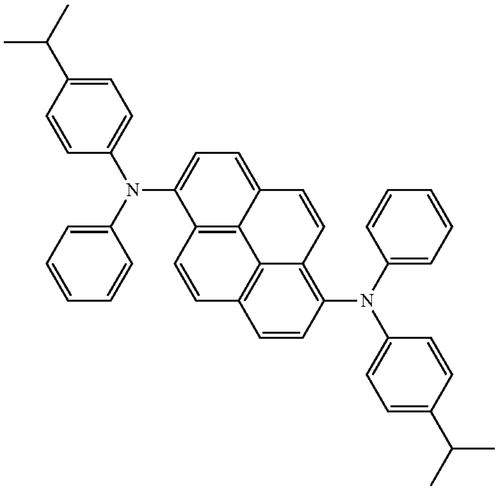

-continued
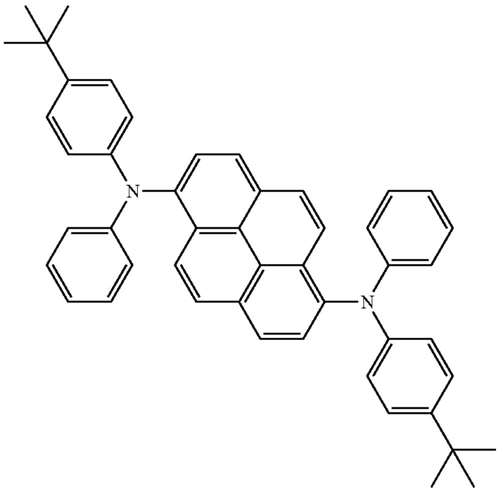
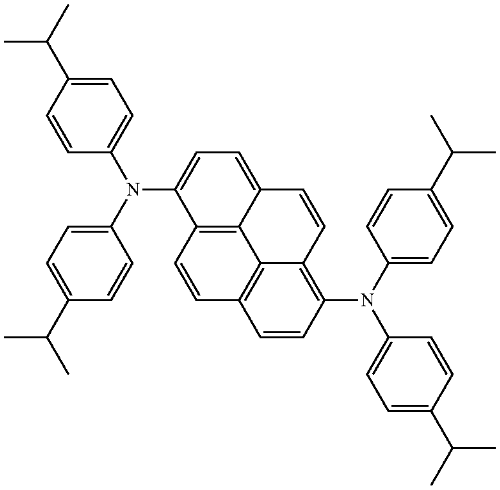
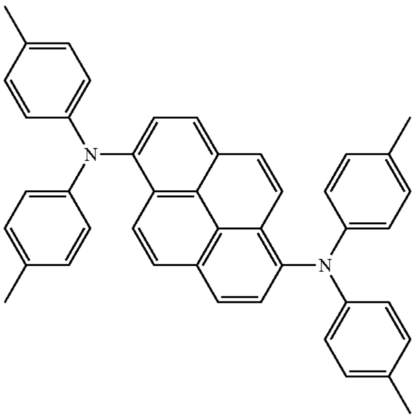
-continued
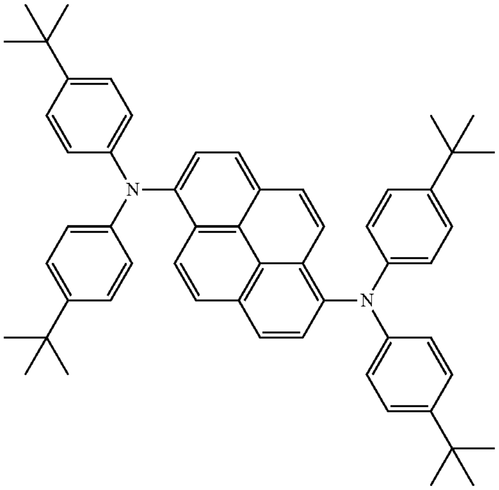
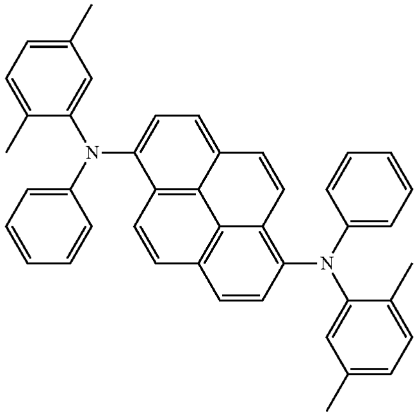
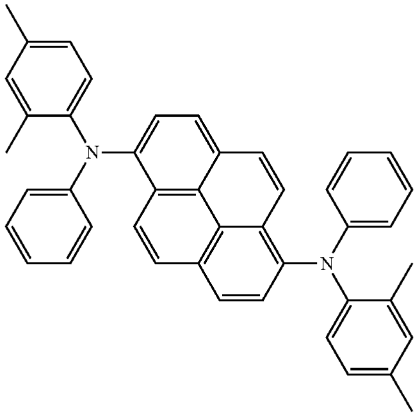

-continued
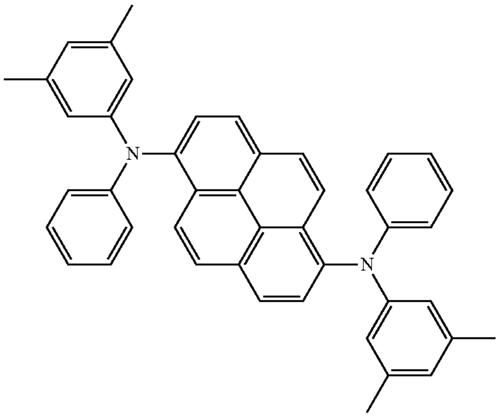
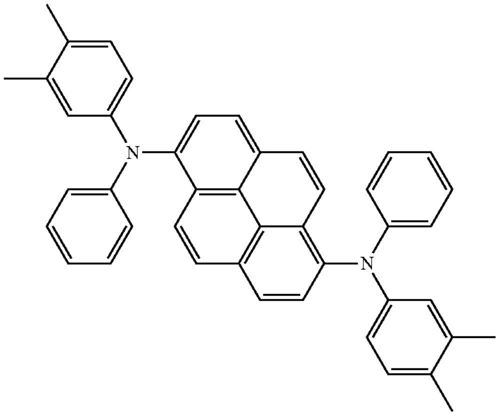
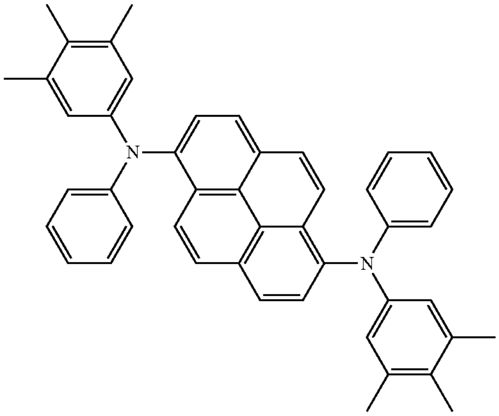
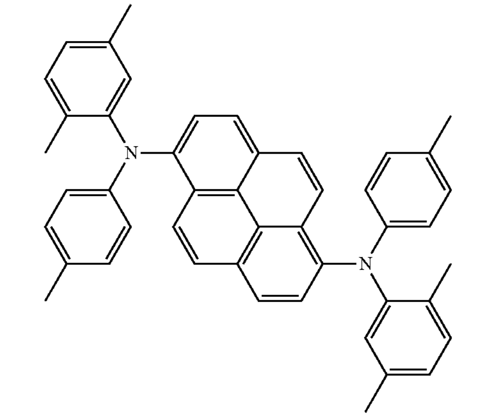
-continued
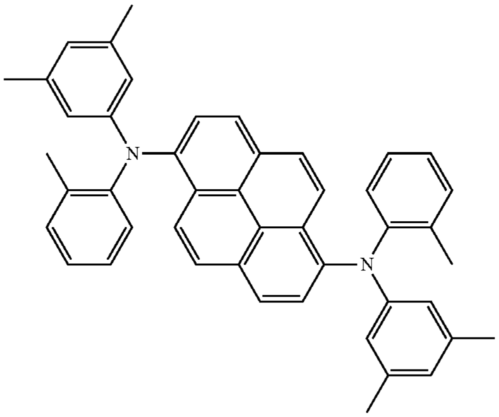
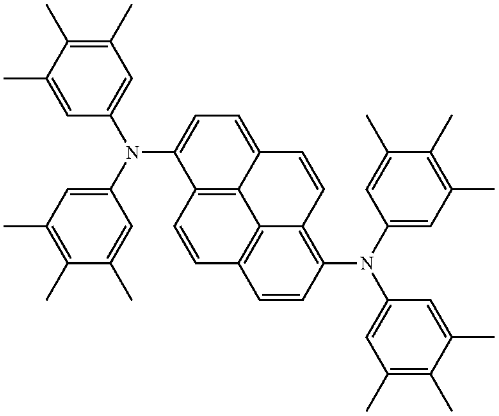
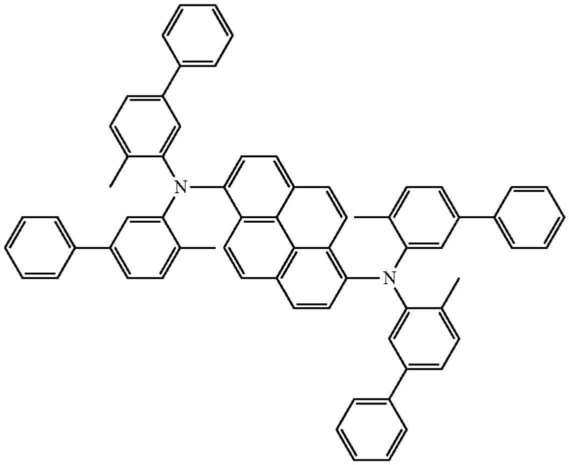

-continued
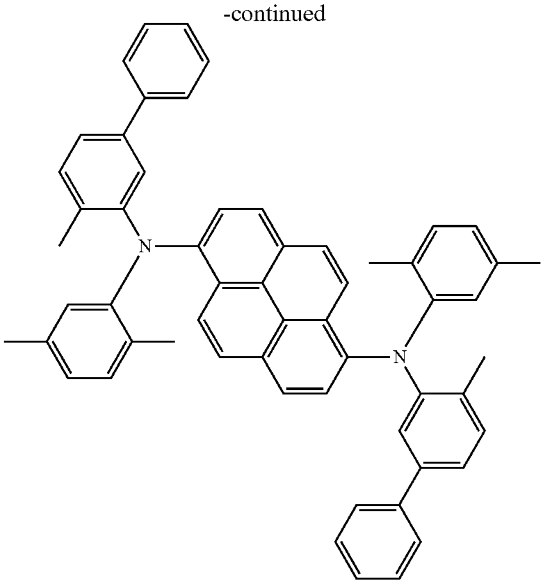
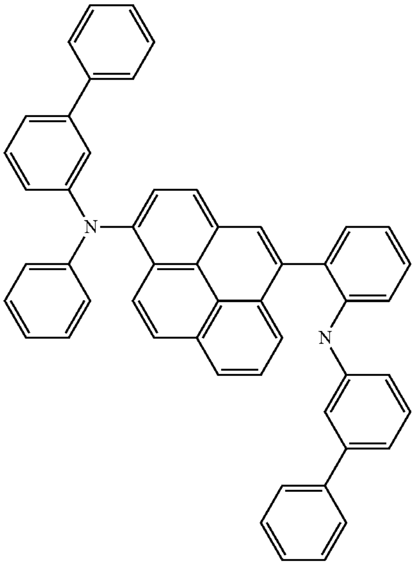
-continued
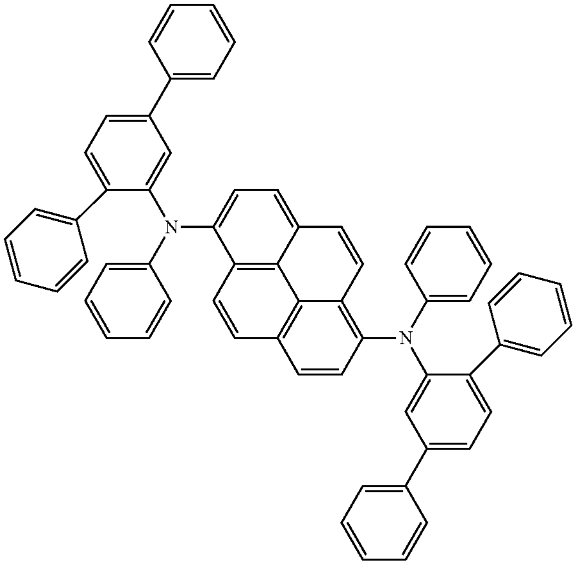
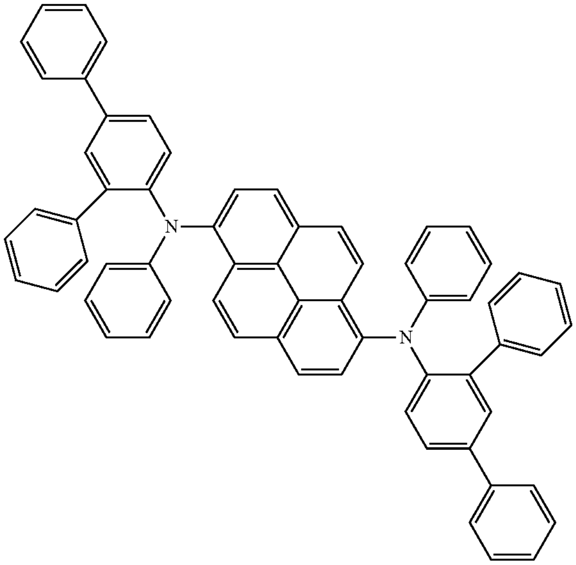
[Formula 125]
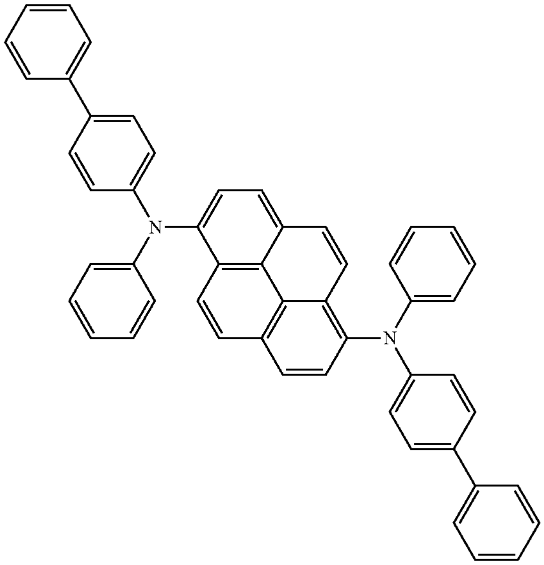
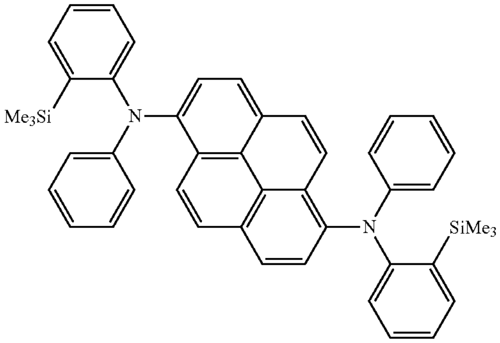

-continued
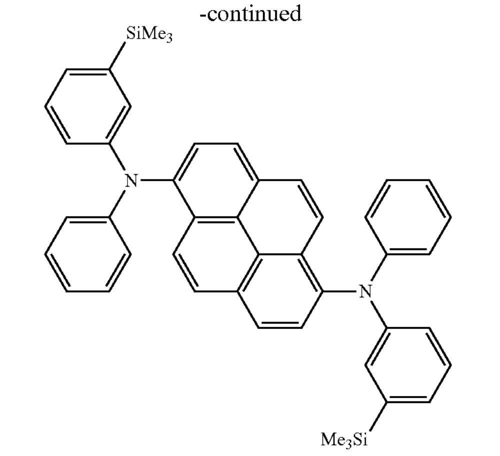
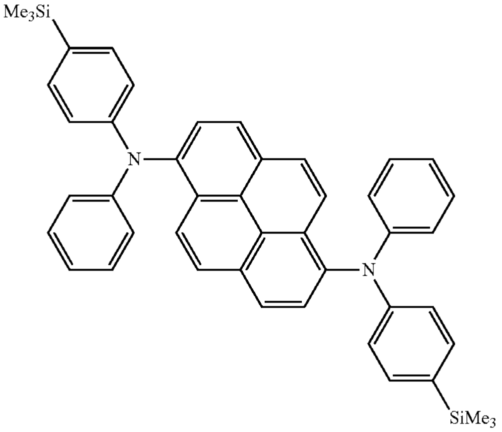
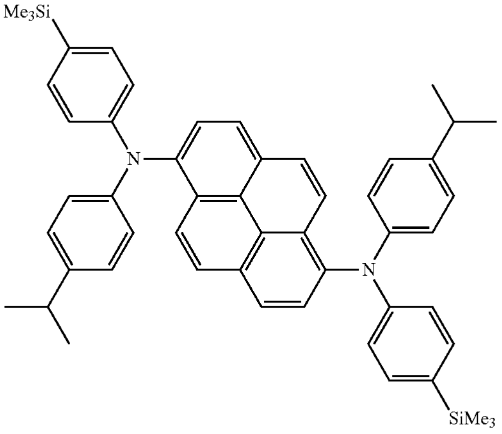
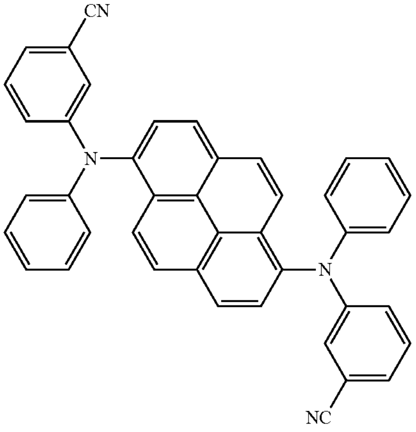
-continued
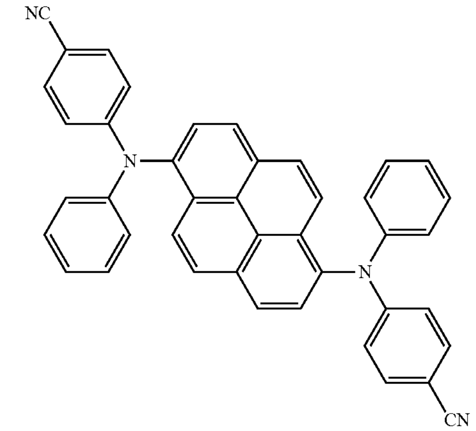
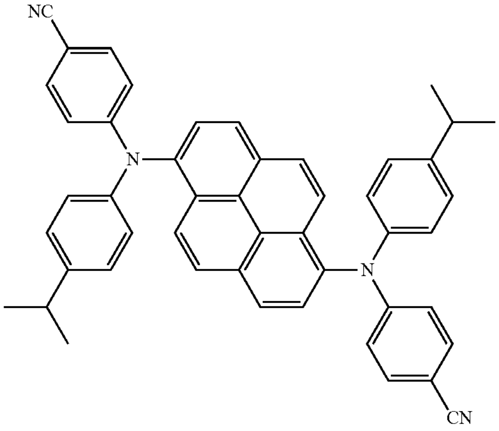
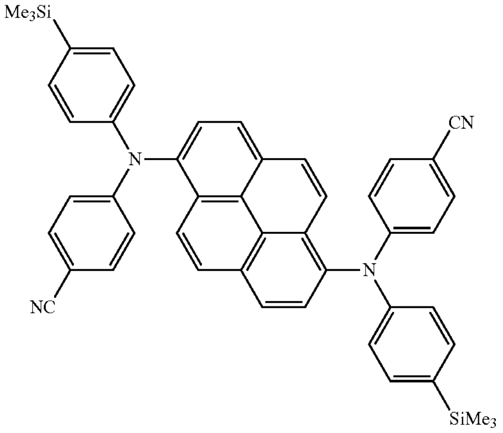
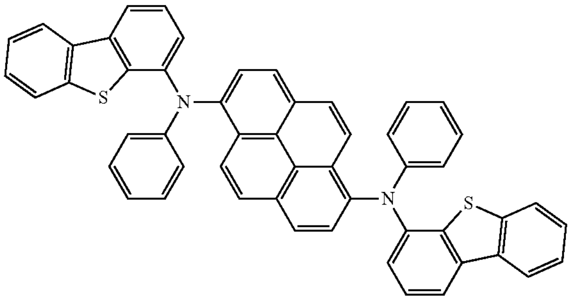

-continued
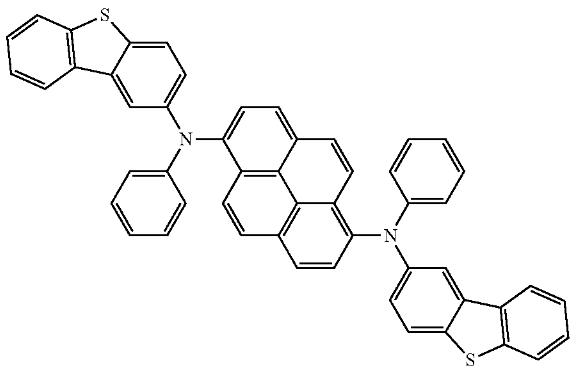
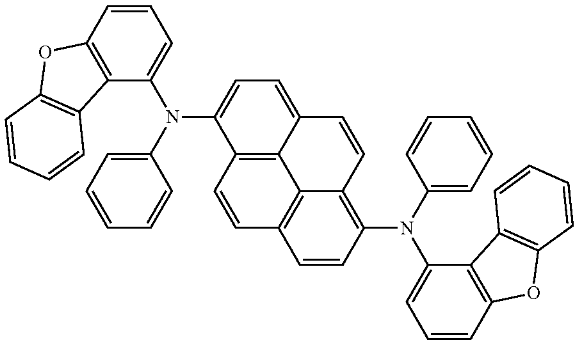
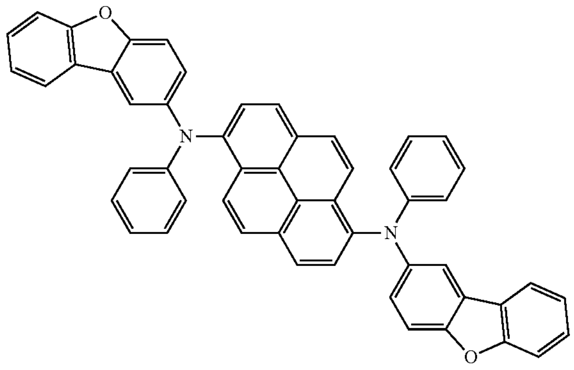
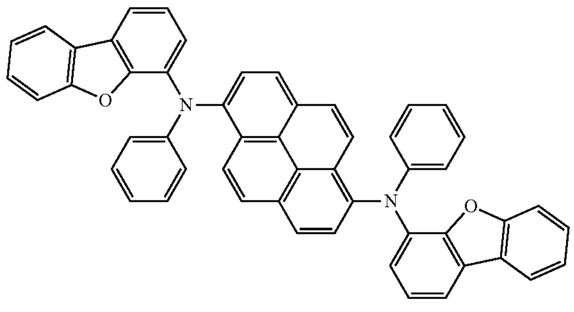
-continued
[Formula 126]
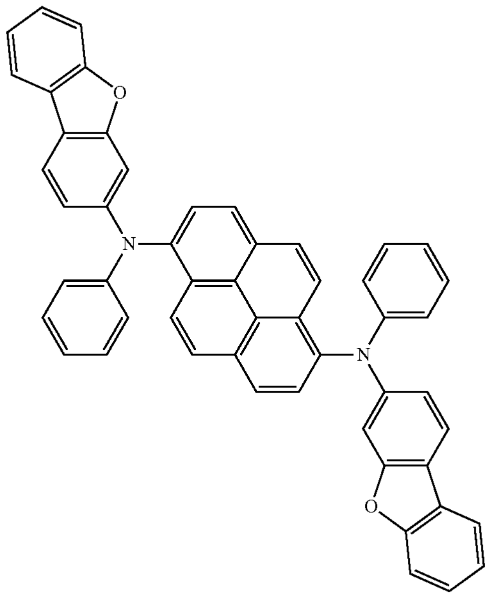
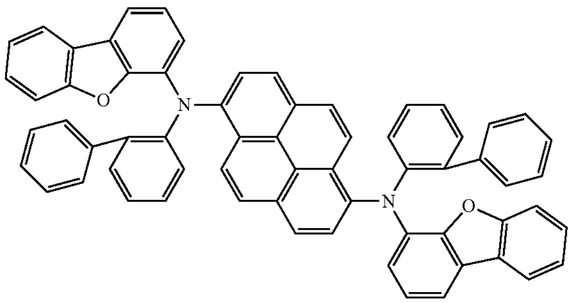
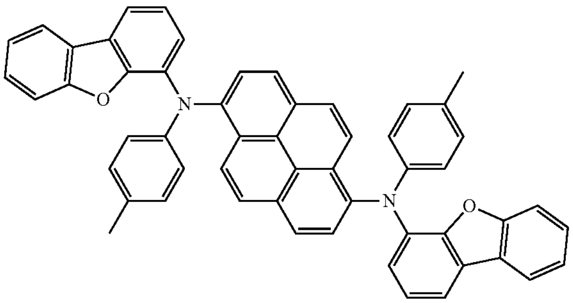
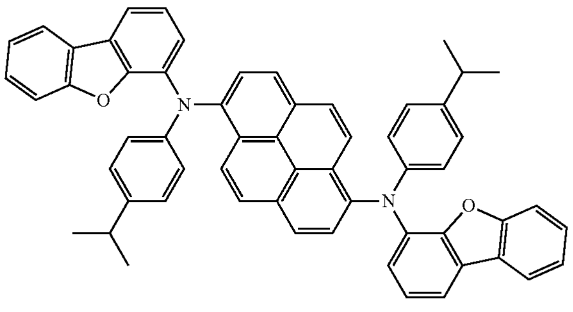

-continued
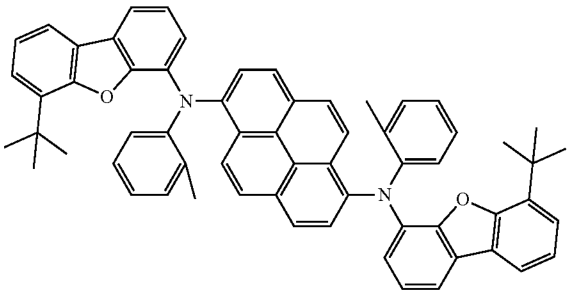
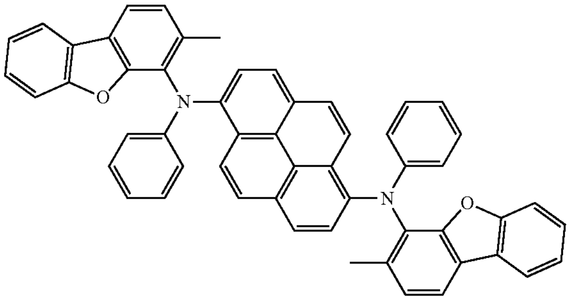
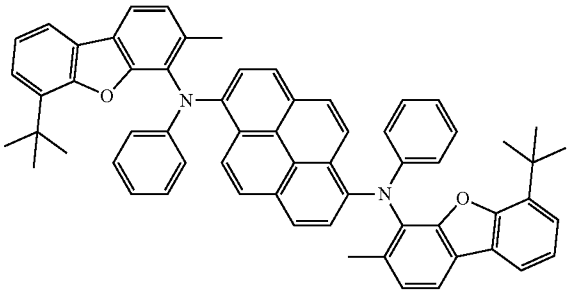
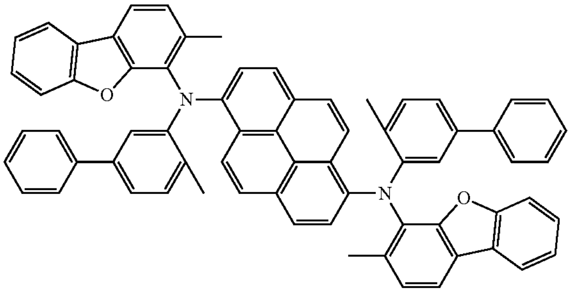
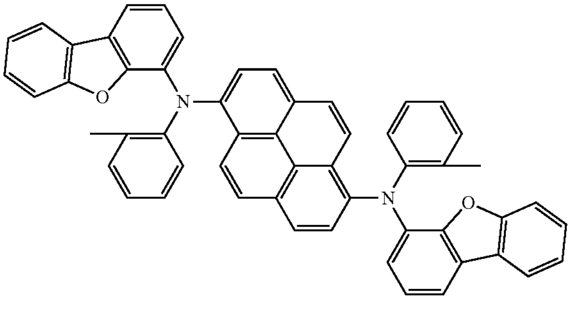
-continued
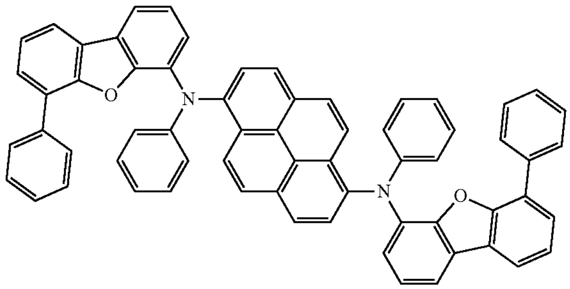
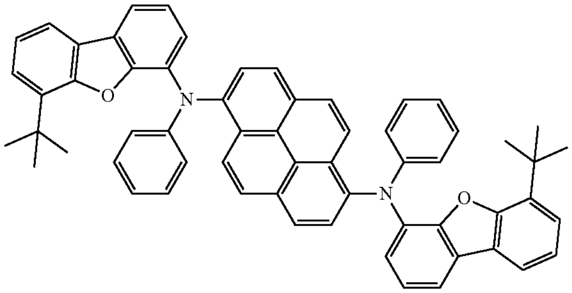
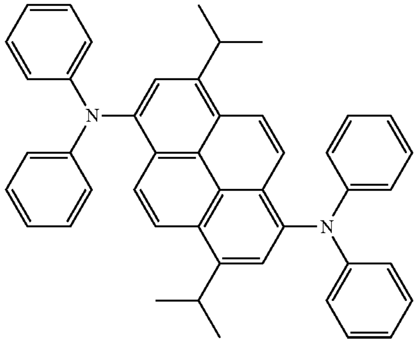
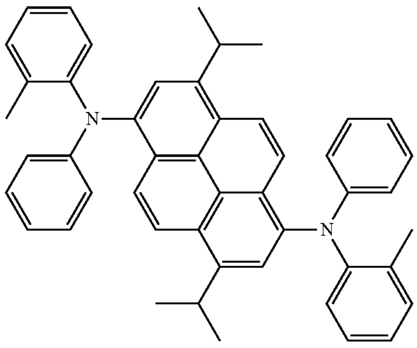
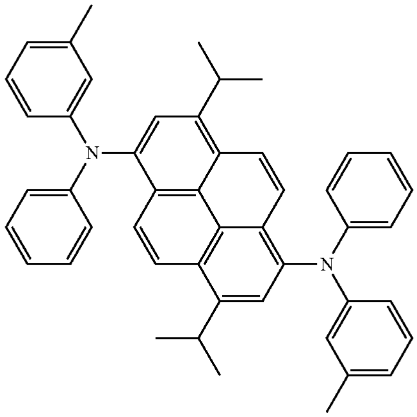

-continued
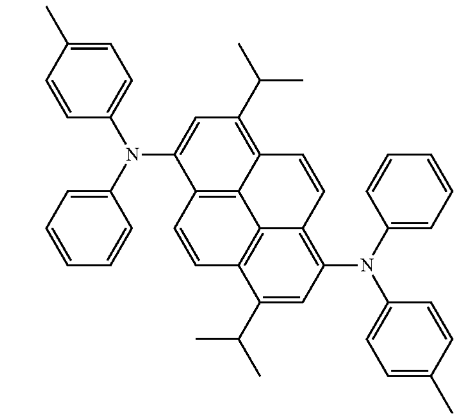
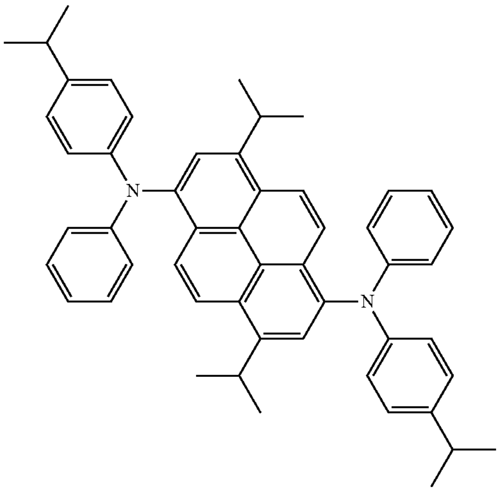
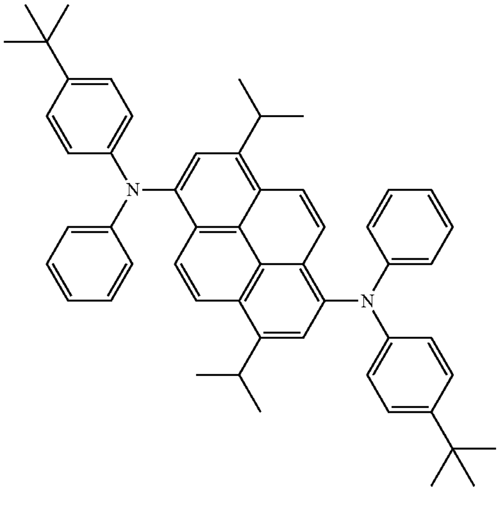
-continued
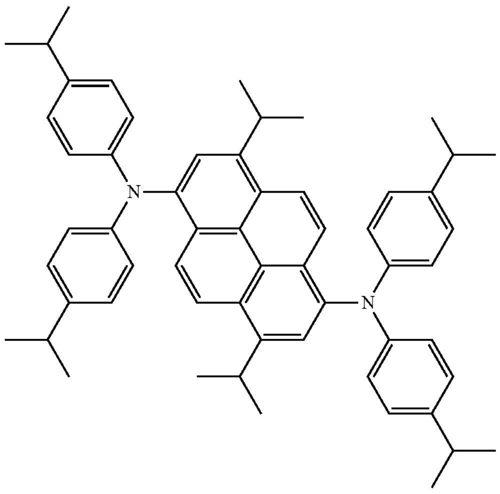
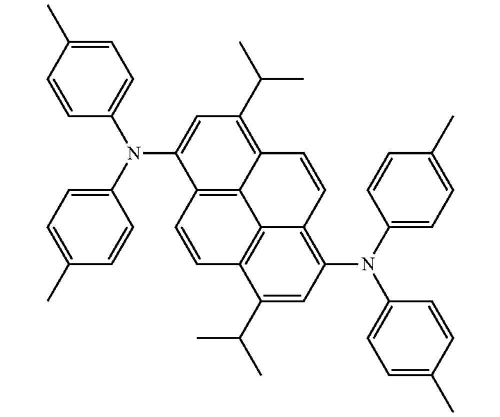
[Formula 127]
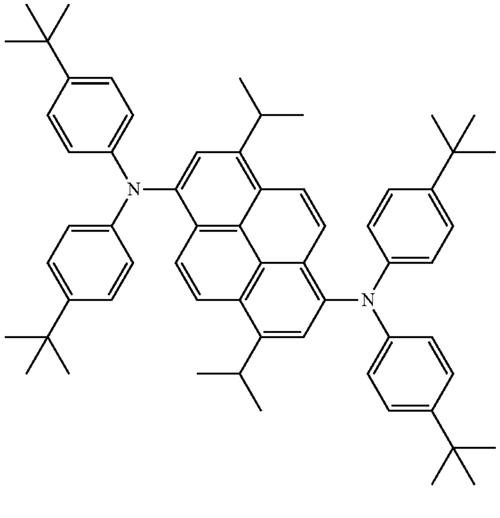

-continued
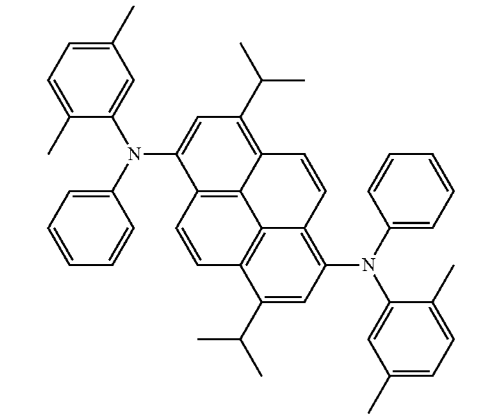
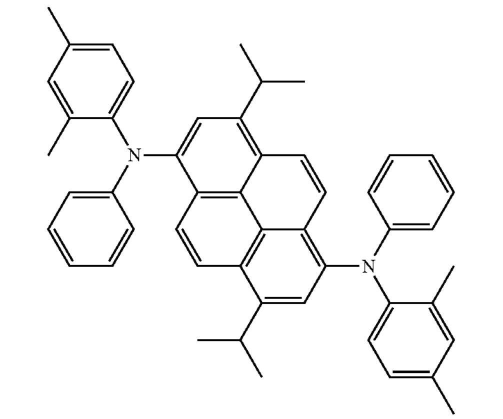
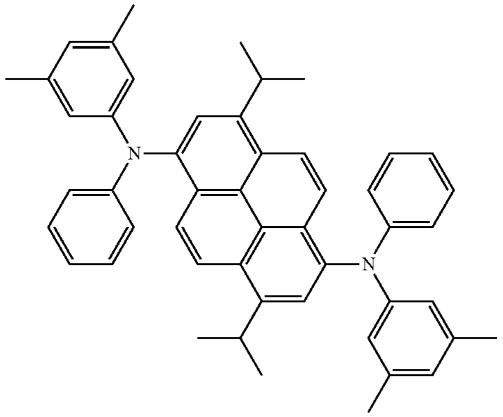
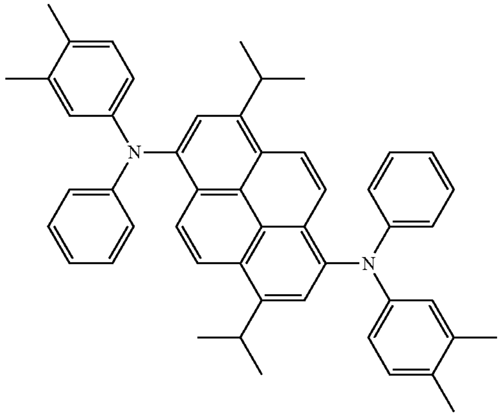
-continued
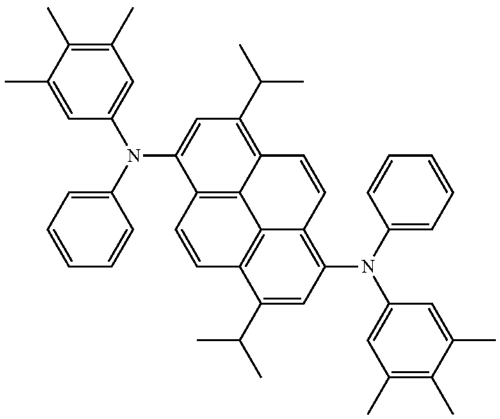
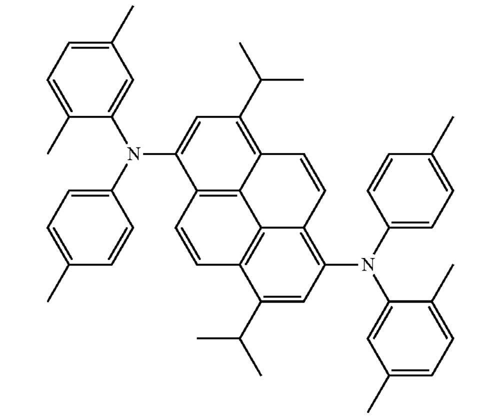
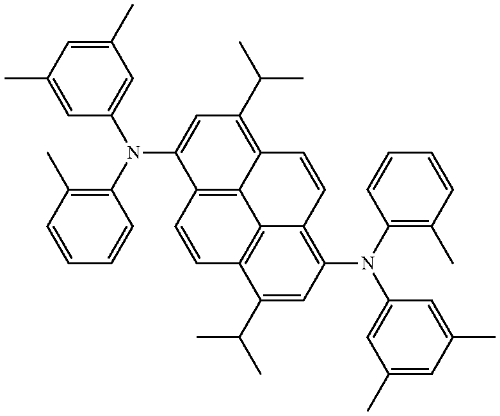
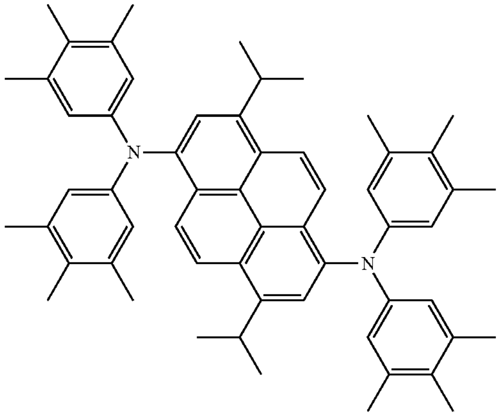

-continued
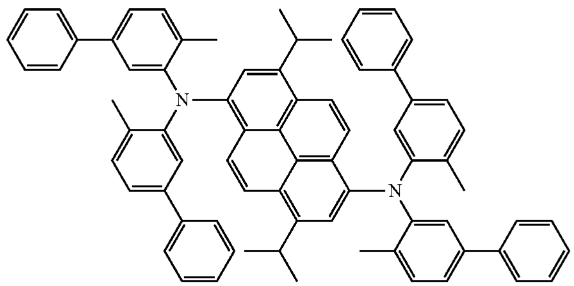
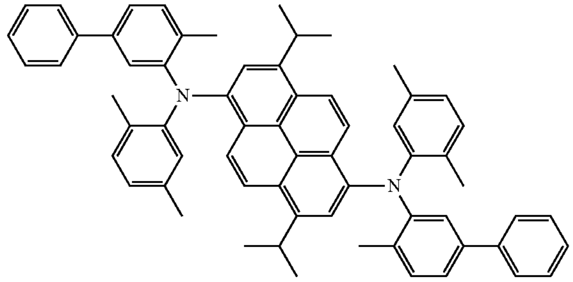
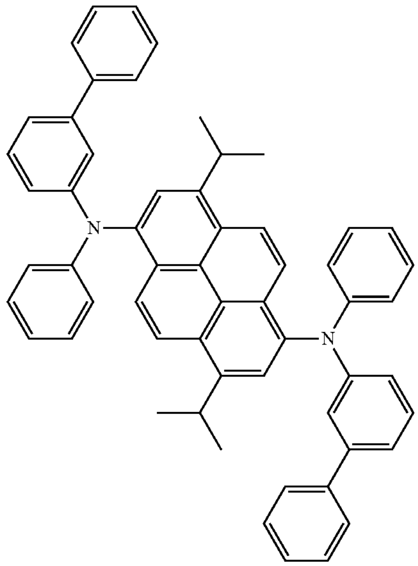
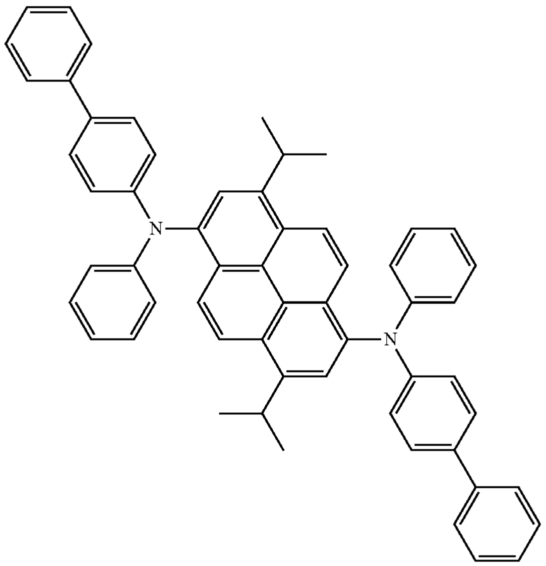
-continued
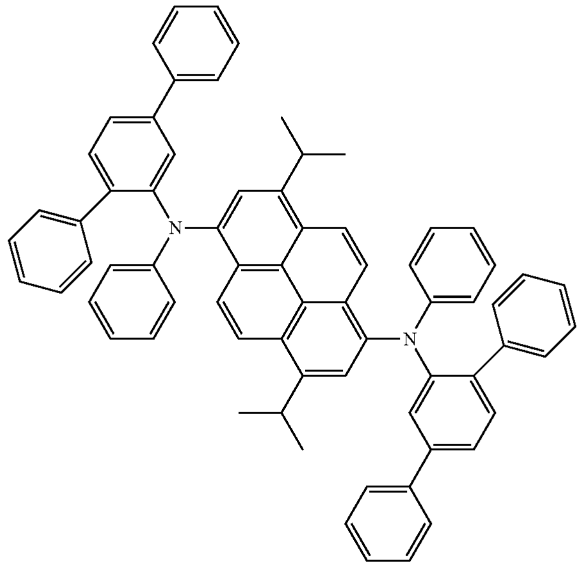
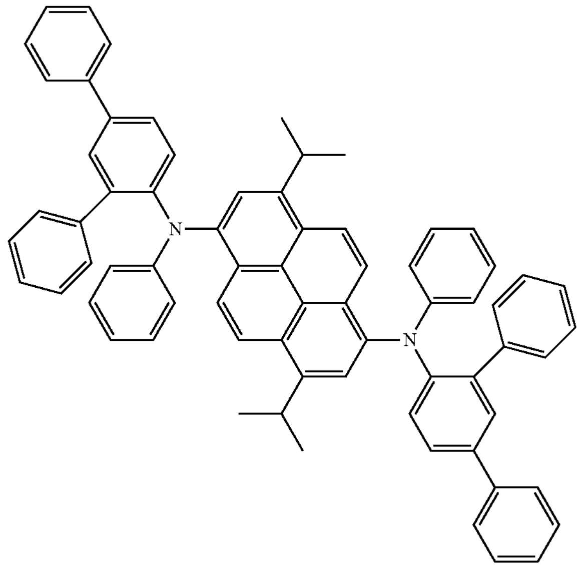
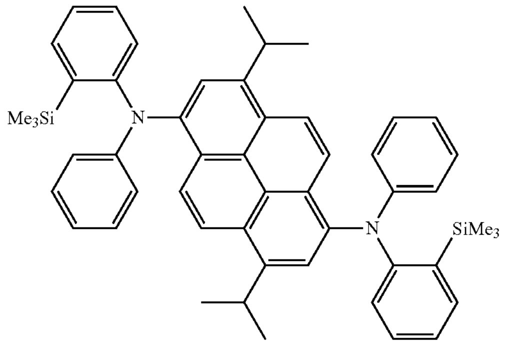

-continued
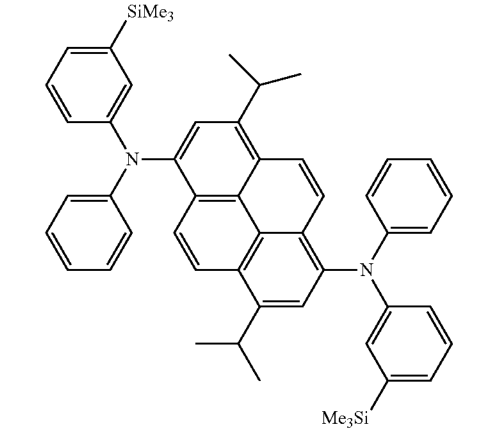
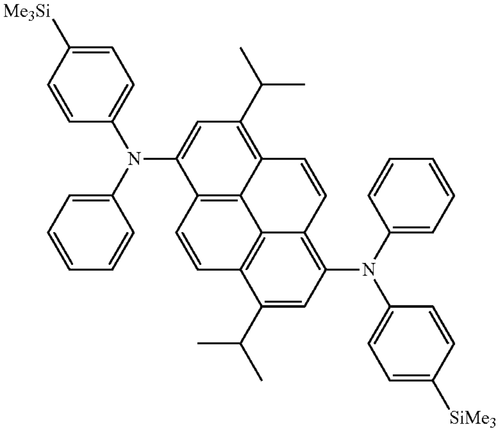
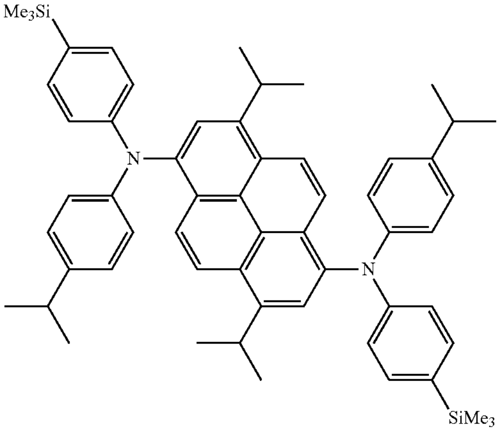
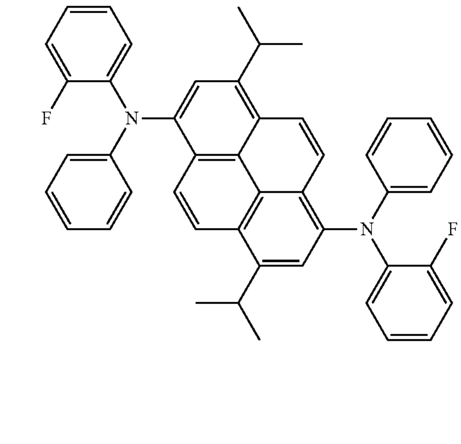
-continued
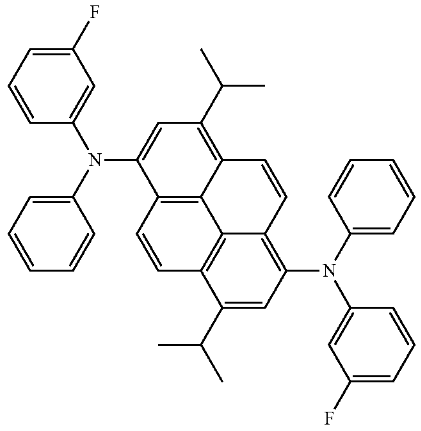
[Formula 128]
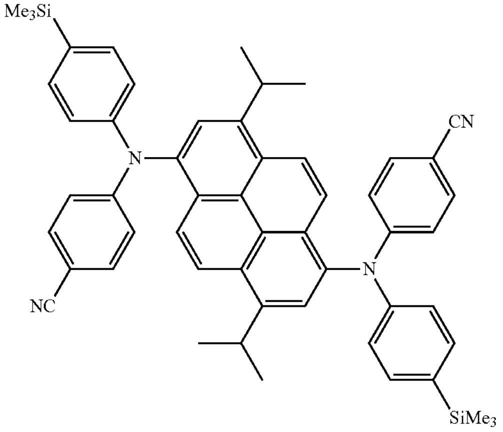
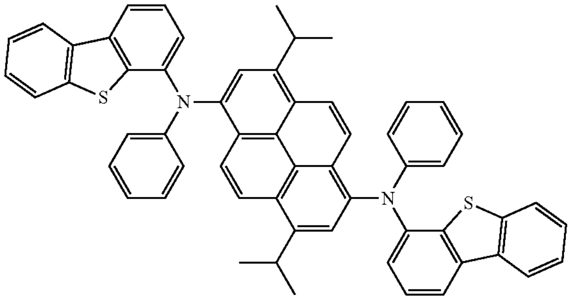
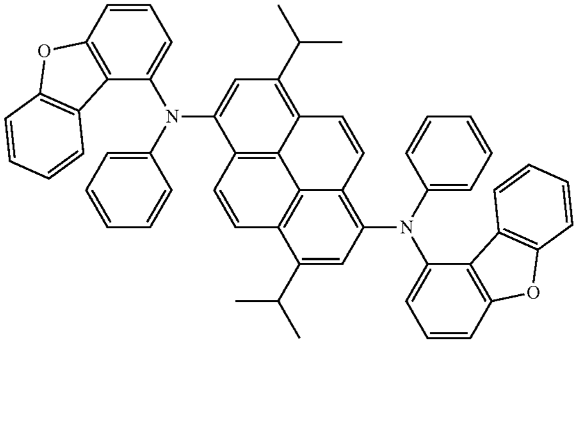

-continued
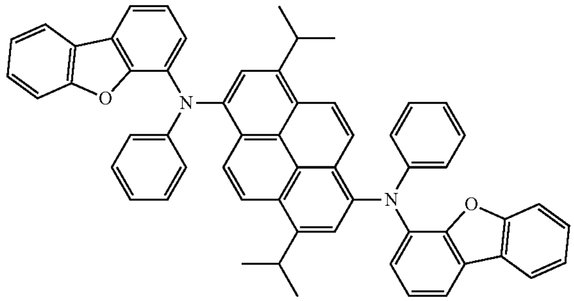
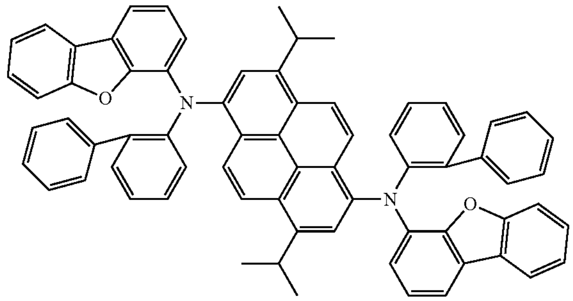
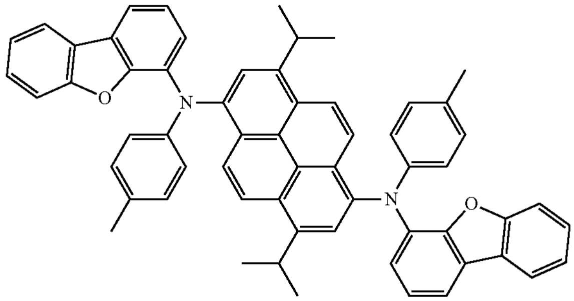
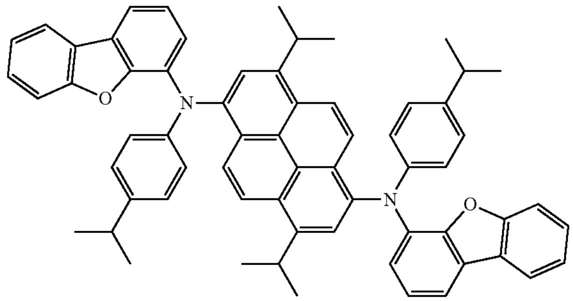
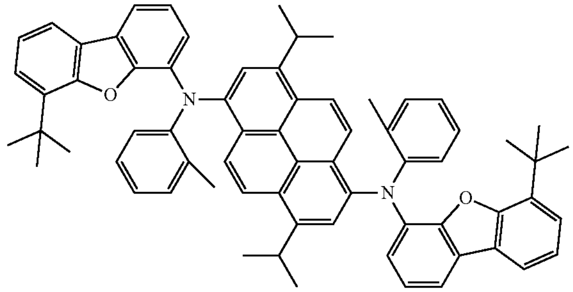
-continued
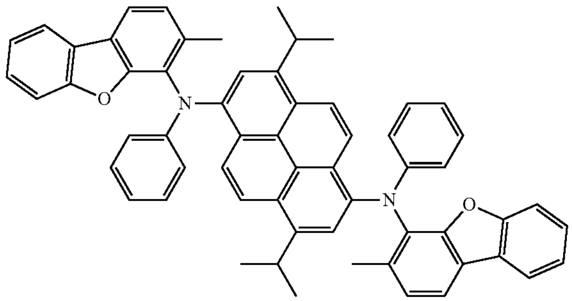
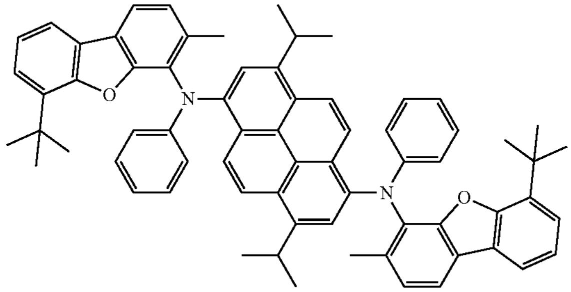
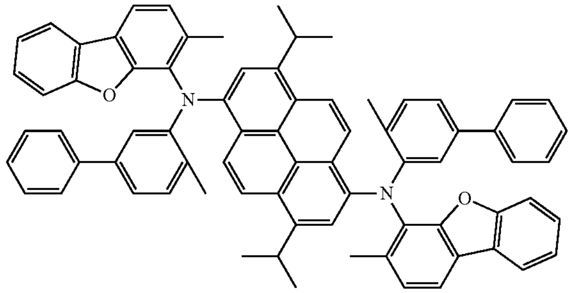
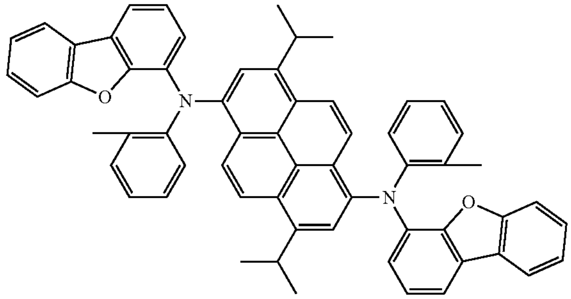
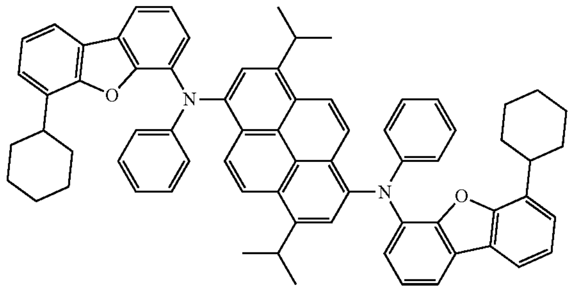

-continued

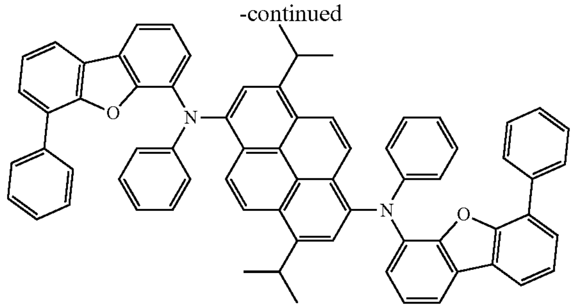

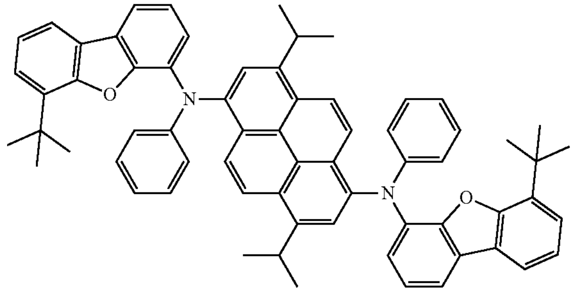 [SMILES: CC(C)c1cc(N(c2ccccc2)c2cccc3c2oc2c(C(C)(C)C)cccc23)c2ccc3c(C(C)C)cc(N(c4ccccc4)c4cccc5c4oc4c(C(C)(C)C)cccc45)c4ccc1c2c34]

Compound Represented by Formula (4)

The compound represented by the formula (4) will be described.

[Formula 129]

(4)

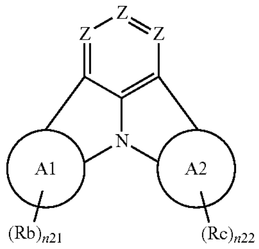

In the formula (4):

Z is each independently CRa or a nitrogen atom;

A1 ring and A2 ring are each independently a substituted or unsubstituted aromatic hydrocarbon ring having 6 to 50 ring carbon atoms, or a substituted or unsubstituted heterocycle having 5 to 50 ring atoms;

when a plurality of Ra are present, at least one combination of adjacent two or more of the plurality of Ra are mutually bonded to form a substituted or unsubstituted monocyclic ring, mutually bonded to form a substituted or unsubstituted fused ring, or not mutually bonded;

n21 and n22 are each independently 0, 1, 2, 3, or 4;

when a plurality of Rb are present, at least one combination of adjacent two or more of the plurality of Rb are mutually bonded to form a substituted or unsubstituted monocyclic ring, mutually bonded to form a substituted or unsubstituted fused ring, or not mutually bonded;

when a plurality of Rc are present, at least one combination of adjacent two or more of the plurality of Rc are mutually bonded to form a substituted or unsubstituted monocyclic ring, mutually bonded to form a substituted or unsubstituted fused ring, or not mutually bonded; and Ra, Rb, and Rc forming neither the monocyclic ring nor the fused ring are each independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms.

The "aromatic hydrocarbon ring" for the A1 ring and A2 ring has the same structure as a compound formed by introducing a hydrogen atom to the "aryl group" described above.

Ring atoms of the "aromatic hydrocarbon ring" for the A1 ring and the A2 ring include two carbon atoms on a fused bicyclic structure at the center of the formula (4)

Specific examples of the "substituted or unsubstituted aromatic hydrocarbon ring having 6 to 50 ring carbon atoms" include a compound formed by introducing a hydrogen atom to the "aryl group" described in the specific example group G1.

The "heterocycle" for the A1 ring and A2 ring has the same structure as a compound formed by introducing a hydrogen atom to the "heterocyclic group" described above.

Ring atoms of the "heterocycle" for the A1 ring and the A2 ring include two carbon atoms on a fused bicyclic structure at the center of the formula (4).

Specific examples of the "substituted or unsubstituted heterocycle having 5 to 50 ring atoms" include a compound formed by introducing a hydrogen atom to the "heterocyclic group" described in the specific example group G2.

Rb is bonded to any one of carbon atoms forming the aromatic hydrocarbon ring for the A1 ring or any one of the atoms forming the heterocycle for the A1 ring.

Rc is bonded to any one of carbon atoms forming the aromatic hydrocarbon ring for the A2 ring or any one of the atoms forming the heterocycle for the A2 ring.

At least one of Ra, Rb, or Rc is preferably a group represented by a formula (4a) below. More preferably, at least two of Ra, Rb, and Rc are groups represented by the formula (4a).

[Formula 130]

(4a)

$$*-L_{401}-Ar_{401}$$

In the formula (4a):

$L_{401}$ is a single bond, a substituted or unsubstituted arylene group having 6 to 30 ring carbon atoms, or a substituted or unsubstituted divalent heterocyclic group having 5 to 30 ring atoms; and $Ar_{401}$ is a substituted or unsubstituted aryl group having 6 to 50 ring carbon atoms, a substituted or unsubstituted heterocyclic group having 5 to 50 ring atoms, or a group represented by a formula (4b) below.

[Formula 131]

(4b)

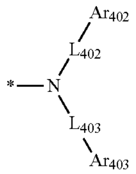

In the formula (4b):

$L_{402}$ and $L_{403}$ are each independently a single bond, a substituted or unsubstituted arylene group having 6 to 30 ring carbon atoms, or a substituted or unsubstituted divalent heterocyclic group having 5 to 30 ring atoms;

a combination of $Ar_{402}$ and $Ar_{403}$ are mutually bonded to form a substituted or unsubstituted monocyclic ring, mutually bonded to form a substituted or unsubstituted fused ring, or not mutually bonded; and $Ar_{402}$ and $Ar_{403}$ forming neither the monocyclic ring nor the fused ring are each independently a substituted or unsubstituted aryl group having 6 to 50 ring carbon atoms, or a substituted or unsubstituted heterocyclic group having 5 to 50 ring atoms.

In an exemplary embodiment, the compound represented by the formula (4) is represented by a formula (42) below.

[Formula 132]

(42)

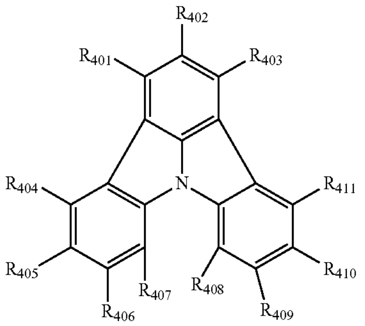

In the formula (42):

at least one combination of adjacent two or more of $R_{401}$ to $R_{411}$ are mutually bonded to form a substituted or unsubstituted monocyclic ring, mutually bonded to form a substituted or unsubstituted fused ring, or not mutually bonded; and $R_{401}$ to $R_{411}$ forming neither the monocyclic ring nor the fused ring are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms.

At least one of $R_{401}$ to $R_{411}$ is preferably a group represented by the formula (4a). More preferably, at least two of $R_{401}$ to $R_{411}$ are each a group represented by the formula (4a).

$R_{404}$ and $R_{411}$ are each preferably a group represented by the formula (4a).

In an exemplary embodiment, the compound represented by the formula (4) is a compound formed by bonding a structure represented by a formula (4-1) or a formula (4-2) below to the A1 ring.

Further, in an exemplary embodiment, the compound represented by the formula (42) is a compound formed by bonding a structure represented by the formula (4-1) or the formula (4-2) to the ring bonded with $R_{404}$ to $R_{407}$.

[Formula 133]

(4-1)

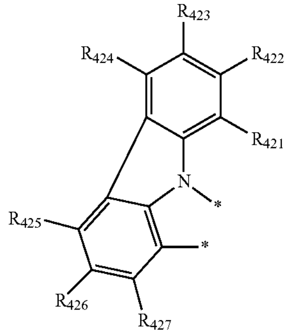

(4-2)

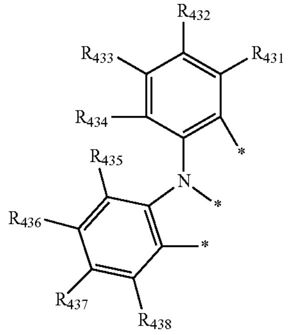

In the formula (4-1), two bonds * are each independently bonded to a ring-forming carbon atom of the aromatic hydrocarbon ring or a ring atom of the heterocycle for the A1 ring in the formula (4) or bonded to one of $R_{404}$ to $R_{407}$ in the formula (42);

in the formula (4-2), three bonds * are each independently bonded to a ring-forming carbon atom of the aromatic hydrocarbon ring or a ring atom of the heterocycle for the A1 ring in the formula (4) or bonded to one of $R_{404}$ to $R_{407}$ in the formula (42);

at least one combination of adjacent two or more of $R_{421}$ to $R_{427}$ are mutually bonded to form a substituted or unsubstituted monocyclic ring, mutually bonded to form a substituted or unsubstituted fused ring, or not mutually bonded;

at least one combination of adjacent two or more of $R_{431}$ to $R_{438}$ are mutually bonded to form a substituted or unsubstituted monocyclic ring, mutually bonded to form a substituted or unsubstituted fused ring, or not mutually bonded; and $R_{421}$ to $R_{427}$ and $R_{431}$ to $R_{438}$ forming neither the monocyclic ring nor the fused ring are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms.

In an exemplary embodiment, the compound represented by the formula (4) is a compound represented by a formula (41-3), a formula (41-4), or a formula (41-5) below.

[Formula 134]

(41-3)

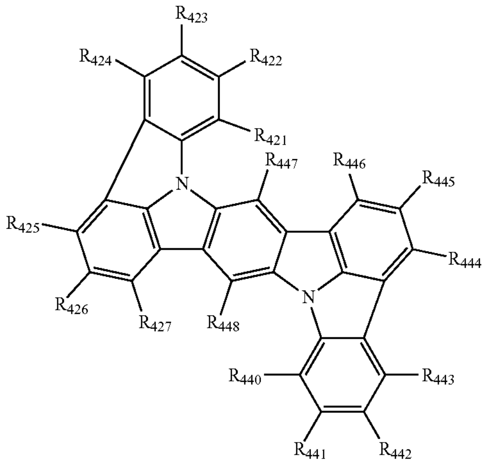

[Formula 135]

(41-4)

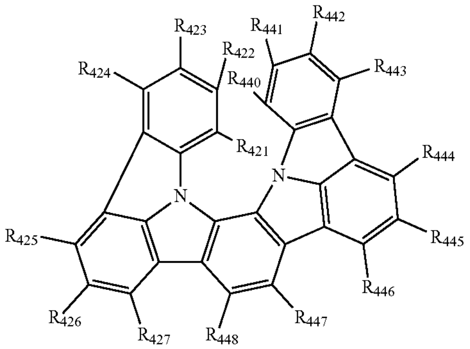

-continued

[Formula 136]

(41-5)

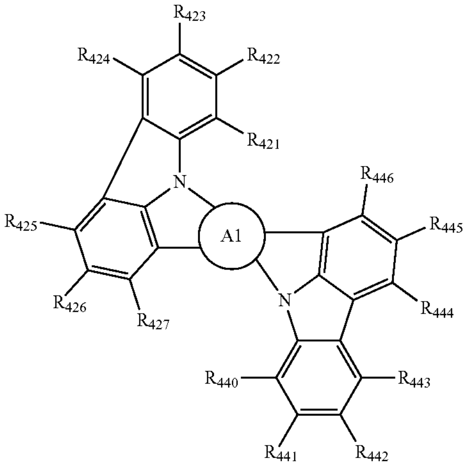

In the formulae (41-3), (41-4) and (41-5):

A1 ring is as defined for the formula (4);

$R_{421}$ to $R_{427}$ each independently represent the same as $R_{421}$ to $R_{427}$ in the formula (4-1); and $R_{440}$ to $R_{448}$ each independently represent the same as $R_{401}$ to $R_{411}$ in the formula (42).

In an exemplary embodiment, a substituted or unsubstituted aromatic hydrocarbon ring having 6 to 50 ring carbon atoms for the A1 ring in the formula (41-5) is a substituted or unsubstituted naphthalene ring, or a substituted or unsubstituted fluorene ring.

In an exemplary embodiment, a substituted or unsubstituted heterocycle having 5 to 50 ring atoms for the A1 ring in the formula (41-5) is a substituted or unsubstituted dibenzofuran ring, a substituted or unsubstituted carbazole ring, or a substituted or unsubstituted dibenzothiophene ring.

In an exemplary embodiment, the compound represented by the formula (4) or the formula (42) is selected from the group consisting of compounds represented by formulae (461) to (467) below.

[Formula 137]

(461)

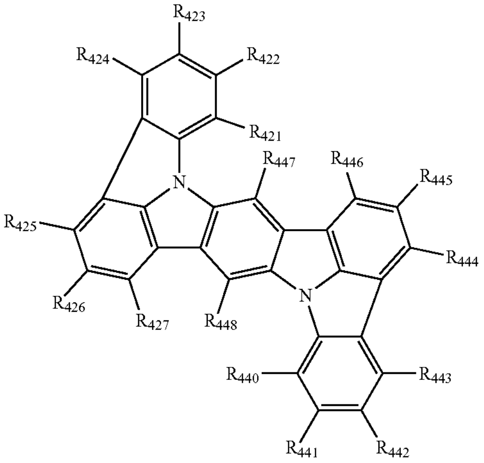

-continued (462)

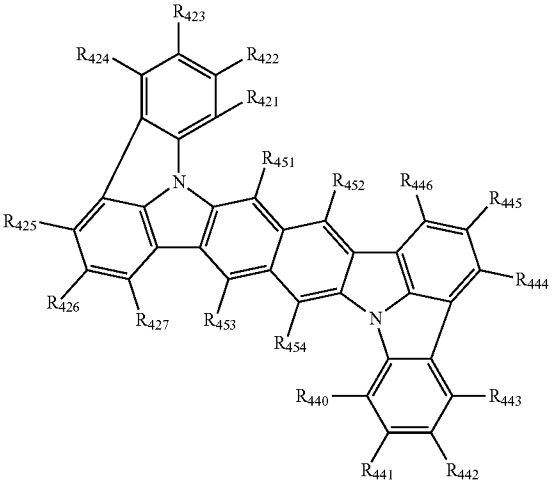

[Formula 138]

(463)

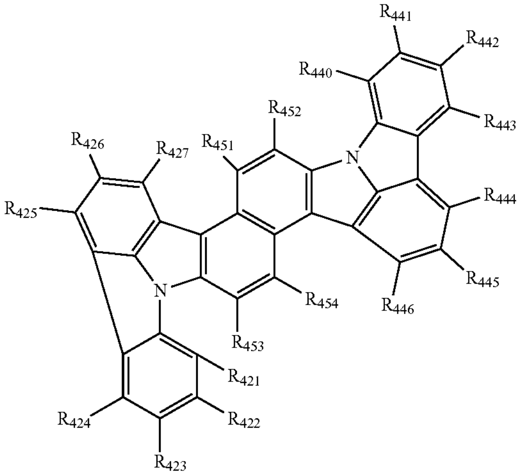

(464)

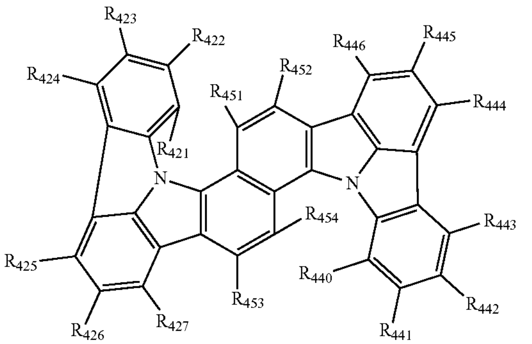

-continued

[Formula 139]

(465)

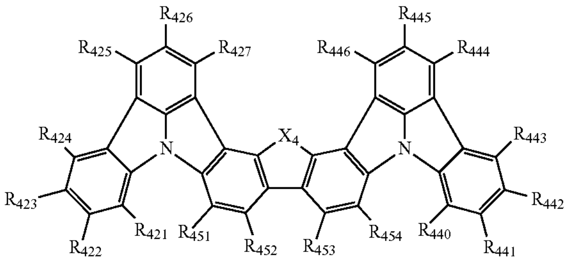

[Formula 140]

(466)

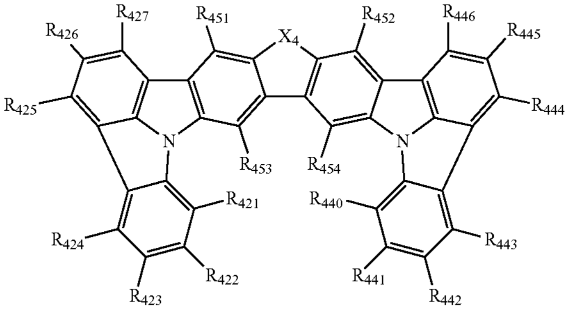

[Formula 141]

(467)

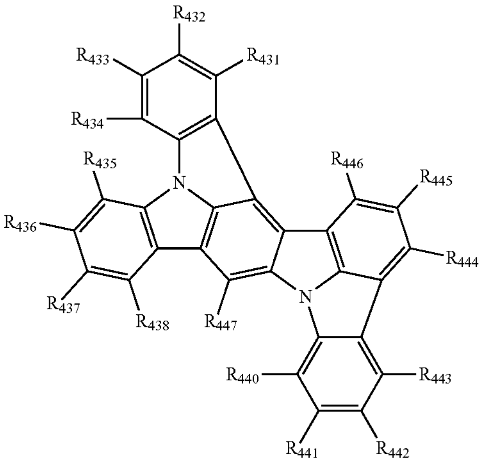

In the formulae (461), (462), (463), (464), (465), (466) and (467):

$R_{421}$ to $R_{427}$ each independently represent the same as $R_{421}$ to $R_{427}$ in the formula (4-1);

$R_{431}$ to $R_{438}$ each independently represent the same as $R_{431}$ to $R_{438}$ in the formula (4-2);

$R_{440}$ to $R_{448}$ and $R_{451}$ to $R_{454}$ each independently represent the same as $R_{401}$ to $R_{411}$ in the formula (42);

$X_4$ is an oxygen atom, $NR_{801}$, or $C(R_{802})(R_{803})$;

$R_{801}$, $R_{802}$, and $R_{803}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

a substituted or unsubstituted alkyl group having 1 to 50 carbon atoms, or a substituted or unsubstituted aryl group having 6 to 50 ring carbon atoms;

when a plurality of $R_{801}$ are present, the plurality of $R_{801}$ are mutually the same or different;

when a plurality of $R_{802}$ are present, the plurality of $R_{802}$ are mutually the same or different; and when a plurality of $R_{803}$ are present, the plurality of $R_{803}$ are mutually the same or different.

In an exemplary embodiment, in a compound represented by the formula (42), at least one combination of adjacent two or more of $R_{401}$ to $R_{411}$ are mutually bonded to form a substituted or unsubstituted monocyclic ring or a substituted or unsubstituted fused ring. The compound represented by the formula (42) in the exemplary embodiment is described in detail as a compound represented by a formula (45).

Compound Represented by Formula (45)

The compound represented by the formula (45) will be described.

[Formula 142]

(45)

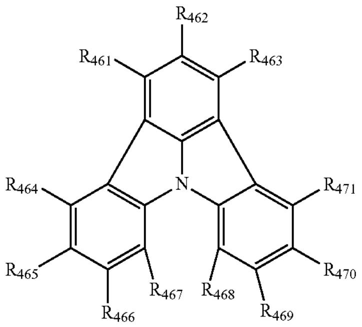

In the formula (45):

two or more of combinations selected from the group consisting of a combination of $R_{461}$ and $R_{462}$, a combination of $R_{462}$ and $R_{463}$, a combination of $R_{464}$ and $R_{465}$, a combination of $R_{465}$ and $R_{466}$, a combination of $R_{466}$ and $R_{467}$, a combination of $R_{468}$ and $R_{469}$, a combination of $R_{469}$ and $R_{470}$, and a combination of $R_{470}$ and $R_{471}$ are mutually bonded to form a substituted or unsubstituted monocyclic ring or a substituted or unsubstituted fused ring;

the combination of $R_{461}$ and $R_{462}$ and the combination of $R_{462}$ and $R_{463}$, the combination of $R_{464}$ and $R_{465}$ and the combination of $R_{465}$ and $R_{466}$, the combination of $R_{465}$ and $R_{466}$ and the combination of $R_{466}$ and $R_{467}$, the combination of $R_{468}$ and $R_{469}$ and the combination of $R_{469}$ and $R_{470}$, and the combination of $R_{469}$ and $R_{470}$ and the combination of $R_{470}$ and $R_{471}$ do not form a ring at the same time;

at least two rings formed by $R_{461}$ to $R_{471}$ are mutually the same or different; and $R_{461}$ to $R_{471}$ forming neither the monocyclic ring nor the fused ring are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms.

In the formula (45), $R_n$ and $R_{n+1}$ (n being an integer selected from 461, 462, 464 to 466, and 468 to 470) are mutually bonded to form a substituted or unsubstituted monocyclic ring or fused ring together with two ring-forming carbon atoms bonded with $R_n$ and $R_{n+1}$. The ring is preferably formed of atoms selected from the group consisting of a carbon atom, an oxygen atom, a sulfur atom, and a nitrogen atom, and is preferably made of 3 to 7, more preferably 5 or 6 atoms.

The number of the above cyclic structures in the compound represented by the formula (45) is, for instance, 2, 3, or 4. The two or more of the cyclic structures may be present on the same benzene ring on the basic skeleton represented by the formula (45) or may be present on different benzene rings. For instance, when three cyclic structures are present, each of the cyclic structures may be present on corresponding one of the three benzene rings of the formula (45).

Examples of the above cyclic structures in the compound represented by the formula (45) include structures represented by formulae (451) to (460) below.

[Formula 143]

(451)

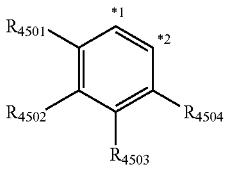

(452)

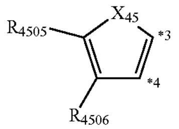

(453)

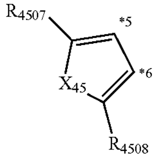

(454)

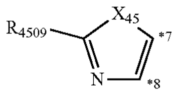

(455)

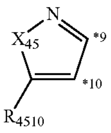

(456)

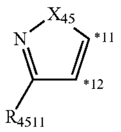

-continued (457)

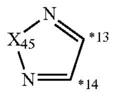

In the formulae (451) to (457):

each combination of *1 and *2, *3 and *4, *5 and *6, *7 and *8, *9 and *10, *11 and *12, and *13 and *14 represent the two ring-forming carbon atoms bonded with $R_n$ and $R_{n+1}$;

the ring-forming carbon atom bonded with $R_n$ may be any one of the two ring-forming carbon atoms represented by *1 and *2, *3 and *4, *5 and *6, *7 and *8, *9 and *10, *11 and *12, and *13 and *14;

$X_{45}$ is $C(R_{4512})(R_{4513})$, $NR_{4514}$, an oxygen atom, or a sulfur atom;

at least one combination of adjacent two or more of $R_{4501}$ to $R_{4506}$ and $R_{4512}$ to $R_{4513}$ are mutually bonded to form a substituted or unsubstituted monocyclic ring, mutually bonded to form a substituted or unsubstituted fused ring, or not mutually bonded; and $R_{4501}$ to $R_{4514}$ forming neither the monocyclic ring nor the fused ring each independently represent the same as $R_{461}$ to $R_{471}$ in the formula (45).

[Formula 144]

(458)

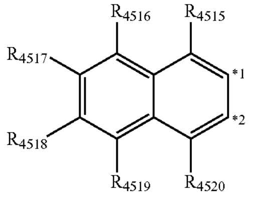

(459)

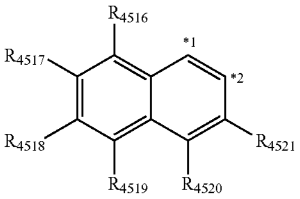

(460)

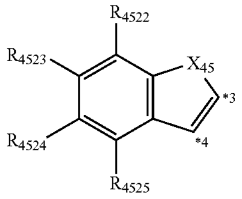

In the formulae (458) to (460):

each combination of *1 and *2, and *3 and *4 represent the two ring-forming carbon atoms bonded with $R_n$ and $R_{n+1}$;

the ring-forming carbon atom bonded with $R_n$ may be any one of the two ring-forming carbon atoms represented by *1 and *2, or *3 and *4;

$X_{45}$ is $C(R_{4512})(R_{4513})$, $NR_{4514}$, an oxygen atom, or a sulfur atom;

at least one combination of adjacent two or more of $R_{4512}$ to $R_{4513}$ and $R_{4515}$ to $R_{4525}$ are mutually bonded to form a substituted or unsubstituted monocyclic ring, mutually bonded to form a substituted or unsubstituted fused ring, or not mutually bonded; and $R_{4512}$ to $R_{4513}$, $R_{4515}$ to $R_{4521}$ and $R_{4522}$ to $R_{4525}$ not forming the monocyclic ring and not forming the fused ring, and $R_{4514}$ each independently represent the same as $R_{461}$ to $R_{471}$ in the formula (45).

In the formula (45), it is preferable that at least one of $R_{462}$, $R_{464}$, $R_{465}$, $R_{470}$ or $R_{471}$ (preferably, at least one of $R_{462}$, $R_{465}$ or $R_{470}$, more preferably $R_{462}$) is a group forming no cyclic structure.

(i) A substituent, if present, for a cyclic structure formed by $R_n$ and $R_{n+1}$ in the formula (45), (ii) $R_{461}$ to $R_{471}$ forming no cyclic structure in the formula (45), and (iii) $R_{4501}$ to $R_{4514}$, $R_{4515}$ to $R_{4525}$ in the formulae (451) to (460) are preferably each independently any one of groups selected from the group consisting of a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —$N(R_{906})(R_{907})$, a substituted or unsubstituted aryl group having 6 to 50 ring carbon atoms, a substituted or unsubstituted heterocyclic group having 5 to 50 ring atoms, or groups represented by formulae (461) to (464).

[Formula 145]

(461)

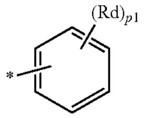

(462)

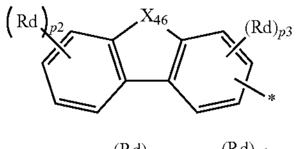

(463)

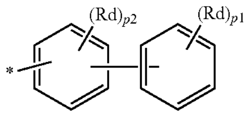

(464)

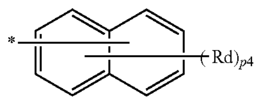

In the formulae (461) to (464):

$R_d$ are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —$Si(R_{901})(R_{902})(R_{903})$, a group represented by —O—$(R_{904})$, a group represented by —S—$(R_{905})$, a group represented by —$N(R_{906})(R_{907})$, a halogen atom, a cyano group, a nitro group, a substituted or unsubstituted aryl group having 6 to 50 ring carbon atoms, or a substituted or unsubstituted heterocyclic group having 5 to 50 ring atoms;

$X_{46}$ is $C(R_{801})(R_{802})$, $NR_{803}$, an oxygen atom or a sulfur atom;

$R_{801}$, $R_{802}$, and $R_{803}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

a substituted or unsubstituted alkyl group having 1 to 50 carbon atoms, or a substituted or unsubstituted aryl group having 6 to 50 ring carbon atoms;

when a plurality of $R_{801}$ are present, the plurality of $R_{801}$ are mutually the same or different;

when a plurality of $R_{802}$ are present, the plurality of $R_{802}$ are mutually the same or different;

when a plurality of $R_{803}$ are present, the plurality of $R_{803}$ are mutually the same or different;

p1 is 5;

p2 is 4;

p3 is 3;

p4 is 7; and

* in the formulae (461) to (464) each independently represent a bonding position to a cyclic structure.

In the third and fourth compounds, $R_{901}$ to $R_{907}$ represent the same as those as described above.

In an exemplary embodiment, the compound represented by the formula (45) is represented by one of formulae (45-1) to (45-6) below.

[Formula 146]

(45-1)

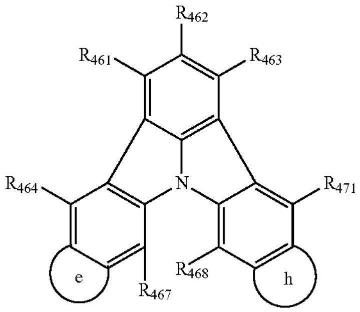

(45-2)

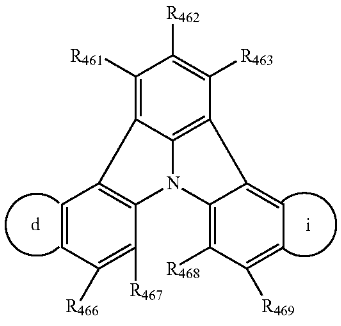

-continued (45-3)

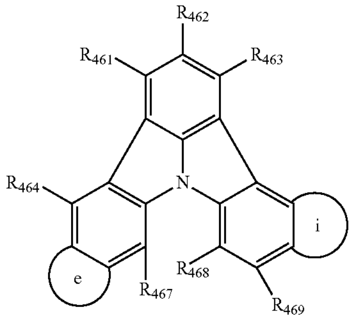

[Formula 147]

(45-4)

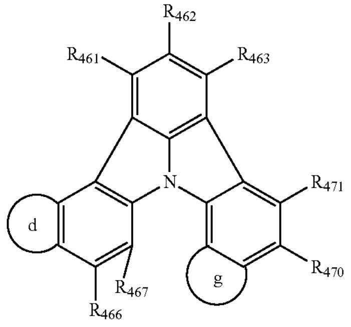

(45-5)

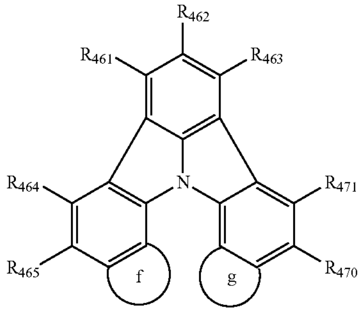

(45-6)

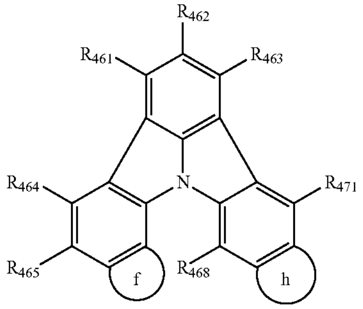

In the formulae (45-1) to (45-6):

rings d to i are each independently a substituted or unsubstituted monocyclic ring or a substituted or unsubstituted fused ring; and $R_{461}$ to $R_{471}$ each independently represent the same as $R_{461}$ to $R_{471}$ in the formula (45).

In an exemplary embodiment, the compound represented by the formula (45) is represented by one of formulae (45-7) to (45-12) below.

[Formula 148]

(45-7)

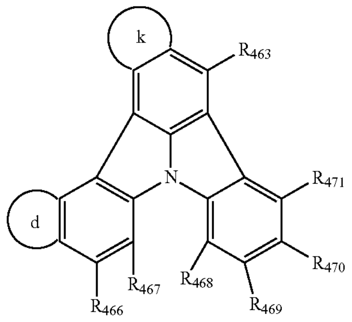

(45-8)

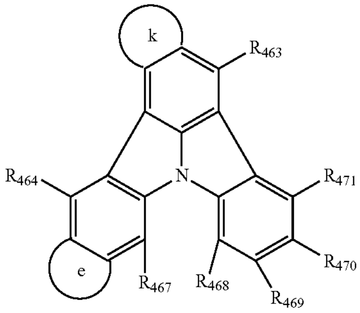

(45-9)

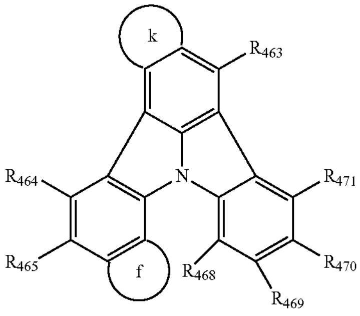

[Formula 149]

(45-10)

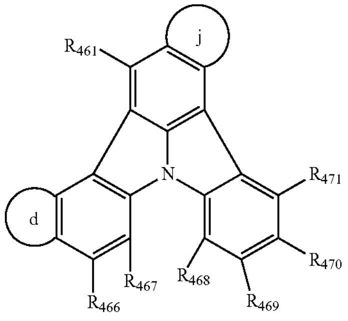

-continued (45-11)

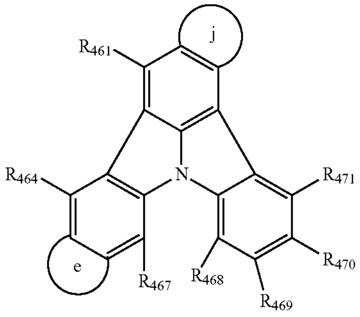

(45-12)

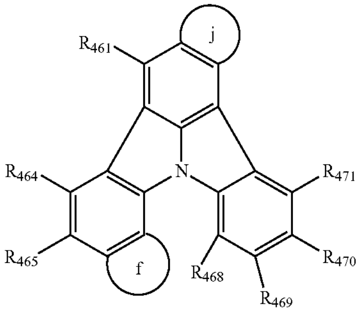

In the formulae (45-7) to (45-12):

rings d to f, k and j are each independently a substituted or unsubstituted monocyclic ring or a substituted or unsubstituted fused ring; and $R_{461}$ to $R_{471}$ each independently represent the same as $R_{481}$ to $R_{471}$ in the formula (45).

In an exemplary embodiment, the compound represented by the formula (45) is represented by one of formulae (45-13) to (45-21) below.

[Formula 150]

(45-13)

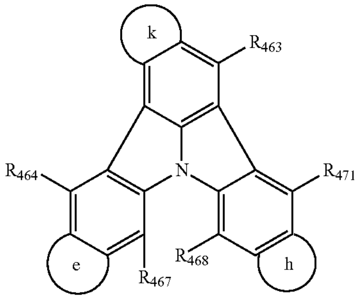

(45-14)

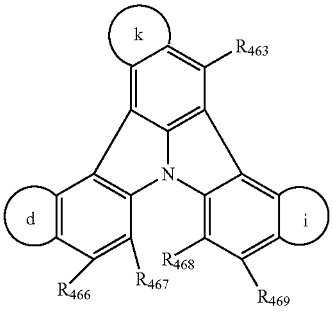

-continued (45-15)

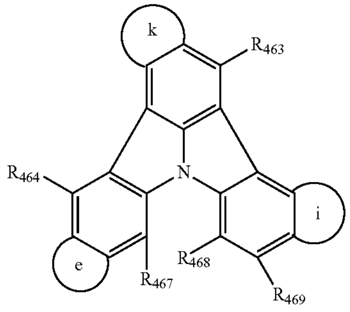

[Formula 151]

(45-16)

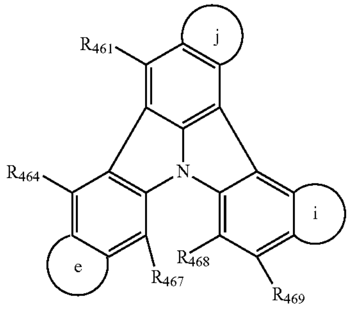

(45-17)

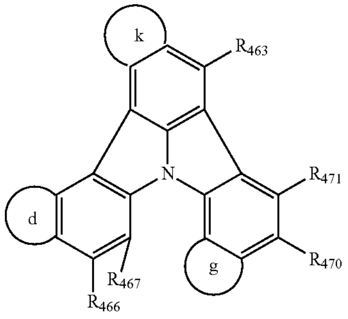

(45-18)

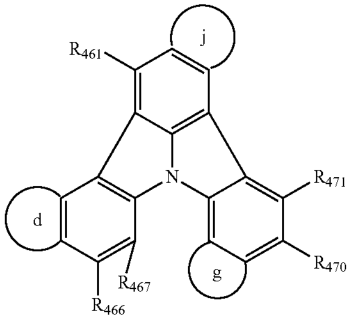

-continued

[Formula 152]

(45-19)

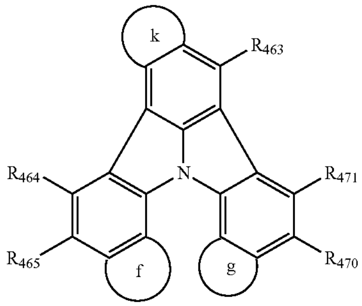

(45-20)

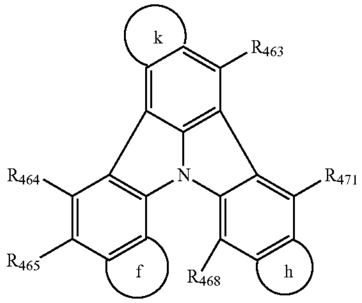

(45-21)

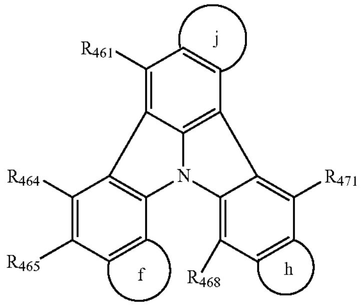

In the formulae (45-13) to (45-21):

rings d to k are each independently a substituted or unsubstituted monocyclic ring or a substituted or unsubstituted fused ring; and $R_{461}$ to $R_{471}$ each independently represent the same as $R_{461}$ to $R_{471}$ in the formula (45).

When the ring g or the ring h further has a substituent, examples of the substituent include a substituted or unsubstituted alkyl group having 1 to 50 carbon atoms, a substituted or unsubstituted aryl group having 6 to 50 ring carbon atoms, a group represented by the formula (461), a group represented by the formula (463), and a group represented by the formula (464).

In an exemplary embodiment, the compound represented by the formula (45) is represented by one of formulae (45-22) to (45-25) below.

[Formula 153]

(45-22)

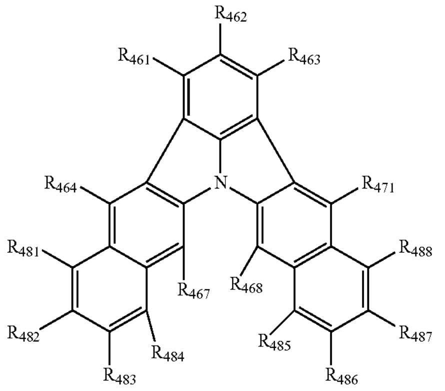

(45-23)

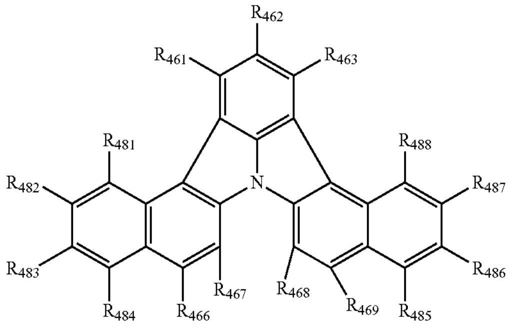

(45-24)

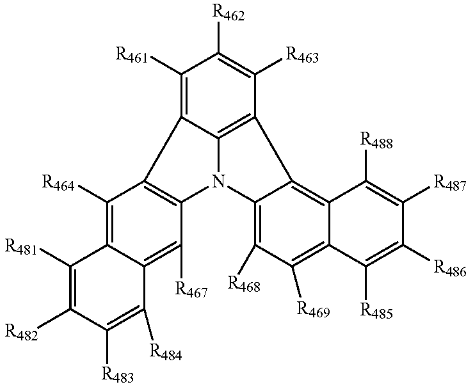

(45-25)

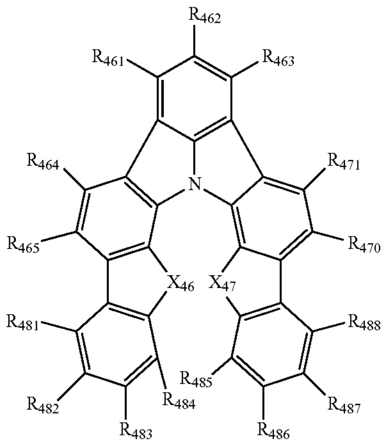

In the formulae (45-22) to (45-25):

$X_{46}$ and $X_{47}$ are each independently $C(R_{801})(R_{802})$, $NR_{803}$, an oxygen atom or a sulfur atom;

$R_{461}$ to $R_{471}$ and $R_{481}$ to $R_{488}$ each independently represent the same as $R_{461}$ to $R_{471}$ of the formula (45);

$R_{801}$, $R_{802}$, and $R_{803}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

a substituted or unsubstituted alkyl group having 1 to 50 carbon atoms, or a substituted or unsubstituted aryl group having 6 to 50 ring carbon atoms;

when a plurality of $R_{801}$ are present, the plurality of $R_{801}$ are mutually the same or different;

when a plurality of $R_{802}$ are present, the plurality of $R_{802}$ are mutually the same or different; and when a plurality of $R_{803}$ are present, the plurality of $R_{803}$ are mutually the same or different.

In an exemplary embodiment, the compound represented by the formula (45) is represented by a formula (45-26) below.

[Formula 154]

(45-26)

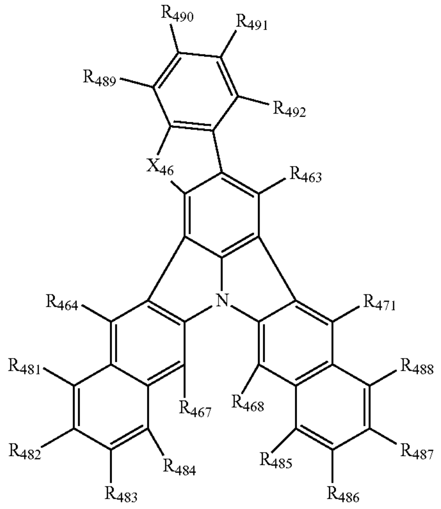

In the formula (45-26):

$X_{46}$ is $C(R_{801})(R_{802})$, $NR_{803}$, an oxygen atom or a sulfur atom;

$R_{463}$, $R_{464}$, $R_{467}$, $R_{468}$, $R_{471}$, and $R_{481}$ to $R_{492}$ each independently represent the same as $R_{461}$ to $R_{471}$ in the formula (45);

$R_{801}$, $R_{802}$, and $R_{803}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

a substituted or unsubstituted alkyl group having 1 to 50 carbon atoms, or a substituted or unsubstituted aryl group having 6 to 50 ring carbon atoms;

when a plurality of $R_{801}$ are present, the plurality of $R_{801}$ are mutually the same or different;

when a plurality of $R_{802}$ are present, the plurality of $R_{802}$ are mutually the same or different; and when a plurality of $R_{803}$ are present, the plurality of $R_{803}$ are mutually the same or different.

Specific examples of the compound represented by the formula (4) include compounds shown below. In the specific examples below, Ph represents a phenyl group, and D represents a deuterium atom.

[Formula 155]

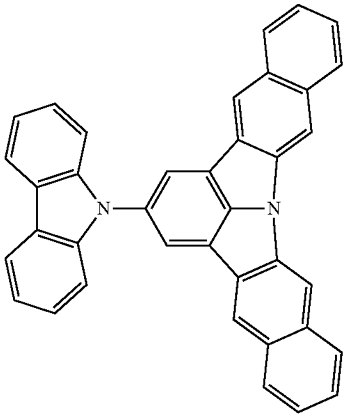

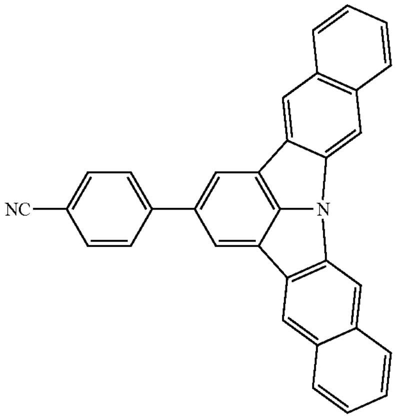

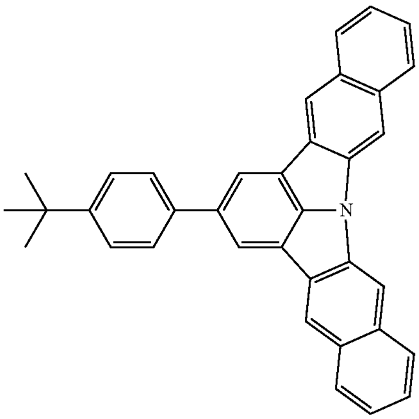

-continued

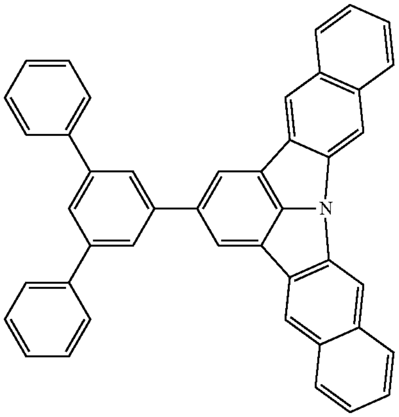

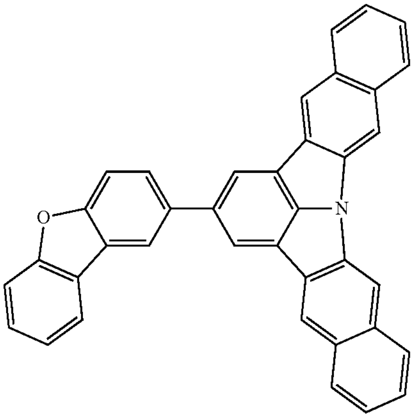

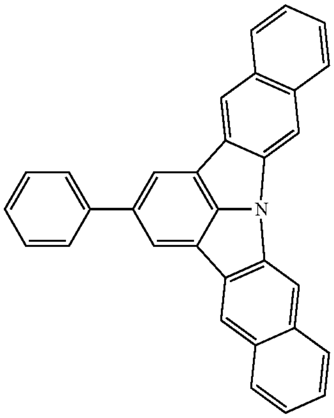

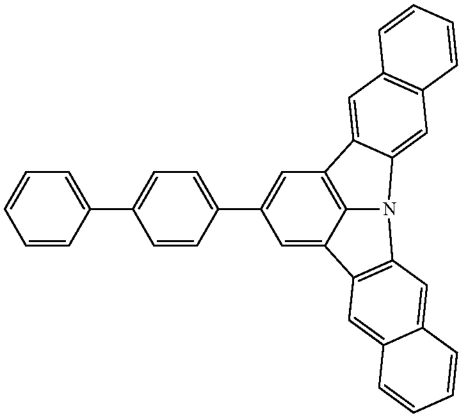

-continued
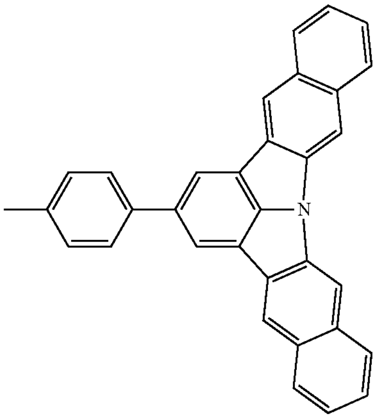
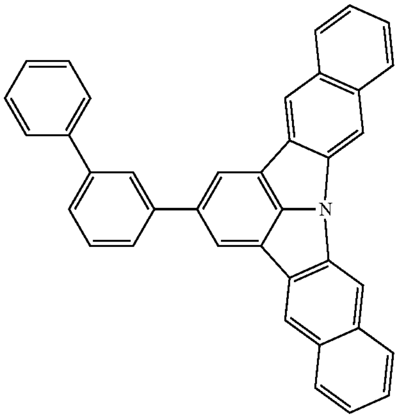
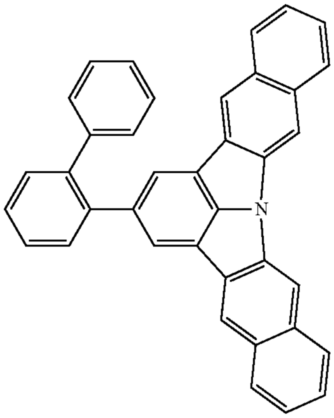
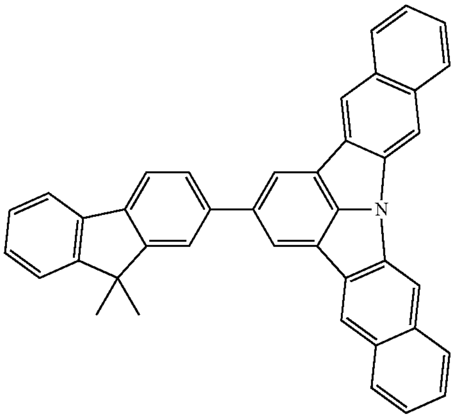
-continued
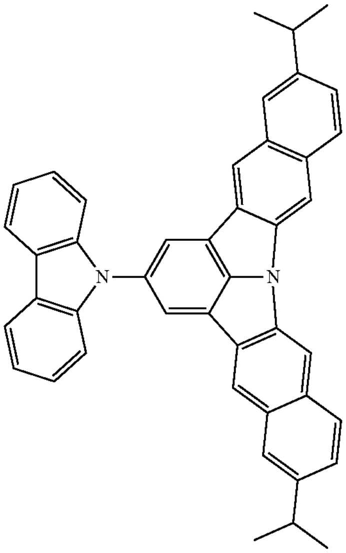
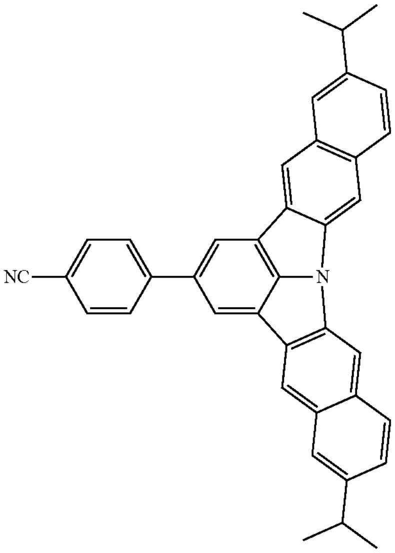
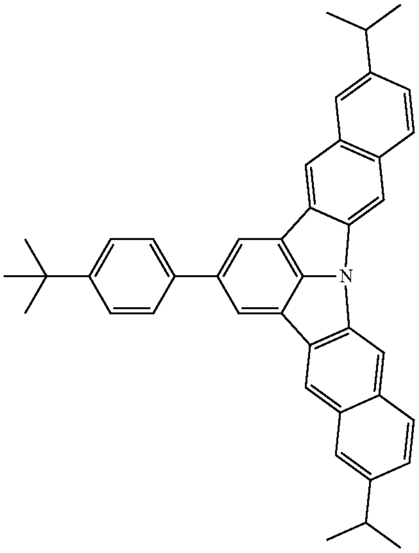

-continued
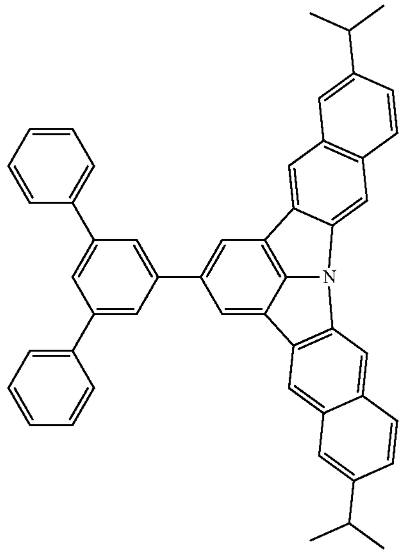
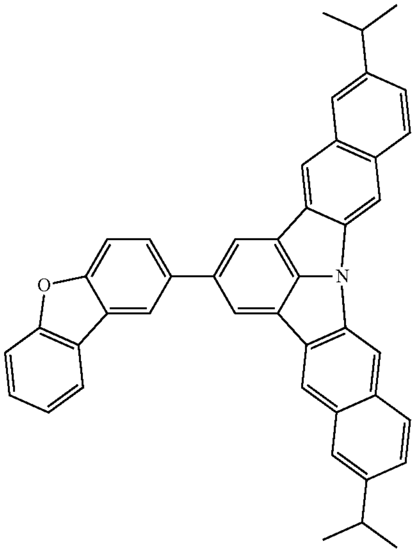
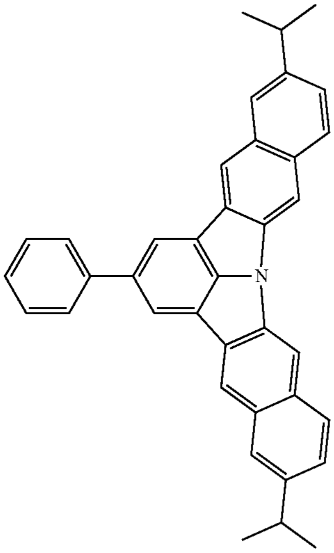
-continued
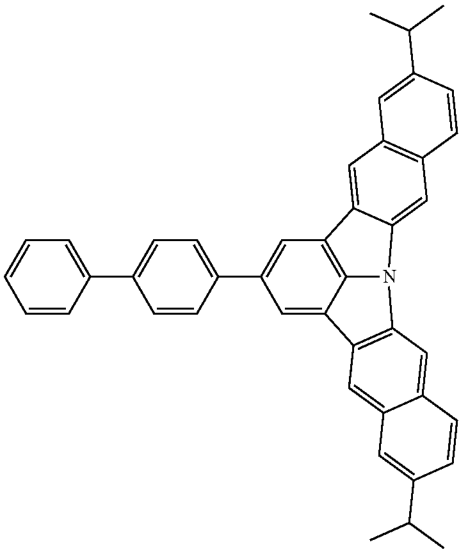
[Formula 156]
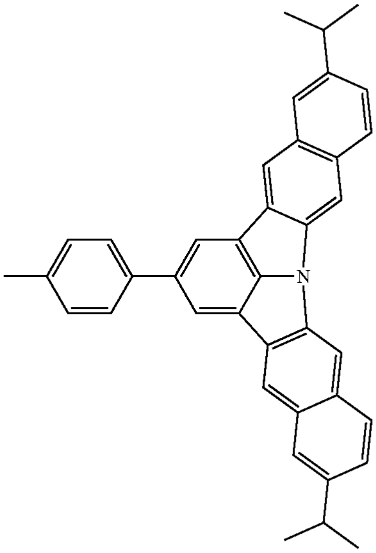
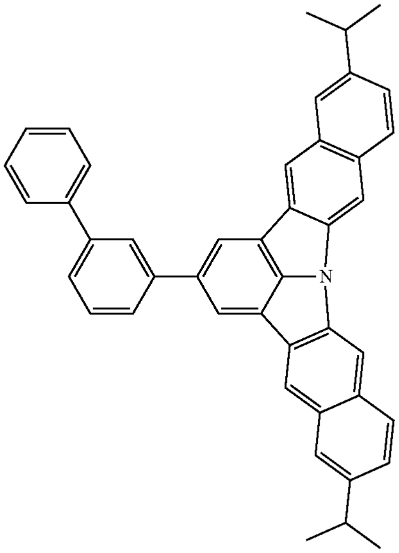

-continued
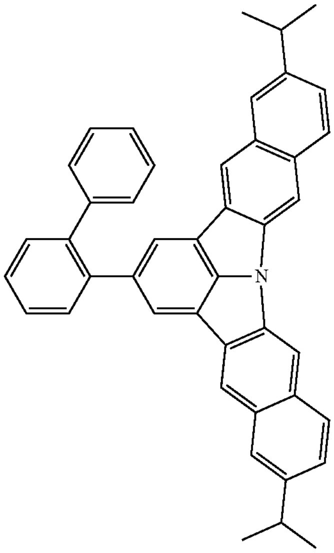
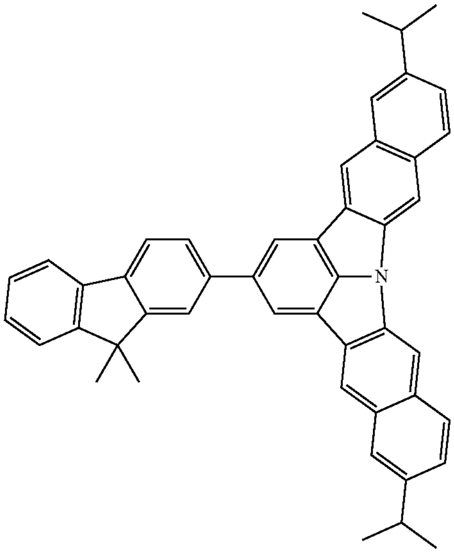
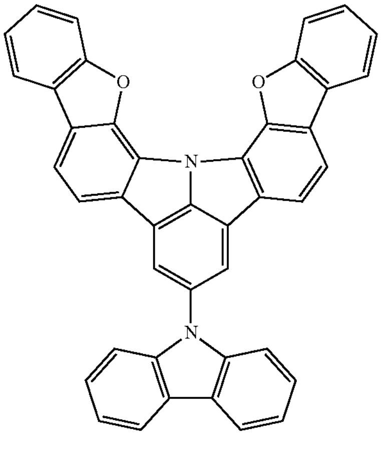
-continued
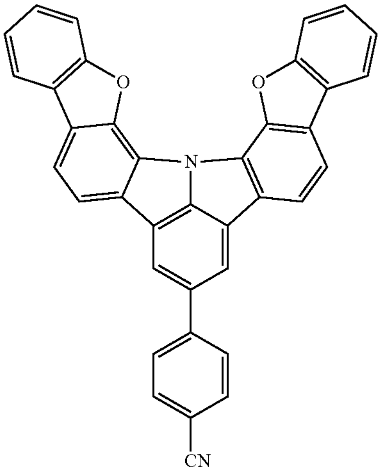
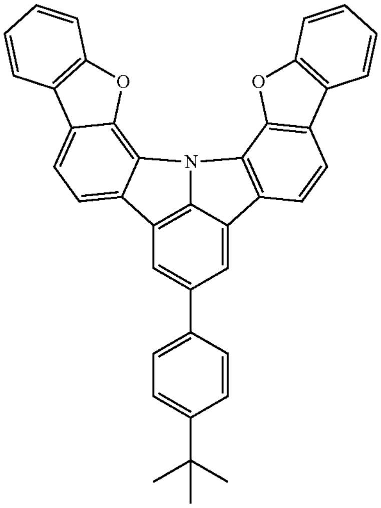
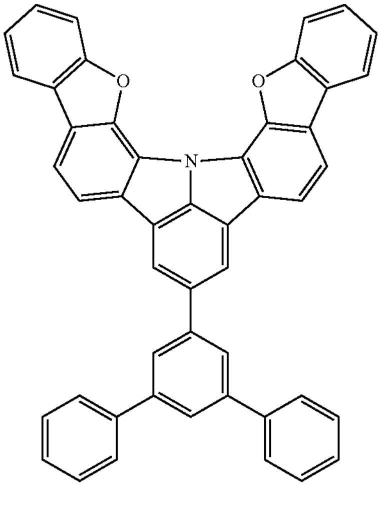

-continued
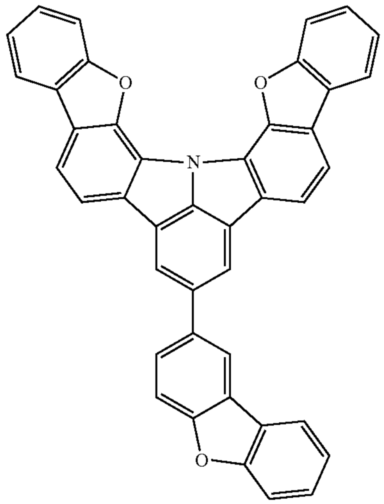
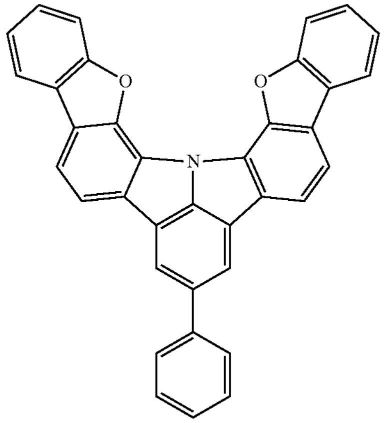
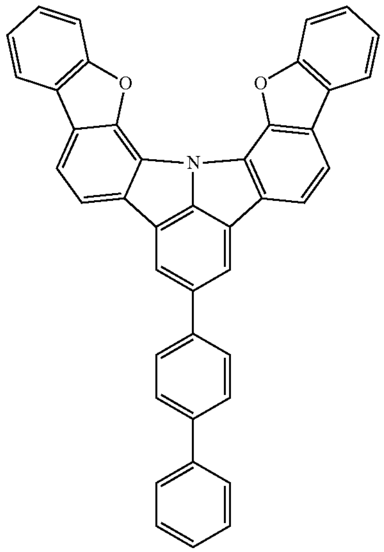
-continued
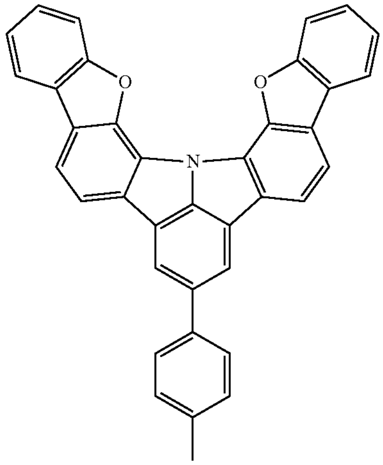
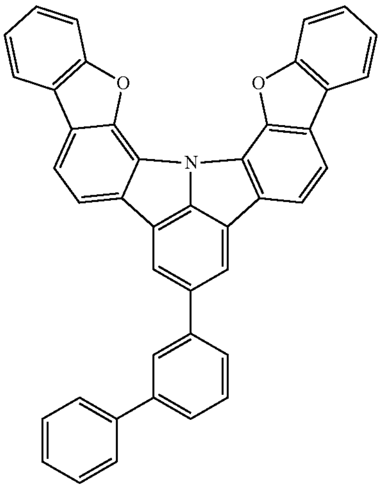
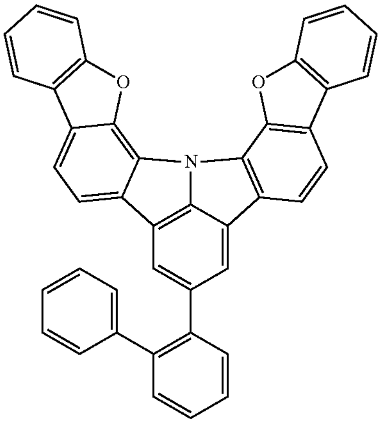

-continued
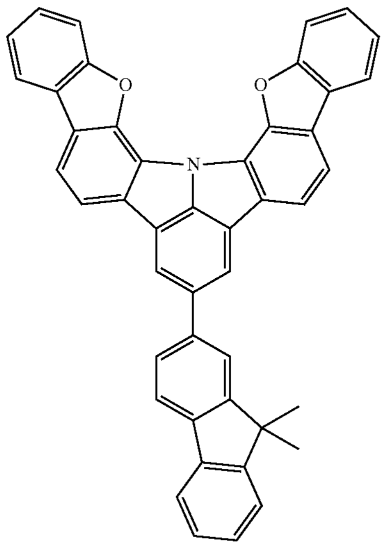
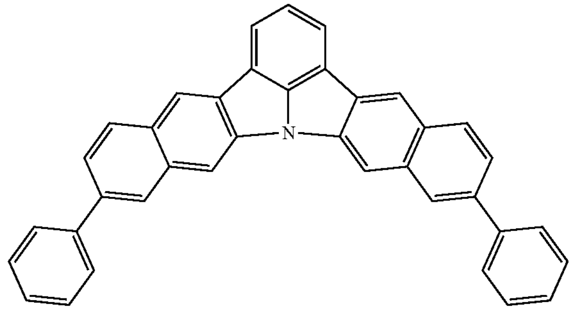
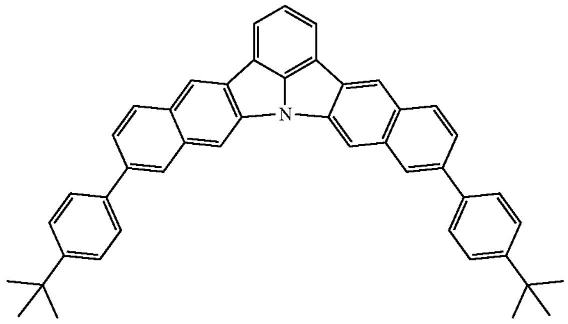
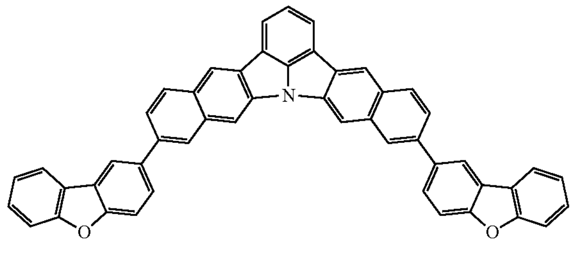
-continued
[Formula 157]
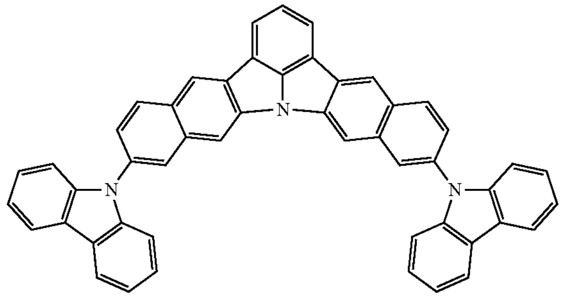
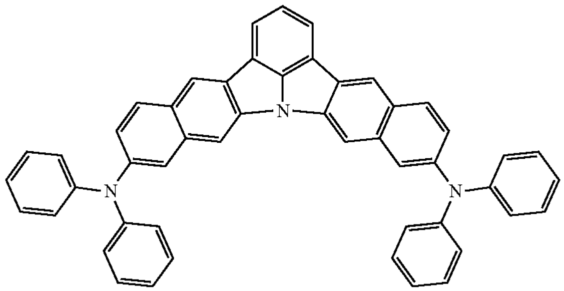
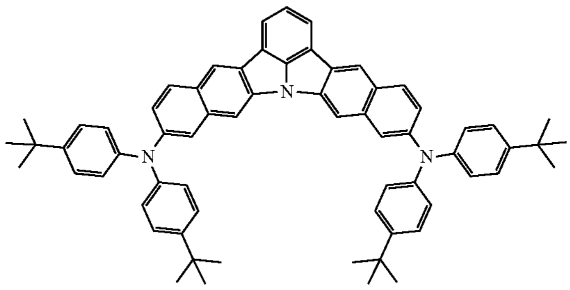
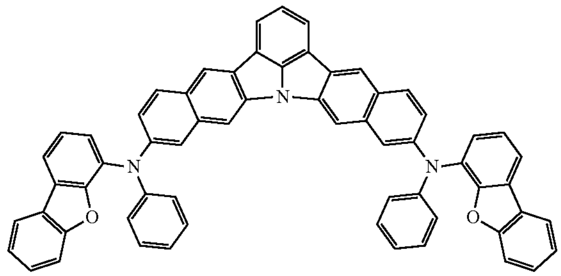
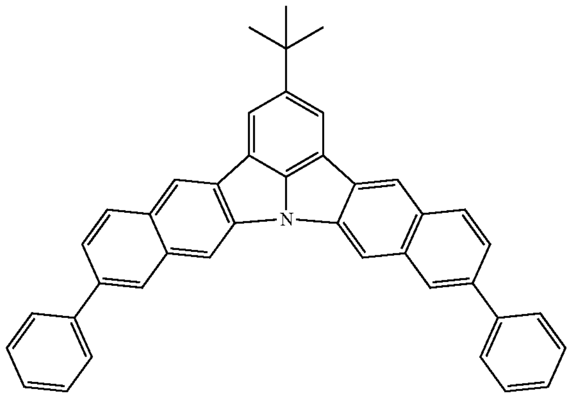

-continued
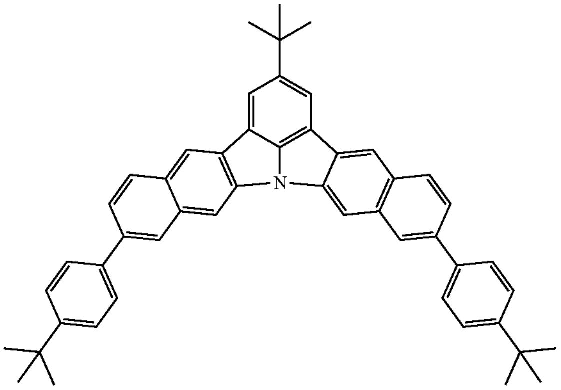
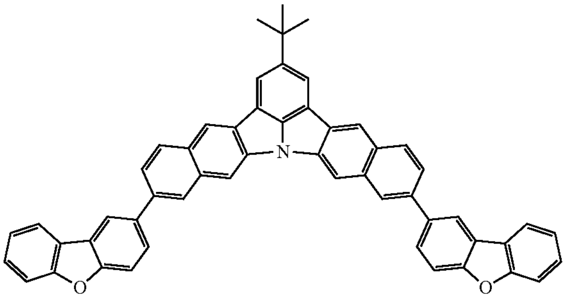
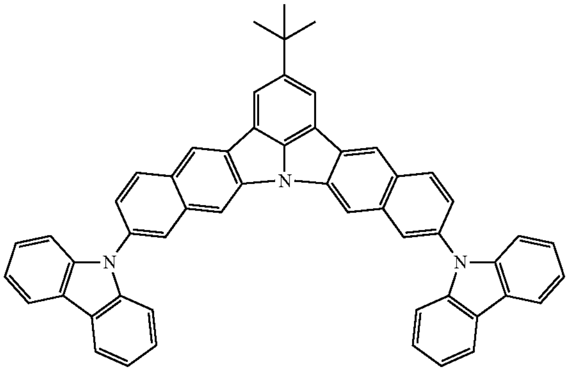
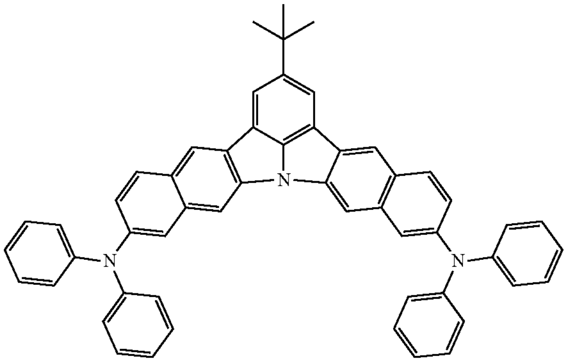
-continued
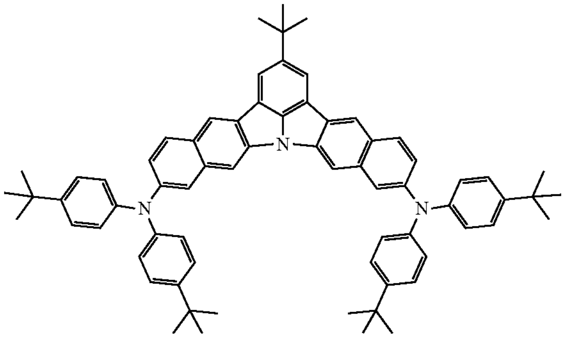
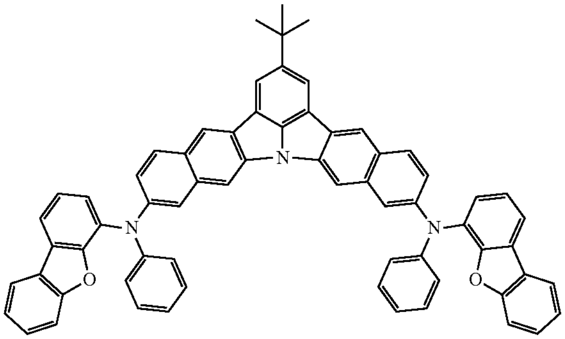
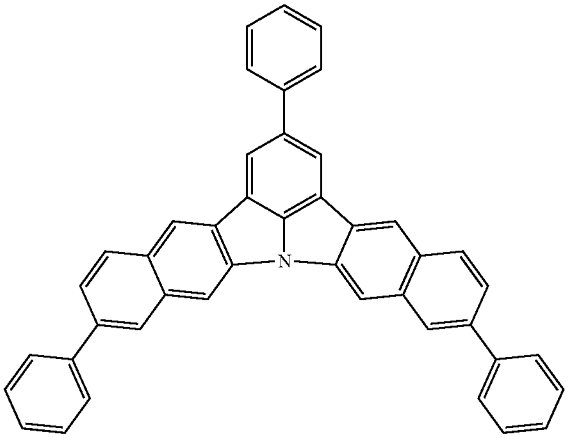
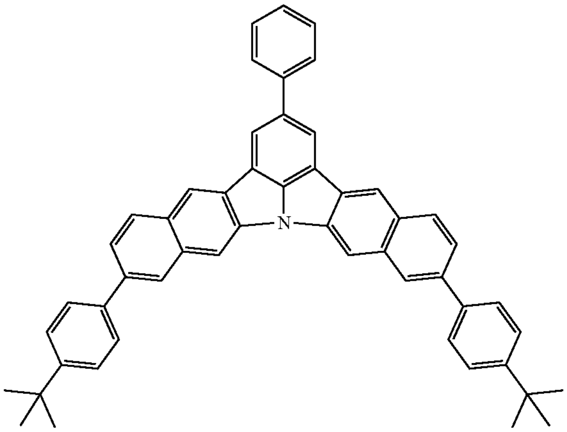

-continued
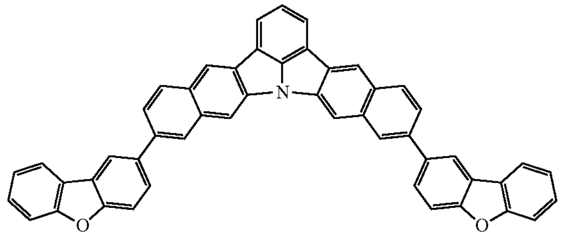
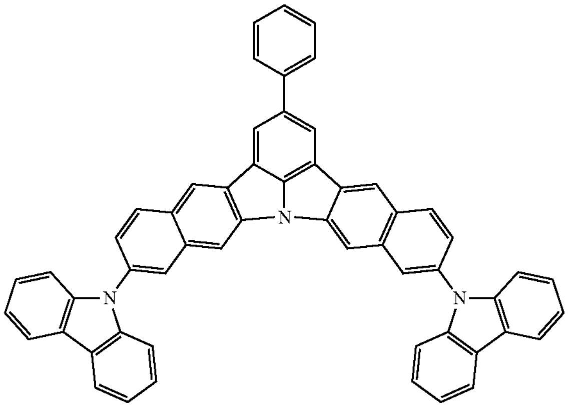
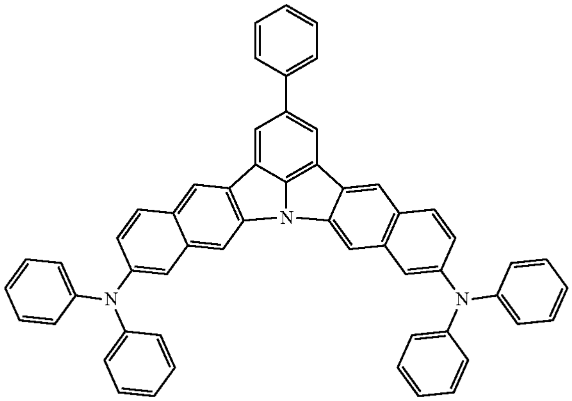
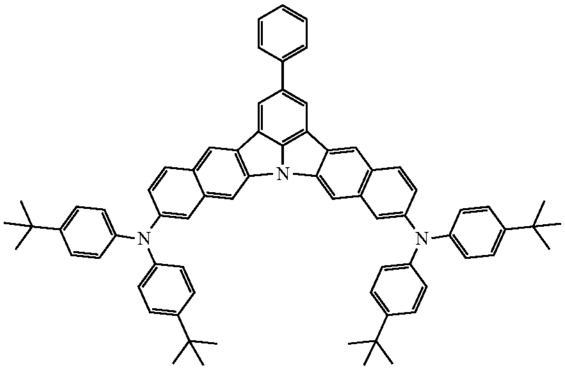
-continued
[Formula 158]
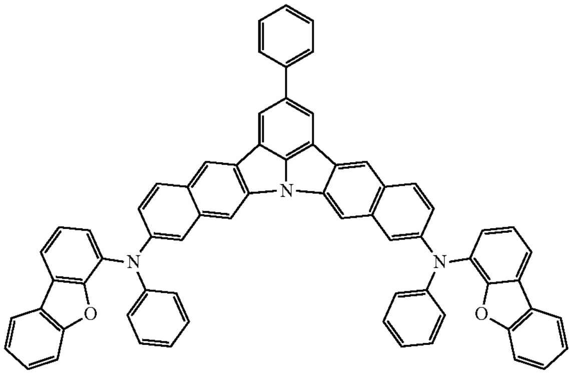
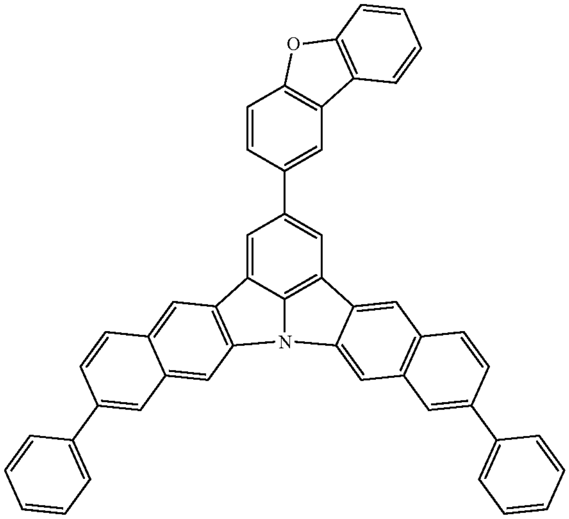
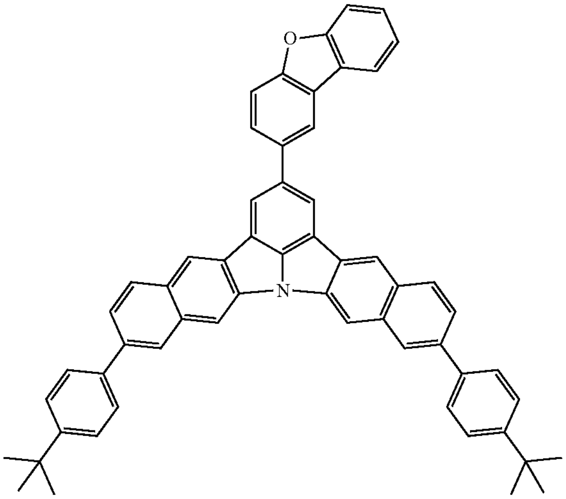

-continued
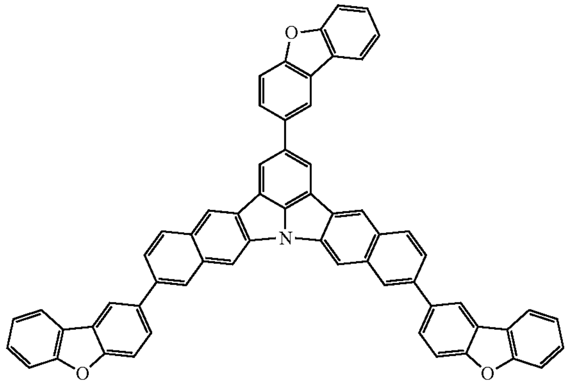
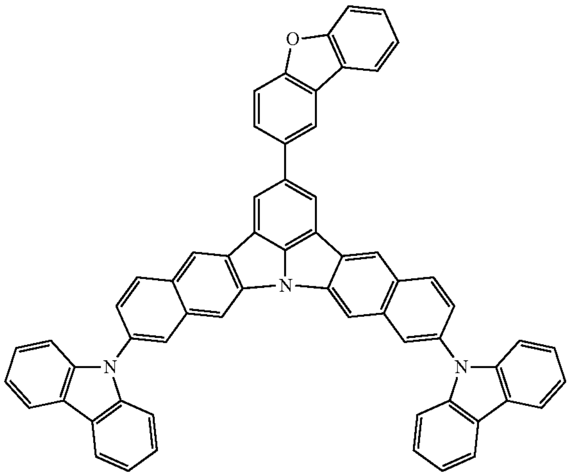
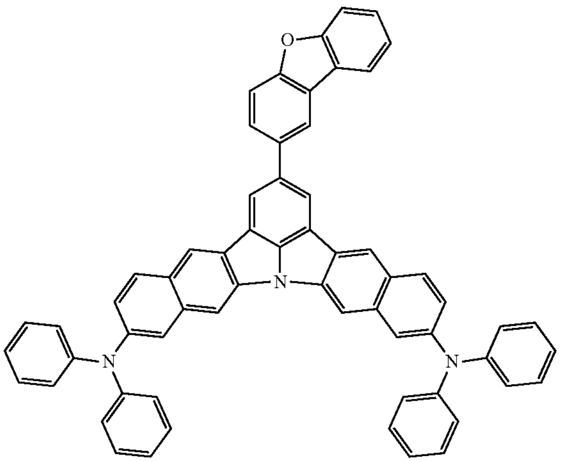
-continued
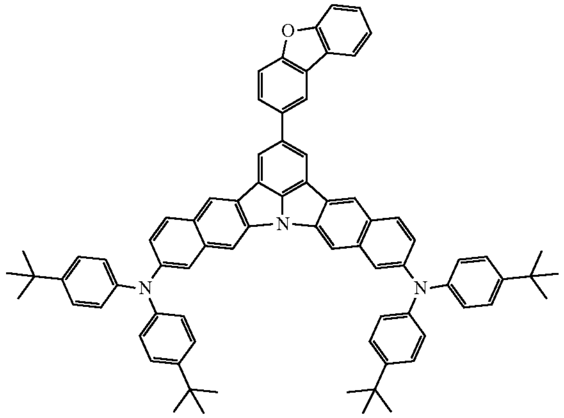
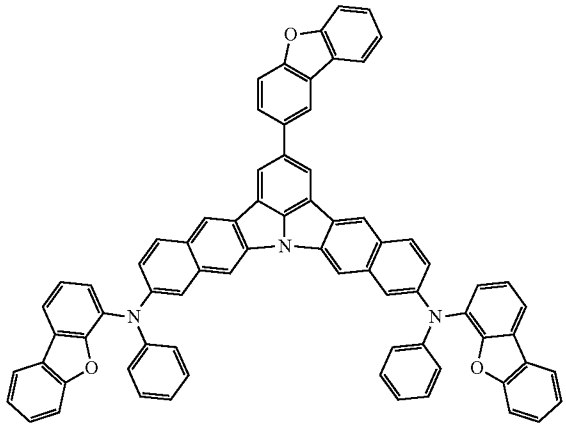
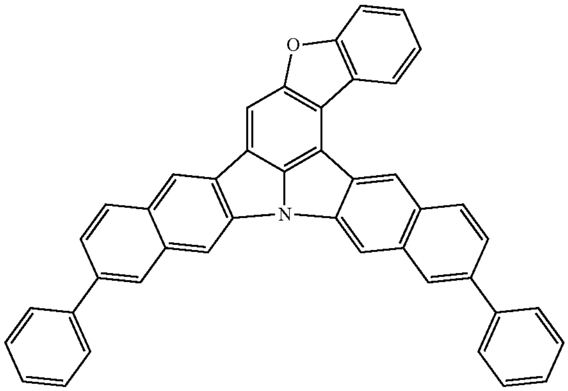
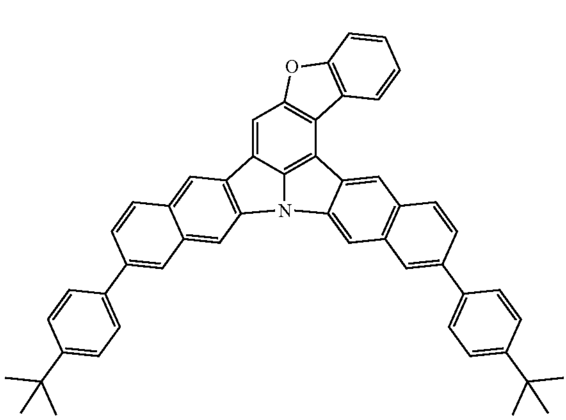

-continued
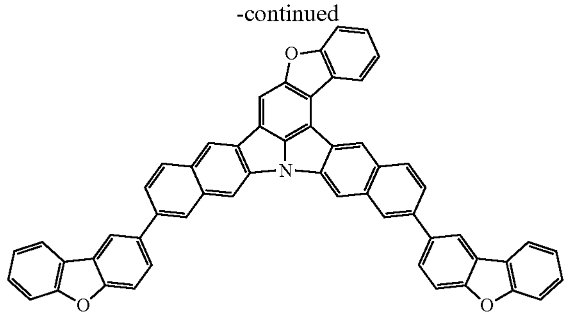
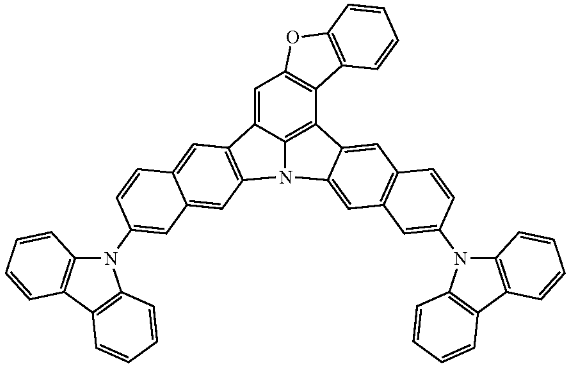
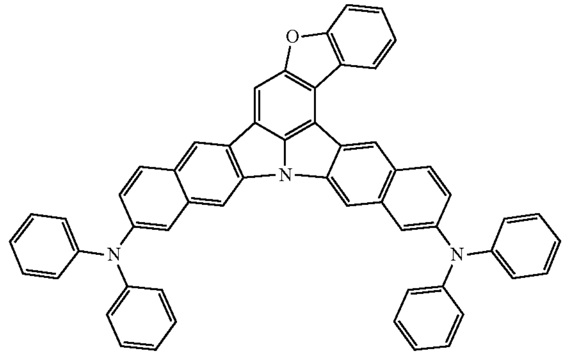
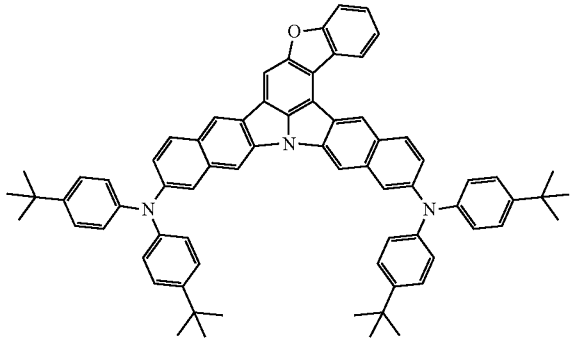
[Formula 159]
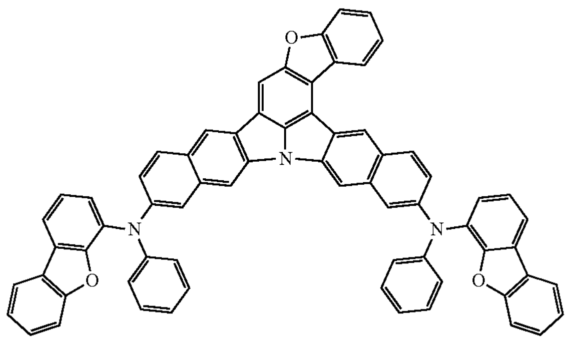
-continued
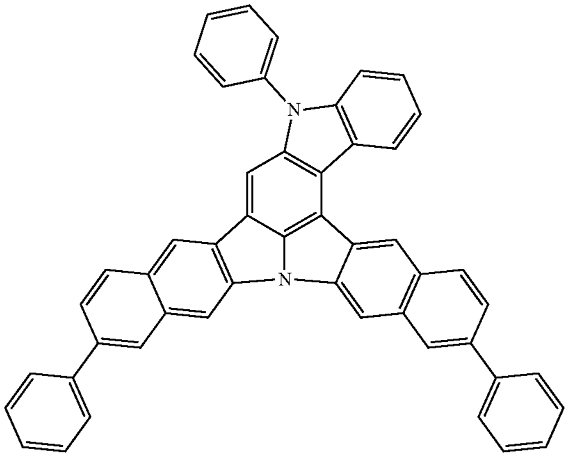
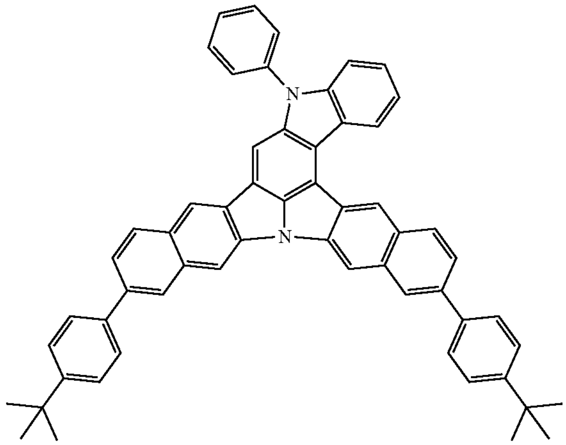
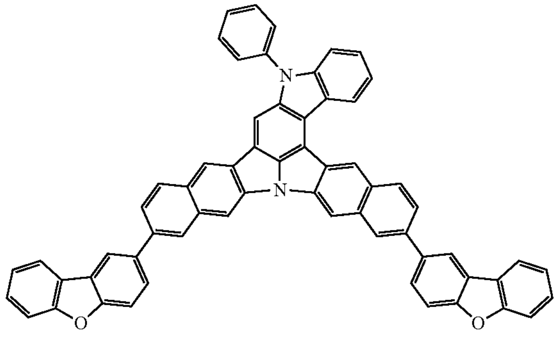
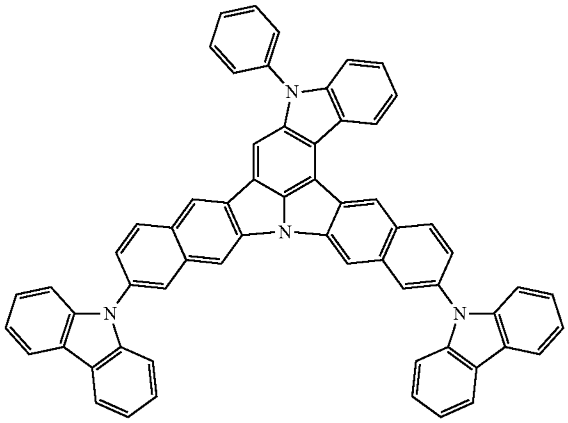

-continued
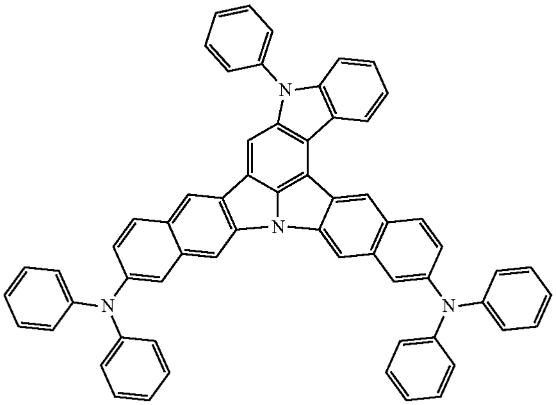
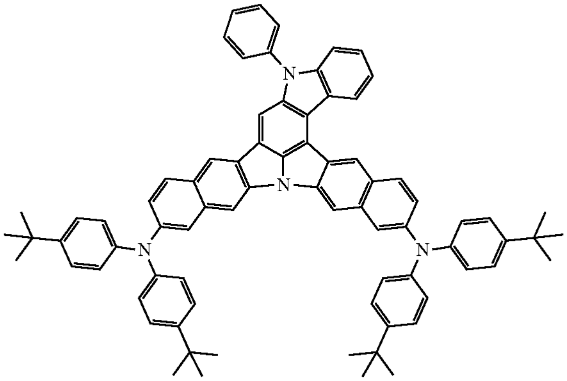
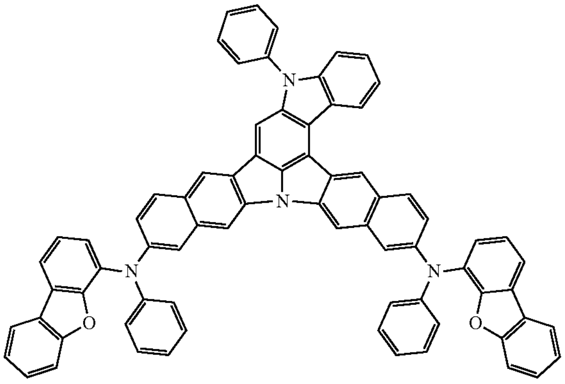
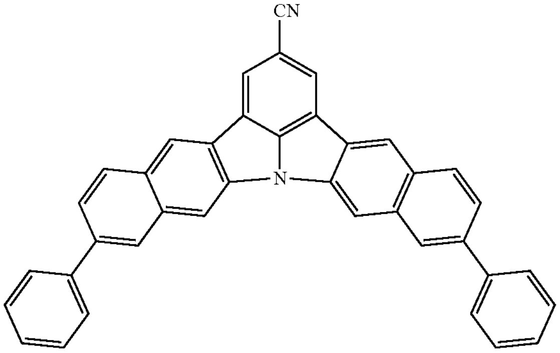
-continued
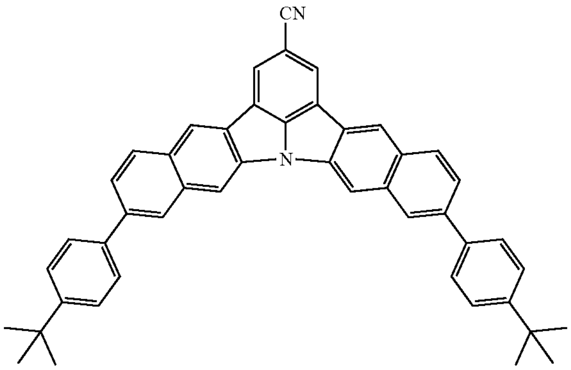
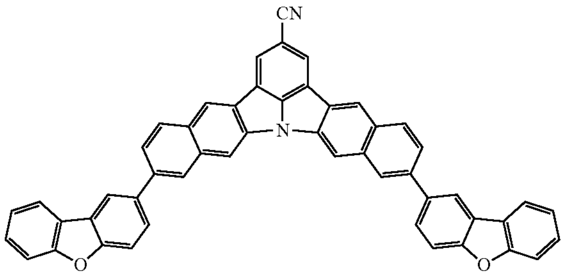
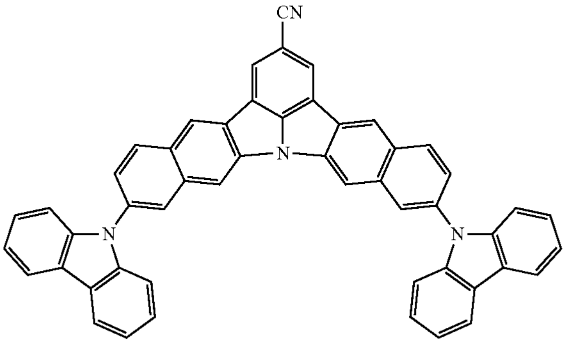
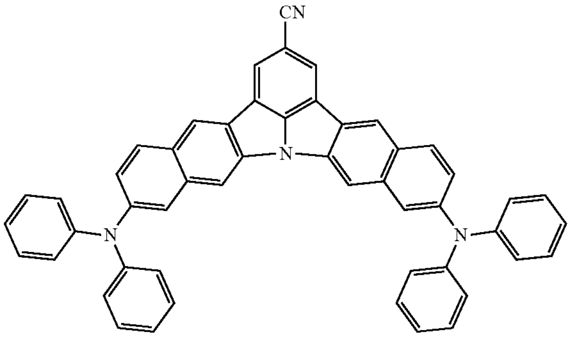
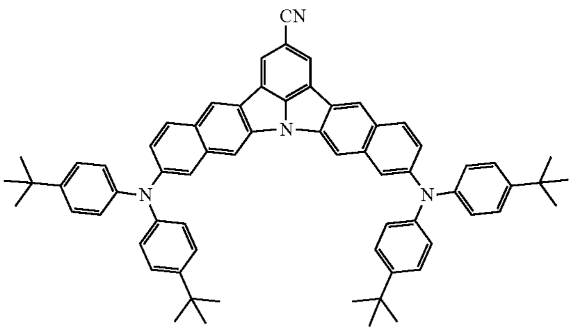

-continued
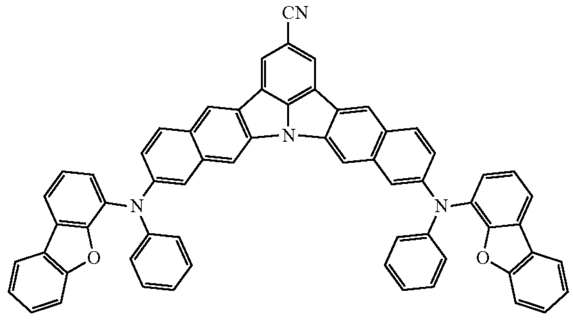
[Formula 160]
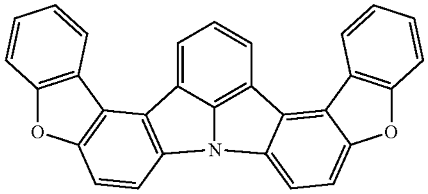
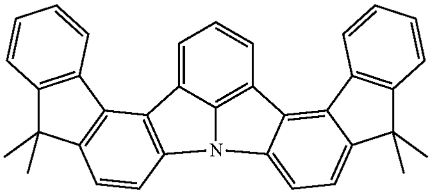
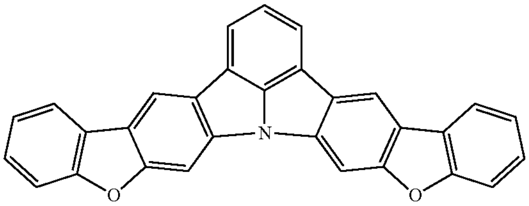
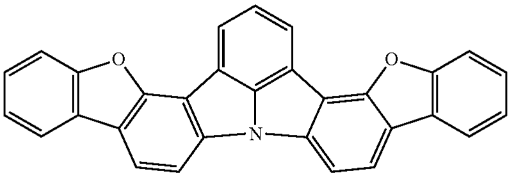
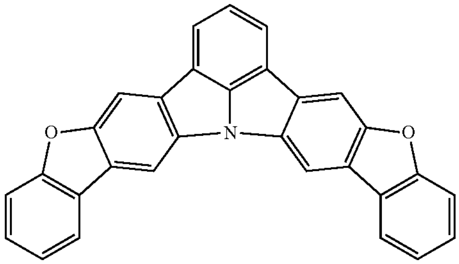
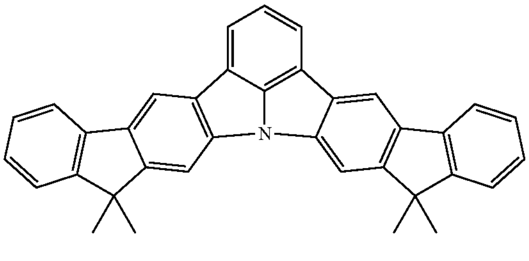
-continued
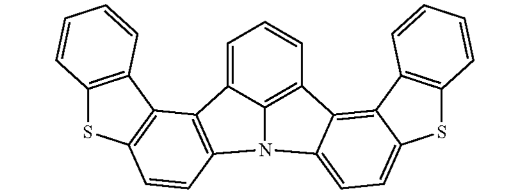
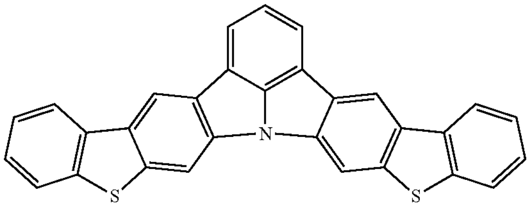
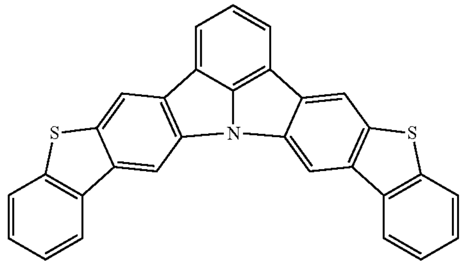
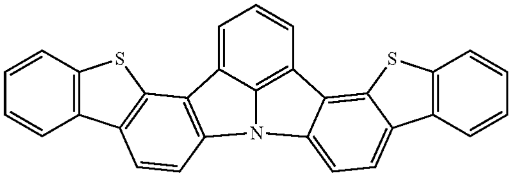
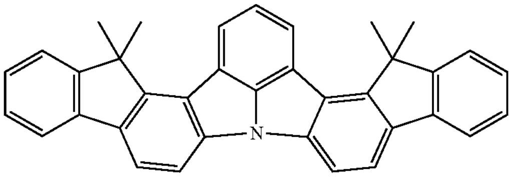
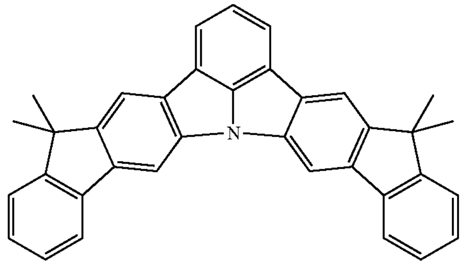
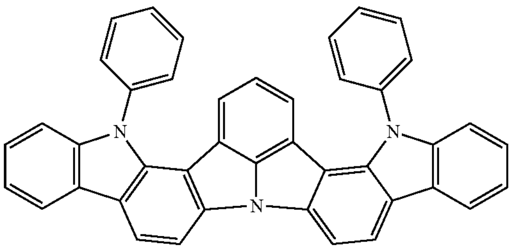

-continued
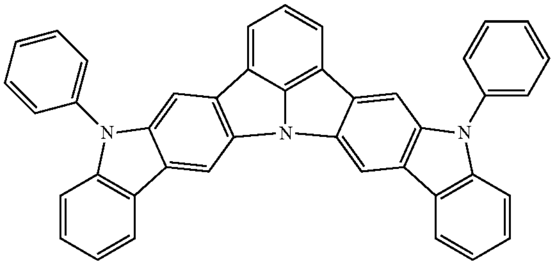
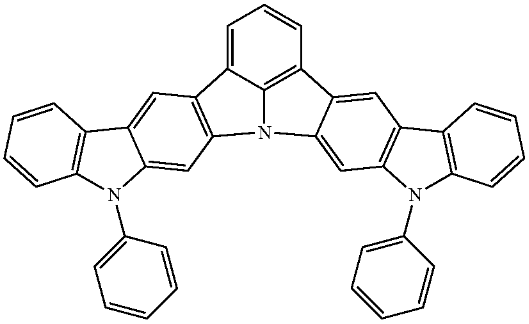
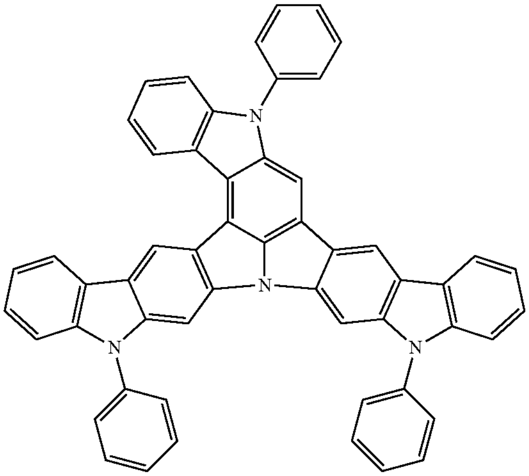
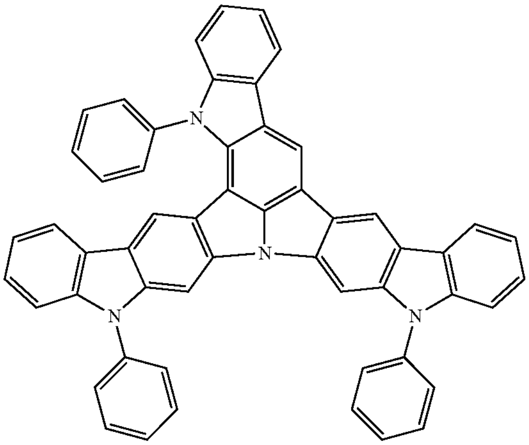
-continued
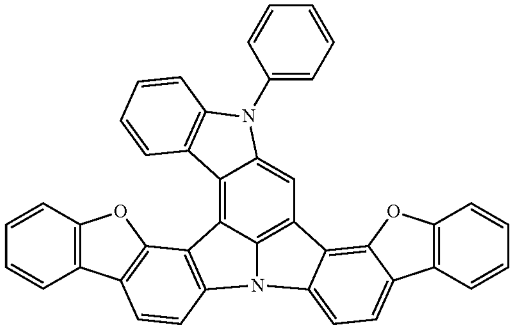
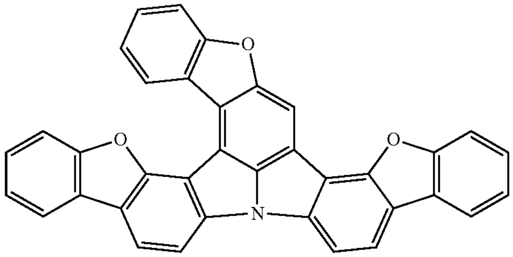
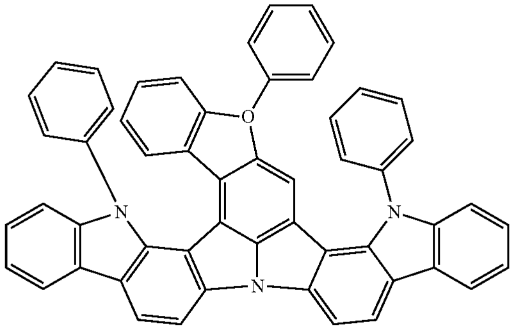
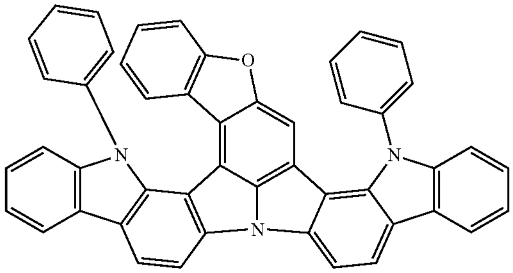
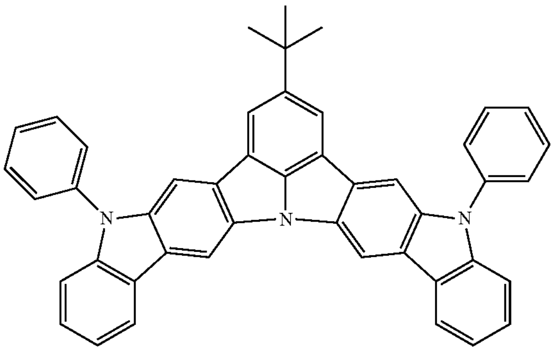

-continued
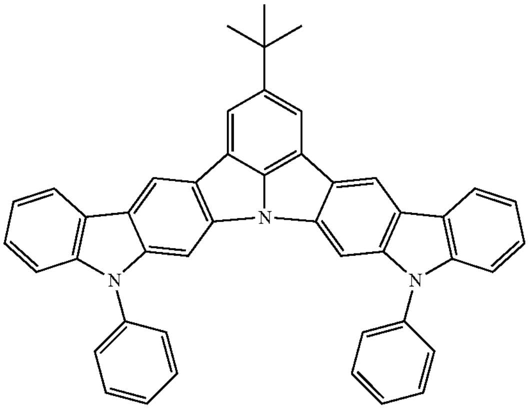
[Formula 161]
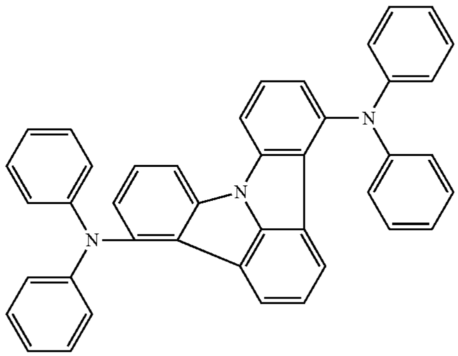
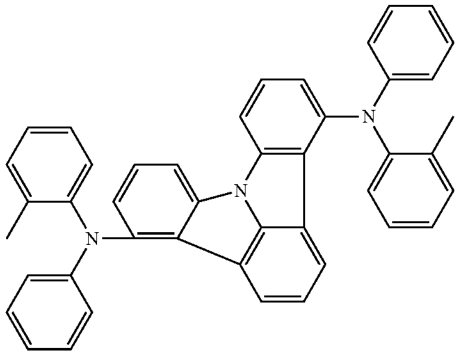
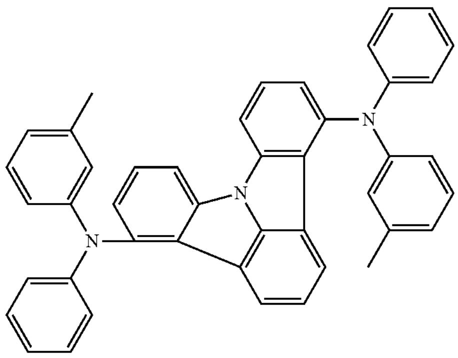
-continued
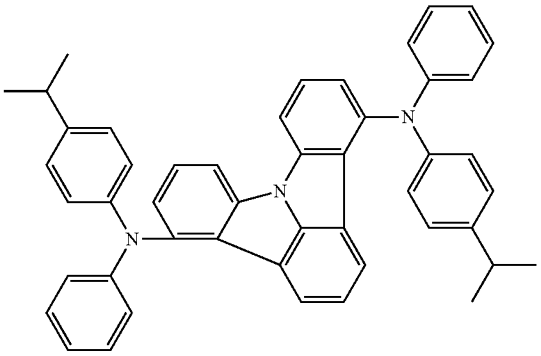
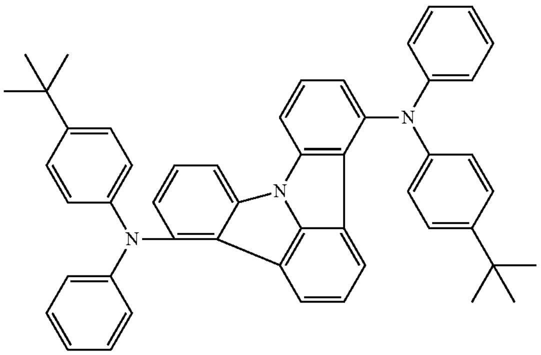
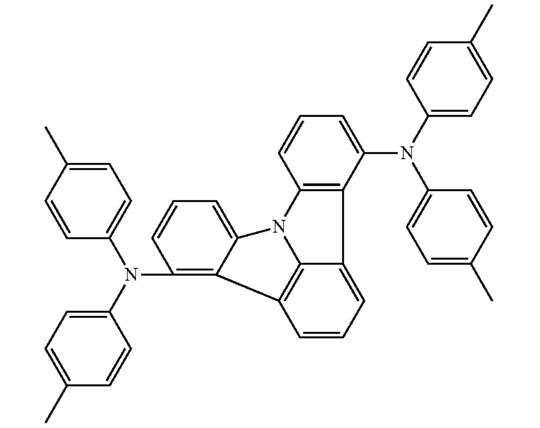
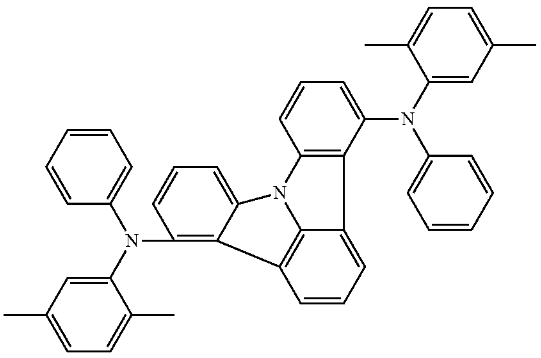

-continued
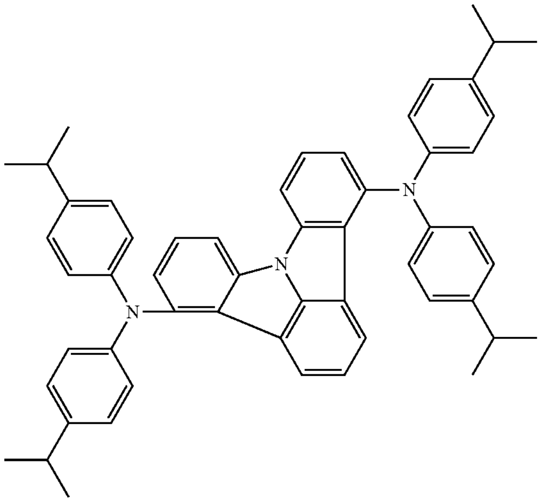
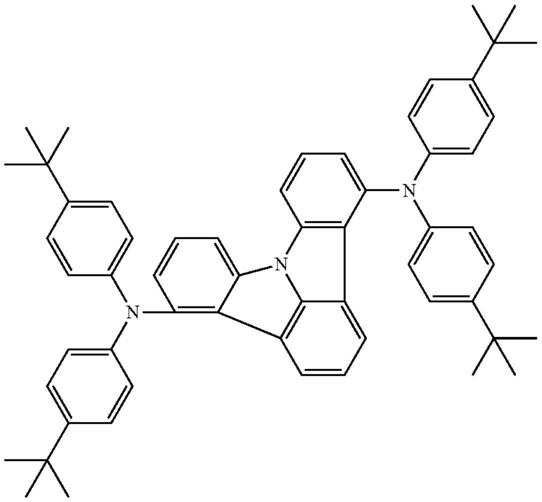
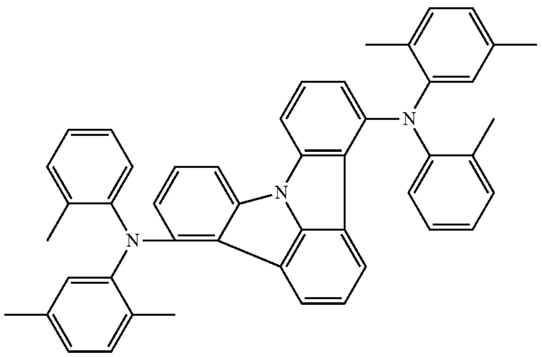
-continued
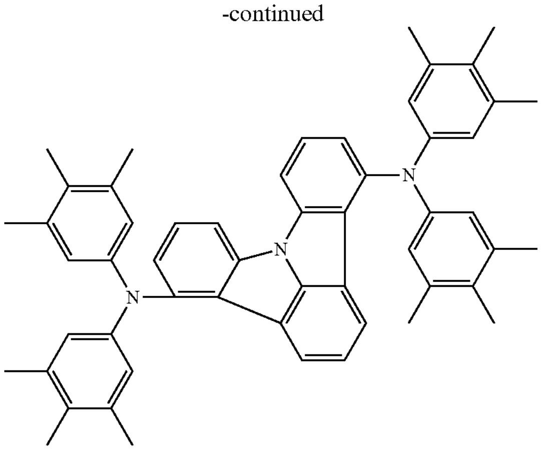
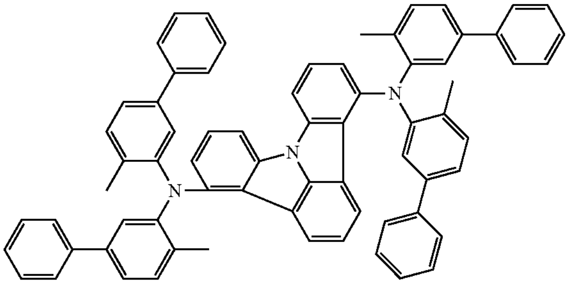
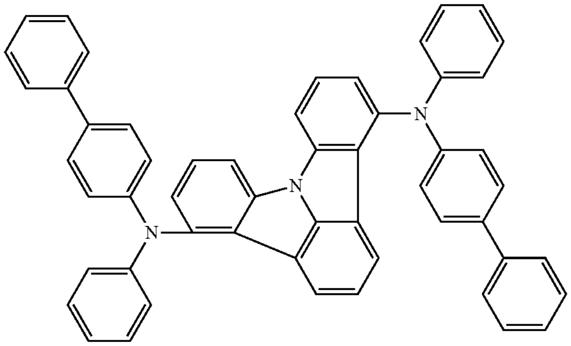
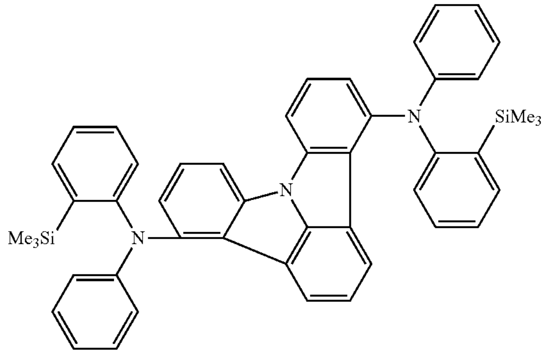
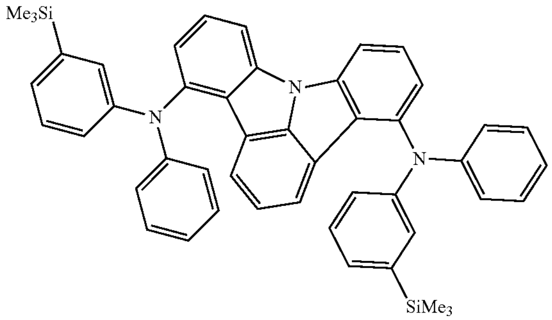

-continued
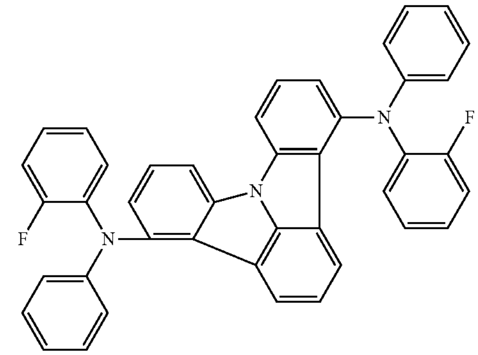
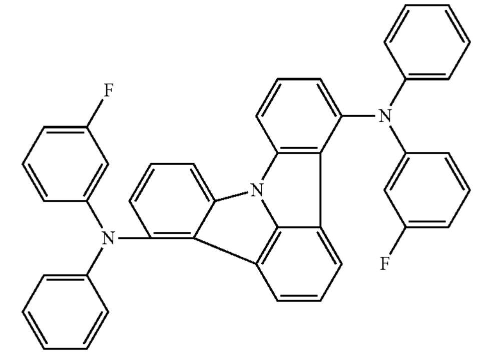
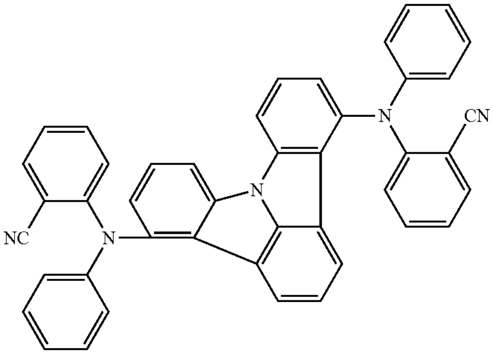
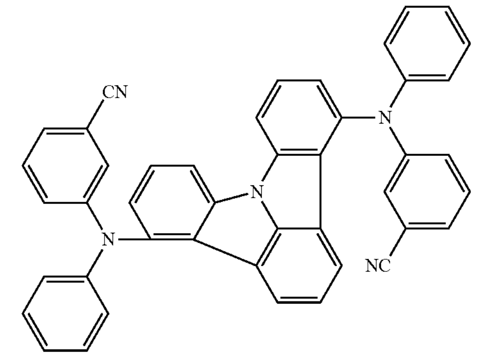
-continued
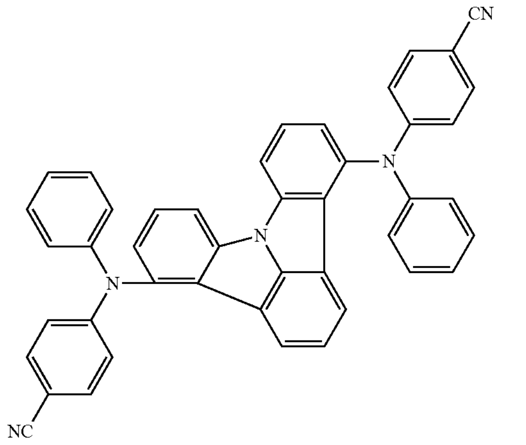
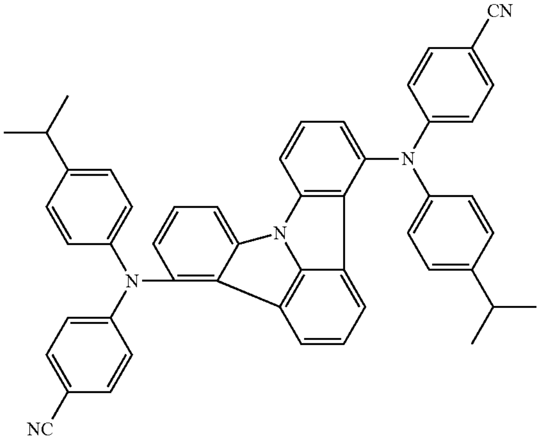
[Formula 162]
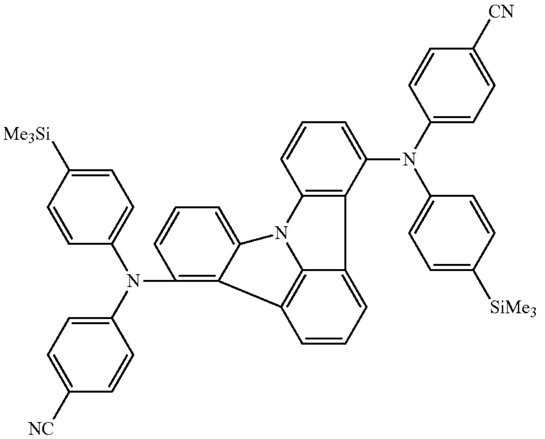
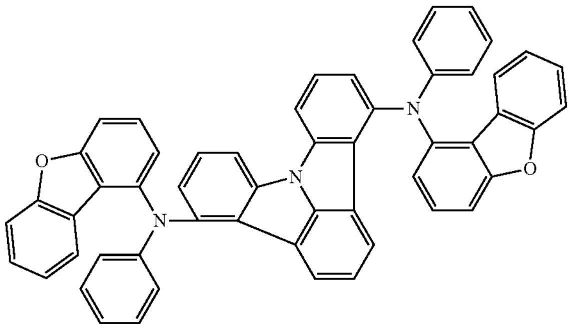

-continued
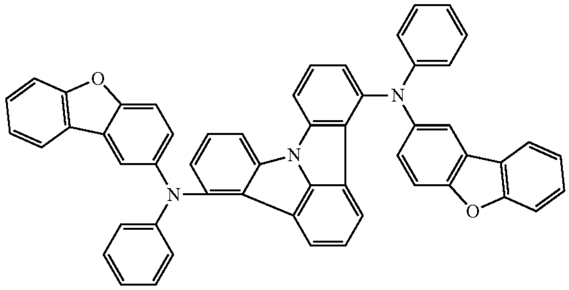
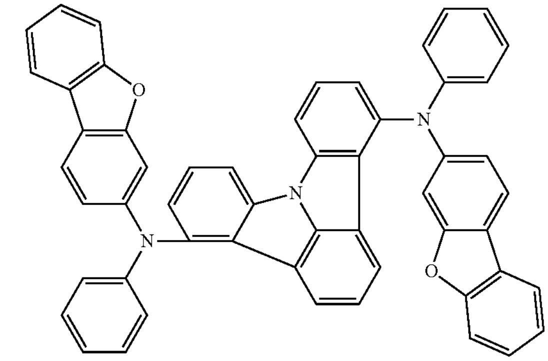
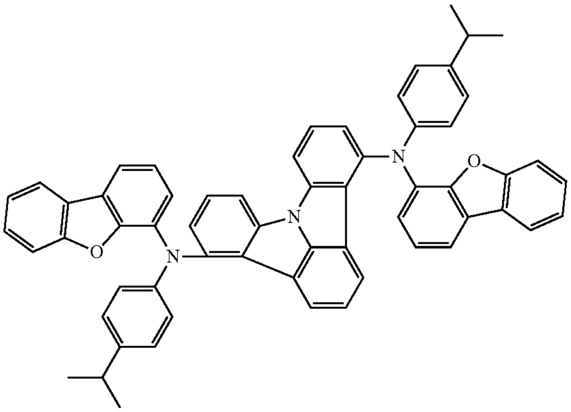
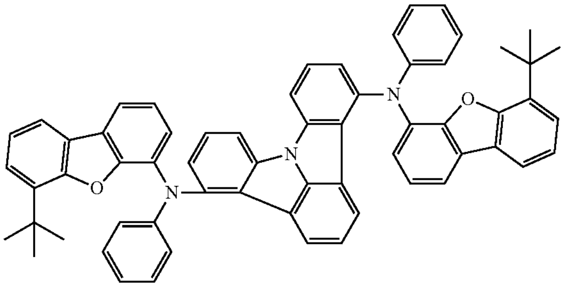
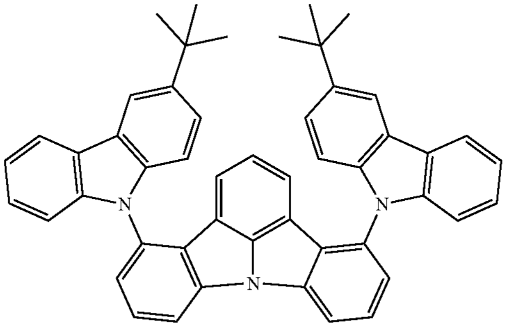
-continued
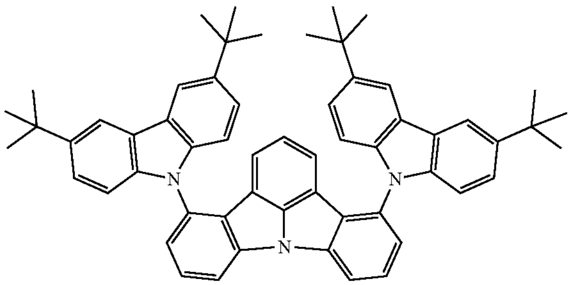
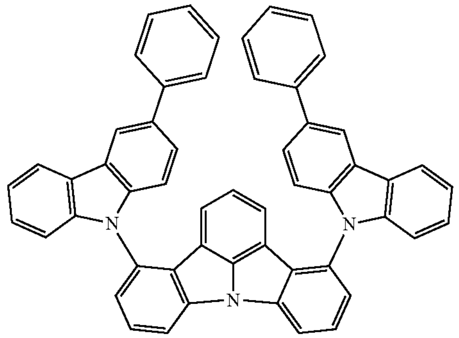
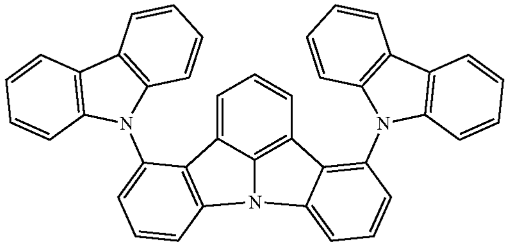
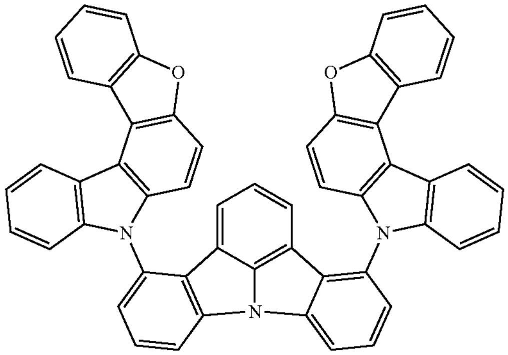
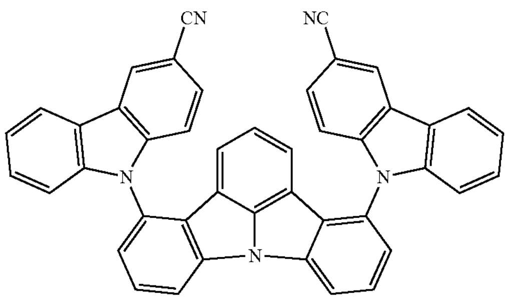

-continued
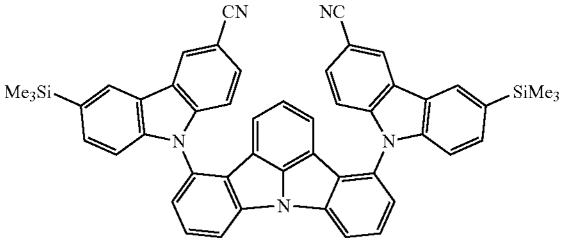
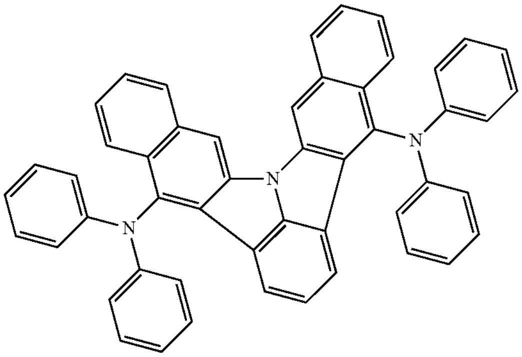
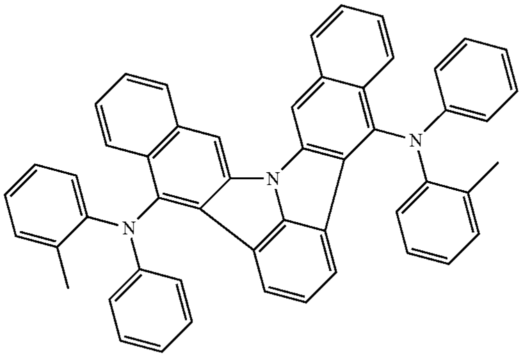
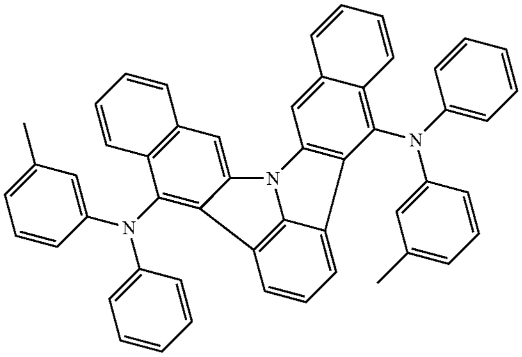
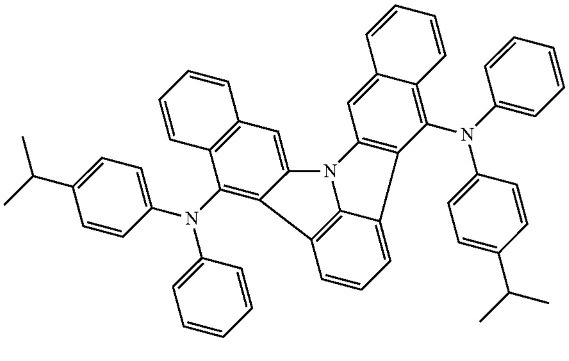
-continued
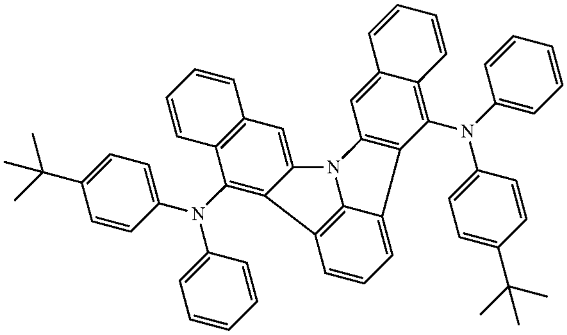
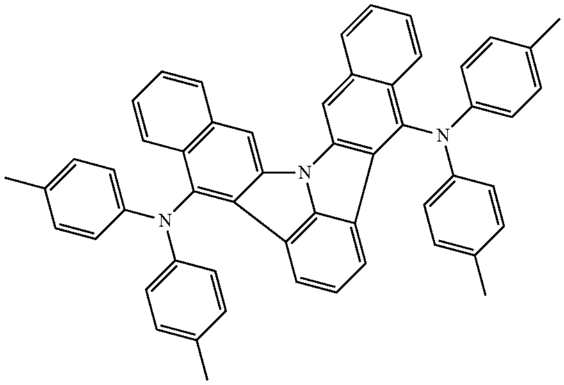
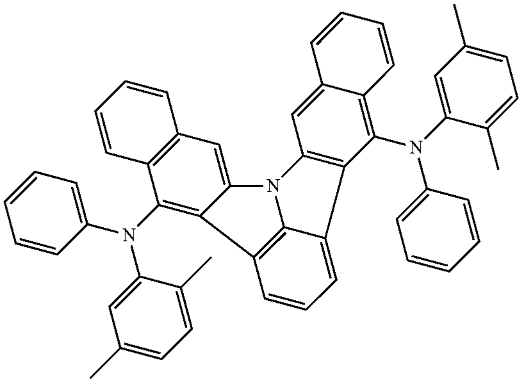
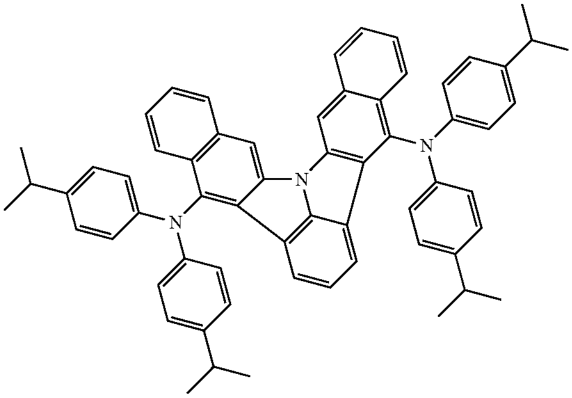

-continued
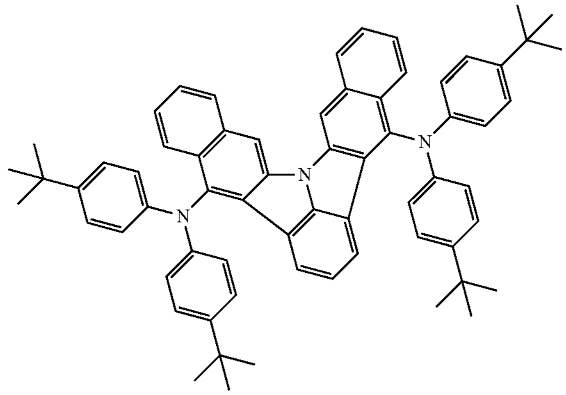
[Formula 163]
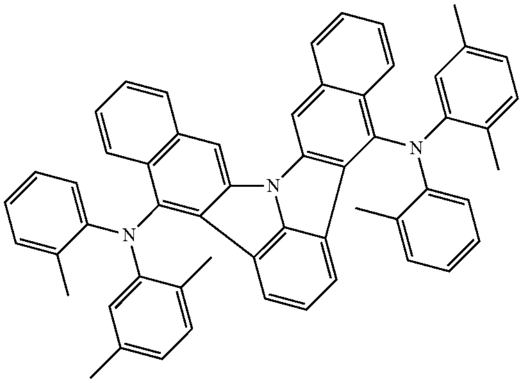
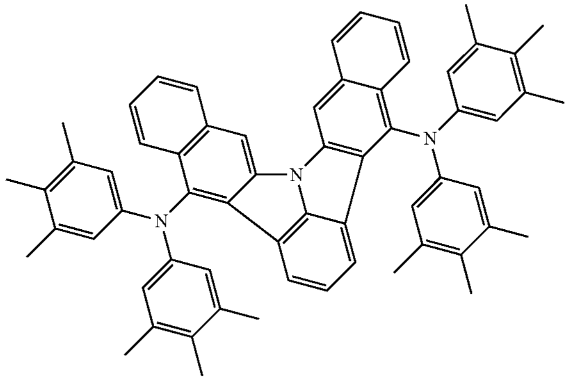
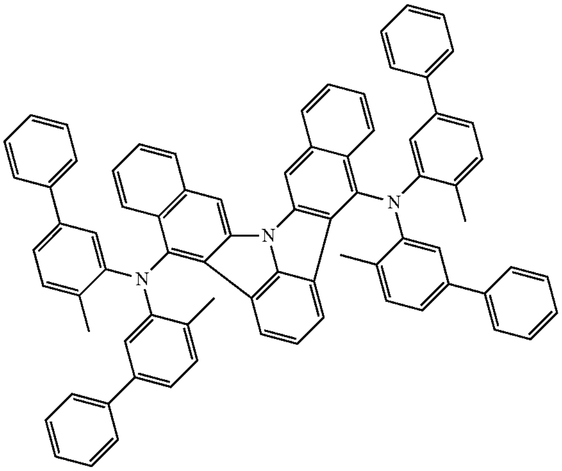
-continued
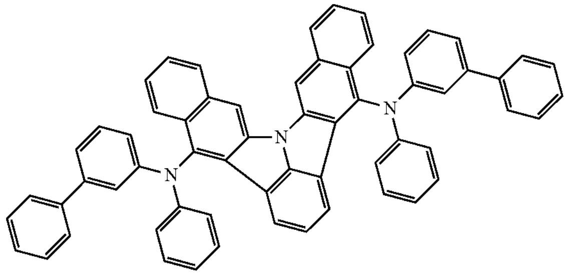
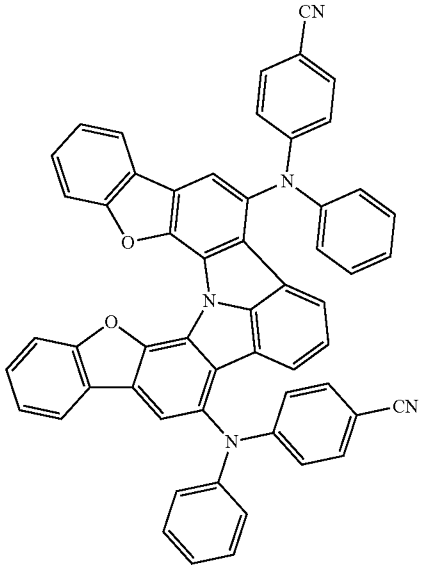
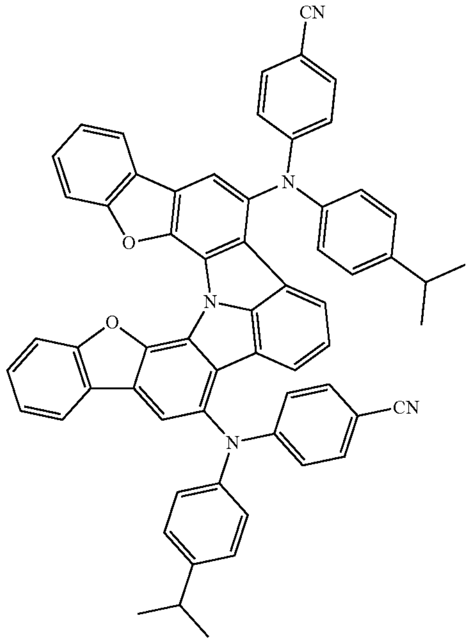

-continued
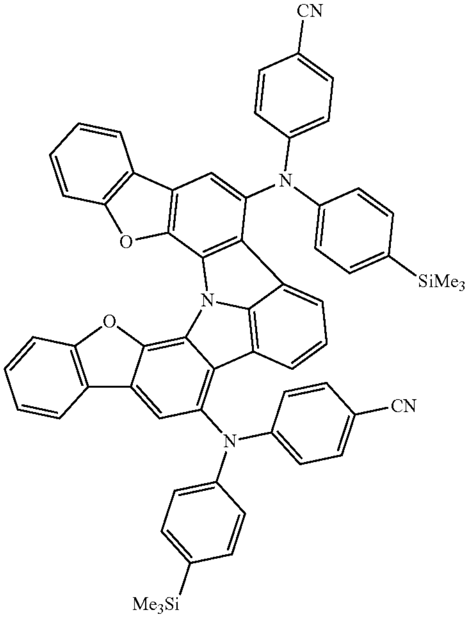
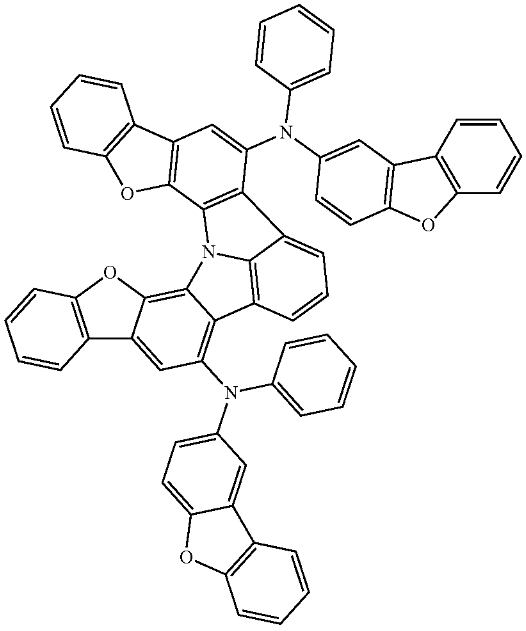
-continued
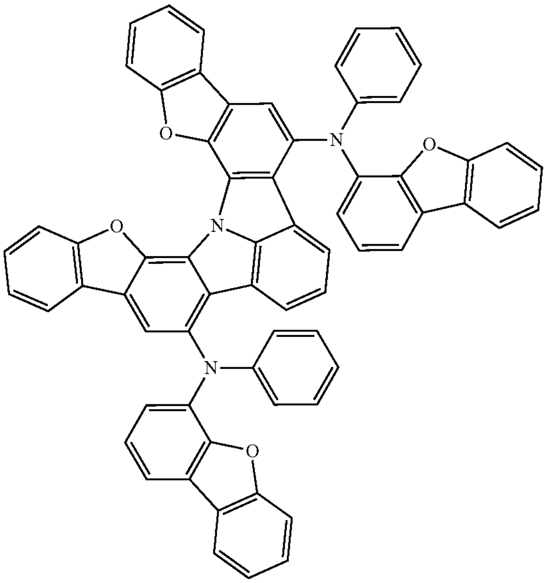
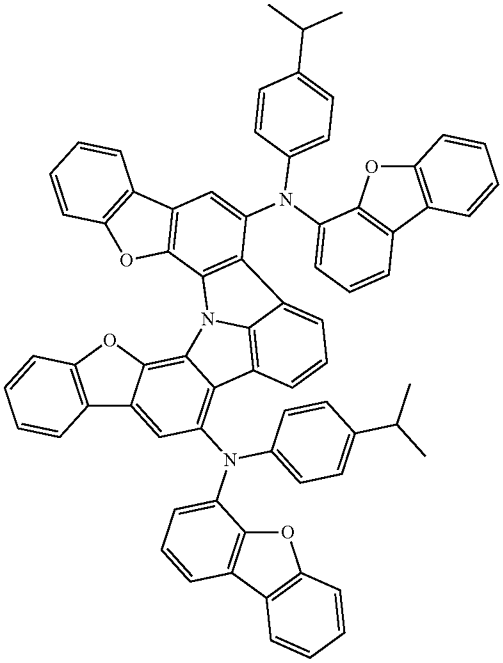

-continued
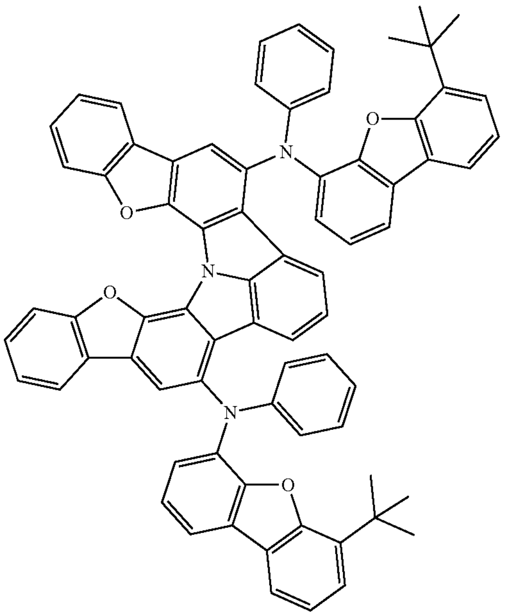 [SMILES: CC(C)(C)c1cccc2c1oc1c(N(c3ccccc3)c3cc4c5ccccc5oc4c4c3c3cccc5c6c(N(c7ccccc7)c7cccc8c7oc7c(C(C)(C)C)cccc78)cc7c8ccccc8oc7c6n4c35)cccc12]
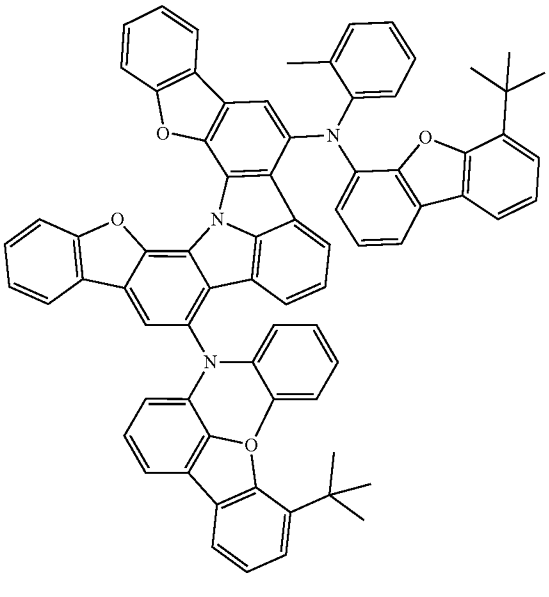
-continued
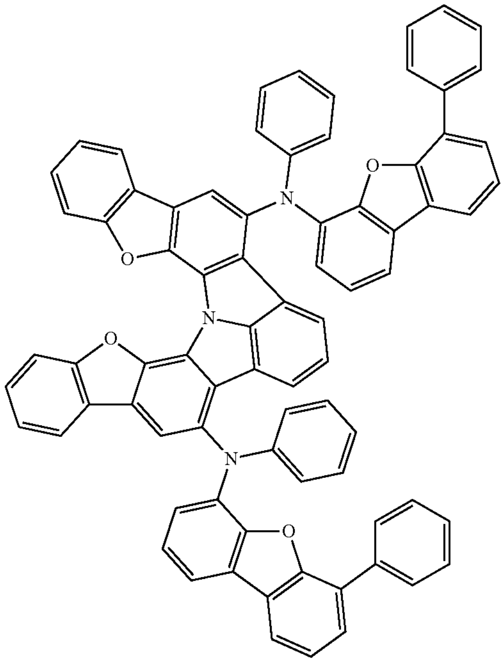
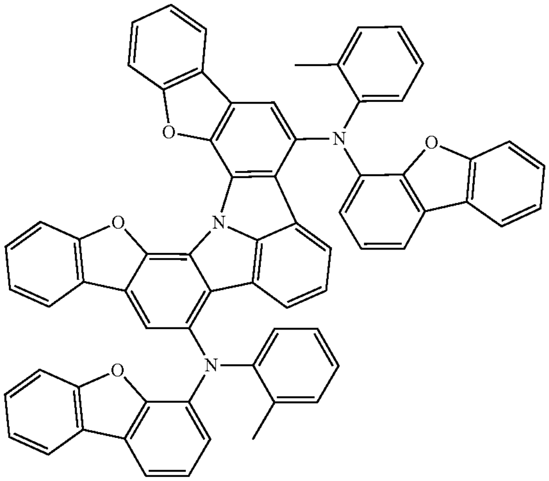
[Formula 164]
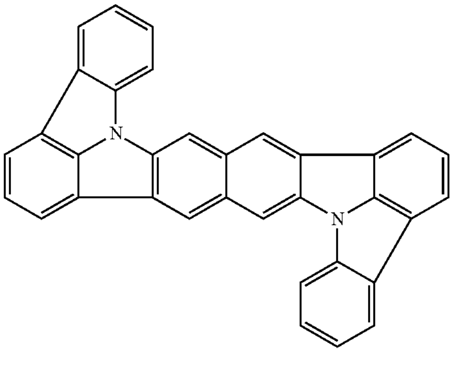

-continued
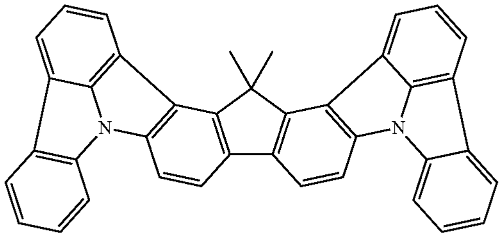
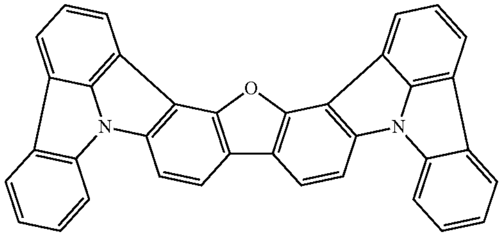
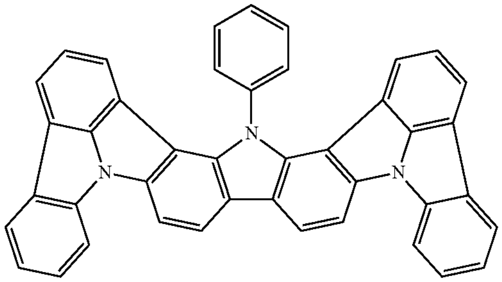
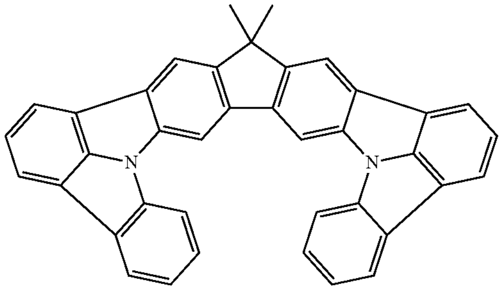
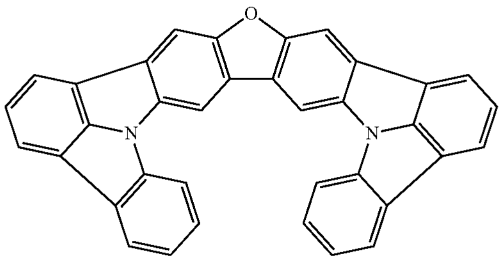
-continued
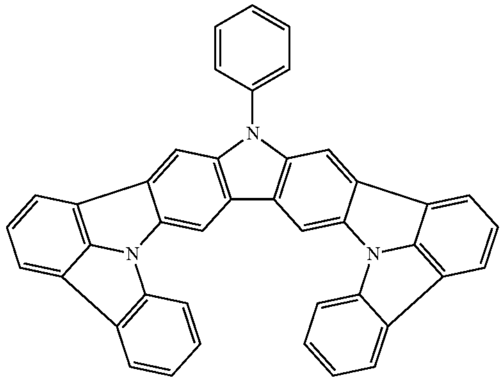
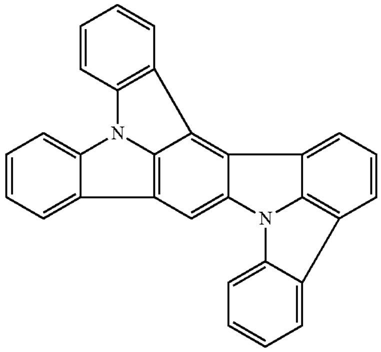
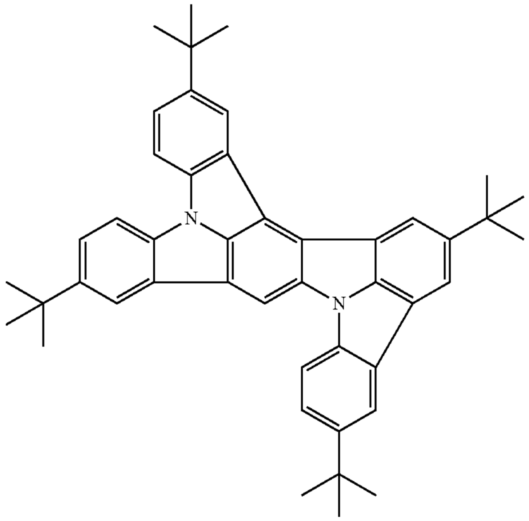
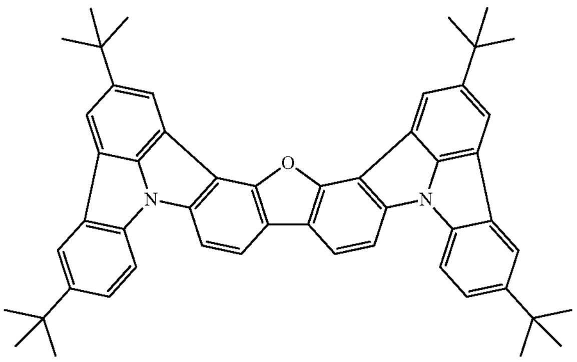

Compound Represented by Formula (5)

The compound represented by the formula (5) will be described. The compound represented by the formula (5) corresponds to a compound represented by the formula (41-3).

[Formula 165]

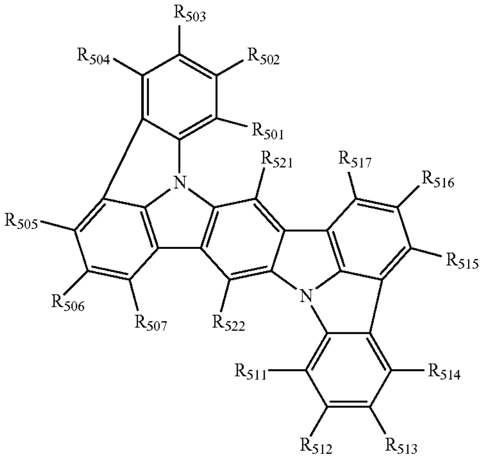

(5)

In the formula (5):

at least one combination of adjacent two or more of $R_{501}$ to $R_{507}$ and $R_{511}$ to $R_{517}$ are mutually bonded to form a substituted or unsubstituted monocyclic ring, mutually bonded to form a substituted or unsubstituted fused ring, or not mutually bonded;

$R_{501}$ to $R_{507}$ and $R_{511}$ to $R_{517}$ forming neither the monocyclic ring nor the fused ring are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms.

$R_{521}$ and $R_{522}$ are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms.

"A combination of adjacent two or more of $R_{501}$ to $R_{507}$ and $R_{511}$ to $R_{517}$" refers to, for instance, a combination of $R_{501}$ and $R_{502}$, a combination of $R_{502}$ and $R_{503}$, a combination of $R_{503}$ and $R_{504}$, a combination of $R_{505}$ and $R_{506}$, a combination of $R_{506}$ and $R_{507}$, and a combination of $R_{501}$, $R_{502}$, and $R_{503}$.

In an exemplary embodiment, at least one, preferably two of $R_{501}$ to $R_{507}$ and $R_{511}$ to $R_{517}$ are groups represented by —N($R_{906}$)($R_{907}$).

In an exemplary embodiment, $R_{501}$ to $R_{507}$ and $R_{511}$ to $R_{517}$ are each independently a hydrogen atom, a substituted or unsubstituted aryl group having 6 to 50 ring carbon atoms, or a substituted or unsubstituted heterocyclic group having 5 to 50 ring atoms.

In an exemplary embodiment, the compound represented by the formula (5) is a compound represented by a formula (52) below.

[Formula 166]

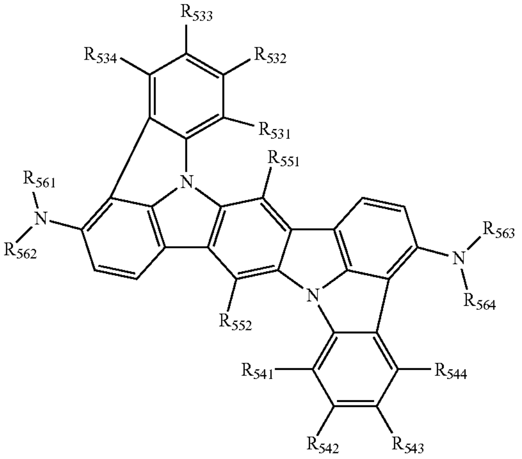

(52)

In the formula (52):

at least one combination of adjacent two or more of $R_{531}$ to $R_{534}$ and $R_{541}$ to $R_{544}$ are mutually bonded to form a substituted or unsubstituted monocyclic ring, mutually bonded to form a substituted or unsubstituted fused ring, or not mutually bonded;

$R_{531}$ to $R_{534}$, $R_{541}$ to $R_{544}$ forming neither the monocyclic ring nor the fused ring, and $R_{551}$ and $R_{552}$ are each independently a hydrogen atom, a substituted or unsubstituted aryl group having 6 to 50 ring carbon atoms, or a substituted or unsubstituted heterocyclic group having 5 to 50 ring atoms; and $R_{561}$ to $R_{564}$ are each independently a substituted or unsubstituted aryl group having 6 to 50 ring carbon atoms, or a substituted or unsubstituted heterocyclic group having 5 to 50 ring atoms.

In an exemplary embodiment, the compound represented by the formula (5) is a compound represented by a formula (53) below.

[Formula 167]

(53)

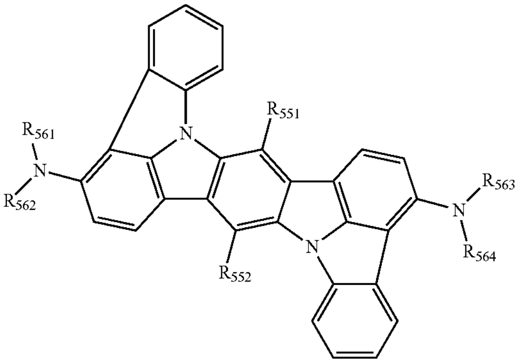

In the formula (53), $R_{551}$, $R_{552}$ and $R_{561}$ to $R_{564}$ each independently represent the same as $R_{551}$, $R_{552}$ and $R_{561}$ to $R_{564}$ in the formula (52).

In an exemplary embodiment, $R_{561}$ to $R_{564}$ in the formulae (52) and (53) are each independently a substituted or unsubstituted aryl group having 6 to 50 ring carbon atoms (preferably a phenyl group).

In an exemplary embodiment, $R_{521}$ and $R_{522}$ in the formula (5) and $R_{551}$ and $R_{552}$ in the formulae (52) and (53) are each a hydrogen atom.

In an exemplary embodiment, a substituent for the "substituted or unsubstituted" group in the formulae (5), (52) and (53) is a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms.

Specific examples of the compound represented by the formula (5) include compounds shown below.

[Formula 168]

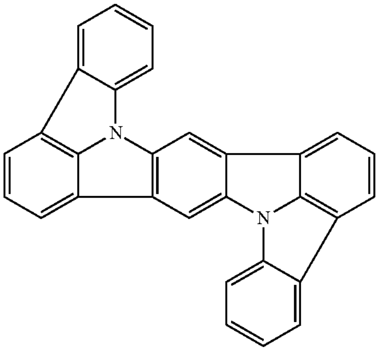

-continued

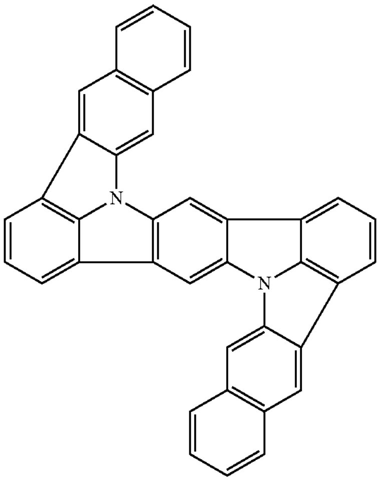

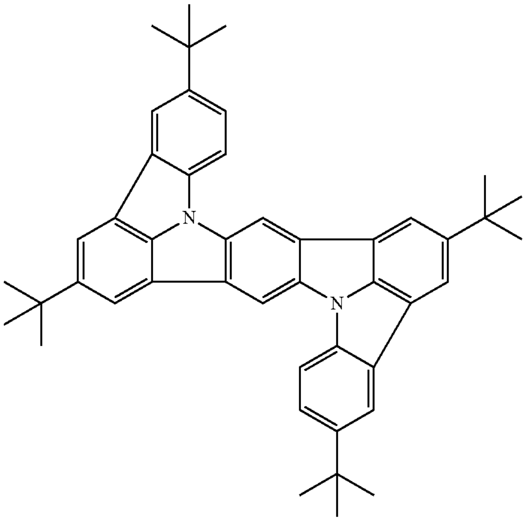

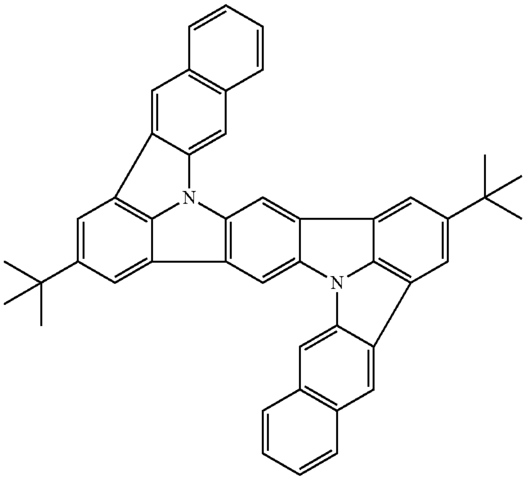

-continued
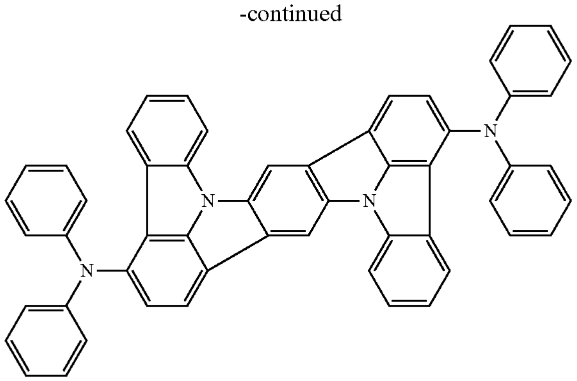
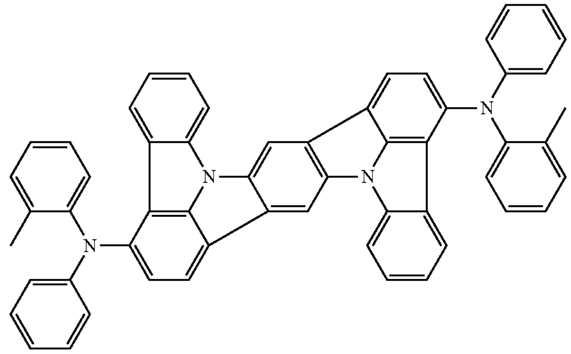
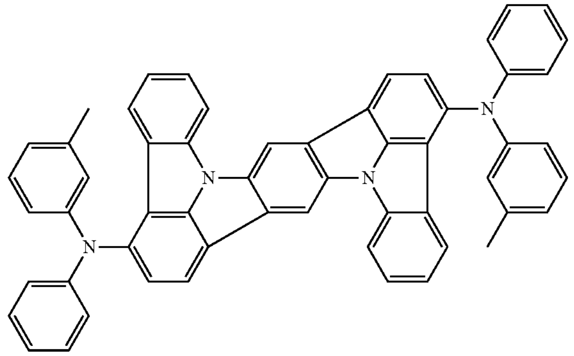
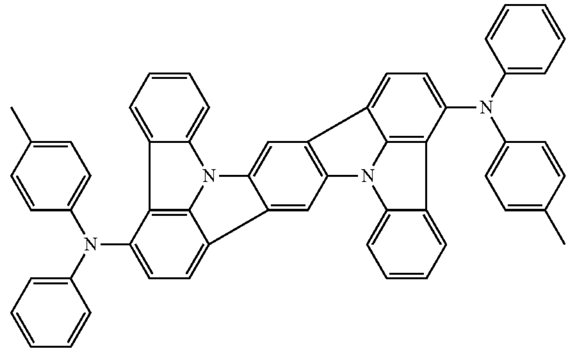
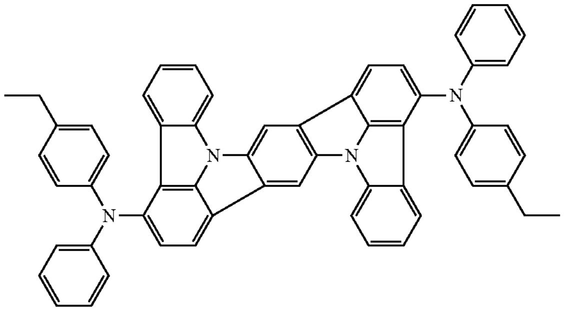
-continued
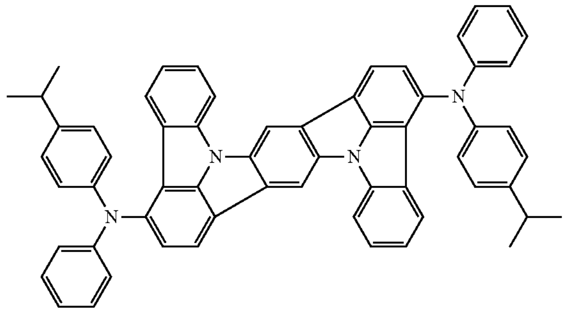
[Formula 169]
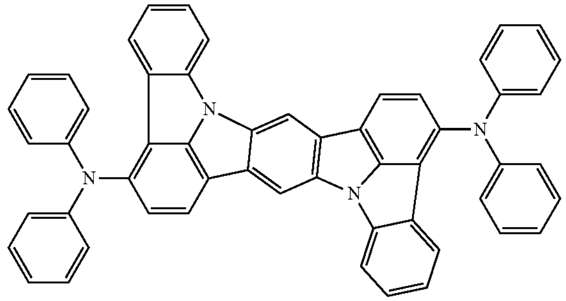
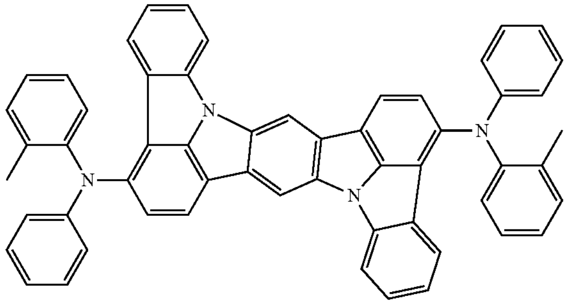
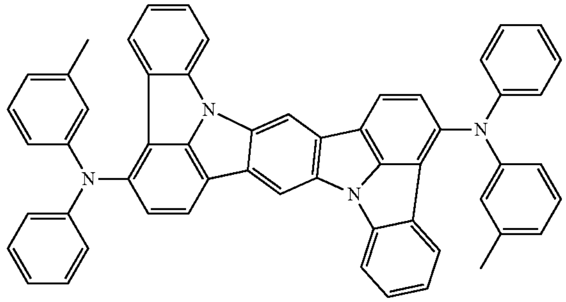
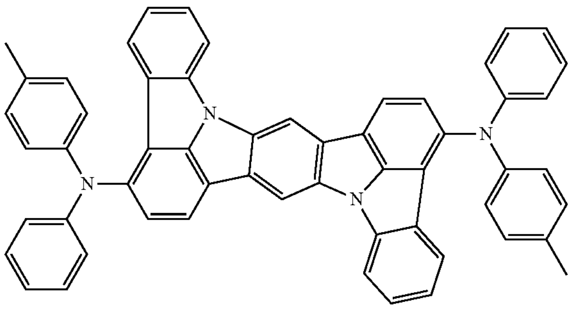

-continued
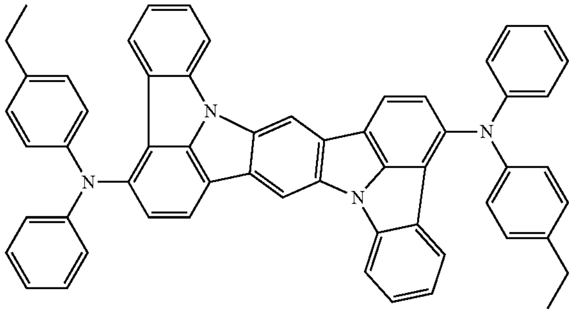
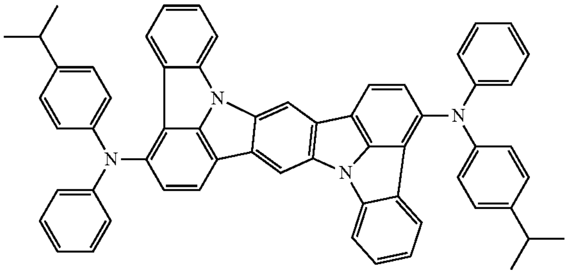
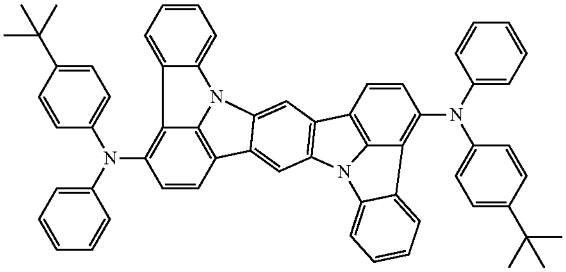
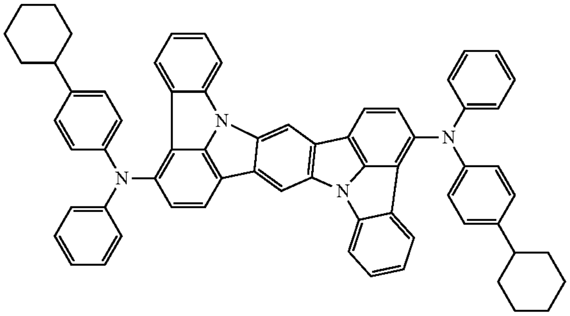
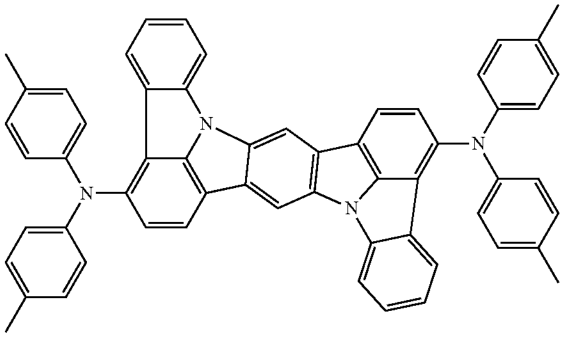
-continued
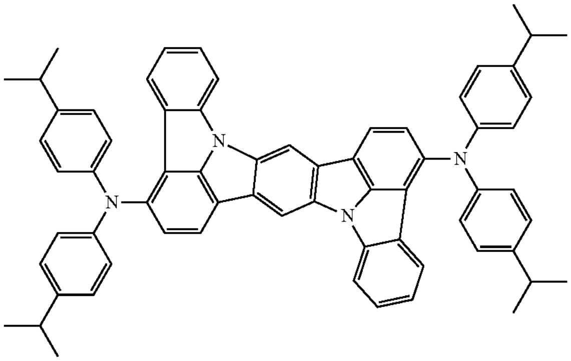
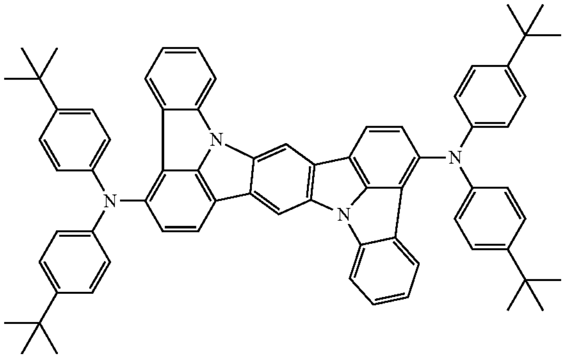
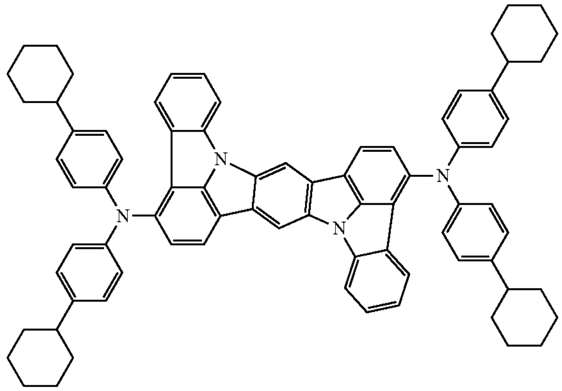
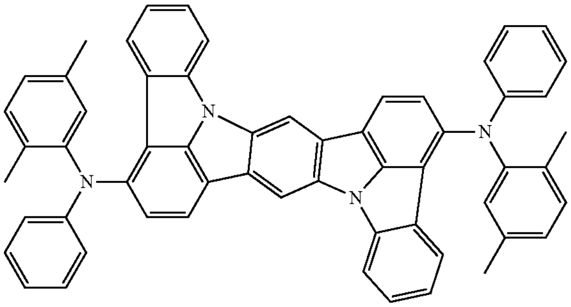
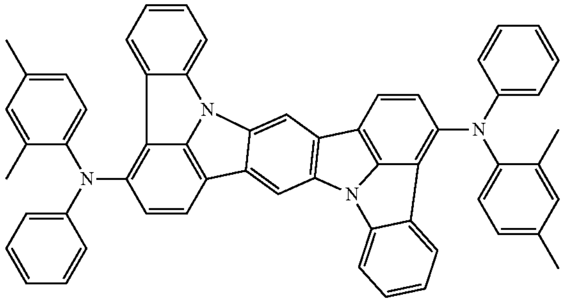

-continued
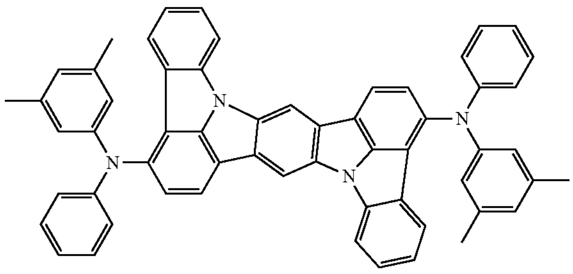
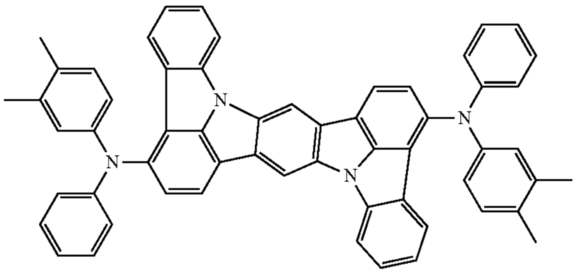
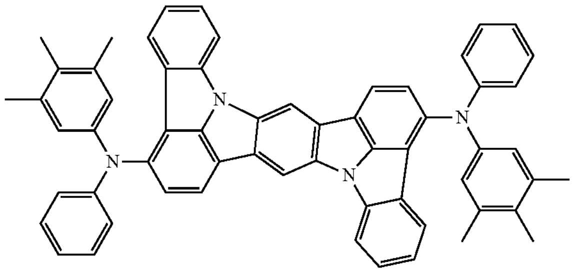
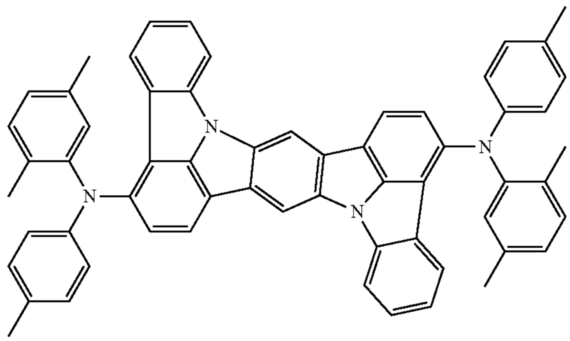
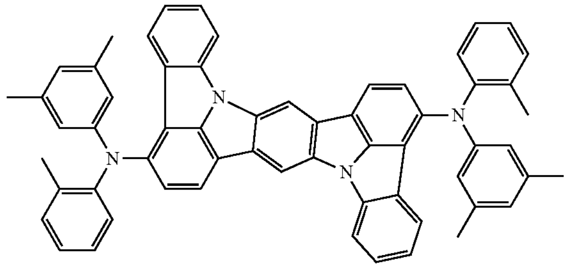
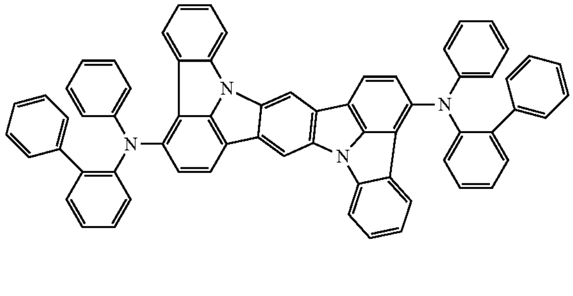
-continued
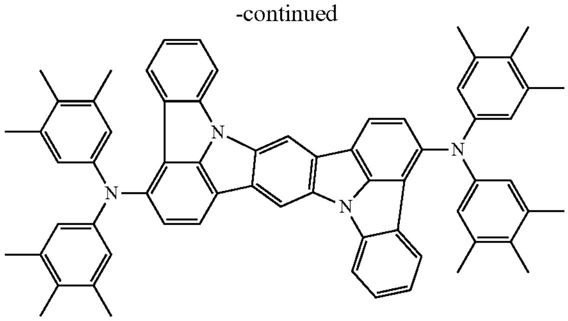
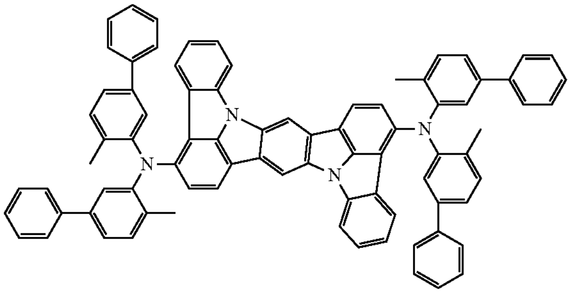
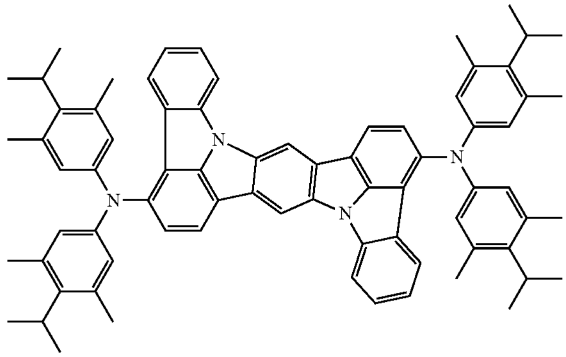
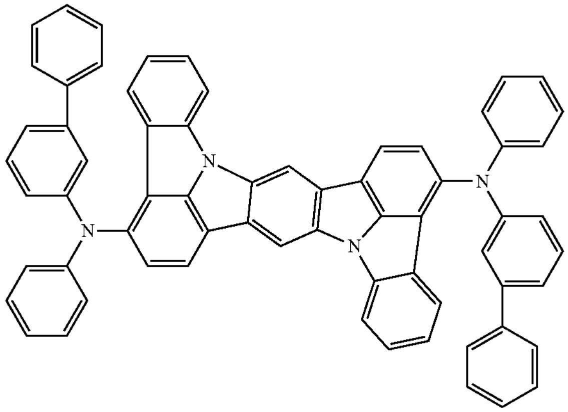
[Formula 170]
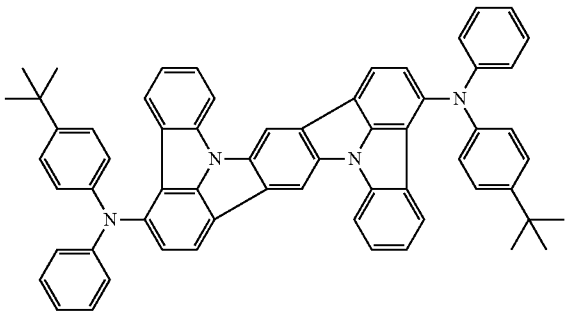

-continued
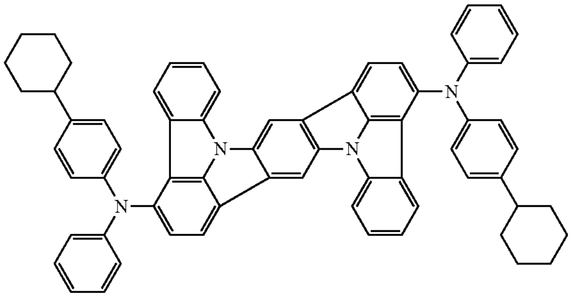
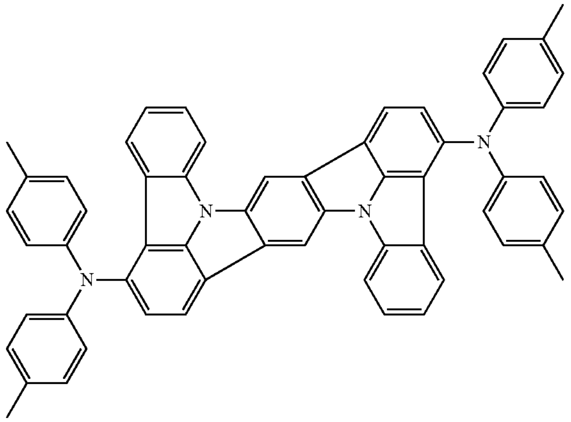
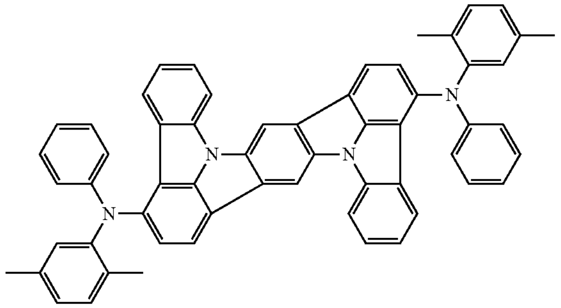
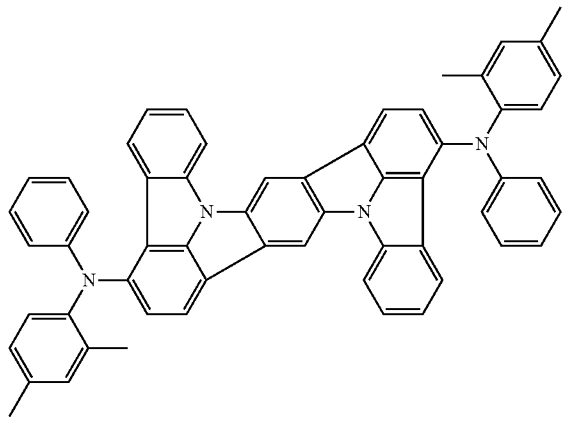
-continued
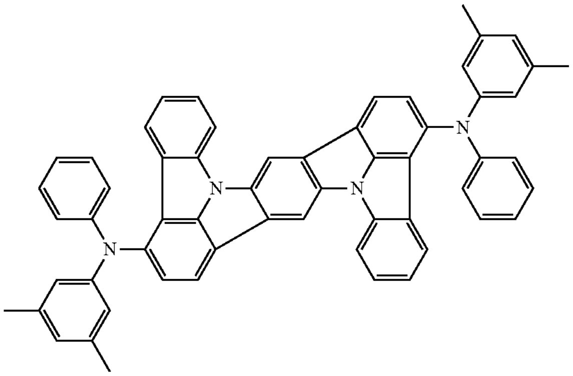
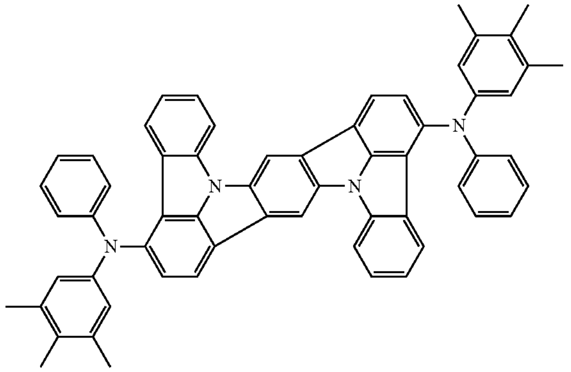
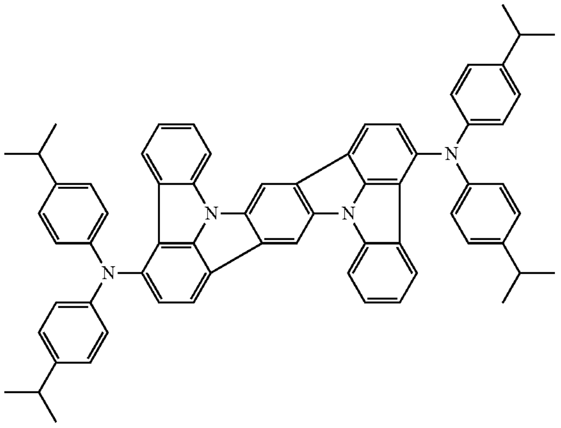
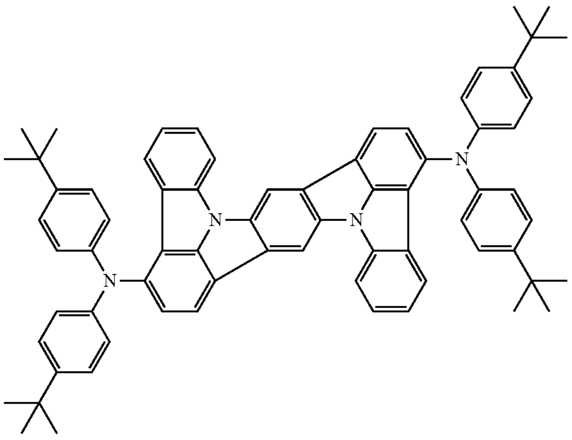

-continued
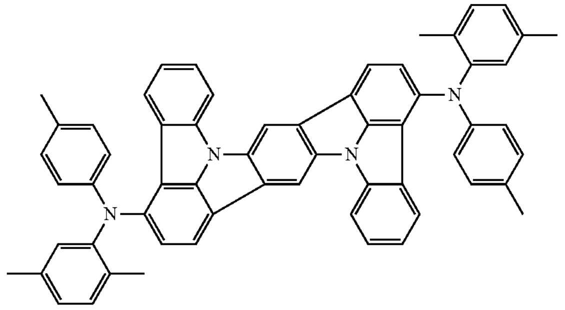
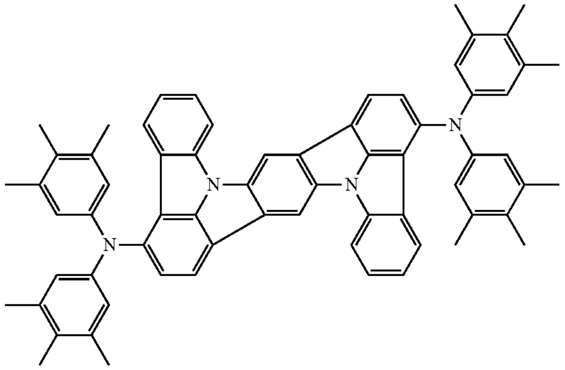
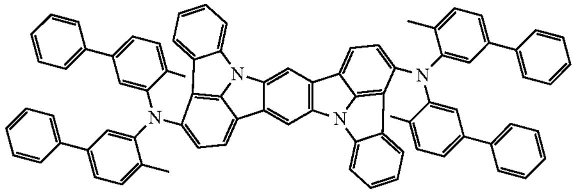
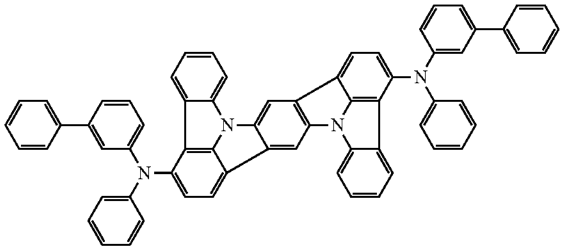
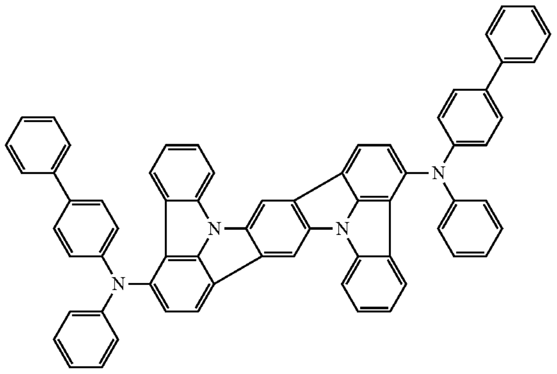
-continued
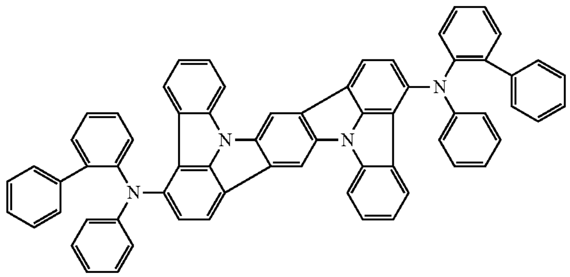
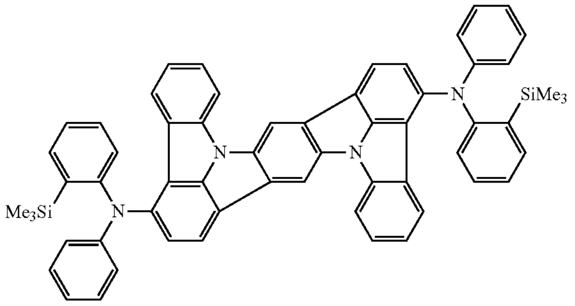
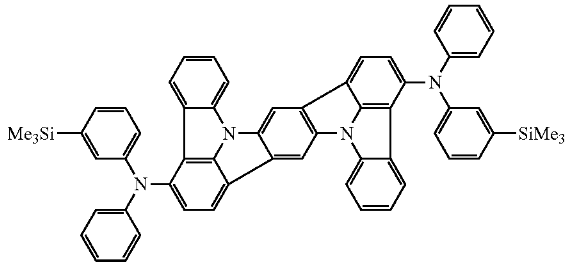
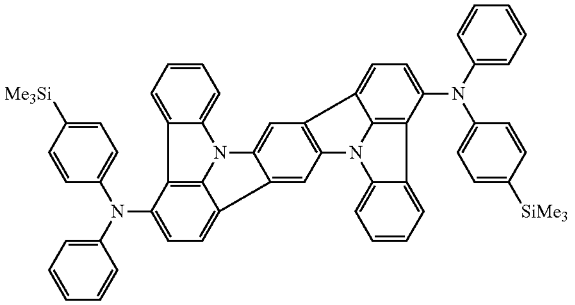
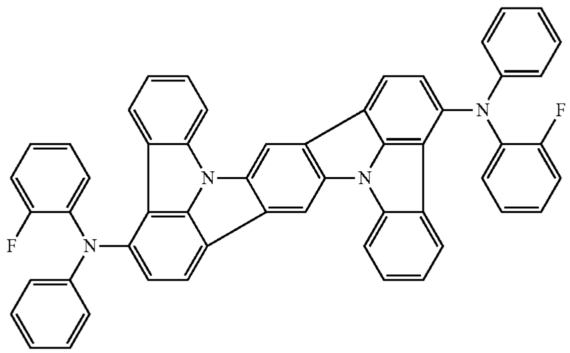

-continued
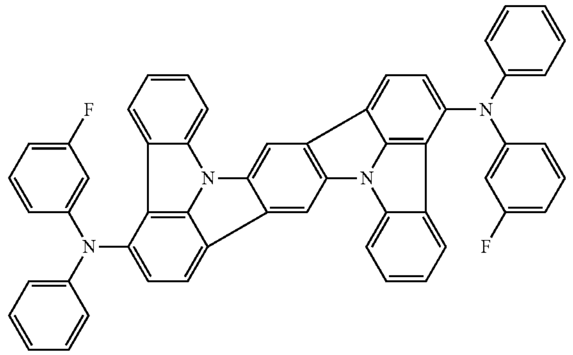
[Formula 171]
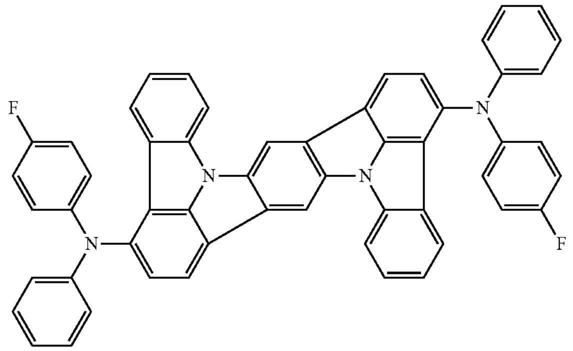
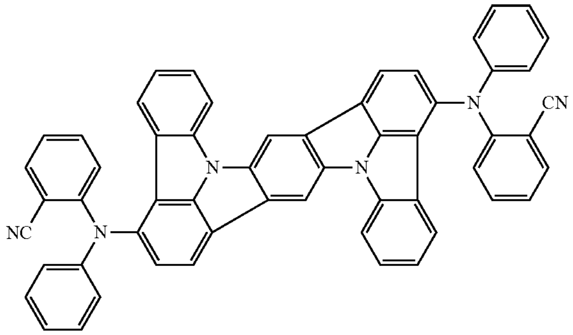
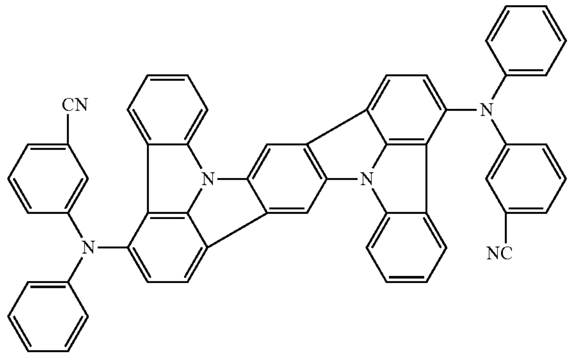
-continued
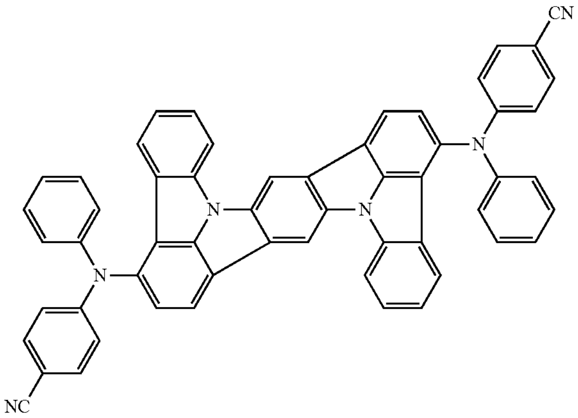
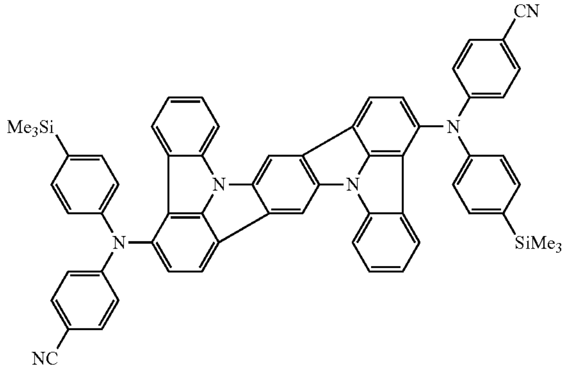
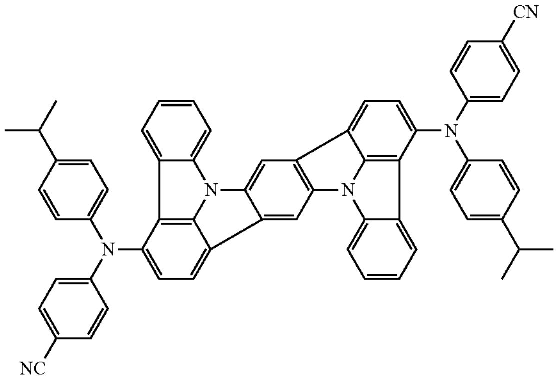
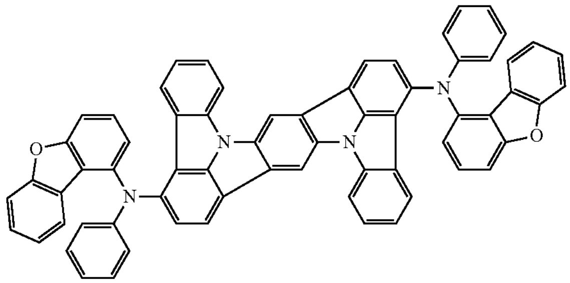
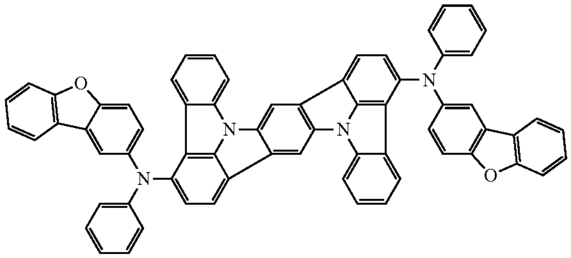

-continued
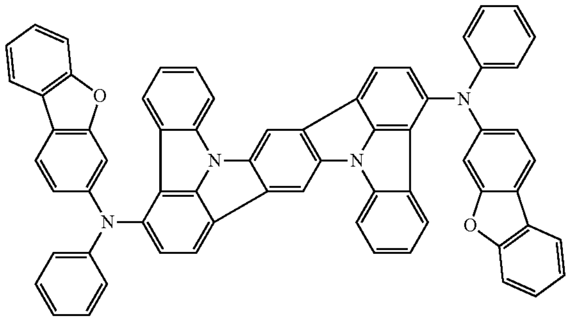
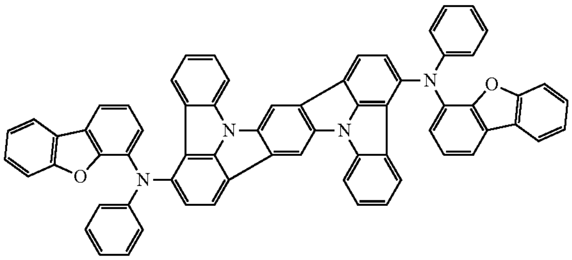
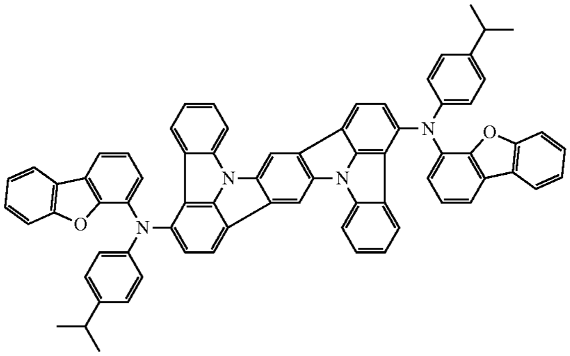
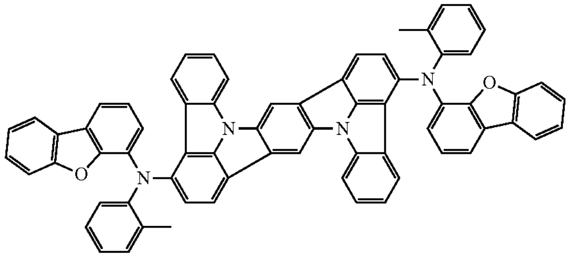
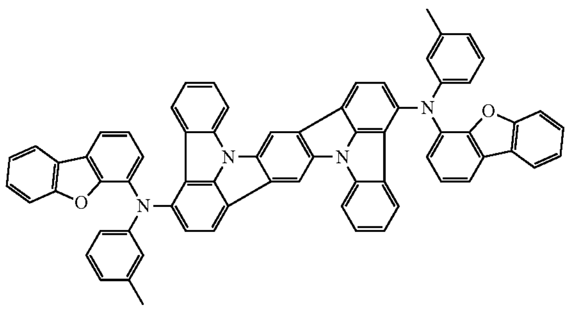
-continued
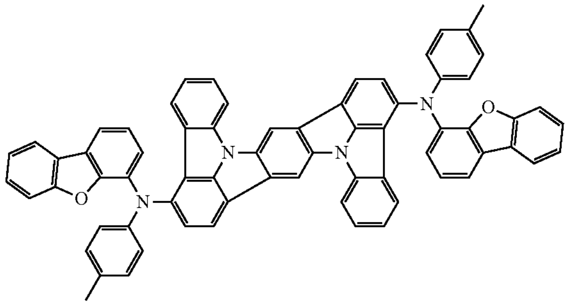
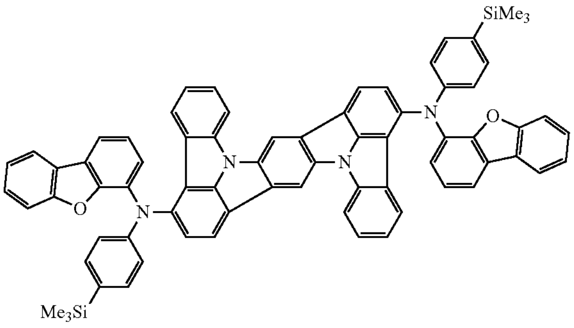
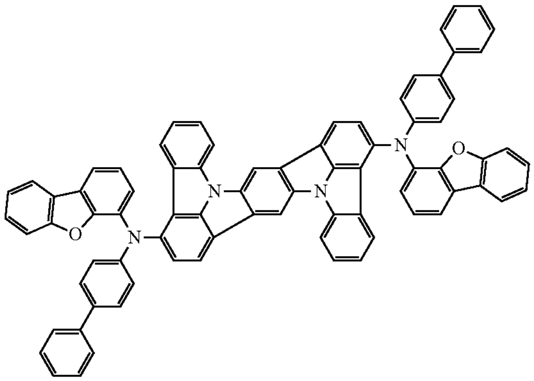
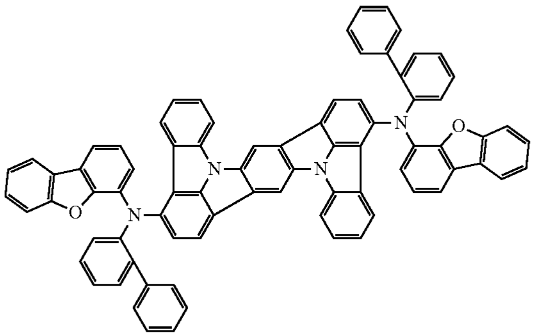
[Formula 172]
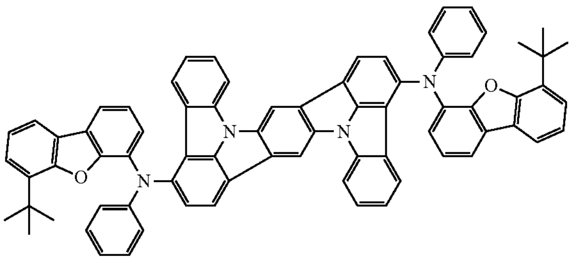

-continued
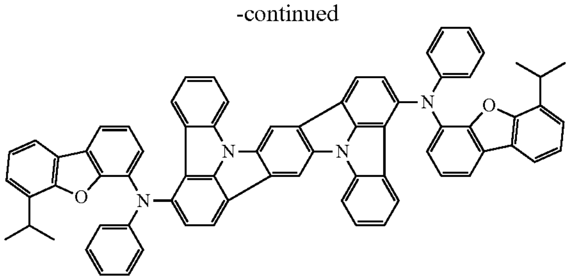
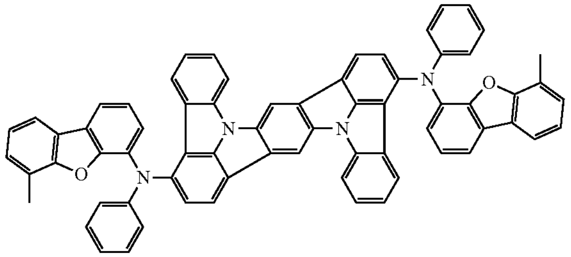
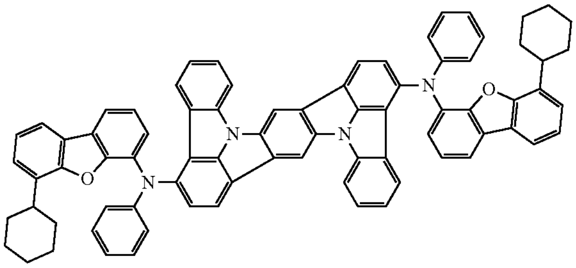
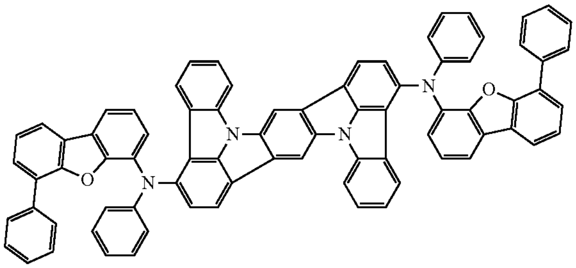
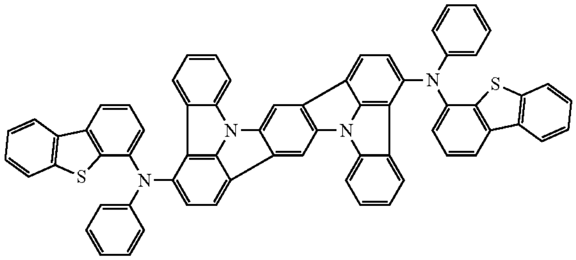
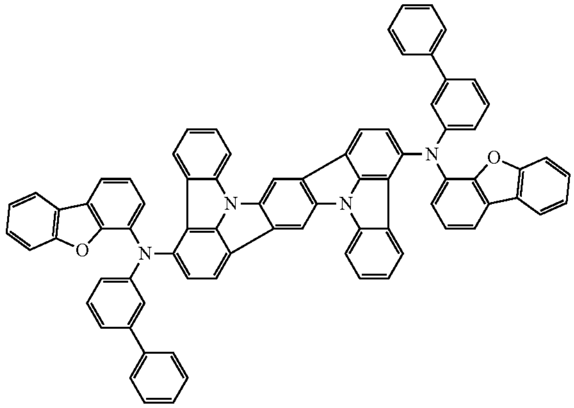
-continued
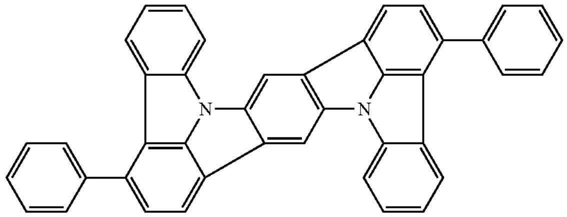
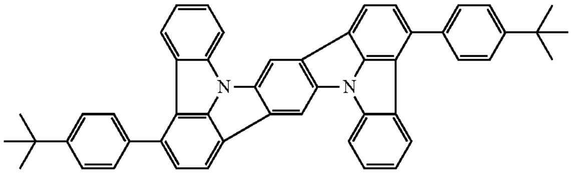
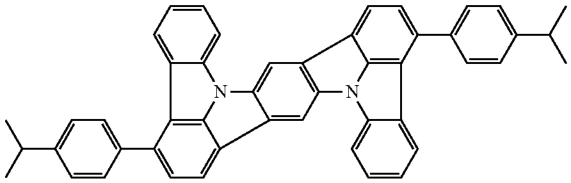
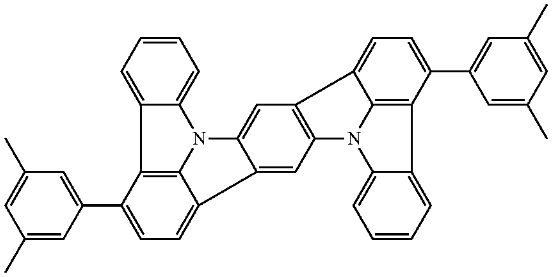
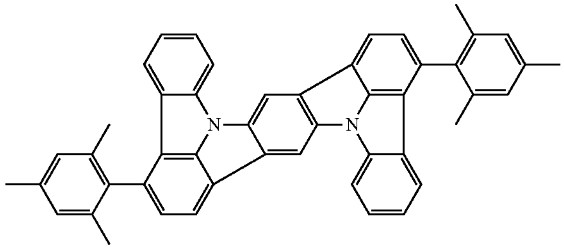
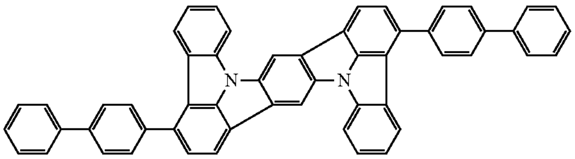
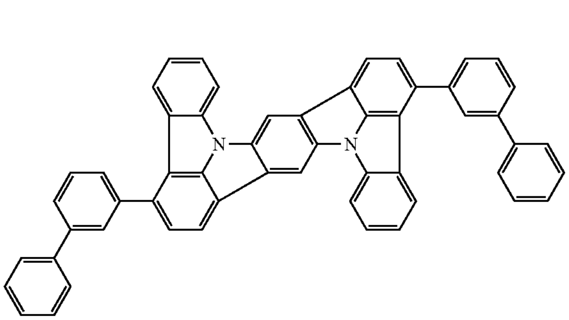

-continued
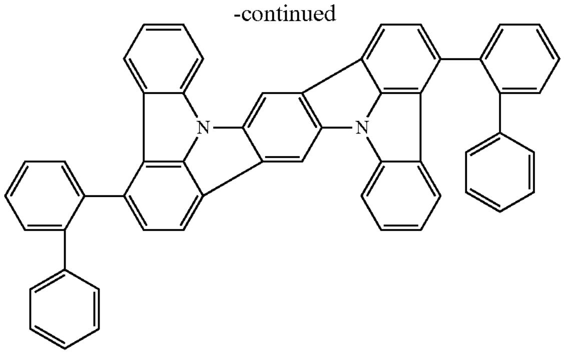
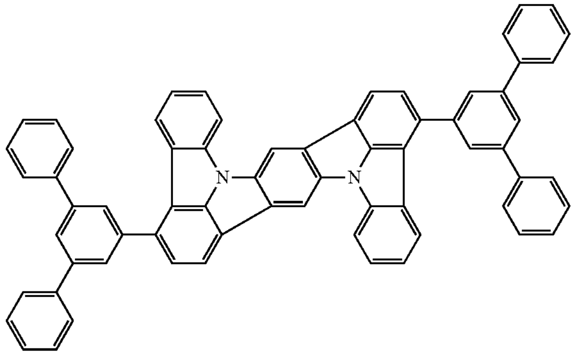
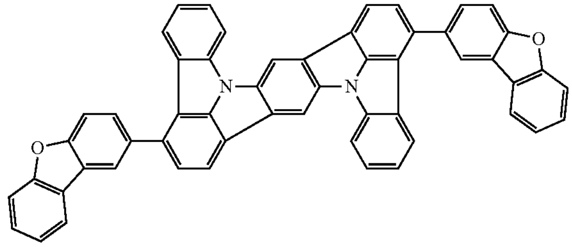
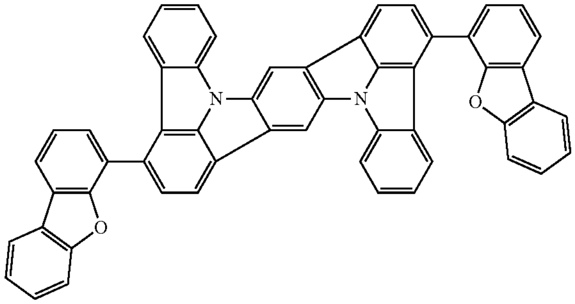
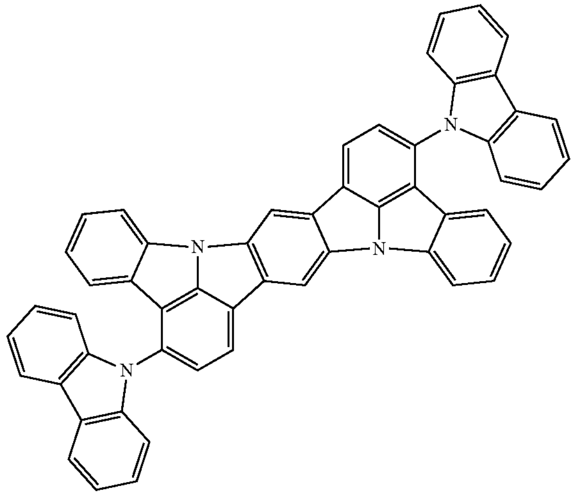
-continued
[Formula 173]
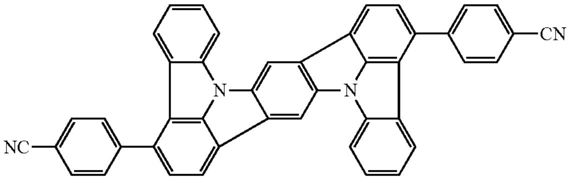
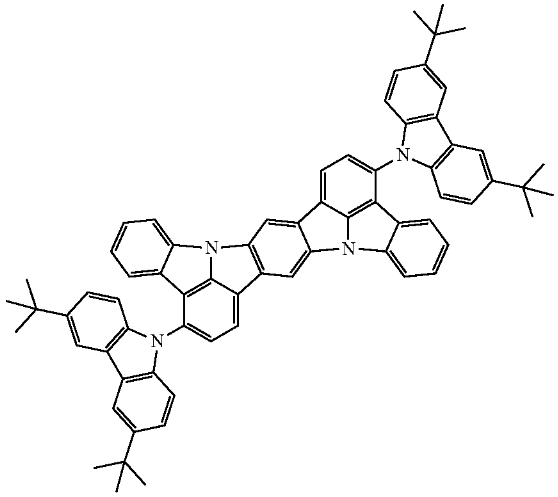
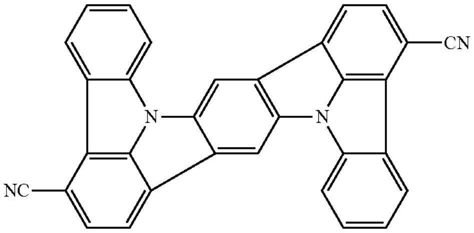
[Formula 174]
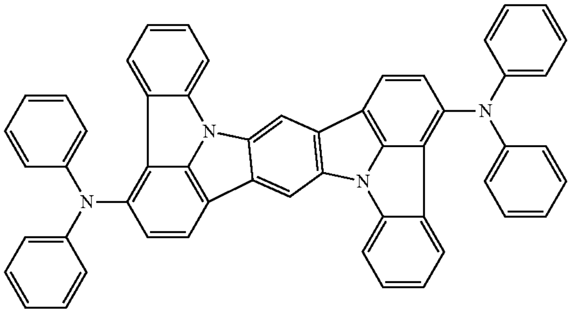
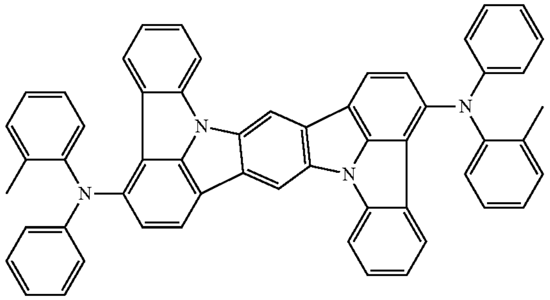

-continued
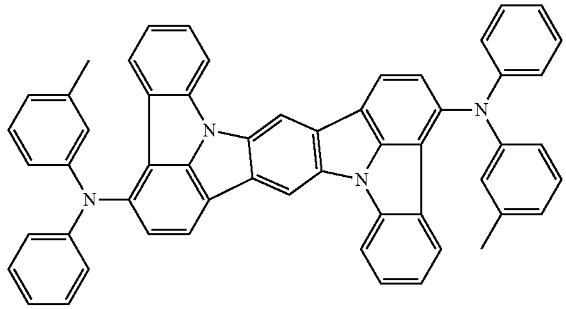
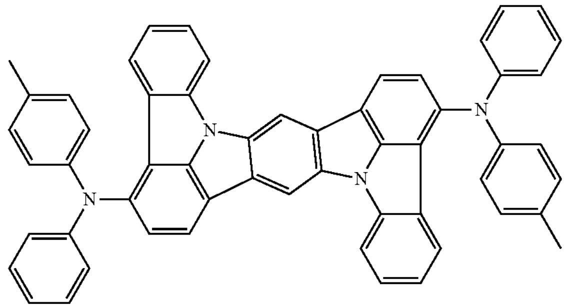
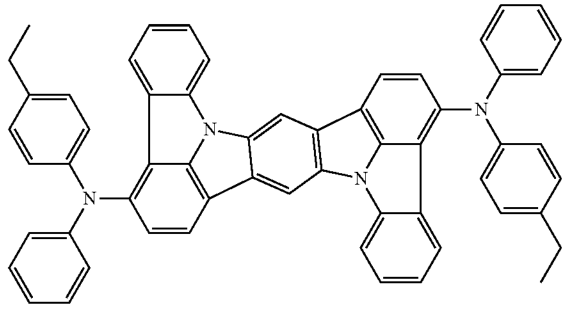
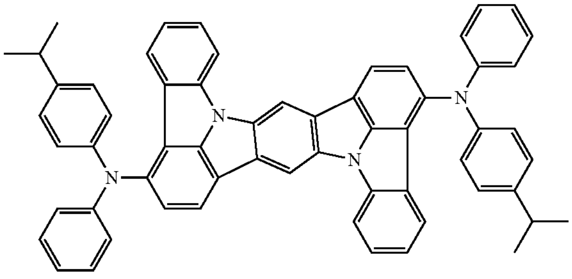
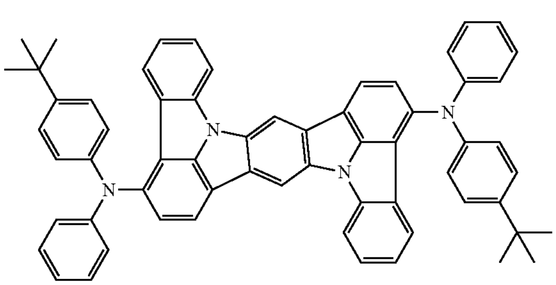
-continued
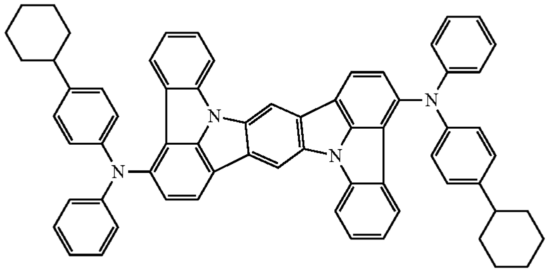
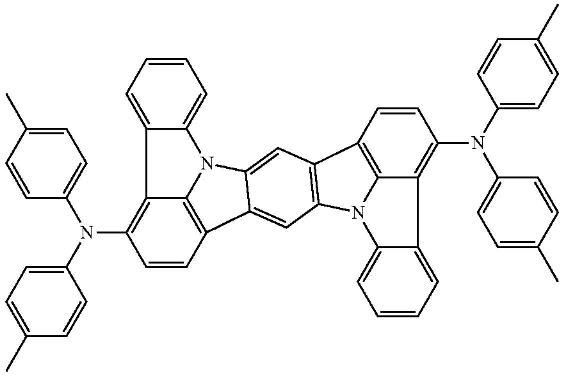
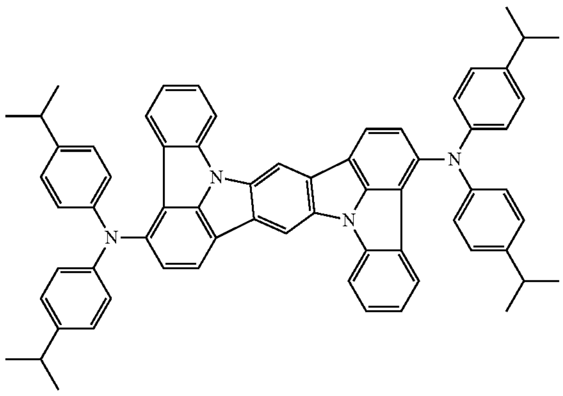
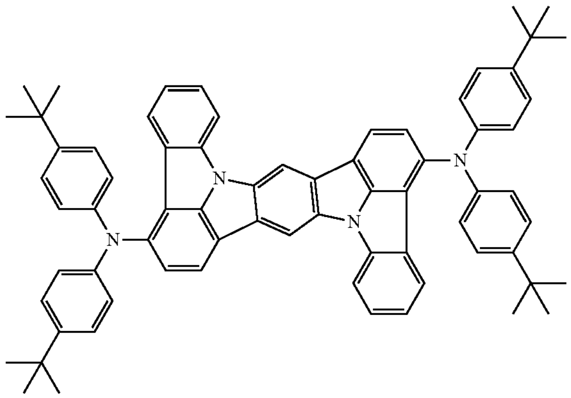

-continued
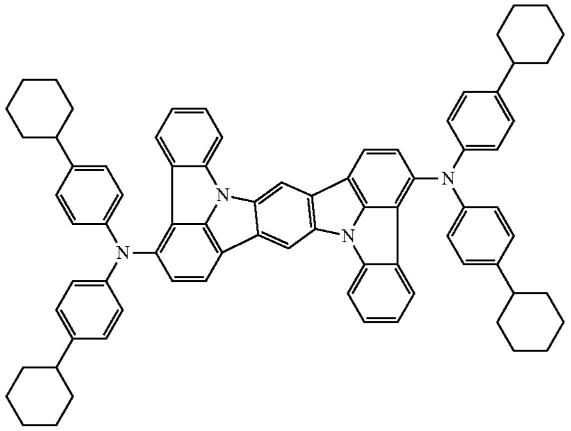
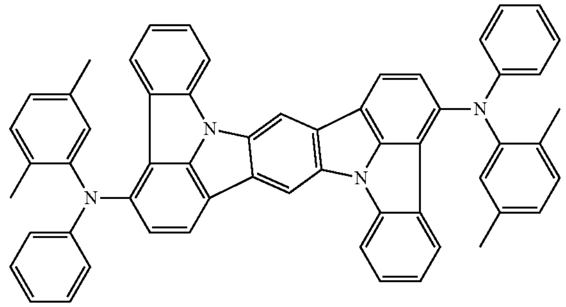
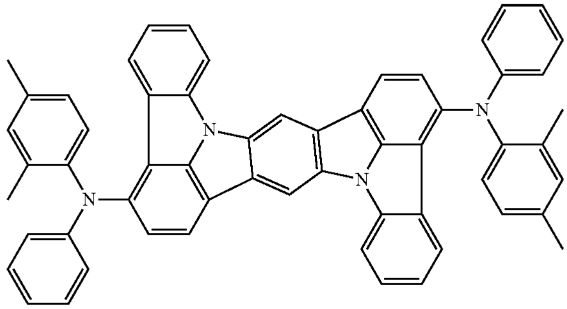
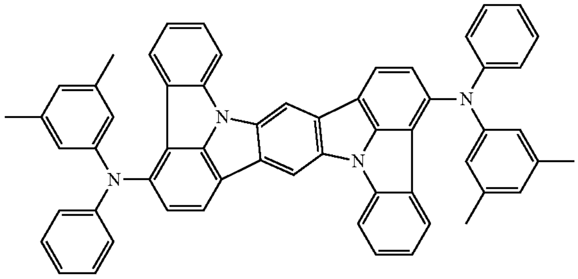
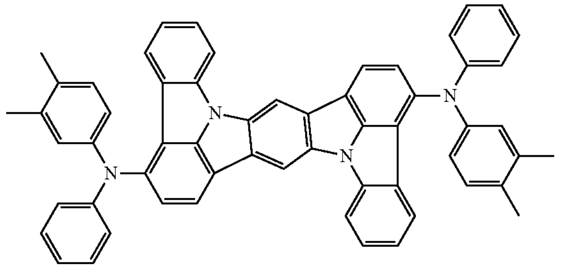
-continued
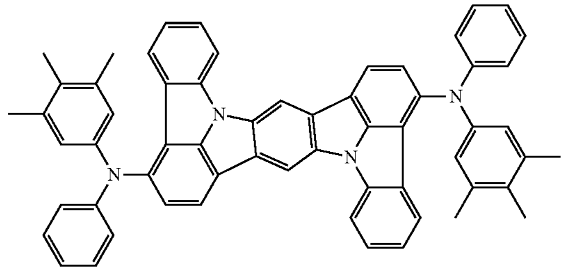
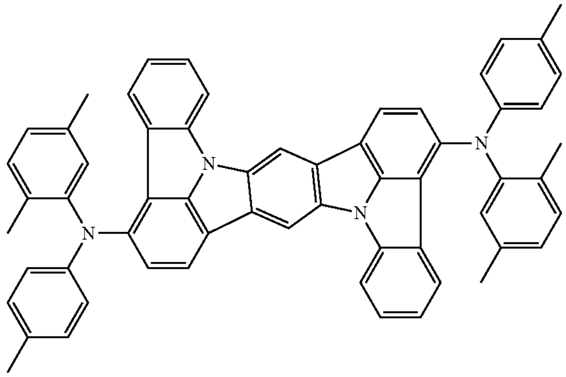
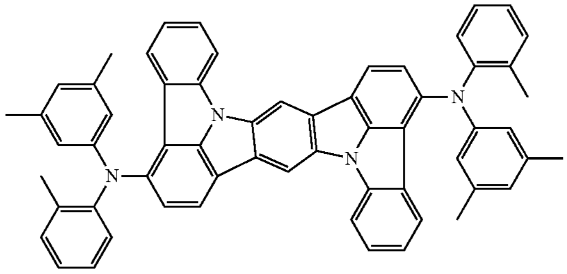
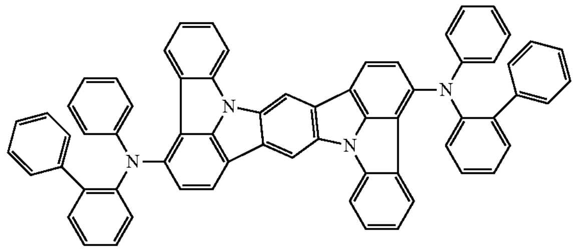
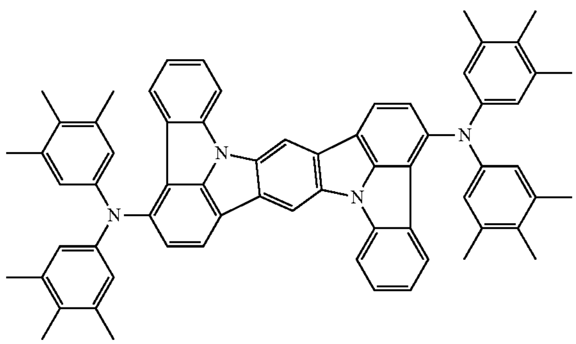

-continued
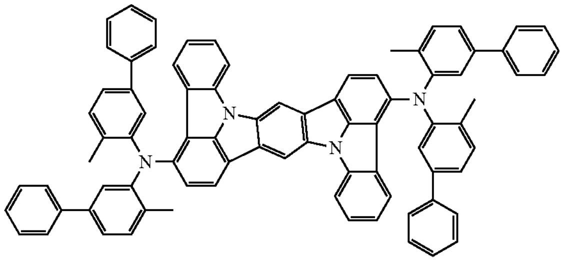
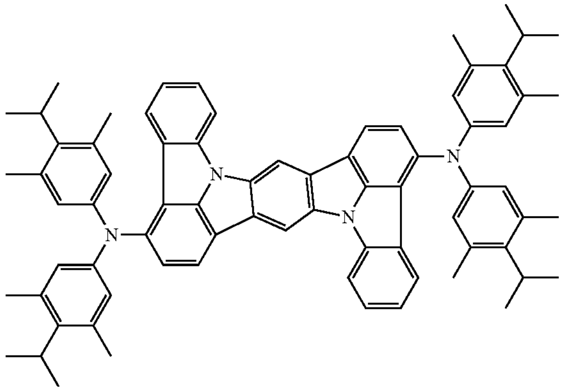
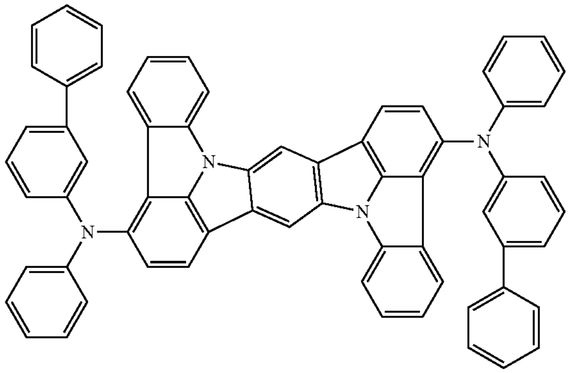
[Formula 175]
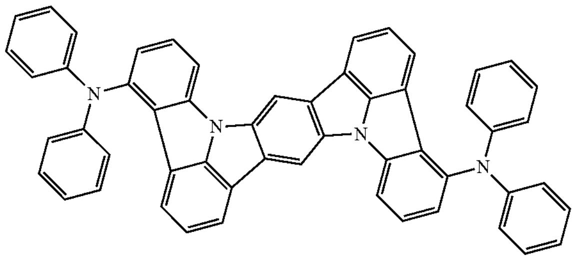
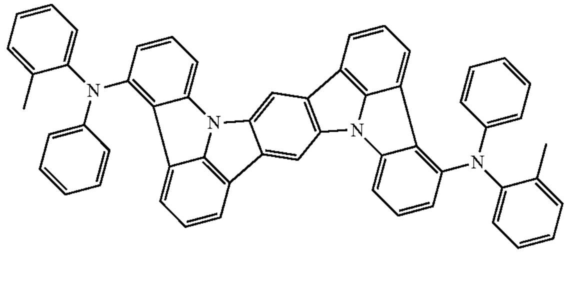
-continued
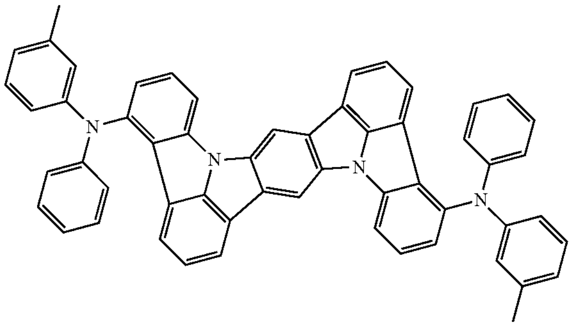
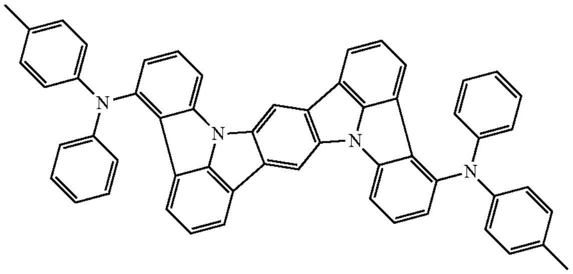
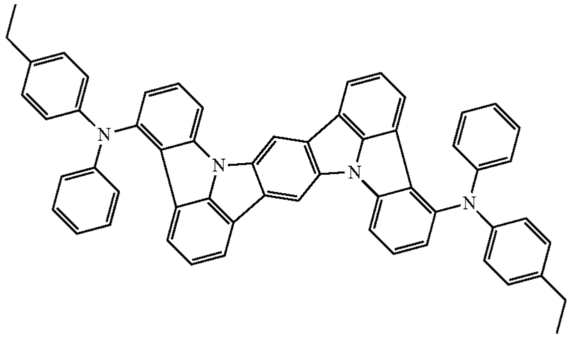
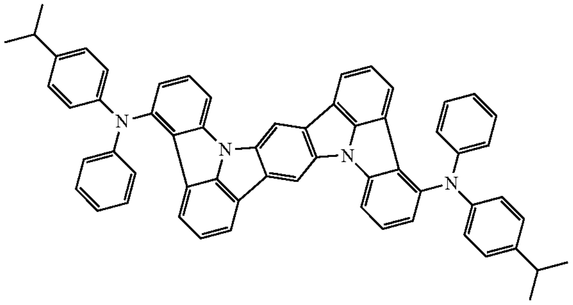
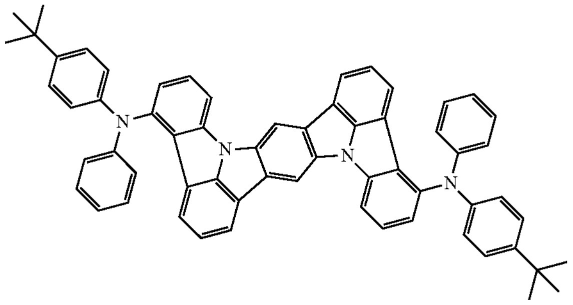

-continued
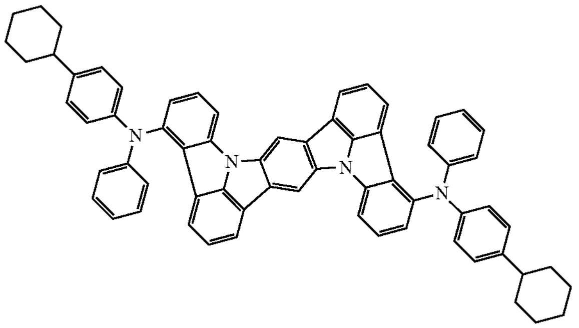
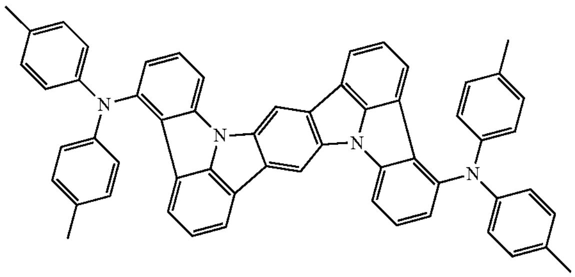
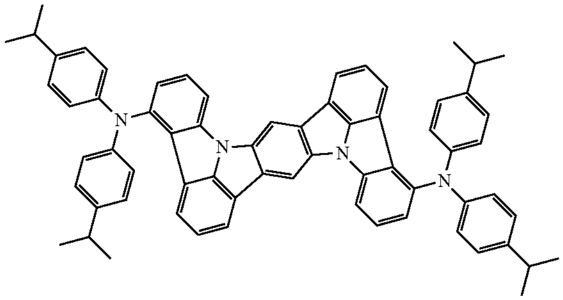
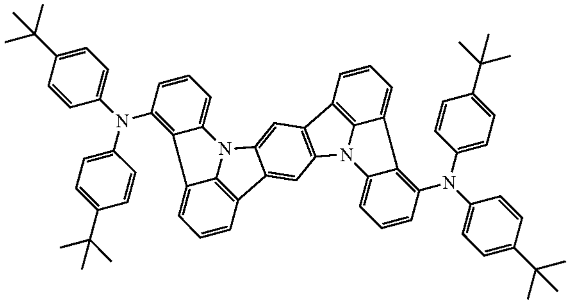
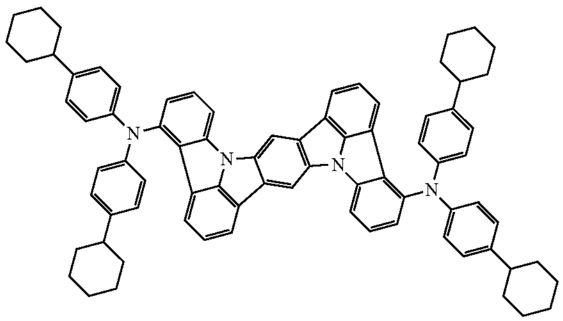
-continued
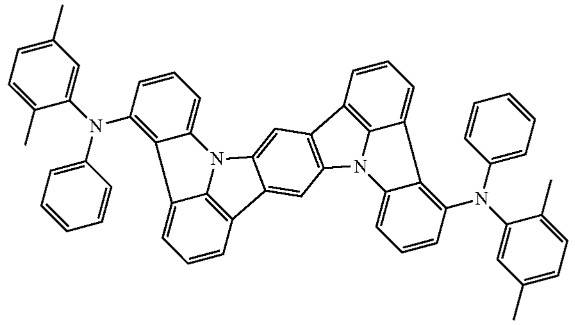
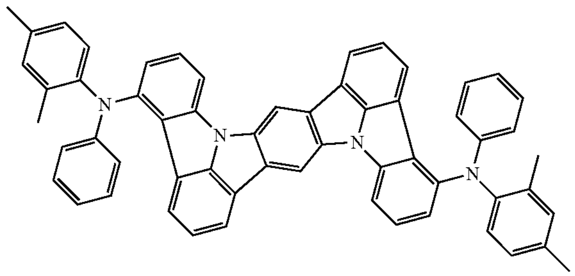
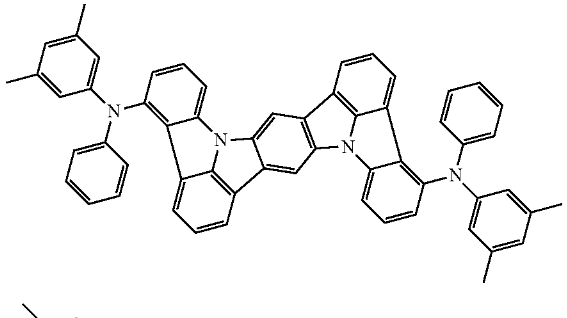
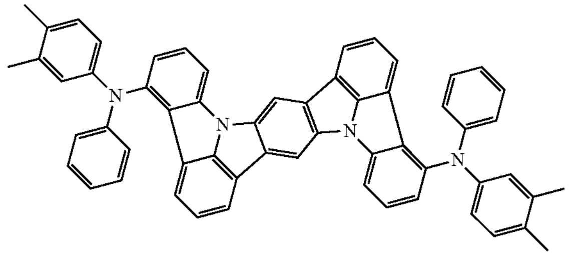
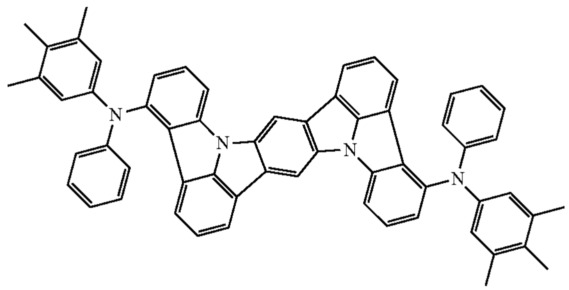

-continued
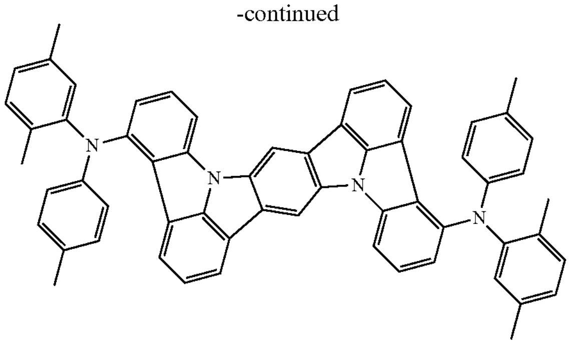
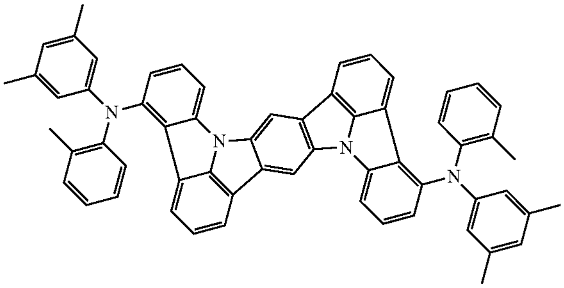
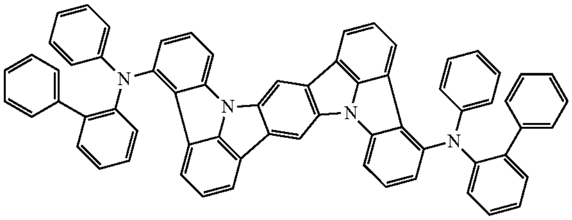
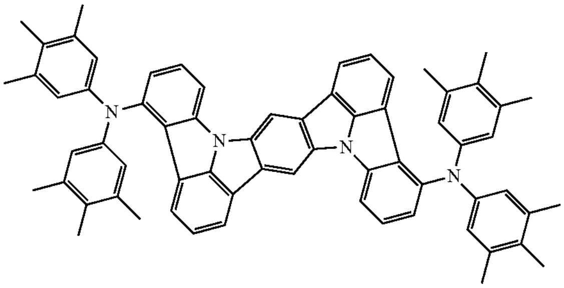
-continued
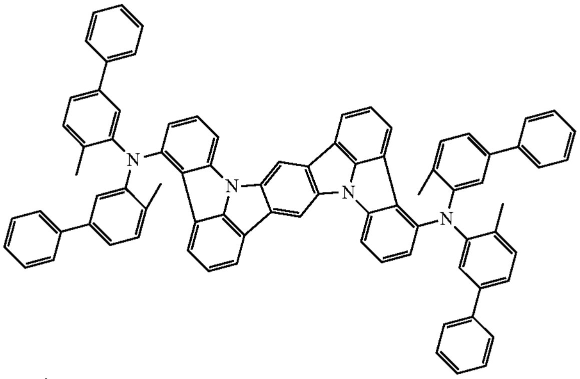
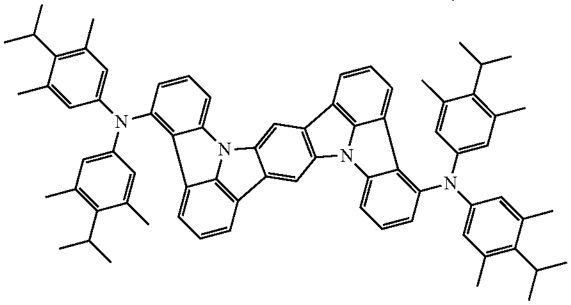
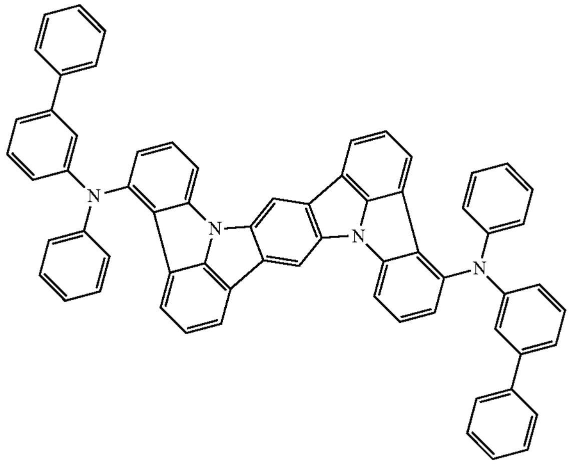
[Formula 176]
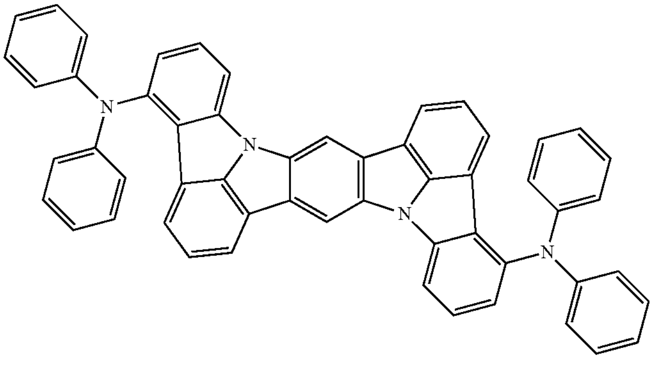

-continued
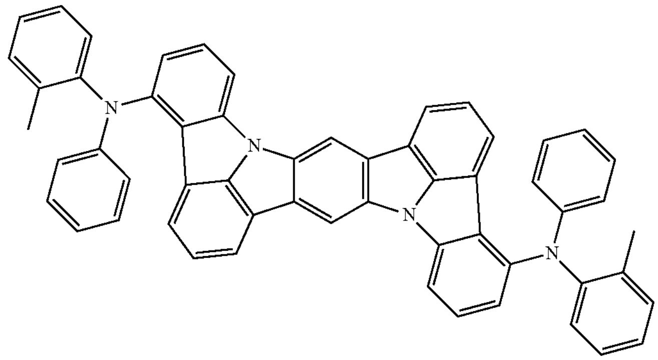
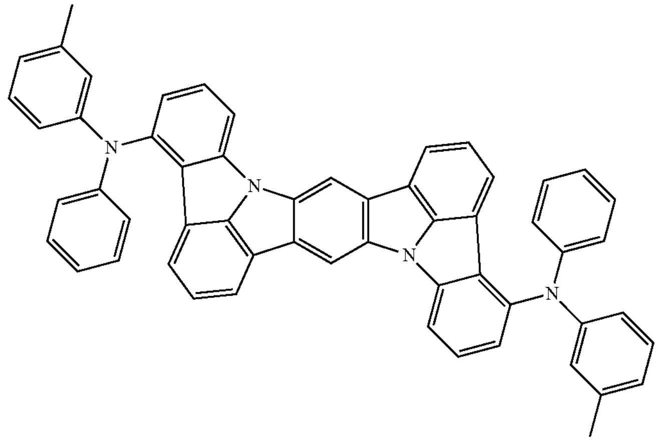
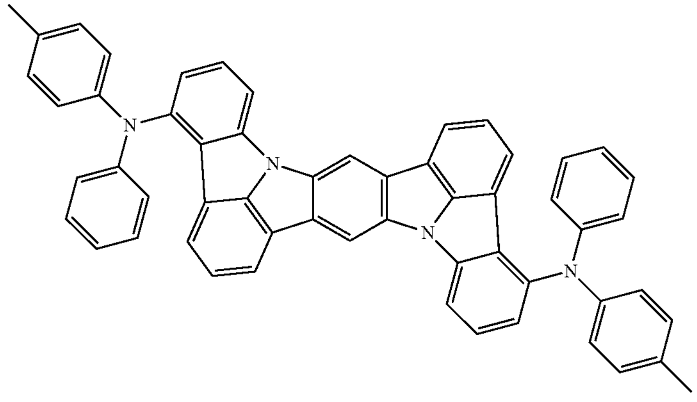
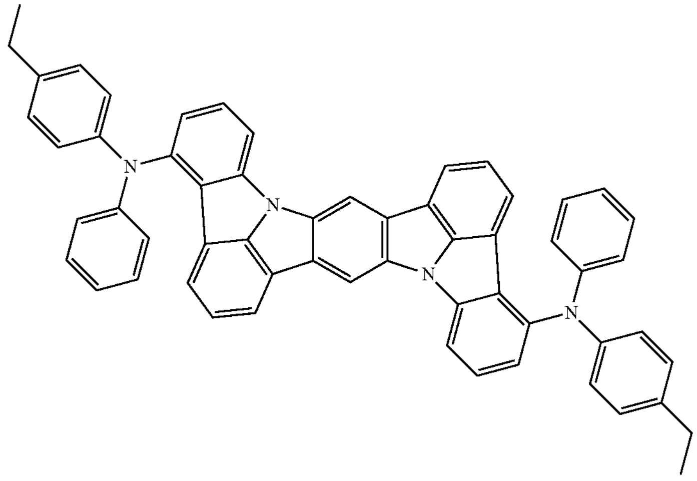

-continued
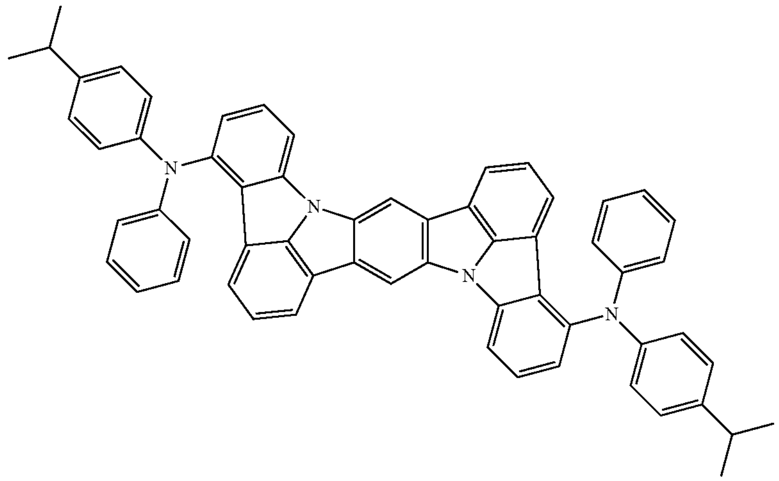
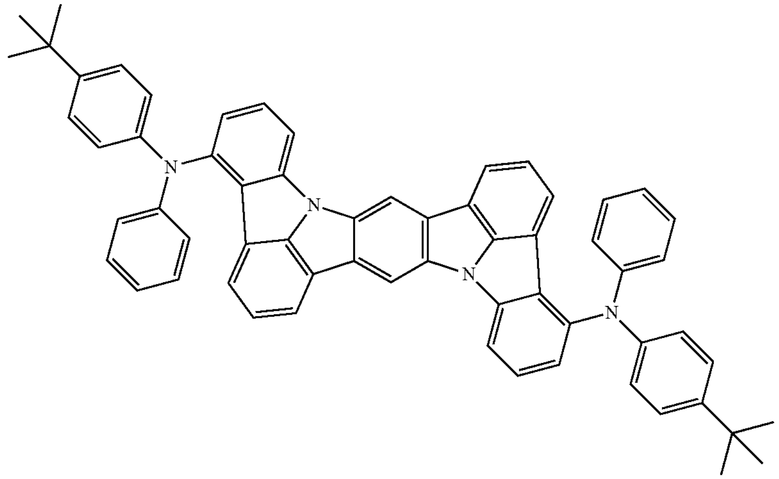
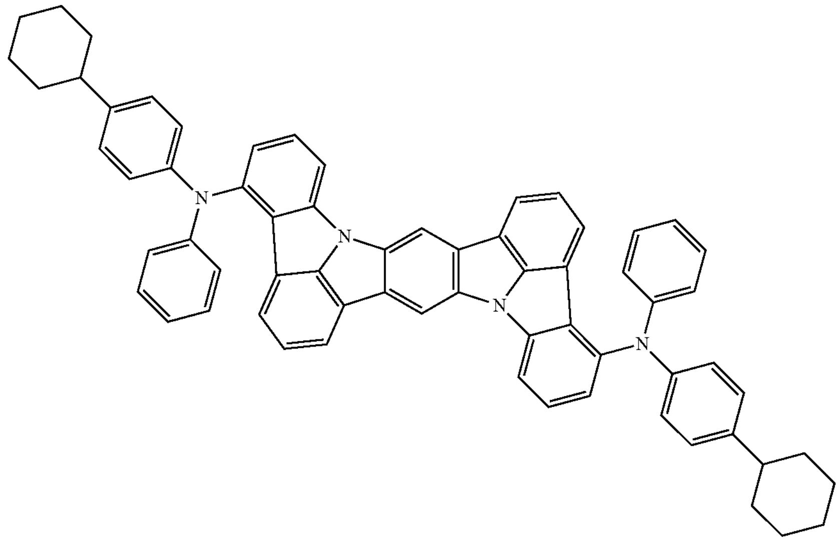

-continued
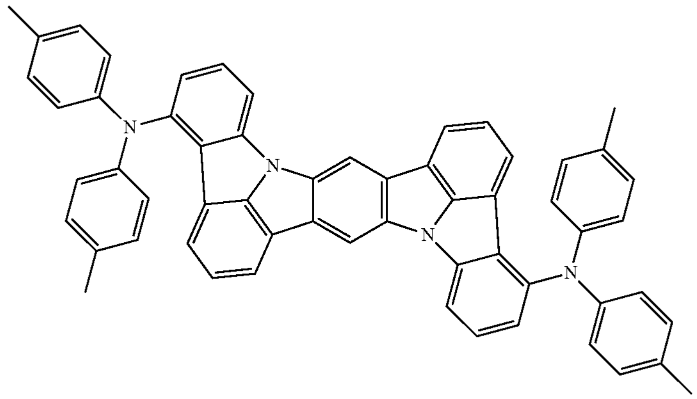
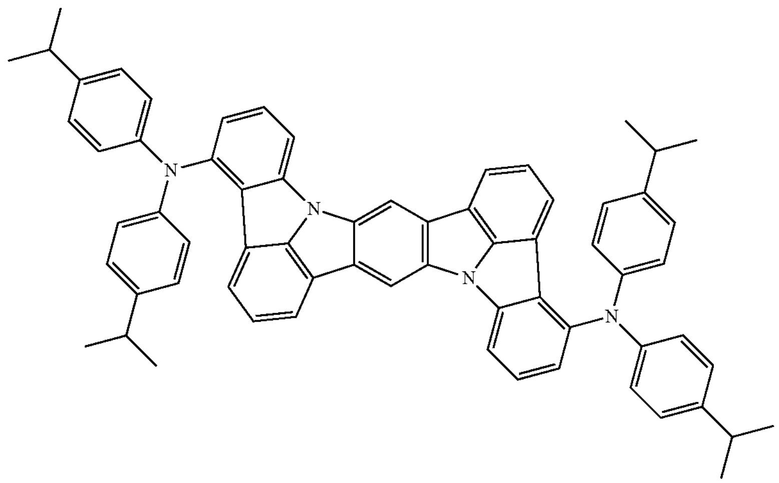
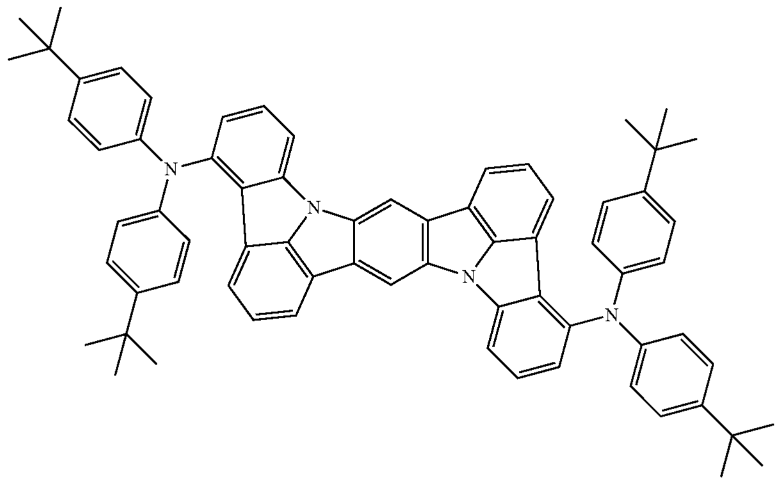

-continued
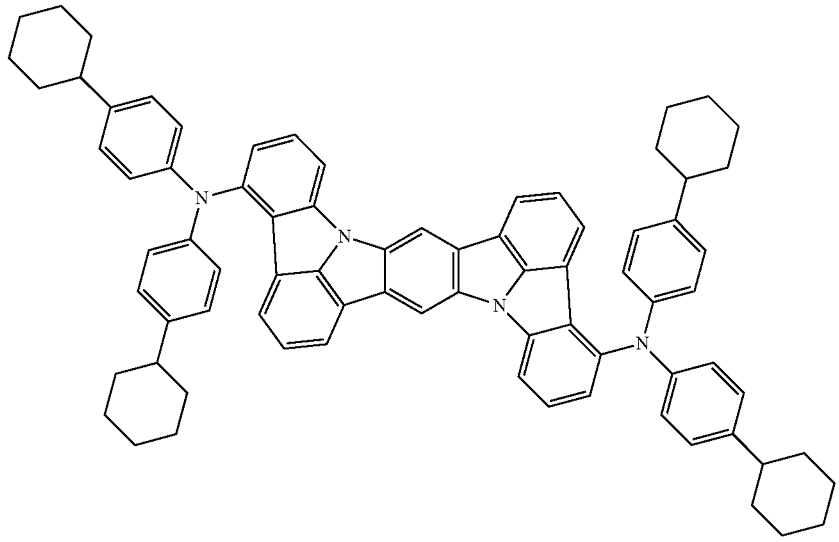
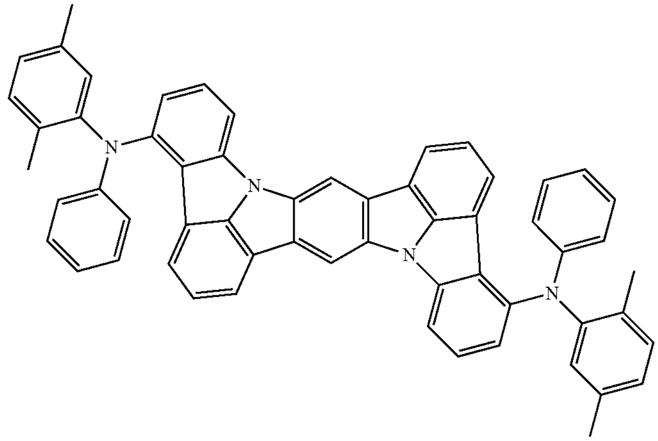
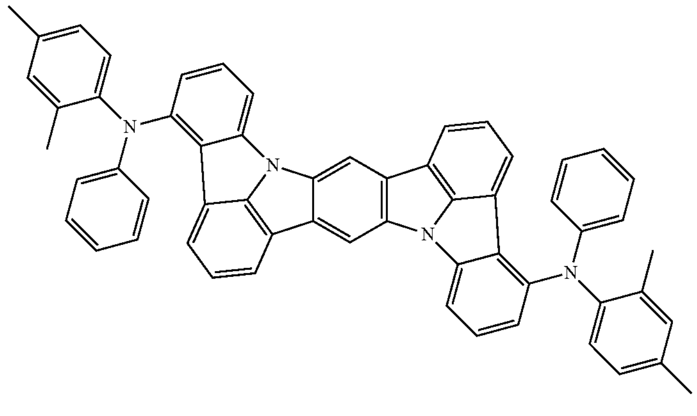

-continued
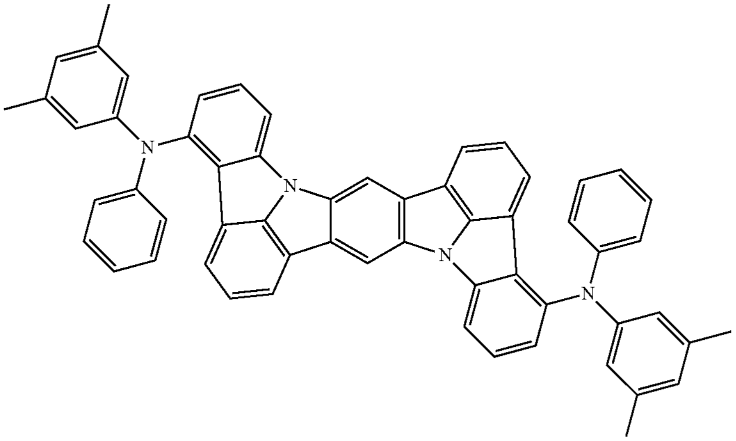
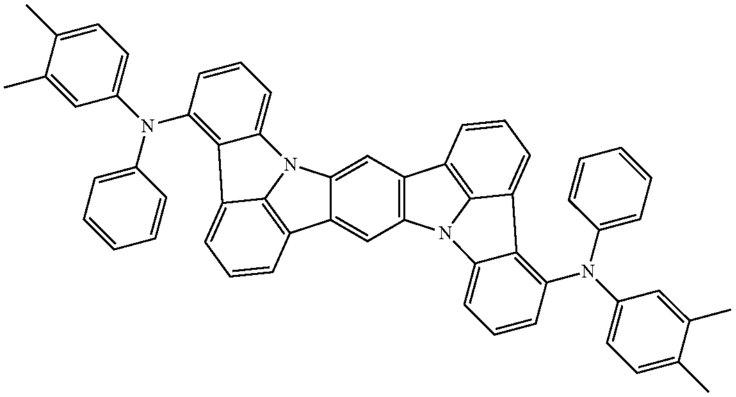
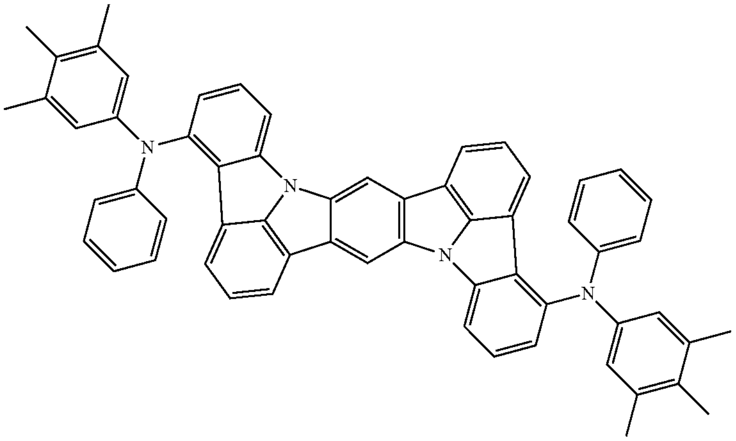
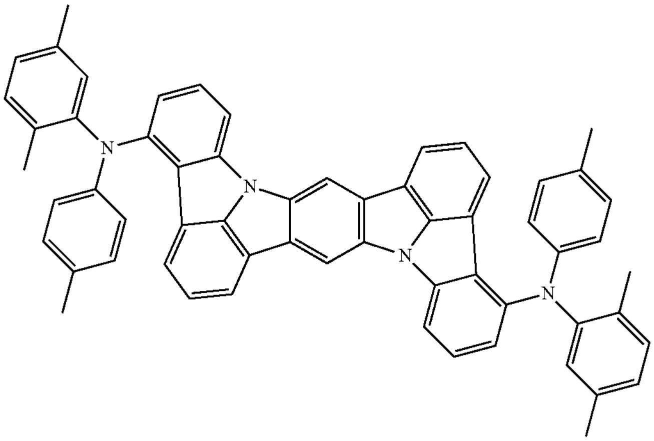

-continued
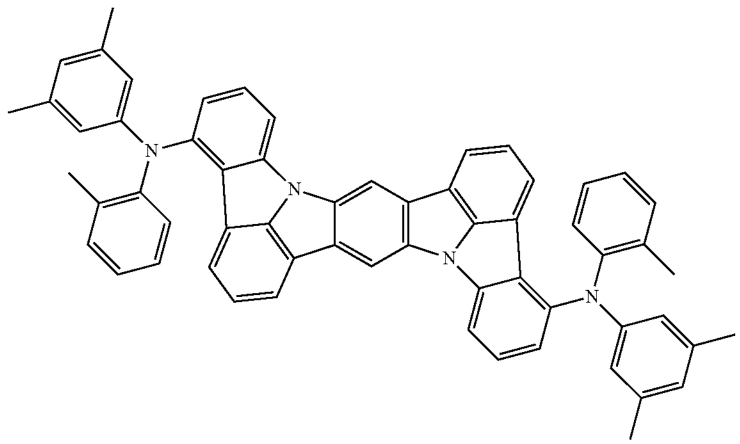
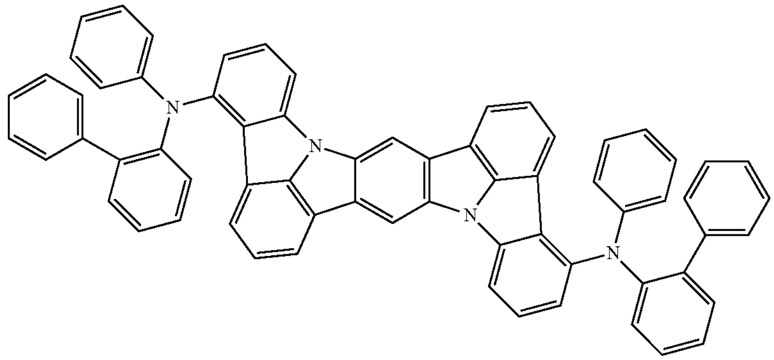
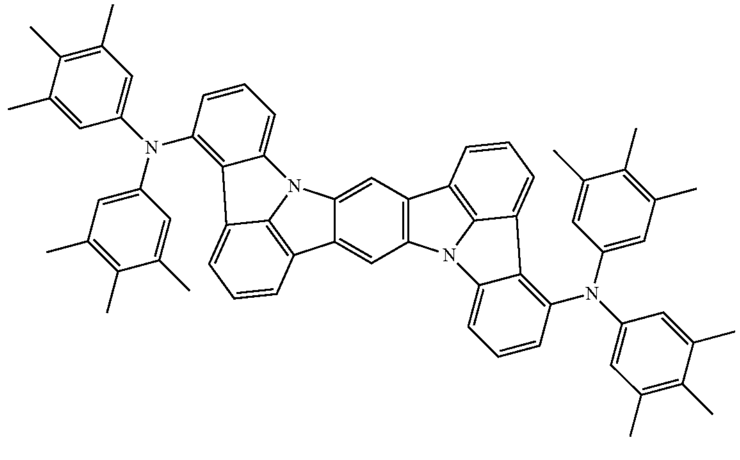

-continued
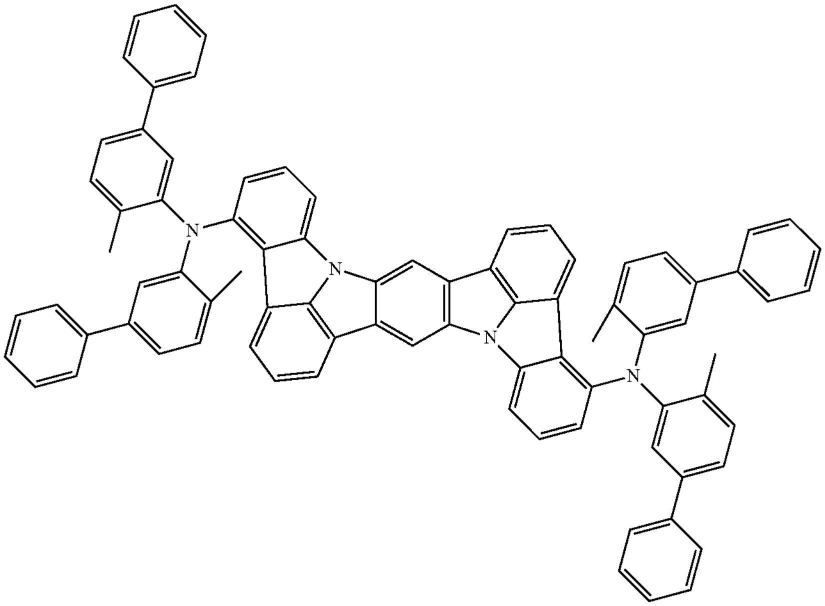
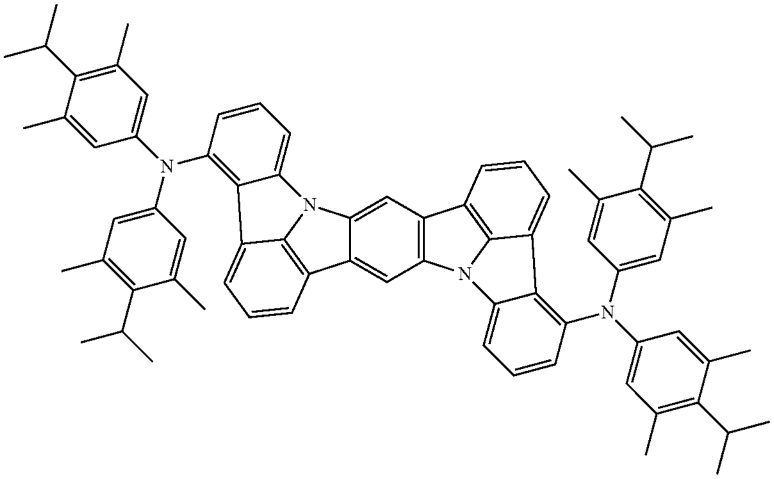
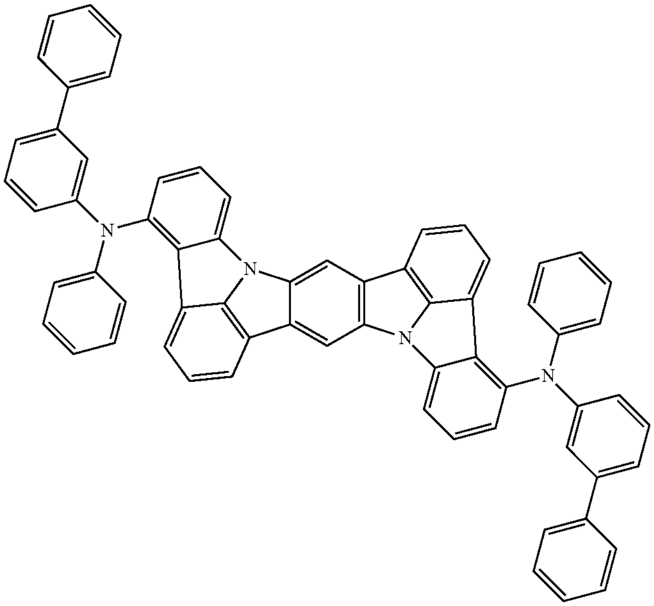

-continued
[Formula 177]
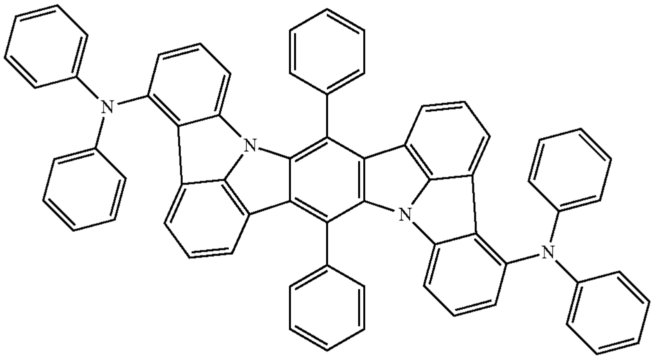
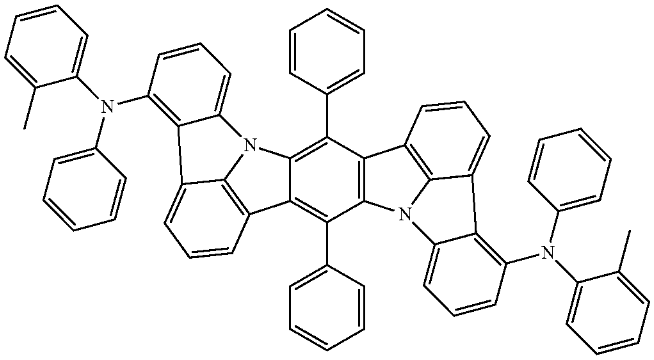
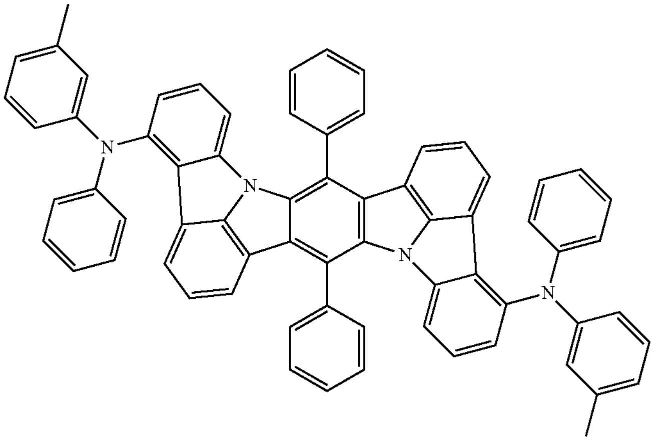
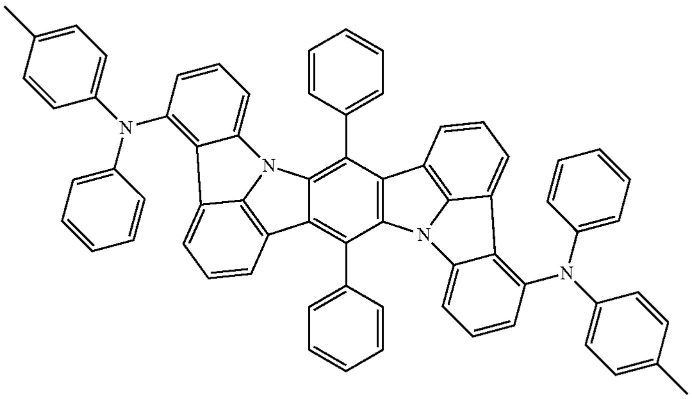

-continued
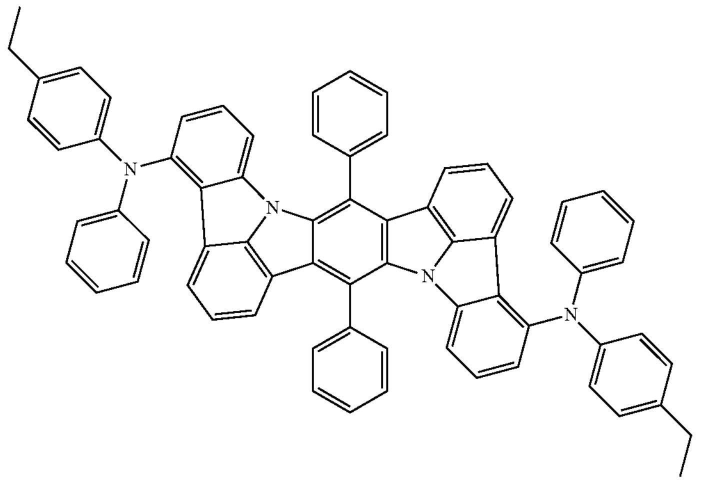
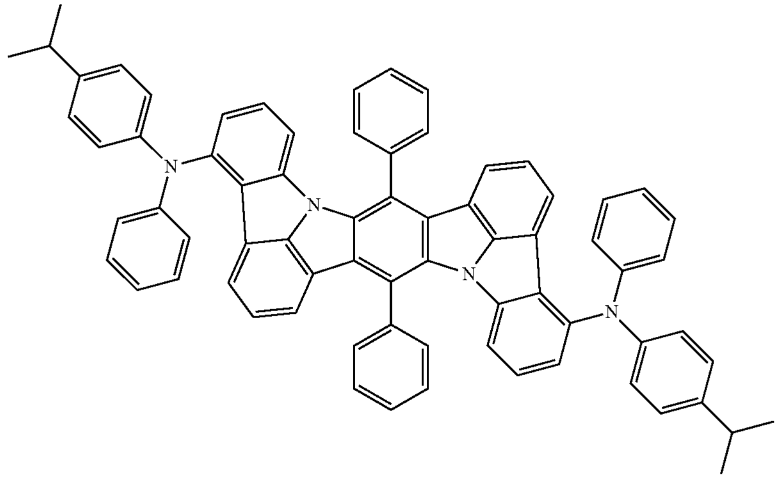
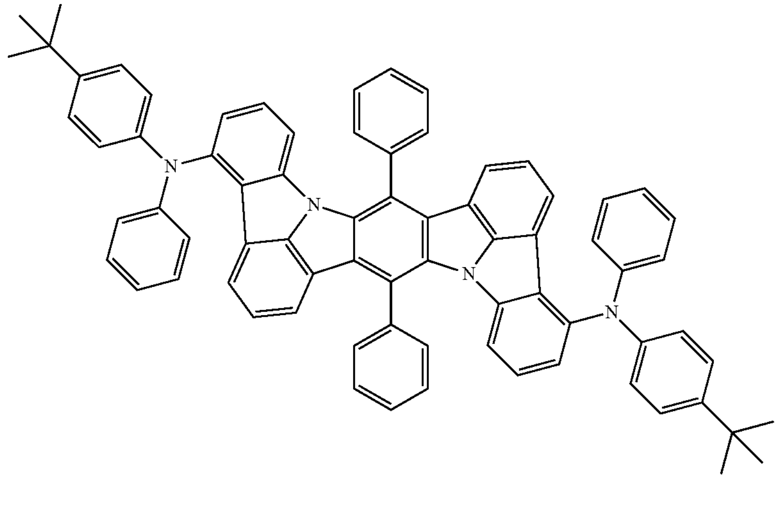

-continued
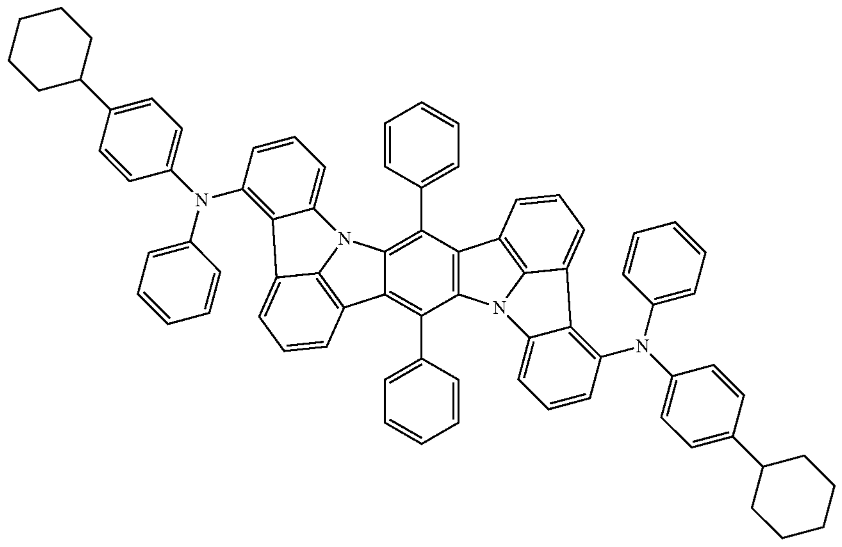
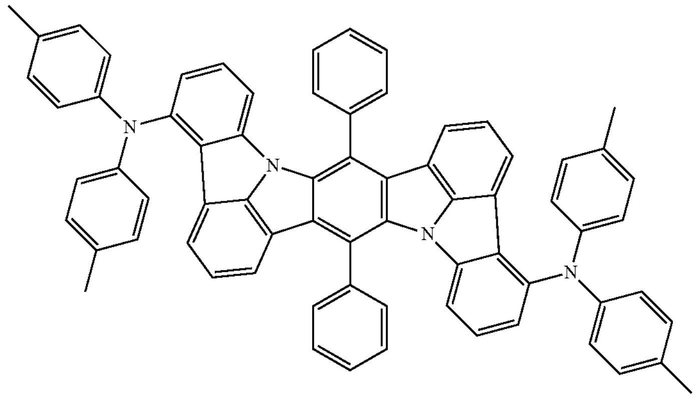
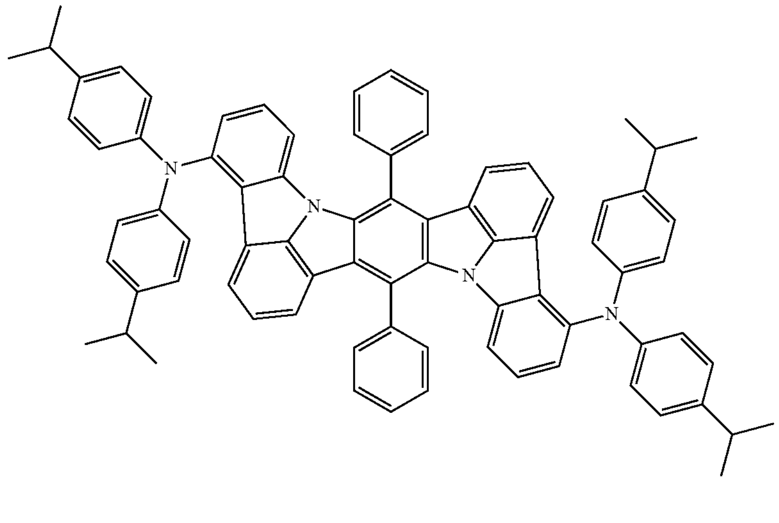

-continued
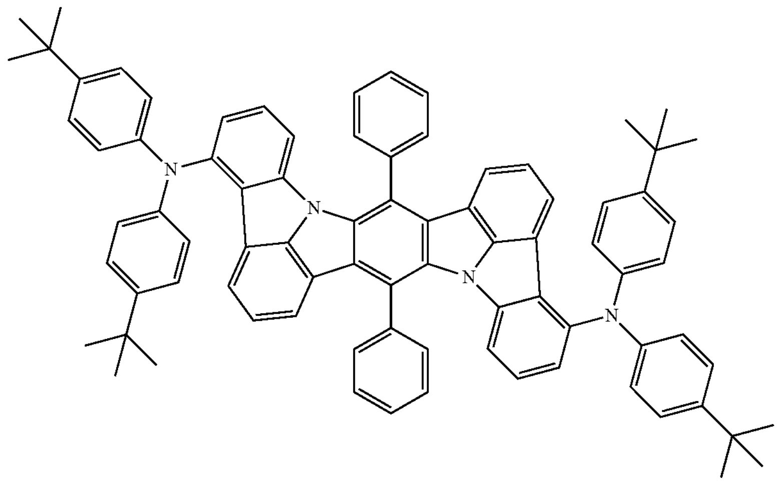
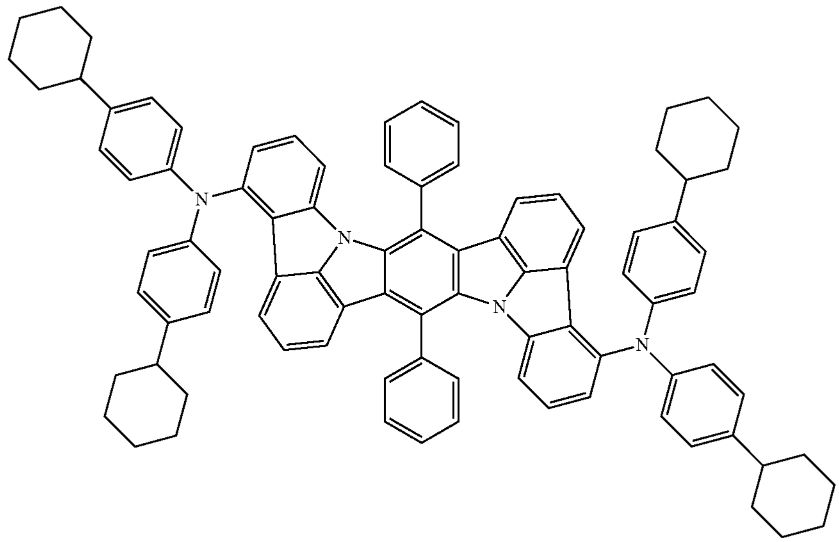
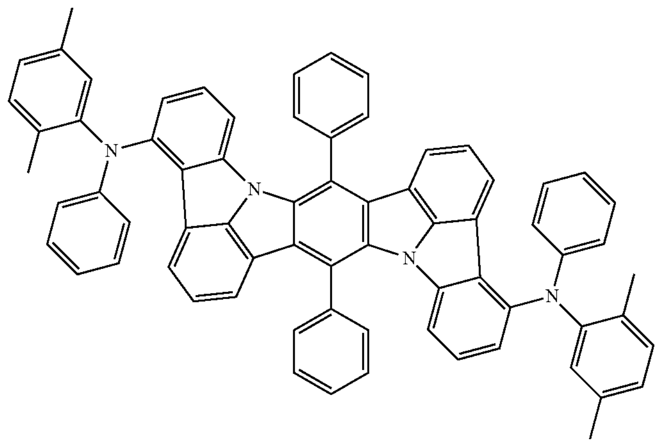

-continued
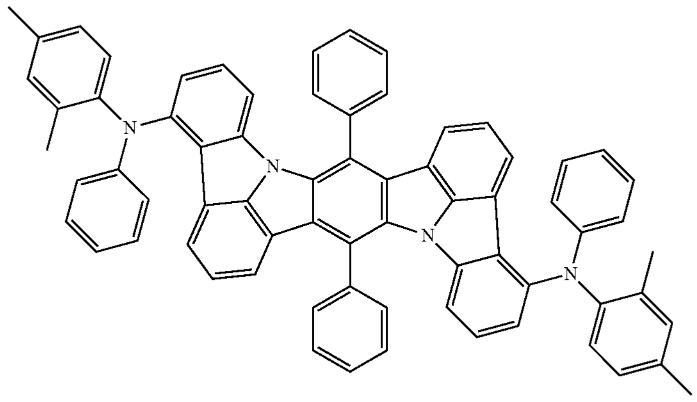
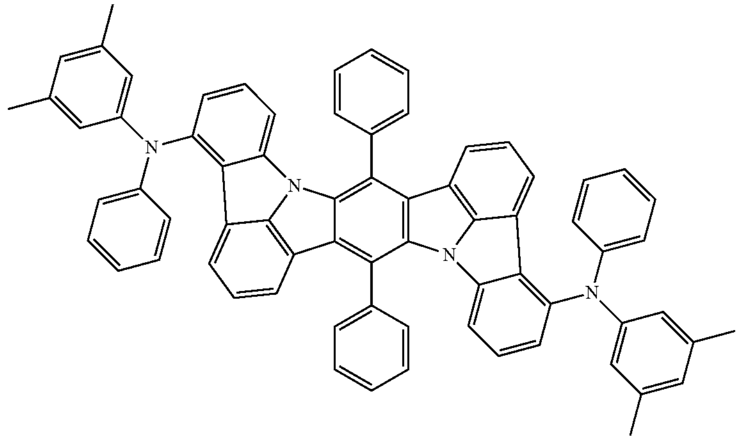
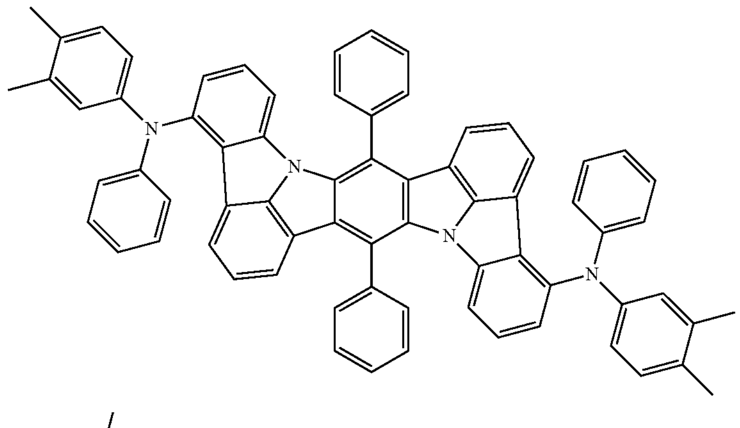
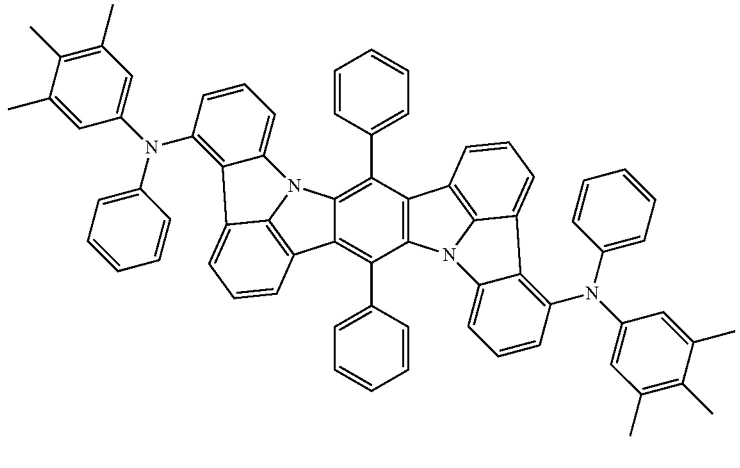

-continued
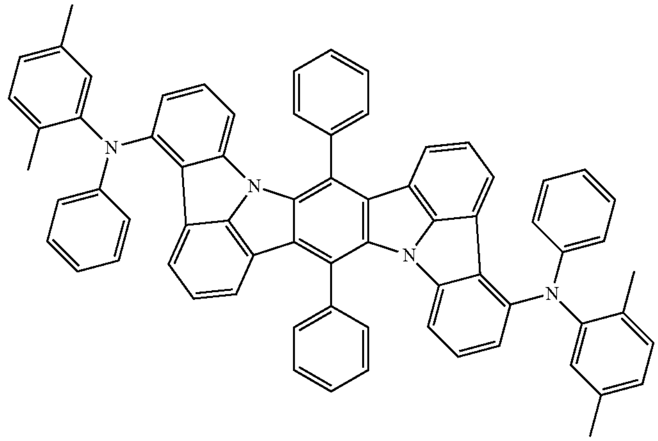
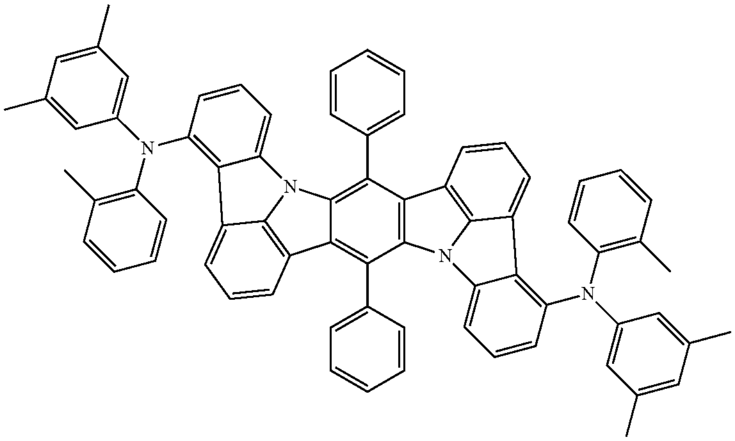
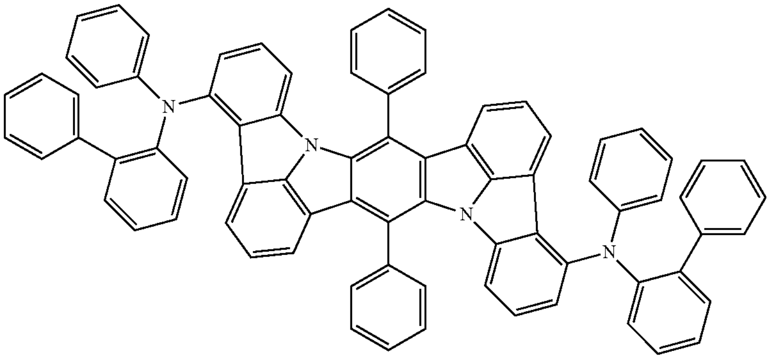
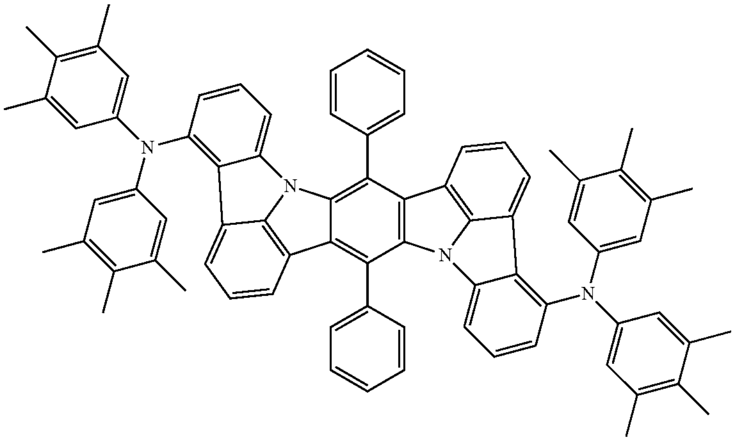

-continued
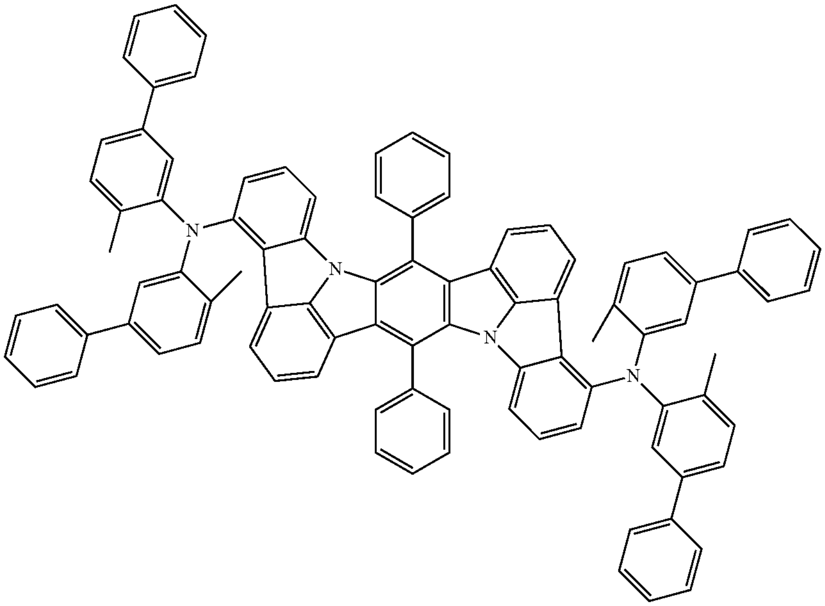
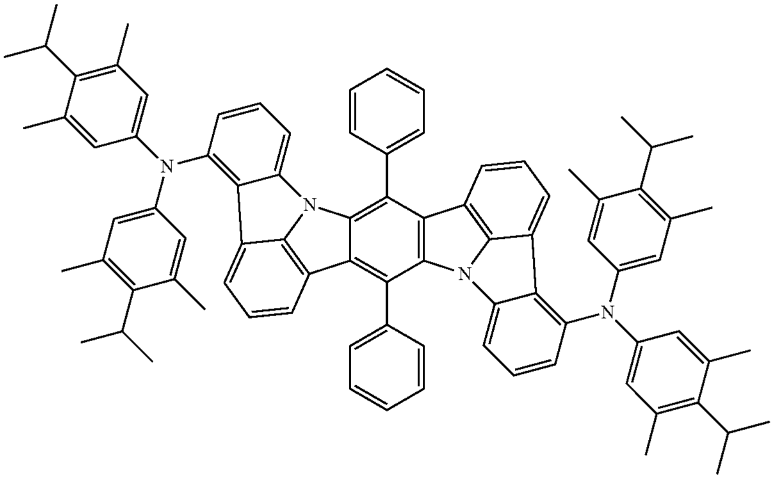
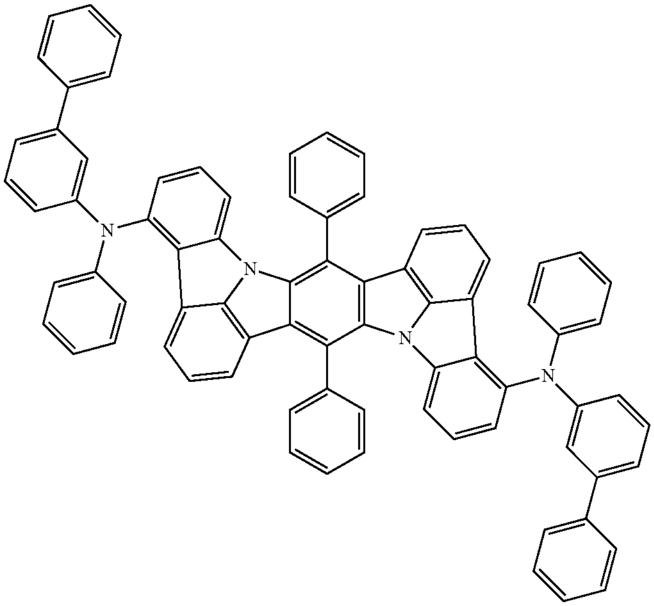

-continued
[Formula 178]
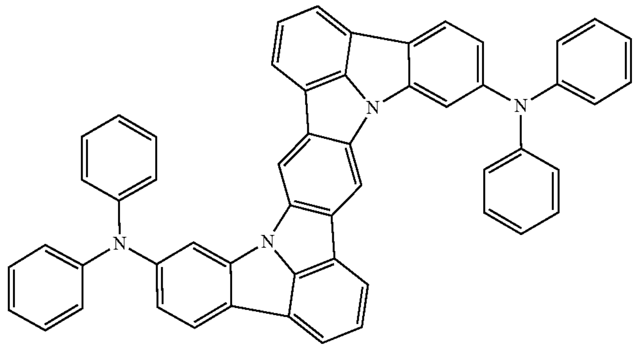
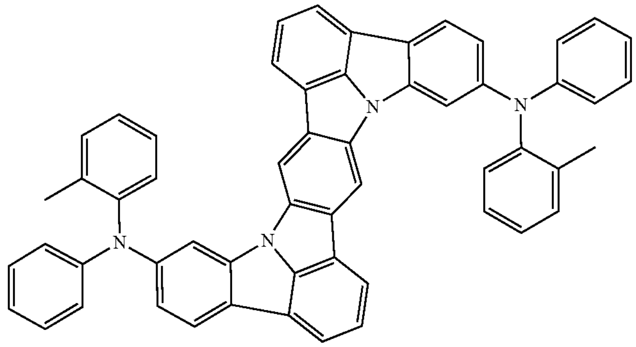
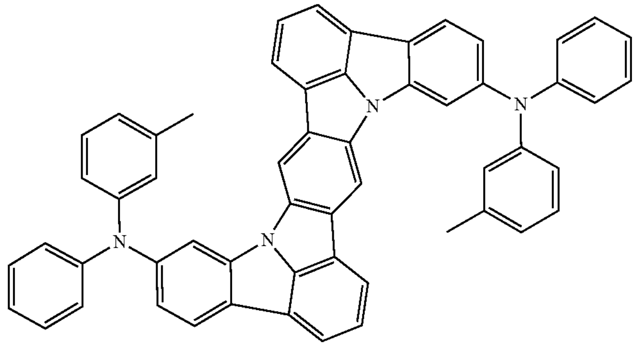
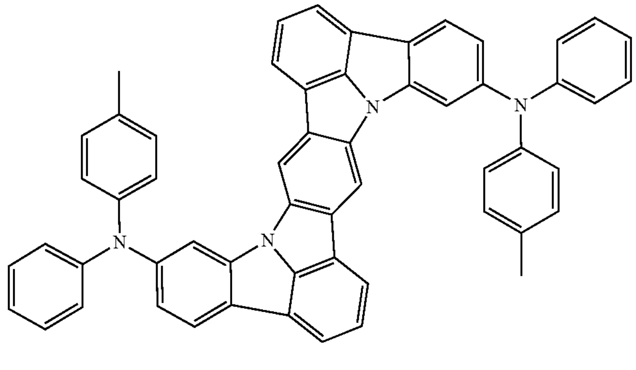

-continued
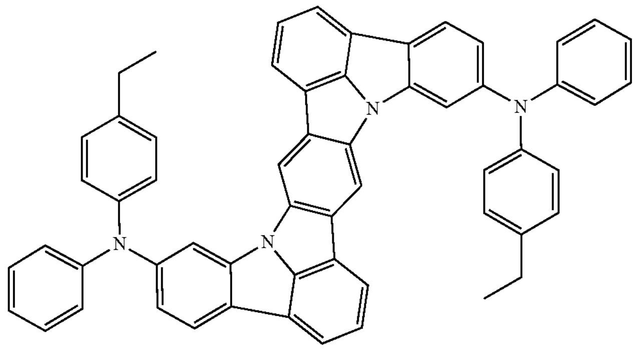
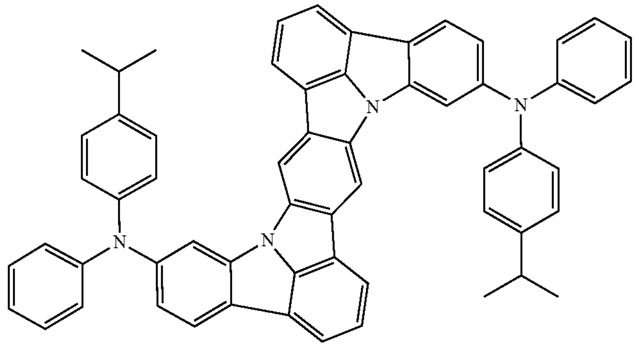
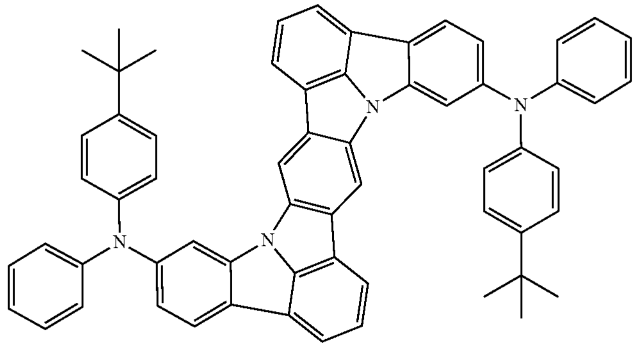
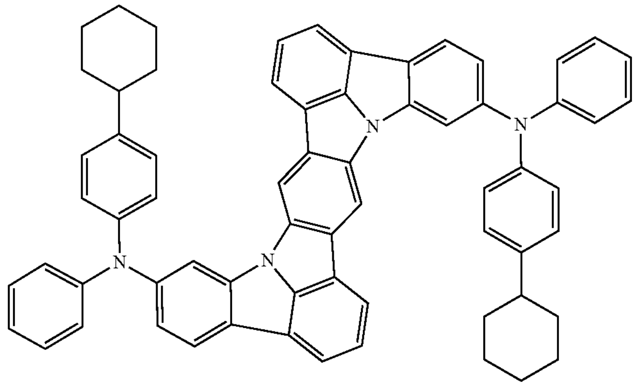

-continued
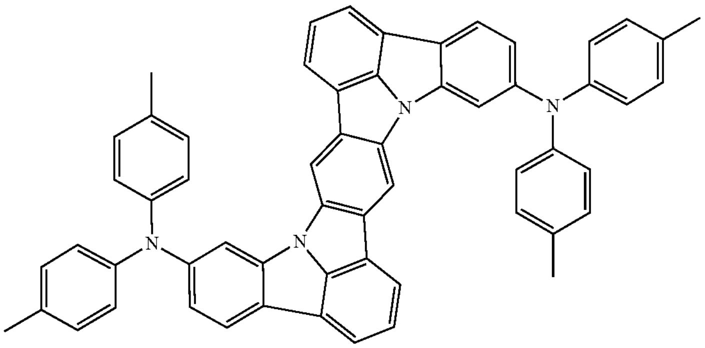
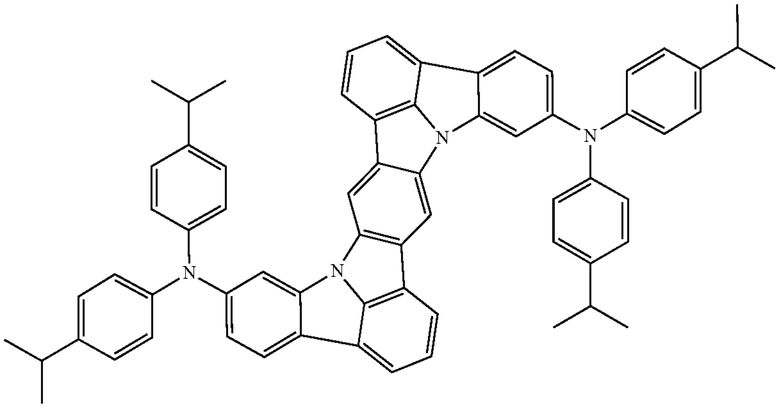
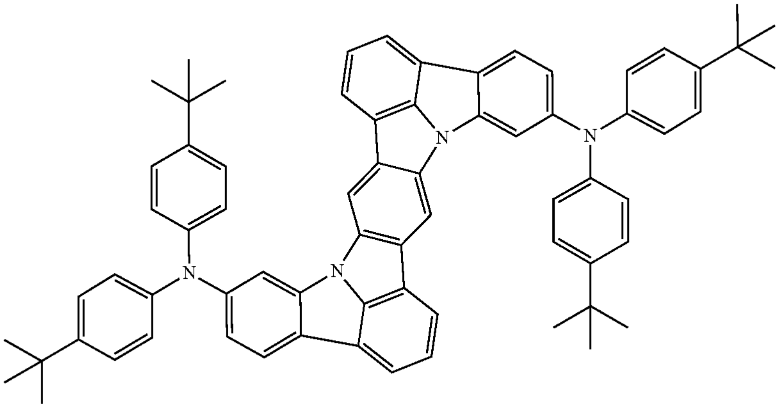
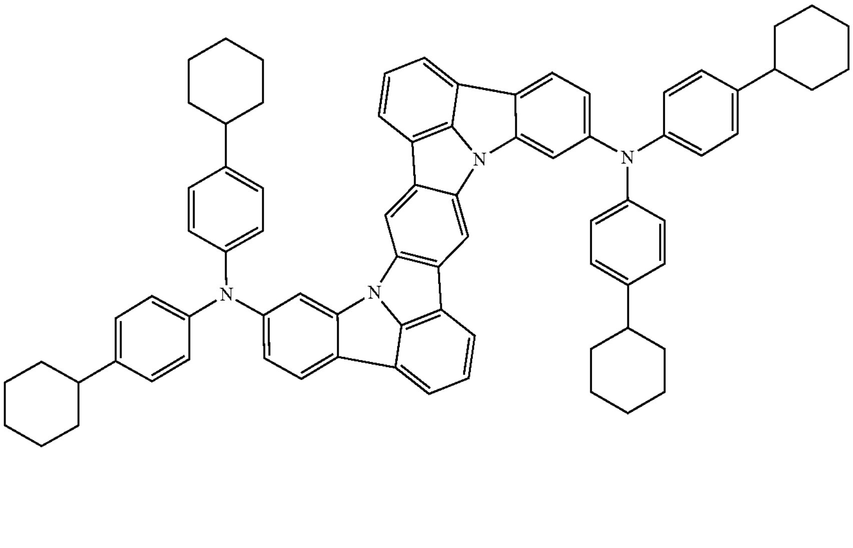

-continued
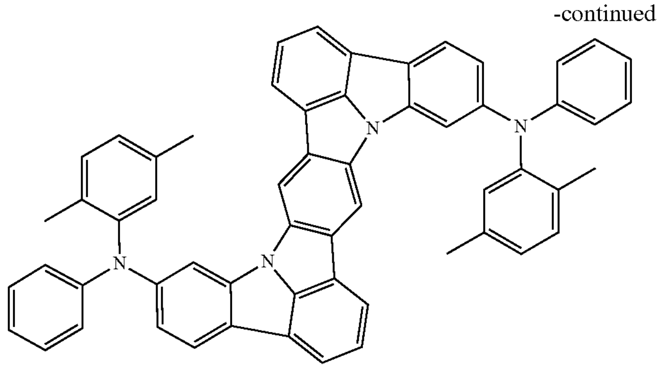
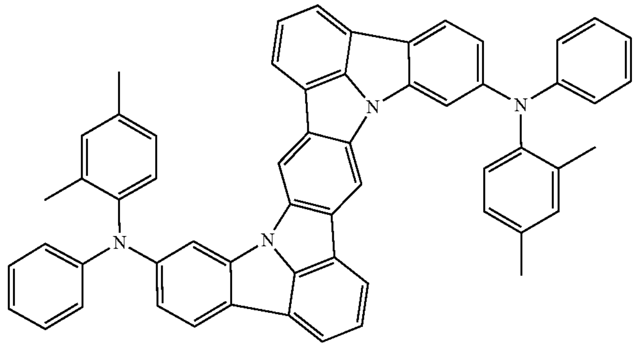
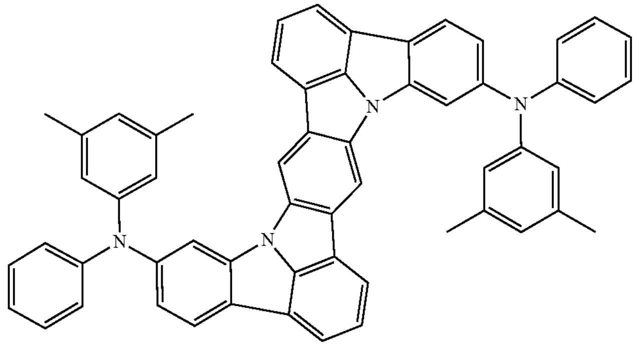
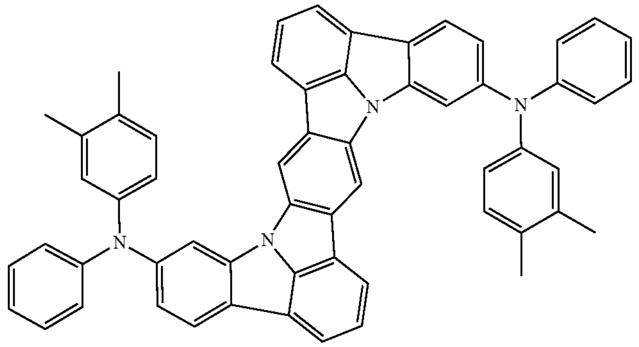
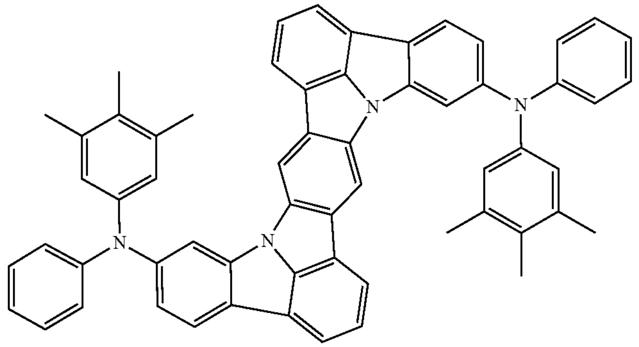

-continued
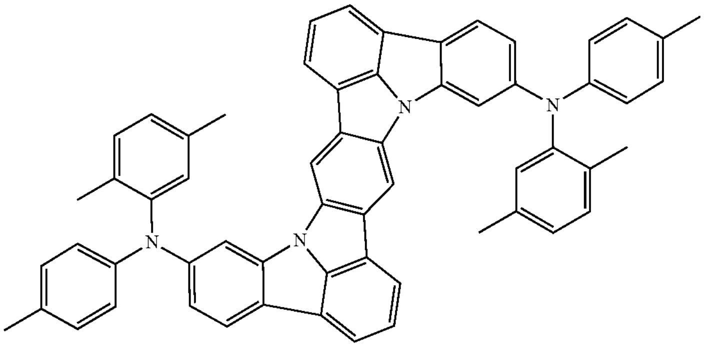
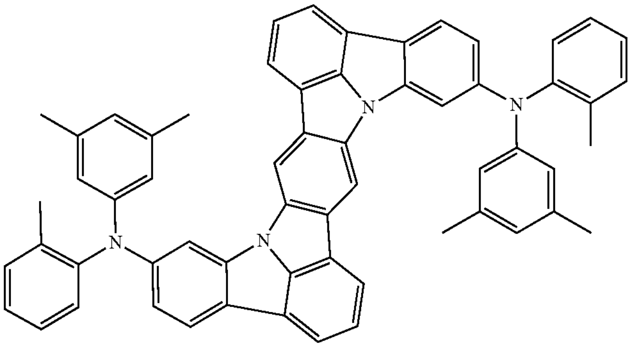
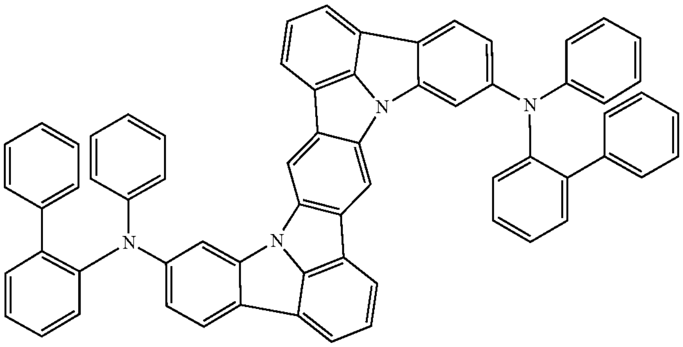
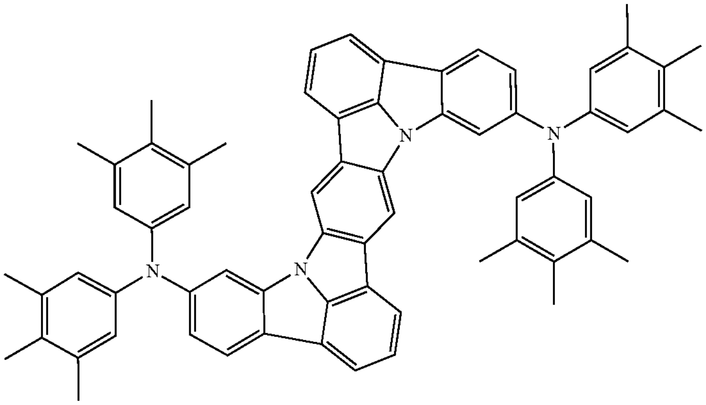

-continued
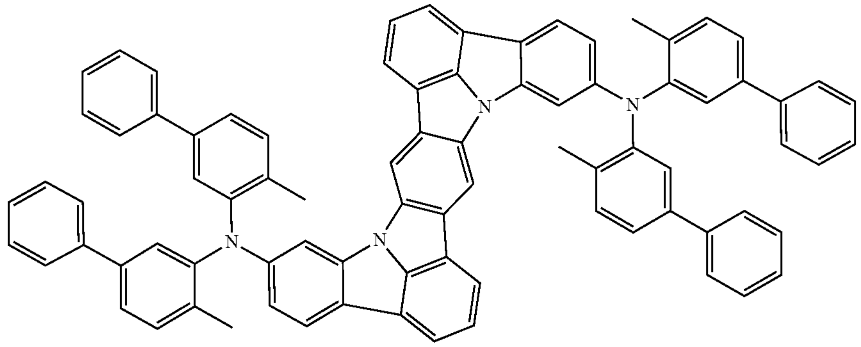
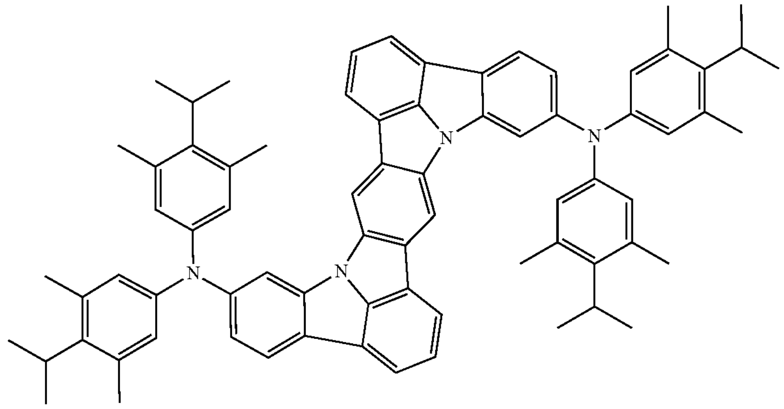
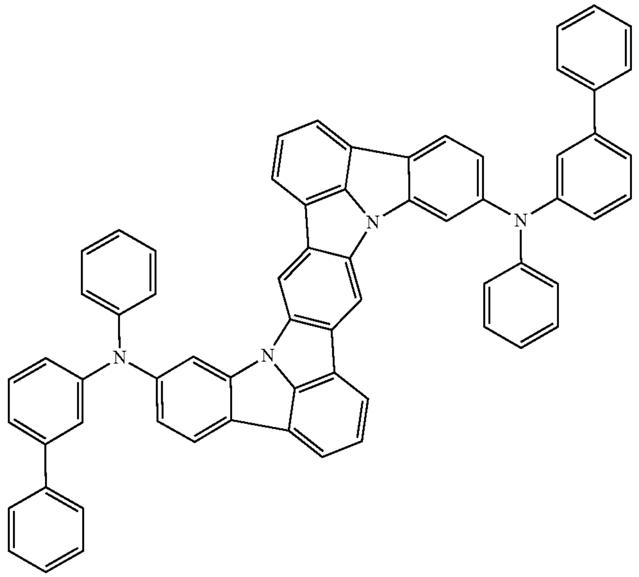

-continued
[Formula 179]
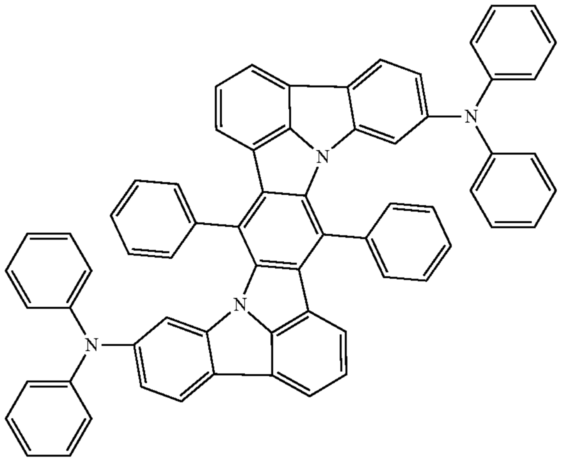
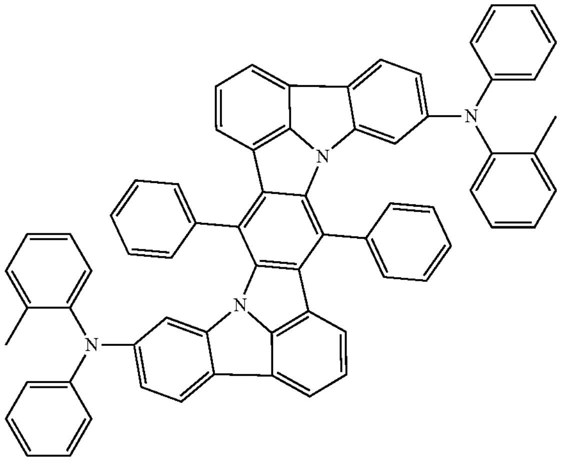
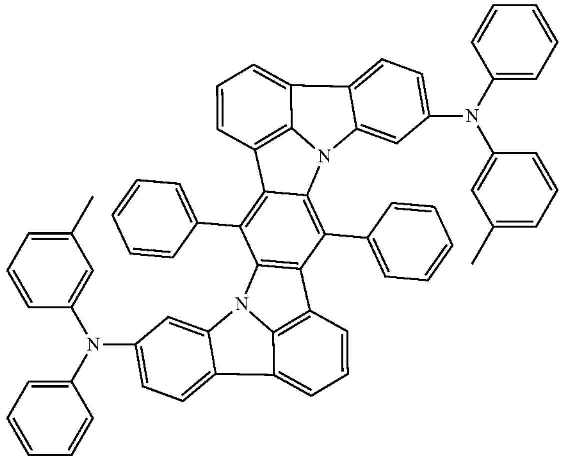
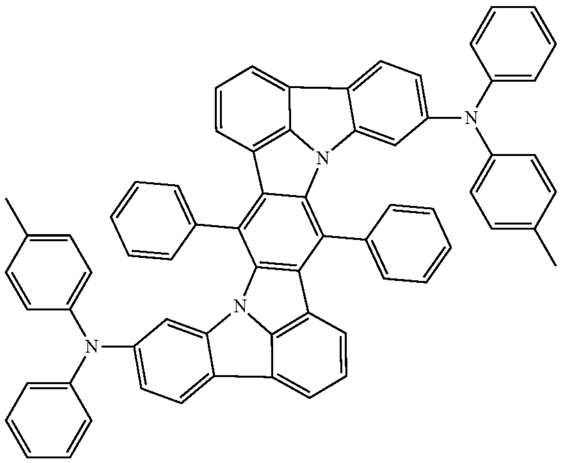
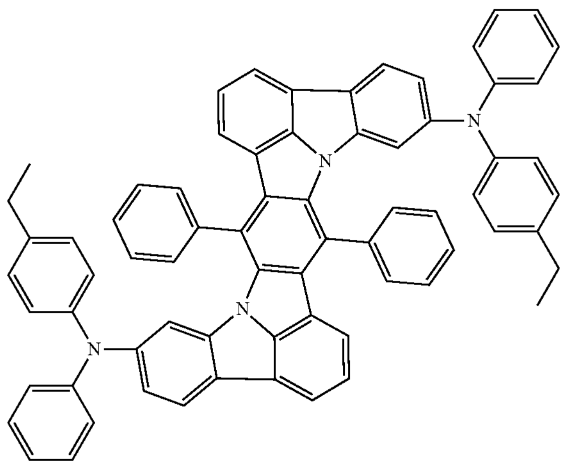

-continued
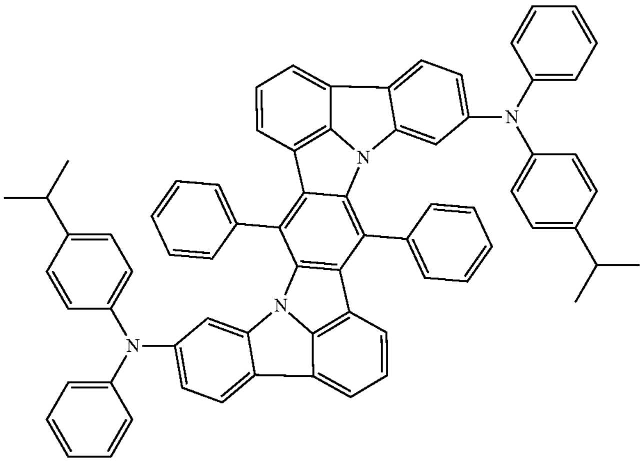
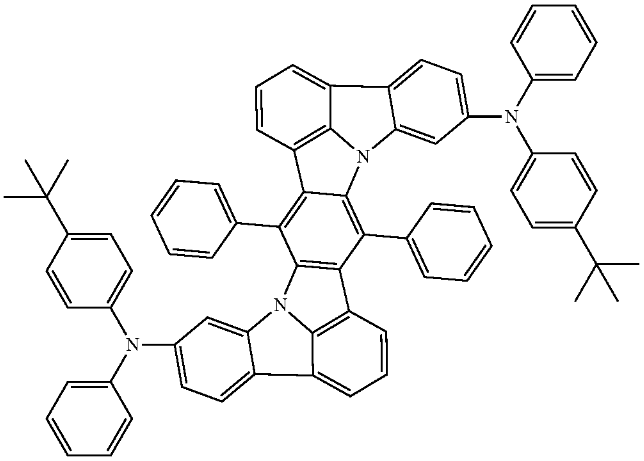
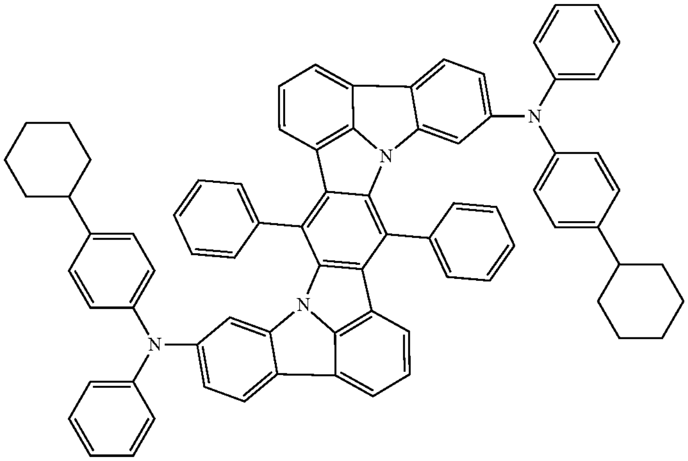

-continued
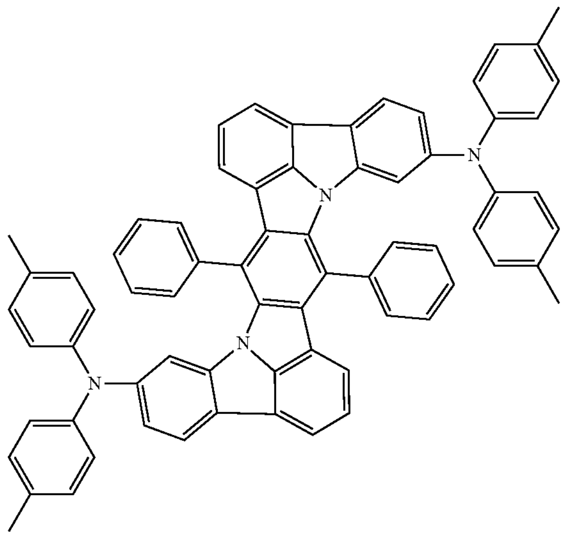
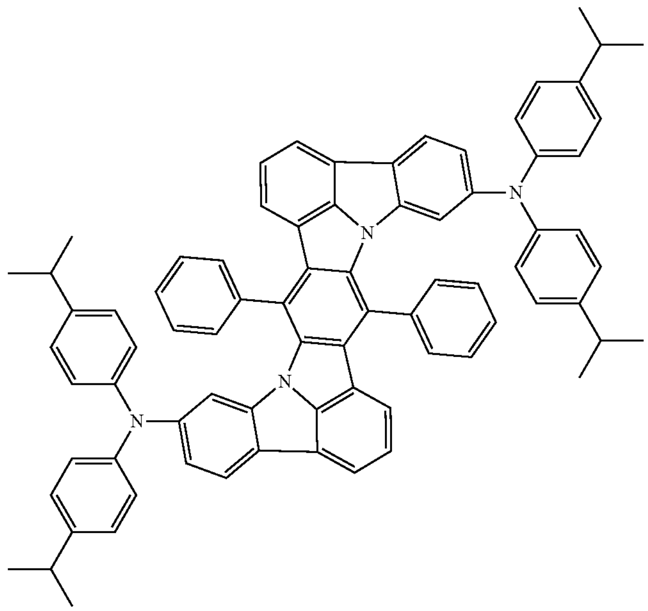

-continued
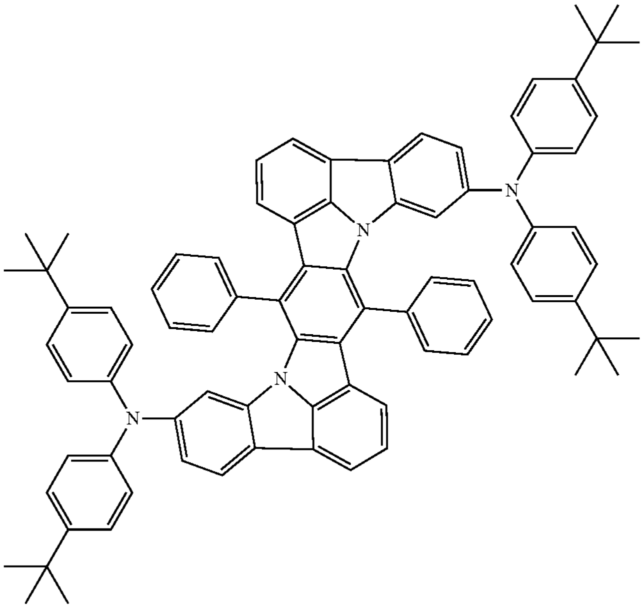
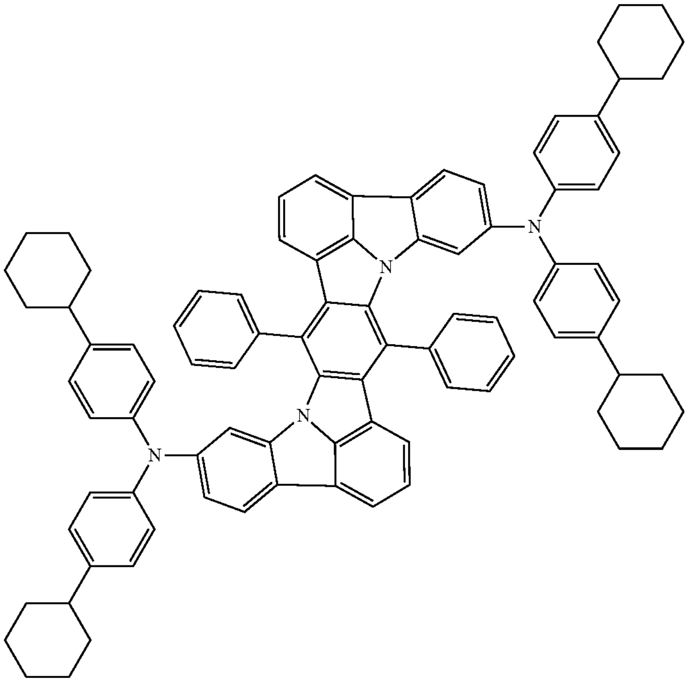

-continued
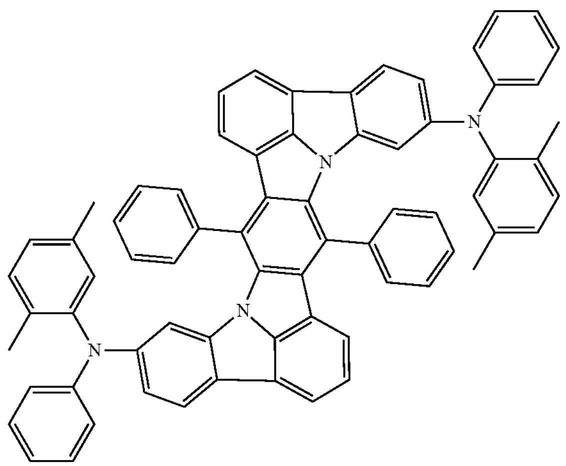
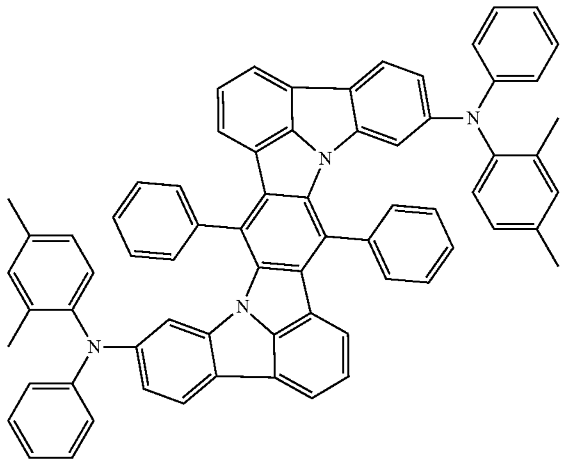
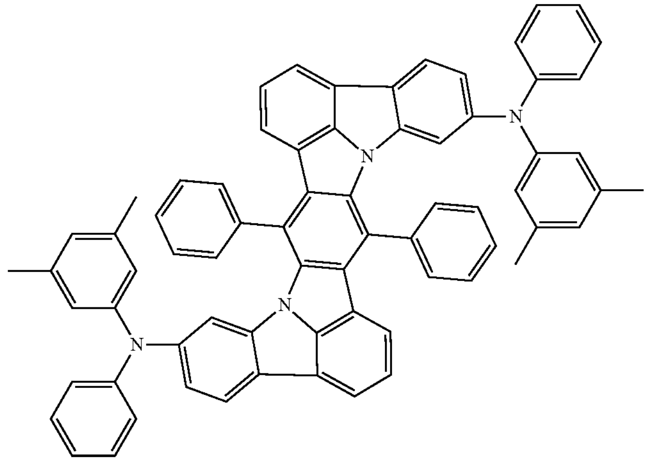
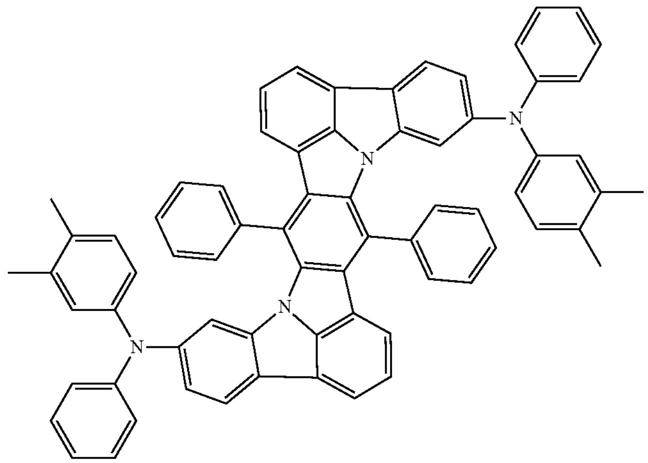

-continued
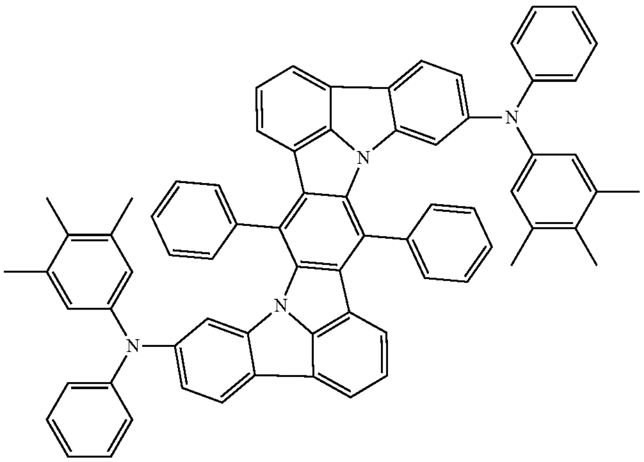
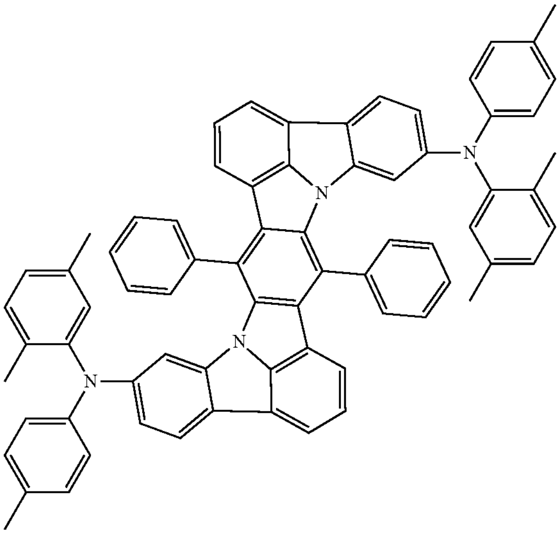
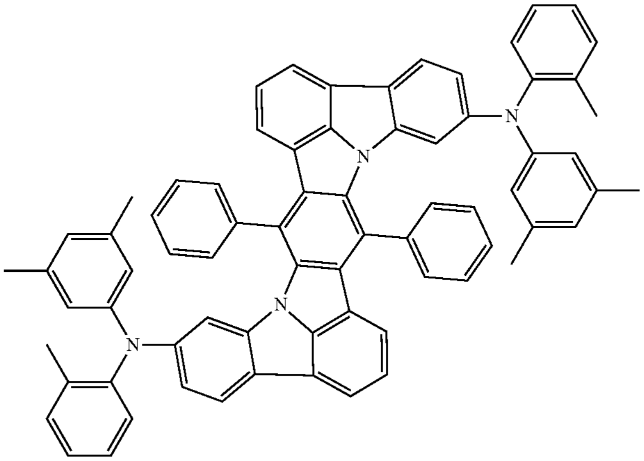
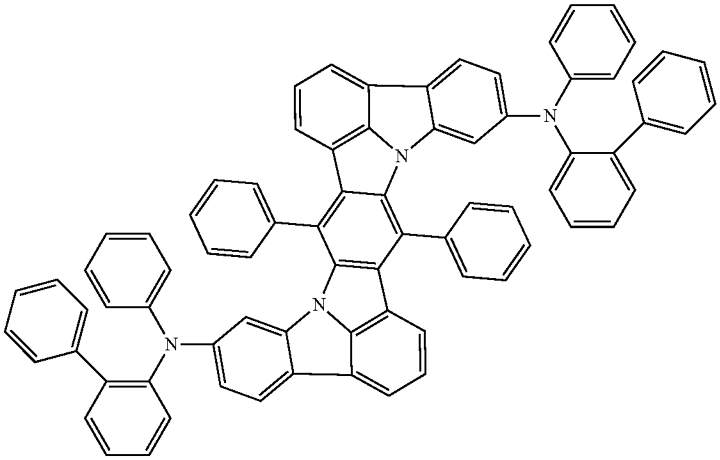

-continued
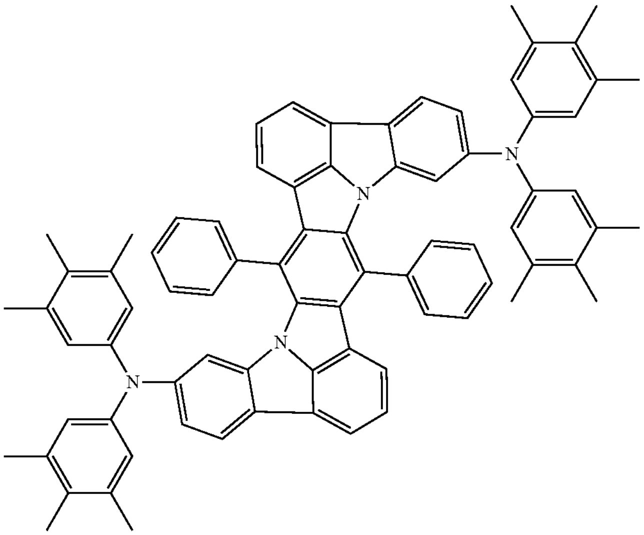
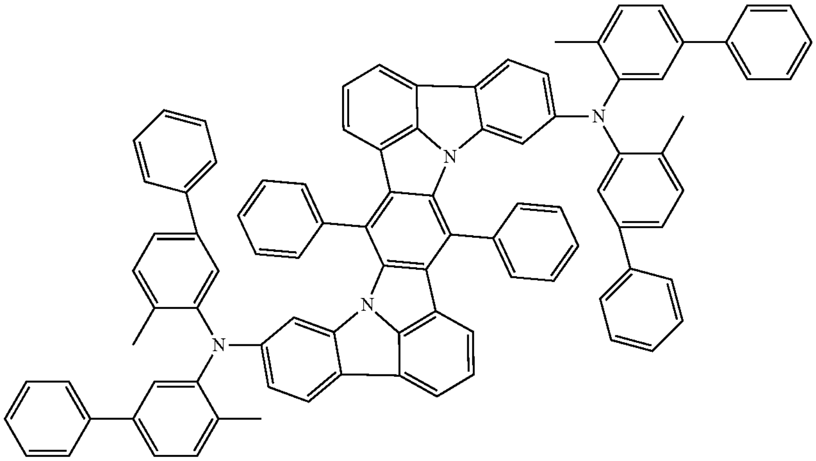
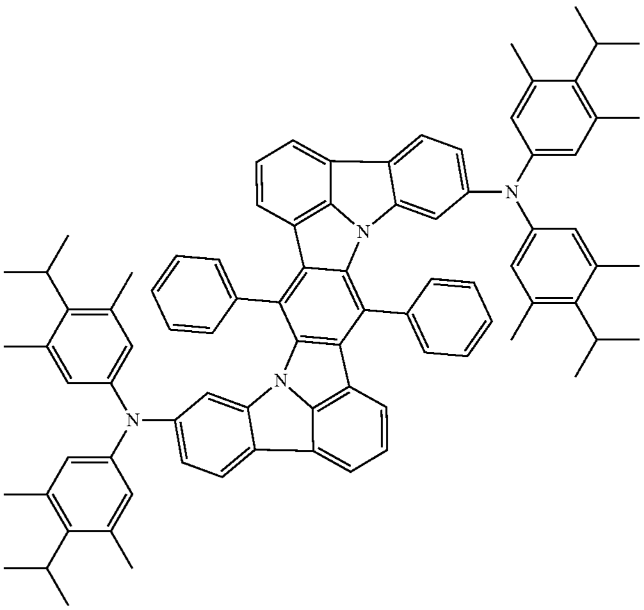

-continued
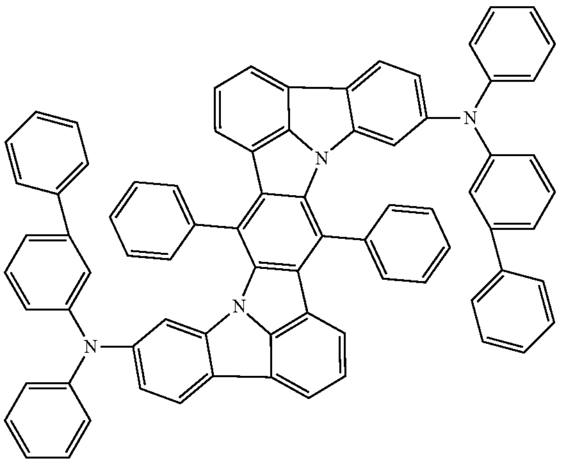
[Formula 180]
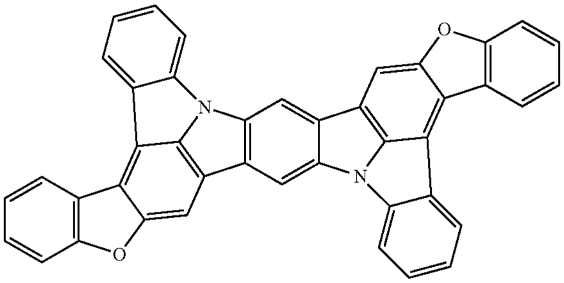
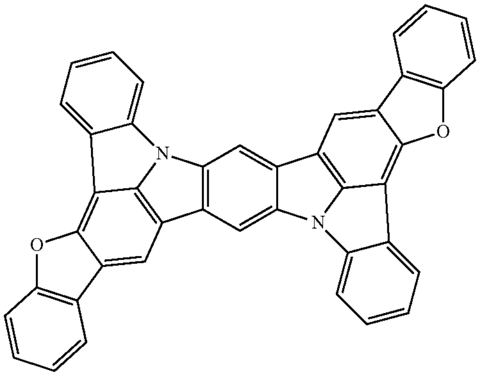
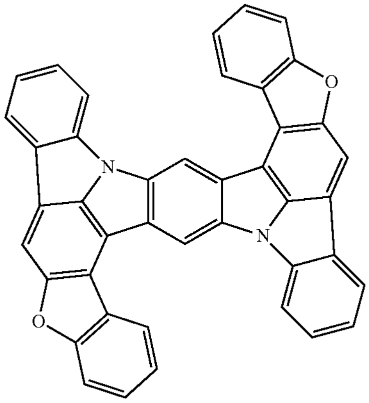
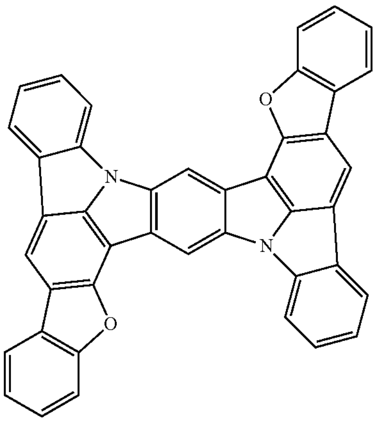
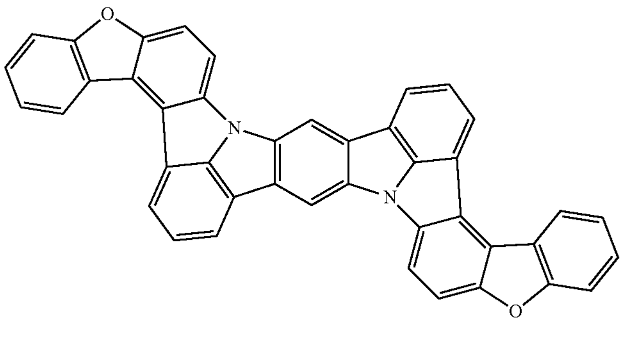

-continued
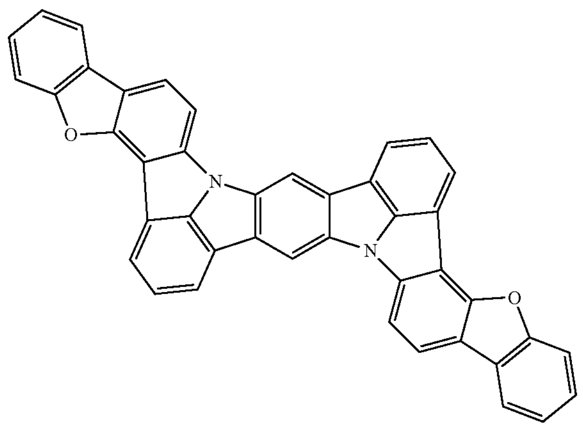
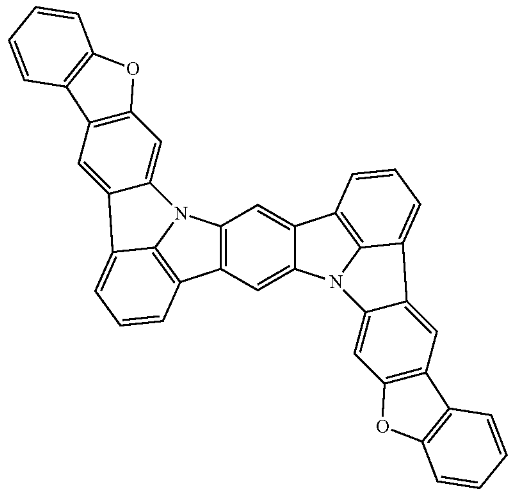
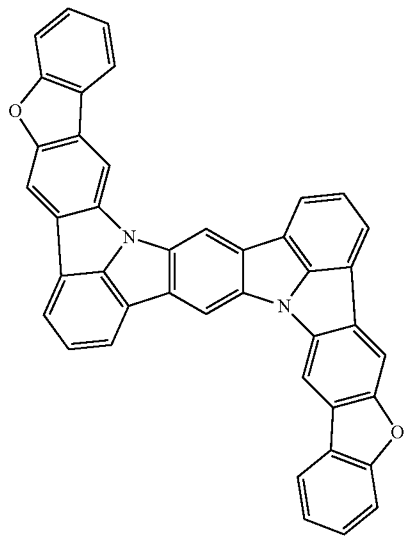
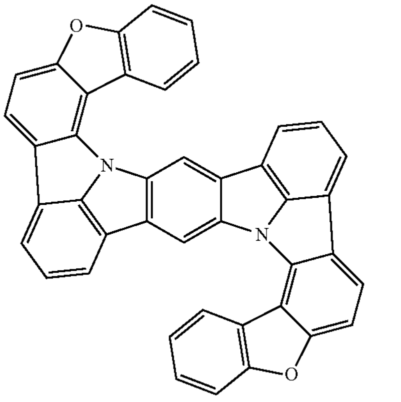
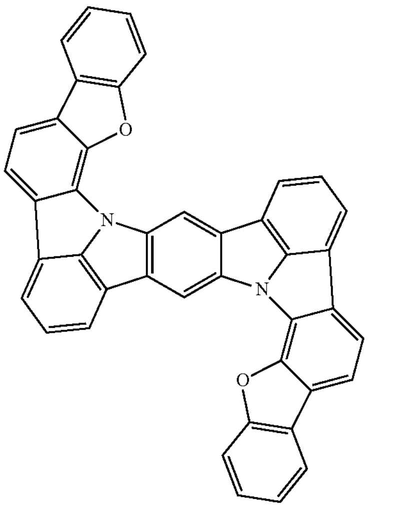
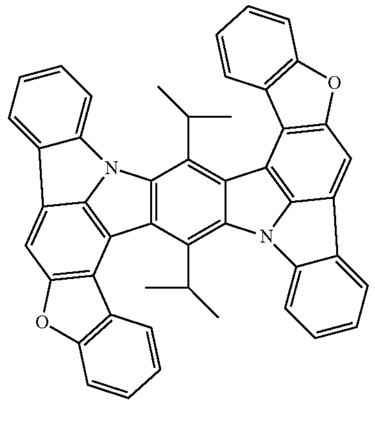
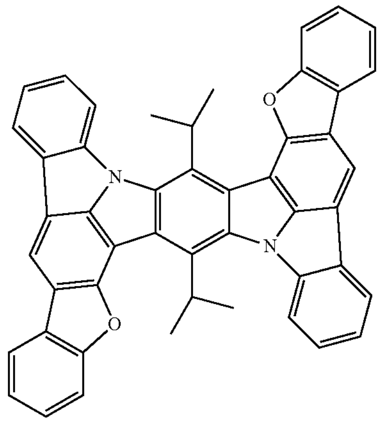

-continued
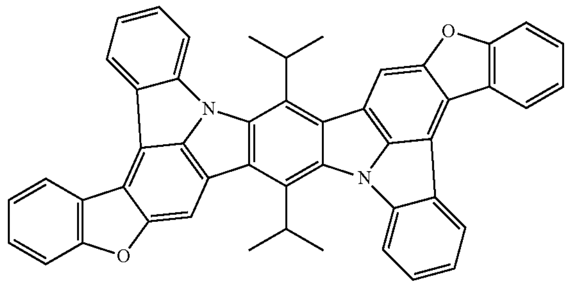
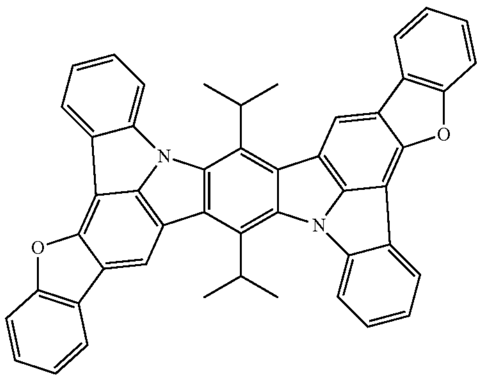
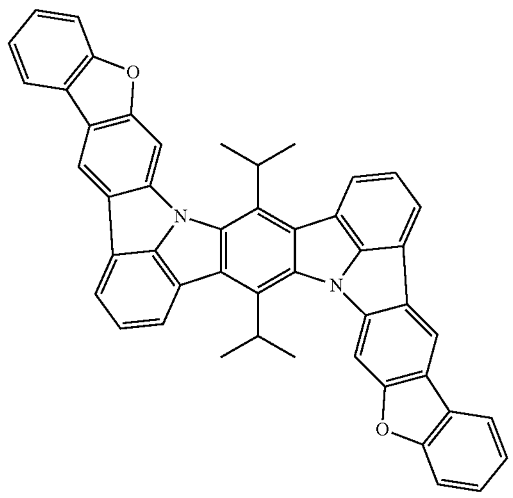
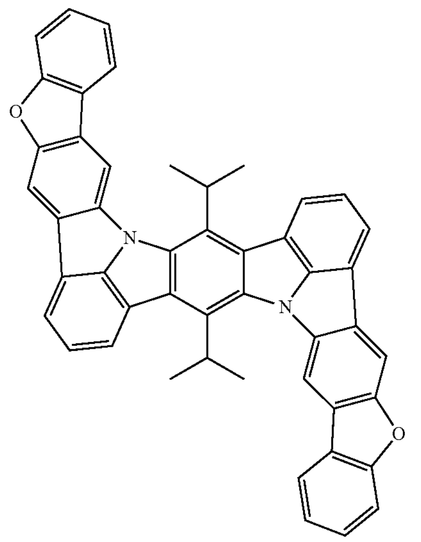
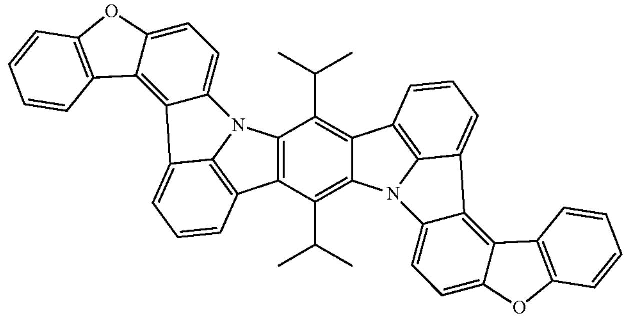

-continued
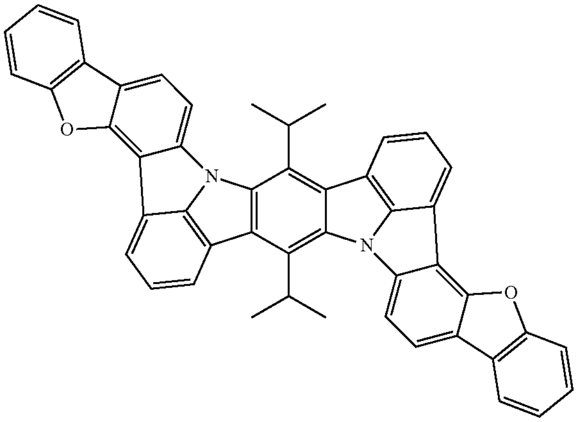
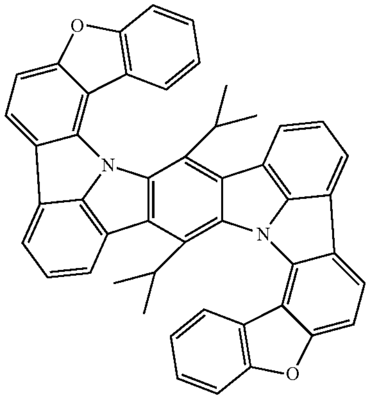
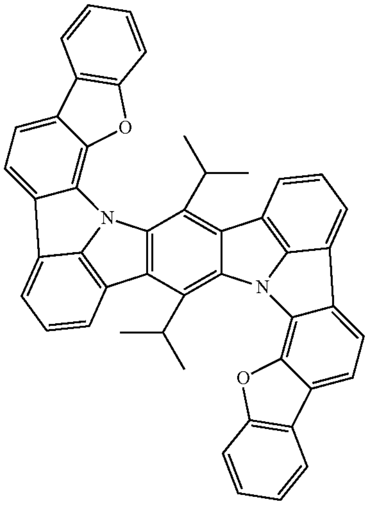
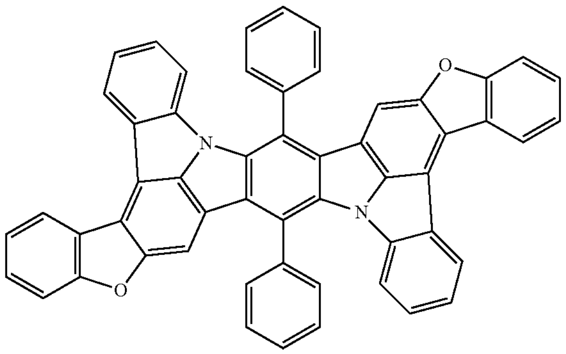
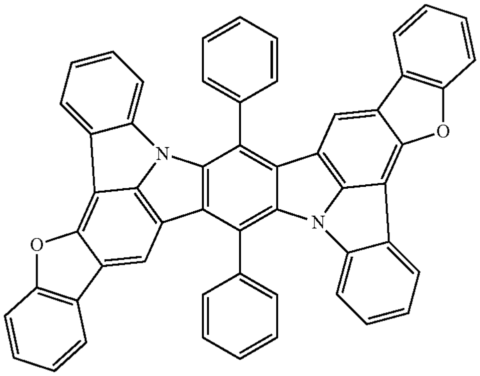
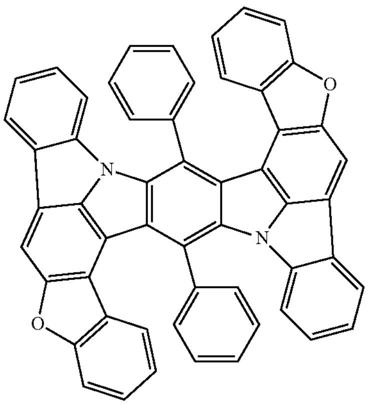

-continued
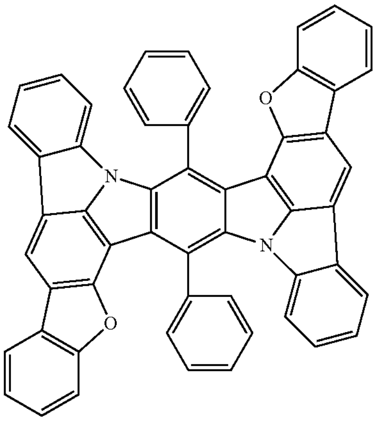
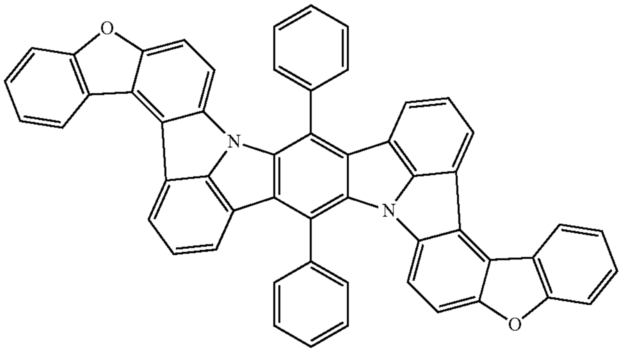
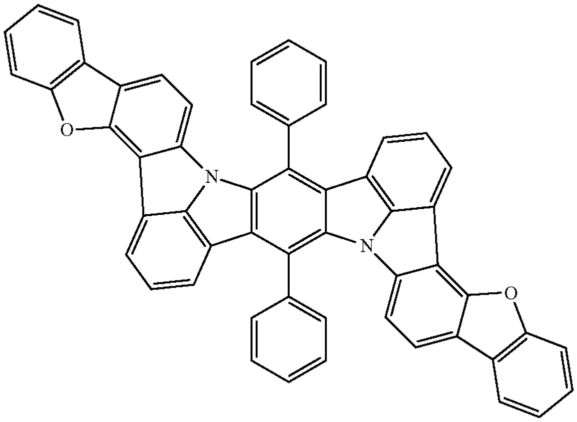
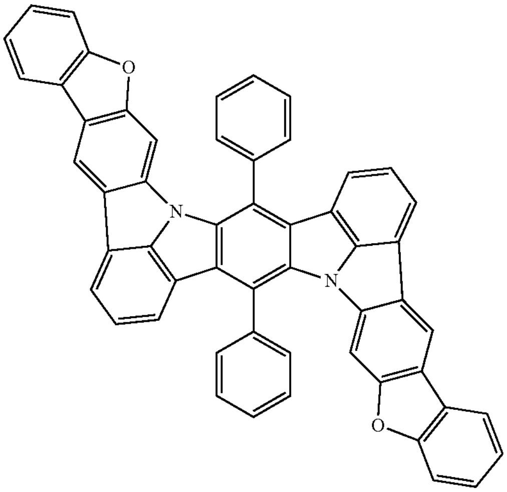
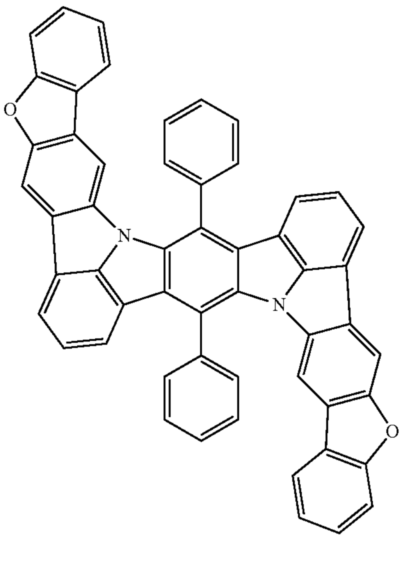

-continued
[Formula 181]
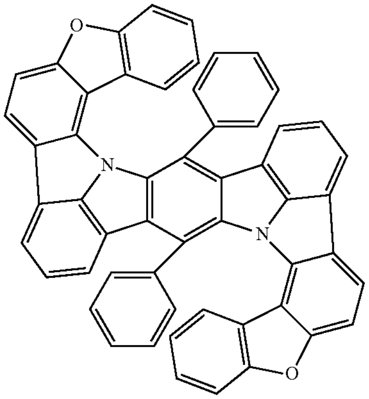
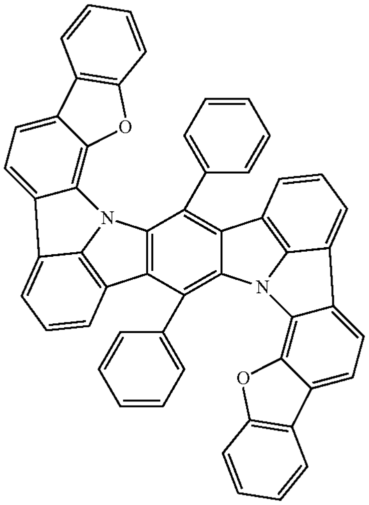
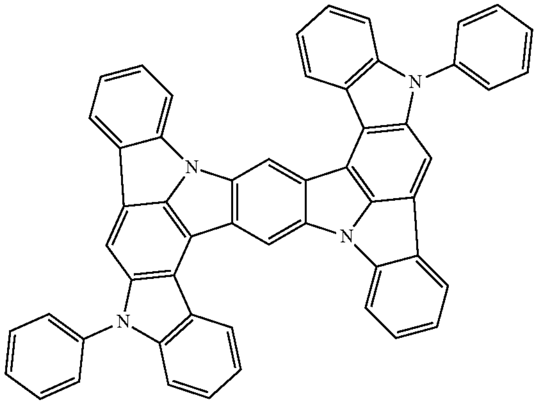
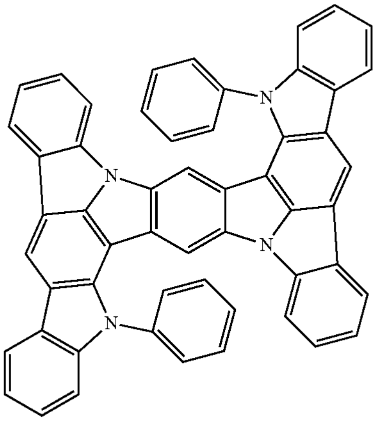
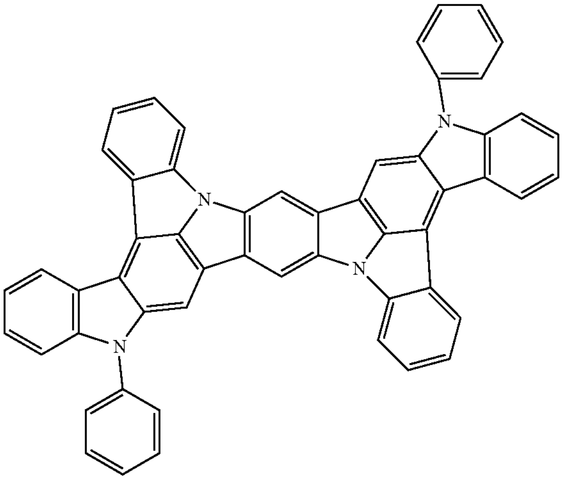

-continued
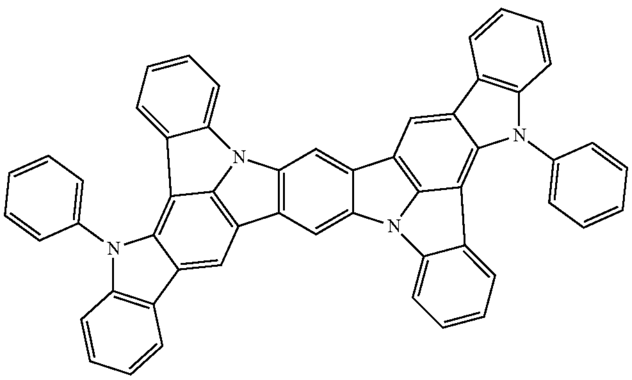
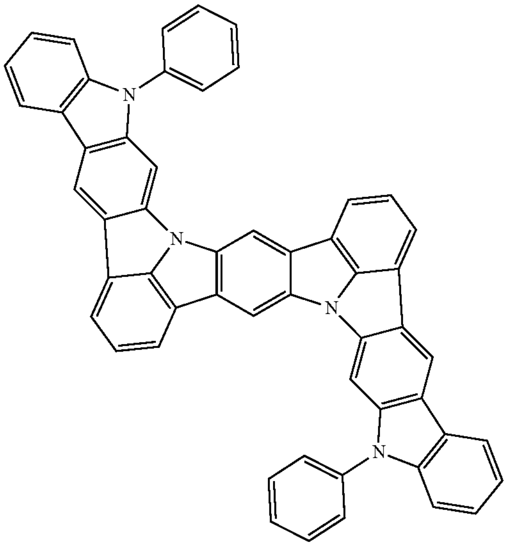
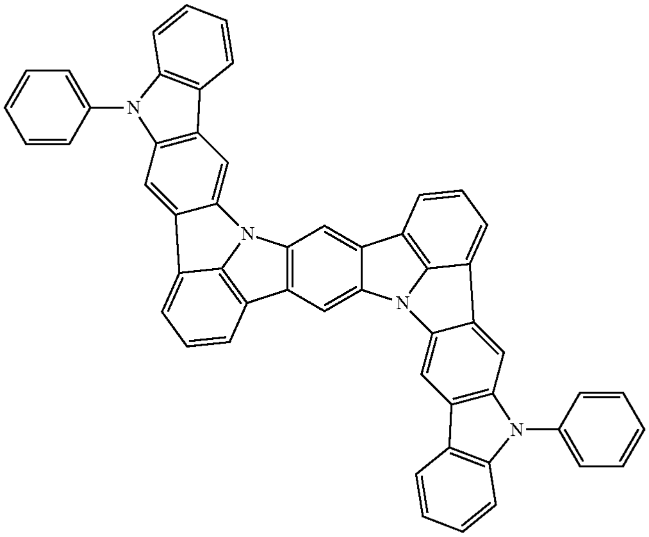
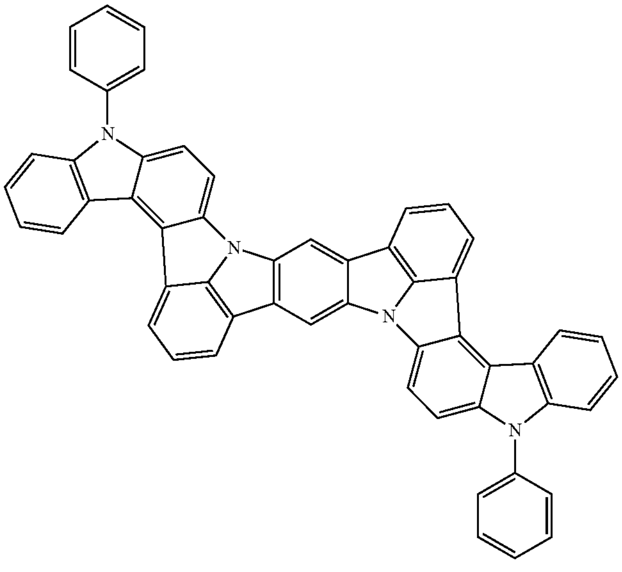

-continued
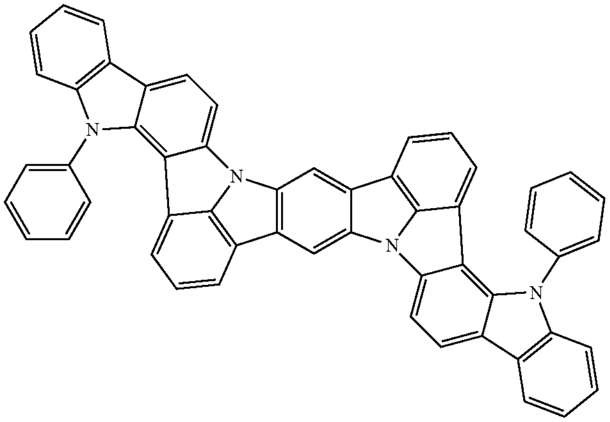
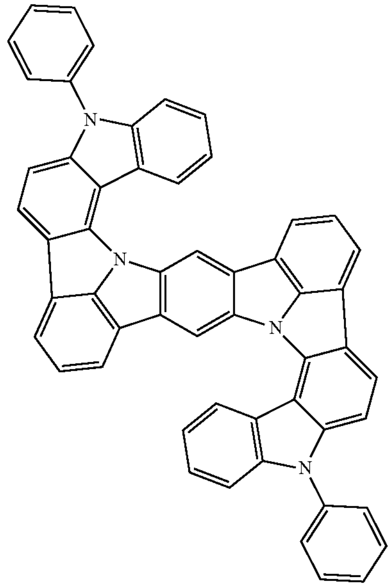
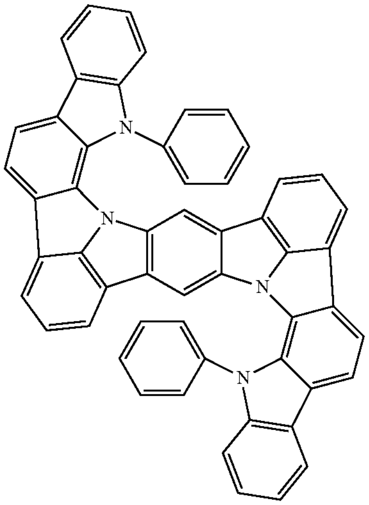
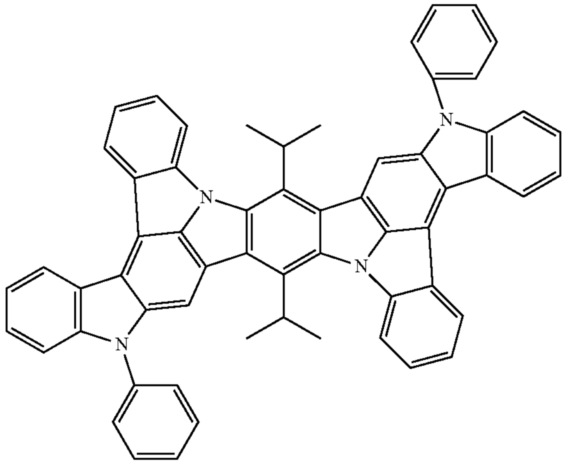
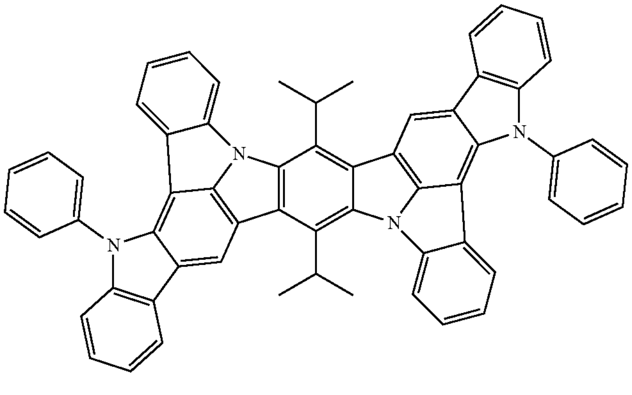
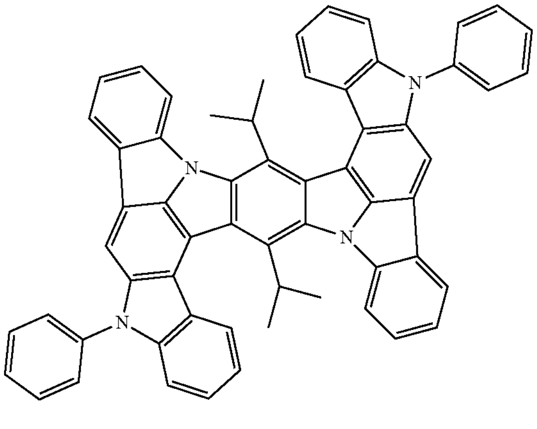

-continued
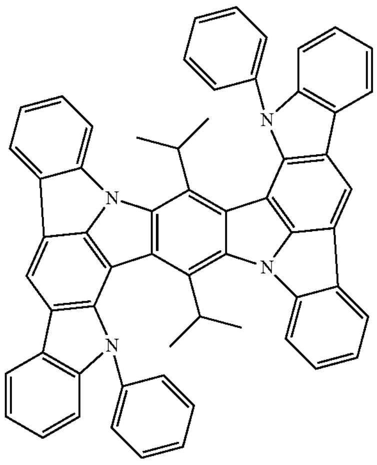
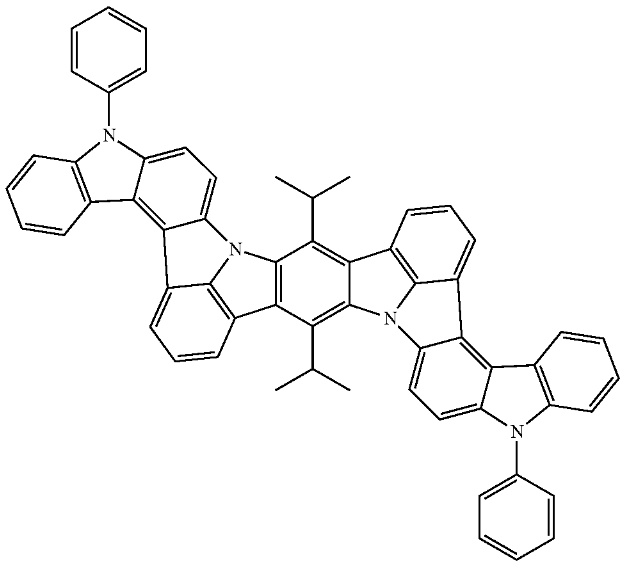
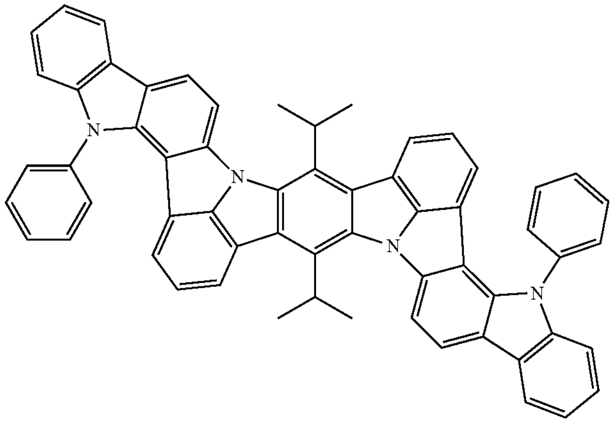
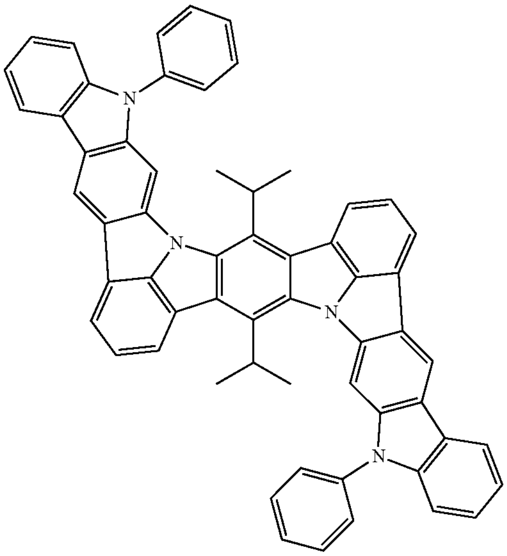
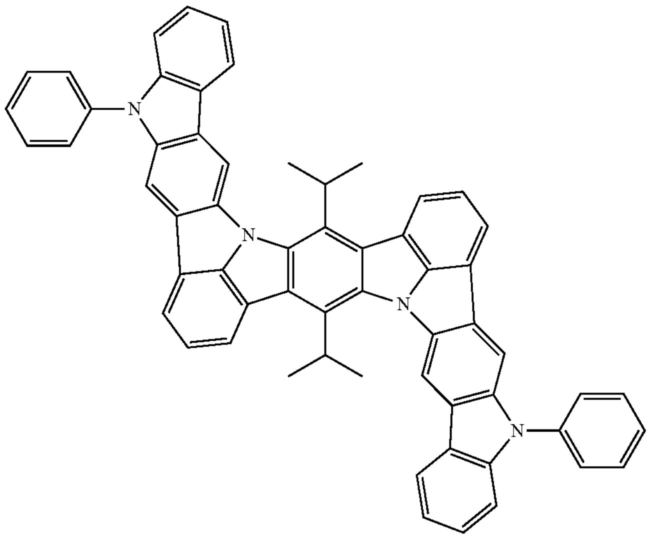
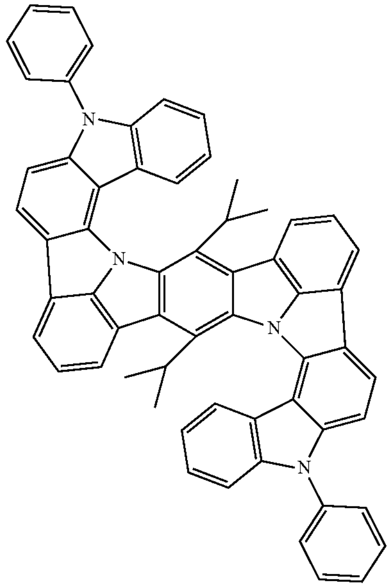

-continued
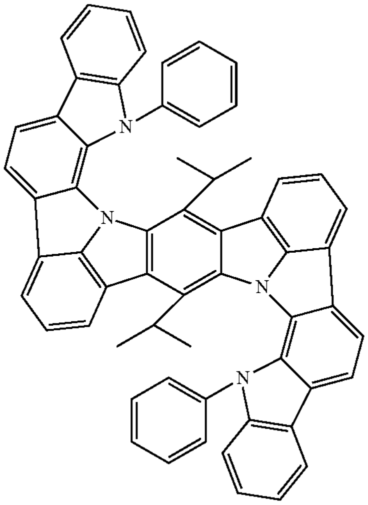
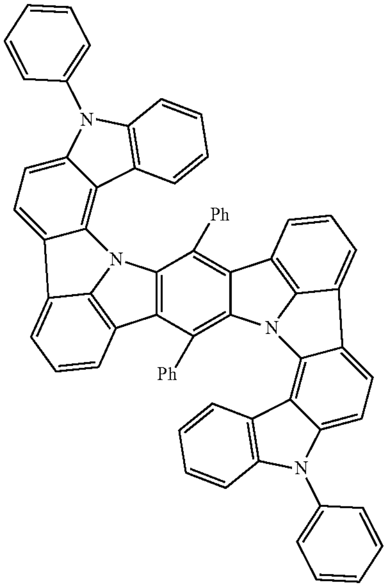
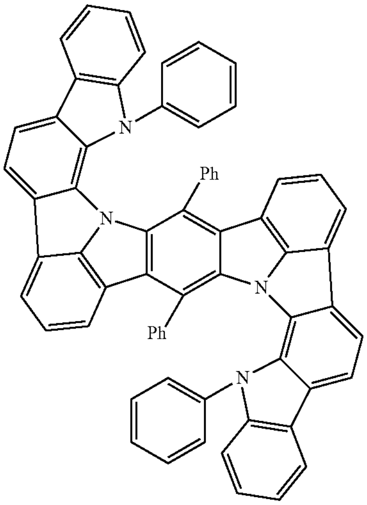
(In the formulae, Ph is a phenyl group.)
[Formula 182]
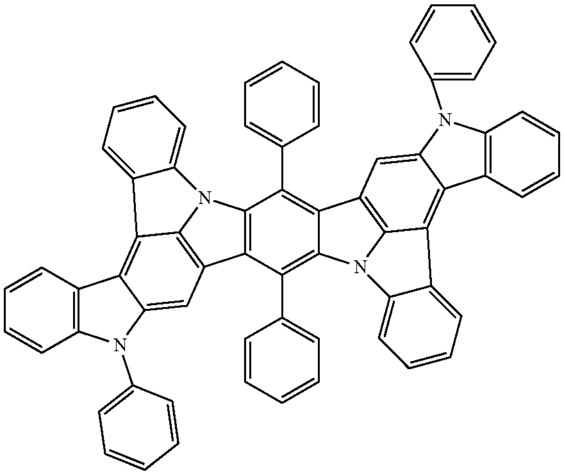
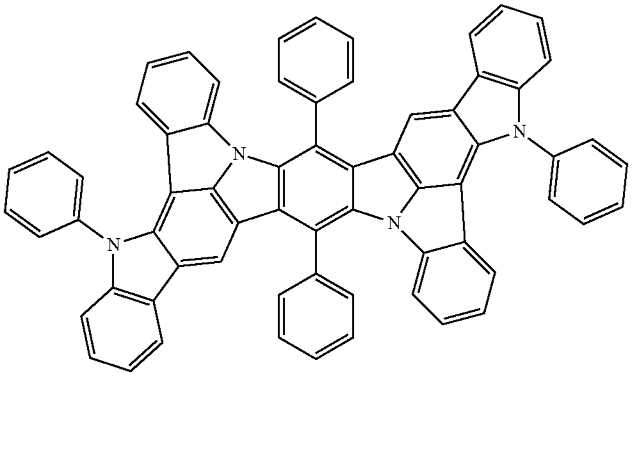
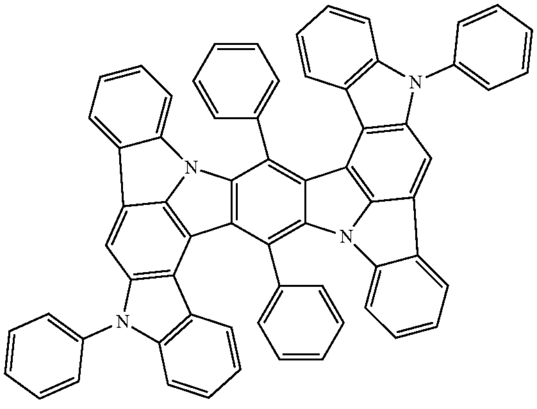

-continued
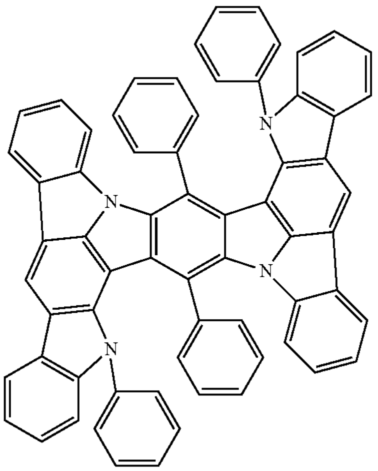
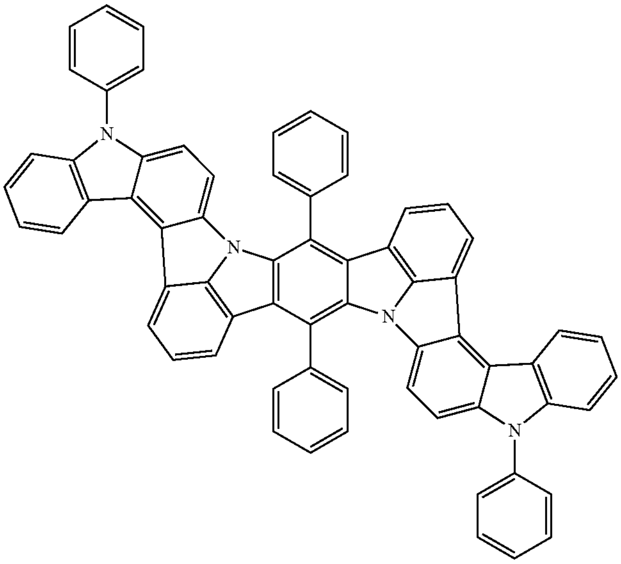
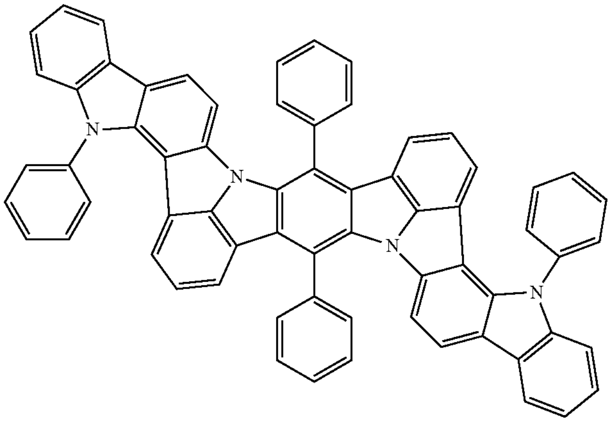
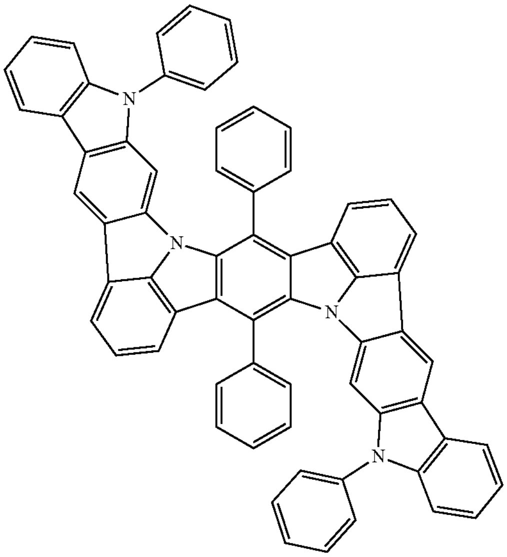
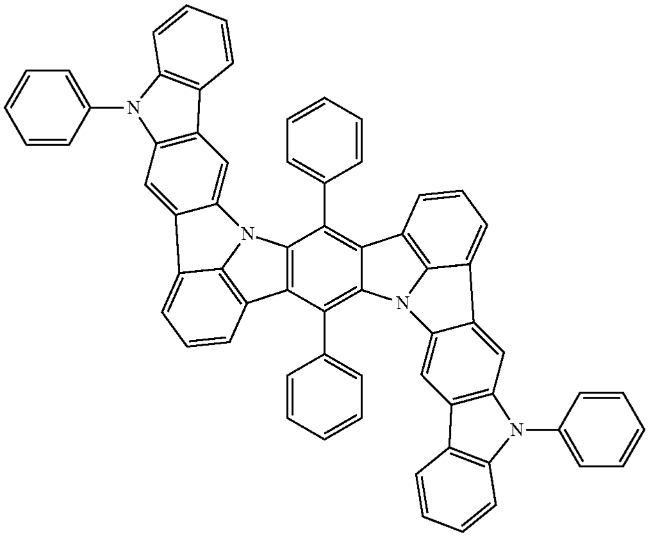

-continued
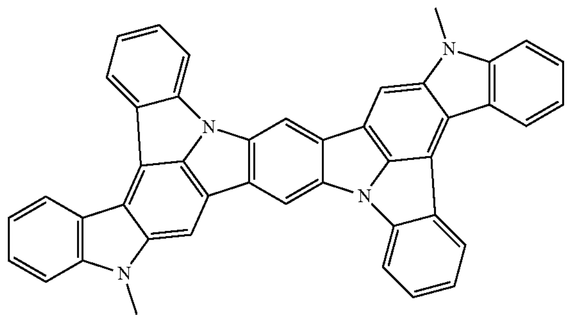
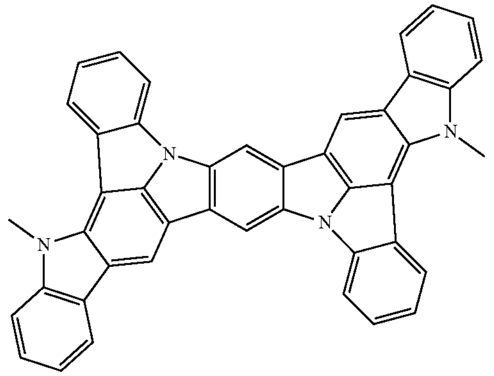
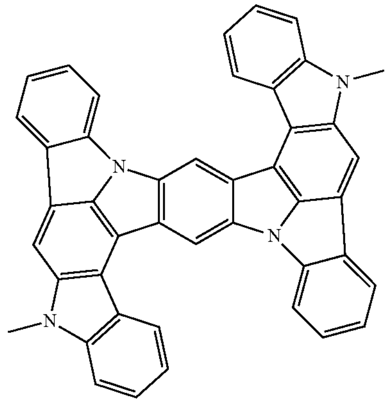
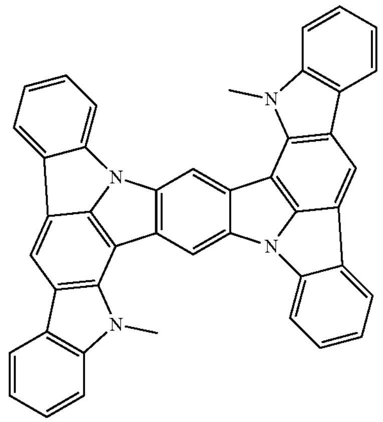
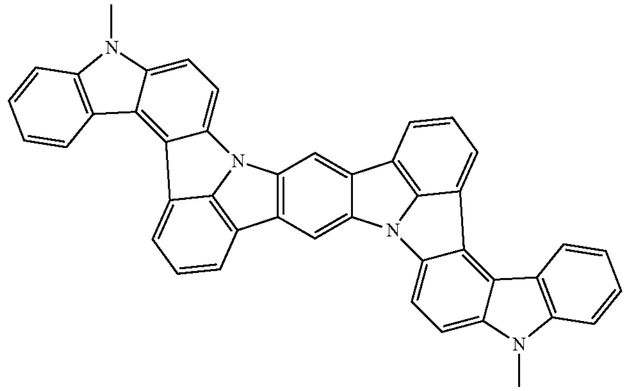
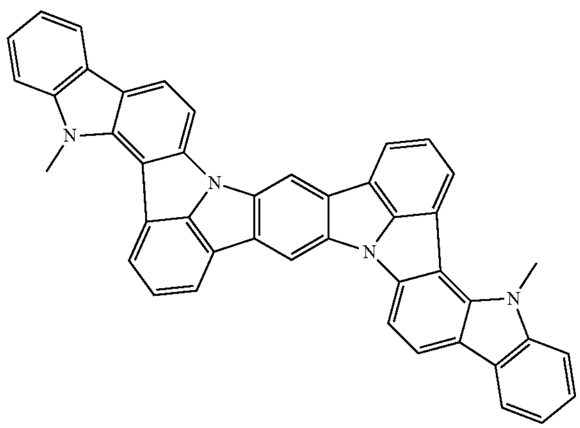

-continued
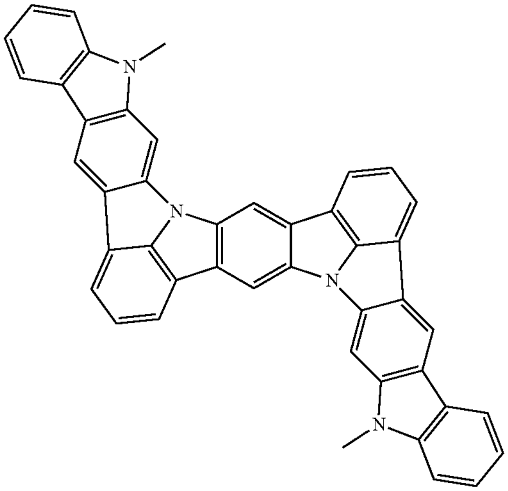
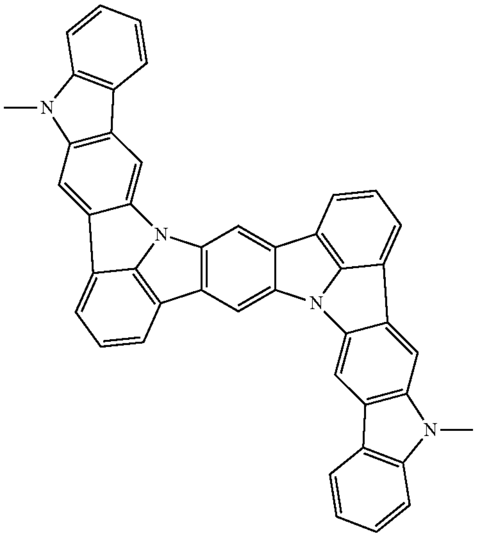
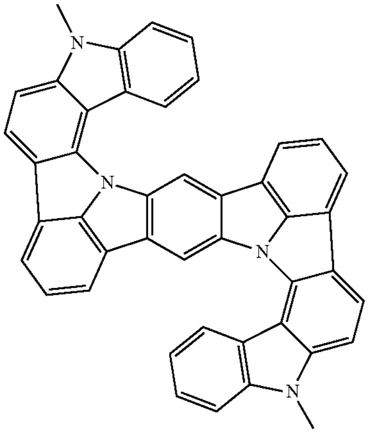
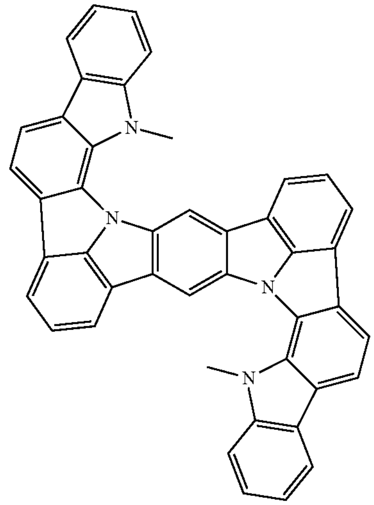
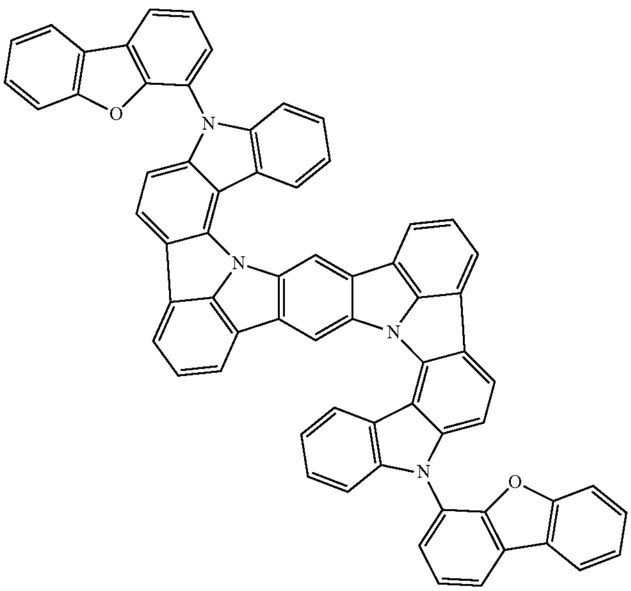
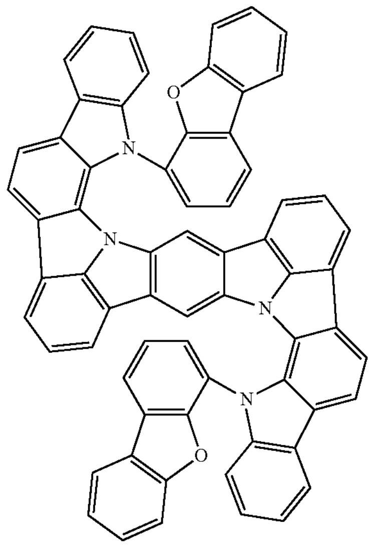

-continued
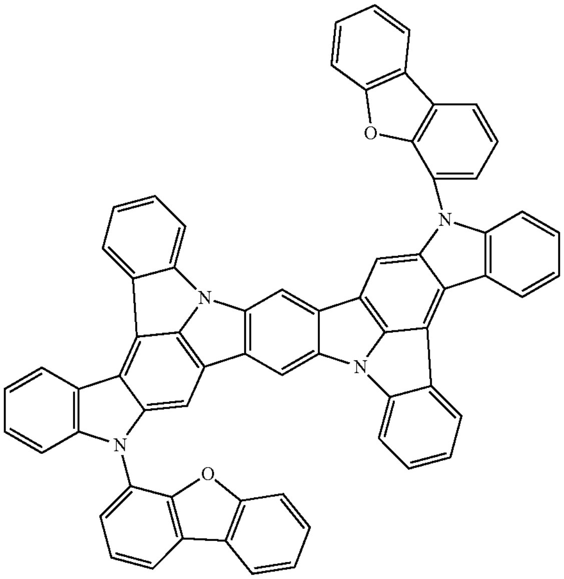
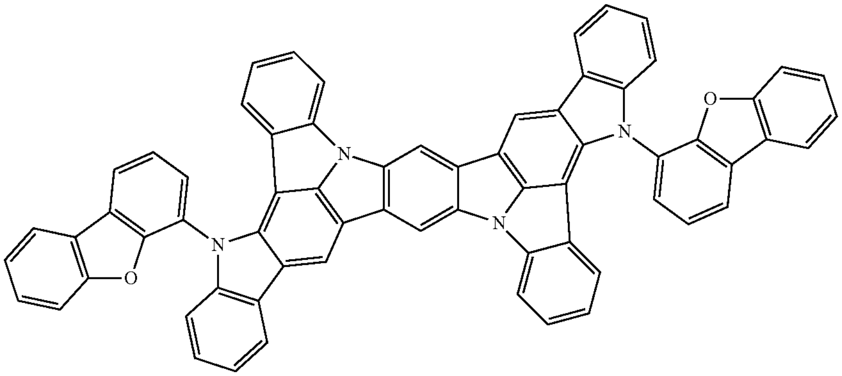
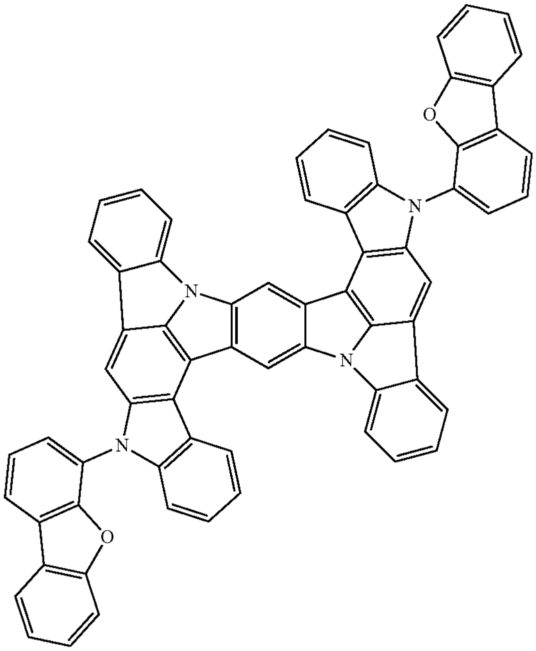
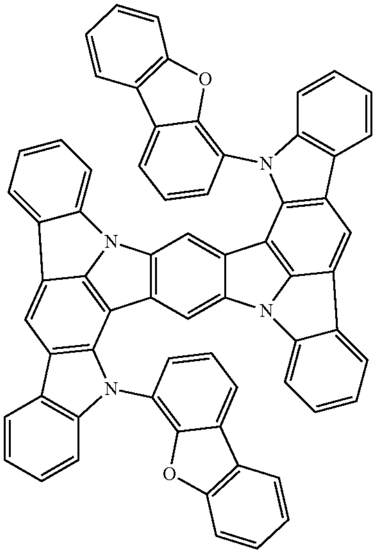

-continued
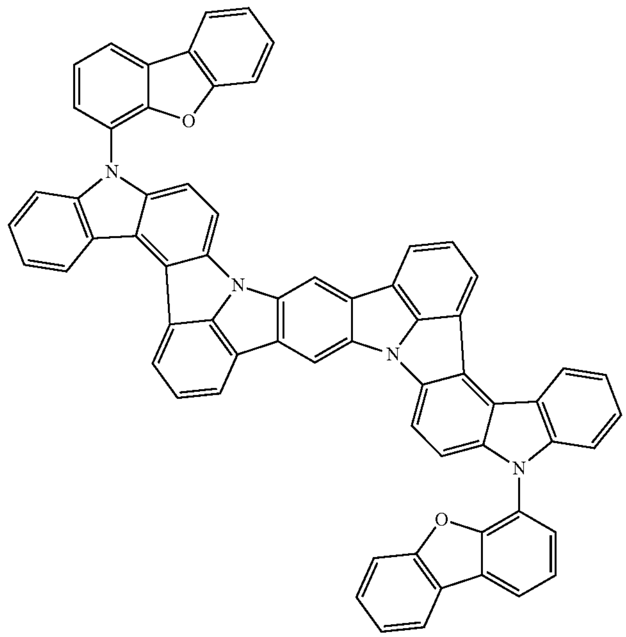
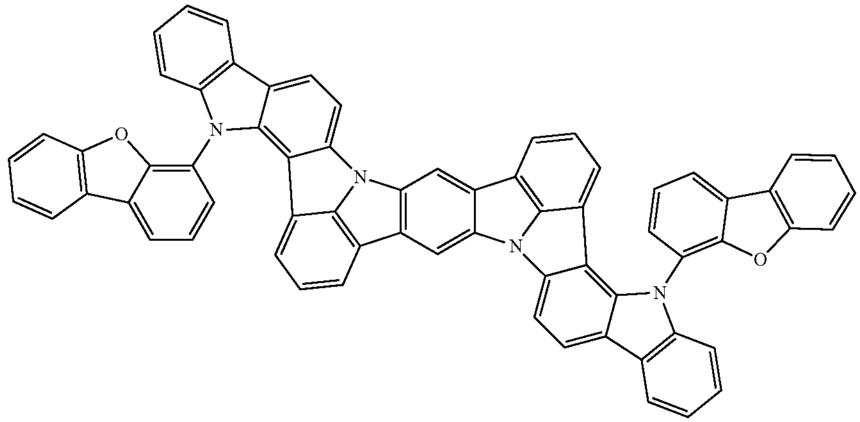
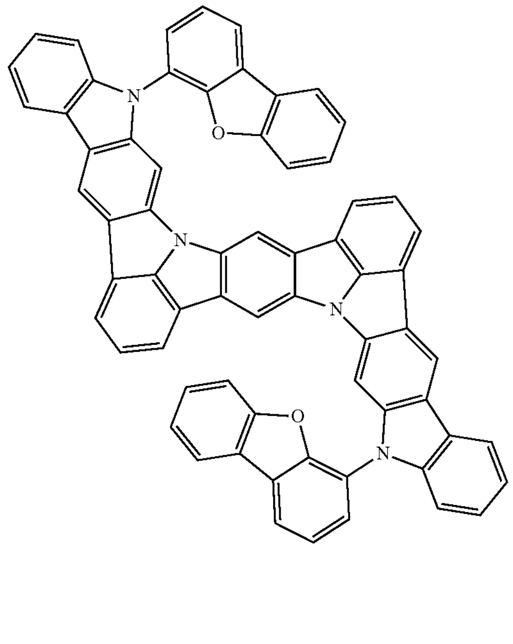

-continued
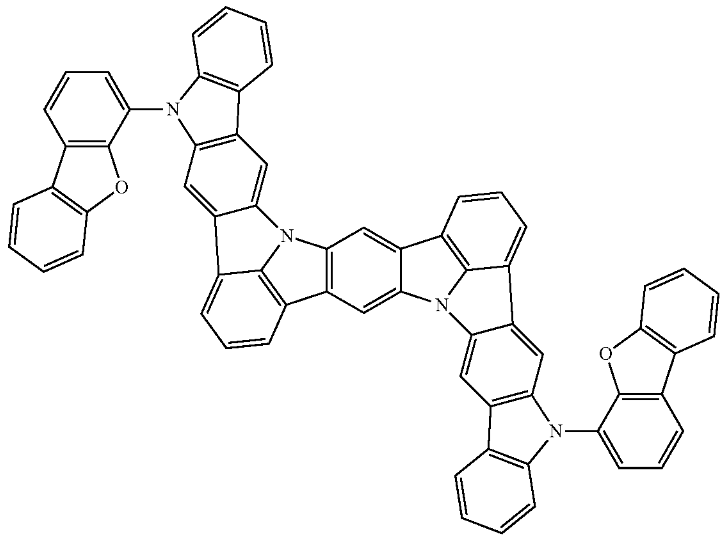
[Formula 183]
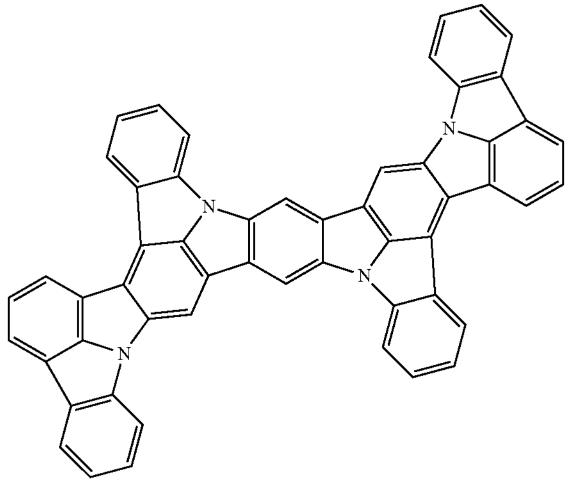
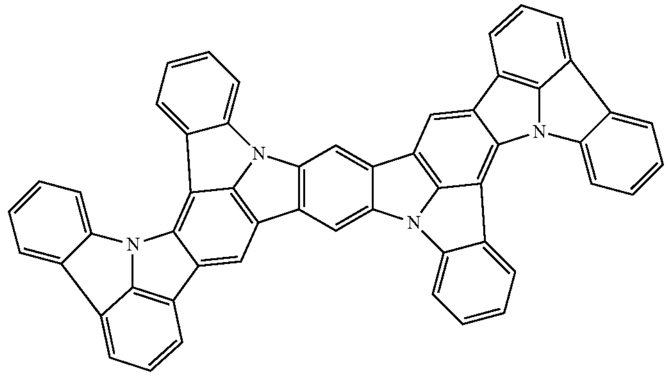
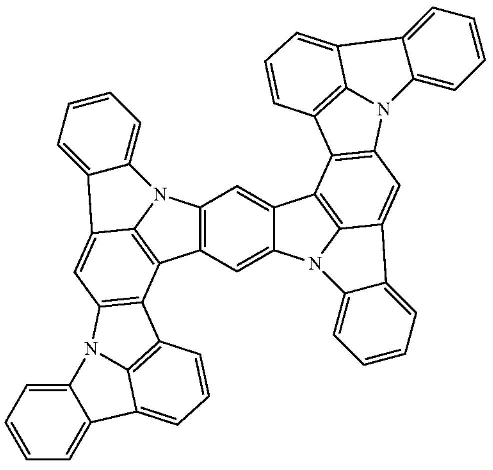

-continued
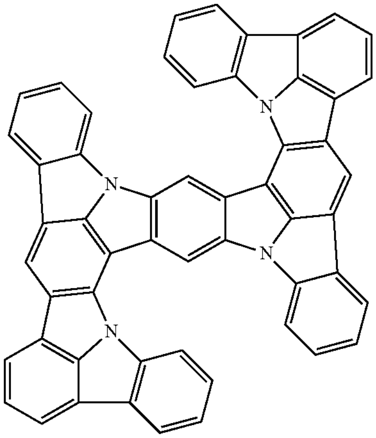
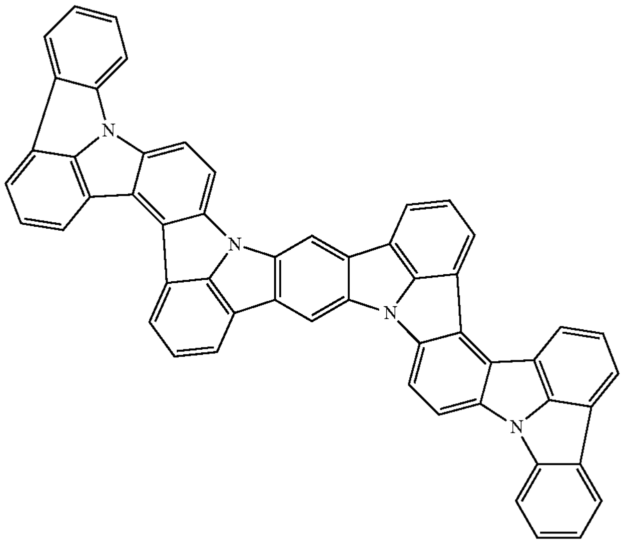
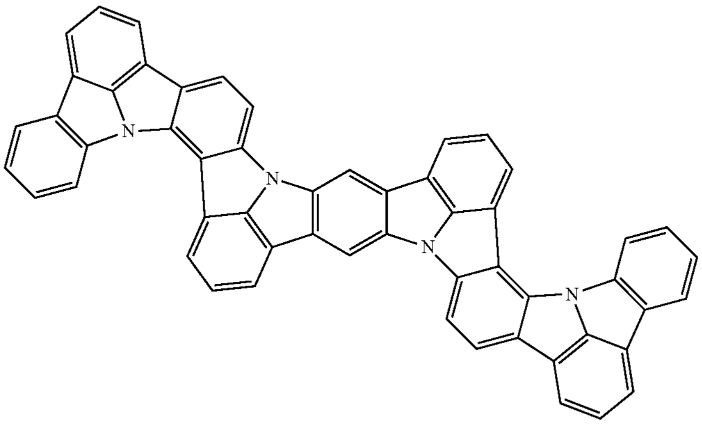
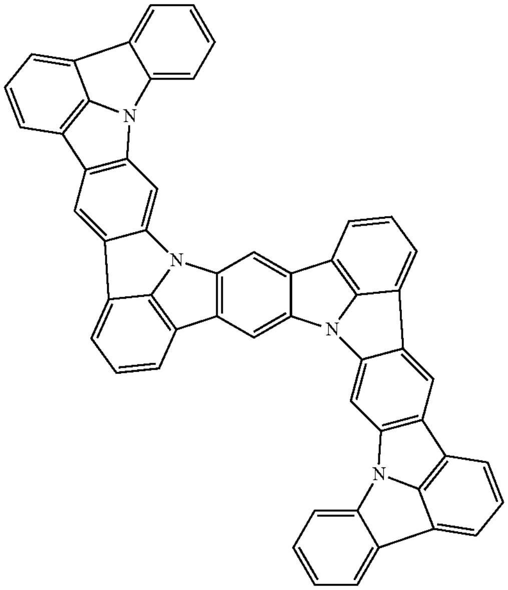
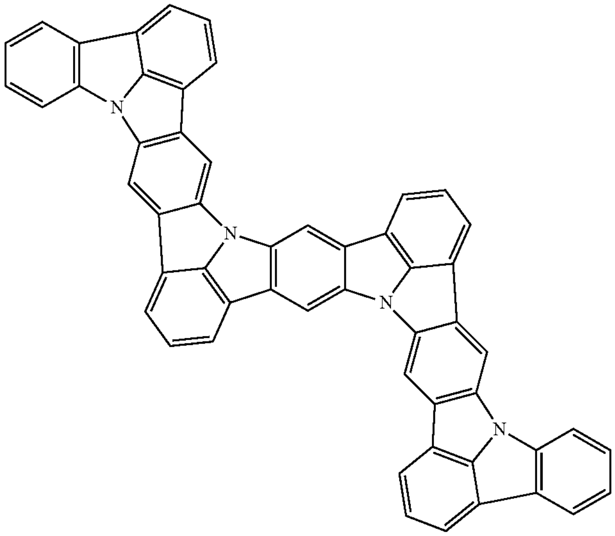

-continued
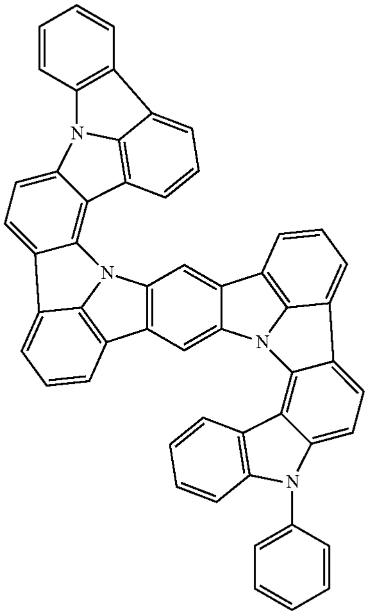
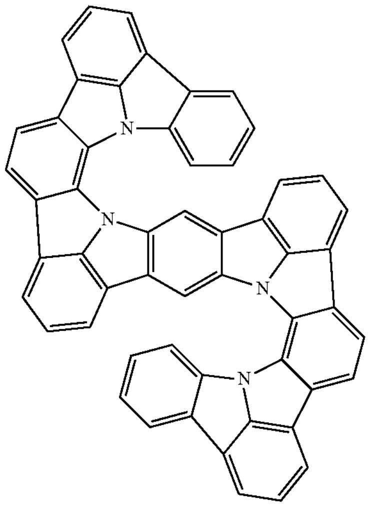
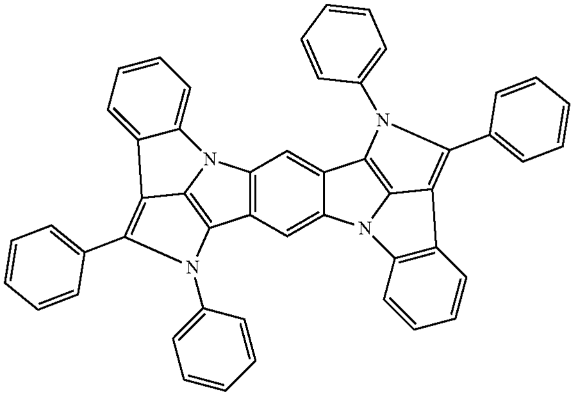
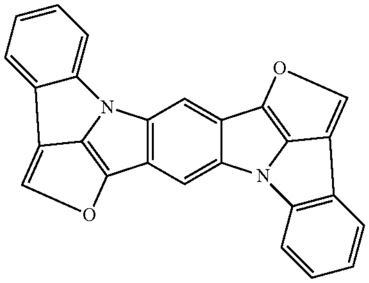
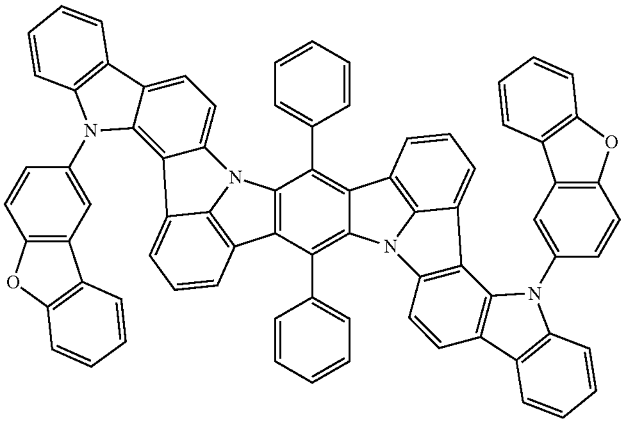

-continued
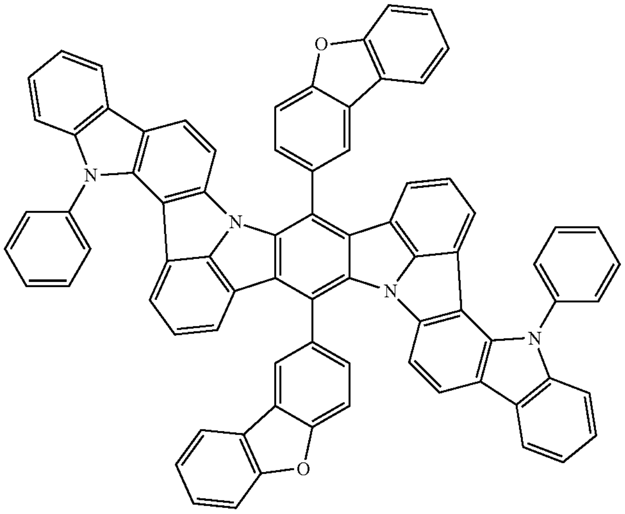
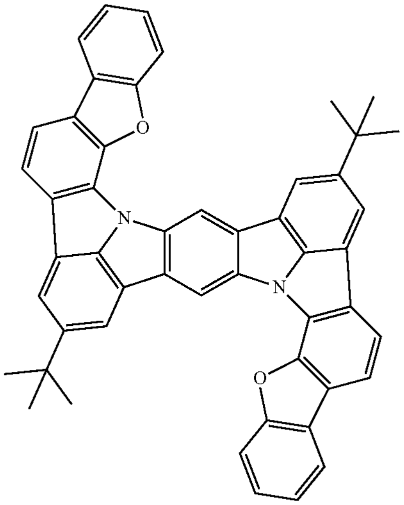
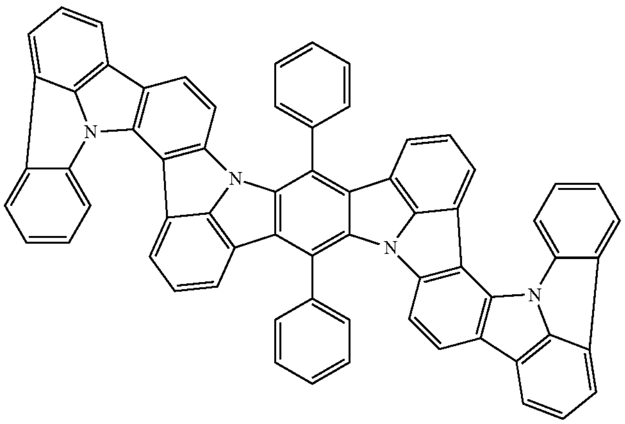
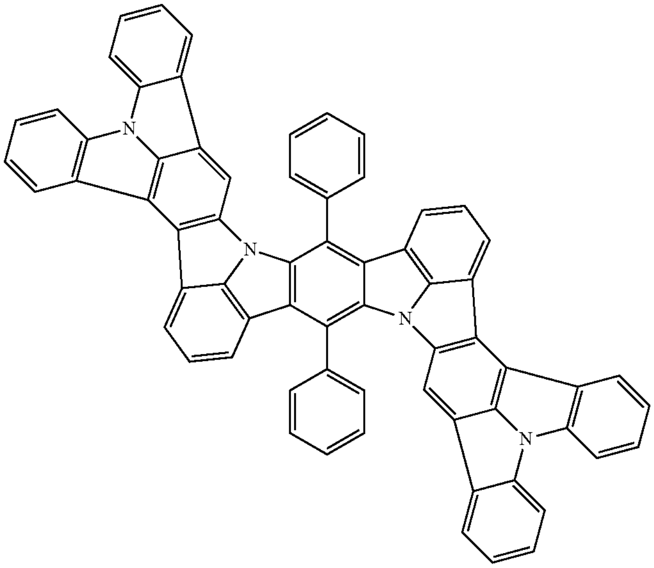

-continued
[Formula 184]
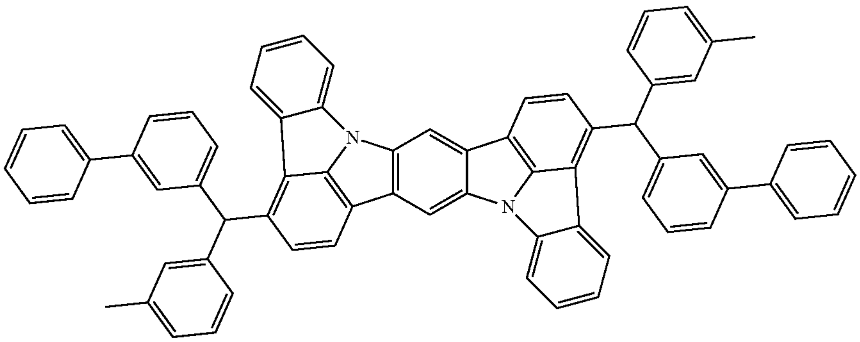
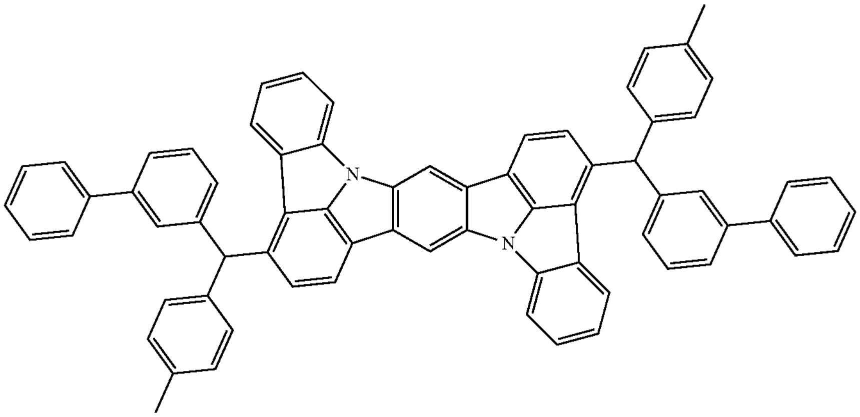
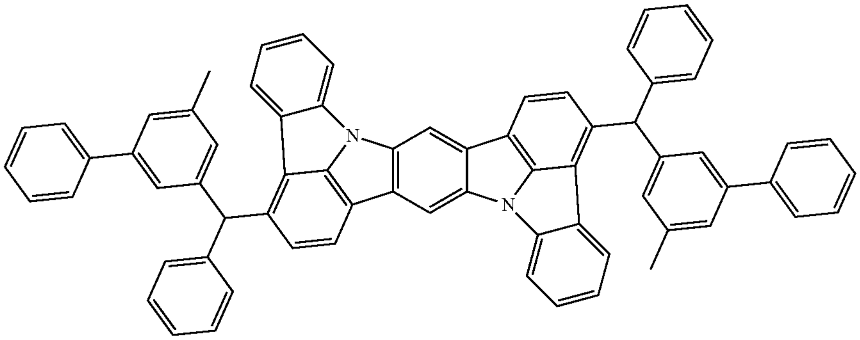
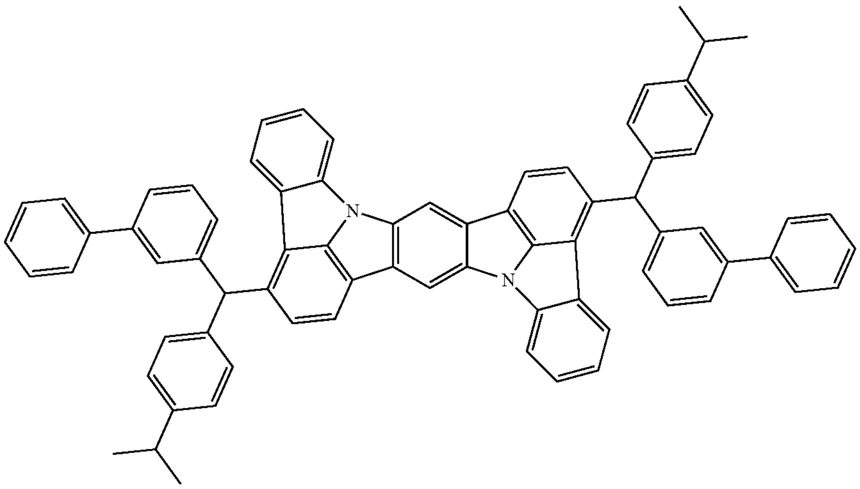

-continued

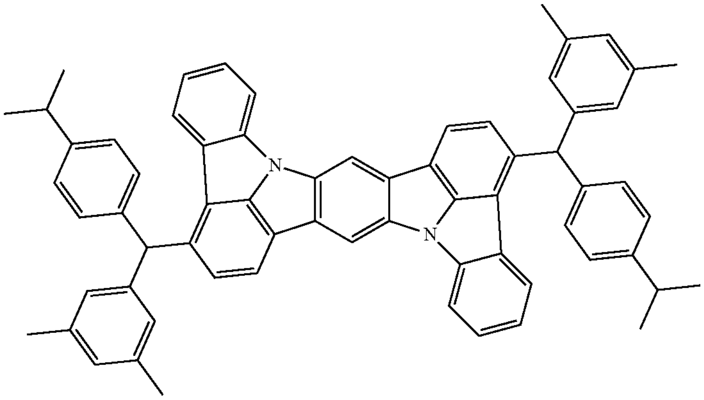

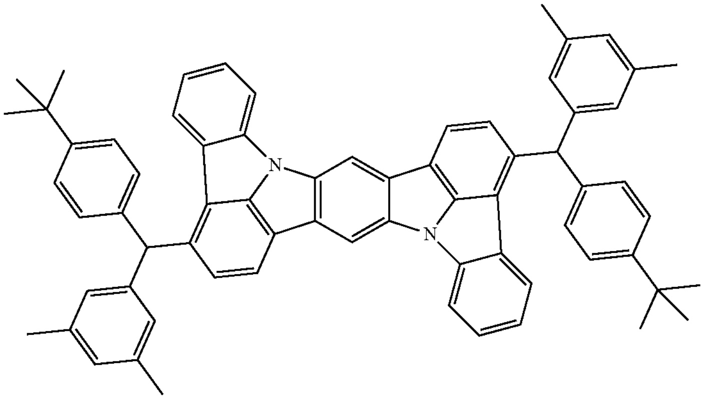

Compound Represented by Formula (6)

The compound represented by the formula (6) will be described.

[Formula 185]

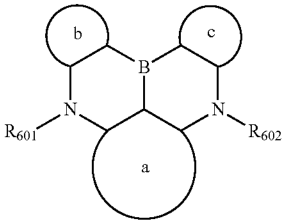

(6)

In the formula (6):

a ring, b ring and c ring are each independently a substituted or unsubstituted aromatic hydrocarbon ring having 6 to 50 ring carbon atoms, or a substituted or unsubstituted heterocycle having 5 to 50 ring atoms;

$R_{601}$ and $R_{602}$ are each independently bonded to the a ring, b ring or c ring to form a substituted or unsubstituted heterocycle, or not bonded thereto to form no substituted or unsubstituted heterocycle; and $R_{601}$ and $R_{602}$ not forming the substituted or unsubstituted heterocycle are each independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms.

The a ring, b ring and c ring are each a ring (a substituted or unsubstituted aromatic hydrocarbon ring having 6 to 50 ring carbon atoms, or a substituted or unsubstituted heterocycle having 5 to 50 ring atoms) fused with a fused bicyclic structure formed of a boron atom and two nitrogen atoms at the center of the formula (6).

The "aromatic hydrocarbon ring" for the a, b, and c rings has the same structure as a compound formed by introducing a hydrogen atom to the "aryl group" described above.

Ring atoms of the "aromatic hydrocarbon ring" for the a ring include three carbon atoms on the fused bicyclic structure at the center of the formula (6).

Ring atoms of the "aromatic hydrocarbon ring" for the b ring and the c ring include two carbon atoms on the fused bicyclic structure at the center of the formula (6).

Specific examples of the "substituted or unsubstituted aromatic hydrocarbon ring having 6 to 50 ring carbon atoms" include a compound formed by introducing a hydrogen atom to the "aryl group" described in the specific example group G1.

The "heterocycle" for the a, b, and c rings has the same structure as a compound formed by introducing a hydrogen atom to the "heterocyclic group" described above.

Ring atoms of the "heterocycle" for the a ring include three carbon atoms on the fused bicyclic structure at the center of the formula (6). Ring atoms of the "heterocycle" for the b ring and c ring include two carbon atoms on the fused bicyclic structure at the center of the formula (6). Specific examples of the "substituted or unsubstituted heterocycle having 5 to 50 ring atoms" include a compound formed by introducing a hydrogen atom to the "heterocyclic group" described in the specific example group G2.

$R_{601}$ and $R_{602}$ are optionally each independently bonded with the a ring, b ring, or c ring to form a substituted or unsubstituted heterocycle. The "heterocycle" in this arrangement includes a nitrogen atom on the fused bicyclic structure at the center of the formula (6). The heterocycle in the above arrangement optionally includes a hetero atom other than the nitrogen atom. $R_{601}$ and $R_{602}$ bonded with the a ring, b ring, or c ring specifically means that atoms forming $R_{601}$ and $R_{602}$ are bonded with atoms forming the a ring, b ring, or c ring. For instance, $R_{601}$ may be bonded with the a ring to form a bicyclic (or tri-or-more cyclic) fused nitrogen-containing heterocycle, in which the ring including $R_{601}$ and the a ring are fused. Specific examples of the nitrogen-containing heterocycle include a compound corresponding to the nitrogen-containing bi(or-more)cyclic fused heterocyclic group in the specific example group G2.

The same applies to $R_{601}$ bonded with the b ring, $R_{602}$ bonded with the a ring, and $R_{602}$ bonded with the c ring.

In an exemplary embodiment, the a ring, b ring and c ring in the formula (6) are each independently a substituted or unsubstituted aromatic hydrocarbon ring having 6 to 50 ring carbon atoms.

In an exemplary embodiment, the a ring, b ring and c ring in the formula (6) are each independently a substituted or unsubstituted benzene ring or a substituted or unsubstituted naphthalene ring.

In an exemplary embodiment, $R_{601}$ and $R_{602}$ in the formula (6) are each independently a substituted or unsubstituted aryl group having 6 to 50 ring carbon atoms, or a substituted or unsubstituted heterocyclic group having 5 to 50 ring atoms, preferably a substituted or unsubstituted aryl group having 6 to 50 ring carbon atoms.

In an exemplary embodiment, the compound represented by the formula (6) is a compound represented by a formula (62) below.

[Formula 186]

(62)

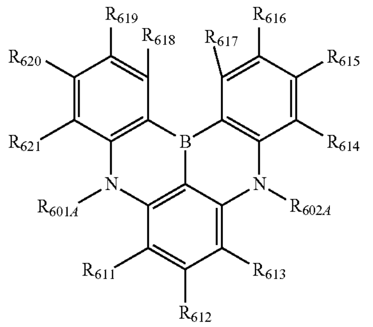

In the formula (62):

$R_{601A}$ is bonded with at least one of $R_{611}$ or $R_{621}$ to form a substituted or unsubstituted heterocycle, or not bonded therewith to form no substituted or unsubstituted heterocycle;

$R_{602A}$ is bonded with at least one of $R_{613}$ or $R_{614}$ to form a substituted or unsubstituted heterocycle, or not bonded therewith to form no substituted or unsubstituted heterocycle;

$R_{601A}$ and $R_{602A}$ not forming the substituted or unsubstituted heterocycle are each independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

at least one combination of adjacent two or more of $R_{611}$ to $R_{621}$ are mutually bonded to form a substituted or unsubstituted monocyclic ring, mutually bonded to form a substituted or unsubstituted fused ring, or not mutually bonded; and $R_{611}$ to $R_{621}$ not forming the substituted or unsubstituted heterocycle, not forming the monocyclic ring, and not forming the fused ring are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $—Si(R_{901})(R_{902})(R_{903})$, a group represented by $—O—(R_{904})$, a group represented by $—S—(R_{905})$, a group represented by $—N(R_{906})(R_{907})$, a halogen atom, a cyano group, a nitro group, a substituted or unsubstituted aryl group having 6 to 50 ring carbon atoms, or a substituted or unsubstituted heterocyclic group having 5 to 50 ring atoms.

$R_{601A}$ and $R_{602A}$ in the formula (62) are groups corresponding to $R_{601}$ and $R_{602}$ in the formula (6), respectively.

For instance, $R_{601A}$ and $R_{611}$ are optionally bonded with each other to form a bicyclic (or tri-or-more cyclic) fused nitrogen-containing heterocycle, in which the ring including $R_{601A}$ and $R_{611}$ and a benzene ring corresponding to the a ring are fused. Specific examples of the nitrogen-containing heterocycle include a compound corresponding to the nitrogen-containing bi(or-more)cyclic fused heterocyclic group in the specific example group G2. The same applies to $R_{601A}$ bonded with $R_{621}$, $R_{602A}$ bonded with $R_{613}$, and $R_{602A}$ bonded with $R_{614}$.

At least one combination of adjacent two or more of $R_{611}$ to $R_{621}$ may be mutually bonded to form a substituted or unsubstituted monocyclic ring, or mutually bonded to form a substituted or unsubstituted fused ring.

For instance, $R_{611}$ and $R_{612}$ are optionally mutually bonded to form a structure in which a benzene ring, indole ring, pyrrole ring, benzofuran ring, benzothiophene ring or the like is fused to the six-membered ring bonded with $R_{611}$ and $R_{612}$, the resultant fused ring forming a naphthalene ring, carbazole ring, indole ring, dibenzofuran ring, or dibenzothiophene ring, respectively.

In an exemplary embodiment, $R_{611}$ to $R_{621}$ not contributing to ring formation are each independently a hydrogen atom, a substituted or unsubstituted alkyl group having 1 to 50 carbon atoms, a substituted or unsubstituted aryl group having 6 to 50 ring carbon atoms, or a substituted or unsubstituted heterocyclic group having 5 to 50 ring atoms.

In an exemplary embodiment, $R_{611}$ to $R_{621}$ not contributing to ring formation are each independently a hydrogen atom, a substituted or unsubstituted aryl group having 6 to 50 ring carbon atoms, or a substituted or unsubstituted heterocyclic group having 5 to 50 ring atoms.

In an exemplary embodiment, $R_{611}$ to $R_{621}$ not contributing to ring formation are each independently a hydrogen atom, or a substituted or unsubstituted alkyl group having 1 to 50 carbon atoms.

In an exemplary embodiment, $R_{611}$ to $R_{621}$ not contributing to ring formation are each independently a hydrogen atom, or a substituted or unsubstituted alkyl group having 1 to 50 carbon atoms, and at least one of $R_{611}$ to $R_{621}$ is a substituted or unsubstituted alkyl group having 1 to 50 carbon atoms.

In an exemplary embodiment, the compound represented by the formula (62) is a compound represented by a formula (63) below.

[Formula 187]

(63)

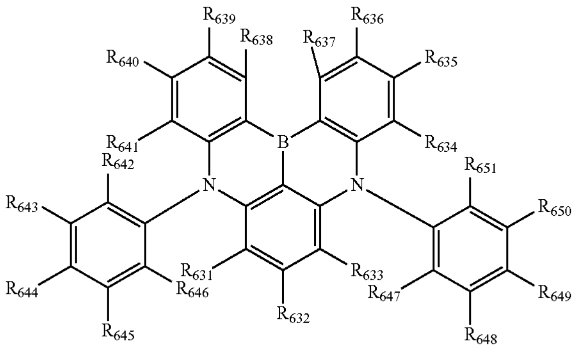

In the formula (63):

$R_{631}$ is bonded with $R_{646}$ to form a substituted or unsubstituted heterocycle, or not bonded therewith to form no substituted or unsubstituted heterocycle;

$R_{633}$ is bonded with $R_{647}$ to form a substituted or unsubstituted heterocycle, or not bonded therewith to form no substituted or unsubstituted heterocycle;

$R_{634}$ is bonded with $R_{651}$ to form a substituted or unsubstituted heterocycle, or not bonded therewith to form no substituted or unsubstituted heterocycle;

$R_{641}$ is bonded with $R_{642}$ to form a substituted or unsubstituted heterocycle, or not bonded therewith to form no substituted or unsubstituted heterocycle;

at least one combination of adjacent two or more of $R_{631}$ to $R_{651}$ are mutually bonded to form a substituted or unsubstituted monocyclic ring, mutually bonded to form a substituted or unsubstituted fused ring, or not mutually bonded; and $R_{631}$ to $R_{651}$ not forming the substituted or unsubstituted heterocycle, not forming the monocyclic ring, and not forming the fused ring are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $-Si(R_{901})(R_{902})(R_{903})$, a group represented by $-O-(R_{904})$, a group represented by $-S-(R_{905})$, a group represented by $-N(R_{906})(R_{907})$, a halogen atom, a cyano group, a nitro group, a substituted or unsubstituted aryl group having 6 to 50 ring carbon atoms, or a substituted or unsubstituted heterocyclic group having 5 to 50 ring atoms.

$R_{631}$ are optionally bonded with $R_{646}$ to form a substituted or unsubstituted heterocycle. For instance, $R_{631}$ and $R_{646}$ are optionally bonded with each other to form a tri-or-more cyclic fused nitrogen-containing heterocycle, in which a benzene ring bonded with $R_{646}$, a ring including a nitrogen atom, and a benzene ring corresponding to the a ring are fused. Specific examples of the nitrogen-containing heterocycle include a compound corresponding to the nitrogen-containing tri(-or-more)cyclic fused heterocyclic group in the specific example group G2. The same applies to $R_{633}$ bonded with $R_{647}$, $R_{634}$ bonded with $R_{651}$, and $R_{641}$ bonded with $R_{642}$.

In an exemplary embodiment, $R_{631}$ to $R_{651}$ not contributing to ring formation are each independently a hydrogen atom, a substituted or unsubstituted alkyl group having 1 to 50 carbon atoms, a substituted or unsubstituted aryl group having 6 to 50 ring carbon atoms, or a substituted or unsubstituted heterocyclic group having 5 to 50 ring atoms.

In an exemplary embodiment, $R_{631}$ to $R_{651}$ not contributing to ring formation are each independently a hydrogen atom, a substituted or unsubstituted aryl group having 6 to 50 ring carbon atoms, or a substituted or unsubstituted heterocyclic group having 5 to 50 ring atoms.

In an exemplary embodiment, $R_{631}$ to $R_{651}$ not contributing to ring formation are each independently a hydrogen atom, or a substituted or unsubstituted alkyl group having 1 to 50 carbon atoms.

In an exemplary embodiment, $R_{631}$ to $R_{651}$ not contributing to ring formation are each independently a hydrogen atom, or a substituted or unsubstituted alkyl group having 1 to 50 carbon atoms, and at least one of $R_{631}$ to $R_{651}$ is a substituted or unsubstituted alkyl group having 1 to 50 carbon atoms.

In an exemplary embodiment, the compound represented by the formula (63) is a compound represented by a formula (63A) below.

[Formula 188]

(63A)

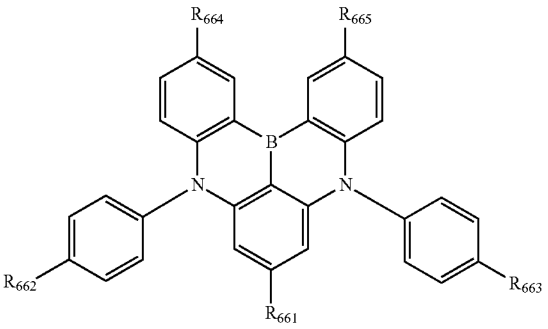

In the formula (63A):

$R_{661}$ is a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, or a substituted or unsubstituted aryl group having 6 to 50 ring carbon atoms; and $R_{662}$ to $R_{665}$ are each independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, or a substituted or unsubstituted aryl group having 6 to 50 ring carbon atoms.

In an exemplary embodiment, $R_{661}$ to $R_{665}$ are each independently a substituted or unsubstituted alkyl group having 1 to 50 carbon atoms, or a substituted or unsubstituted aryl group having 6 to 50 ring carbon atoms.

In an exemplary embodiment, $R_{661}$ to $R_{665}$ are each independently a substituted or unsubstituted alkyl group having 1 to 50 carbon atoms.

In an exemplary embodiment, the compound represented by the formula (63) is a compound represented by a formula (63B) below.

[Formula 189]

(63B)

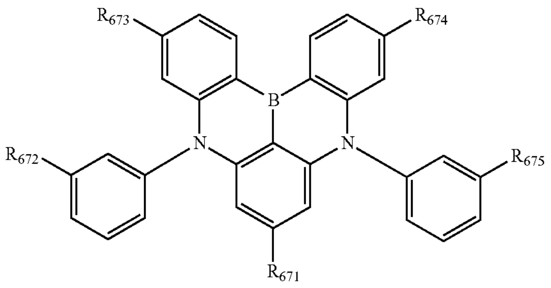

In the formula (63B):

$R_{671}$ and $R_{672}$ are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —N($R_{906}$)($R_{907}$), or a substituted or unsubstituted aryl group having 6 to 50 ring carbon atoms; and $R_{673}$ to $R_{675}$ are each independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —N($R_{906}$)($R_{907}$), or a substituted or unsubstituted aryl group having 6 to 50 ring carbon atoms.

In an exemplary embodiment, the compound represented by the formula (63) is a compound represented by a formula (63B') below.

[Formula 190]

(63B')

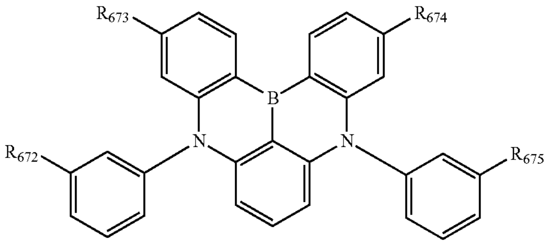

In the formula (63B'), $R_{672}$ to $R_{675}$ each independently represent the same as $R_{672}$ to $R_{675}$ in the formula (63B).

In an exemplary embodiment, at least one of $R_{671}$ to $R_{675}$ is a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —N($R_{906}$)($R_{907}$), or a substituted or unsubstituted aryl group having 6 to 50 ring carbon atoms.

In an exemplary embodiment: $R_{672}$ is a hydrogen atom, a substituted or unsubstituted alkyl group having 1 to 50 carbon atoms, a group represented by —N($R_{906}$)($R_{907}$), or a substituted or unsubstituted aryl group having 6 to 50 ring carbon atoms; and $R_{671}$ and $R_{673}$ to $R_{675}$ are each independently a substituted or unsubstituted alkyl group having 1 to 50 carbon atoms, a group represented by —N($R_{906}$)($R_{907}$), or a substituted or unsubstituted aryl group having 6 to 50 ring carbon atoms.

In an exemplary embodiment, the compound represented by the formula (63) is a compound represented by a formula (63C) below.

[Formula 191]

(63C)

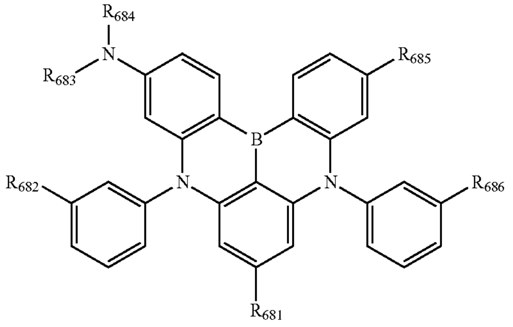

In the formula (63C):

$R_{681}$ and $R_{682}$ are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, or a substituted or unsubstituted aryl group having 6 to 50 ring carbon atoms.

$R_{683}$ to $R_{686}$ are each independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, or a substituted or unsubstituted aryl group having 6 to 50 ring carbon atoms.

In an exemplary embodiment, the compound represented by the formula (63) is a compound represented by a formula (63C') below.

[Formula 192]

(63C')

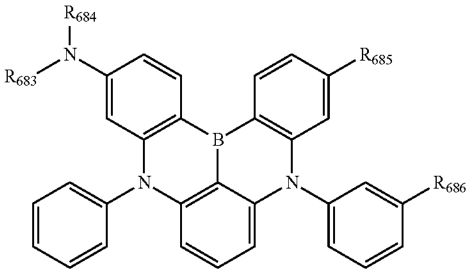

In the formula (63C'), $R_{683}$ to $R_{686}$ each independently represent the same as $R_{683}$ to $R_{686}$ in the formula (63C).

In an exemplary embodiment, $R_{681}$ to $R_{686}$ are each independently a substituted or unsubstituted alkyl group having 1 to 50 carbon atoms, or a substituted or unsubstituted aryl group having 6 to 50 ring carbon atoms.

In an exemplary embodiment, $R_{681}$ to $R_{686}$ are each independently a substituted or unsubstituted aryl group having 6 to 50 ring carbon atoms.

The compound represented by the formula (6) is producible by initially bonding the a ring, b ring and c ring with linking groups (a group including N—$R_{601}$ and a group including N—$R_{602}$) to form an intermediate (first reaction), and bonding the a ring, b ring and c ring with a linking group (a group including a boron atom) to form a final product (second reaction). In the first reaction, an amination reaction (e.g. Buchwald-Hartwig reaction) is applicable. In the second reaction, Tandem Hetero-Friedel-Crafts Reactions or the like is applicable.

Specific examples of the compound represented by the formula (6) are shown below. It should however be noted that these specific examples are merely exemplary and do not limit the compound represented by the formula (6).

[Formula 193]

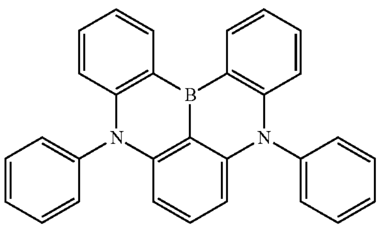

-continued

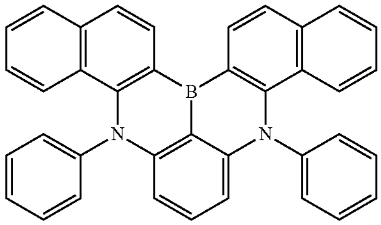

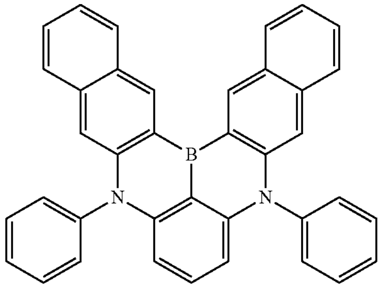

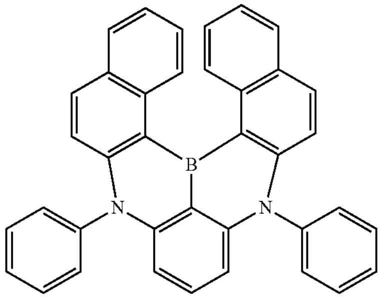

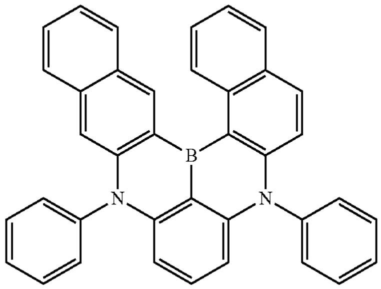

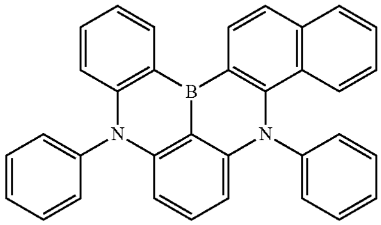

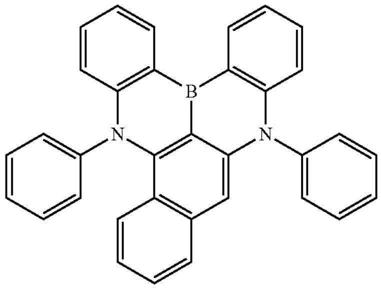

-continued
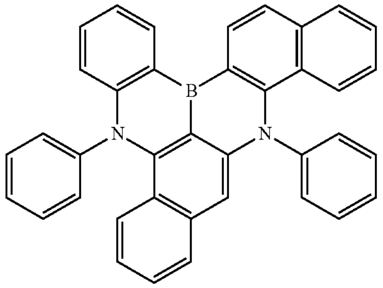
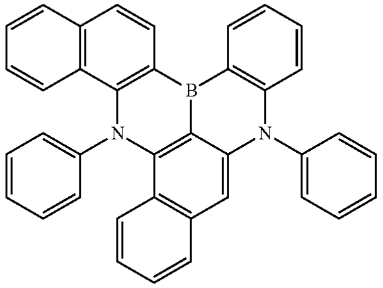
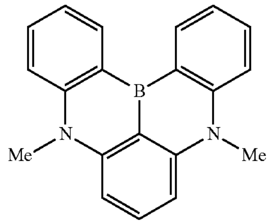
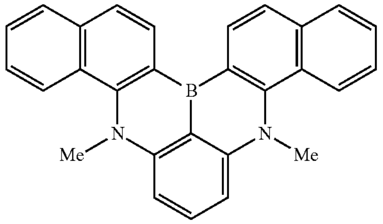
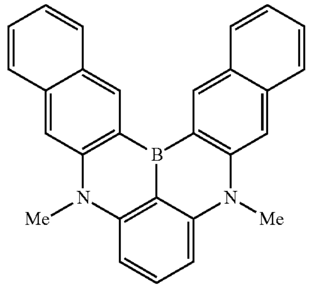
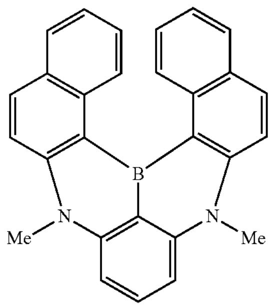
-continued
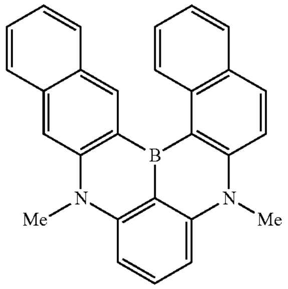
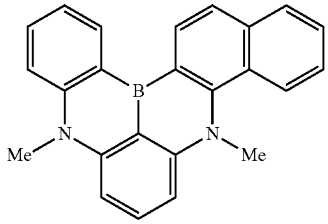
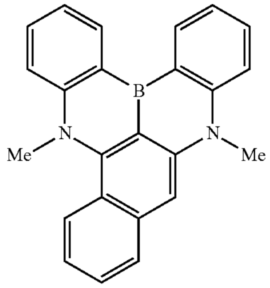
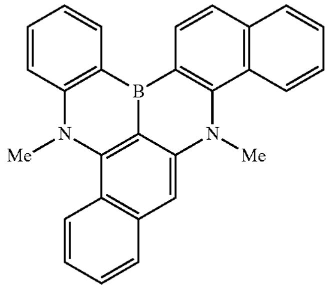
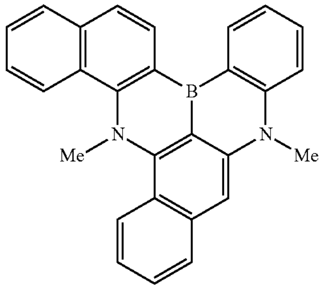

-continued
[Formula 194]
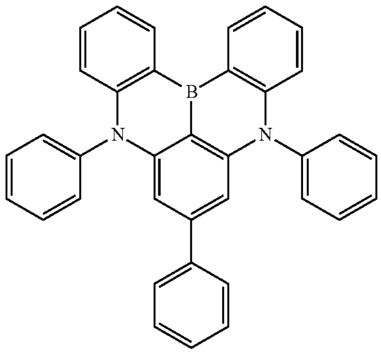
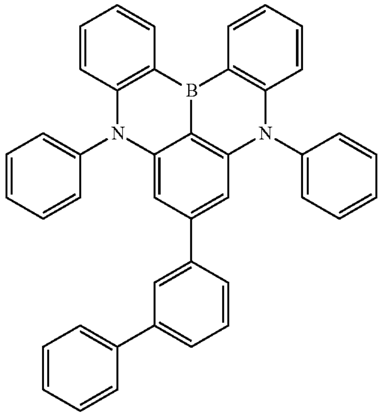
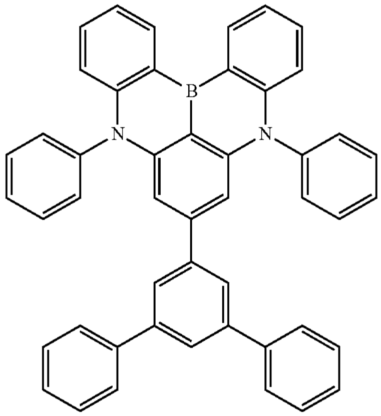
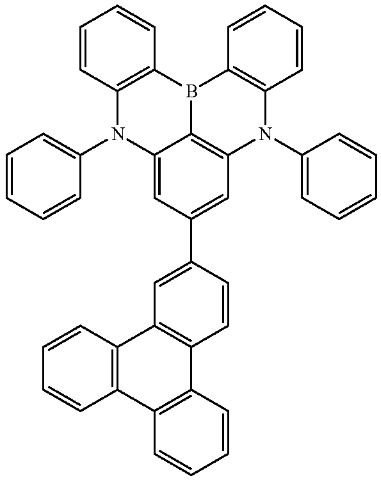
-continued
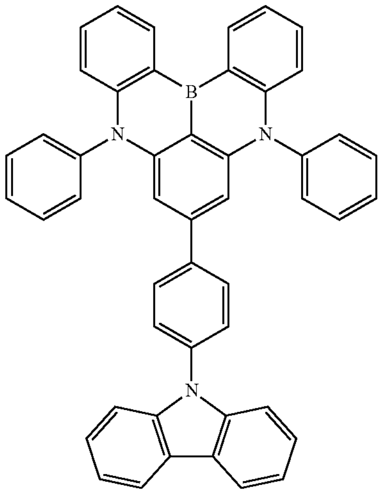
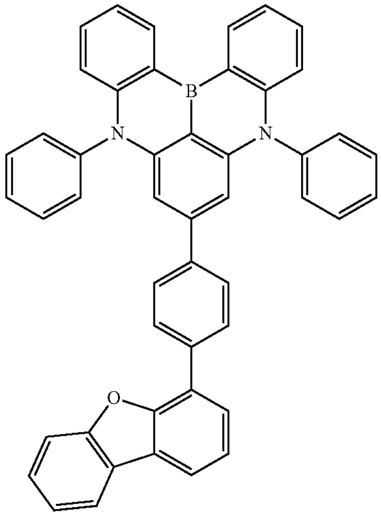
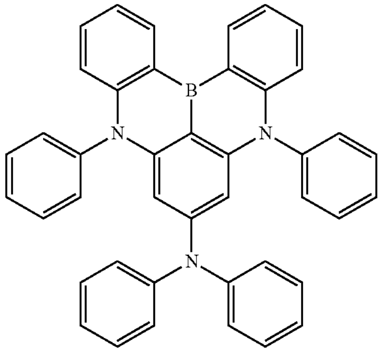
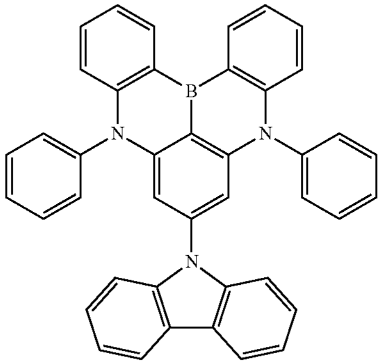

-continued
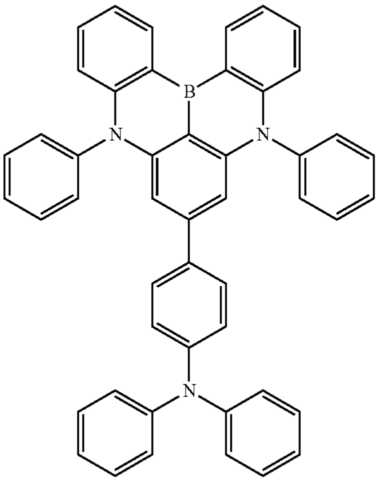
[Formula 195]
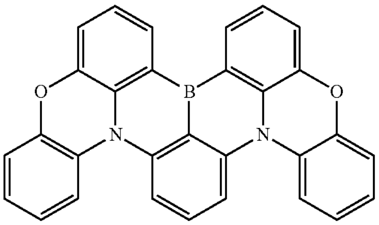
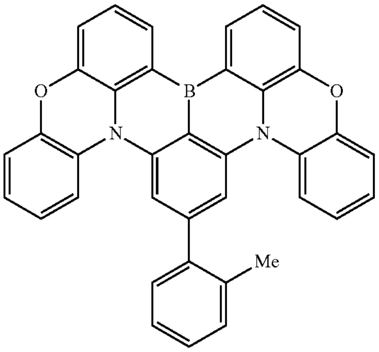
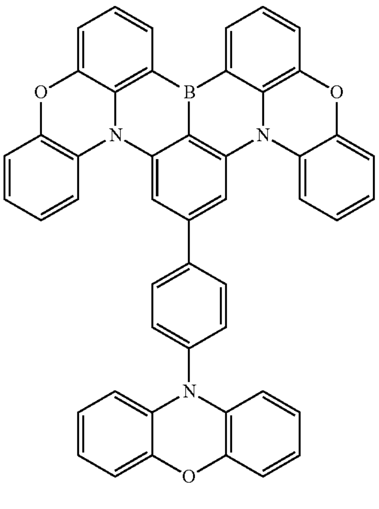
-continued
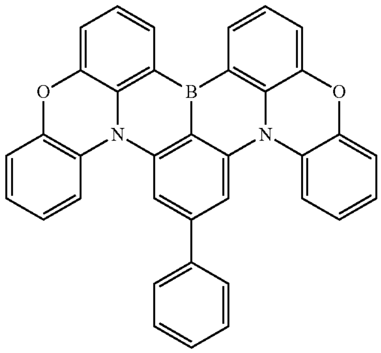
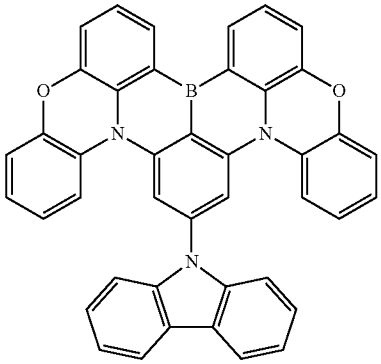
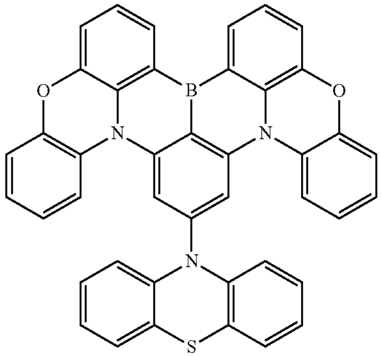
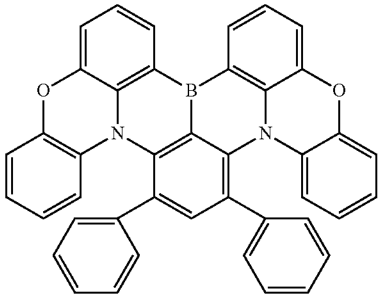
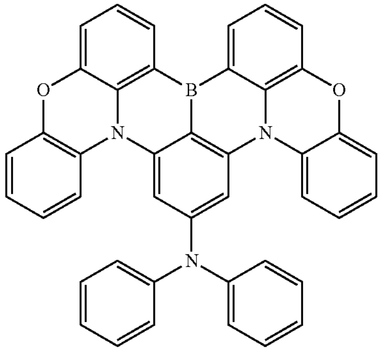

-continued
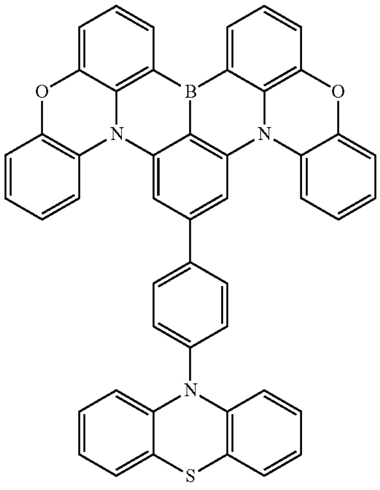
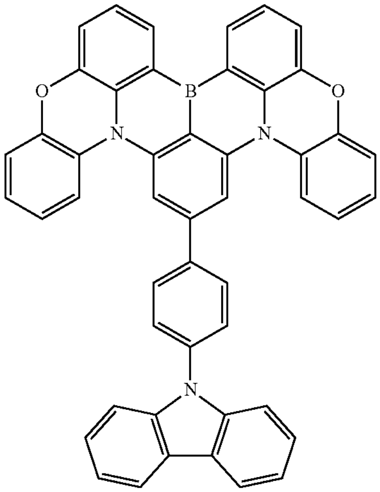
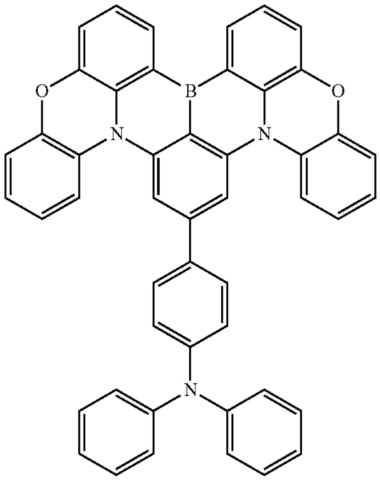
-continued
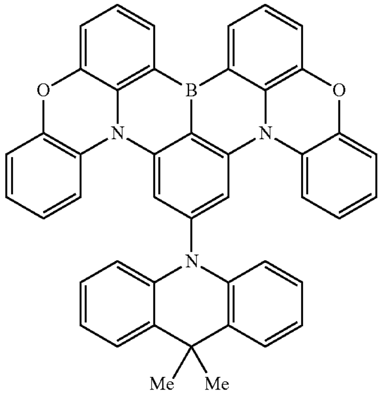
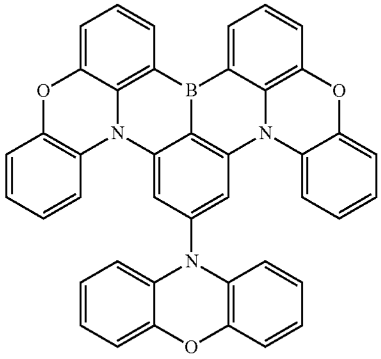
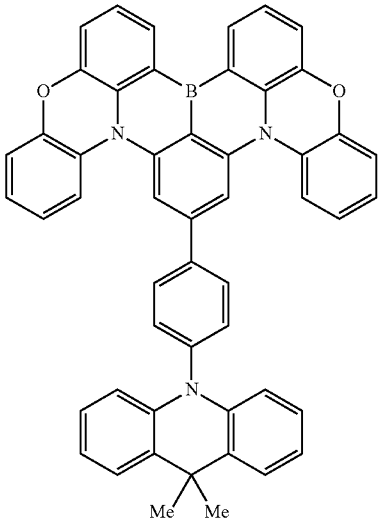
[Formula 196]
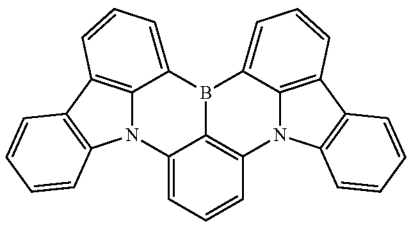

-continued
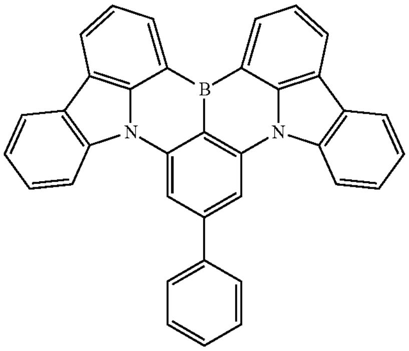
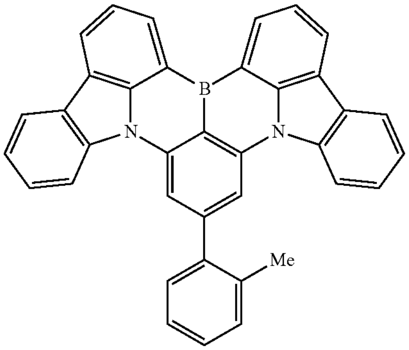
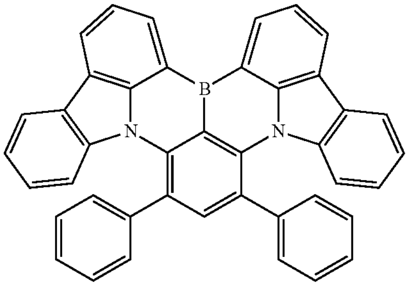
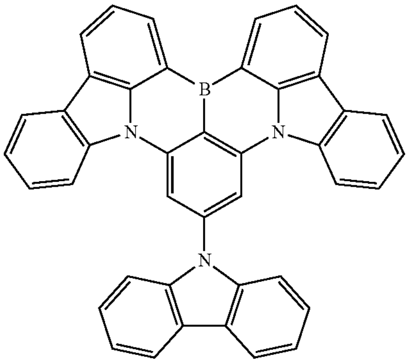
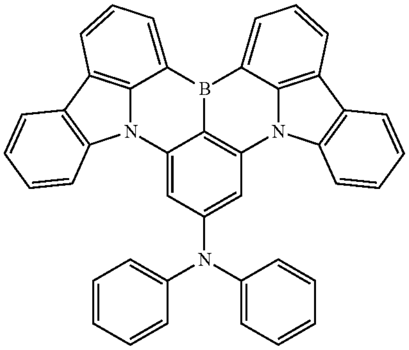
-continued
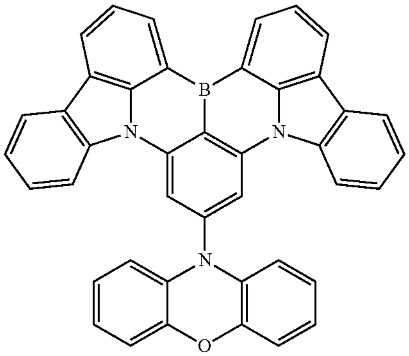
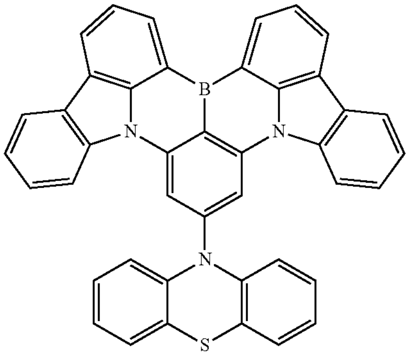
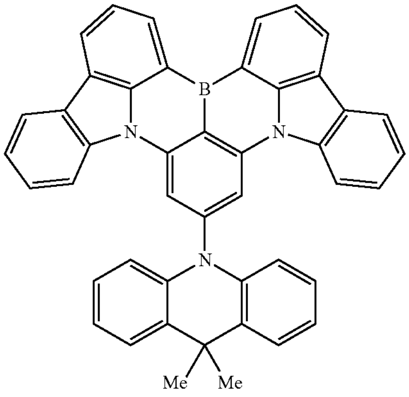
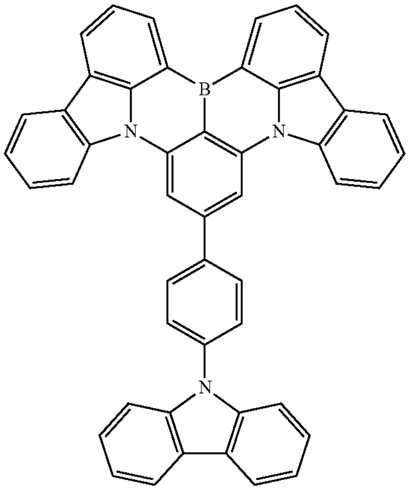

-continued
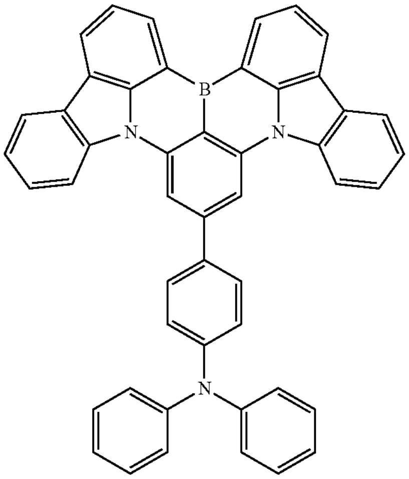
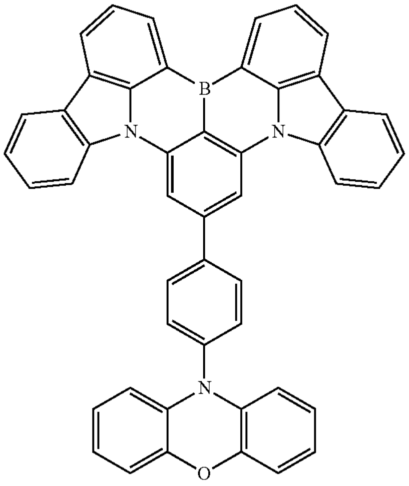
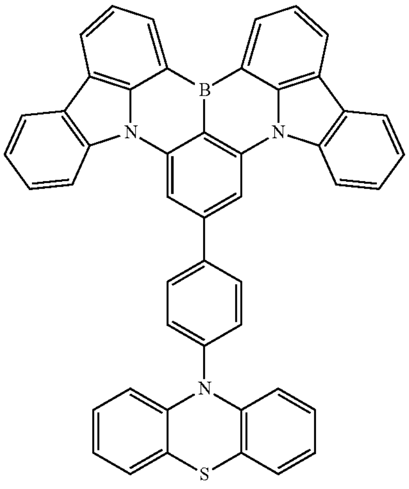
-continued
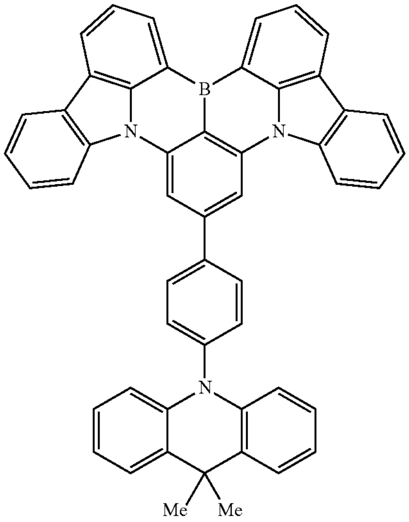
[Formula 197]
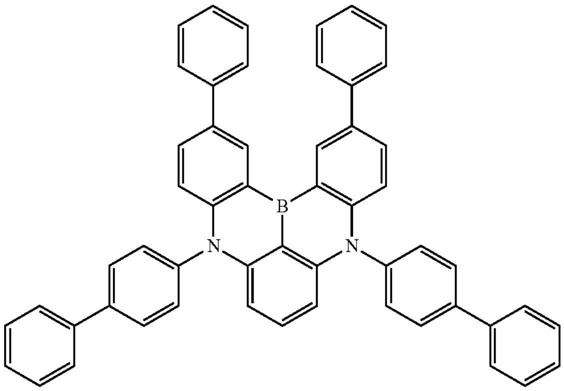
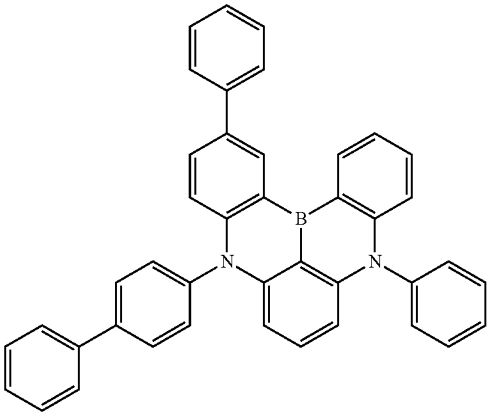
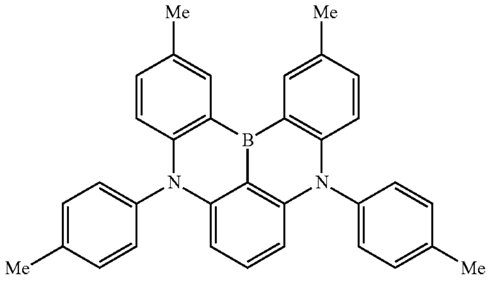

-continued
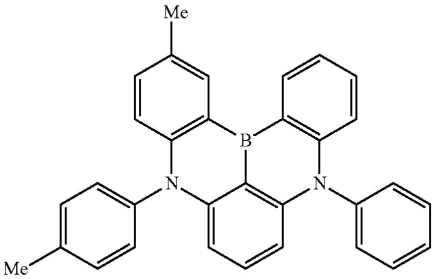
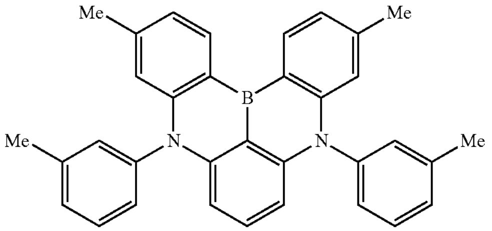
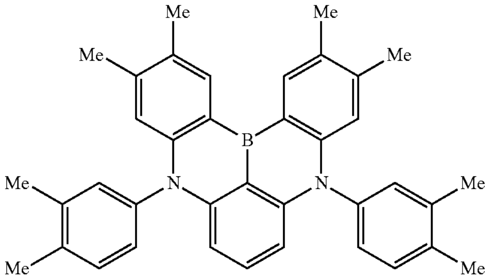
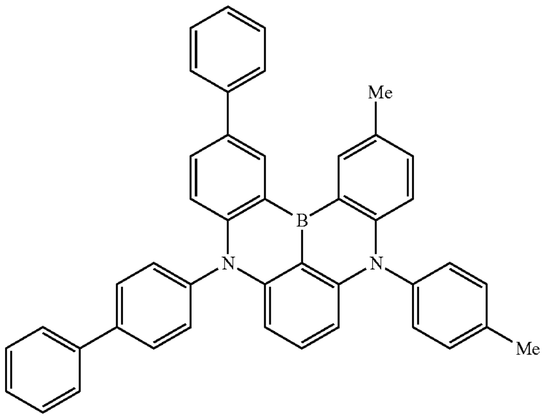
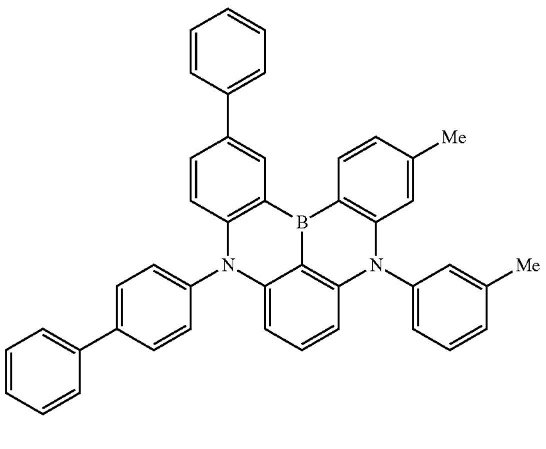
-continued
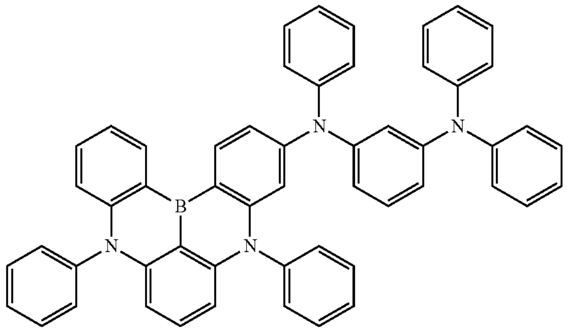
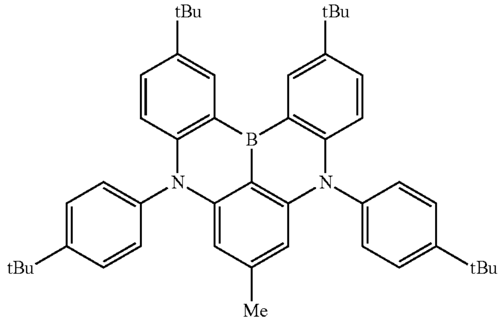
[Formula 198]
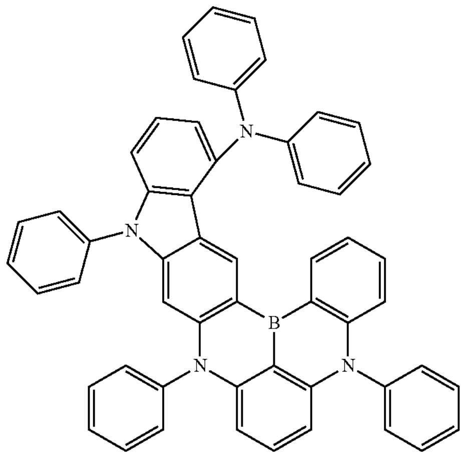
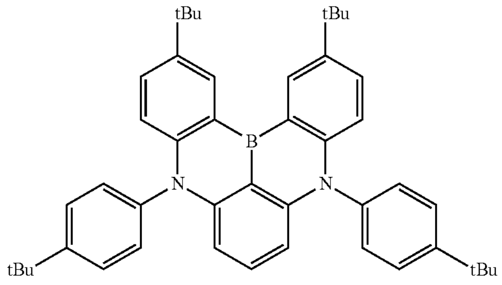
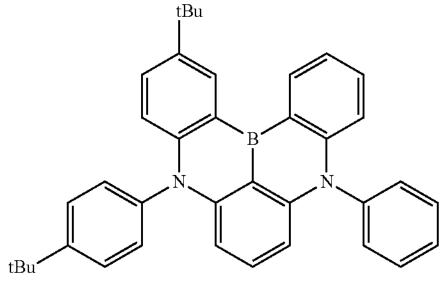

-continued
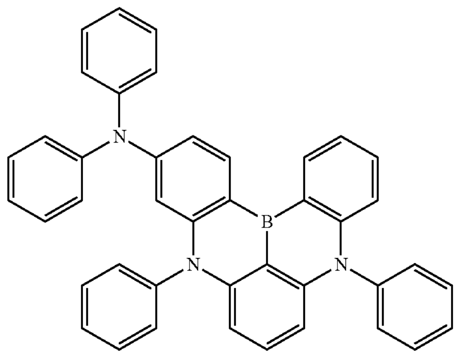
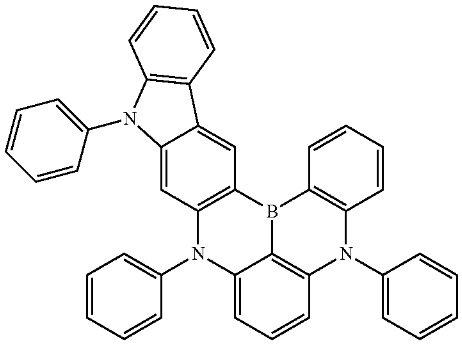
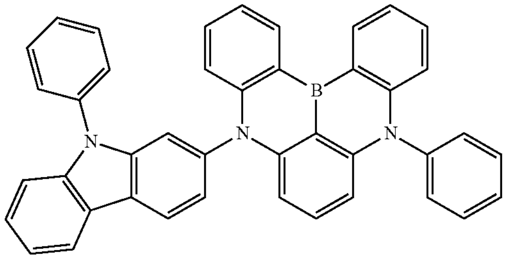
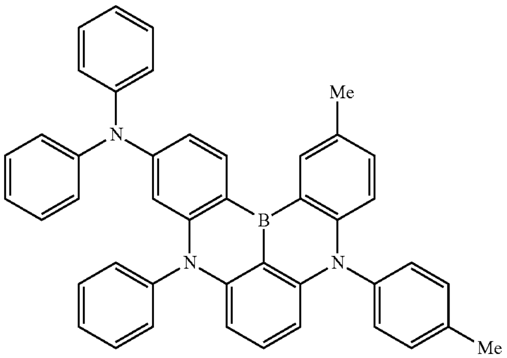
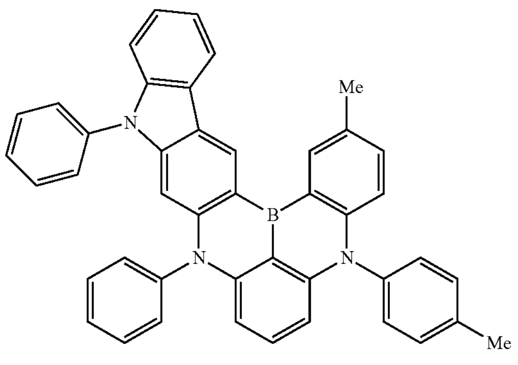
-continued
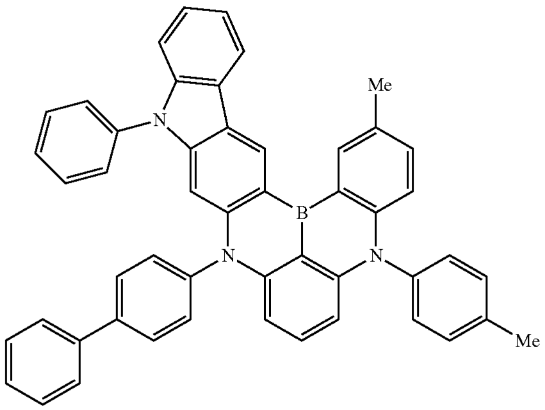
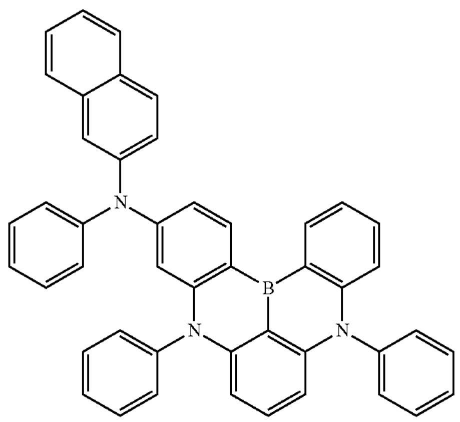
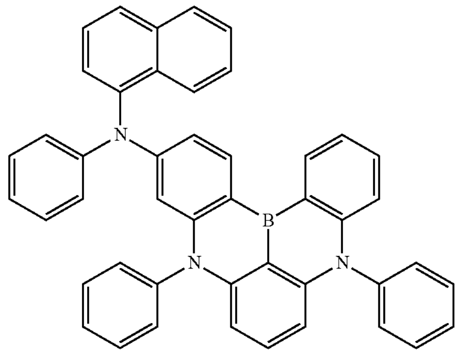
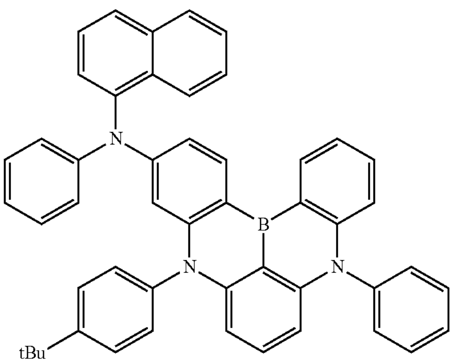

-continued
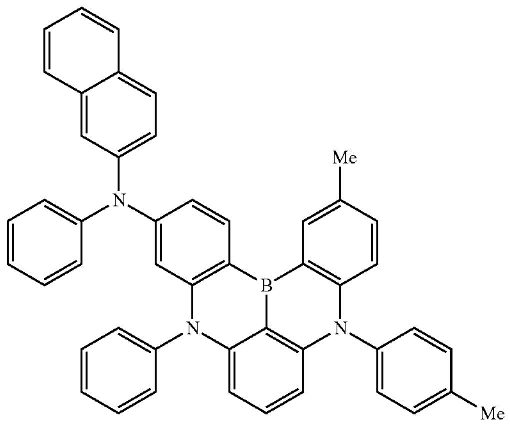
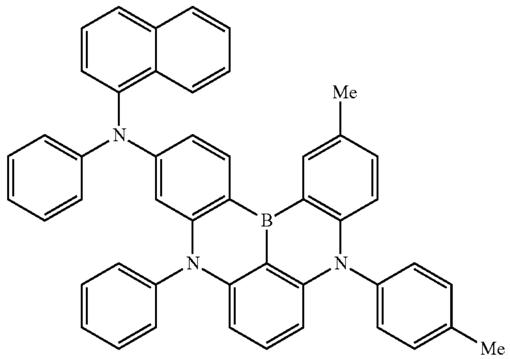
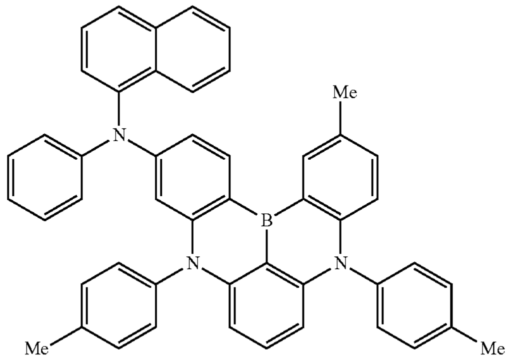
-continued
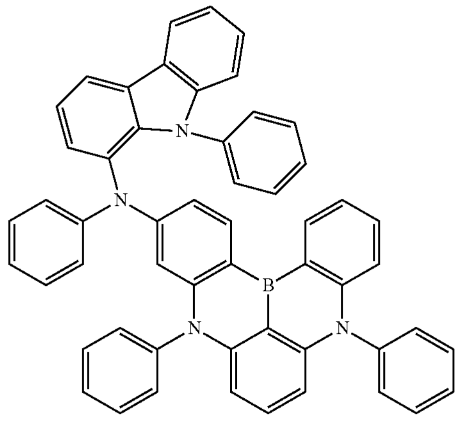
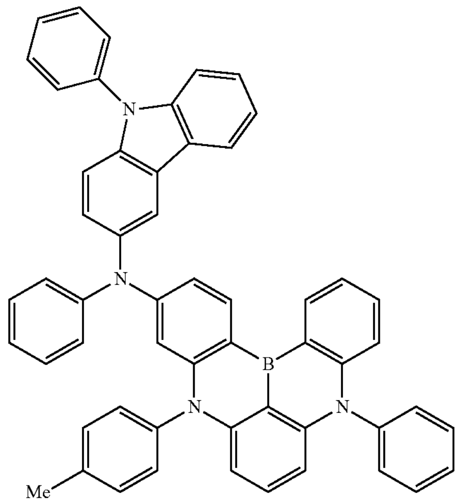
[Formula 199]
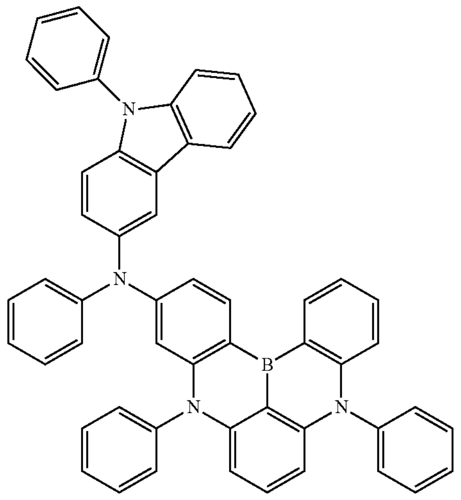
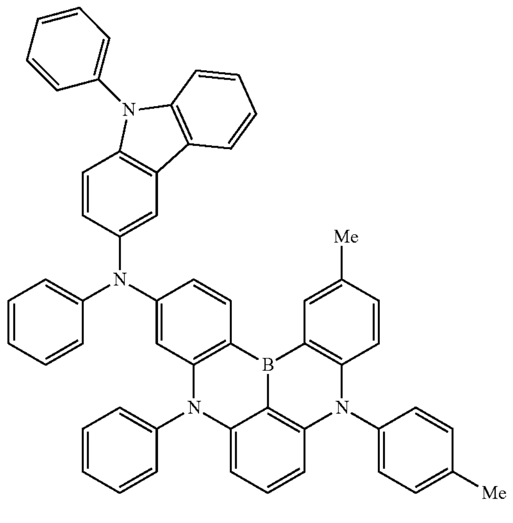

-continued
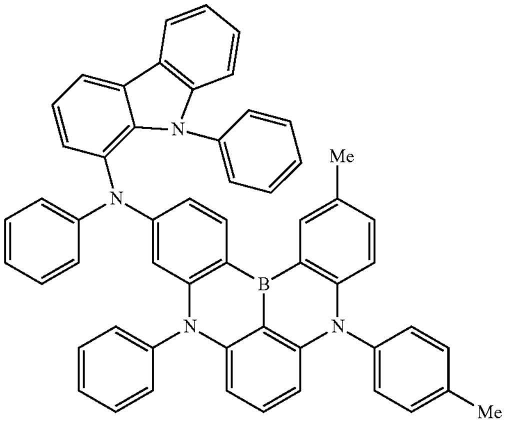
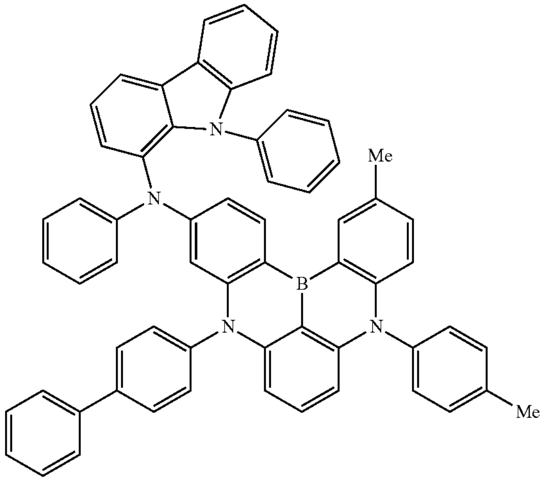
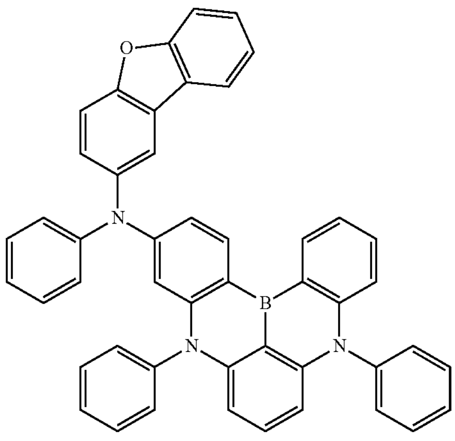
-continued
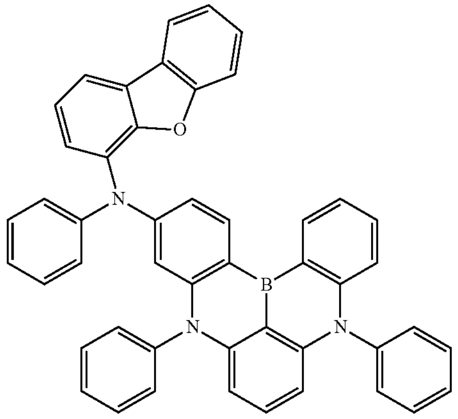
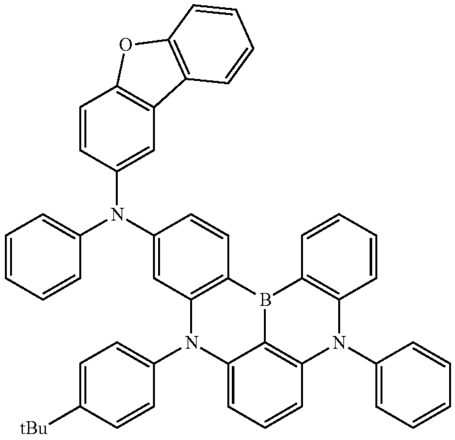
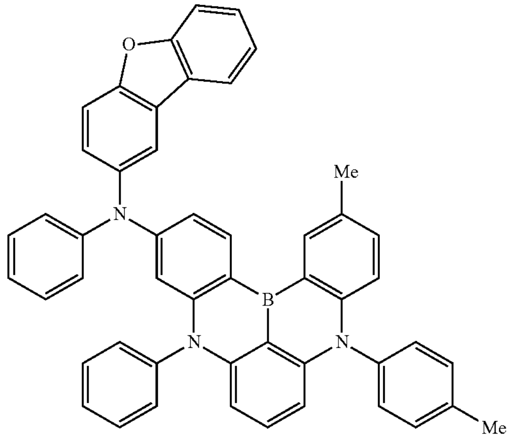
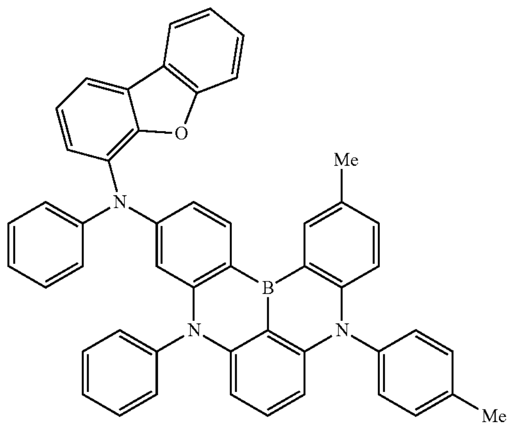

-continued
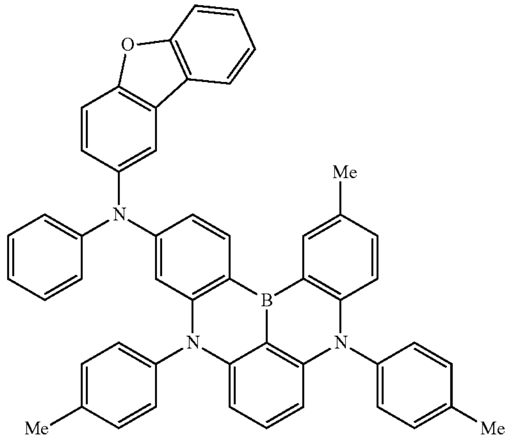
[Formula 200]
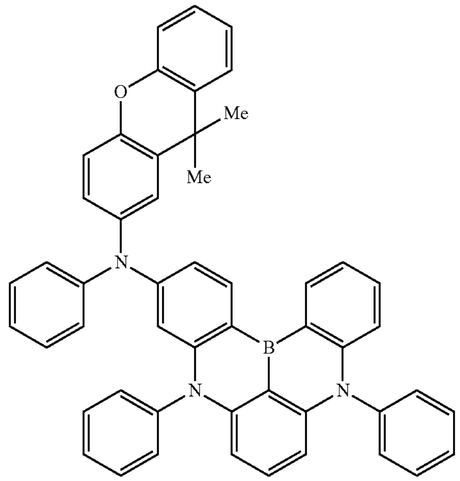
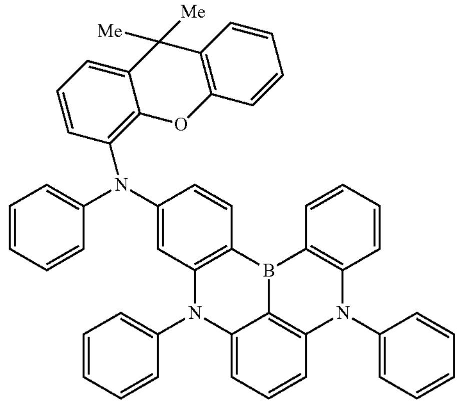
-continued
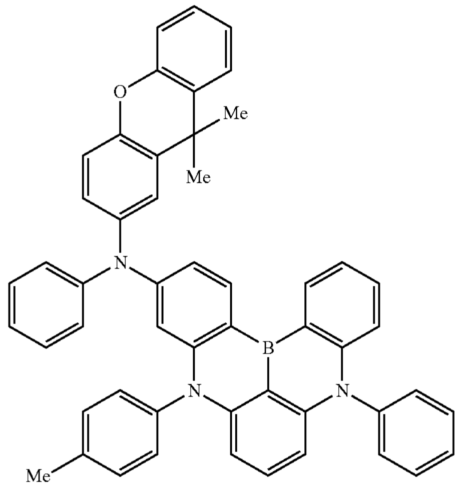
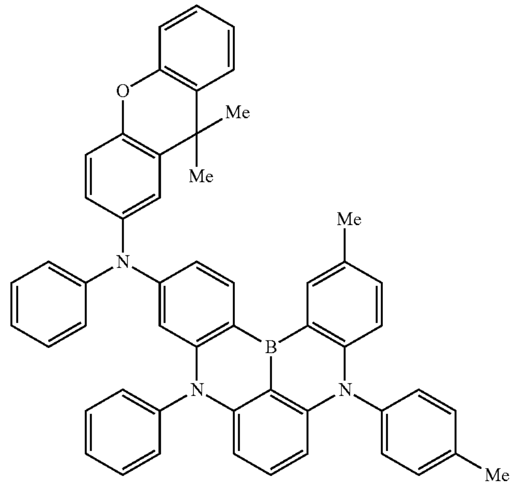
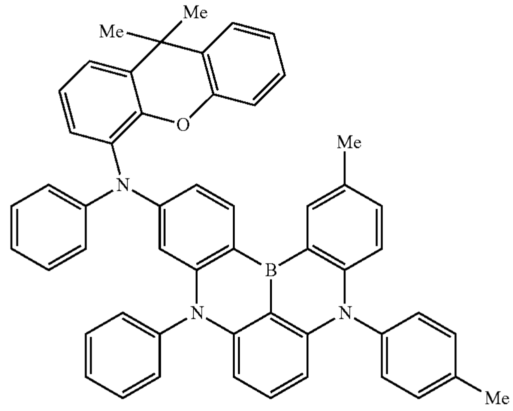

-continued
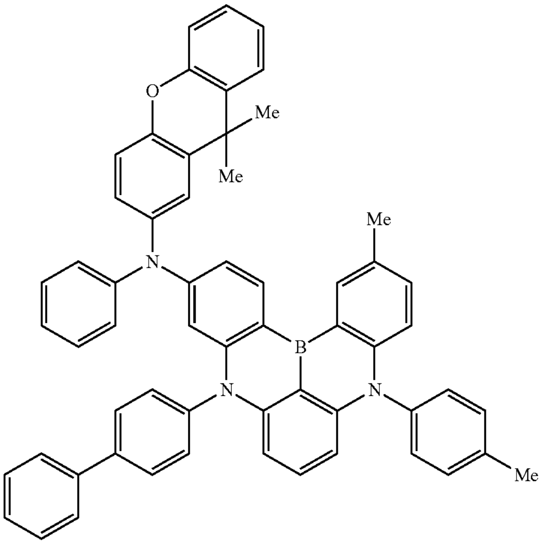
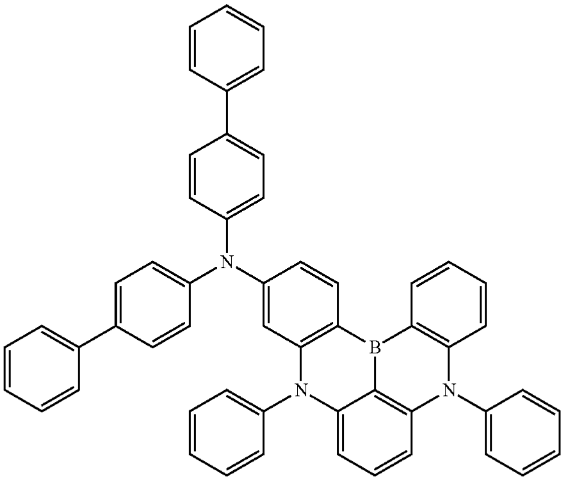
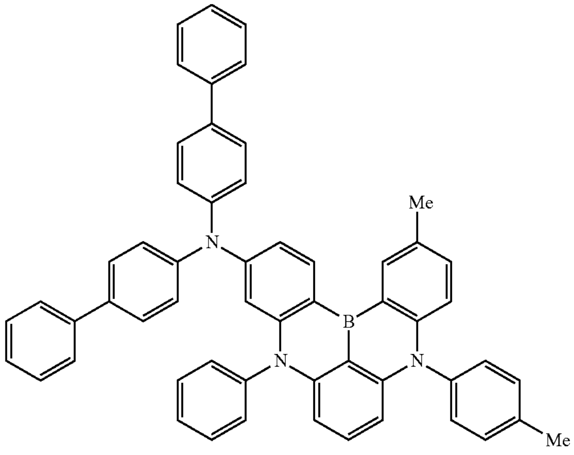
-continued
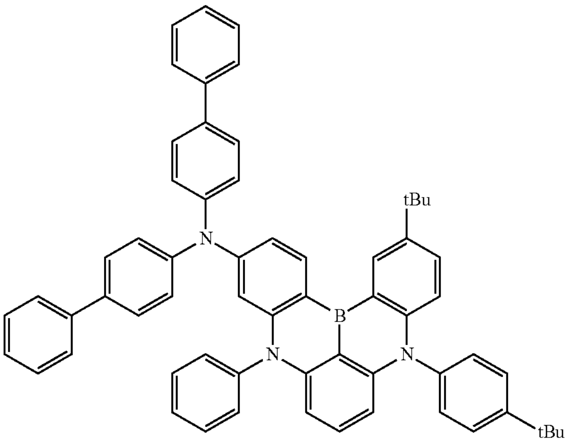
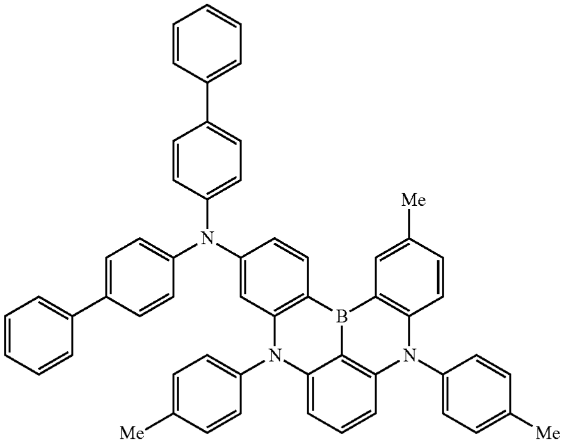
[Formula 201]
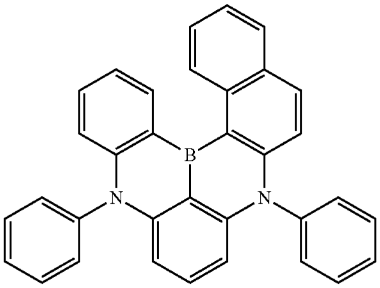
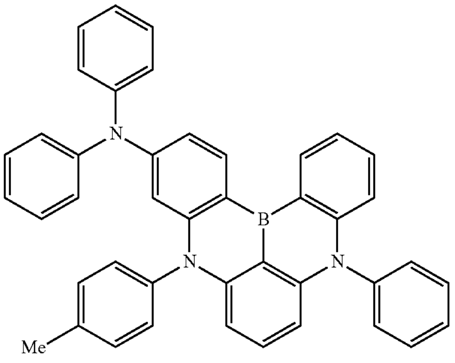

-continued
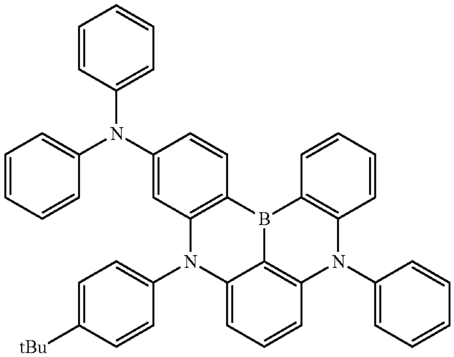
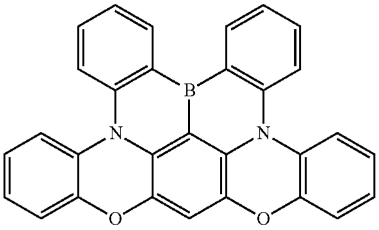
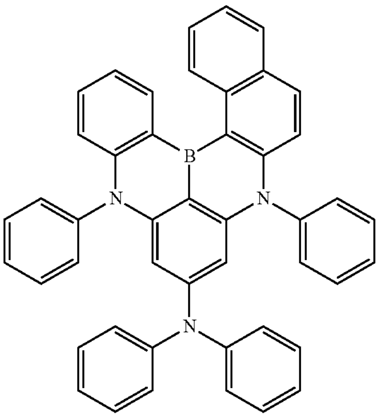
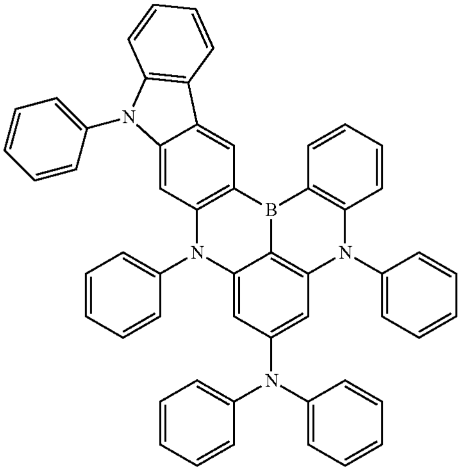
-continued
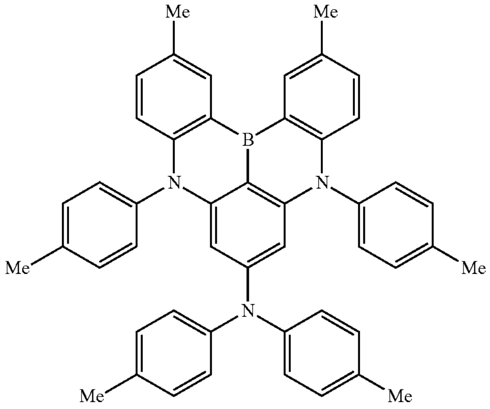
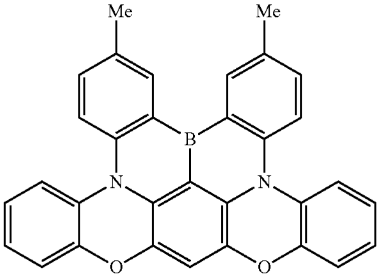
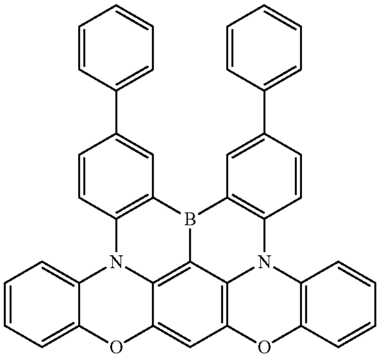
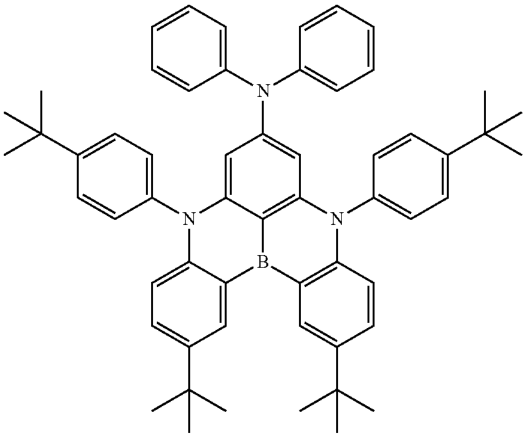

-continued
[Formula 202]
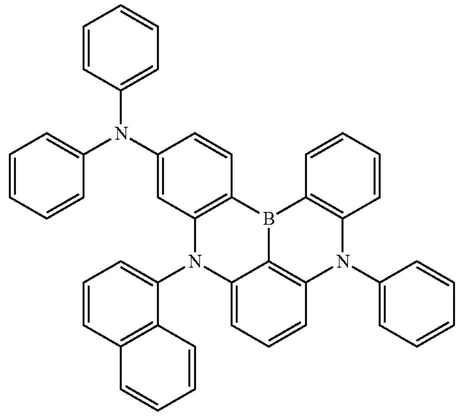
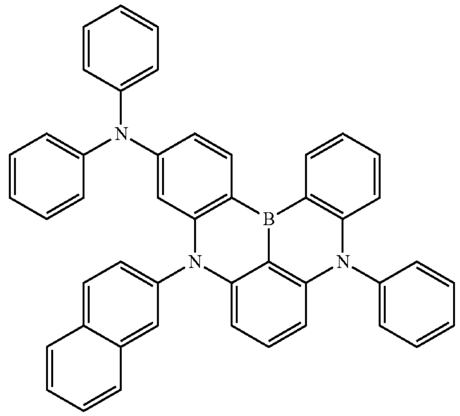
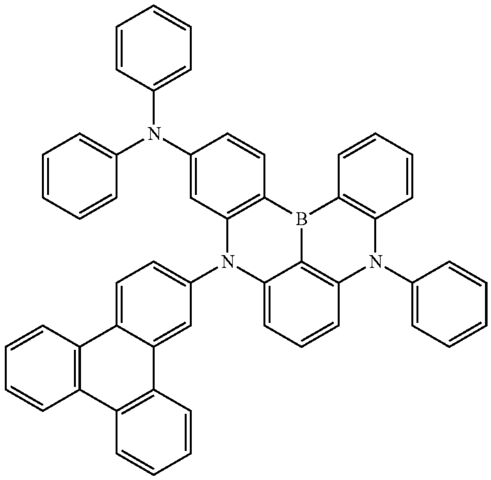
-continued
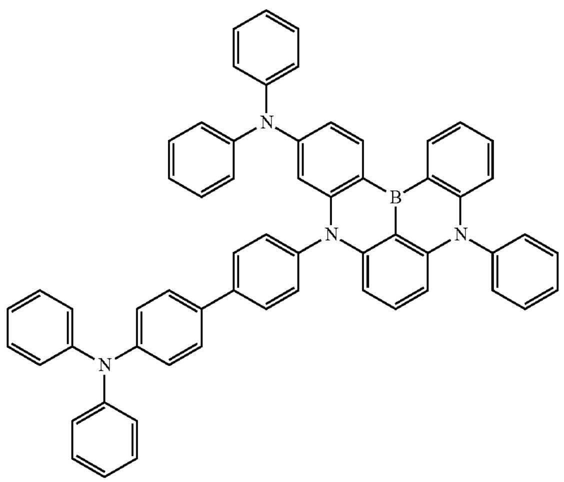
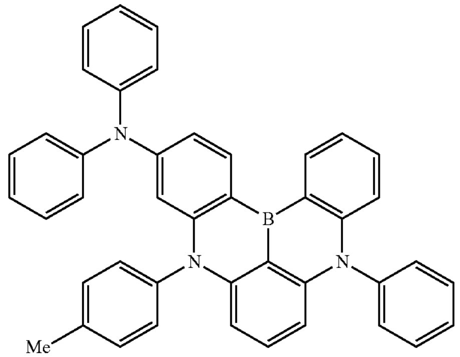
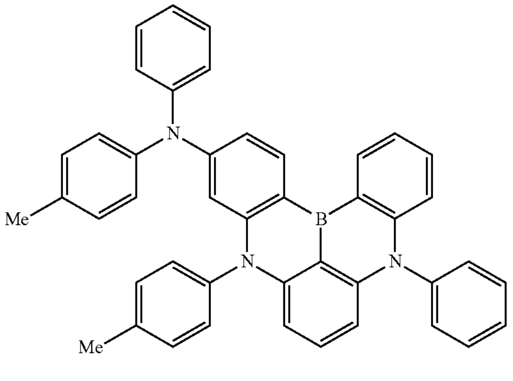
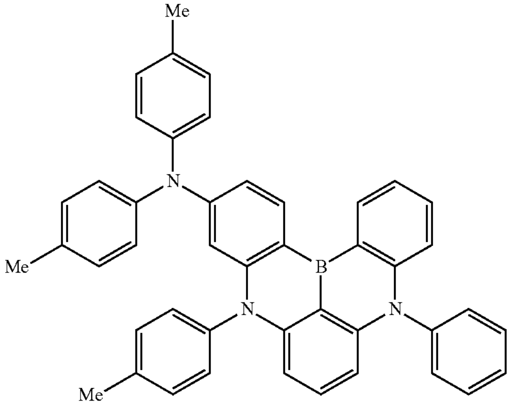

-continued
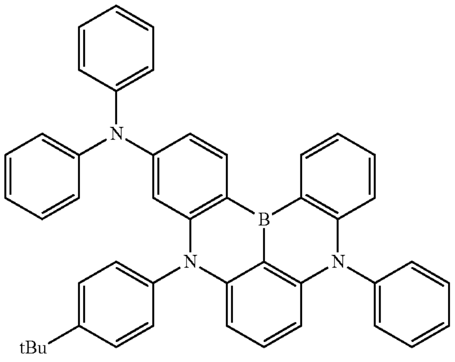
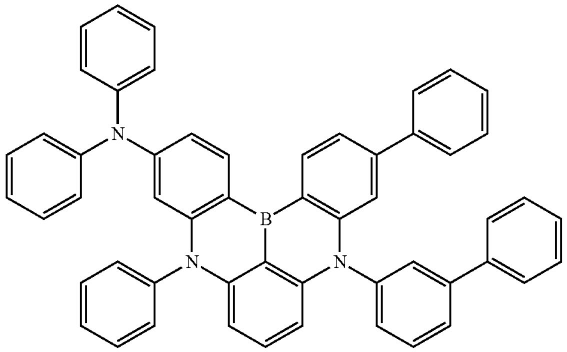
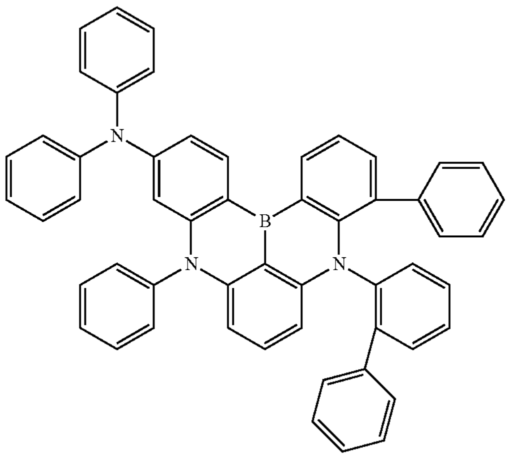
-continued
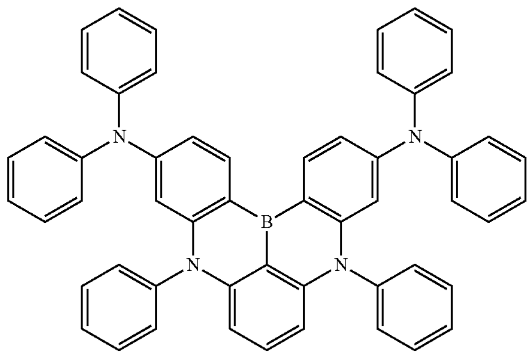
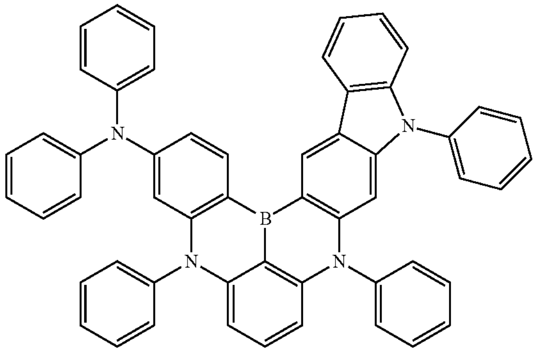
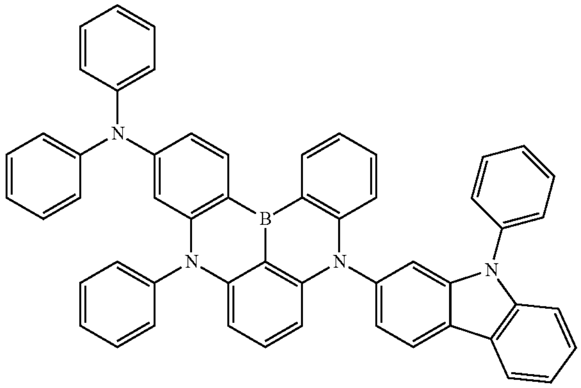
[Formula 203]
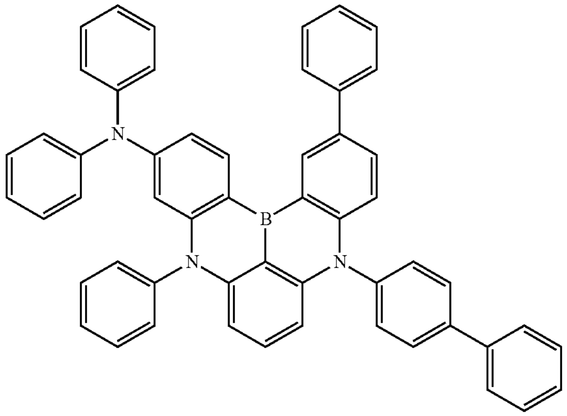
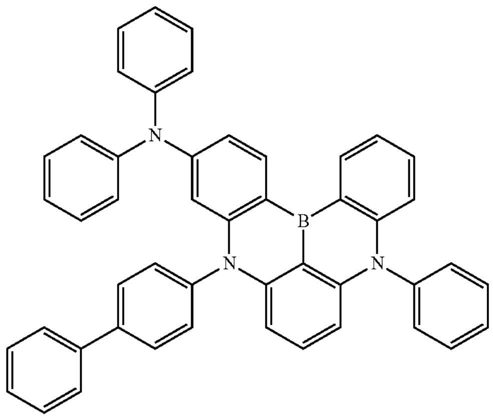

-continued
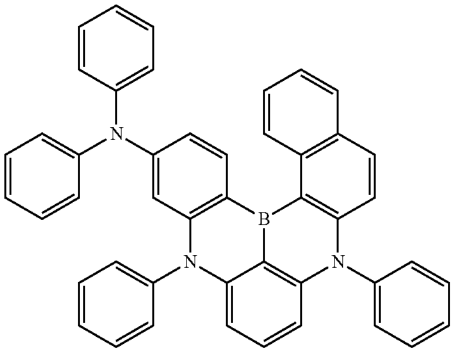
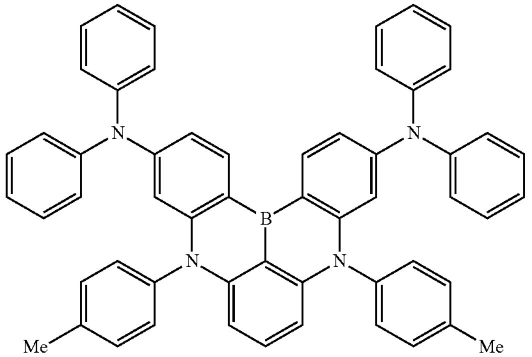
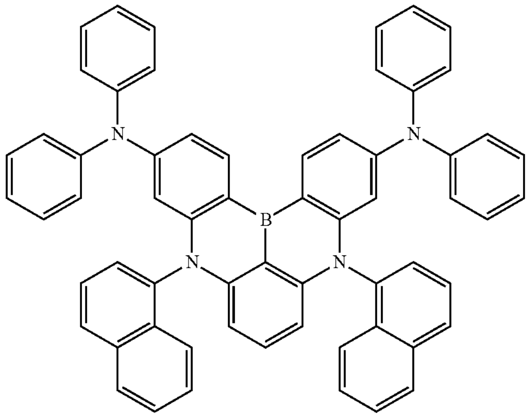
[Formula 204]
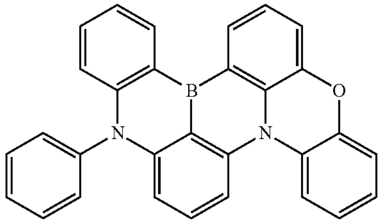
-continued
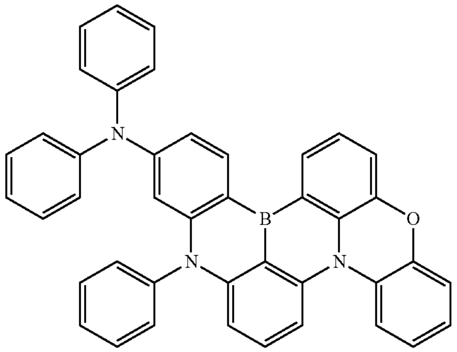
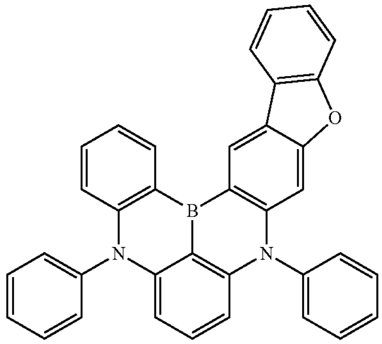
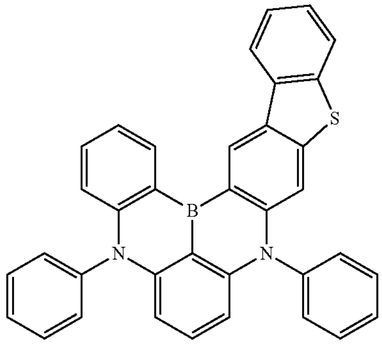
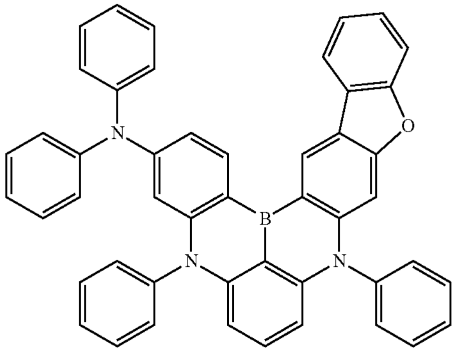
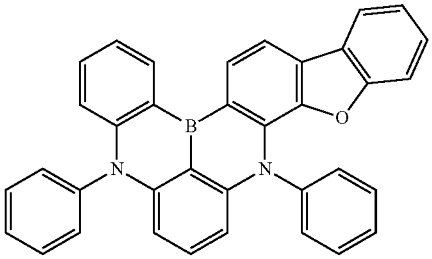

-continued

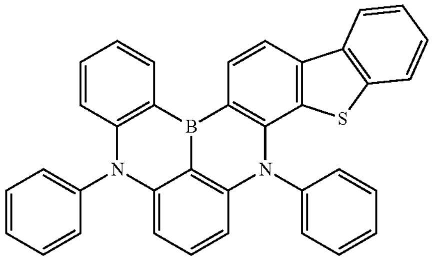

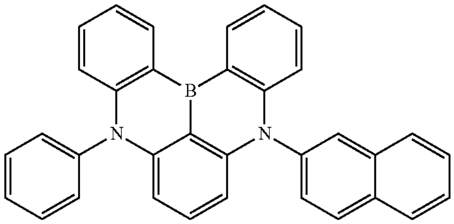

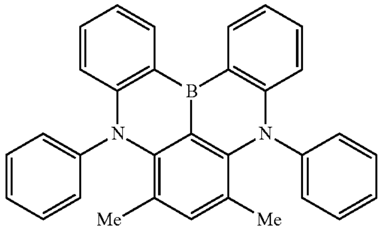

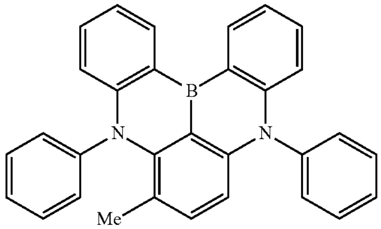

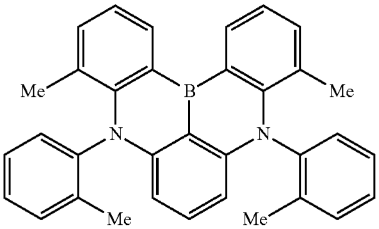

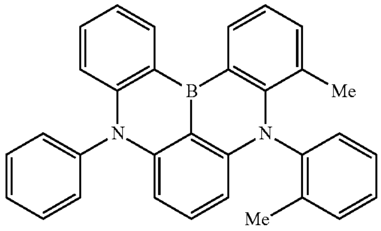

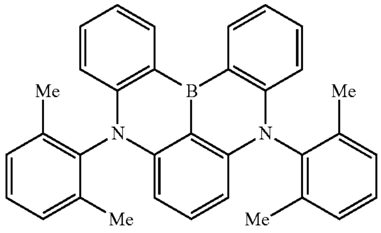

-continued

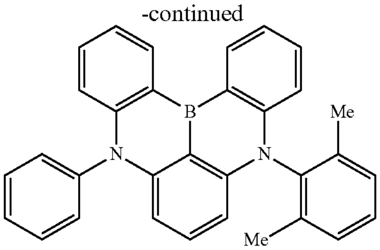

Compound Represented by Formula (7)

The compound represented by the formula (7) will be described below.

[Formula 205]

(7)

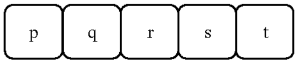

[Formula 206]

(72)

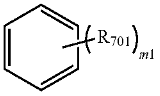

(73)

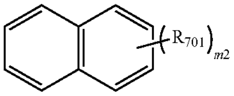

(74)

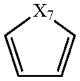

(75)

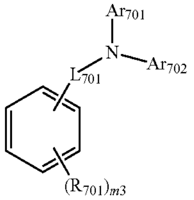

(76)

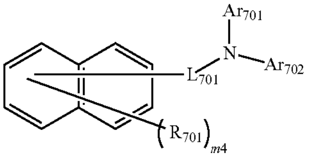

In the formula (7):

r ring is a ring represented by the formula (72) or the formula (73), the r ring being fused with adjacent ring(s) at any position(s);

q ring and s ring are each independently a ring represented by the formula (74) and fused with adjacent ring(s) at any position(s);

p ring and t ring are each independently a structure represented by the formula (75) or the formula (76) and fused with adjacent ring(s) at any position(s); $X_7$ is an oxygen atom, a sulfur atom, or $NR_{702}$;

when a plurality of $R_{701}$ are present, adjacent ones of the plurality of $R_{701}$ are mutually bonded to form a substituted or unsubstituted monocyclic ring, mutually bonded to form a substituted or unsubstituted fused ring, or not mutually bonded;

$R_{701}$ and $R_{702}$ forming neither the monocyclic ring nor the fused ring are each independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms;

$Ar_{701}$ and $Ar_{702}$ are each independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

$L_{701}$ is a substituted or unsubstituted alkylene group having 1 to 50 carbon atoms, a substituted or unsubstituted alkenylene group having 2 to 50 carbon atoms, a substituted or unsubstituted alkynylene group having 2 to 50 carbon atoms, a substituted or unsubstituted cycloalkylene group having 3 to 50 ring carbon atoms, a substituted or unsubstituted arylene group having 6 to 50 ring carbon atoms, or a substituted or unsubstituted divalent heterocyclic group having 5 to 50 ring atoms;

mL is 0, 1, or 2;

m2 is 0, 1, 2, 3, or 4;

m3 is each independently 0, 1, 2, or 3;

m4 is each independently 0, 1, 2, 3, 4, or 5;

when a plurality of $R_{701}$ are present, the plurality of $R_{701}$ are mutually the same or different;

when a plurality of $X_7$ are present, the plurality of $X_7$ are mutually the same or different;

when a plurality of $R_{702}$ are present, the plurality of $R_{702}$ are mutually the same or different;

when a plurality of $Ar_{701}$ are present, the plurality of $Ar_{701}$ are mutually the same or different;

when a plurality of $Ar_{702}$ are present, the plurality of $Ar_{702}$ are mutually the same or different; and when a plurality of $L_{701}$ are present, the plurality of $L_{701}$ are mutually the same or different.

In the formula (7), each of the p ring, q ring, r ring, s ring, and t ring is fused with an adjacent ring(s) sharing two carbon atoms. The fused position and orientation are not limited but may be defined as required.

In an exemplary embodiment, in the formula (72) or the formula (73) representing the r ring, m1=0 or m2=0 is satisfied.

In an exemplary embodiment, the compound represented by the formula (7) is represented by any one of formulae (71-1) to (71-6) below.

[Formula 207]

(71-1)

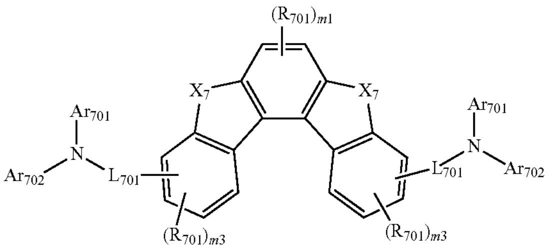

[Formula 208]

(71-2)

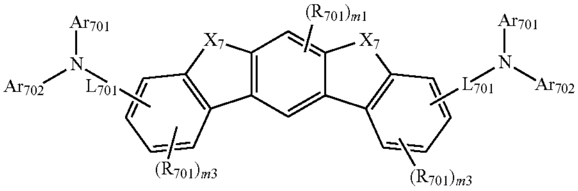

[Formula 209]

(71-3)

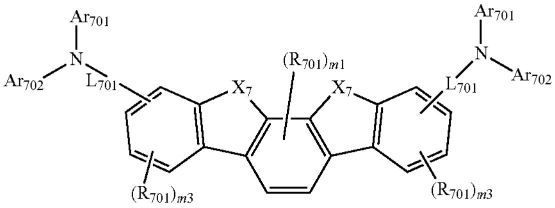

[Formula 210]

(71-4)

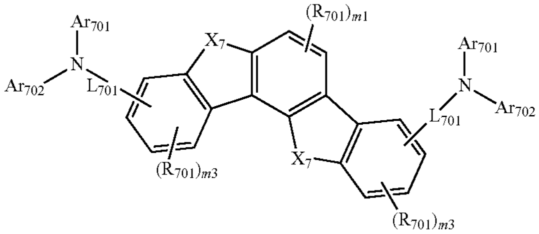

-continued

[Formula 211]

(71-5)

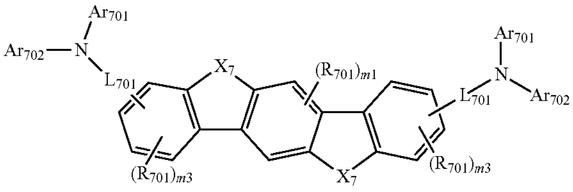

[Formula 212]

(71-6)

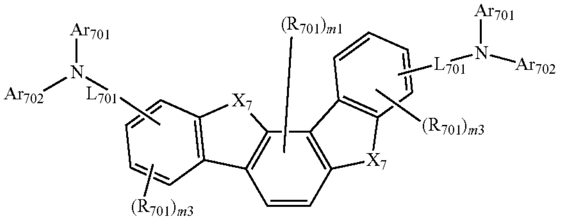

In the formulae (71-1) to (71-6), $R_{701}$, $X_7$, $Ar_{701}$, $Ar_{702}$, $L_{701}$, m1, and m3 respectively represent the same as $R_{701}$, $X_7$, $Ar_{701}$, $Ar_{702}$, $L_{701}$, m1, and m3 in the formula (7).

In an exemplary embodiment, the compound represented by the formula (7) is represented by any one of formulae (71-11) to (71-13) below.

[Formula 213]

(71-11)

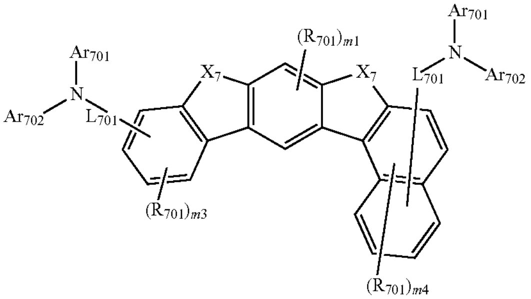

[Formula 214]

(71-12)

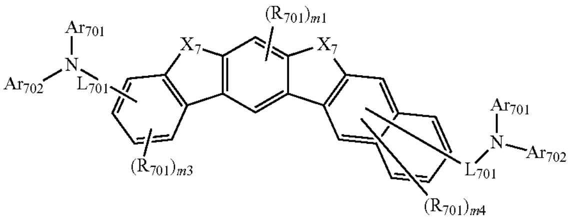

-continued

[Formula 215]

(71-13)

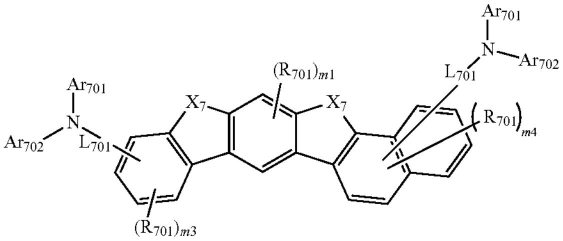

In the formulae (71-11) to (71-13), $R_{701}$, $X_7$, $Ar_{701}$, $Ar_{702}$, $L_{701}$, m1, m3 and m4 respectively represent the same as $R_{701}$, $X_7$, $Ar_{701}$, $Ar_{702}$, $L_{701}$, m1, m3 and m4 in the formula (7).

In an exemplary embodiment, the compound represented by the formula (7) is represented by any one of formulae (71-21) to (71-25) below.

[Formula 216]

(71-21)

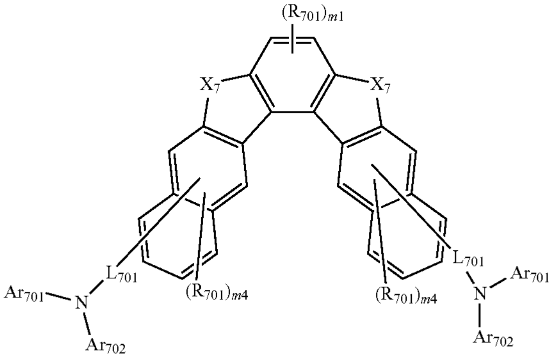

[Formula 217]

(71-22)

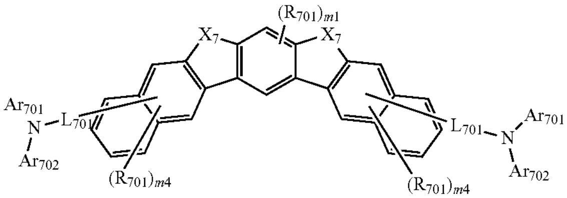

-continued
[Formula 218]
(71-23)
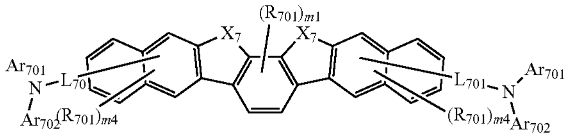
[Formula 219]
(71-24)
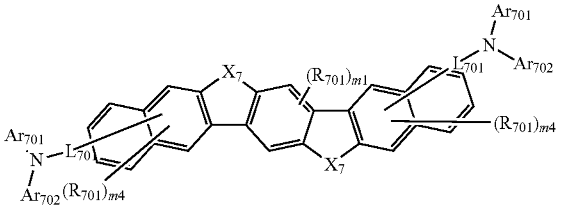
-continued
[Formula 220]
(71-25)
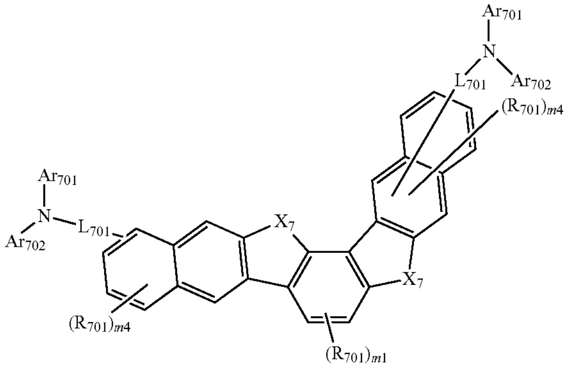
In the formulae (71-21) to (71-25), $R_{701}$, $X_7$, $Ar_{701}$, $Ar_{702}$, $L_{701}$, m1, and m4 respectively represent the same as $R_{701}$, $X_7$, $Ar_{701}$, $Ar_{702}$, $L_{701}$, m1, and m4 in the formula (7).
In an exemplary embodiment, the compound represented by the formula (7) is represented by any one of formulae (71-31) to (71-33) below.
[Formula 221]
(71-31)
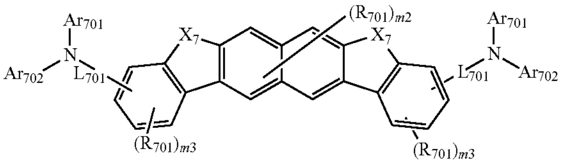
[Formula 222]
(71-32)
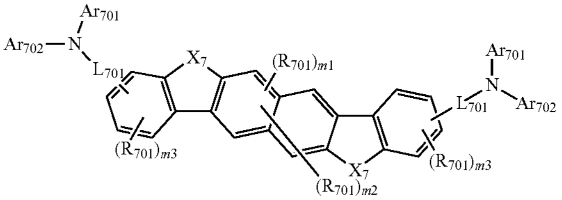
[Formula 223]
(71-33)
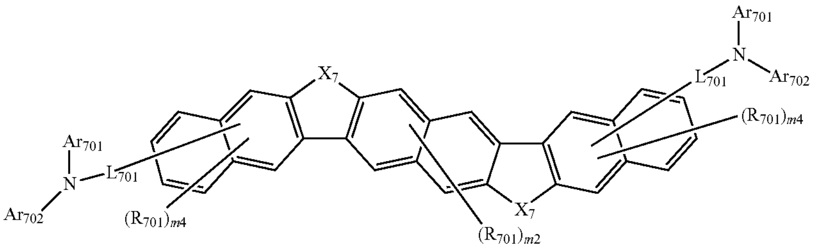

In the formulae (71-31) to (71-33), $R_{701}$, $X_7$, $Ar_{701}$, $Ar_{702}$, $L_{701}$, and m2 to m4 respectively represent the same as $R_{701}$, $X_7$, $Ar_{701}$, $Ar_{702}$, $L_{701}$, and m2 to m4 in the formula (7).

In an exemplary embodiment, $Ar_{701}$ and $Ar_{702}$ are each independently a substituted or unsubstituted aryl group having 6 to 50 ring carbon atoms.

In an exemplary embodiment, one of $Ar_{701}$ and $Ar_{702}$ is a substituted or unsubstituted aryl group having 6 to 50 ring carbon atoms, and the other of $Ar_{701}$ and $Ar_{702}$ is a substituted or unsubstituted heterocyclic group having 5 to 50 ring atoms.

Specific examples of the compound represented by the formula (7) include compounds shown below.

[Formula 224]

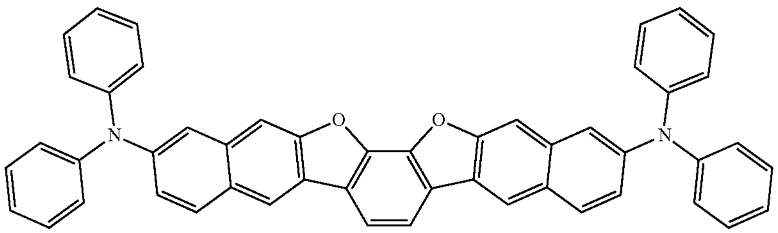

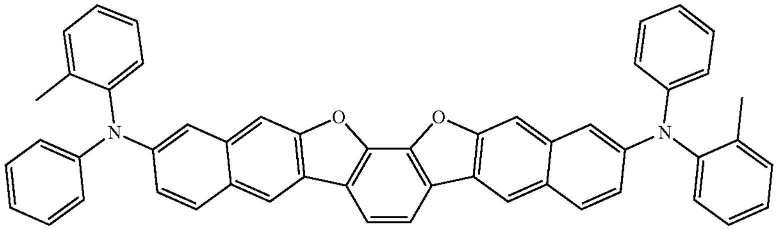

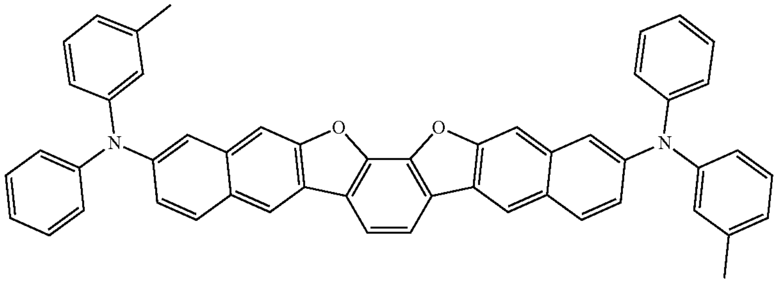

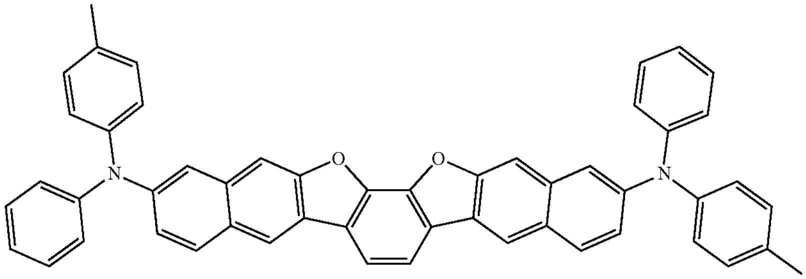

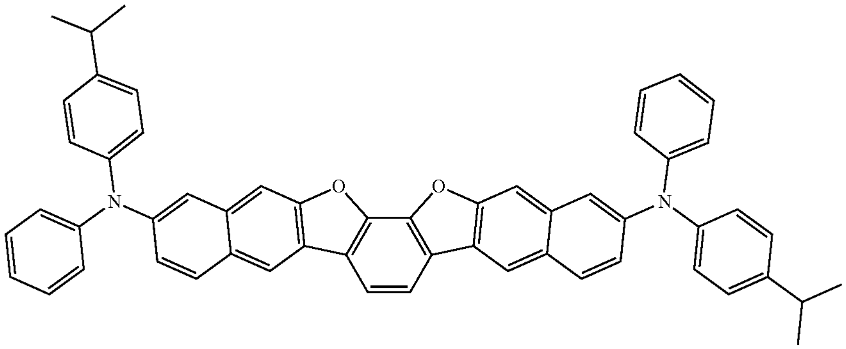

-continued
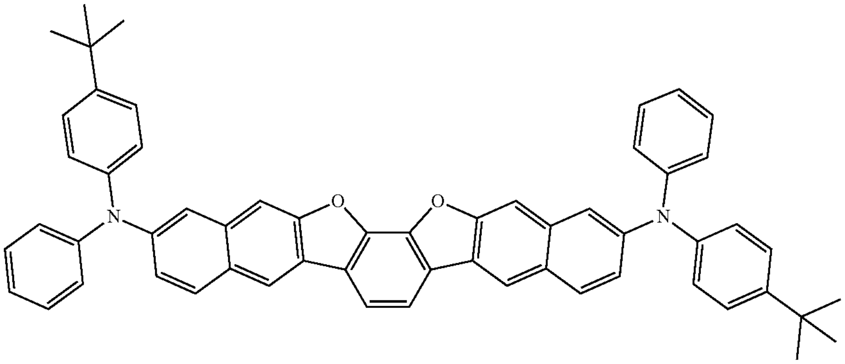
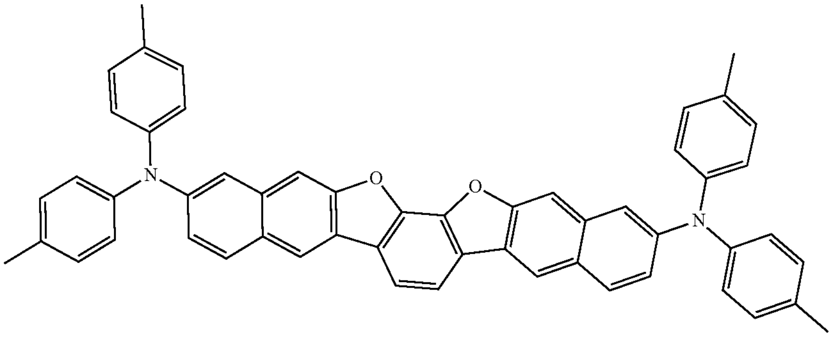
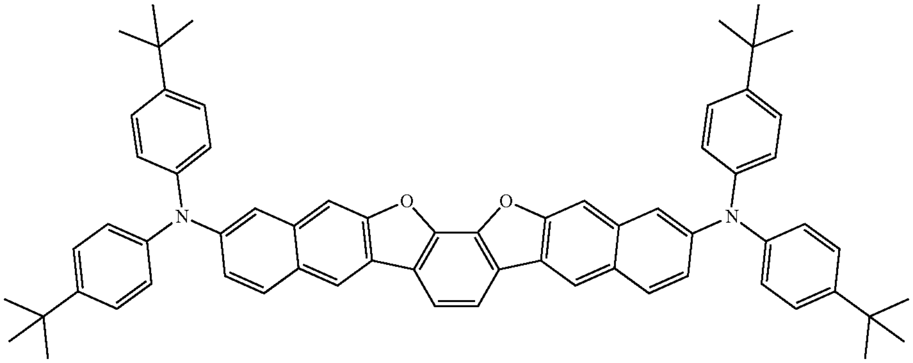
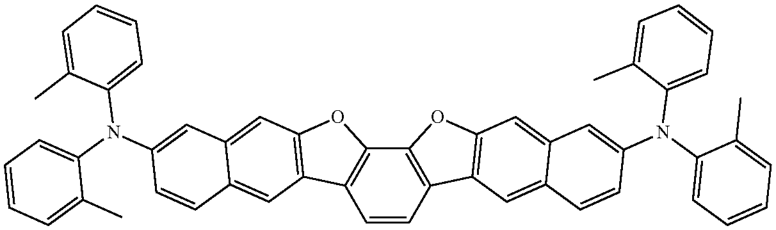
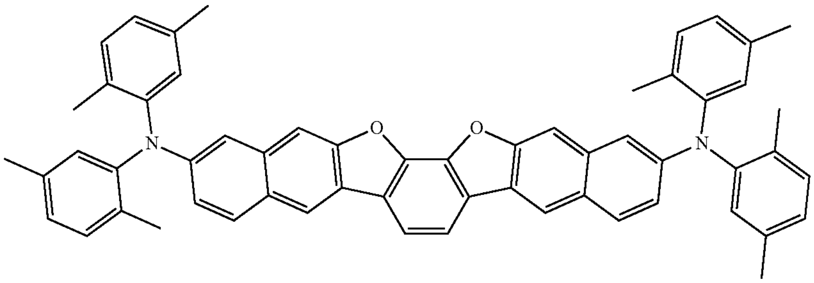

-continued
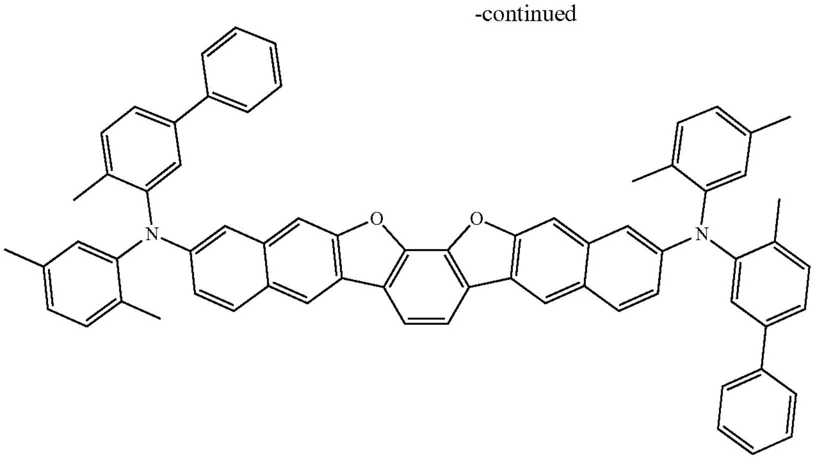
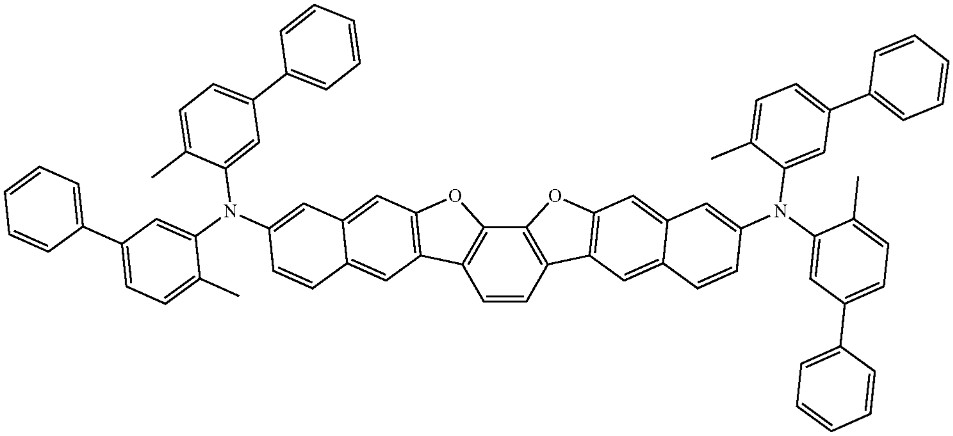
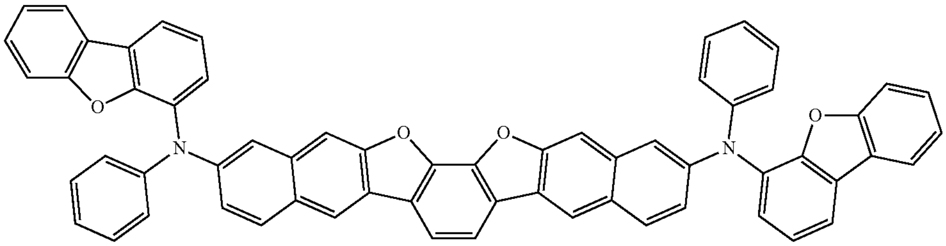
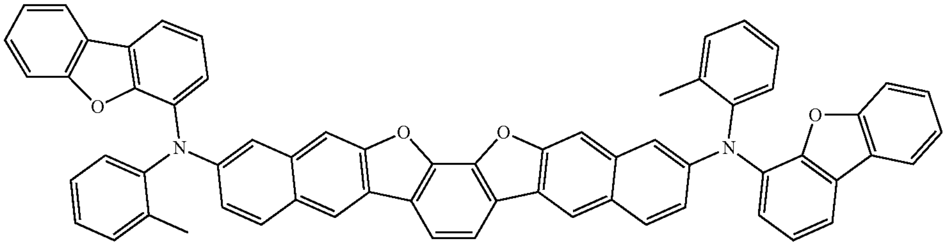
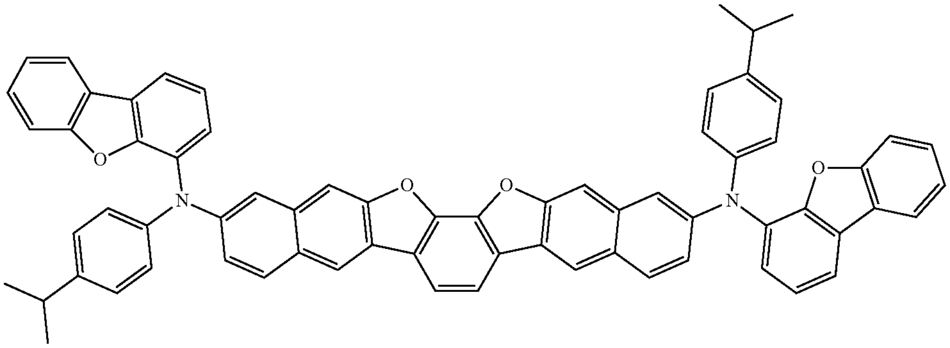

-continued
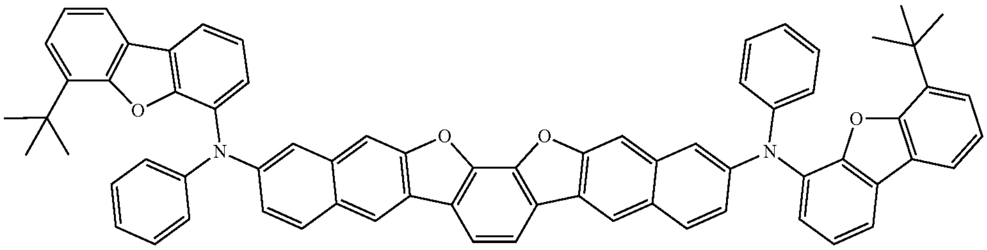
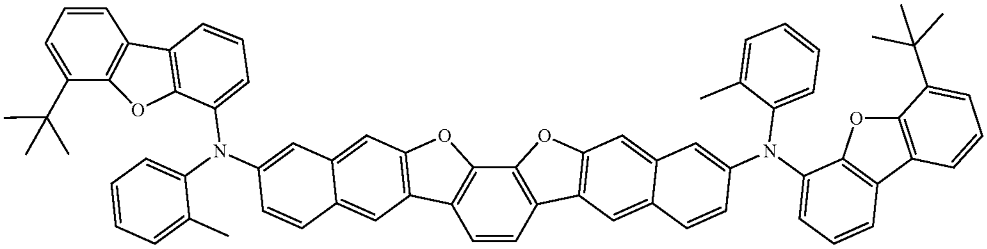
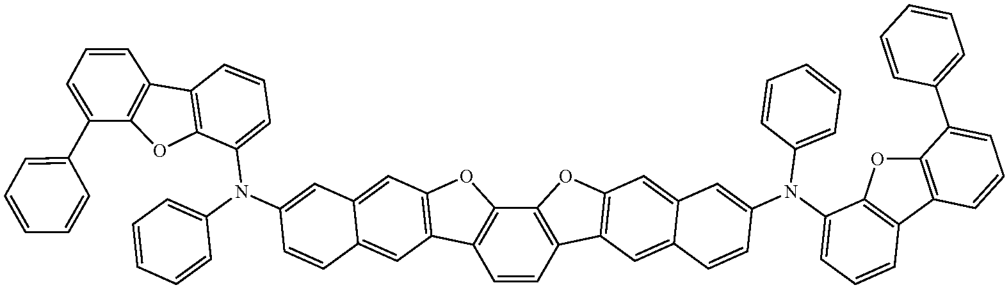
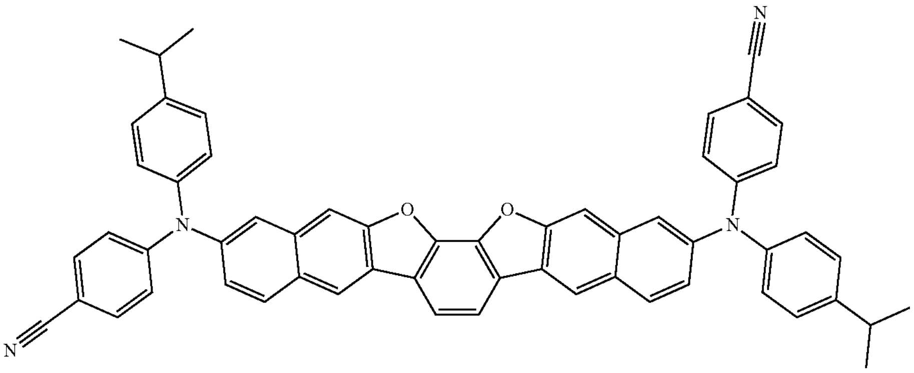
[Formula 225]
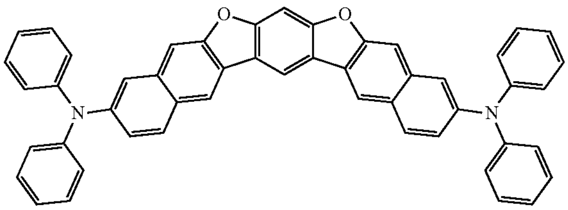
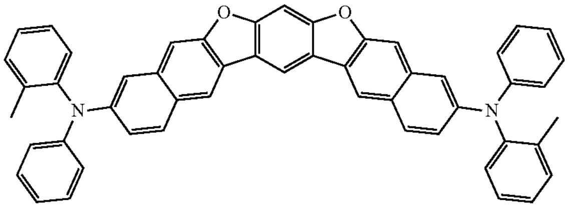

-continued
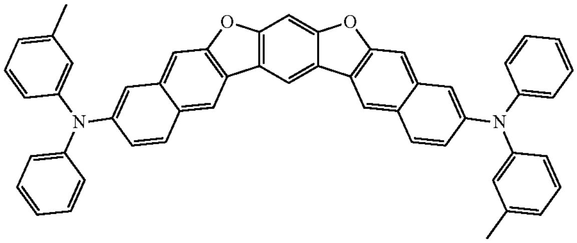
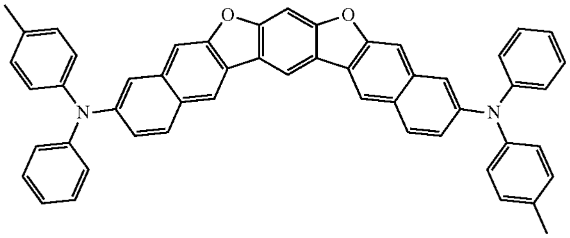
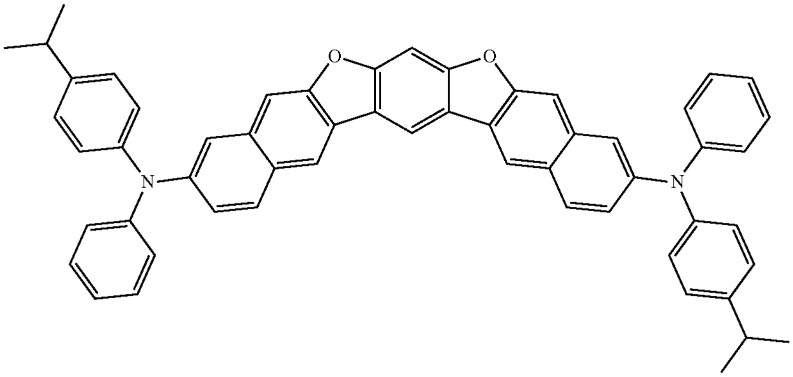
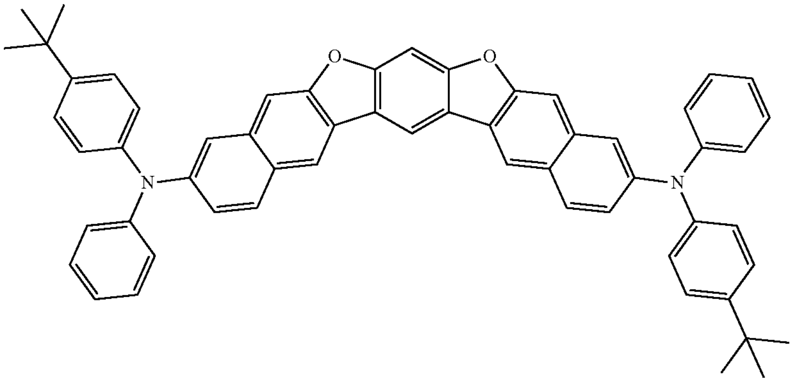
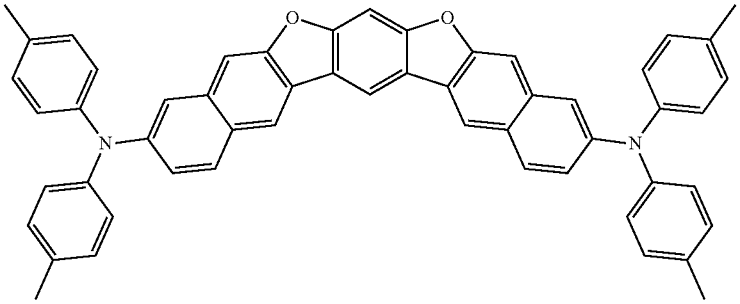

-continued
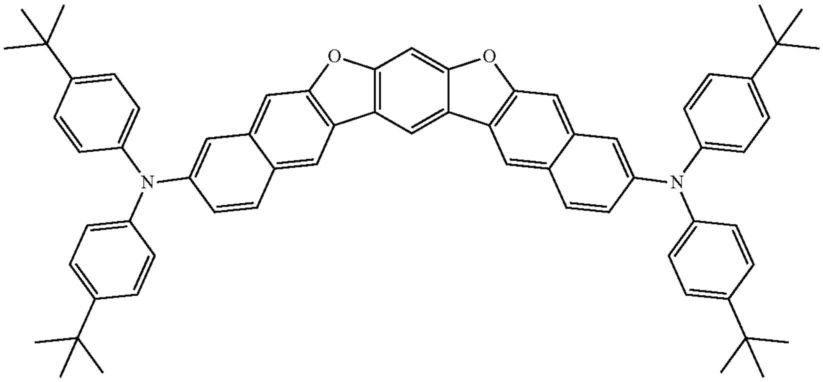
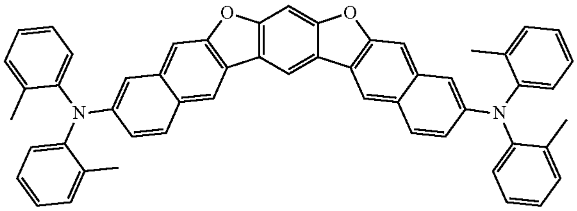
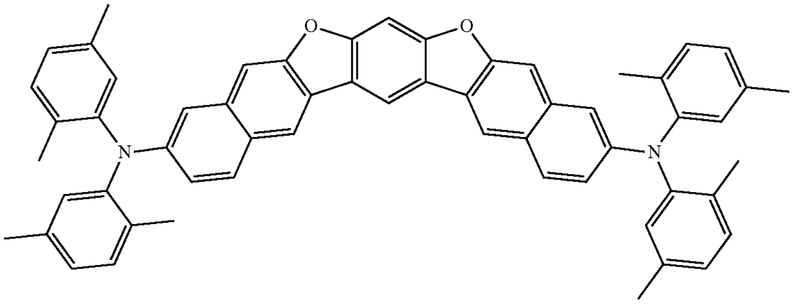
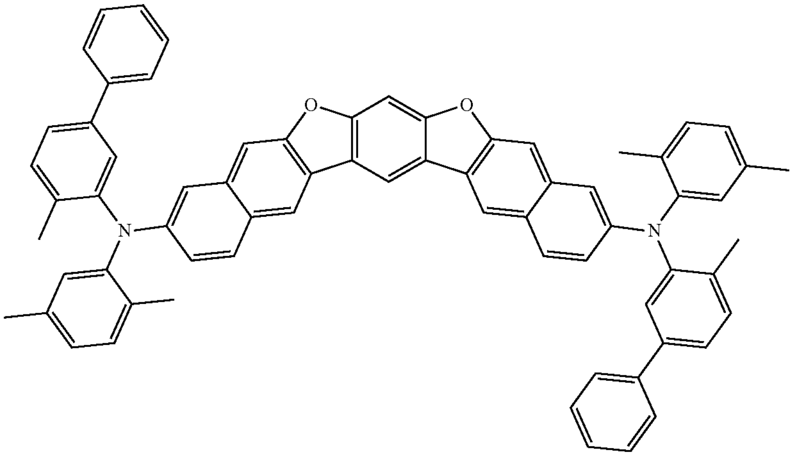

-continued
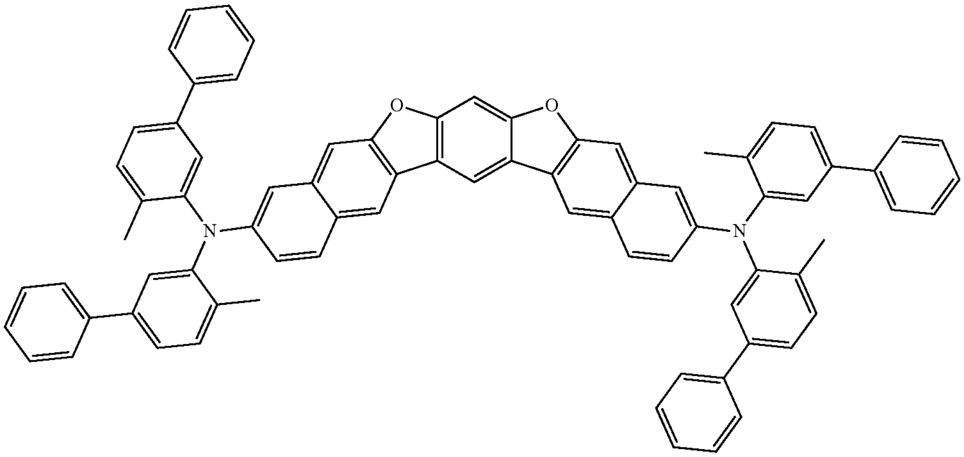
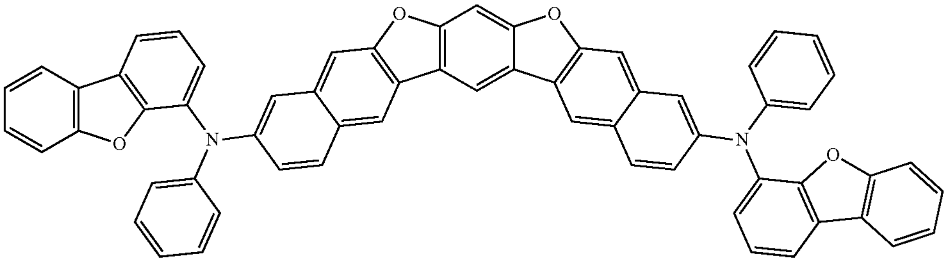
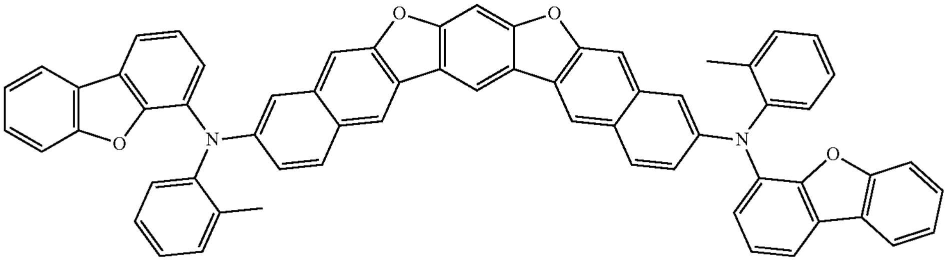
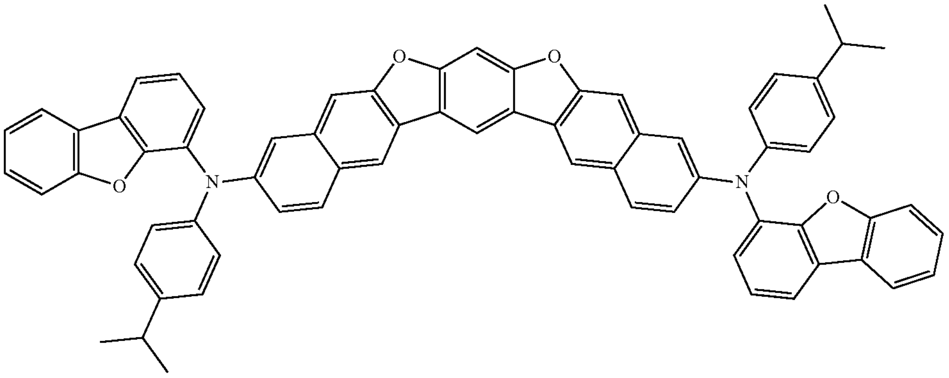
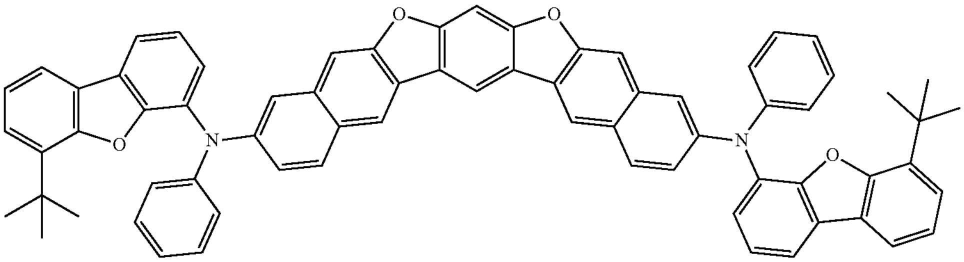

-continued
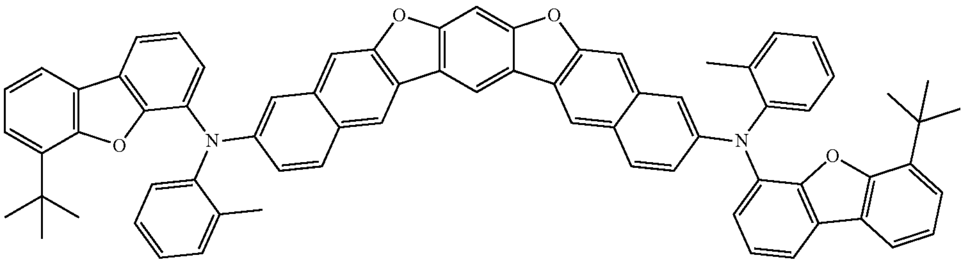
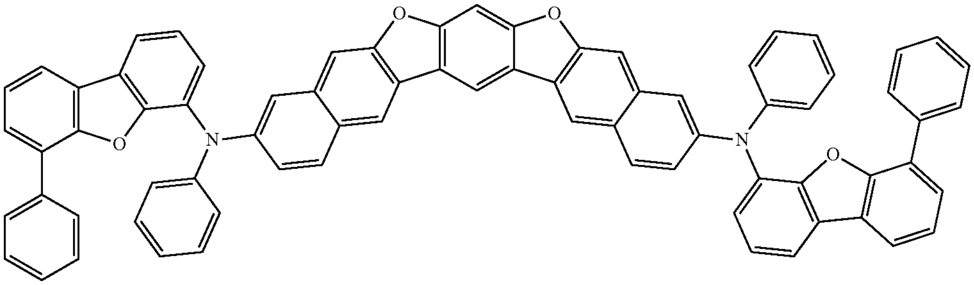
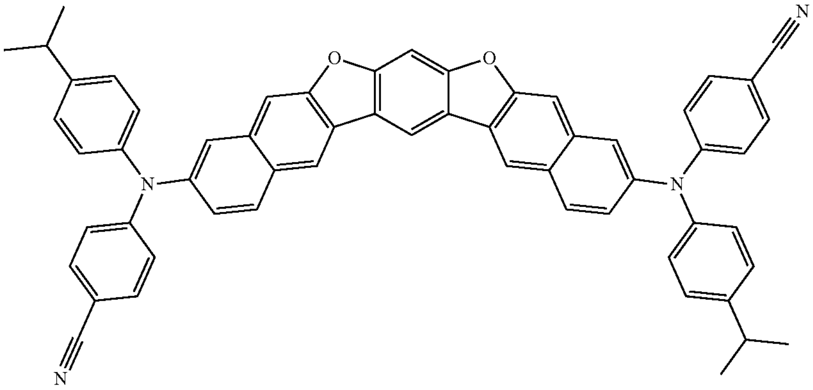
[Formula 226]
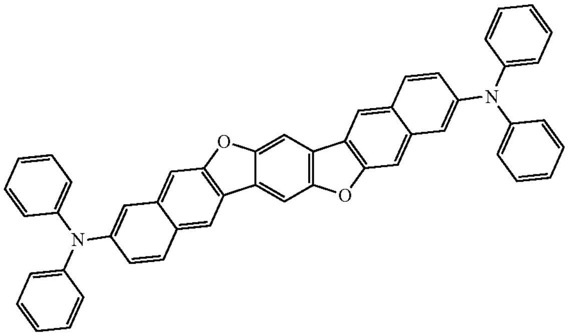
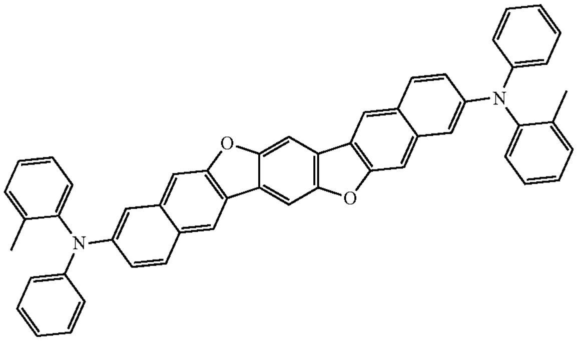

-continued
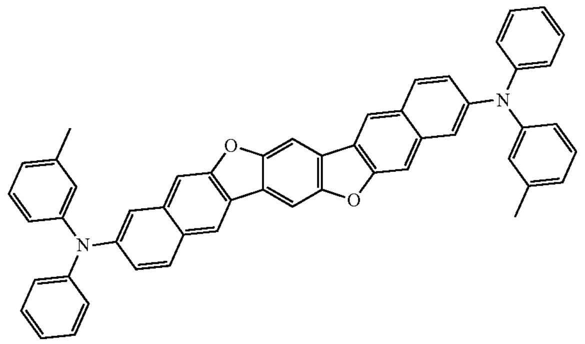
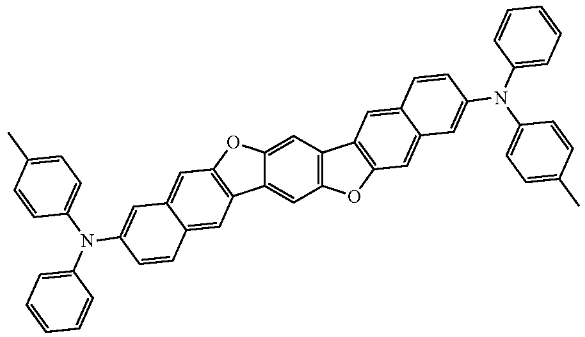
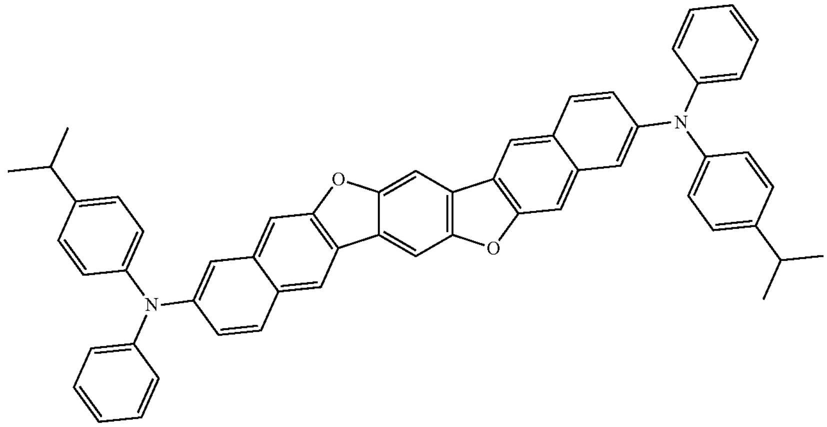
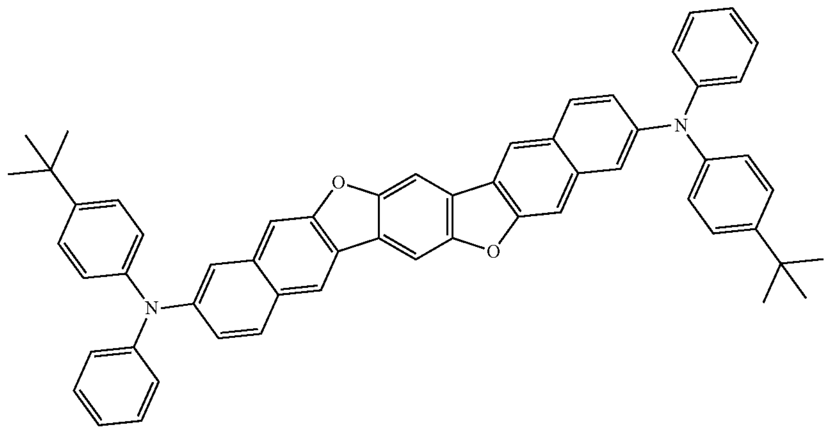

-continued
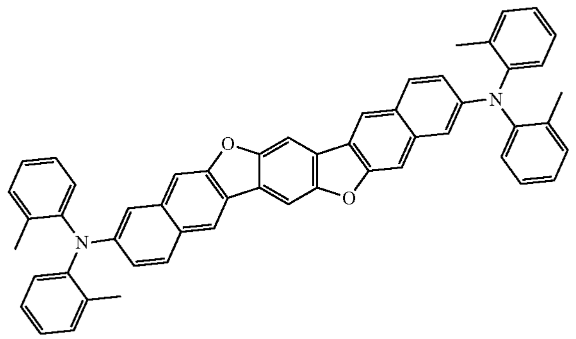
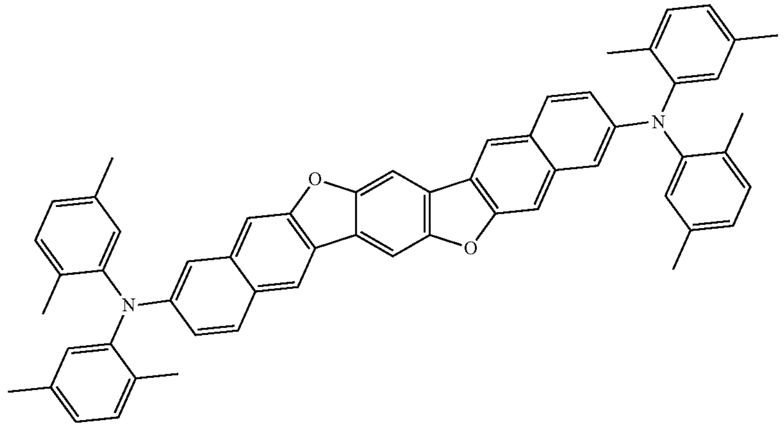
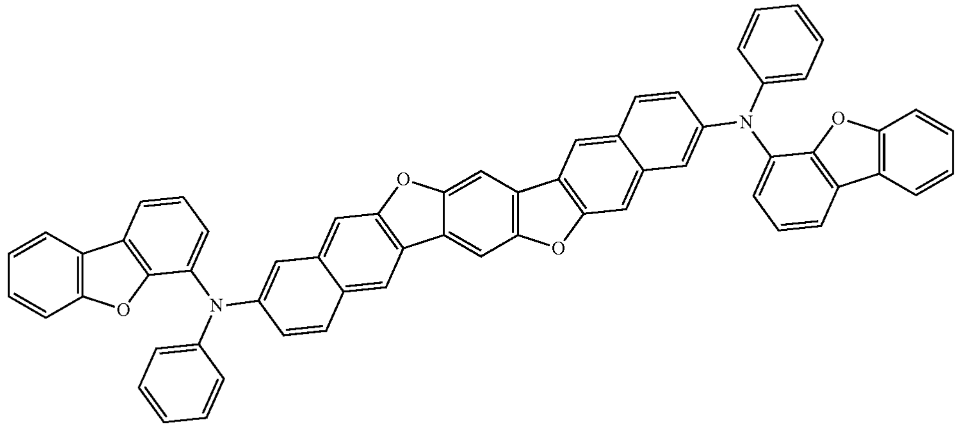
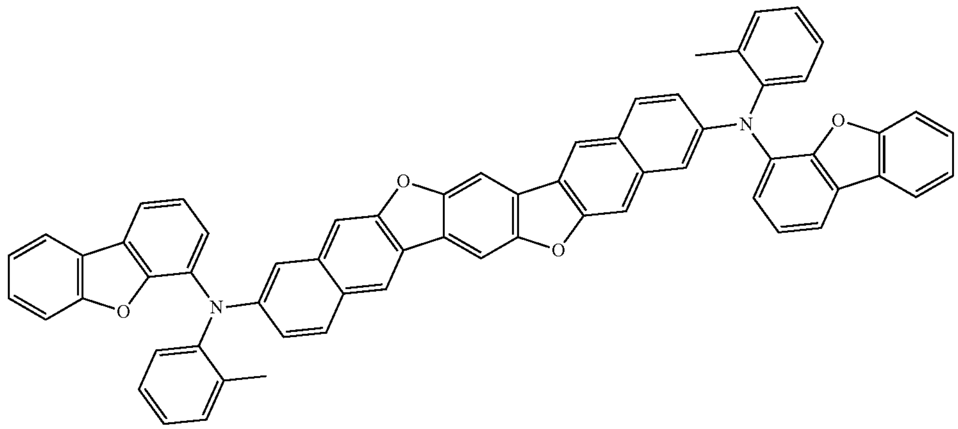

-continued
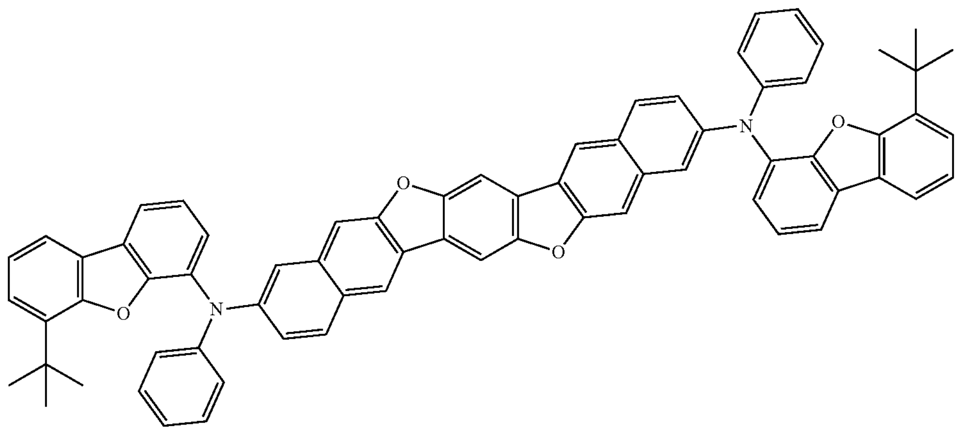
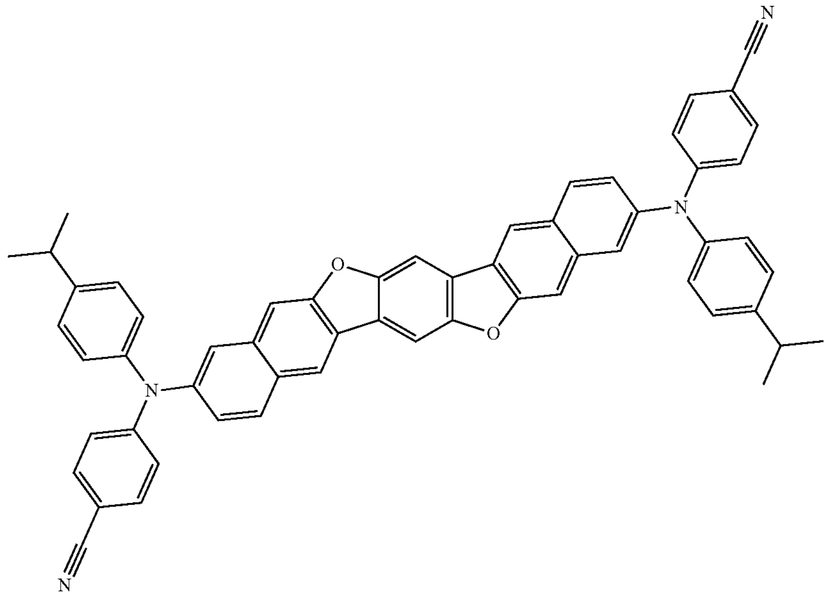
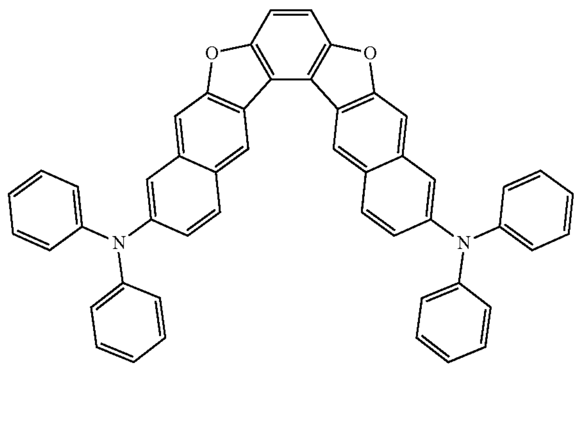

-continued
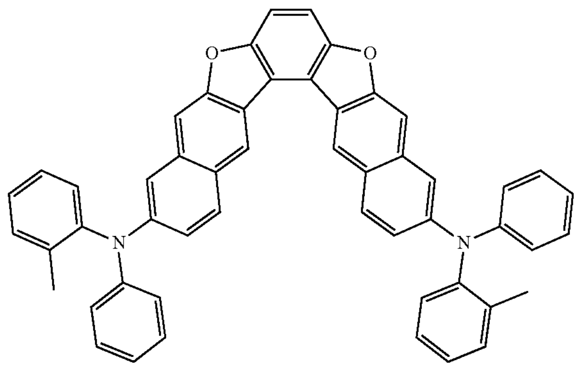
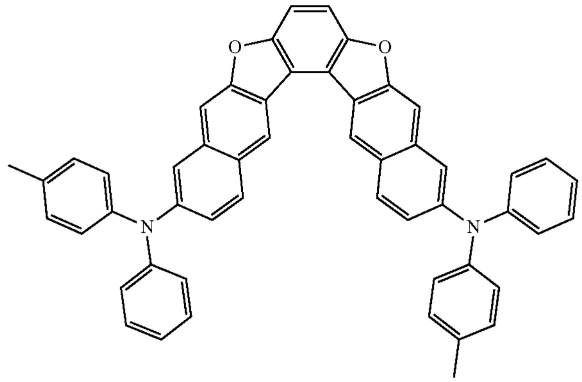
[Formula 227]
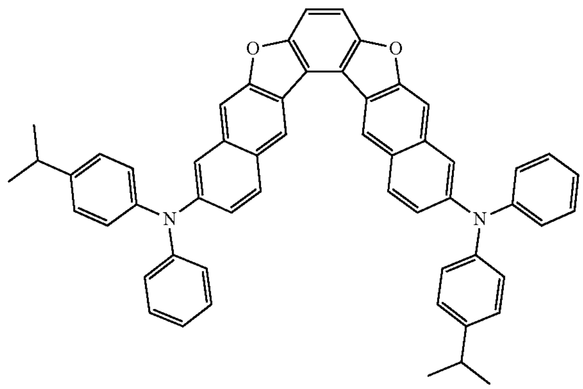
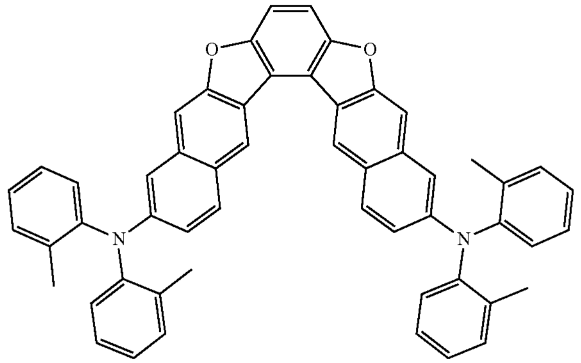

-continued
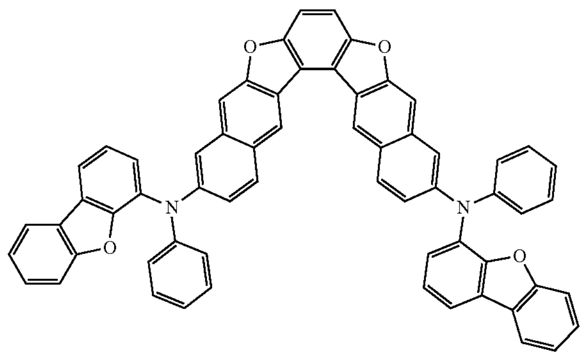
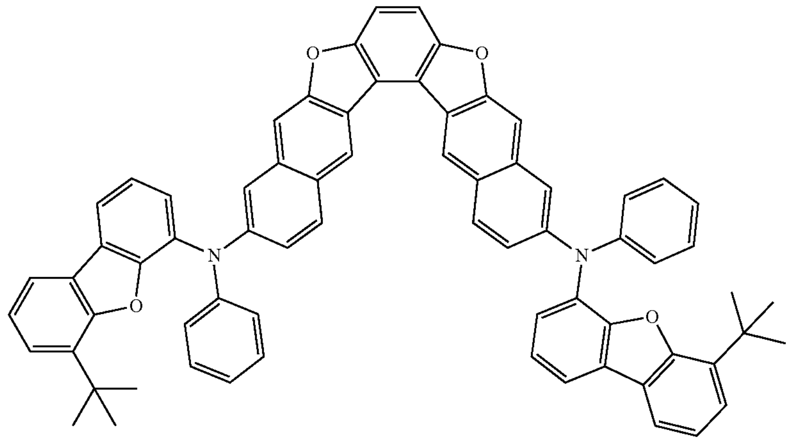
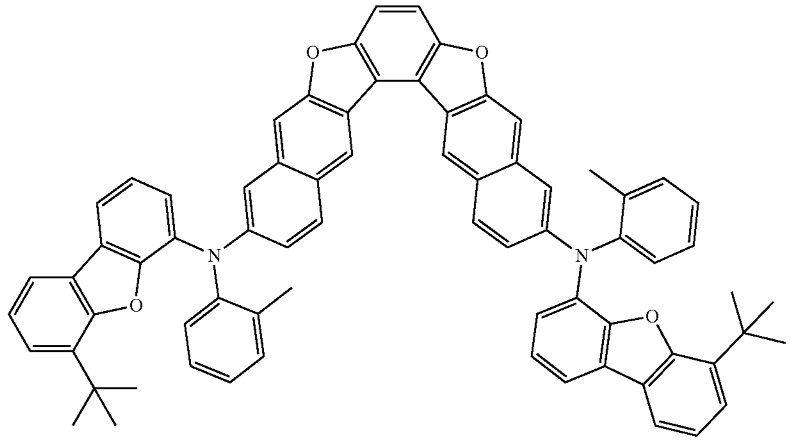
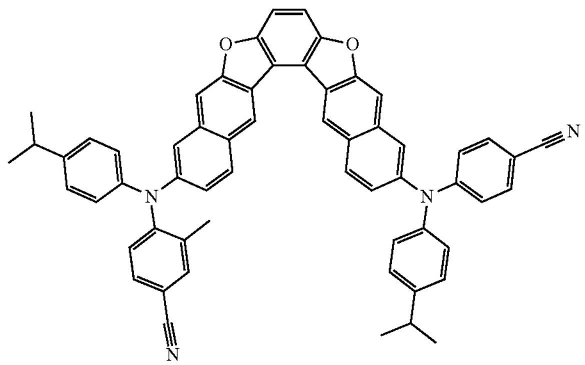

-continued
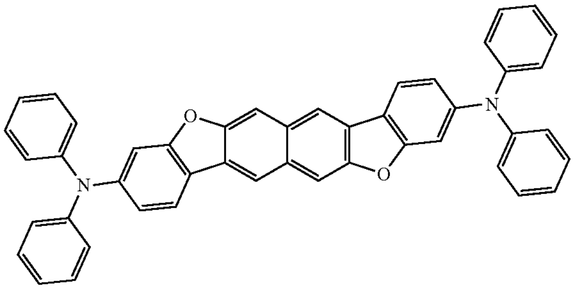
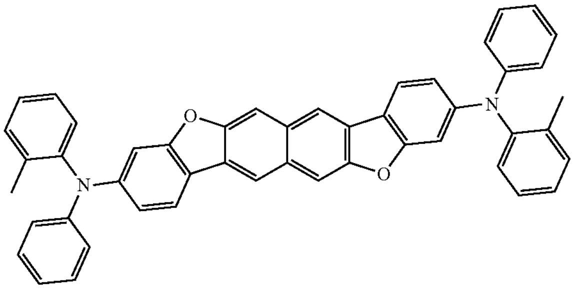
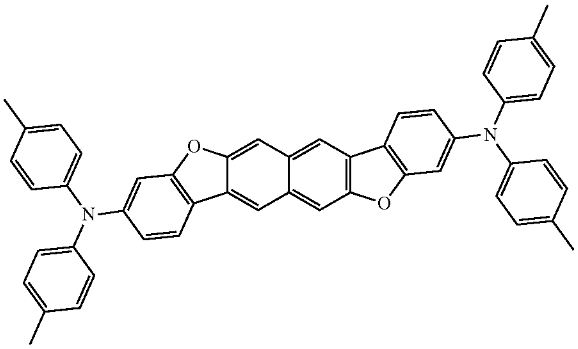
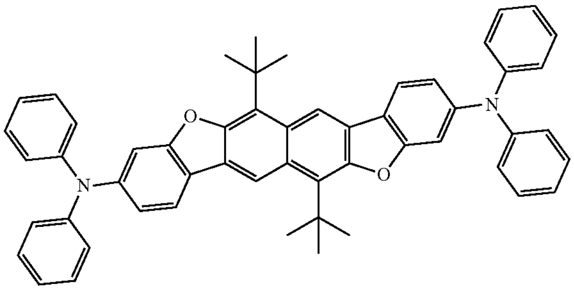
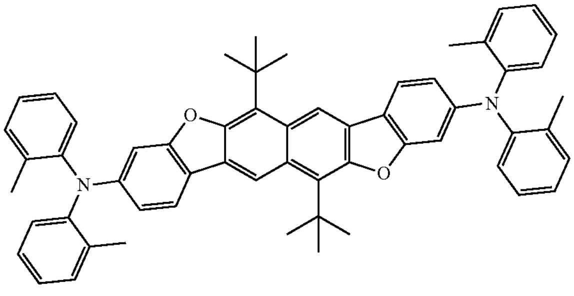

-continued
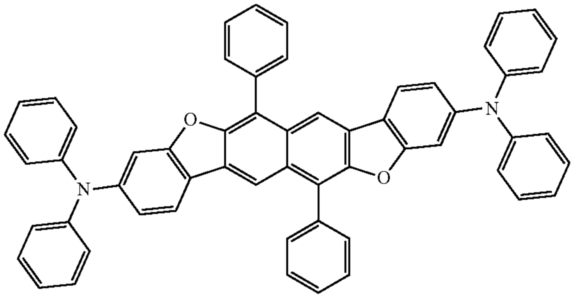
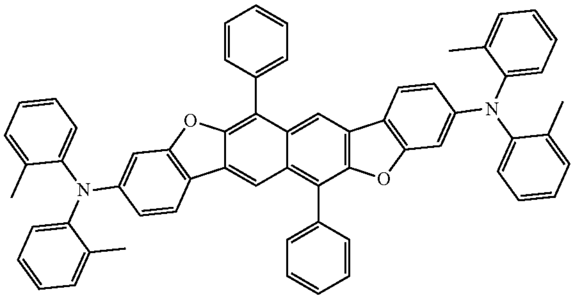
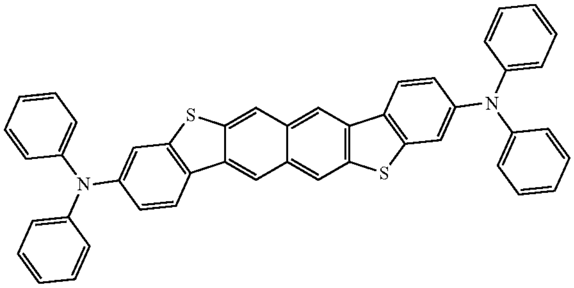
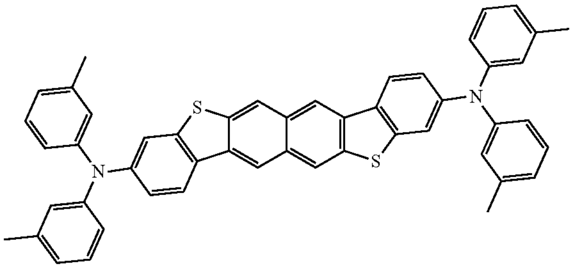
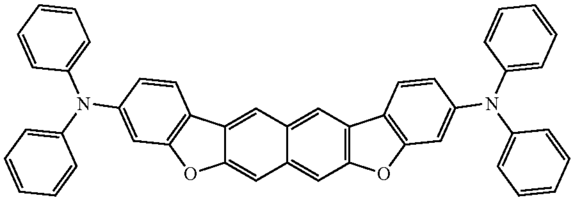
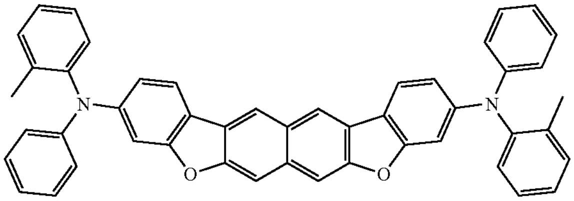

-continued
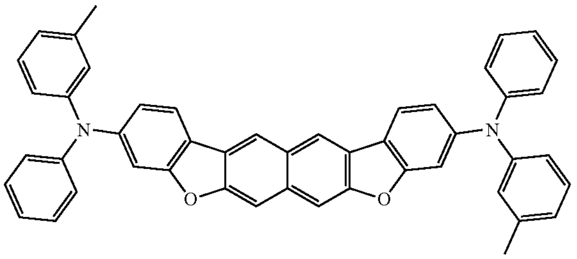
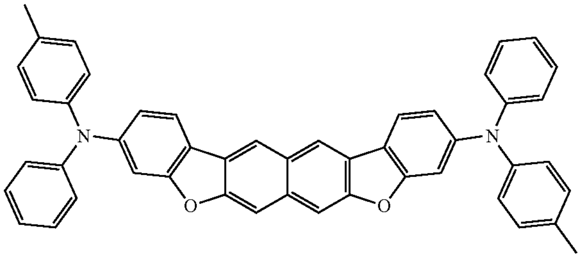
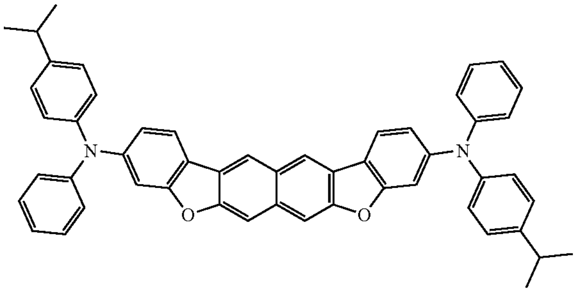
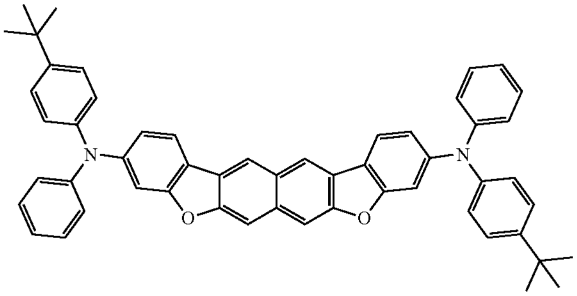
[Formula 228]
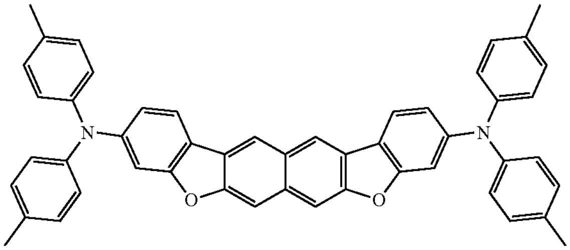
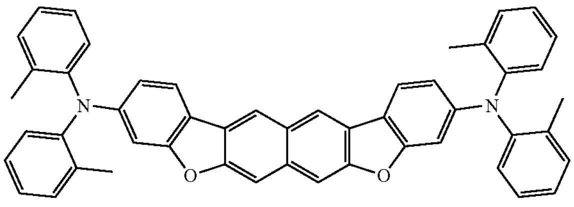

-continued
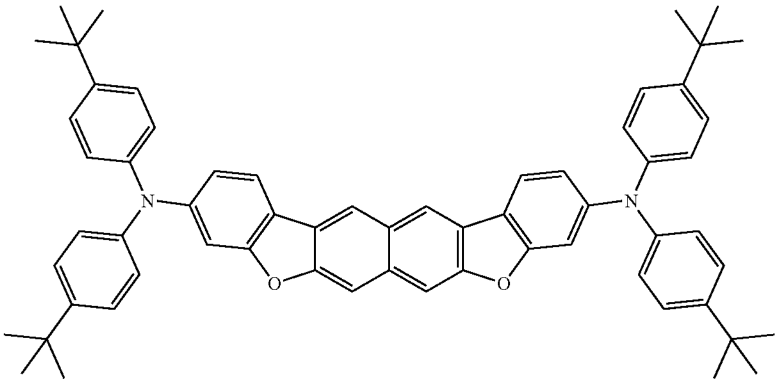
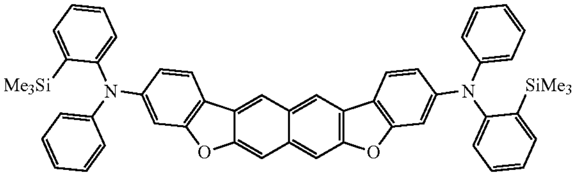
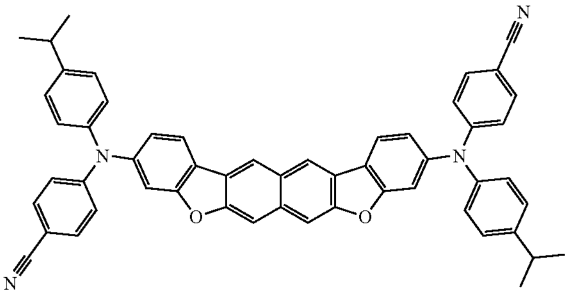
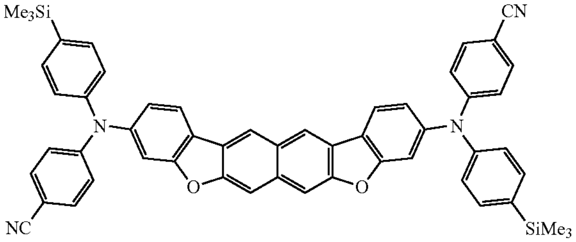
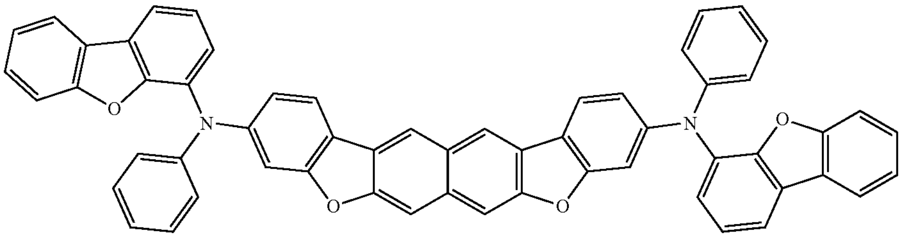
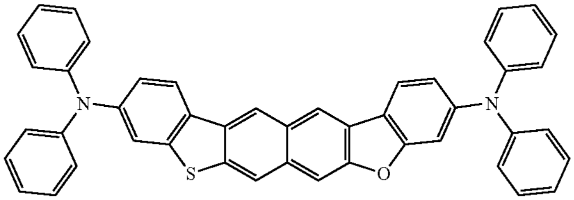

-continued
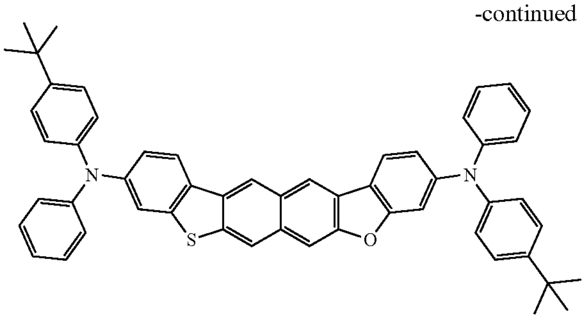
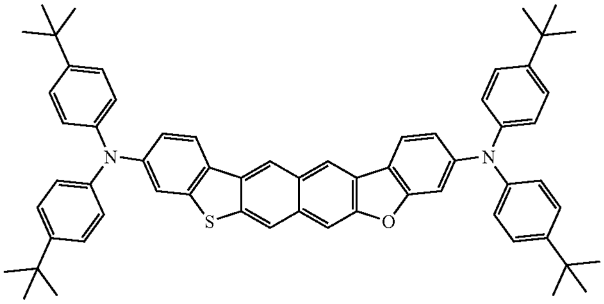
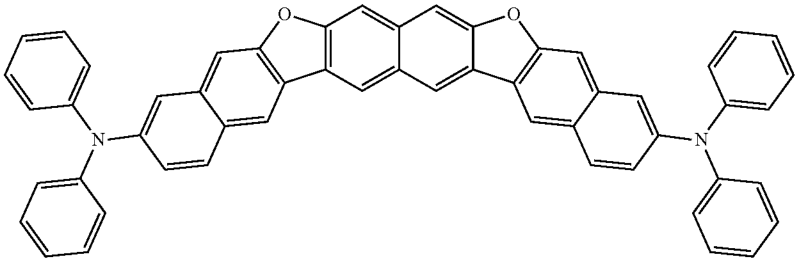
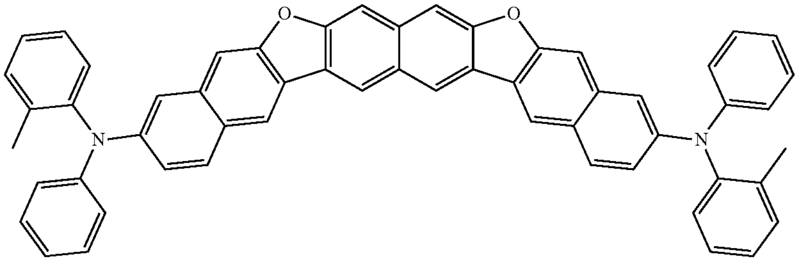
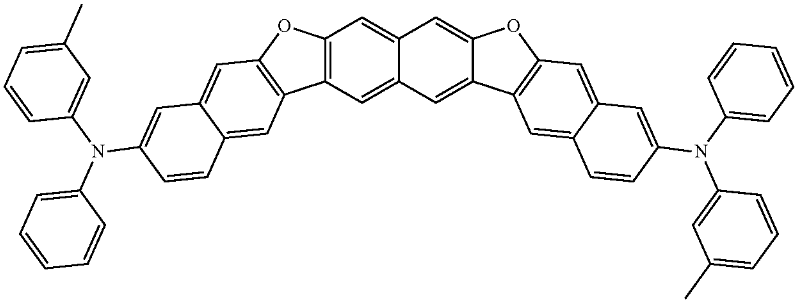
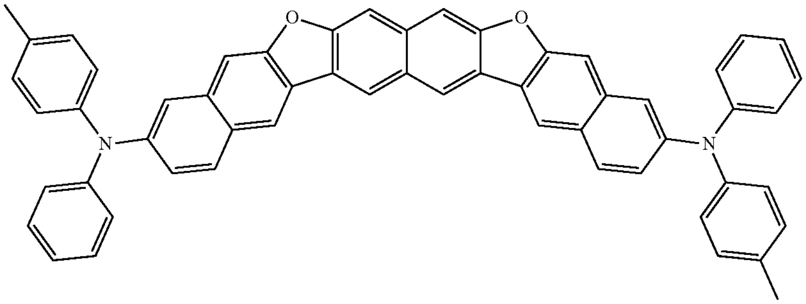

-continued
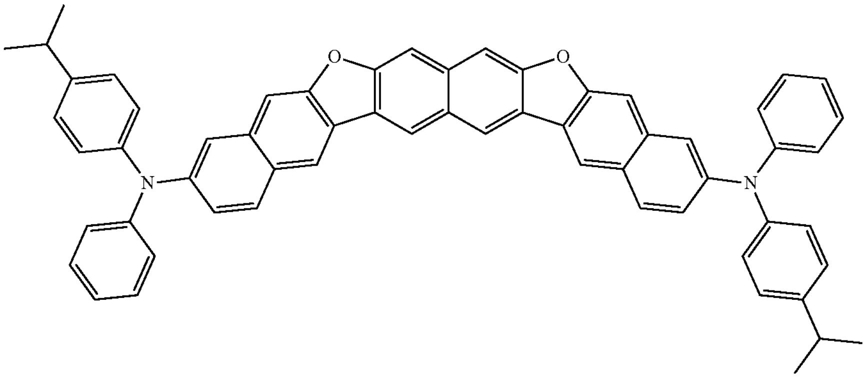
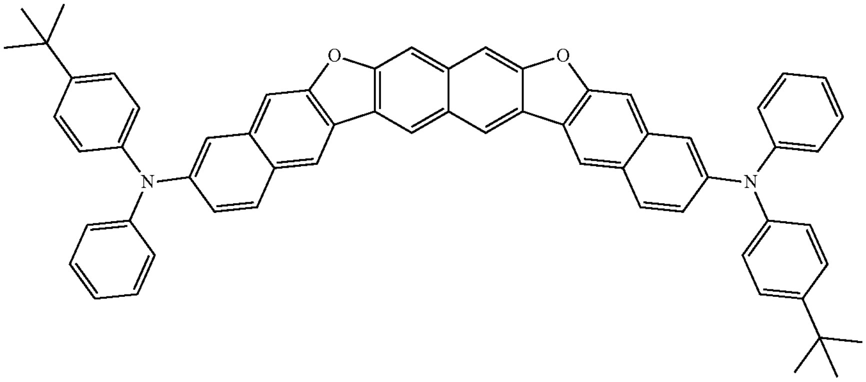
[Formula 229]
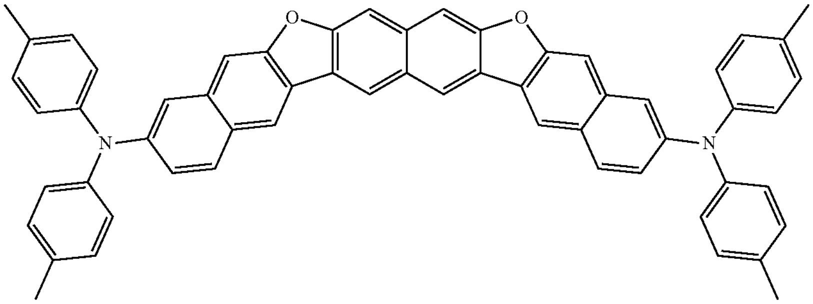
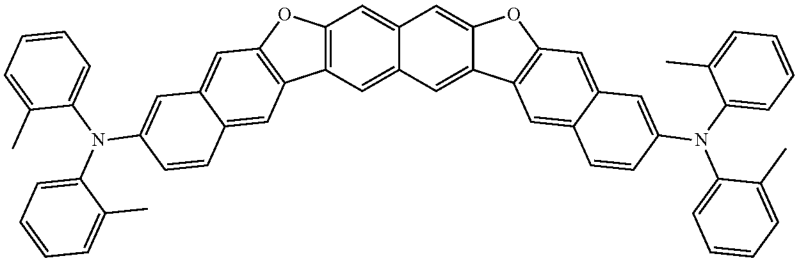

-continued
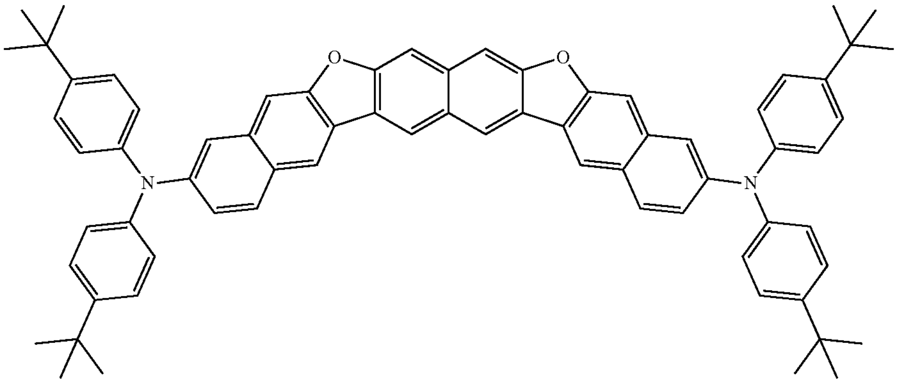
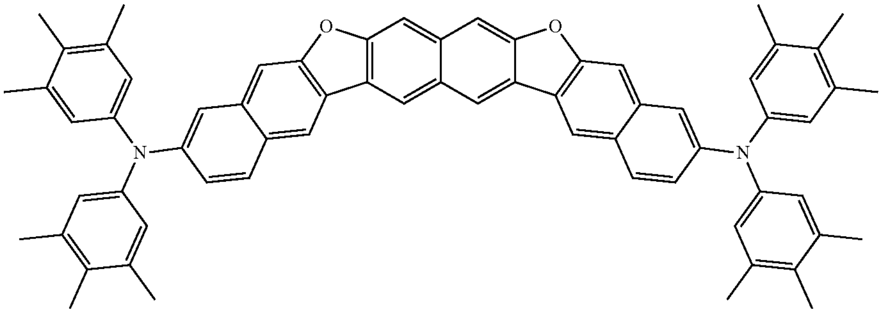
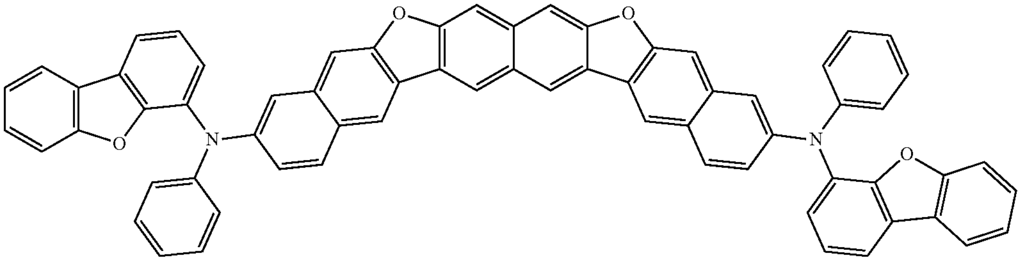
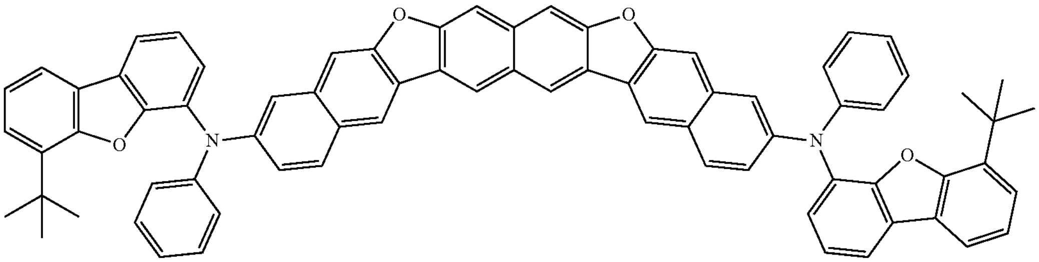

Compound Represented by Formula (8)

The compound represented by the formula (8) will be described below.

[Formula 230]

(8)

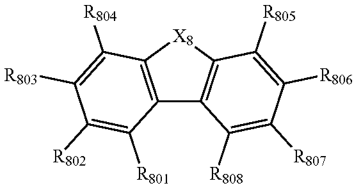

In the formula (8):

at least one combination of $R_{801}$ and $R_{802}$, $R_{802}$ and $R_{803}$, or $R_{803}$ and $R_{804}$ are mutually bonded to form a divalent group represented by a formula (82) below; and at least one combination of $R_{805}$ and $R_{806}$, $R_{806}$ and $R_{807}$, or $R_{807}$ and $R_{808}$ are mutually bonded to form a divalent group represented by a formula (83) below.

[Formula 231]

(82)

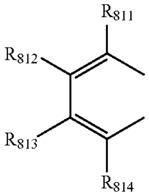

(83)

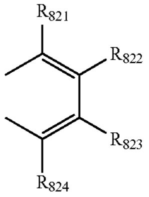

At least one of $R_{801}$ to $R_{804}$ not forming the divalent group represented by the formula (82) or $R_{811}$ to $R_{814}$ is a monovalent group represented by a formula (84) below;

at least one of $R_{805}$ to $R_{808}$ not forming the divalent group represented by the formula (83) or $R_{821}$ to $R_{824}$ is a monovalent group represented by a formula (84) below;

$X_8$ is an oxygen atom, a sulfur atom, or $NR_{809}$; and $R_{801}$ to $R_{808}$ not forming the divalent group represented by the formula (82) or (83) and not being the monovalent group represented by the formula (84), $R_{811}$ to $R_{814}$ and $R_{821}$ to $R_{824}$ not being the monovalent group represented by the formula (84), and $R_{809}$ are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —$Si(R_{901})(R_{902})(R_{903})$, a group represented by —O—$(R_{904})$, a group represented by —S—$(R_{905})$, a group represented by —$N(R_{906})(R_{907})$, a halogen atom, a cyano group, a nitro group, a substituted or unsubstituted aryl group having 6 to 50 ring carbon atoms, or a substituted or unsubstituted heterocyclic group having 5 to 50 ring atoms.

[Formula 232]

(84)

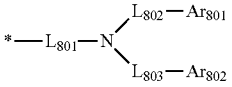

In the formula (84):

$Ar_{801}$ and $Ar_{802}$ are each independently a substituted or unsubstituted aryl group having 6 to 50 ring carbon atoms, or a substituted or unsubstituted heterocyclic group having 5 to 50 ring atoms;

$L_{801}$ to $L_{803}$ are each independently a single bond, a substituted or unsubstituted arylene group having 6 to 30 ring carbon atoms, a substituted or unsubstituted divalent heterocyclic group having 5 to 30 ring atoms, or a divalent linking group formed by bonding two, three or four groups selected from the group consisting of a substituted or unsubstituted arylene group having 6 to 30 ring carbon atoms and a substituted or unsubstituted divalent heterocyclic group having 5 to 30 ring atoms; and

* in the formula (84) represents a bonding position to a cyclic structure represented by the formula (8) or a bonding position to a group represented by the formula (82) or (83).

In the formula (8), the positions for the divalent group represented by the formula (82) and the divalent group represented by the formula (83) to be formed are not specifically limited but the divalent groups may be formed at any possible positions on $R_{801}$ to $R_{808}$.

In an exemplary embodiment, the compound represented by the formula (8) is represented by any one of formulae (81-1) to (81-6) below.

[Formula 233]

(81-1)

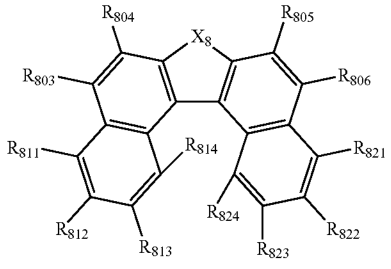

(81-2)

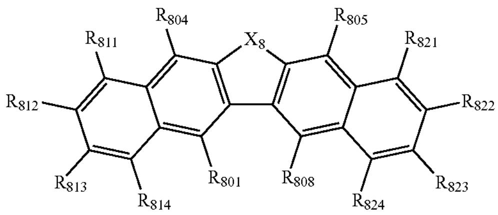

-continued

[Formula 234]

(81-3)

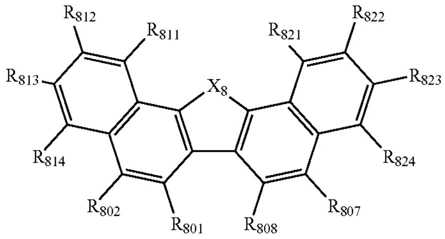

(81-4)

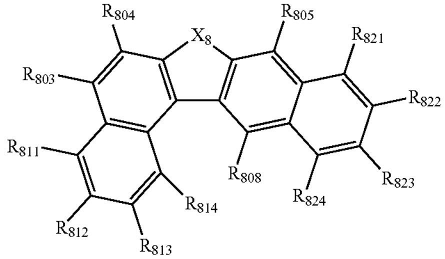

[Formula 235]

(81-5)

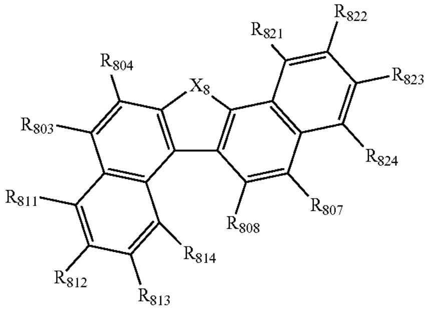

(81-6)

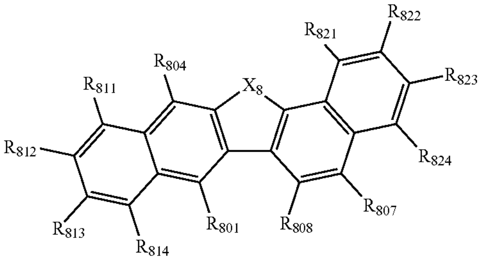

In the formulae (81-1) to (81-6):

$X_8$ represents the same as $X_8$ in the formula (8);

at least two of $R_{801}$ to $R_{824}$ are each a monovalent group represented by the formula (84); and $R_{801}$ to $R_{824}$ that are not the monovalent group represented by the formula (84) are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms.

In an exemplary embodiment, the compound represented by the formula (8) is represented by any one of formulae (81-7) to (81-18) below.

[Formula 236]

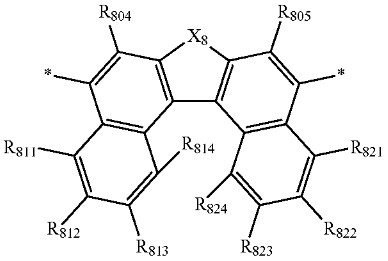

(81-7)

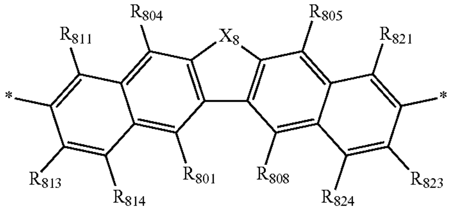

(81-8)

[Formula 237]

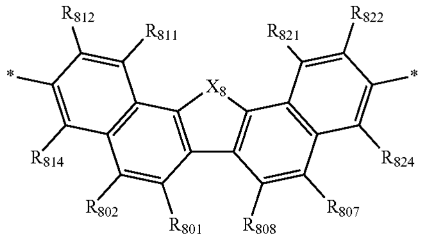

(81-9)

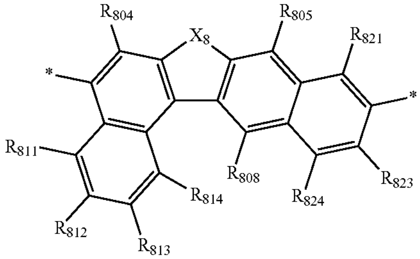

(81-10)

-continued

[Formula 238]

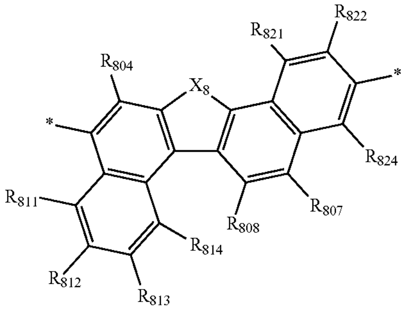

(81-11)

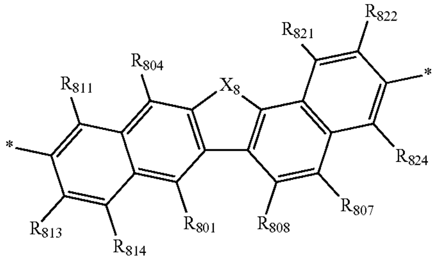

(81-12)

[Formula 239]

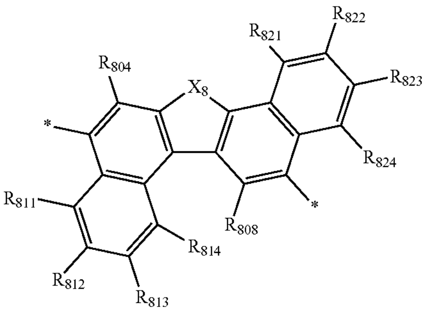

(81-13)

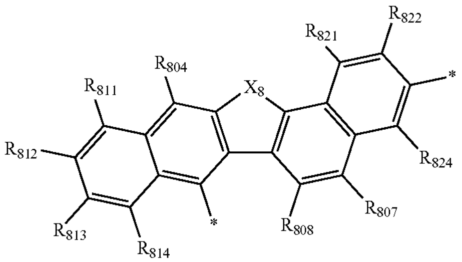

(81-14)

[Formula 240]

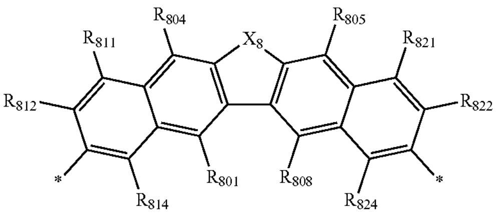

(81-15)

-continued

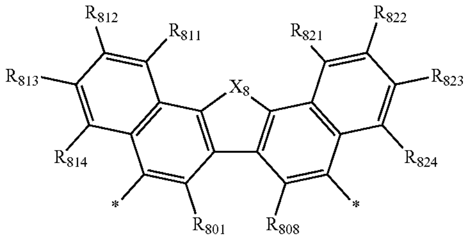

(81-16)

[Formula 241]

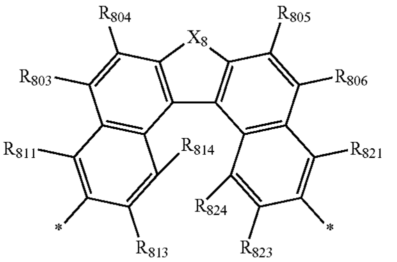

(81-17)

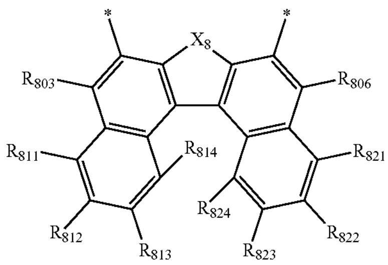

(81-18)

In the formulae (81-7) to (81-18):

$X_8$ represents the same as $X_8$ in the formula (8);

* is a single bond bonded to a monovalent group represented by the formula (84); and $R_{801}$ to $R_{824}$ each independently represent the same as $R_{801}$ to $R_{824}$ in the formulae (81-1) to (81-6) that are not the monovalent group represented by the formula (84).

$R_{801}$ to Roos not forming the divalent group represented by the formula (82) or (83) and not being the monovalent group represented by the formula (84), and $R_{811}$ to $R_{814}$ and $R_{821}$ to $R_{824}$ not being the monovalent group represented by the formula (84) are preferably each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms.

The monovalent group represented by the formula (84) is preferably represented by a formula (85) or (86) below.

[Formula 242]

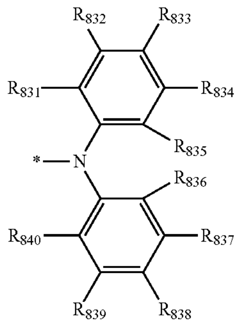

(85)

In the formula (85):

$R_{831}$ to $R_{840}$ are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms; and

* in the formula (85) represents the same as * in the formula (84).

[Formula 243]

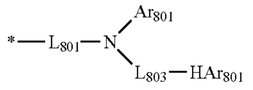

(86)

In the formula (86):

$Ar_{801}$, $L_{801}$, and Laos represent the same as $Ar_{801}$, $L_{801}$, and $L_{803}$ in the formula (84); and $HAr_{801}$ is a structure represented by a formula (87) below.

[Formula 244]

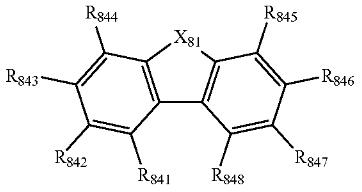

(87)

In the formula (87):

$X_{81}$ is an oxygen atom or a sulfur atom;

one of $R_{841}$ to $R_{848}$ is a single bond with $L_{803}$; and $R_{841}$ to $R_{848}$ not being the single bond are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms.

Specific examples of the compound represented by the formula (8) include compounds shown below as well as the compounds disclosed in WO 2014/104144.

[Formula 245]

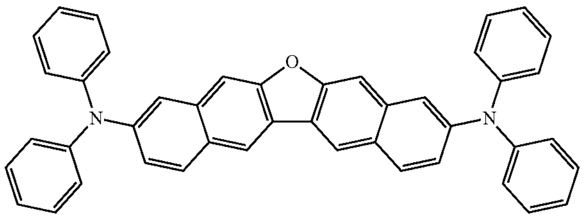

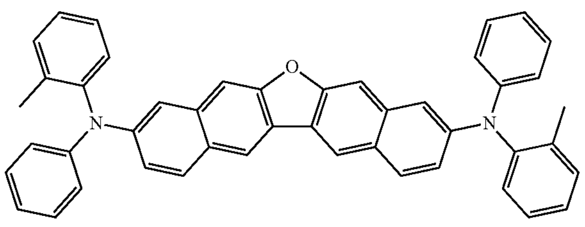

-continued
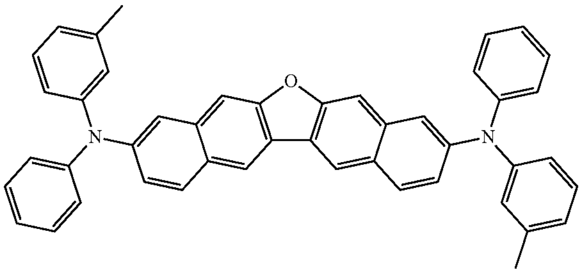
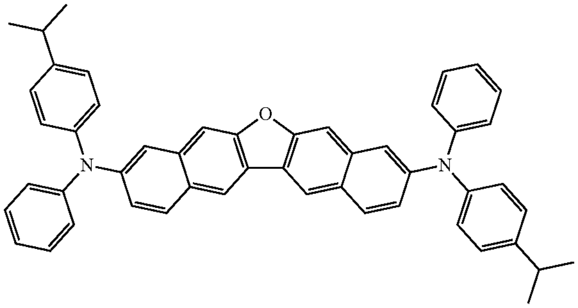
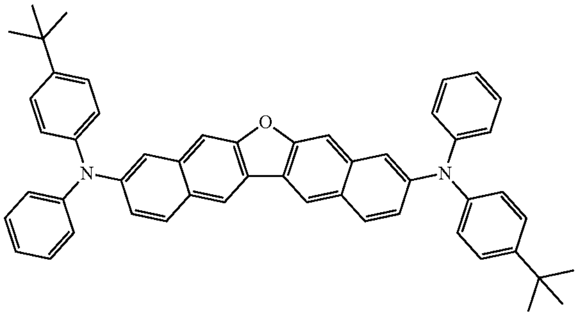
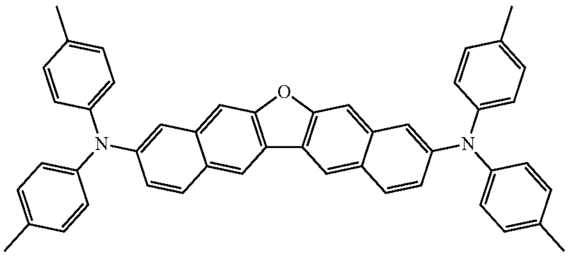
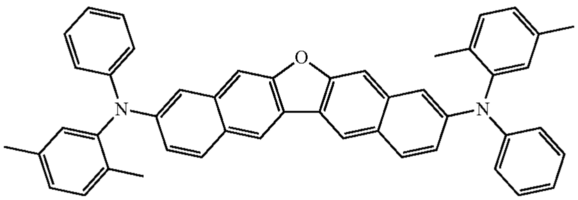
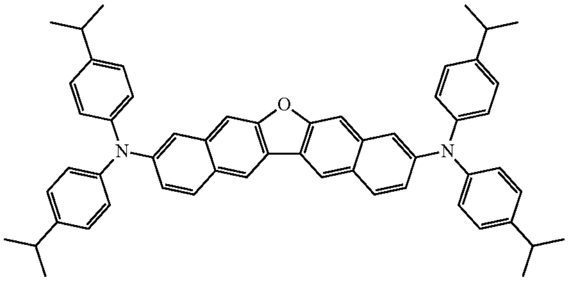

-continued
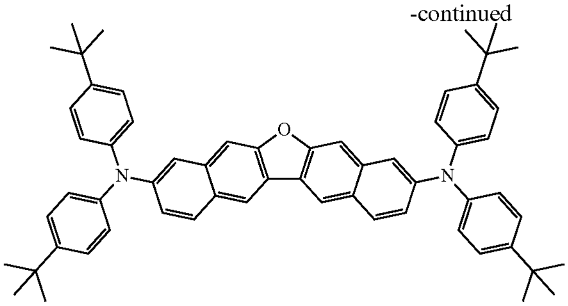
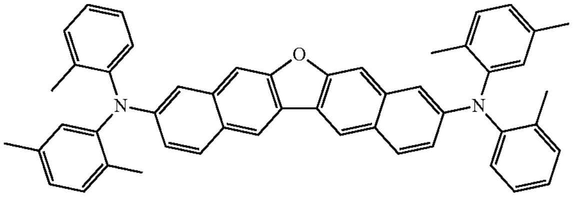
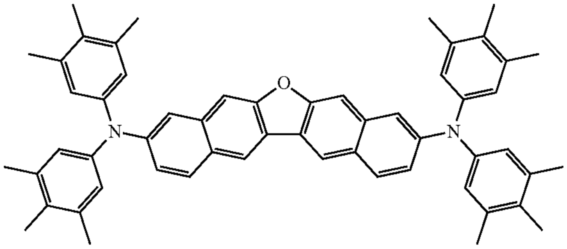
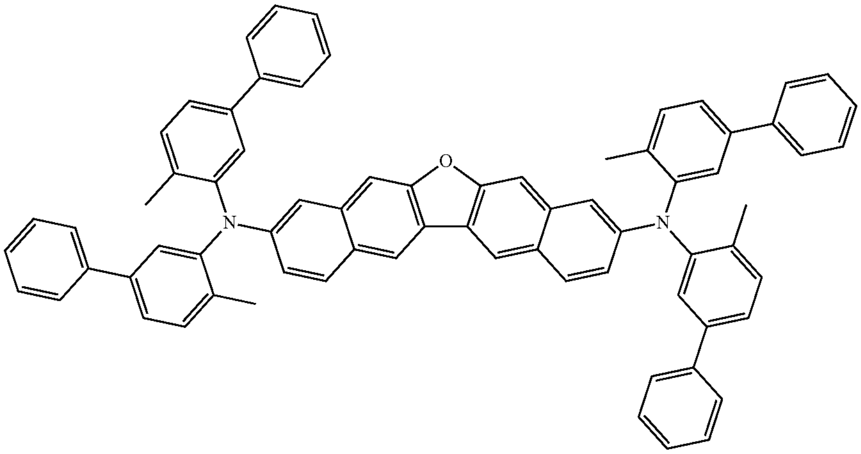
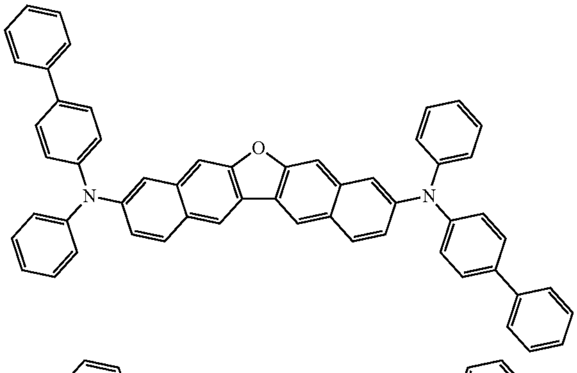
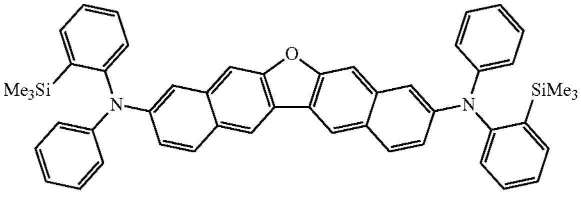

-continued
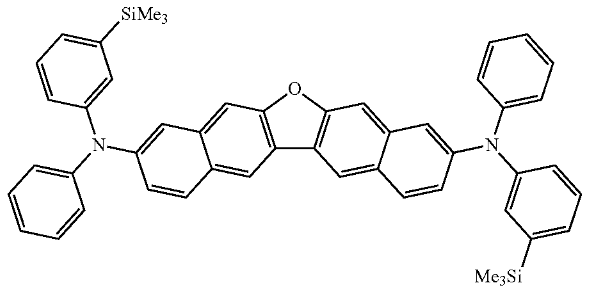
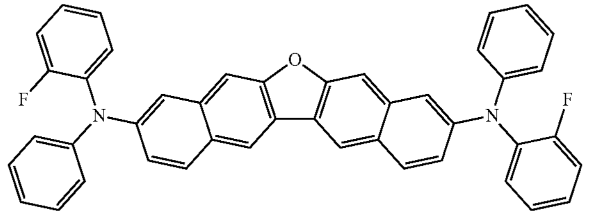
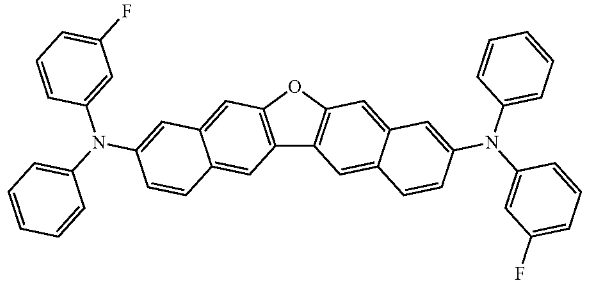
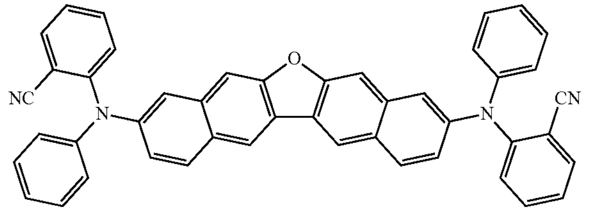
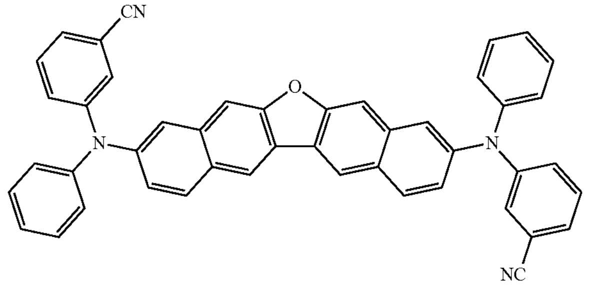
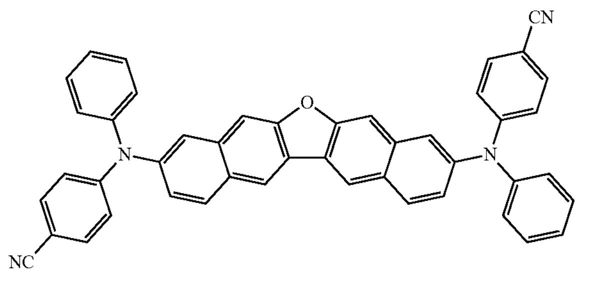

-continued
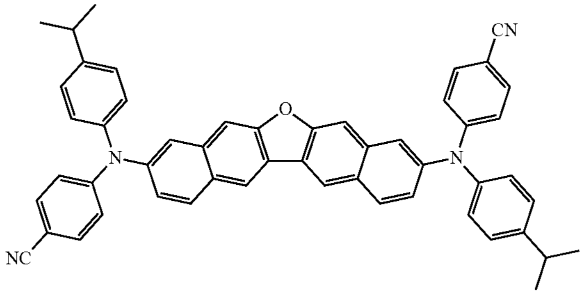
[Formula 246]
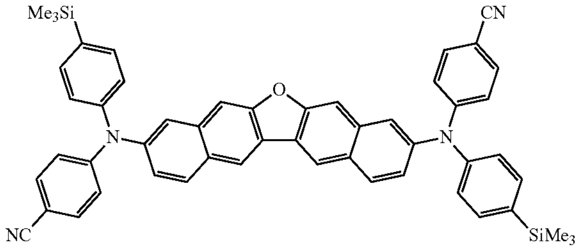
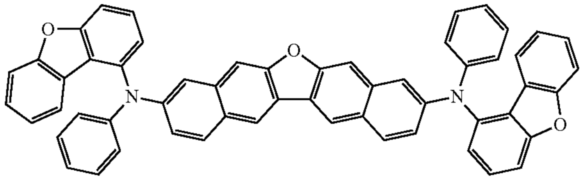
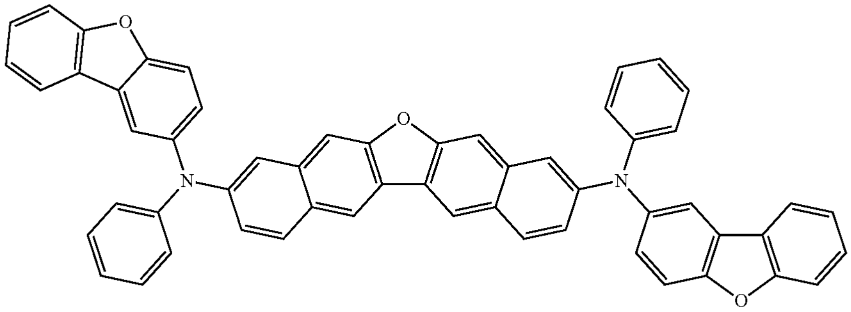
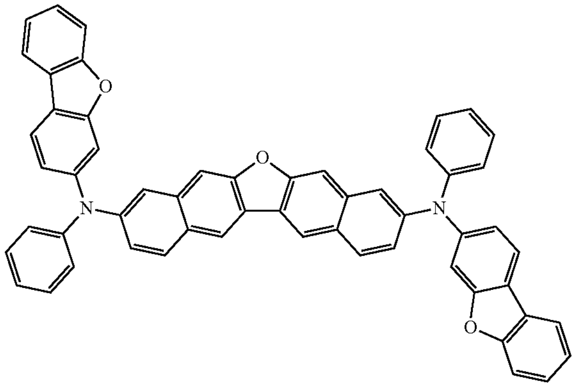
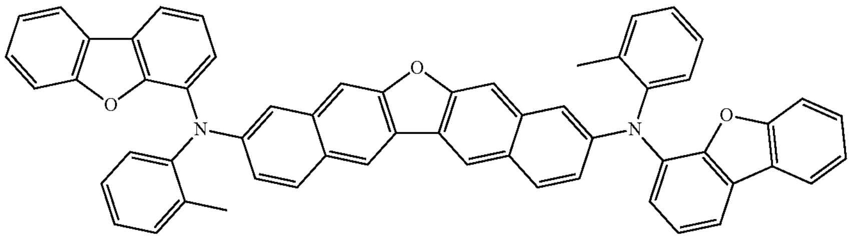

-continued
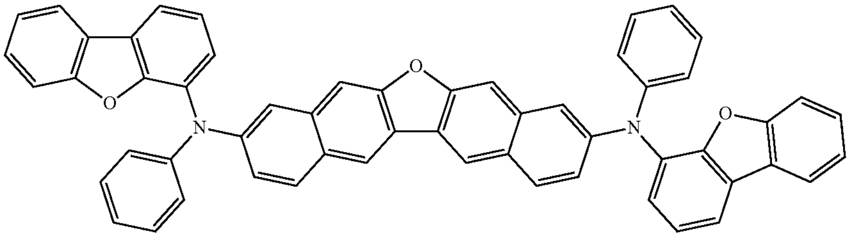
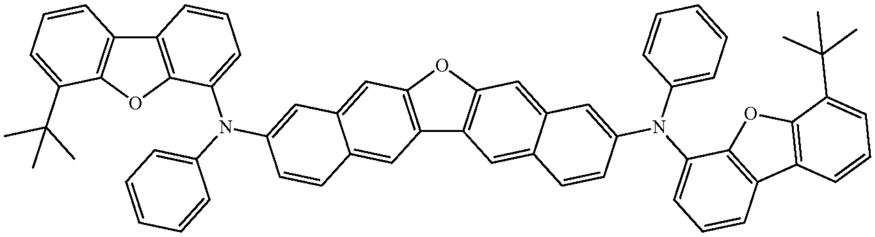
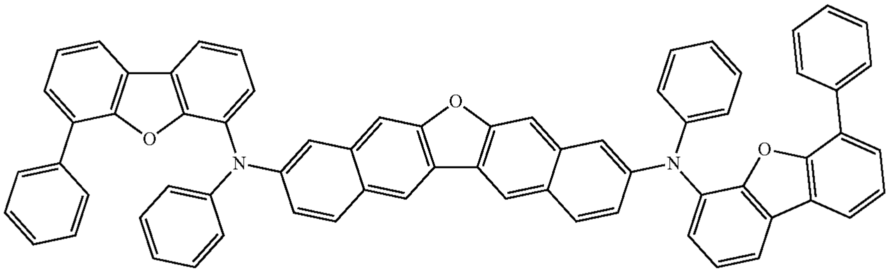
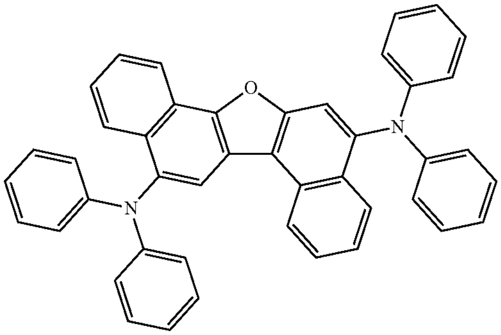
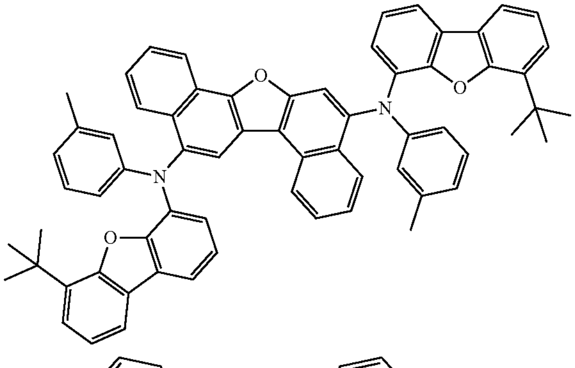
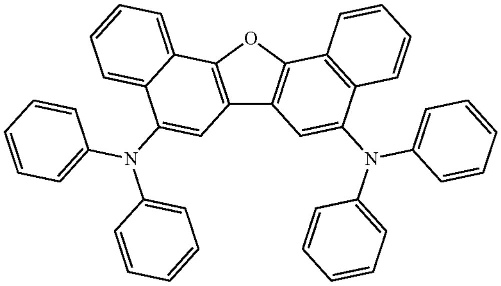

-continued
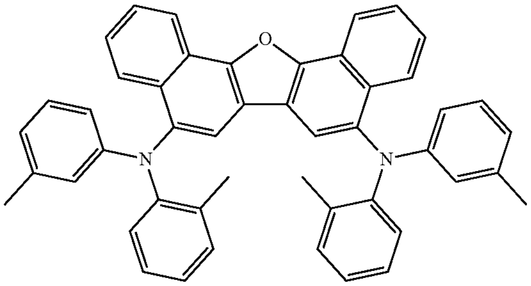
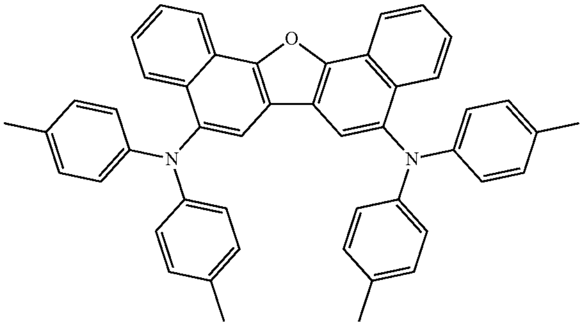
[Formula 247]
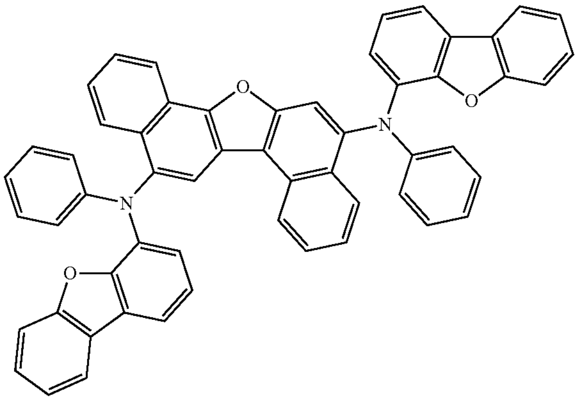
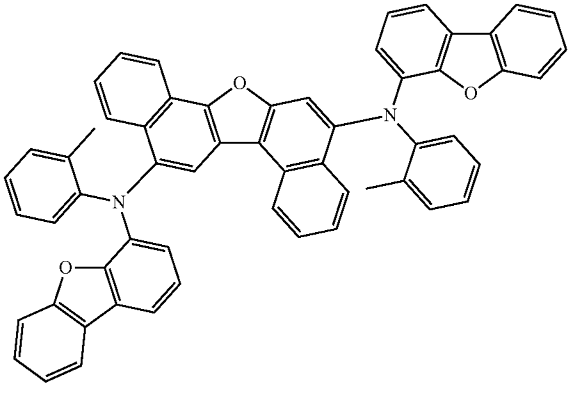

-continued
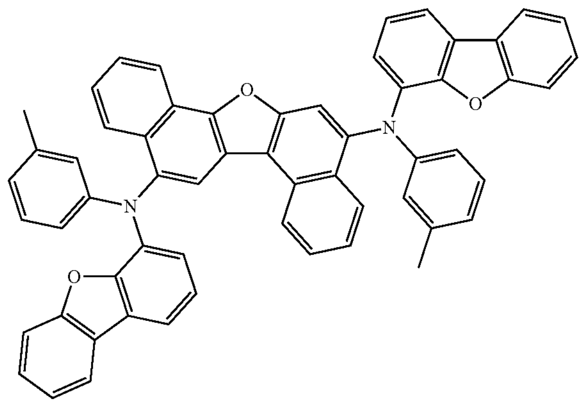
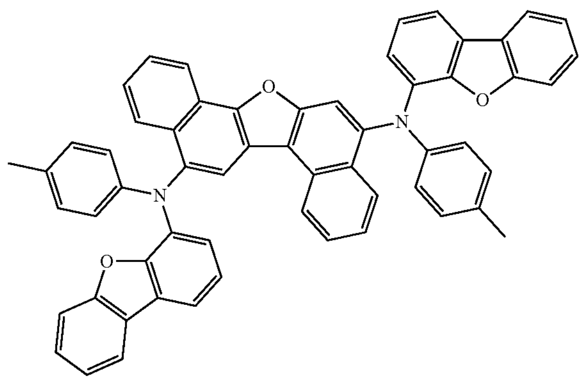
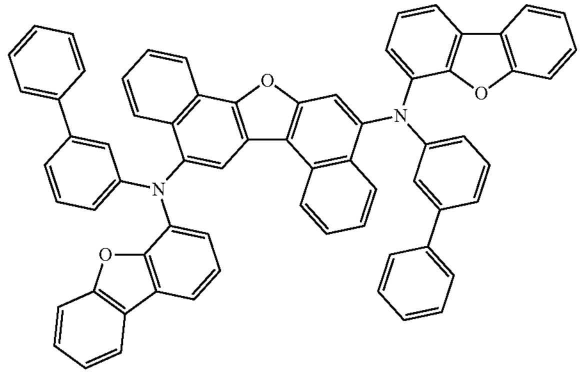
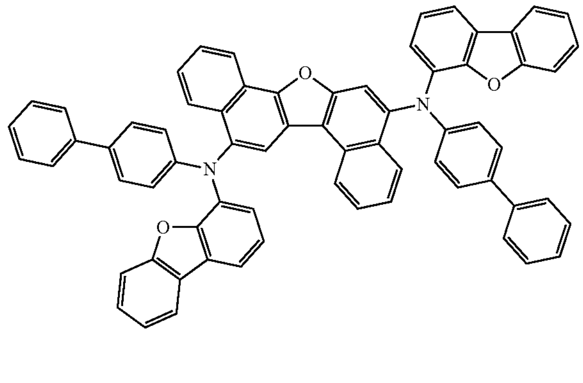

-continued
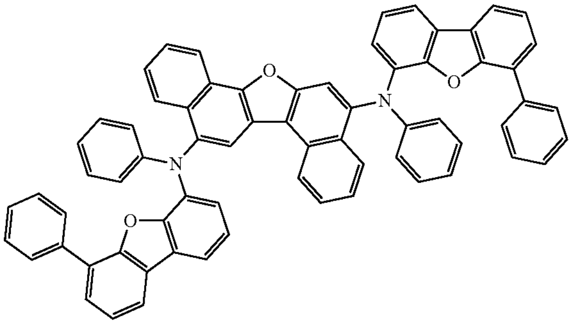
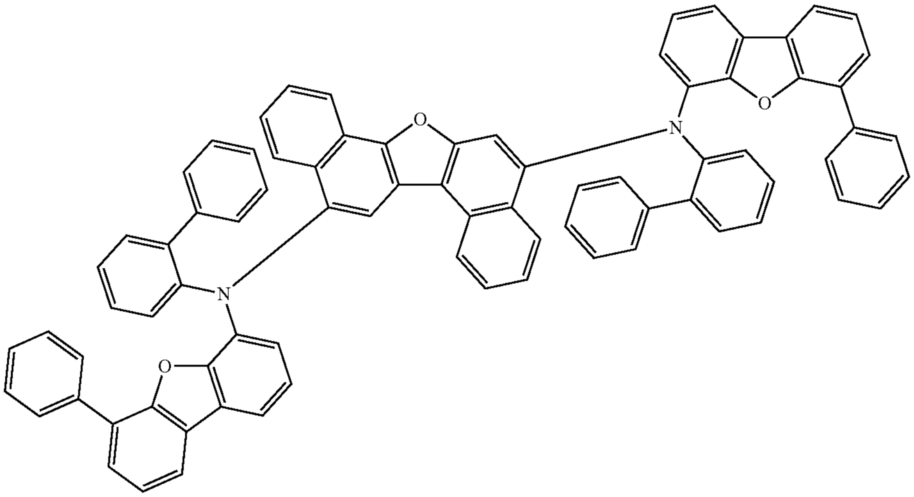
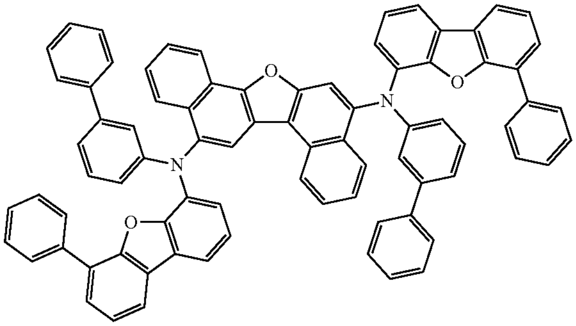
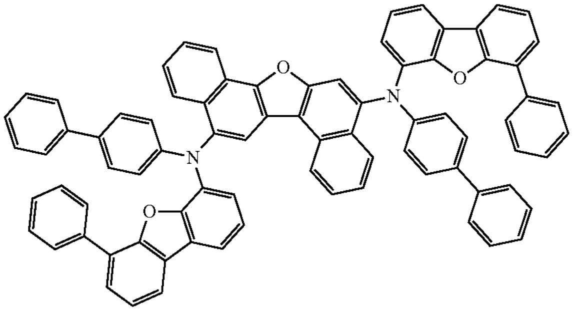

-continued
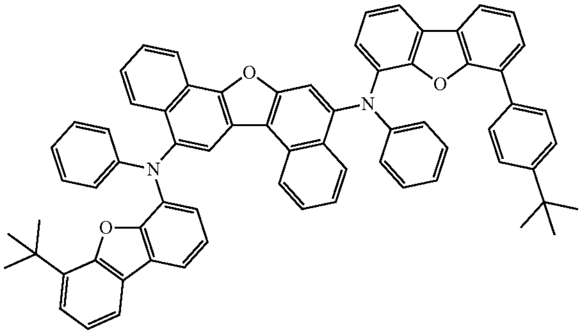
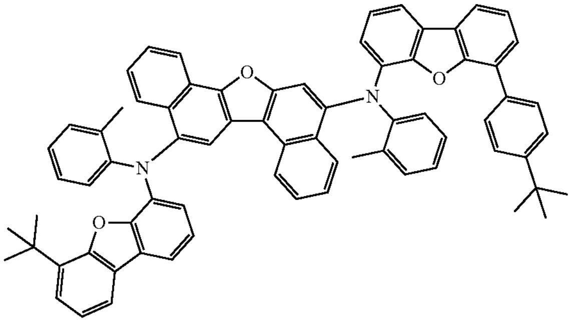
[Formula 248]
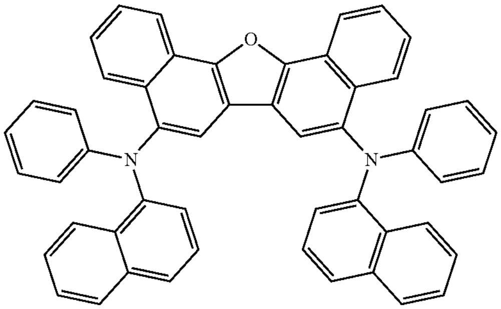
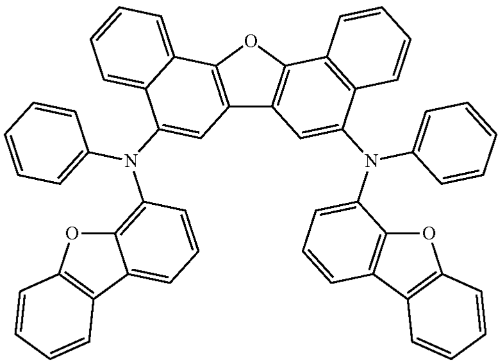

-continued
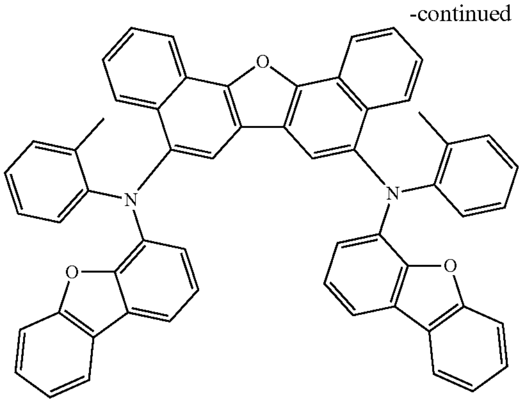
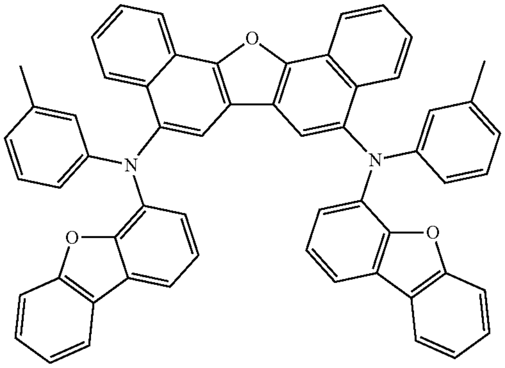
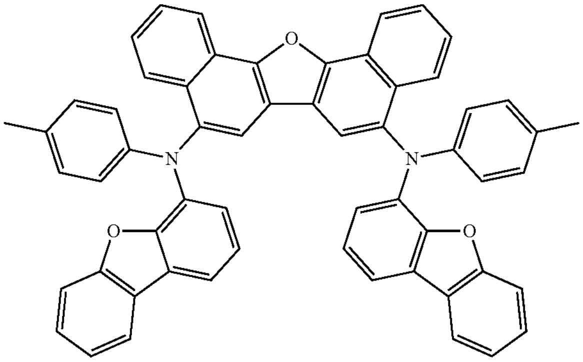
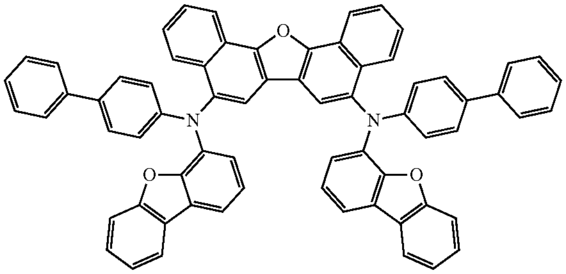
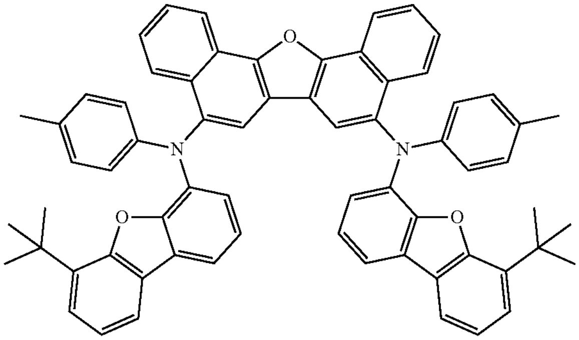

-continued
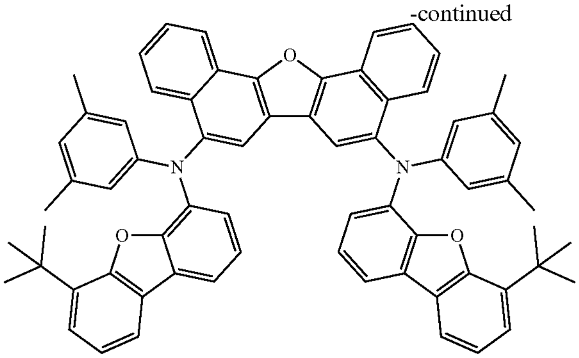
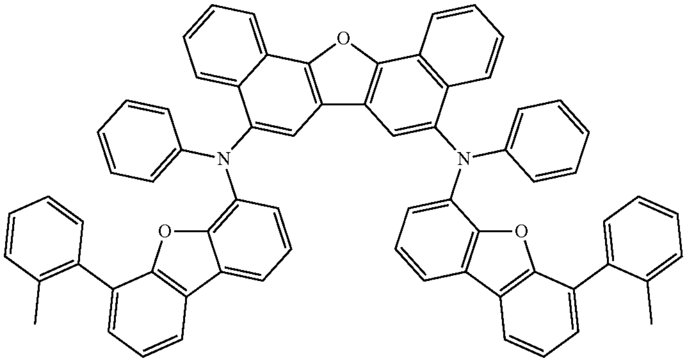
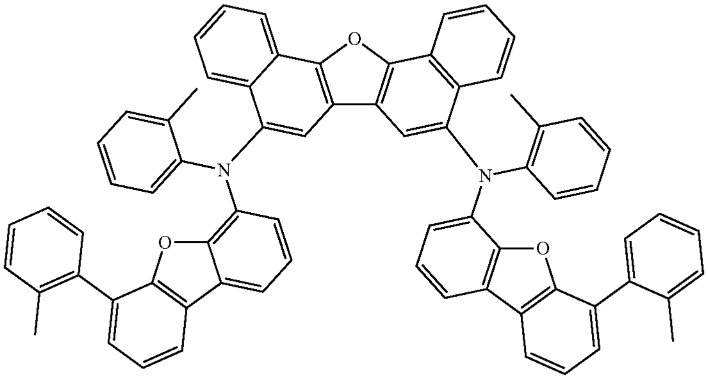
[Formula 249]
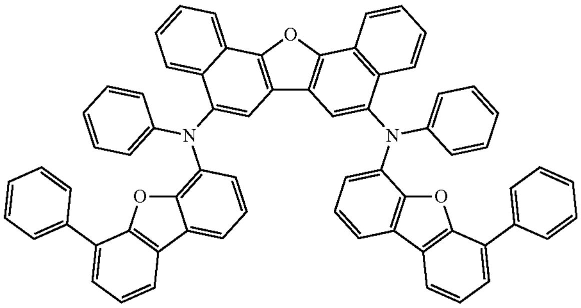
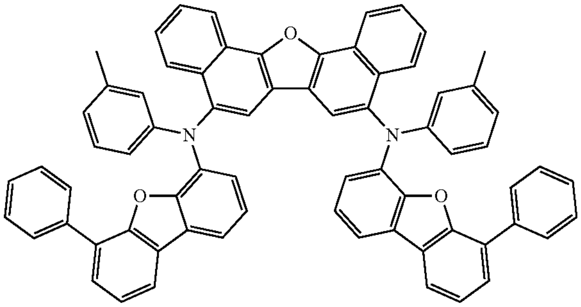

-continued
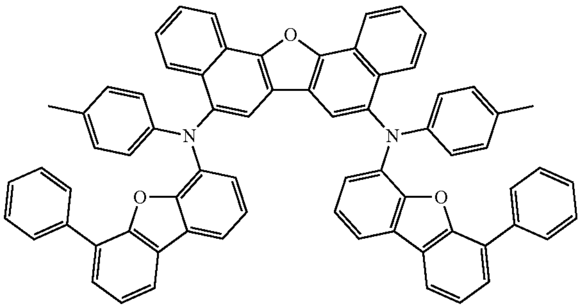
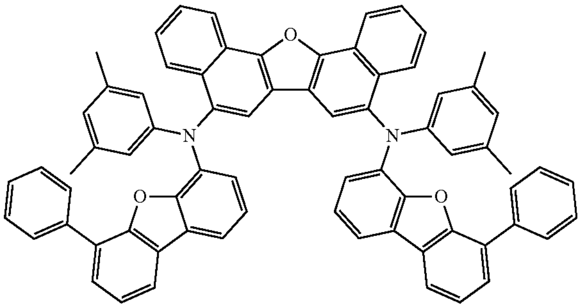
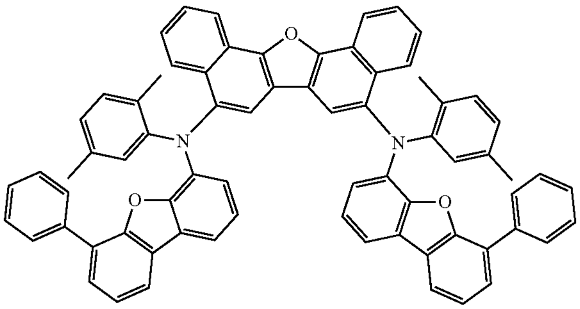
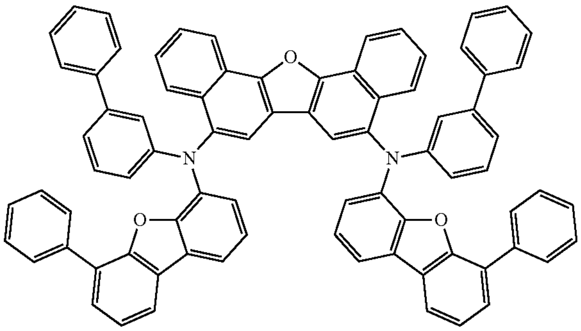
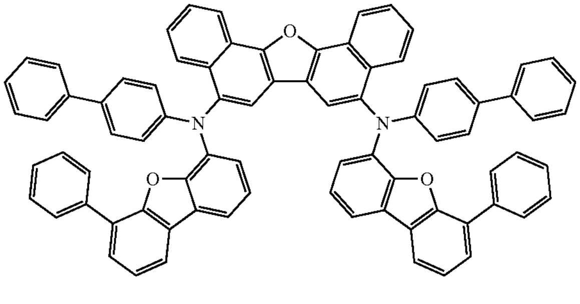

-continued
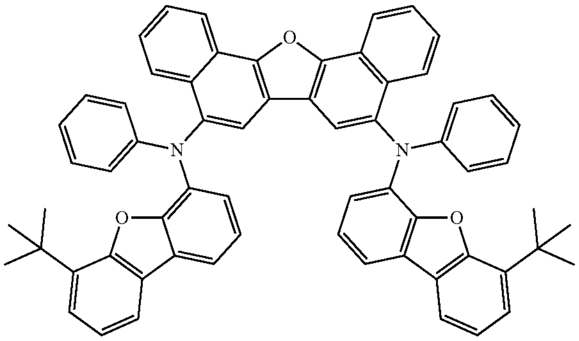
[Formula 250]
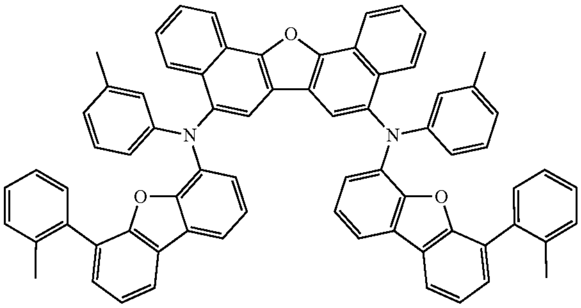
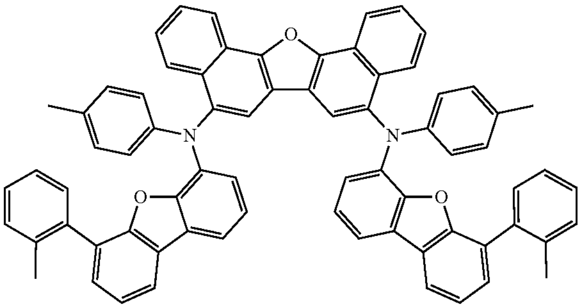
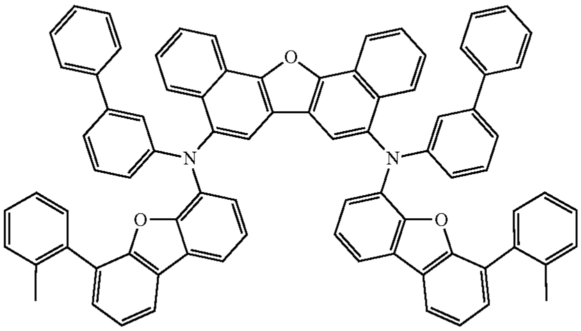
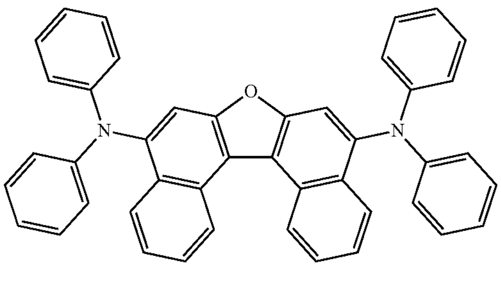

-continued
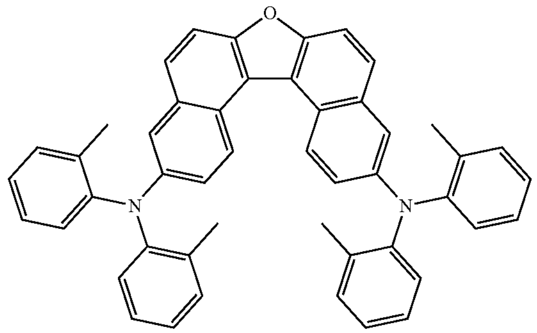
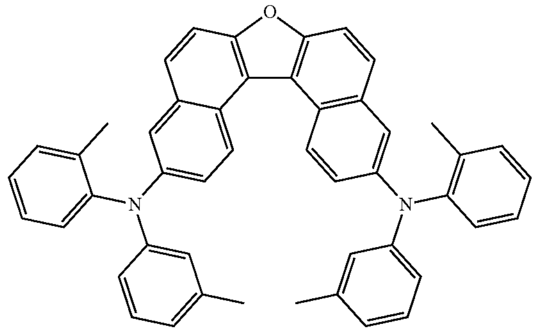
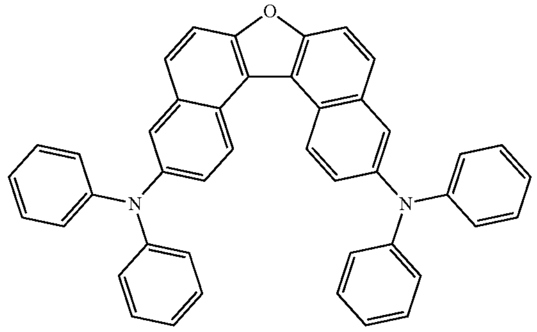
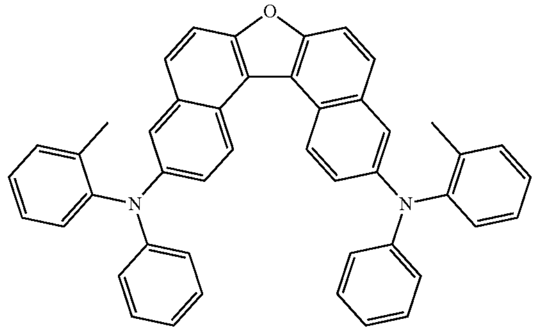
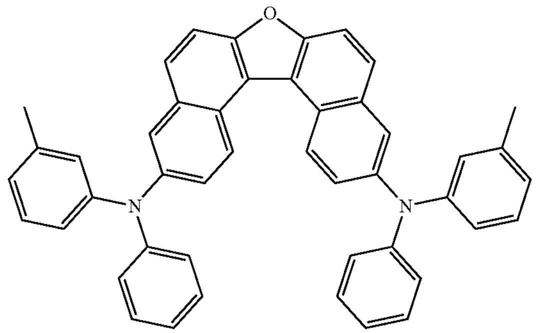

-continued
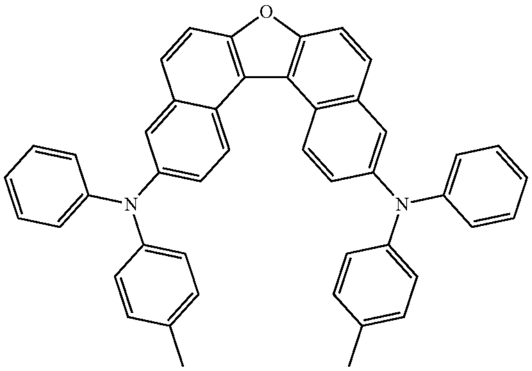
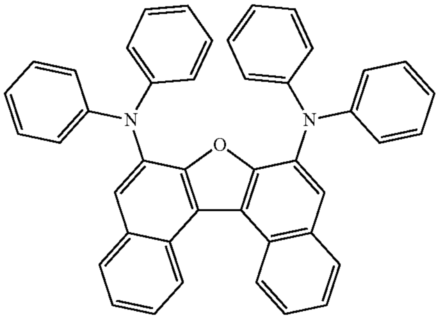
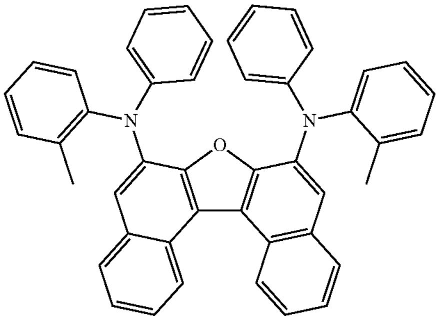
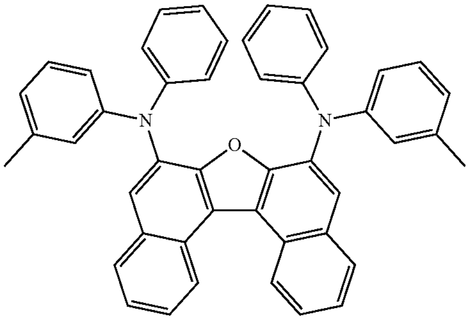
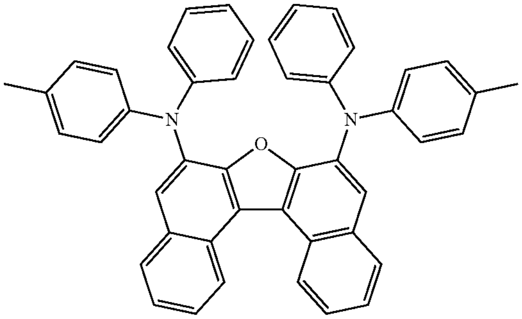

-continued

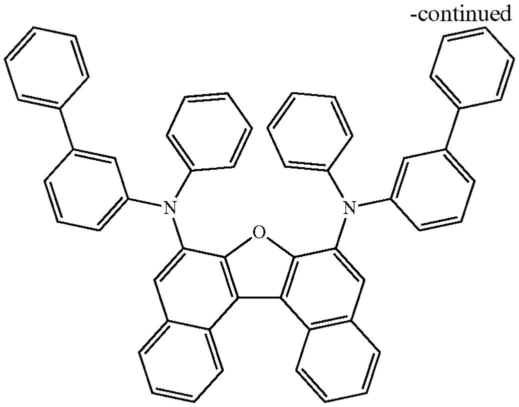

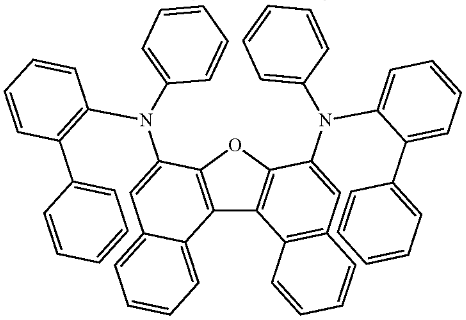

Compound Represented by Formula (9)

The compound represented by the formula (9) will be described below.

[Formula 251]

(9)

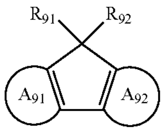

In the formula (9):

A91 ring and A92 ring are each independently a substituted or unsubstituted aromatic hydrocarbon ring having 6 to 50 ring carbon atoms, or a substituted or unsubstituted heterocycle having 5 to 50 ring atoms; and at least one of A91 ring or A92 ring is bonded with * in a structure represented by a formula (92) below.

[化252]

(92)

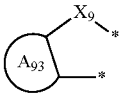

In the formula (92):

A93 ring is a substituted or unsubstituted aromatic hydrocarbon ring having 6 to 50 ring carbon atoms, or a substituted or unsubstituted heterocycle having 5 to 50 ring atoms;

$X_9$ is $NR_{93}$, $C(R_{94})(R_{95})$, $Si(R_{96})(R_{97})$, $Ge(R_{98})(R_{99})$, an oxygen atom, a sulfur atom, or a selenium atom;

$R_{91}$ and $R_{92}$ are mutually bonded to form a substituted or unsubstituted monocyclic ring, mutually bonded to form a substituted or unsubstituted fused ring, or not mutually bonded; and $R_{91}$ and $R_{92}$ not forming the monocyclic ring and not forming the fused ring, and $R_{93}$ to $R_{99}$ are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $-Si(R_{901})(R_{902})(R_{903})$, a group represented by $-O-(R_{904})$, a group represented by $-S-(R_{905})$, a group represented by $-N(R_{906})(R_{907})$, a halogen atom, a cyano group, a nitro group, a substituted or unsubstituted aryl group having 6 to 50 ring carbon atoms, or a substituted or unsubstituted heterocyclic group having 5 to 50 ring atoms.

At least one ring selected from the group consisting of A91 ring and A92 ring is bonded to a bond * of a structure represented by the formula (92). In other words, the ring-forming carbon atoms of the aromatic hydrocarbon ring or the ring atoms of the heterocycle of the A91 ring in an exemplary embodiment are bonded to the bonds * in a structure represented by the formula (92). Further, the ring-forming carbon atoms of the aromatic hydrocarbon ring or the ring atoms of the heterocycle of the A92 ring in an exemplary embodiment are bonded to the bonds * in a structure represented by the formula (92).

In an exemplary embodiment, a group represented by a formula (93) below is bonded to one or both of the A91 ring and A92 ring.

[Formula 253]

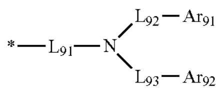

(93)

In the formula (93):

$Ar_{91}$ and $Ar_{92}$ are each independently a substituted or unsubstituted aryl group having 6 to 50 ring carbon atoms, or a substituted or unsubstituted heterocyclic group having 5 to 50 ring atoms;

$L_{91}$ to $L_{93}$ are each independently a single bond, a substituted or unsubstituted arylene group having 6 to 30 ring carbon atoms, a substituted or unsubstituted divalent heterocyclic group having 5 to 30 ring atoms, or a divalent linking group formed by bonding two, three or four groups selected from the group consisting of a substituted or unsubstituted arylene group having 6 to 30 ring carbon atoms and a substituted or unsubstituted divalent heterocyclic group having 5 to 30 ring atoms; and

* in the formula (93) represents a bonding position to one of A91 ring and A92 ring.

In an exemplary embodiment, in addition to the A91 ring, the ring-forming carbon atoms of the aromatic hydrocarbon ring or the ring atoms of the heterocycle of the A92 ring are bonded to * in a structure represented by the formula (92). In this case, the moieties represented by the formula (92) may be mutually the same or different.

In an exemplary embodiment, $R_{91}$ and $R_{92}$ are each independently a substituted or unsubstituted aryl group having 6 to 50 ring carbon atoms.

In an exemplary embodiment, $R_{91}$ and $R_{92}$ are mutually bonded to form a fluorene structure.

In an exemplary embodiment, the rings A91 and A92 are each independently a substituted or unsubstituted aromatic hydrocarbon ring having 6 to 50 ring carbon atoms, example of which is a substituted or unsubstituted benzene ring.

In an exemplary embodiment, the ring A93 is a substituted or unsubstituted aromatic hydrocarbon ring having 6 to 50 ring carbon atoms, example of which is a substituted or unsubstituted benzene ring.

In an exemplary embodiment, $X_9$ is an oxygen atom or a sulfur atom.

Specific examples of the compound represented by the formula (9) include compounds shown below.

[Formula 254]

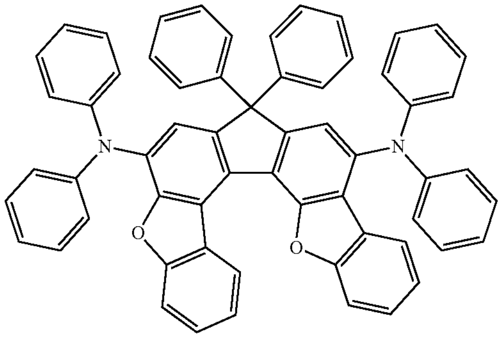

-continued

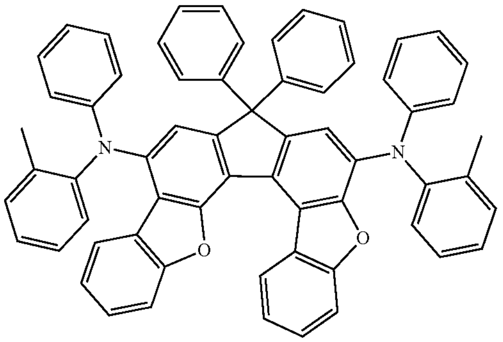

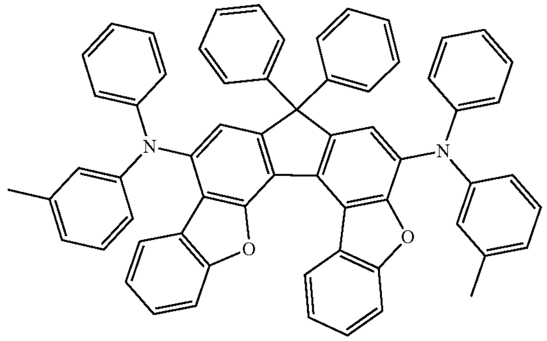

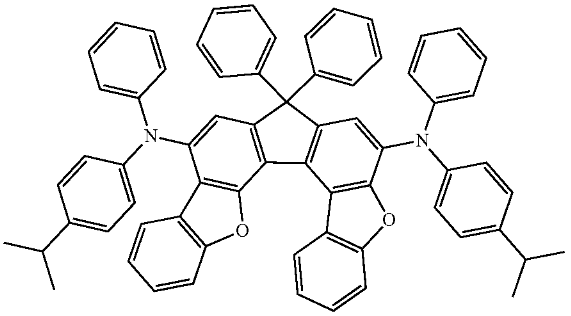

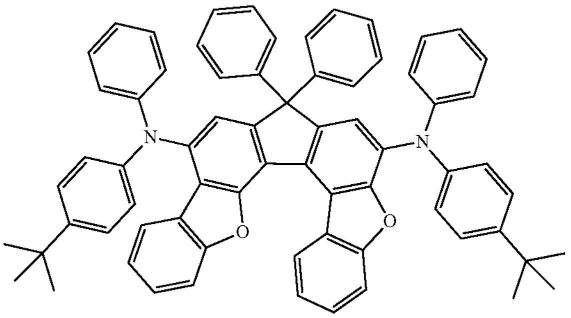

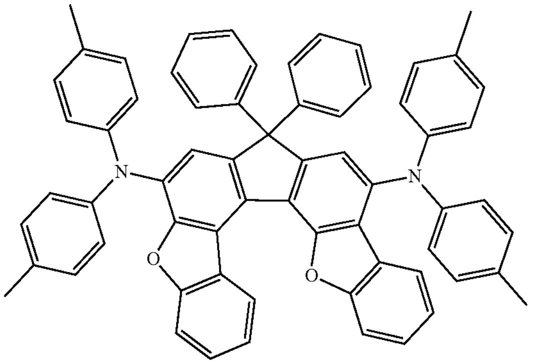

-continued
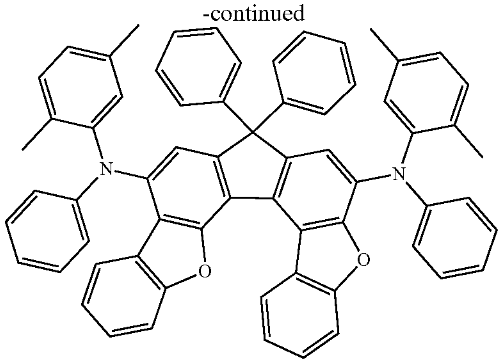
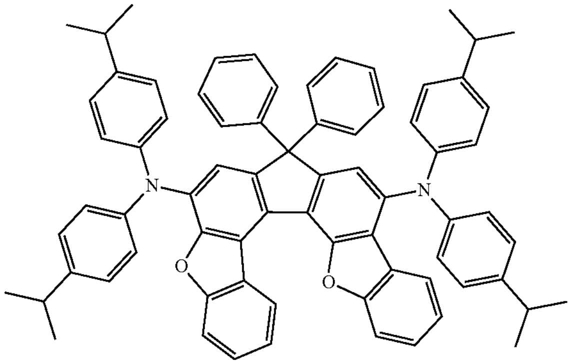
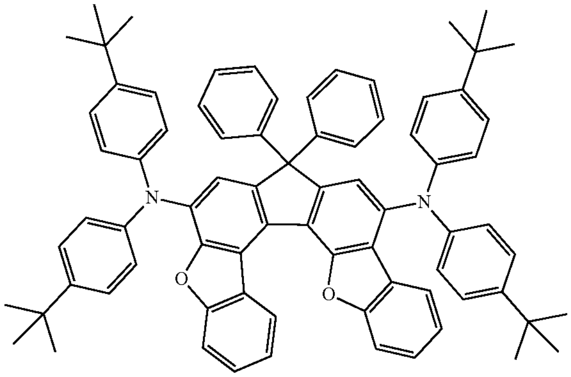
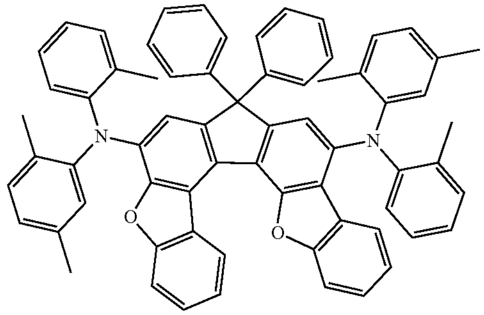
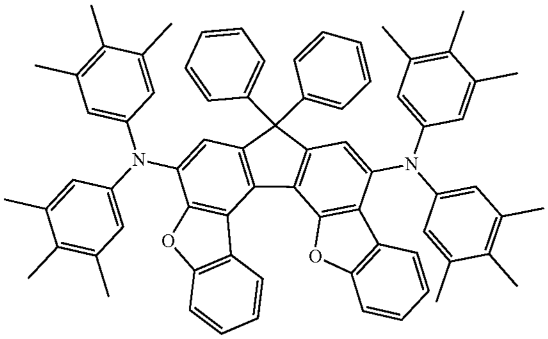
-continued
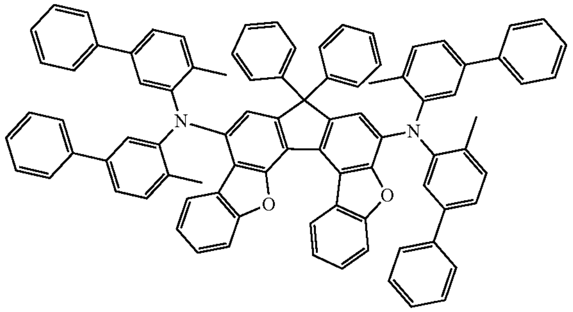
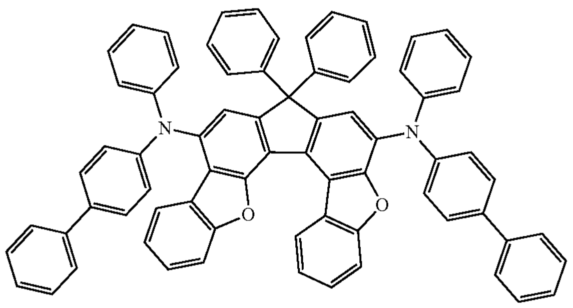
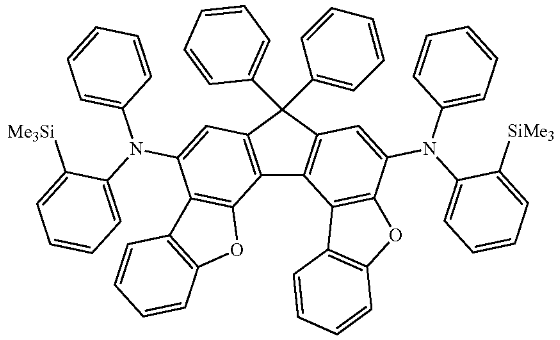
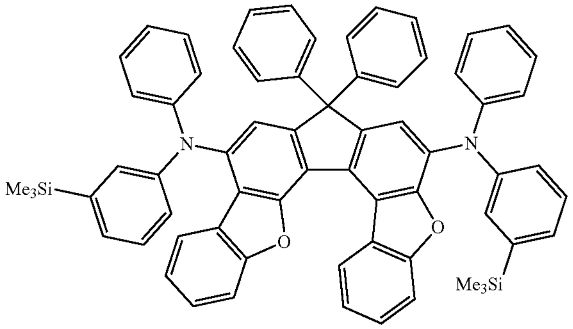
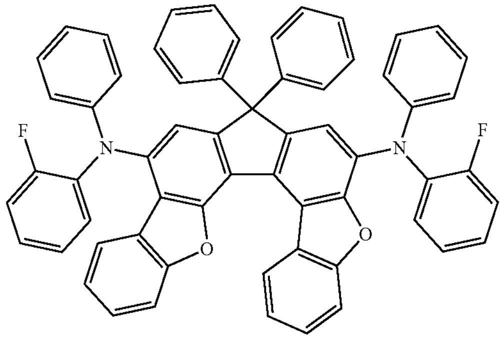

-continued
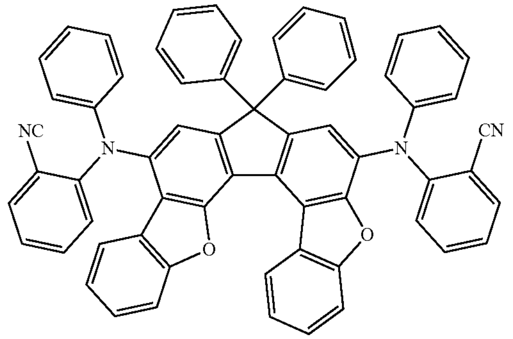
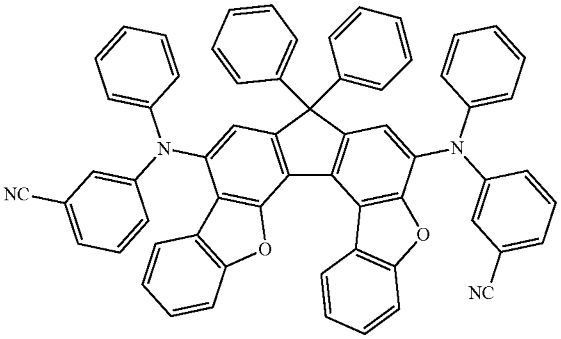
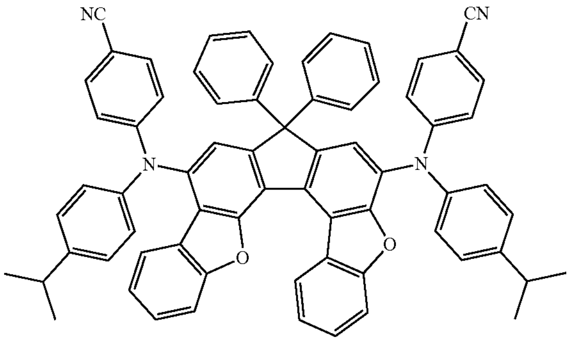
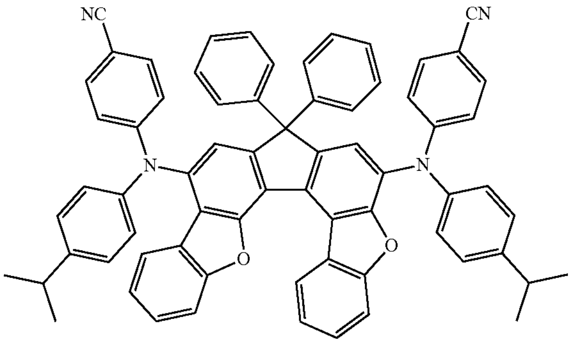
-continued
[Formula 255]
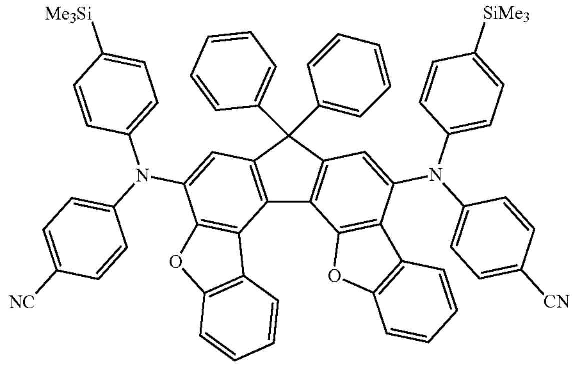
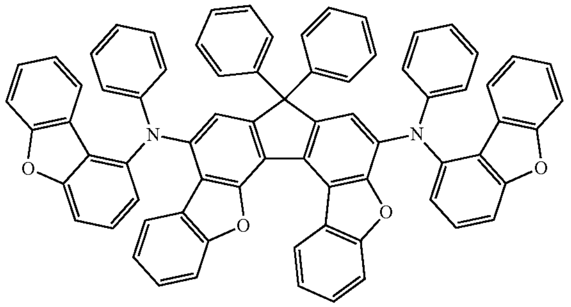
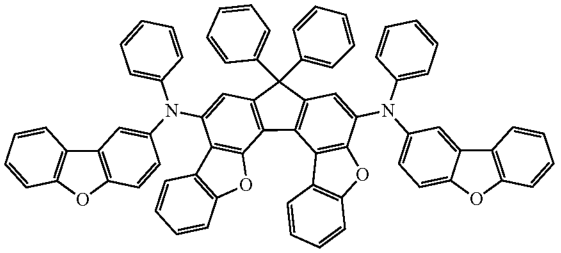
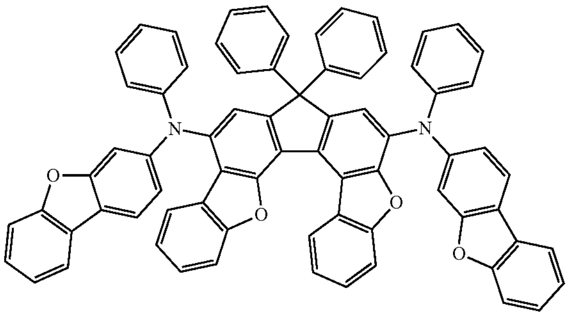
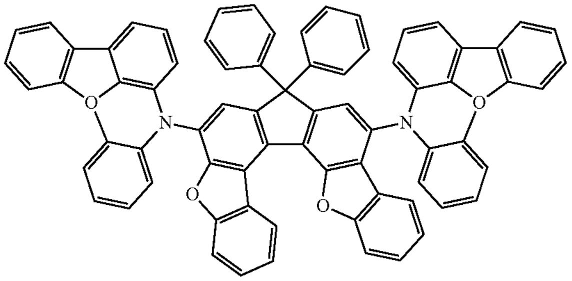

-continued
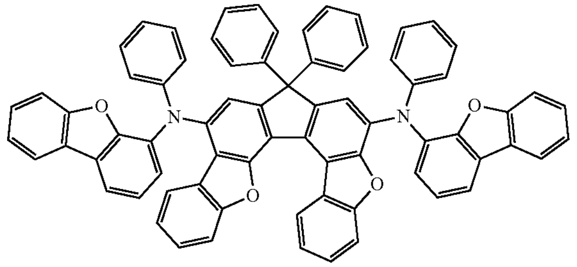
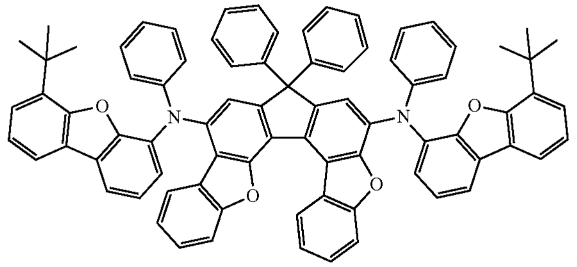
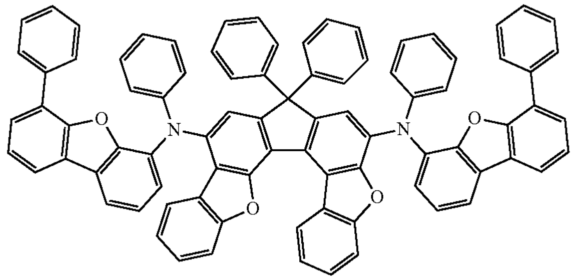
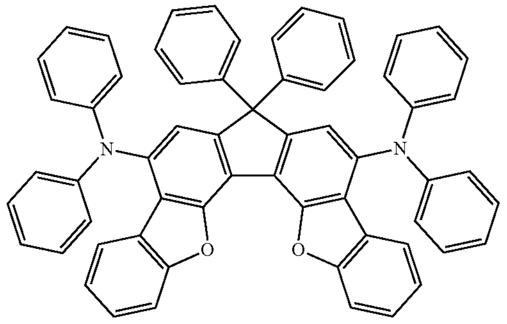
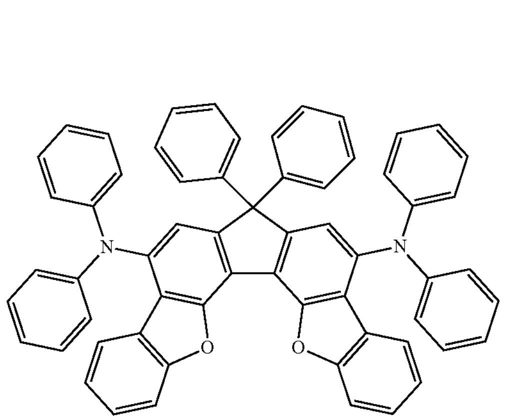
-continued
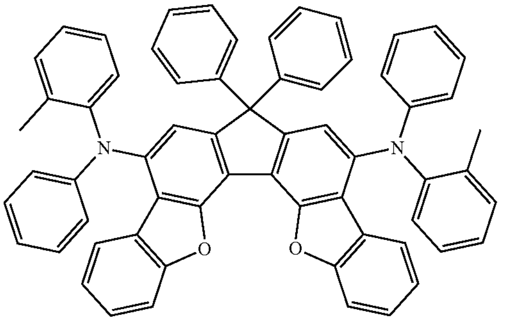
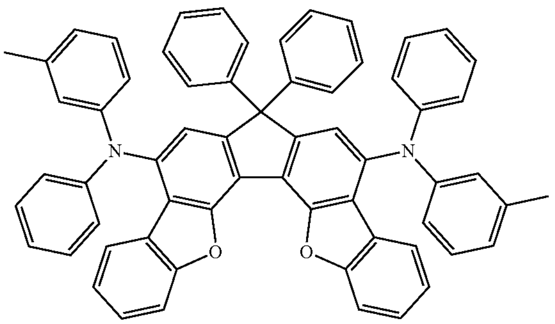
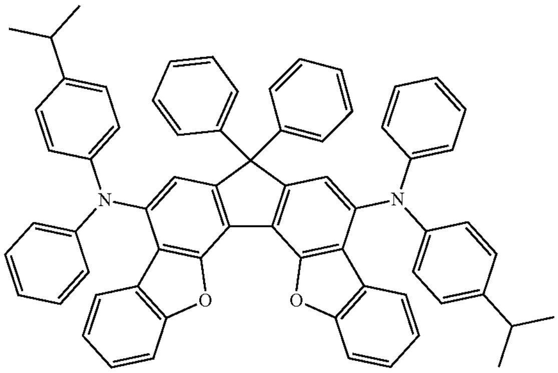
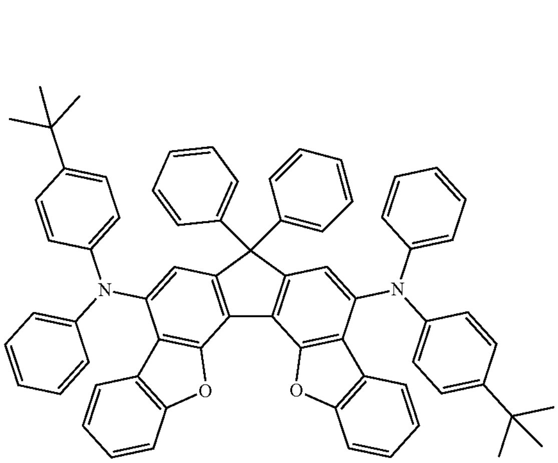

-continued
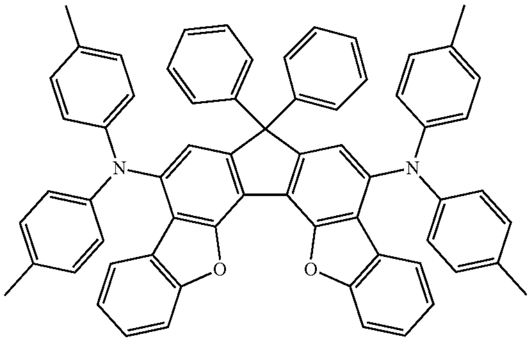
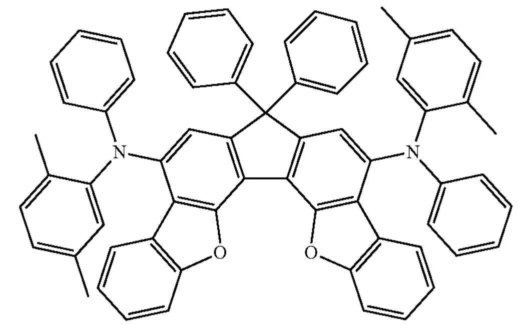
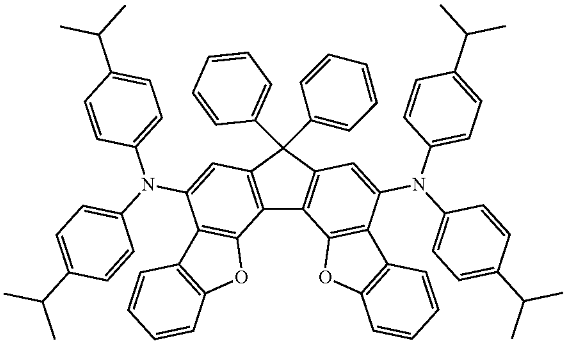
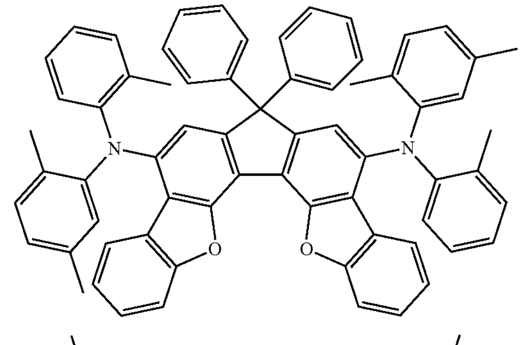
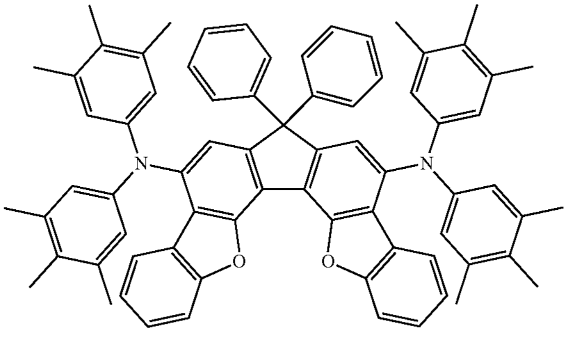
-continued
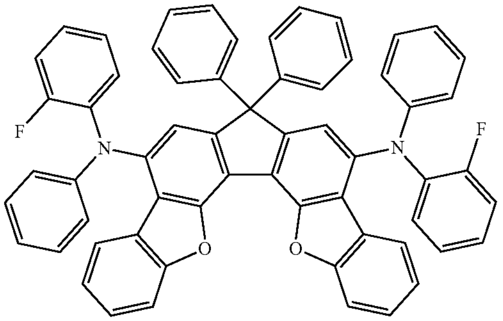
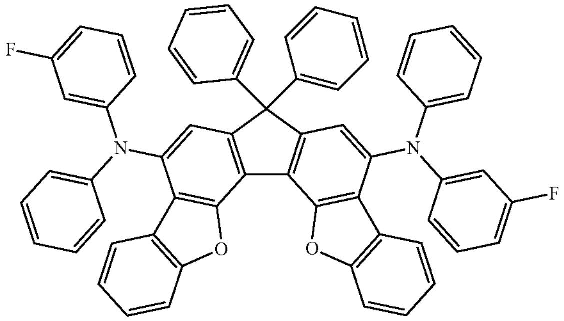
[Formula 256]
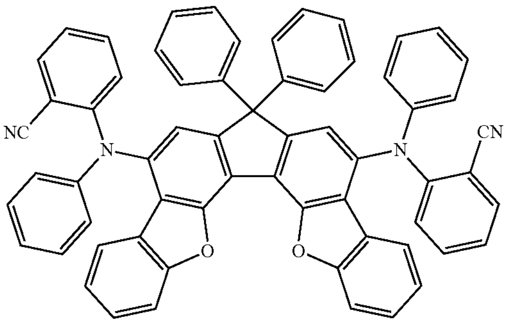
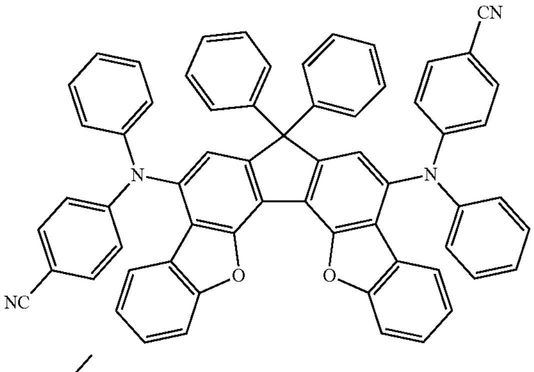
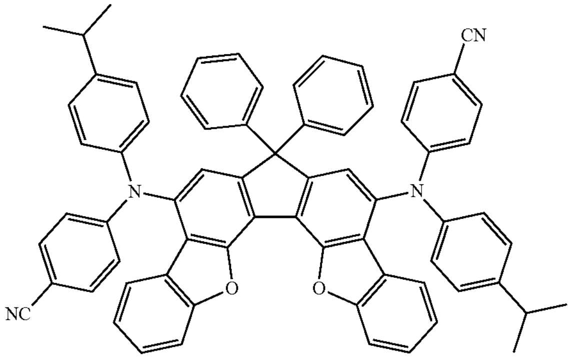

-continued
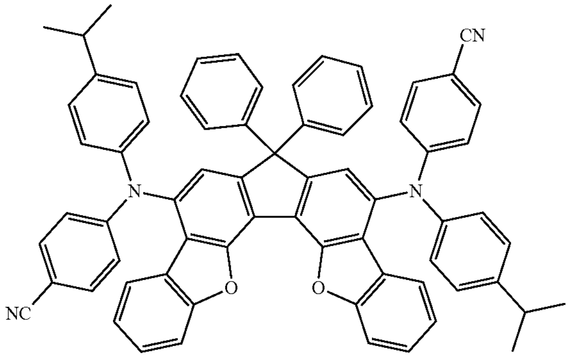
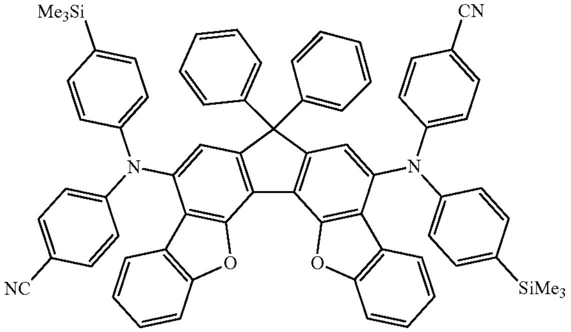
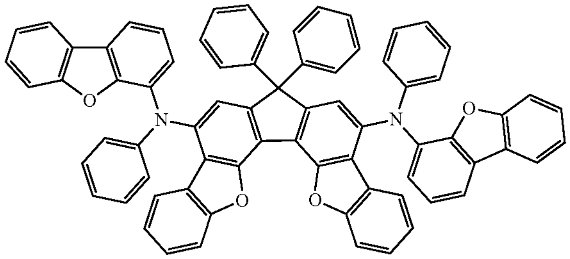
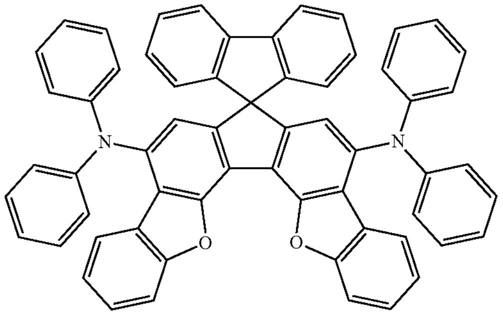
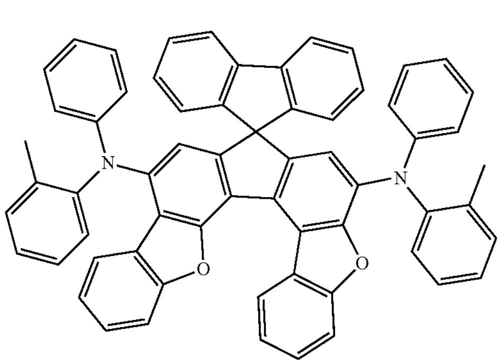
-continued
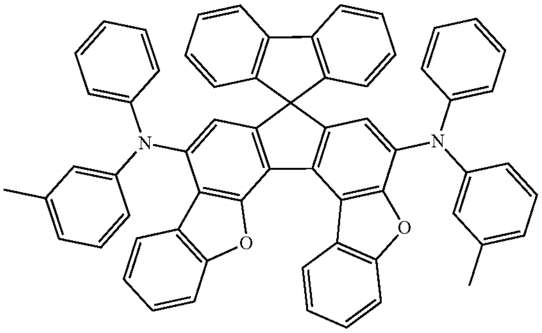
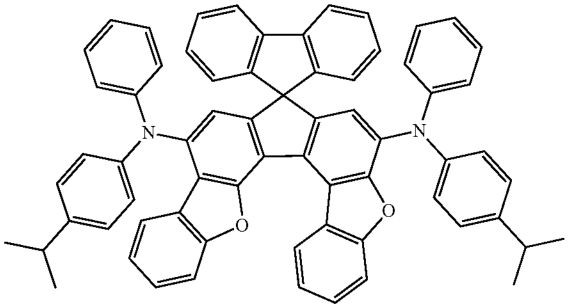
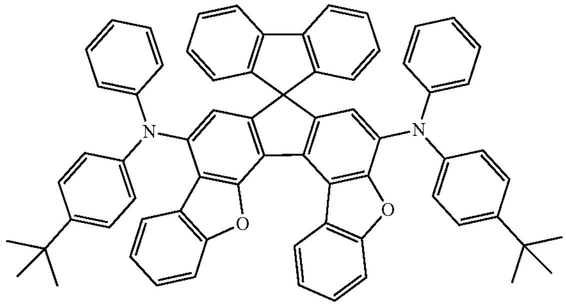
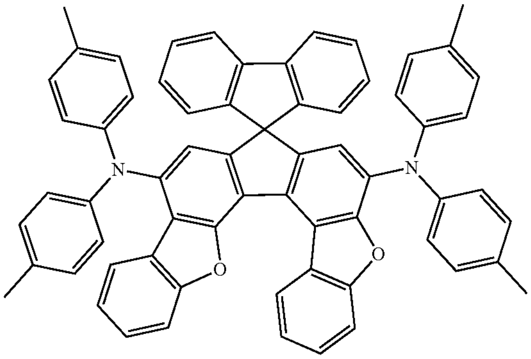
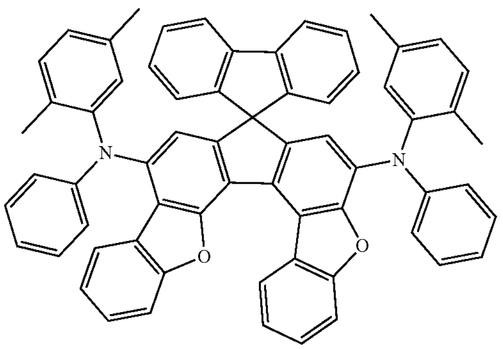

-continued
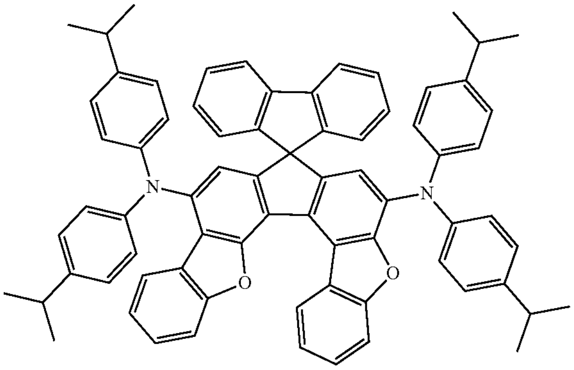
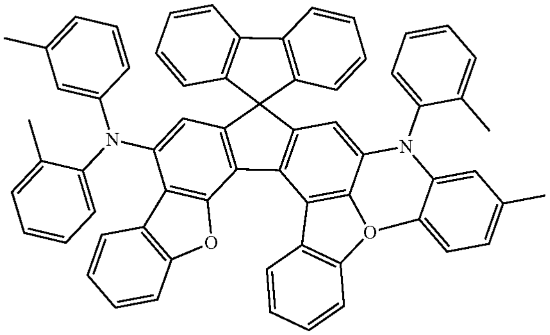
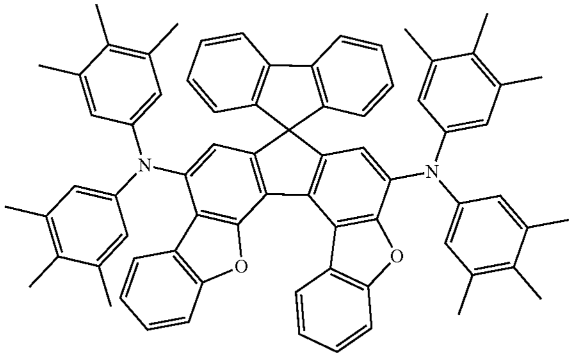
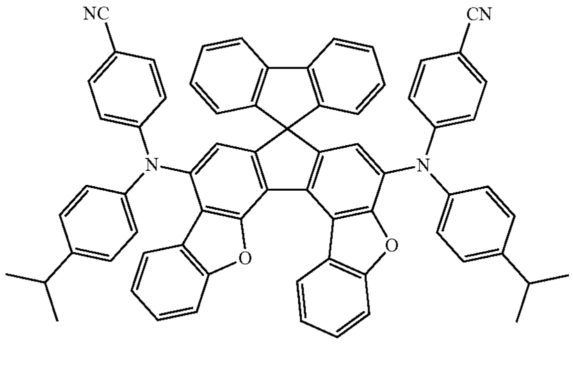
-continued
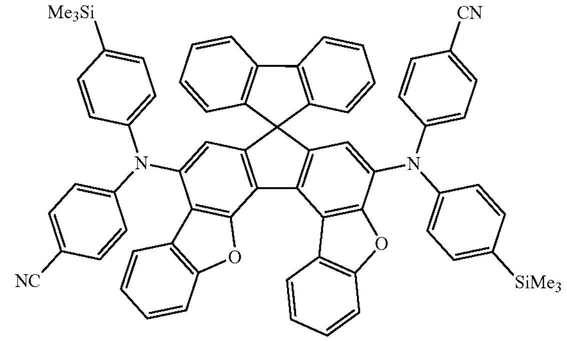
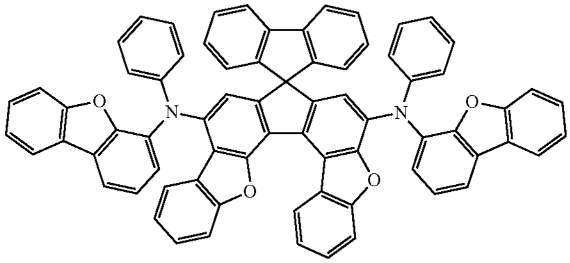
[Formula 257]
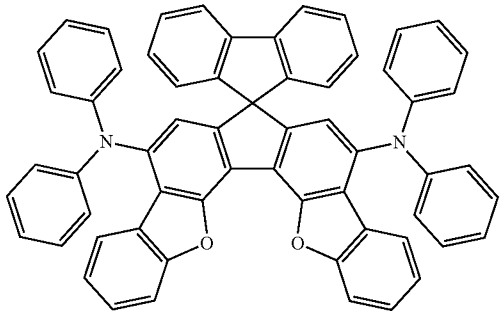
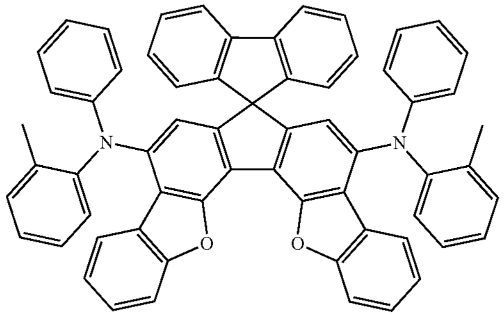
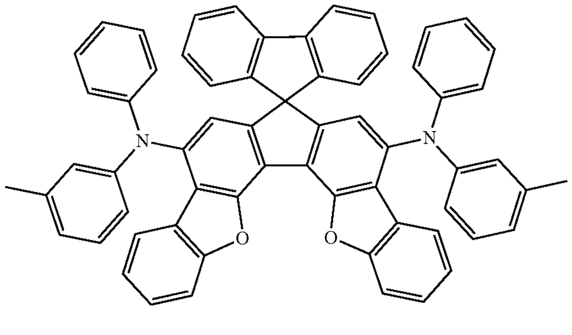

-continued

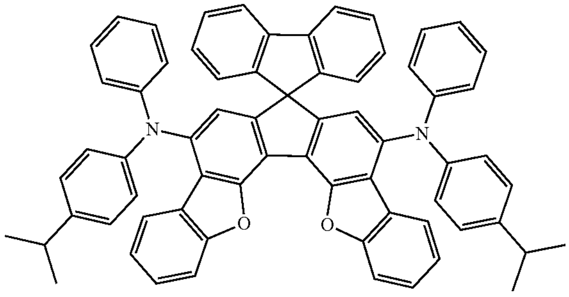

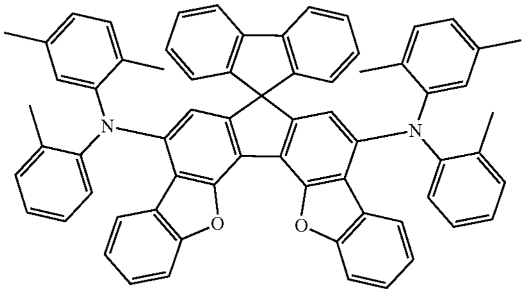

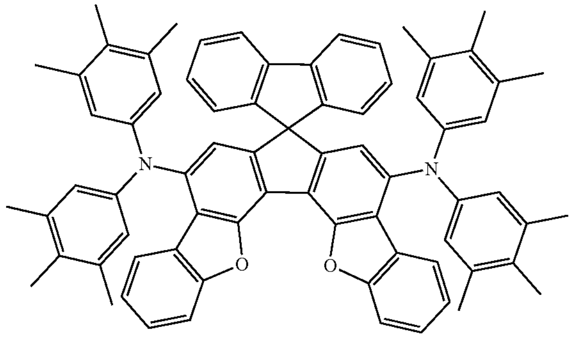

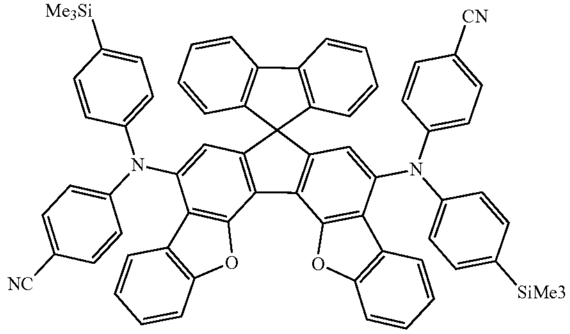

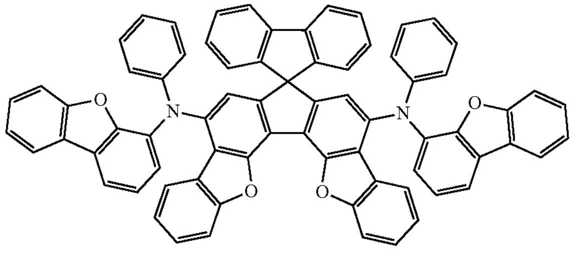

Compound Represented by Formula (10)

The compound represented by the formula (10) will be described below.

[Formula 258]

(10)

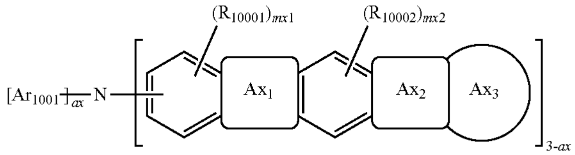

[Formula 259]

(10a)

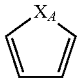

(10b)

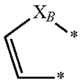

In the formula (10):

$Ax_1$ ring is a ring represented by the formula (10a) and fused with adjacent ring(s) at any position(s);

$Ax_2$ ring is a ring represented by the formula (10b) and fused with adjacent ring(s) at any position(s);

two * in the formula (10b) are bonded to $Ax_3$ ring at any position(s);

$X_A$ and $X_B$ are each independently $C(R_{1003})(R_{1004})$, $Si(R_{1005})(R_{1006})$, an oxygen atom or a sulfur atom;

$Ax_3$ ring is a substituted or unsubstituted aromatic hydrocarbon ring having 6 to 50 ring carbon atoms, or a substituted or unsubstituted heterocycle having 5 to 50 ring atoms;

$Ar_{1001}$ is a substituted or unsubstituted aryl group having 6 to 50 ring carbon atoms, or a substituted or unsubstituted heterocyclic group having 5 to 50 ring atoms;

$R_{1001}$ to $R_{1006}$ are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $—Si(R_{901})(R_{902})(R_{903})$, a group represented by $—O—(R_{904})$, a group represented by $—S—(R_{905})$, a group represented by $—N(R_{906})(R_{907})$, a halogen atom, a cyano group, a nitro group, a substituted or unsubstituted aryl group having 6 to 50 ring carbon atoms, or a substituted or unsubstituted heterocyclic group having 5 to 50 ring atoms;

mx1 is 3, mx2 is 2;

a plurality of $R_{1001}$ are mutually the same or different;

a plurality of $R_{1002}$ are mutually the same or different;

ax is 0, 1, or 2;

when ax is 0 or 1, the structures enclosed by brackets indicated by "3-ax" are mutually the same or different; and when ax is 2, a plurality of $Ar_{1001}$ are mutually the same or different.

In an exemplary embodiment, $Ar_{1001}$ is a substituted or unsubstituted aryl group having 6 to 50 ring carbon atoms.

In an exemplary embodiment, $Ax_3$ ring is a substituted or unsubstituted aromatic hydrocarbon ring having 6 to 50 ring carbon atoms, example of which is a substituted or unsubstituted benzene ring, a substituted or unsubstituted naphthalene ring, or a substituted or unsubstituted anthracene ring.

In an exemplary embodiment, $R_{1003}$ and $R_{1004}$ are each independently a substituted or unsubstituted alkyl group having 1 to 50 carbon atoms.

In an exemplary embodiment, ax is 1.

Specific examples of the compound represented by the formula (10) include compounds shown below.

[Formula 260]

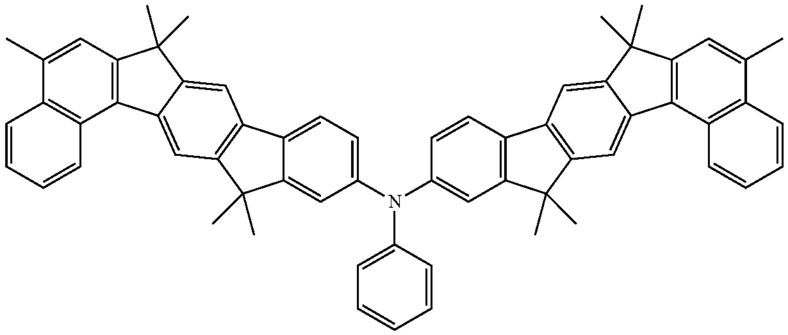

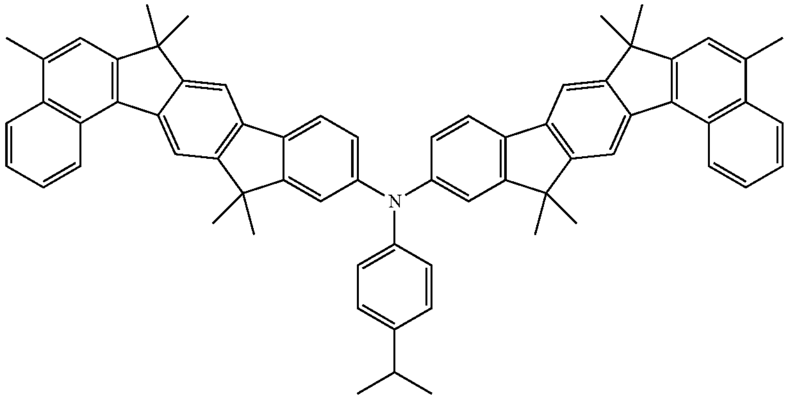

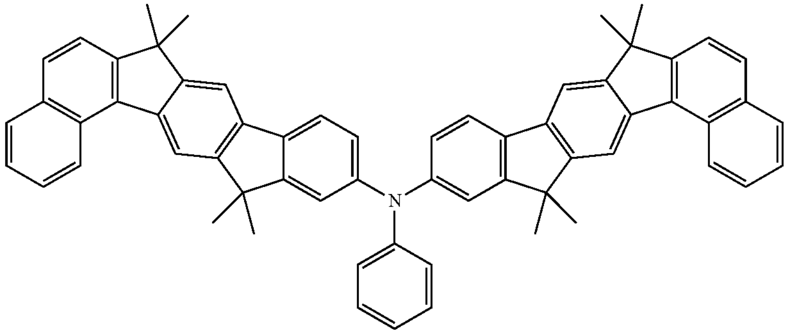

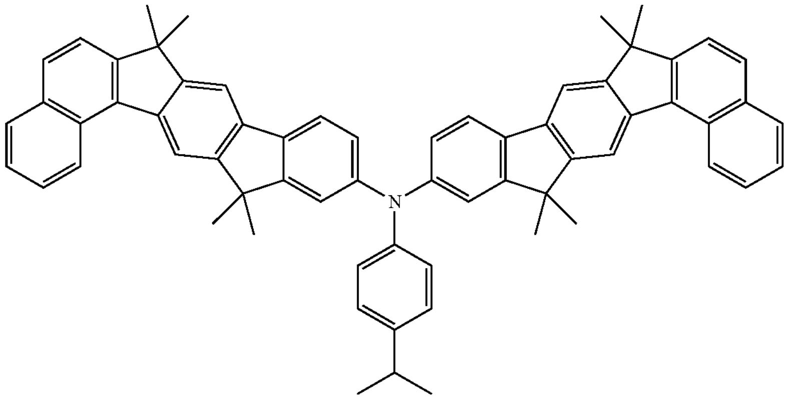

-continued
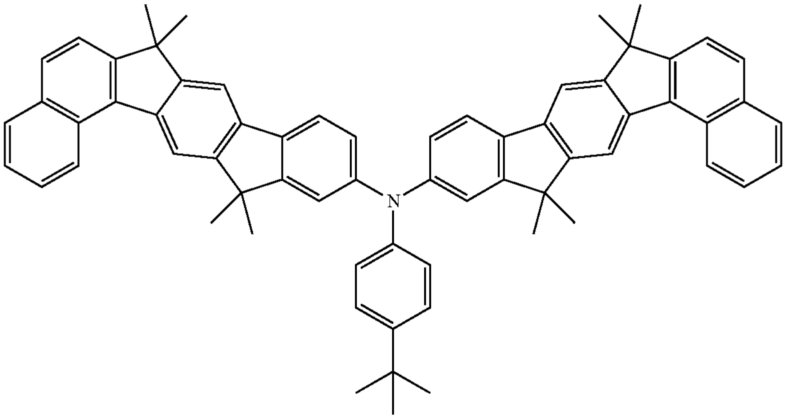
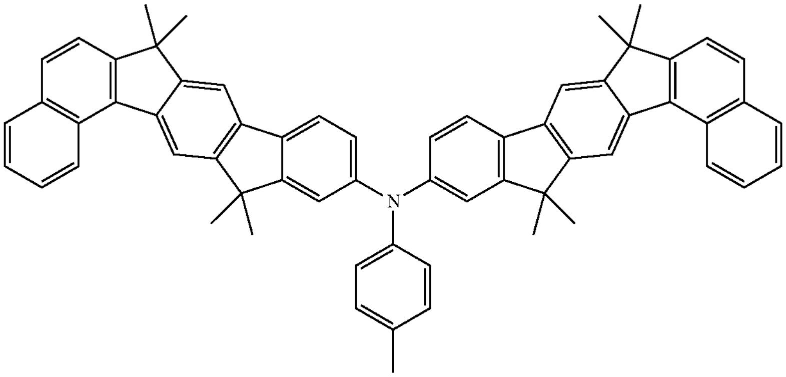
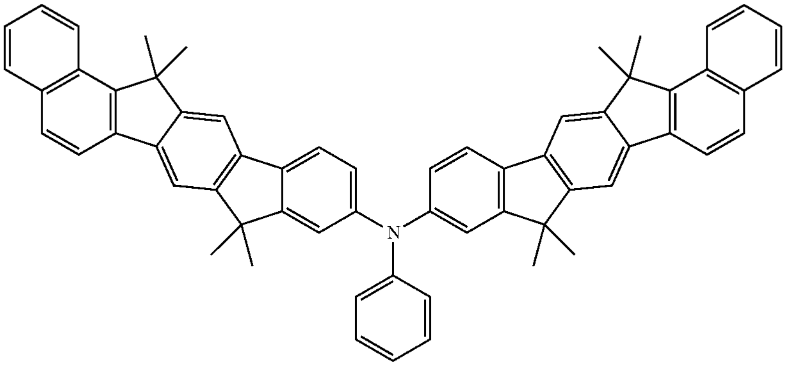
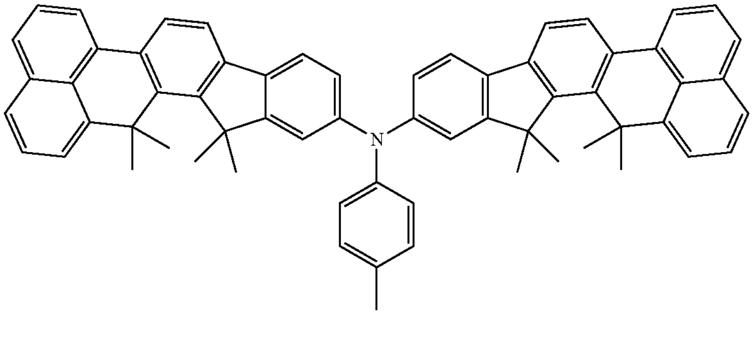

-continued
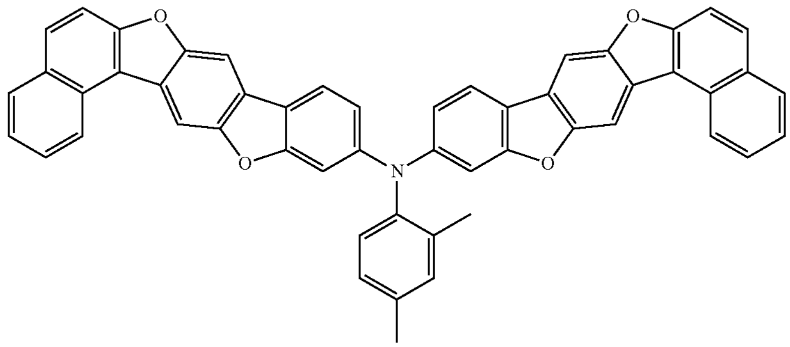
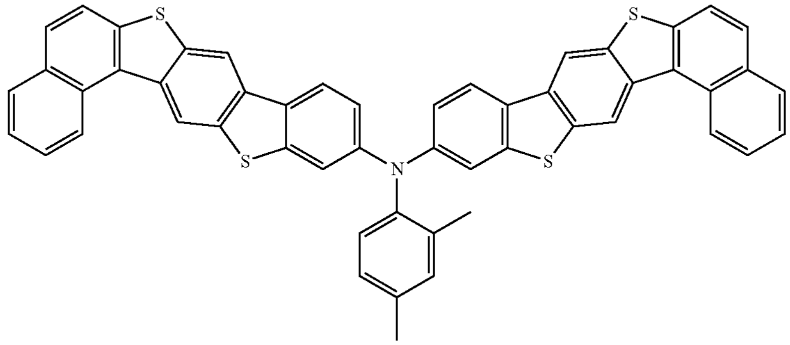
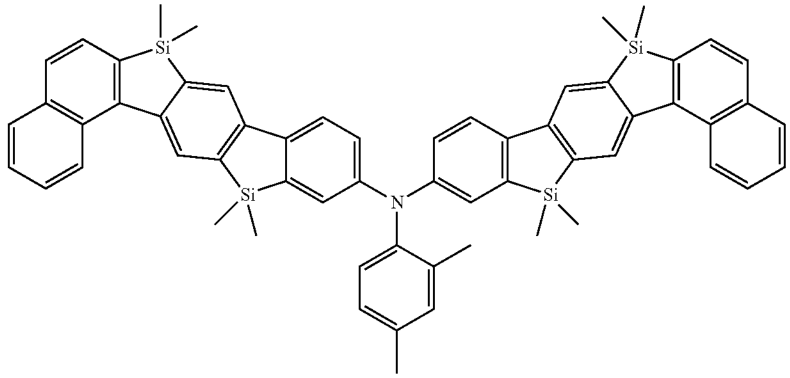

In an exemplary embodiment, the emitting layer contains, as at least one of the third compound or the fourth compound, at least one compound selected from the group consisting of a compound represented by the formula (4), a compound represented by the formula (5), a compound represented by the formula (7), a compound represented by the formula (8), a compound represented by the formula (9), and a compound represented by a formula (63a) below.

[Formula 261]

(63a)

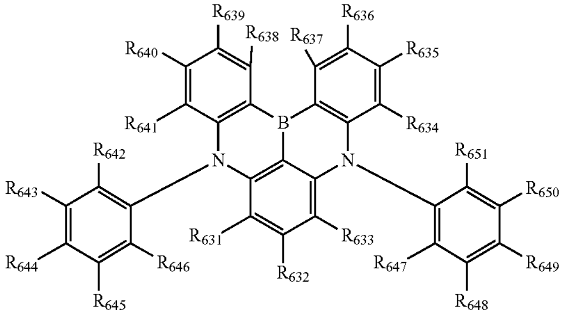

In the formula (63A):

$R_{631}$ is bonded with $R_{646}$ to form a substituted or unsubstituted heterocycle, or not bonded therewith to form no substituted or unsubstituted heterocycle;

$R_{633}$ is bonded with $R_{647}$ to form a substituted or unsubstituted heterocycle, or not bonded therewith to form no substituted or unsubstituted heterocycle;

$R_{634}$ is bonded with $R_{651}$ to form a substituted or unsubstituted heterocycle, or not bonded therewith to form no substituted or unsubstituted heterocycle;

$R_{641}$ is bonded with $R_{642}$ to form a substituted or unsubstituted heterocycle, or not bonded therewith to form no substituted or unsubstituted heterocycle;

at least one combination of adjacent two or more of $R_{631}$ to $R_{651}$ are mutually bonded to form a substituted or unsubstituted monocyclic ring, mutually bonded to form a substituted or unsubstituted fused ring, or not mutually bonded;

$R_{631}$ to $R_{651}$ not forming the substituted or unsubstituted heterocycle, not forming the monocyclic ring, and not forming the fused ring are each independently a hydrogen atom, a halogen atom, a cyano group, a nitro group, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a substituted or unsubstituted aryl group having 6 to 50 ring carbon atoms, or a substituted or unsubstituted heterocyclic group having 5 to 50 ring atoms; and at least one of $R_{631}$ to $R_{651}$ not forming the substituted or unsubstituted heterocycle, not forming the monocyclic ring and not forming the fused ring are a halogen atom, a cyano group, a nitro group, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms.

In an exemplary embodiment, the compound represented by the formula (4) is a compound represented by the formula (41-3), the formula (41-4), or the formula (41-5), the A1 ring in the formula (41-5) being a substituted or unsubstituted fused aromatic hydrocarbon ring having 10 to 50 ring carbon atoms, or a substituted or unsubstituted fused heterocycle having 8 to 50 ring atoms.

In an exemplary embodiment, the substituted or unsubstituted fused aromatic hydrocarbon ring having 10 to 50 ring carbon atoms in the formulae (41-3), (41-4) and (41-5) is a substituted or unsubstituted naphthalene ring, a substituted or unsubstituted anthracene ring, or a substituted or unsubstituted fluorene ring; and the substituted or unsubstituted fused heterocycle having 8 to 50 ring atoms is a substituted or unsubstituted dibenzofuran ring, a substituted or unsubstituted carbazole ring, or a substituted or unsubstituted dibenzothiophene ring.

In an exemplary embodiment, the substituted or unsubstituted fused aromatic hydrocarbon ring having 10 to 50 ring carbon atoms in the formula (41-3), (41-4) or (41-5) is a substituted or unsubstituted naphthalene ring, or a substituted or unsubstituted fluorene ring; and the substituted or unsubstituted fused heterocycle having 8 to 50 ring atoms is a substituted or unsubstituted dibenzofuran ring, a substituted or unsubstituted carbazole ring, or a substituted or unsubstituted dibenzothiophene ring.

In an exemplary embodiment, the compound represented by the formula (4) is selected from the group consisting of a compound represented by a formula (461) below, a compound represented by a formula (462) below, a compound represented by a formula (463) below, a compound represented by a formula (464) below, a compound represented by a formula (465) below, a compound represented by a formula (466) below, and a compound represented by a formula (467) below.

[Formula 262]

(461)

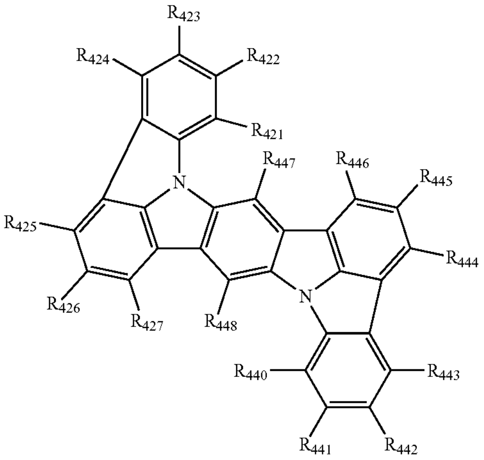

-continued (462)

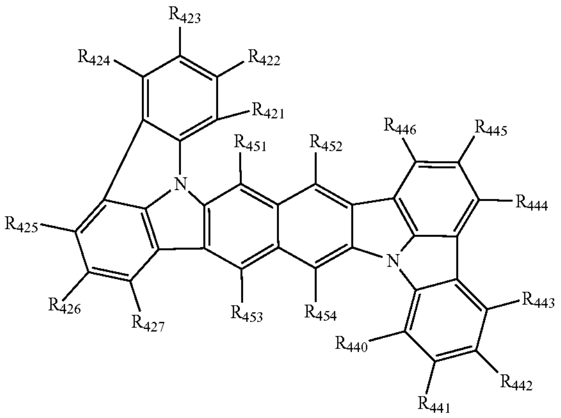

[Formula 263]

(463)

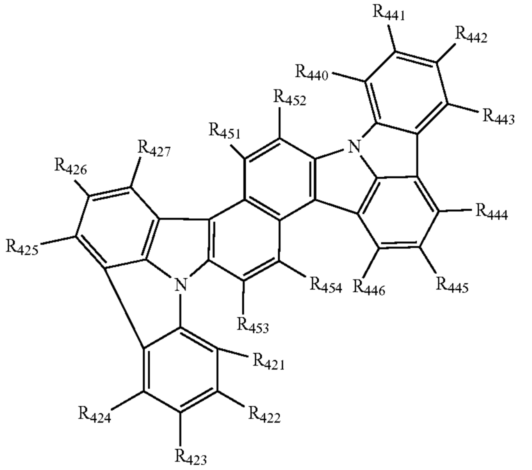

(464)

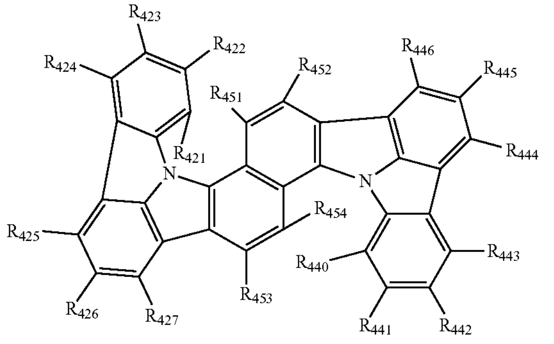

[Formula 264]

(465)

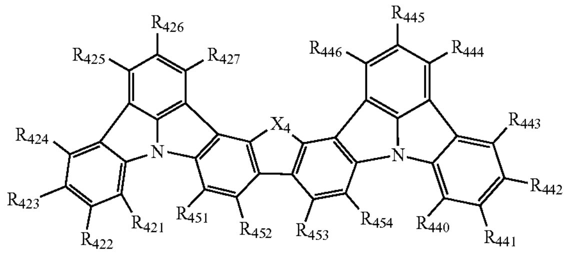

-continued

[Formula 265]

(466)

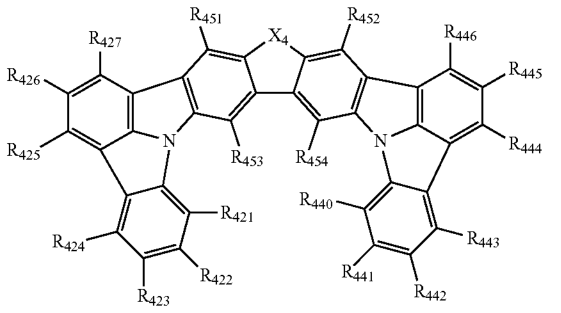

[Formula 266]

(467)

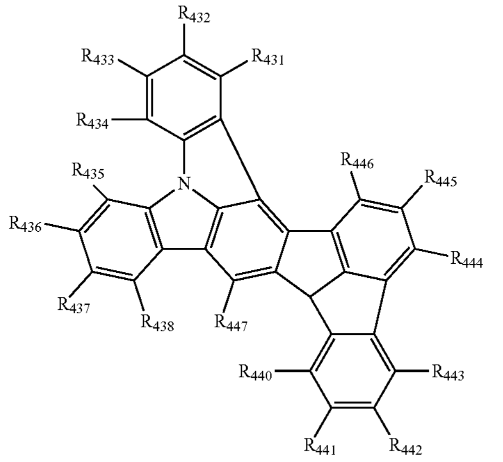

In the formulae (461) to (467):

at least one combination of adjacent two or more of $R_{421}$ to $R_{427}$, $R_{431}$ to $R_{436}$, $R_{440}$ to $R_{448}$, and $R_{451}$ to $R_{454}$ are mutually bonded to form a substituted or unsubstituted monocyclic ring, mutually bonded to form a substituted or unsubstituted fused ring, or not mutually bonded;

$R_{437}$, $R_{438}$, and $R_{421}$ to $R_{427}$, $R_{431}$ to $R_{436}$, $R_{440}$ to $R_{448}$, and $R_{451}$ to $R_{454}$ forming neither the monocyclic ring nor the fused ring are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms;

$X_4$ is an oxygen atom, $NR_{801}$, or $C(R_{802})(R_{803})$;

$R_{801}$, $R_{802}$, and $R_{803}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

a substituted or unsubstituted alkyl group having 1 to 50 carbon atoms, or a substituted or unsubstituted aryl group having 6 to 50 ring carbon atoms;

when a plurality of $R_{801}$ are present, the plurality of $R_{801}$ are mutually the same or different;

when a plurality of $R_{802}$ are present, the plurality of $R_{802}$ are mutually the same or different; and when a plurality of $R_{803}$ are present, the plurality of $R_{803}$ are mutually the same or different.

In an exemplary embodiment, $R_{421}$ to $R_{427}$ and $R_{440}$ to $R_{448}$ are each independently a hydrogen atom, a substituted or unsubstituted aryl group having 6 to 50 ring carbon atoms, or a substituted or unsubstituted heterocyclic group having 5 to 50 ring atoms.

In an exemplary embodiment, $R_{421}$ to $R_{427}$ and $R_{440}$ to $R_{447}$ are each independently selected from the group consisting of a hydrogen atom, a substituted or unsubstituted aryl group having 6 to 18 ring carbon atoms, and a substituted or unsubstituted heterocyclic group having 5 to 18 ring atoms.

In an exemplary embodiment, the compound represented by the formula (41-3) is a compound represented by a formula (41-3-1) below.

[Formula 267]

(41-3-1)

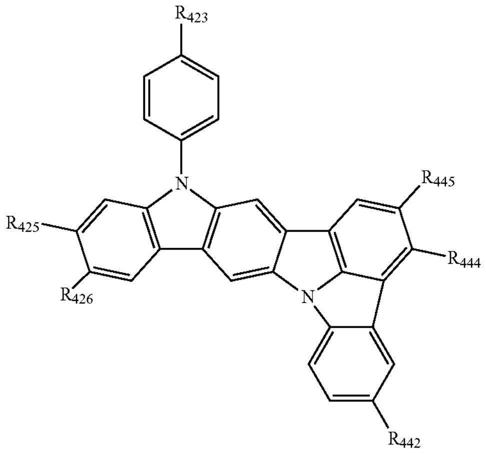

In the formula (41-3-1), $R_{423}$, $R_{425}$, $R_{426}$, $R_{442}$, $R_{444}$ and $R_{445}$ each independently represent the same as $R_{423}$, $R_{425}$, $R_{426}$, $R_{442}$, $R_{444}$ and $R_{445}$ in the formula (41-3).

In an exemplary embodiment, the compound represented by the formula (41-3) is a compound represented by a formula (41-3-2) below.

[Formula 268]

(41-3-2)

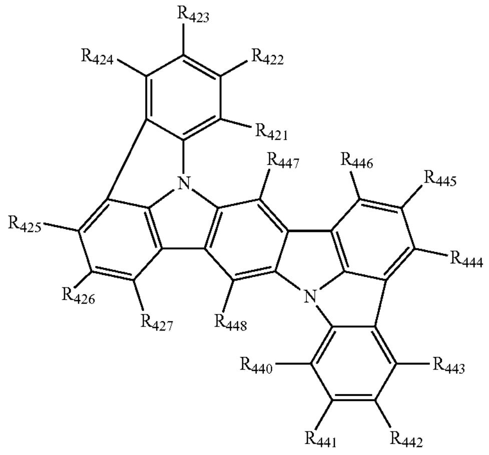

In the formula (41-3-2), $R_{421}$ to $R_{427}$ and $R_{440}$ to $R_{448}$ each independently represent the same as $R_{421}$ to $R_{427}$ and $R_{440}$ to $R_{448}$ in the formula (41-3); and at least one of $R_{421}$ to $R_{427}$ or $R_{440}$ to $R_{446}$ is a group represented by —$N(R_{906})(R_{907})$.

In an exemplary embodiment, two of $R_{421}$ to $R_{427}$ and $R_{440}$ to $R_{448}$ in the formula (41-3-2) are each a group represented by —$N(R_{906})(R_{907})$.

In an exemplary embodiment, the compound represented by the formula (41-3-2) is a compound represented by a formula (41-3-3) below.

[Formula 269]

(41-3-3)

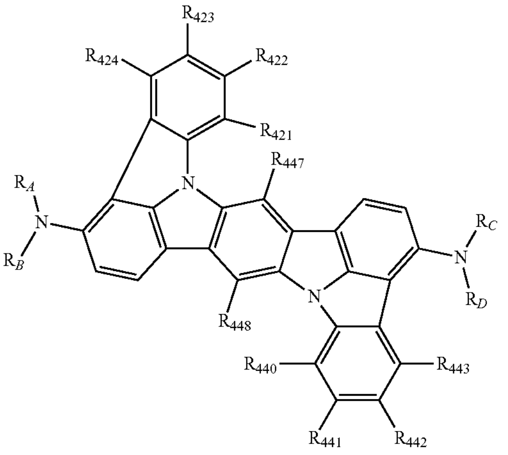

In the formula (41-3-3), $R_{421}$ to $R_{424}$, $R_{440}$ to $R_{443}$, $R_{447}$, and $R_{448}$ each independently represent the same as $R_{421}$ to $R_{424}$, $R_{440}$ to $R_{443}$, $R_{447}$, and $R_{448}$ in the formula (41-3); and $R_A$, $R_B$, $R_C$, and $R_D$ are each independently a substituted or unsubstituted aryl group having 6 to 18 ring carbon atoms, or a substituted or unsubstituted heterocyclic group having 5 to 18 ring atoms.

In an exemplary embodiment, the compound represented by the formula (41-3-3) is a compound represented by a formula (41-3-4) below.

[Formula 270]

(41-3-4)

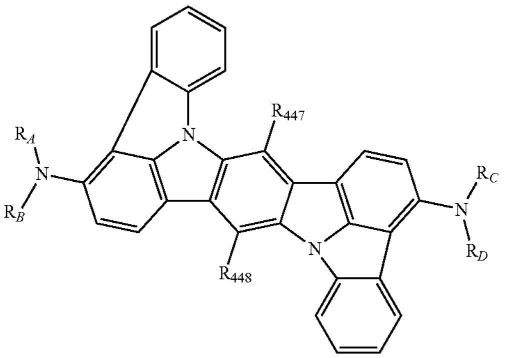

In the formula (41-3-4), $R_{447}$, $R_{448}$, $R_A$, $R_B$, $R_C$ and $R_D$ each independently represent the same as $R_{447}$, $R_{448}$, $R_A$, $R_B$, $R_C$ and $R_D$ in the formula (41-3-3).

In an exemplary embodiment, $R_A$, $R_B$, $R_C$, and $R_D$ are each independently a substituted or unsubstituted aryl group having 6 to 18 ring carbon atoms.

In an exemplary embodiment, $R_A$, $R_B$, $R_C$, and $R_D$ are each independently a substituted or unsubstituted phenyl group.

In an exemplary embodiment, $R_{447}$ and $R_{448}$ are each a hydrogen atom.

In an exemplary embodiment, a substituent for "substituted or unsubstituted" group in each of the formulae is an unsubstituted alkyl group having 1 to 50 carbon atoms, an unsubstituted alkenyl group having 2 to 50 carbon atoms, an unsubstituted alkynyl group having 2 to 50 carbon atoms, an unsubstituted cycloalkyl group having 3 to 50 ring carbon atoms, —Si($R_{901a}$)($R_{902a}$)($R_{903a}$), —O—($R_{904a}$), —S—($R_{905a}$), —N($R_{906}$a)($R_{907a}$), a halogen atom, a cyano group, a nitro group, an unsubstituted aryl group having 6 to 50 ring carbon atoms, or an unsubstituted heterocyclic group having 5 to 50 ring atoms;

$R_{901a}$ to $R_{907a}$ are each independently a hydrogen atom, an unsubstituted alkyl group having 1 to 50 carbon atoms, an unsubstituted aryl group having 6 to 50 ring carbon atoms, or an unsubstituted heterocyclic group having 5 to 50 ring atoms;

when two or more $R_{901a}$ are present, the two or more $R_{901a}$ are mutually the same or different;

when two or more $R_{902a}$ are present, the two or more $R_{902a}$ are mutually the same or different;

when two or more $R_{903a}$ are present, the two or more $R_{903a}$ are mutually the same or different;

when two or more $R_{904a}$ are present, the two or more $R_{904a}$ are mutually the same or different;

when two or more $R_{905a}$ are present, the two or more $R_{905a}$ are mutually the same or different;

when two or more $R_{906a}$ are present, the two or more $R_{906a}$ are mutually the same or different; and when two or more $R_{907a}$ are present, the two or more $R_{907a}$ are mutually the same or different.

In an exemplary embodiment, a substituent for "substituted or unsubstituted" group in each of the formulae is an unsubstituted alkyl group having 1 to 50 carbon atoms, an unsubstituted aryl group having 6 to 50 ring carbon atoms, or an unsubstituted heterocyclic group having 5 to 50 ring atoms.

In an exemplary embodiment, a substituent for "substituted or unsubstituted" group in each of the formulae is an unsubstituted alkyl group having 1 to 18 carbon atoms, an unsubstituted aryl group having 6 to 18 ring carbon atoms, or an unsubstituted heterocyclic group having 5 to 18 ring atoms.

In the organic EL device according to the exemplary embodiment, the second emitting layer preferably further contains the fourth compound that luminesces and the fourth compound is more preferably a fluorescent compound.

The fourth compound is preferably a compound that emits light having a maximum peak wavelength in a range from 430 nm to 480 nm, more preferably a compound that emits fluorescence having a maximum peak wavelength in a range from 430 nm to 480 nm.

In the organic EL device according to the exemplary embodiment, the first emitting layer preferably further contains the third compound that luminesces and the third compound is more preferably a fluorescent compound.

The third compound is preferably a compound that emits light having a maximum peak wavelength in a range from 430 nm to 480 nm, more preferably a compound that emits fluorescence having a maximum peak wavelength in a range from 430 nm to 480 nm.

A measurement method of the maximum peak wavelength of a compound is as follows. A toluene solution of a measurement target compound at a concentration ranging from $10^{-6}$ mol/L to $10^{-5}$ mol/L is prepared and put in a quartz cell. An emission spectrum (ordinate axis: emission intensity, abscissa axis: wavelength) of the thus-obtained sample is measured at a normal temperature (300K). The emission spectrum is measurable using a spectrophotometer (machine name: F-7000) manufactured by Hitachi High-Tech Science Corporation. It should be noted that the machine for measuring the emission spectrum is not limited to the machine used herein.

A peak wavelength of the emission spectrum exhibiting the maximum luminous intensity is defined as a maximum emission peak wavelength. Herein, the maximum peak wavelength of fluorescence is occasionally referred to as a maximum fluorescence peak wavelength (FL-peak).

When the first emitting layer of the organic EL device according to the exemplary embodiment contains the first compound and the third compound, the first compound is preferably a host material (sometimes referred to as a matrix material) and the third compound is preferably a dopant material (sometimes referred to as a guest material, emitter, or luminescent material).

In the organic EL device according to the exemplary embodiment, a triplet energy $T_1$(H1) of the first host material and a triplet energy $T_1$(H2) of the second host material preferably satisfy a relationship of a numerical formula (Numerical Formula 3) below.

(Numerical Formula 3)

$$T_1(H1) > T_1(H2)$$

In an arrangement of the exemplary embodiment, an organic electroluminescence device with improved luminous efficiency can be provided.

Conventionally, Triplet-Triplet-Annihilation (sometimes referred to as TTA) is known as a technique for enhancing the luminous efficiency of the organic electroluminescence device. TTA is a mechanism in which triplet excitons collide with one another to generate singlet excitons. It should be noted that the TTA mechanism is also occasionally referred to as a TTF mechanism as described in WO2010/134350.

The TTF phenomenon will be described. Holes injected from an anode and electrons injected from a cathode are recombined in an emitting layer to generate excitons. As for the spin state, as is conventionally known, singlet excitons account for 25% and triplet excitons account for 75%. In a conventionally known fluorescent device, light is emitted when singlet excitons of 25% are relaxed to the ground state. The remaining triplet excitons of 75% are returned to the ground state without emitting light through a thermal deactivation process. Accordingly, the theoretical limit value of the internal quantum efficiency of a conventional fluorescent device is believed to be 25%.

Meanwhile, the behavior of triplet excitons generated within an organic substance has been theoretically examined. According to S. M. Bachilo et al. (J. Phys. Chem. A, 104, 7711 (2000)), assuming that high-order excitons such as quintet excitons are quickly returned to triplet excitons, triplet excitons (hereinafter abbreviated as $^3A^*$) collide with one another with an increase in the density thereof, whereby a reaction shown by the following formula occurs. In the formula, $^1A$ represents the ground state and $^1A^*$ represents the lowest singlet excitons.

$$^3A^* + {}^3A^* \longrightarrow (4/9)^1A + (1/9)^1A^* + (13/9)^3A^*$$

In other words, $5^3A^* \rightarrow 4^1A + 1A^*$ is satisfied, and it is expected that, among triplet excitons initially generated, which account for 75%, one fifth thereof (i.e., 20%) is changed to singlet excitons. Accordingly, the amount of singlet excitons which contribute to emission is 40%, which is a value obtained by adding 15% (75%×(⅕)=15%) to 25%, which is the amount ratio of initially generated singlet excitons. At this time, a ratio of luminous intensity derived from TTF (TTF ratio) relative to the total luminous intensity is 15/40, i.e., 37.5%. Assuming that singlet excitons are generated by collision of initially generated triplet excitons accounting for 75% (i.e., one singlet exciton is generated from two triplet excitons), a significantly high internal quantum efficiency of 62.5% is obtained, which is a value obtained by adding 37.5% (75%×(½)=37.5%) to 25% (the amount ratio of initially generated singlet excitons). At this time, the TTF ratio is 37.5/62.5=60%.

In the organic electroluminescence device according to an arrangement of the exemplary embodiment, it is considered that triplet excitons generated by recombination of holes and electrons in the first emitting layer and present on an interface between the first emitting layer and organic layer(s) in direct contact therewith are not likely to be quenched even under the presence of excessive carriers on the interface between the first emitting layer and the organic layer(s). For instance, the presence of a recombination region locally on an interface between the first emitting layer and a hole transporting layer or an electron blocking layer is considered to cause quenching by excessive electrons. Meanwhile, the presence of a recombination region locally on an interface between the first emitting layer and an electron transporting layer or a hole blocking layer is considered to cause quenching by excessive holes.

The organic electroluminescence device according to an arrangement of the exemplary embodiment includes at least two emitting layers (i.e., the first emitting layer and the second emitting layer) which satisfy a predetermined relationship. The triplet energy $T_1(H1)$ of the first host material in the first emitting layer and the triplet energy $T_1(H2)$ of the second host material in the second emitting layer satisfy the relationship of the numerical formula (Numerical Formula 3).

By including the first emitting layer and the second emitting layer so as to satisfy the numerical formula (Numerical Formula 3), triplet excitons generated in the first emitting layer can transfer to the second emitting layer without being quenched by excessive carriers and be inhibited from back-transferring from the second emitting layer to the first emitting layer. Consequently, the second emitting layer exhibits the TTF mechanism to efficiently generate singlet excitons, thereby improving luminous efficiency.

Accordingly, the organic electroluminescence device includes, as different regions, the first emitting layer mainly generating triplet excitons and the second emitting layer mainly exhibiting the TTF mechanism using triplet excitons having transferred from the first emitting layer, and a difference in triplet energy is provided by using a compound having a smaller triplet energy than that of the first host material in the first emitting layer as the second host material in the second emitting layer, thereby improving the luminous efficiency.

In the organic EL device according to the exemplary embodiment, it is preferable that the triplet energy $T_1(H1)$ of the first host material and the triplet energy $T_1(H2)$ of the second host material satisfy a relationship of a numerical formula (Numerical Formula 3A) below.

(Numerical Formula 3A)

$$T_1(H1) - T_1(H2) > 0.03 \text{ eV}$$

When the first emitting layer of the organic EL device according to the exemplary embodiment contains the first host material (first compound) and the third compound, a singlet energy $S_1(H1)$ of the first host material (first compound) and a singlet energy $S_1(D3)$ of the third compound preferably satisfy a relationship of a numerical formula (Numerical Formula 1) below.

(Numerical Formula 1)

$$S_1(H1) > S_1(D3)$$

When the first host material and the third compound satisfy the relationship of the numerical formula (Numerical formula 1), singlet excitons generated on the first host material easily energy-transfer from the first host material to the third compound, thereby contributing to fluorescence of the third compound.

In the organic EL device according to the exemplary embodiment, it is preferable that the triplet energy $T_1(H1)$ of the first host material and a triplet energy $T_1(D3)$ of the third compound satisfy a relationship of a numerical formula (Numerical Formula 4) below.

(Numerical Formula 4)

$$T_1(D3) > T_1(H1)$$

When the first host material and the third compound satisfy the relationship of the numerical formula (Numerical Formula 4), triplet excitons generated in the first emitting layer are transferred not onto the third compound having higher triplet energy but onto the first host material, thereby being easily transferred to the second emitting layer.

The organic EL device according to the exemplary embodiment preferably satisfies a relationship of a numerical formula (Numerical Formula 4B) below.

(Numerical Formula 4B)

$$T_1(D3) > T_1(H1) > T_1(H2)$$

When the second emitting layer of the organic EL device according to the exemplary embodiment contains the second compound and the fourth compound, the second compound is preferably a host material (sometimes referred to as a matrix material) and the fourth compound is preferably a dopant material (sometimes referred to as a guest material, emitter, or luminescent material).

When the second emitting layer of the organic EL device according to the exemplary embodiment contains the second host material (second compound) and the fourth compound, a singlet energy $S_1(H2)$ of the second host material (second compound) and a singlet energy $S_1(D4)$ of the fourth compound preferably satisfy a relationship of a numerical formula (Numerical Formula 2) below.

(Numerical Formula 2)

$$S_1(H2) > S_1(D4)$$

In the organic EL device according to the exemplary embodiment, when the fourth compound and the second host material satisfy the relationship of the numerical formula (Numerical Formula 2), due to the singlet energy of the fourth compound being smaller than the singlet energy of the second host material, singlet excitons generated by the TTF phenomenon energy-transfer from the second host material to the fourth compound, thereby contributing to fluorescence of the fourth compound.

In the organic EL device according to the exemplary embodiment, a triplet energy $T_1(D4)$ of the fourth compound and the triplet energy $T_1(H2)$ of the second host material preferably satisfy a relationship of a numerical formula (Numerical Formula 5) below.

(Numerical Formula 5)

$$T_1(D4) > T_1(H2)$$

In the organic EL device according to the exemplary embodiment, when the fourth compound and the second host material satisfy the relationship of the numerical formula (Numerical Formula 5), in transfer of triplet excitons generated in the first emitting layer to the second emitting layer, the triplet excitons energy-transfer not onto the fourth compound having higher triplet energy but onto molecules of the second host material. In addition, triplet excitons generated by recombination of holes and electrons on the second host material do not transfer to the fourth compound having higher triplet energy. Triplet excitons generated by recombination on molecules of the fourth compound quickly energy-transfer to molecules of the second host material.

Triplet excitons in the second host material do not transfer to the fourth compound but efficiently collide with one another on the second host material to generate singlet excitons by the TTF phenomenon.

Triplet Energy $T_1$

A method of measuring triplet energy $T_1$ is exemplified by a method below.

A measurement target compound is dissolved in EPA (diethylether:isopentane:ethanol=5:5:2 in volume ratio) so as to fall within a range from 10-5 mol/L to 10-4 mol/L, and the obtained solution is put in a quartz cell to provide a measurement sample. A phosphorescence spectrum (ordinate axis: phosphorescent luminous intensity, abscissa axis: wavelength) of the measurement sample is measured at a low temperature (77K). A tangent is drawn to the rise of the phosphorescence spectrum close to the short-wavelength region. An energy amount is calculated by a conversion equation (F1) below on a basis of a wavelength value λedge [nm] at an intersection of the tangent and the abscissa axis. The calculated energy amount is defined as triplet energy $T_1$.

$$T_1\ [eV] = 1239.85/\lambda edge \quad \text{Conversion Equation (F1)}$$

The tangent to the rise of the phosphorescence spectrum close to the short-wavelength region is drawn as follows. While moving on a curve of the phosphorescence spectrum from the short-wavelength region to the local maximum value closest to the short-wavelength region among the local maximum values of the phosphorescence spectrum, a tangent is checked at each point on the curve toward the long-wavelength of the phosphorescence spectrum. An inclination of the tangent is increased along the rise of the curve (i.e., a value of the ordinate axis is increased). A tangent drawn at a point of the local maximum inclination (i.e., a tangent at an inflection point) is defined as the tangent to the rise of the phosphorescence spectrum close to the short-wavelength region.

A local maximum point where a peak intensity is 15% or less of the maximum peak intensity of the spectrum is not counted as the above-mentioned local maximum peak intensity closest to the short-wavelength region. The tangent drawn at a point that is closest to the local maximum peak intensity closest to the short-wavelength region and where the inclination of the curve is the local maximum is defined as a tangent to the rise of the phosphorescence spectrum close to the short-wavelength region.

For phosphorescence measurement, a spectrophotofluorometer body F-4500 (manufactured by Hitachi High-Technologies Corporation) is usable. The measurement instrument is not limited to this arrangement. A combination of a cooling unit, a low temperature container, an excitation light source and a light-receiving unit may be used for measurement.

Singlet Energy $S_1$

A method of measuring a singlet energy $S_1$ with use of a solution (occasionally referred to as a solution method) is exemplified by a method below.

A toluene solution of a measurement target compound at a concentration ranging from 10-5 mol/L to 10-4 mol/L is prepared and put in a quartz cell. An absorption spectrum (ordinate axis: absorption intensity, abscissa axis: wavelength) of the thus-obtained sample is measured at a normal temperature (300K). A tangent is drawn to the fall of the absorption spectrum close to the long-wavelength region, and a wavelength value λedge (nm) at an intersection of the tangent and the abscissa axis is assigned to a conversion equation (F2) below to calculate the singlet energy.

$$S_1\ [\text{eV}] = 1239.85/\lambda\text{edge} \quad \text{Conversion Equation (F2)}$$

Any device for measuring absorption spectrum is usable. For instance, a spectrophotometer (U3310 manufactured by Hitachi, Ltd.) is usable.

The tangent to the fall of the absorption spectrum close to the long-wavelength region is drawn as follows. While moving on a curve of the absorption spectrum from the local maximum value closest to the long-wavelength region, among the local maximum values of the absorption spectrum, in a long-wavelength direction, a tangent at each point on the curve is checked. An inclination of the tangent is decreased and increased in a repeated manner as the curve falls (i.e., a value of the ordinate axis is decreased). A tangent drawn at a point where the inclination of the curve is the local minimum closest to the long-wavelength region (except when absorbance is 0.1 or less) is defined as the tangent to the fall of the absorption spectrum close to the long-wavelength region.

The local maximum absorbance of 0.2 or less is not counted as the above-mentioned local maximum absorbance closest to the long-wavelength region.

The first emitting layer and the second emitting layer preferably do not contain a phosphorescent material (dopant material).

The first emitting layer and the second emitting layer preferably do not contain a heavy metal complex and a phosphorescent rare earth metal complex. Examples of the heavy metal complex herein include iridium complex, osmium complex, and platinum complex.

Further, the first emitting layer and the second emitting layer also preferably do not contain a metal complex.

Film Thickness of Emitting Layer

A film thickness of the emitting layer of the organic EL device according to the exemplary embodiment is preferably in a range from 5 nm to 50 nm, more preferably in a range from 7 nm to 50 nm, further preferably in a range from 10 nm to 50 nm. When the film thickness of the emitting layer is 5 nm or more, the emitting layer is easily formable and chromaticity is easily adjustable. When the film thickness of the emitting layer is 50 nm or less, a rise in the drive voltage is easily reducible.

Content Ratios of Compounds in Emitting Layer

When the first emitting layer contains the first compound and the third compound, a content ratio of each of the first compound and the third compound in the first emitting layer preferably falls, for instance, within a range below.

The content ratio of the first compound is preferably in a range from 80 mass % to 99 mass %, more preferably in a range from 90 mass % to 99 mass %, further preferably in a range from 95 mass % to 99 mass %.

The content ratio of the third compound is preferably in a range from 1 mass % to 10 mass %, more preferably in a range from 1 mass % to 7 mass %, further preferably in a range from 1 mass % to 5 mass %.

The upper limit of the total of the content ratios of the first compound and the third compound in the first emitting layer is 100 mass %.

It is not excluded that the first emitting layer of the exemplary embodiment further contains a material(s) other than the first and third compounds.

The first emitting layer may contain a single type of the first compound or may contain two or more types of the first compound. The first emitting layer may contain a single type of the third compound or may contain two or more types of the third compound.

When the second emitting layer contains the second compound and the fourth compound, a content ratio of each of the second compound and the fourth compound in the second emitting layer preferably falls, for instance, within a range below.

The content ratio of the second compound is preferably in a range from 80 mass % to 99 mass %, more preferably in a range from 90 mass % to 99 mass %, further preferably in a range from 95 mass % to 99 mass %.

The content ratio of the fourth compound is preferably in a range from 1 mass % to 10 mass %, more preferably in a range from 1 mass % to 7 mass %, further preferably in a range from 1 mass % to 5 mass %.

The upper limit of the total of the content ratios of the second compound and the fourth compound in the second emitting layer is 100 mass %.

It is not excluded that the second emitting layer of the exemplary embodiment further contains a material(s) other than the second and fourth compounds.

The second emitting layer may contain a single type of the second compound or may contain two or more types of the second compound. The second emitting layer may contain a single type of the fourth compound or may contain two or more types of the fourth compound.

In the organic EL device according to the exemplary embodiment, the first emitting layer and the second emitting layer are preferably in direct contact with each other.

Herein, a layer arrangement in which the first emitting layer and the second emitting layer are in direct contact with each other can include one of embodiments ($LS_1$), (LS2) and (LS3) below.

($LS_1$) An embodiment in which a region containing both the first host material and the second host material is generated in a process of vapor-depositing the compound of the first emitting layer and vapor-depositing the compound of the second emitting layer, and is present on the interface between the first emitting layer and the second emitting layer.

(LS2) An embodiment in which in a case of containing an emitting compound in the first emitting layer and the second emitting layer, a region containing all of the first host material, the second host material and the emitting compound is generated in a process of vapor-depositing the compound of the first emitting layer and vapor-depositing the compound of the second emitting layer, and is present on the interface between the first emitting layer and the second emitting layer.

(LS3) An embodiment in which in a case of containing an emitting compound in the first emitting layer and the second emitting layer, a region containing the emitting compound, a region containing the first host material or a region containing the second host material is generated in a process of vapor-depositing the compound of the first emitting layer and vapor-depositing the compound of the second emitting layer, and is present on the interface between the first emitting layer and the second emitting layer.

When the first emitting layer and the second emitting layer are not in direct contact with each other in the organic EL device according to the exemplary embodiment, at least one organic layer may be provided between the first emitting layer and the second emitting layer.

Interposed Layer

The organic EL device according to the exemplary embodiment may include an interposed layer as an organic layer disposed between the first emitting layer and the second emitting layer.

In the exemplary embodiment, in order to inhibit an overlap between a Singlet emitting region and a TTF emitting region, the interposed layer contains no emitting compound or may contain an emitting compound in an insubstantial amount provided that the overlap can be inhibited.

For instance, the interposed layer contains 0 mass % of an emitting compound. Alternatively, for instance, the interposed layer may contain an emitting compound provided that the emitting compound contained is a component accidentally mixed in a manufacturing process or a component contained as impurities in a material.

For instance, when the interposed layer consists of a material A, a material B, and a material C, the content ratios of the materials A, B, and C in the interposed layer are each 10 mass % or more, and the total of the content ratios of the materials A, B, and C is 100 mass %.

In the following, the interposed layer is occasionally referred to as a "non-doped layer". A layer containing an emitting compound is occasionally referred to as a "doped layer".

It is considered that the Singlet emitting region and the TTF emitting region are typically likely to be separated from each other in layered emitting layers, thus improving luminous efficiency.

In the organic EL device according to the exemplary embodiment, when the interposed layer (non-doped layer) is disposed between the first emitting layer and the second emitting layer in the emitting region, it is expected that a region where the Singlet emitting region and the TTF emitting region overlap with each other is reduced to inhibit a decrease in TTF efficiency caused by collision between triplet excitons and carriers. That is, it is considered that providing the interposed layer (non-doped layer) between the emitting layers contributes to the improvement in the efficiency of TTF emission.

The interposed layer is the non-doped layer.

The interposed layer contains no metal atom. The interposed layer thus contains no metal complex.

The interposed layer contains an interposed layer material. The interposed layer material is not an emitting compound.

The interposed layer material may be any material except for the emitting compound.

Examples of the interposed layer material include: 1) a heterocyclic compound such as an oxadiazole derivative, benzimidazole derivative, or phenanthroline derivative; 2) a fused aromatic compound such as a carbazole derivative, anthracene derivative, phenanthrene derivative, pyrene derivative or chrysene derivative; and 3) an aromatic amine compound such as a triarylamine derivative or a fused polycyclic aromatic amine derivative.

One or both of the first host material and the second host material may be used as the interposed layer material. The interposed layer material may be any material provided that the Singlet emitting region and the TTF emitting region are separated from each other and the Singlet emission and the TTF emission are not hindered.

In the organic EL device according to the exemplary embodiment, the respective content ratios of all the materials forming the interposed layer in the interposed layer are 10 mass % or more.

The interposed layer contains the interposed layer material as a material forming the interposed layer.

The interposed layer preferably contains 60 mass % or more of the interposed layer material, more preferably contains 70 mass % or more of the interposed layer material, further preferably contains 80 mass % or more of the interposed layer material, more further preferably 90 mass % or more of the interposed layer material, still further more preferably 95 mass % or more of the interposed layer material, with respect to the total mass of the interposed layer.

The interposed layer may contain a single type of the interposed layer material or may contain two or more types of the interposed layer material.

When the interposed layer contains two or more types of the interposed layer material, an upper limit of the total of the content ratios of the two or more types of the interposed layer material is 100 mass %.

It should be noted that the interposed layer of the exemplary embodiment may further contain material(s) other than the interposed layer material.

The interposed layer may be provided in the form of a single layer or a laminate of two or more layers.

As long as the overlap between the Singlet emitting region and the TTF emitting region is inhibited, a film thickness of the interposed layer is not particularly limited but each layer in the interposed layer is preferably in a range from 3 nm to 15 nm, more preferably in a range from 5 nm to 10 nm.

The interposed layer having a film thickness of 3 nm or more easily separates the Singlet emitting region from the emitting region derived from TTF.

The interposed layer having a film thickness of 15 nm or less easily inhibits a phenomenon where the host material of the interposed layer emits light.

An arrangement of the organic EL device 1 will be further described. It should be noted that the reference numerals will be sometimes omitted below.

Substrate

The substrate is used as a support for the organic EL device. For instance, glass, quartz, plastics and the like are usable for the substrate. A flexible substrate is also usable. The flexible substrate is a bendable substrate, which is exemplified by a plastic substrate. Examples of the material for the plastic substrate include polycarbonate, polyarylate, polyethersulfone, polypropylene, polyester, polyvinyl fluoride, polyvinyl chloride, polyimide, and polyethylene naphthalate. Moreover, an inorganic vapor deposition film is also usable.

Anode

Metal, an alloy, an electrically conductive compound, a mixture thereof, or the like having a large work function (specifically, 4.0 eV or more) is preferably used as the anode formed on the substrate. Specific examples of the material include ITO (Indium Tin Oxide), indium oxide-tin oxide containing silicon or silicon oxide, indium oxide-zinc oxide, indium oxide containing tungsten oxide and zinc oxide, and graphene. In addition, gold (Au), platinum (Pt), nickel (Ni), tungsten (W), chrome (Cr), molybdenum (Mo), iron (Fe), cobalt (Co), copper (Cu), palladium (Pd), titanium (Ti), and nitrides of a metal material (e.g., titanium nitride) are usable.

The material is typically formed into a film by a sputtering method. For instance, the indium oxide-zinc oxide can be formed into a film by the sputtering method using a target in which zinc oxide in a range from 1 mass % to 10 mass % is added to indium oxide. Moreover, for instance, the indium oxide containing tungsten oxide and zinc oxide can be formed by the sputtering method using a target in which tungsten oxide in a range from 0.5 mass % to 5 mass % and zinc oxide in a range from 0.1 mass % to 1 mass % are added to indium oxide. In addition, the anode may be formed by a vacuum deposition method, a coating method, an inkjet method, a spin coating method or the like.

Among the organic layers formed on the anode, since the hole injecting layer adjacent to the anode is formed of a composite material into which holes are easily injectable irrespective of the work function of the anode, a material usable as an electrode material (e.g., metal, an alloy, an electroconductive compound, a mixture thereof, and the elements belonging to the group 1 or 2 of the periodic table) is also usable for the anode.

A material having a small work function such as elements belonging to Groups 1 and 2 in the periodic table of the elements, specifically, an alkali metal such as lithium (Li) and cesium (Cs), an alkaline earth metal such as magnesium (Mg), calcium (Ca) and strontium (Sr), alloys (e.g., MgAg and AlLi) including the alkali metal or the alkaline earth metal, a rare earth metal such as europium (Eu) and ytterbium (Yb), alloys including the rare earth metal are also usable for the anode. It should be noted that the vacuum deposition method and the sputtering method are usable for forming the anode using the alkali metal, alkaline earth metal and the alloy thereof. Further, when a silver paste is used for the anode, the coating method and the inkjet method are usable.

Cathode

It is preferable to use metal, an alloy, an electroconductive compound, a mixture thereof, or the like having a small work function (specifically, 3.8 eV or less) for the cathode. Examples of the material for the cathode include elements belonging to Groups 1 and 2 in the periodic table of the elements, specifically, the alkali metal such as lithium (Li) and cesium (Cs), the alkaline earth metal such as magnesium (Mg), calcium (Ca) and strontium (Sr), alloys (e.g., MgAg and AlLi) including the alkali metal or the alkaline earth metal, the rare earth metal such as europium (Eu) and ytterbium (Yb), and alloys including the rare earth metal.

It should be noted that the vacuum deposition method and the sputtering method are usable for forming the cathode using the alkali metal, alkaline earth metal and the alloy thereof. Further, when a silver paste is used for the cathode, the coating method and the inkjet method are usable.

By providing the electron injecting layer, various conductive materials such as Al, Ag, ITO, graphene, and indium oxide-tin oxide containing silicon or silicon oxide may be used for forming the cathode regardless of the work function. The conductive materials can be formed into a film using the sputtering method, inkjet method, spin coating method and the like.

Hole Injecting Layer

The hole injecting layer is a layer containing a substance exhibiting a high hole injectability. Examples of the substance exhibiting a high hole injectability include molybdenum oxide, titanium oxide, vanadium oxide, rhenium oxide, ruthenium oxide, chrome oxide, zirconium oxide, hafnium oxide, tantalum oxide, silver oxide, tungsten oxide, and manganese oxide.

In addition, the examples of the highly hole-injectable substance further include: an aromatic amine compound, which is a low-molecule organic compound, such as 4,4',4"-tris(N,N-diphenylamino)triphenylamine (abbreviation: TDATA), 4,4',4"-tris[N-(3-methylphenyl)-N-phenylamino] triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazole-3-yl)-N-phenylamino]-9-phenylcarbazole (abbreviation: PCzPCA1), 3,6-bis[N-(9-phenylcarbazole-3-yl)-N-phenylamino]-9-phenylcarbazole (abbreviation: PCzPCA2), and 3-[N-(1-naphthyl)-N-(9-phenylcarbazole-3-yl)amino]-9-phenylcarbazole (abbreviation: PCzPCN1); and dipyrazino[2,3-f:20,30-h]quinoxaline-2,3,6,7,10,11-hexacarbonitrile (HAT-CN).

In addition, a high polymer compound (e.g., oligomer, dendrimer and polymer) is usable as the substance exhibiting a high hole injectability. Examples of the high-molecule compound include poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), and poly[N,N'-bis(4-butylphenyl)-N, N'-bis(phenyl)benzidine] (abbreviation: Poly-TPD). Moreover, an acid-added high polymer compound such as poly(3,4-ethylenedioxythiophene)/poly(styrene sulfonic acid) (PEDOT/PSS) and polyaniline/poly(styrene sulfonic acid) (PAni/PSS) are also usable.

Hole Transporting Layer

The hole transporting layer is a layer containing a highly hole-transporting substance. An aromatic amine compound, carbazole derivative, anthracene derivative and the like are usable for the hole transporting layer. Specific examples of a material for the hole transporting layer include an aromatic amine compound such as 4,4'-bis[N-(1-naphthyl)-N-phenylamino]biphenyl (abbreviation: NPB), N, N'-bis(3-methylphenyl)-N, N'-diphenyl-[1,1'-biphenyl]-4,4'-diamine (abbreviation: TPD), 4-phenyl-4'-(9-phenylfluorene-9-yl) triphenylamine (abbreviation: BAFLP), 4,4'-bis[N-(9,9-dimethylfluorene-2-yl)-N-phenylamino]biphenyl (abbreviation: DFLDPBi), 4,4',4"-tris(N,N-diphenylamino) triphenylamine (abbreviation: TDATA), 4,4',4"-tris[N-(3-methylphenyl)-N-phenylamino]triphenylamine (abbreviation: MTDATA), and 4,4'-bis[N-(spiro-9,9'-bifluorene-2-yl)-N-phenylamino]biphenyl (abbreviation: BSPB). The above-described substances mostly have a hole mobility of 10-6 $cm^2/(V\cdot s)$ or more.

For the hole transporting layer, a carbazole derivative such as CBP, 9-[4-(N-carbazolyl)]phenyl-10-phenylanthracene (CzPA), and 9-phenyl-3-[4-(10-phenyl-9-anthryl)phenyl]-9H-carbazole (PCzPA) and an anthracene derivative such as t-BuDNA, DNA, and DPAnth may be used. A high polymer compound such as poly(N-vinylcarbazole) (abbreviation: PVK) and poly(4-vinyltriphenylamine) (abbreviation: PVTPA) is also usable.

However, in addition to the above substances, any substance exhibiting a higher hole transportability than an electron transportability may be used. It should be noted that the layer containing the substance exhibiting a high hole transportability may be not only a single layer but also a laminate of two or more layers formed of the above substance(s).

Electron Transporting Layer

The electron transporting layer is a layer containing a highly electron-transporting substance. For the electron transporting layer, 1) a metal complex such as an aluminum complex, beryllium complex, and zinc complex, 2) a hetero aromatic compound such as imidazole derivative, benzimidazole derivative, azine derivative, carbazole derivative, and phenanthroline derivative, and 3) a high polymer compound are usable. Specifically, as a low-molecule organic compound, a metal complex such as Alq, tris(4-methyl-8-quinolinato)aluminum (abbreviation: $Almq_3$), bis(10-hydroxybenzo[h]quinolinato)beryllium (abbreviation: $BeBq_2$), BAlq, Znq, ZnPBO and ZnBTZ is usable. In addition to the metal complex, a heteroaromatic compound such as 2-(4-biphenylyl)-5-(4-tert-butylphenyl)-1,3,4-oxadiazole (abbreviation: PBD), 1,3-bis[5-(ptert-butylphenyl)-1,3,4-oxadiazole-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), and 4,4'-bis(5-methylbenzoxazole-2-yl)stilbene (abbreviation: BzOs) is usable. In the exemplary embodiment, a benzimidazole compound is preferably usable. The above-described substances mostly have an electron mobility of $10^{-6}$ $cm^2/Vs$ or more. It should be noted that any substance other than the above substance may be used for the electron transporting layer as long as the substance exhibits a higher electron transportability than the hole transportability. The electron transporting layer may be provided in the form of a single layer or a laminate of two or more layers of the above substance(s).

Specific examples of the compound usable for the electron transporting layer include compounds below. It should however be noted that the invention is not limited to the specific examples of the compound.

[Formula 271]

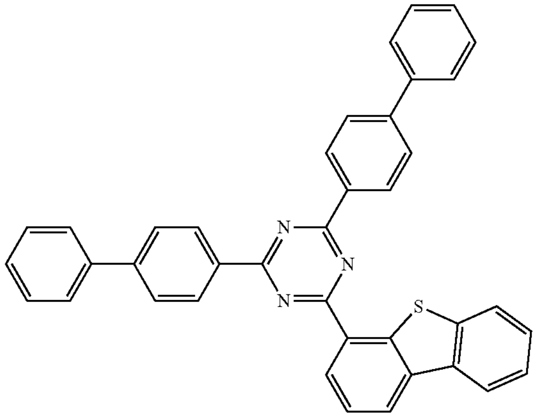

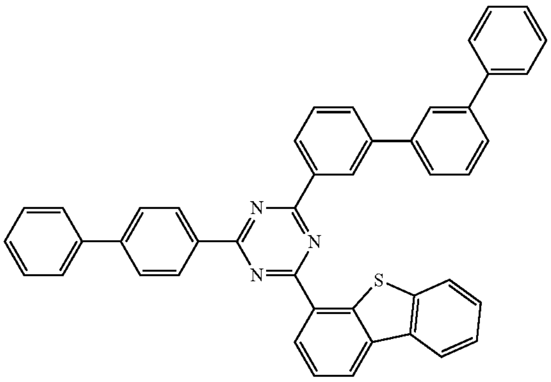

-continued

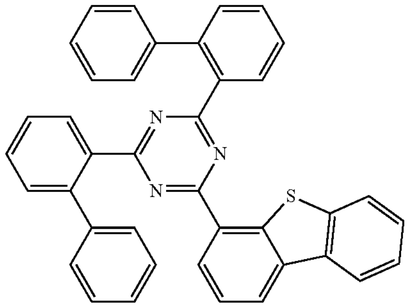

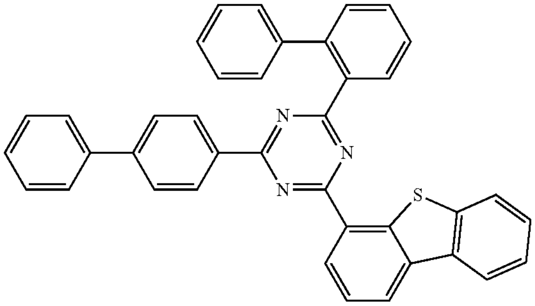

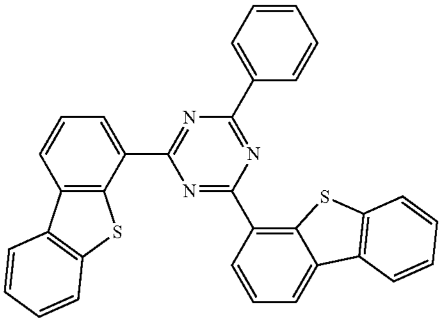

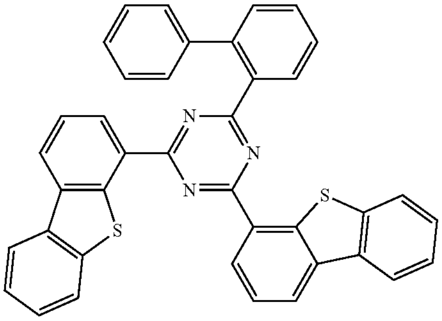

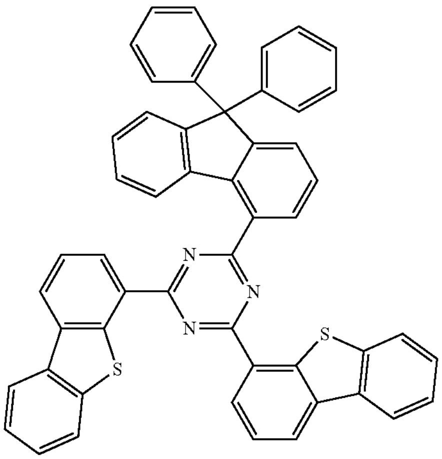

-continued

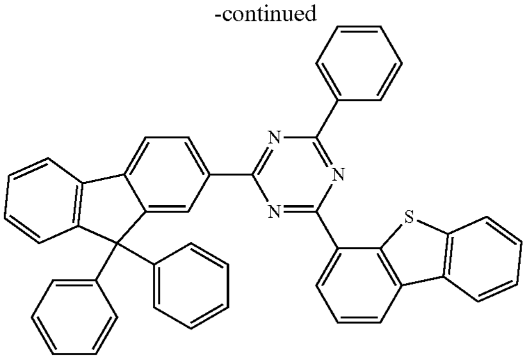

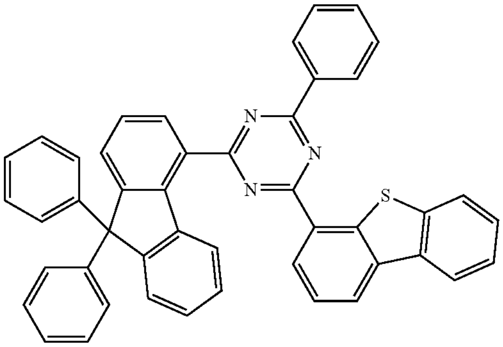

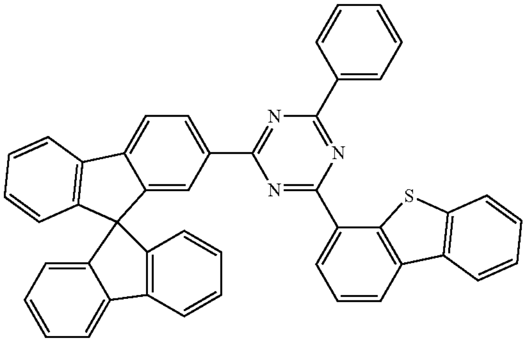

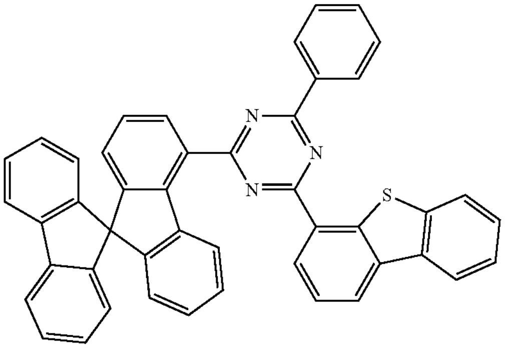

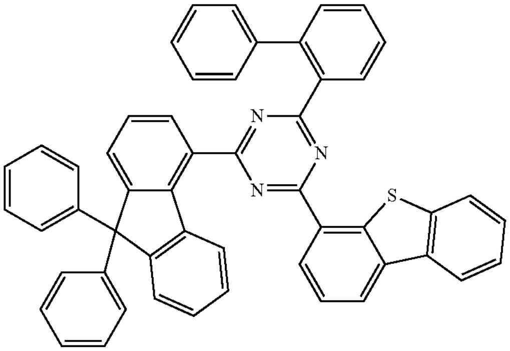

-continued

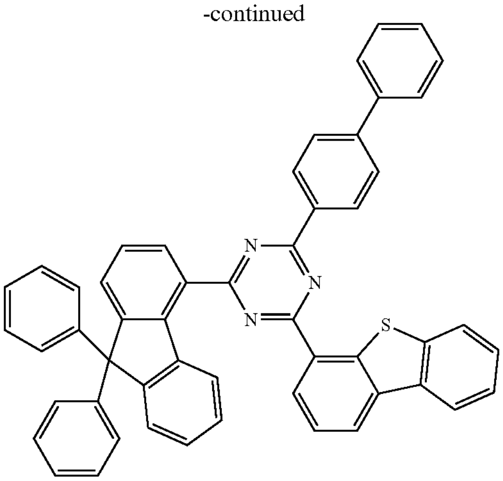

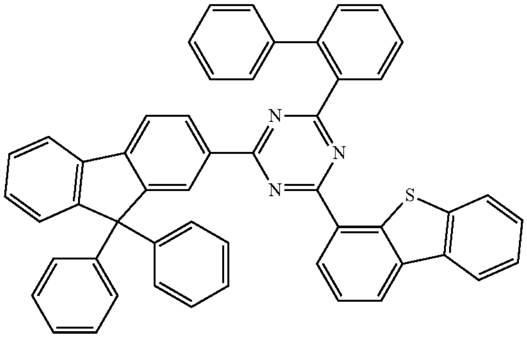

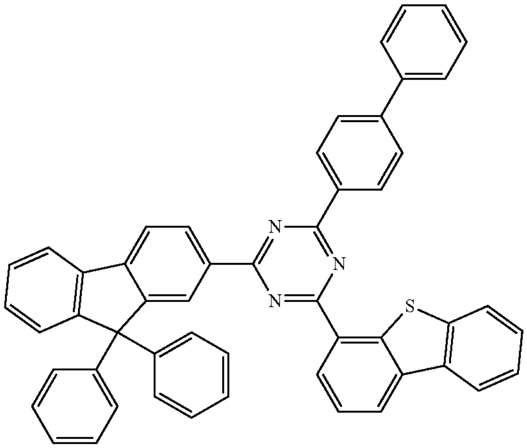

Further, a high polymer compound is usable for the electron transporting layer. For instance, poly[(9,9-dihexylfluorene-2,7-diyl)-co-(pyridine-3,5-diyl)] (abbreviation: PF-Py), poly[(9,9-dioctylfluorene-2,7-diyl)-co-(2,2'-bipyridine-6,6'-diyl)] (abbreviation: PF-BPy) and the like are usable.

Electron Injecting Layer

The electron injecting layer is a layer containing a highly electron-injectable substance. Examples of a material for the electron injecting layer include an alkali metal, alkaline earth metal and a compound thereof, examples of which include lithium (Li), cesium (Cs), calcium (Ca), lithium fluoride (LiF), cesium fluoride (CsF), calcium fluoride ($CaF_2$), and lithium oxide (LiOx). In addition, the alkali metal, alkaline earth metal or the compound thereof may be added to the substance exhibiting the electron transportability in use. Specifically, for instance, magnesium (Mg) added to Alq may be used. In this case, the electrons can be more efficiently injected from the cathode.

Alternatively, the electron injecting layer may be provided by a composite material in a form of a mixture of the organic compound and the electron donor. Such a composite material exhibits excellent electron injectability and electron transportability since electrons are generated in the organic compound by the electron donor. In this case, the organic compound is preferably a material excellent in transporting the generated electrons. Specifically, the above examples (e.g., the metal complex and the hetero aromatic compound) of the substance forming the electron transporting layer are usable. As the electron donor, any substance exhibiting electron donating property to the organic compound is usable. Specifically, the electron donor is preferably alkali metal, alkaline earth metal and rare earth metal such as lithium, cesium, magnesium, calcium, erbium and ytterbium. The electron donor is also preferably alkali metal oxide and alkaline earth metal oxide such as lithium oxide, calcium oxide, and barium oxide. Moreover, a Lewis base such as magnesium oxide is usable. Further, the organic compound such as tetrathiafulvalene (abbreviation: TTF) is usable.

Layer Formation Method

A method for forming each layer of the organic EL device in the exemplary embodiment is subject to no limitation except for the above particular description. However, known methods of dry film-forming such as vacuum deposition, sputtering, plasma or ion plating and wet film-forming such as spin coating, dipping, flow coating or ink-jet are applicable.

Film Thickness

A film thickness of each of the organic layers of the organic EL device in the exemplary embodiment is not limited unless otherwise specified in the above. In general, the thickness preferably ranges from several nanometers to 1 μm because excessively small film thickness is likely to cause defects (e.g. pin holes) and excessively large thickness leads to the necessity of applying high voltage and consequent reduction in efficiency.

According to the exemplary embodiment, an organic electroluminescence device with improved device performance can be provided.

In an arrangement according to the exemplary embodiment, an organic electroluminescence device with improved luminous efficiency can be provided. In the organic EL device according to the exemplary embodiment, the first compound represented by the formula (1) or the like may be a compound having a fused fluoranthene ring (i.e., a compound in which at least one combination of adjacent two or more of $R_{101}$ to $R_{110}$ are mutually bonded to form a substituted or unsubstituted monocyclic ring, or mutually bonded to form a substituted or unsubstituted fused ring). In this case, by layering the first emitting layer containing this first compound as the first host material and the second emitting layer containing the second host material, the organic EL device has an improved luminous efficiency. When the first emitting layer and the second emitting layer are in direct contact with each other, the luminous efficiency is easily improvable.

In an arrangement of the exemplary embodiment, an organic electroluminescence device emitting light with a long lifetime can be provided. In the organic EL device according to the exemplary embodiment, the first compound represented by the formula (1) or the like may be a compound having a non-fused fluoranthene ring (i.e., a compound in which none of combinations of adjacent two or more of $R_{101}$ to $R_{110}$ are mutually bonded). In this case, by layering the first emitting layer containing this first compound as the first host material and the second emitting layer containing the second host material, the host materials are prevented from being locally deteriorated by a generated excited state and the organic EL device thus emits light with a long lifetime. When the first emitting layer and the second emitting layer are in direct contact with each other, light emission with a long lifetime is easily achievable.

The organic EL device according to the exemplary embodiment is drivable at a low voltage.

Second Exemplary Embodiment

Compound

A compound according to a second exemplary embodiment is a compound represented by a formula (151) below and having at least one group represented by a formula (152) below. The compound according to the second exemplary embodiment is a compound that may also correspond to an arrangement of the first compound serving as the first host material in the first exemplary embodiment.

[Formula 272]

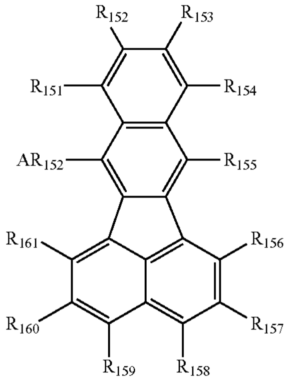

(151)

$$*-L_{151}-Ar_{151} \quad (152)$$

In the formula (151):

at least one of $R_{151}$ to $R_{155}$ is a group represented by the formula (152);

$R_{151}$ to $R_{154}$ not being the group represented by the formula (152) are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $-Si(R_{901})(R_{902})(R_{903})$, a group represented by $-O-(R_{904})$, a group represented by $-S-(R_{905})$, a substituted or unsubstituted aralkyl group having 7 to 50 carbon atoms, a group represented by $-C(=O)R_{801}$, a group represented by $-COOR_{802}$, a halogen atom, a cyano group, a nitro group, a substituted or unsubstituted aryl group having 6 to 50 ring carbon atoms, or a substituted or unsubstituted heterocyclic group having 5 to 50 ring atoms;

$R_{155}$ not being the group represented by the formula (152) is a substituted or unsubstituted aryl group having 6 to 50 ring carbon atoms, or a substituted or unsubstituted heterocyclic group having 5 to 50 ring atoms;

$R_{156}$ to $R_{161}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a substituted or unsubstituted aralkyl group having 7 to 50 carbon atoms, a group represented by —C(=O)$R_{801}$, a group represented by —COO$R_{802}$, a halogen atom, a cyano group, or a nitro group; $Ar_{152}$ is an unsubstituted aryl group having 6 to 50 ring carbon atoms; and when $R_{155}$ is a group represented by the formula (152), $Ar_{152}$ is a group different from $R_{155}$, in the formula (152):

$Ar_{151}$ is an aryl group including four or more six-membered rings, or a heterocyclic group including one or more oxygen atoms and having 5 to 50 ring atoms;

$L_{151}$ is a single bond, a substituted or unsubstituted arylene group having 6 to 50 ring carbon atoms, or a substituted or unsubstituted divalent heterocyclic group having 5 to 50 ring atoms;

when two or more $L_{151}$ are present, the two or more $L_{151}$ are mutually the same or different;

when two or more $Ar_{151}$ are present, the two or more $Ar_{151}$ are mutually the same or different; and

* in the formula (152) represents a bonding position to a ring represented by the formula (151).

In the compound represented by the formula (151), $R_{901}$, $R_{902}$, $R_{903}$, $R_{904}$, $R_{905}$, $R_{801}$ and $R_{802}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

when a plurality of $R_{901}$ are present, the plurality of $R_{901}$ are mutually the same or different;

when a plurality of $R_{902}$ are present, the plurality of $R_{902}$ are mutually the same or different;

when a plurality of $R_{903}$ are present, the plurality of $R_{903}$ are mutually the same or different;

when a plurality of $R_{904}$ are present, the plurality of $R_{904}$ are mutually the same or different;

when a plurality of $R_{905}$ are present, the plurality of $R_{905}$ are mutually the same or different;

when a plurality of $R_{801}$ are present, the plurality of $R_{801}$ are mutually the same or different; and when a plurality of $R_{802}$ are present, the plurality of $R_{802}$ are mutually the same or different.

The aryl group including four or more six-membered rings as $Ar_{151}$ is a fused aryl group in which four or more six-membered rings are fused to each other. The aryl group including four or more six-membered rings is exemplified by a pyrenyl group, a benzanthryl group, a chrysenyl group or a triphenyl group. Further, for instance, a phenyl group, a naphthyl group or an anthryl group is an aryl group including three or less six-membered rings.

The compound according to the exemplary embodiment preferably has one group represented by the formula (152).

In the compound according to the exemplary embodiment, $R_{153}$ or $R_{155}$ is preferably a group represented by the formula (152).

The compound according to the exemplary embodiment is preferably a compound represented by a formula (151A) or (151B) below.

[Formula 273]

(151A)

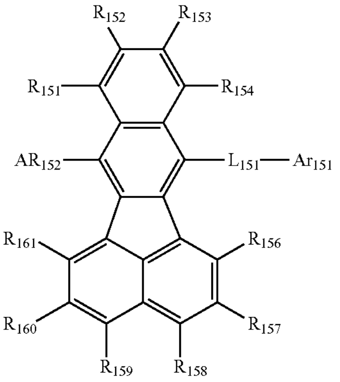

(151B)

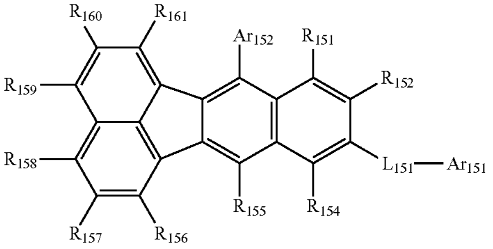

In the formulae (151A) and (151B): $R_{151}$ to $R_{161}$ and $Ar_{152}$ respectively represent the same as $R_{151}$ to $R_{161}$ and $Ar_{152}$ in the formula (151); and $Ar_{151}$ and $L_{151}$ respectively represent the same as $Ar_{151}$ and $L_{151}$ in the formula (152).

In the exemplary embodiment, the compound represented by the formula (151) is preferably a compound represented by a formula (153), (154), (155), (156), (157), (158), (159) or (160) below.

[Formula 274]

(153)

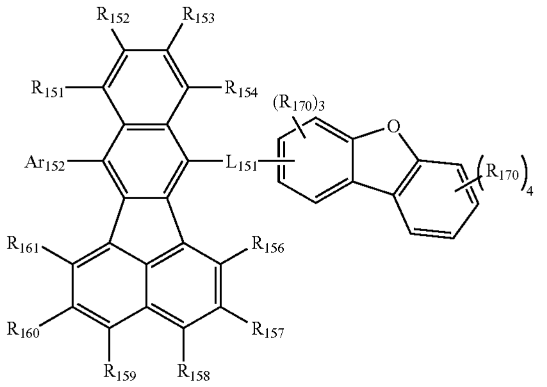

-continued (154)

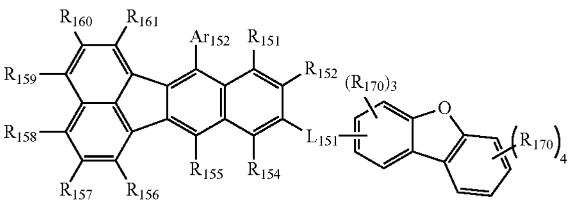

In the formulae (153) and (154): $R_{151}$ to $R_{161}$, $Ar_{152}$ and $L_{151}$ respectively represent the same as $R_{151}$ to $R_{161}$, $Ar_{152}$ and List in the formulae (151) and (152);

$R_{170}$ represents the same as $R_{151}$ to $R_{154}$ not being the group represented by the formula (152); and a plurality of $R_{170}$ are mutually the same or different.

[Formula 275]

(155)

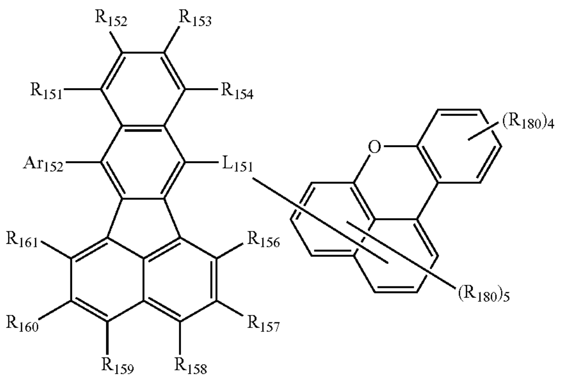

(156)

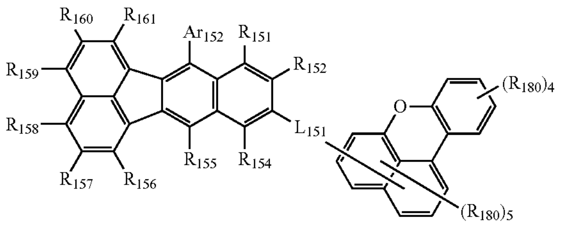

[Formula 276]

(157)

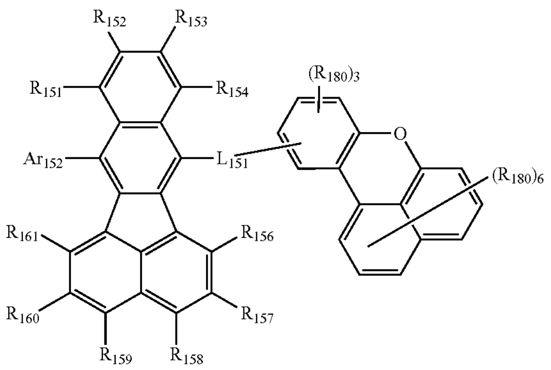

-continued (158)

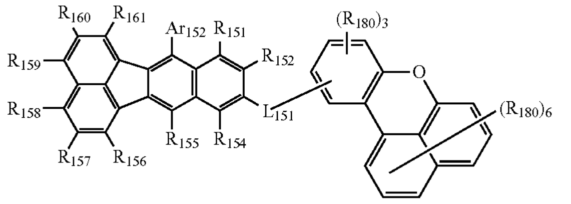

In the formulae (155), (156), (157) and (158): $R_{151}$ to $R_{161}$, $Ar_{152}$ and $L_{151}$ respectively represent the same as $R_{151}$ to $R_{161}$, $Ar_{152}$ and $L_{151}$ in the formulae (151) and (152);

$R_{180}$ represents the same as $R_{151}$ to $R_{154}$ not being the group represented by the formula (152); and a plurality of $R_{180}$ are mutually the same or different.

[Formula 277]

(159)

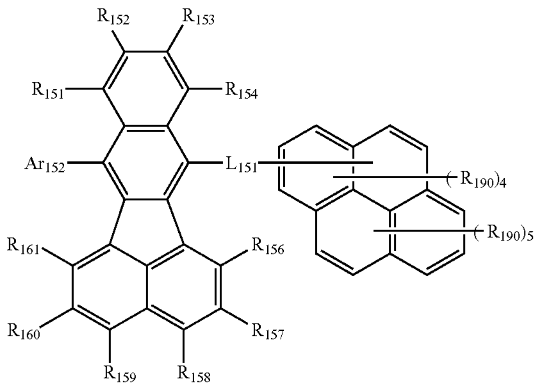

(160)

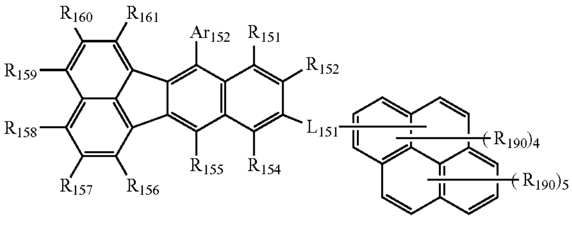

In the formulae (159) and (160): $R_{151}$ to $R_{161}$, $Ar_{152}$ and $L_{151}$ respectively represent the same as $R_{151}$ to $R_{161}$, $Ar_{152}$ and $L_{151}$ in the formulae (151) and (152);

$R_{190}$ represents the same as $R_{151}$ to $R_{154}$ not being the group represented by the formula (152); and a plurality of $R_{190}$ are mutually the same or different.

In the formulae (153) to (160), $L_{151}$, $R_{170}$, $R_{180}$ and $R_{190}$ are each independently bonded to a carbon atom of any of the six-membered rings.

$R_{170}$, $R_{180}$ and $R_{190}$ are preferably each independently a hydrogen atom or a substituted or unsubstituted alkyl group having 1 to 50 carbon atoms.

$R_{170}$, $R_{180}$ and $R_{190}$ are each preferably a hydrogen atom.

The compound according to the exemplary embodiment is also preferably a compound represented by a formula (153A) or (154A) below.

[Formula 278]

(153A)

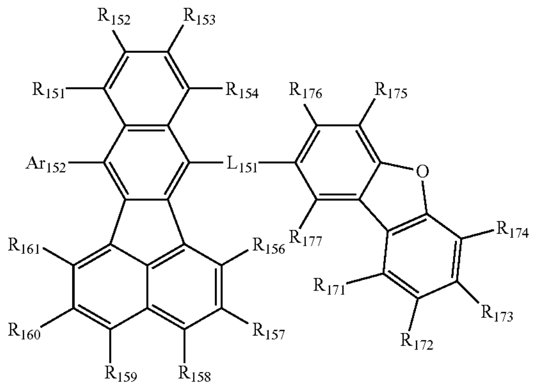

(154A)

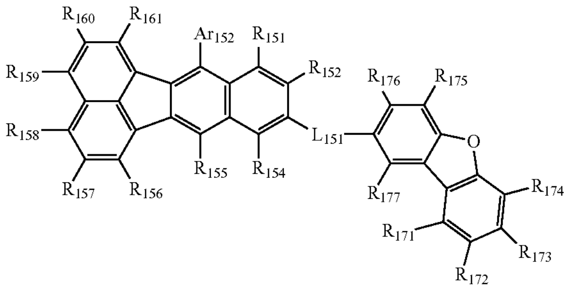

In the formulae (153A) and (154A): $R_{151}$ to $R_{161}$, $Ar_{152}$ and $L_{151}$ respectively represent the same as $R_{151}$ to $R_{161}$, $Ar_{152}$ and $L_{151}$ in the formulae (151) and (152); and $R_{171}$ to $R_{177}$ each independently represent the same as $R_{151}$ to $R_{154}$ not being the group represented by the formula (152).

The compound according to the exemplary embodiment is also preferably a compound represented by a formula (155A) or (157A) below.

[Formula 279]

(155A)

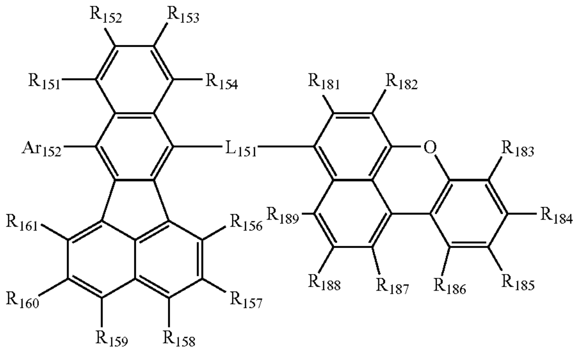

-continued (157A)

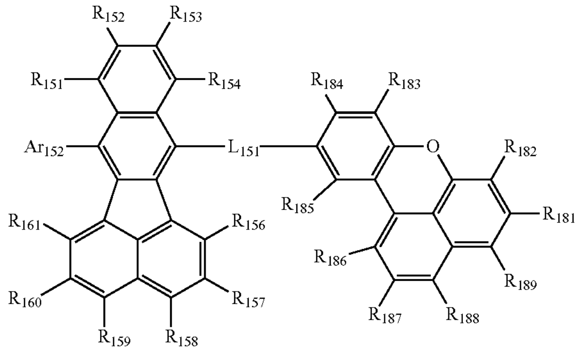

In the formulae (155A) and (157A): $R_{151}$ to $R_{161}$, $Ar_{152}$ and $L_{151}$ respectively represent the same as $R_{151}$ to $R_{161}$, $Ar_{152}$ and $L_{151}$ in the formulae (151) and (152); and $R_{181}$ to $R_{189}$ each independently represent the same as $R_{151}$ to $R_{154}$ not being the group represented by the formula (152).

The compound according to the exemplary embodiment is also preferably a compound represented by a formula (159A) or (160A) below.

[Formula 280]

(159A)

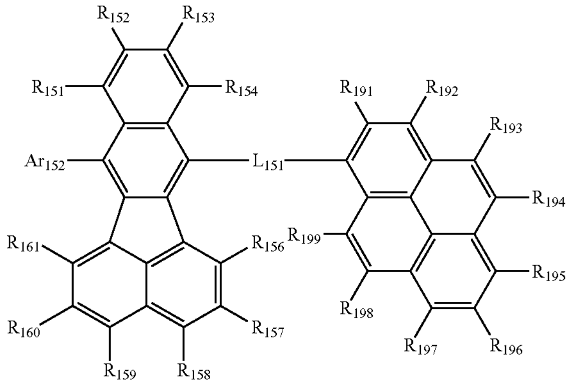

(160A)

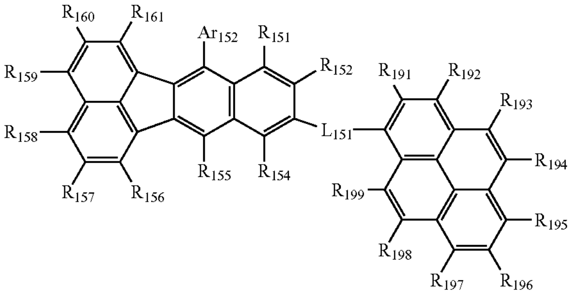

In the formulae (159A) and (160A): $R_{151}$ to $R_{161}$, $Ar_{152}$ and $L_{151}$ respectively represent the same as $R_{151}$ to $R_{161}$, $Ar_{152}$ and $L_{151}$ in the formulae (151) and (152); and $R_{191}$ to $R_{199}$ each independently represent the same as $R_{151}$ to $R_{154}$ not being the group represented by the formula (152).

In the compound according to the exemplary embodiment, $Ar_{152}$ is preferably an unsubstituted phenyl group, an unsubstituted naphthyl group, an unsubstituted biphenyl group, or an unsubstituted terphenyl group.

In the compound according to the exemplary embodiment, $L_{151}$ is preferably a single bond or a substituted or unsubstituted arylene group having 6 to 50 ring carbon atoms.

In the compound according to the exemplary embodiment, $L_{151}$ is more preferably a single bond or a substituted or unsubstituted phenylene group.

In the compound according to the exemplary embodiment, $R_{156}$ to $R_{161}$ are each preferably a hydrogen atom.

In the compound according to the exemplary embodiment, $R_{151}$ to $R_{155}$ not being the group represented by the formula (152) are preferably each independently a hydrogen atom or a substituted or unsubstituted alkyl group having 1 to 50 carbon atoms.

In the compound according to the exemplary embodiment, $R_{151}$ to $R_{155}$ not being the group represented by the formula (152) are each preferably a hydrogen atom.

Manufacturing Method of Compound Represented by Formula (151)

The compound represented by the formula (151) can be manufactured by application of known substitution reactions and materials depending on a target compound, in accordance with or based on synthesis methods described later in Examples.

Specific Examples of Compound Represented by Formula (151)

Specific examples of the compound represented by the formula (151) include compounds shown as the specific examples of the first compound in the first exemplary embodiment and falling under the definition range of the formula (151).

The compound according to the exemplary embodiment is usable as an organic-electroluminescence-device material.

The compound according to the exemplary embodiment is also usable for at least any of one or more organic layers provided between an anode and a cathode of an organic EL device. An organic EL device containing the compound according to the exemplary embodiment includes an anode, a cathode, and one or more organic layers provided between the anode and the cathode, in which preferably, at least any of the organic layers contains the compound according to the exemplary embodiment; more preferably, an emitting layer as the organic layer contains the compound according to the exemplary embodiment; further preferably, the emitting layer contains the compound according to the exemplary embodiment as a host material.

Further, the compound according to the exemplary embodiment is also usable as the first host material (first compound) for the organic EL device according to the first exemplary embodiment. An organic EL device containing the compound according to the second exemplary embodiment as the first host material according to the first exemplary embodiment includes: an anode; a cathode; a first emitting layer provided between the anode and the cathode; and a second emitting layer provided between the anode and the cathode, in which the first emitting layer contains, as the first host material, the first compound represented by the formula (151) and having at least one group represented by the formula (152), the second emitting layer contains the second host material, and the first host material and the second host material are mutually different.

According to the exemplary embodiment, a compound capable of improving performance of an organic electroluminescence device can be provided.

Third Exemplary Embodiment

Electronic Device

An electronic device according to a third exemplary embodiment is installed with any one of the organic EL devices according to the above exemplary embodiment. Examples of the electronic device include a display device and a light-emitting unit. Examples of the display device include a display component (e.g., an organic EL panel module), TV, mobile phone, tablet and personal computer. Examples of the light-emitting unit include an illuminator and a vehicle light.

Modification of Embodiment(s)

The scope of the invention is not limited by the above-described exemplary embodiments but includes any modification and improvement as long as such modification and improvement are compatible with the invention.

For instance, the number of emitting layers is not limited to two, and more than two emitting layers may be provided and layered with each other. When the organic EL device includes more than two emitting layers, it is only necessary that at least two of the emitting layers should satisfy the requirements mentioned in the above exemplary embodiment. For instance, the rest of the emitting layers may be a fluorescent emitting layer or a phosphorescent emitting layer with use of emission caused by electron transfer from the triplet excited state directly to the ground state.

When the organic EL device includes a plurality of emitting layers, these emitting layers may be mutually adjacently provided, or may form a so-called tandem organic EL device, in which a plurality of emitting units are layered via an intermediate layer.

An example of the organic EL device three or more emitting layers is a tandem organic EL device below.

An organic electroluminescence device includes: an anode; a cathode; a first emitting layer provided between the anode and the cathode; a second emitting layer provided between the anode and the cathode; and a third emitting layer provided between the anode and the cathode and being not in direct contact with any of the first emitting layer and the second emitting layer, in which the first emitting layer contains, as the first host material, the first compound represented by the formula (1) and having at least one group represented by the formula (11), and the second emitting layer contains the second compound represented by the formula (2) as the second host material.

In this tandem organic EL device, the first emitting layer and the second emitting layer are preferably in direct contact with each other. In the tandem organic EL device, the second emitting layer is preferably provided between the first emitting layer and the cathode. The compounds described in the above exemplary embodiments are usable as the first host material, the second host material and the emitting compound.

In the tandem organic EL device, the third emitting layer also preferably contains the first compound.

In the tandem organic EL device, the third emitting layer also preferably contains the second compound.

The tandem organic EL device preferably includes an intermediate layer between the third emitting layer and the first emitting layer and/or an intermediate layer between the third emitting layer and the second emitting layer.

The intermediate layer is generally also referred to as an intermediate electrode, intermediate conductive layer, charge generating layer, electron drawing layer, connection layer, or intermediate insulative layer.

The intermediate layer supplies electrons to a layer that is close to the anode with respect to the intermediate layer, and supplies holes to a layer that is close to the cathode with respect to the intermediate layer. The intermediate layer can be made of a known material. The intermediate layer may be a single layer, or may be provided by two or more layers. A unit made of two or more intermediate layers is sometimes referred to as an intermediate unit. The compositions of the plurality of intermediate layers of the intermediate unit are mutually the same or different.

Further, a plurality of layers including the emitting layer that are disposed between the intermediate layer/intermediate unit and the anode/cathode are occasionally referred to as an emitting unit. Examples of the device arrangement of the organic EL device including a plurality of emitting units include (TND1) to (TND4) below.

(TND1) anode/first emitting unit/intermediate layer/second emitting unit/cathode (TND2) anode/first emitting unit/intermediate unit/second emitting unit/cathode (TND3) anode/first emitting unit/first intermediate layer/second emitting unit/second intermediate layer/third emitting unit/cathode (TND4) anode/first emitting unit/first intermediate unit/second emitting unit/second intermediate unit/third emitting unit/cathode The number of the emitting units and the intermediate layers (or intermediate units) is not limited to the examples shown above.

The first emitting layer and the second emitting layer are preferably included in at least one of the first emitting unit, the second emitting unit, or the third emitting unit.

The first emitting layer and the second emitting layer are also preferably included in all of the emitting units of the organic EL device.

For instance, a blocking layer may be provided adjacent to at least one of a side of the emitting layer close to the anode or a side of the emitting layer close to the cathode. The blocking layer is preferably provided in contact with the emitting layer to block at least any of holes, electrons, excitons or combinations thereof.

For instance, when the blocking layer is provided in contact with the side of the emitting layer close to the cathode, the blocking layer permits transport of electrons and blocks holes from reaching a layer provided closer to the cathode (e.g., the electron transporting layer) beyond the blocking layer. When the organic EL device includes the electron transporting layer, the blocking layer is preferably interposed between the emitting layer and the electron transporting layer.

When the blocking layer is provided in contact with the side of the emitting layer close to the anode, the blocking layer permits transport of holes and blocks electrons from reaching a layer provided closer to the anode (e.g., the hole transporting layer) beyond the blocking layer. When the organic EL device includes the hole transporting layer, the blocking layer is preferably interposed between the emitting layer and the hole transporting layer.

Alternatively, the blocking layer may be provided adjacent to the emitting layer so that excitation energy does not leak out from the emitting layer toward neighboring layer(s). The blocking layer blocks excitons generated in the emitting layer from being transferred to a layer(s) (e.g., the electron transporting layer and the hole transporting layer) closer to the electrode(s) beyond the blocking layer.

The emitting layer is preferably bonded with the blocking layer.

Specific structure, shape and the like of the components in the invention may be designed in any manner as long as an object of the invention can be achieved.

EXAMPLES

The invention will be described in further detail with reference to Examples. It should be noted that the scope of the invention is by no means limited to Examples.

Compounds

Structures of compounds represented by the formula (1) or (151) and used for manufacturing organic EL devices in Examples are shown below.

[Formula 281]

BH1-1

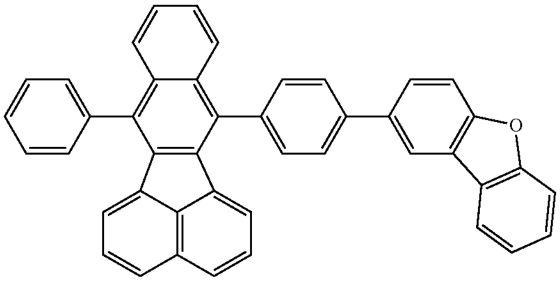

[Formula 282]

1BH-2

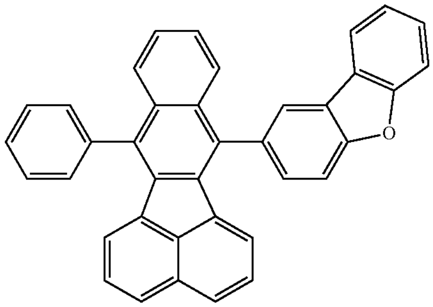

1BH-3

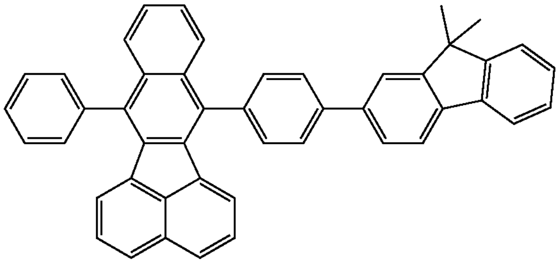

1BH-4

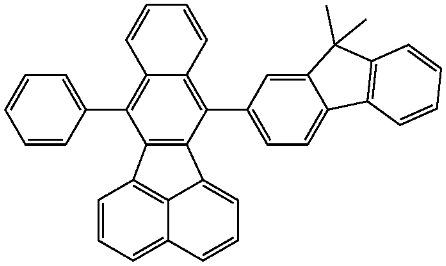

-continued
1BH-5
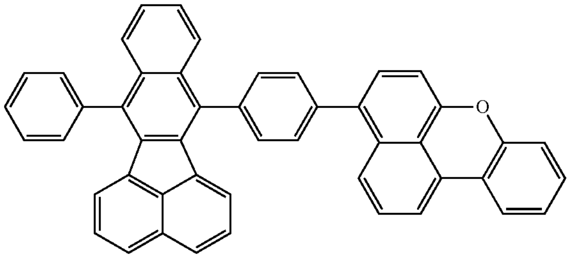
1BH-6
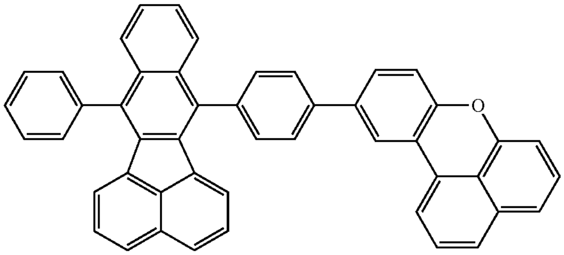
1BH-7
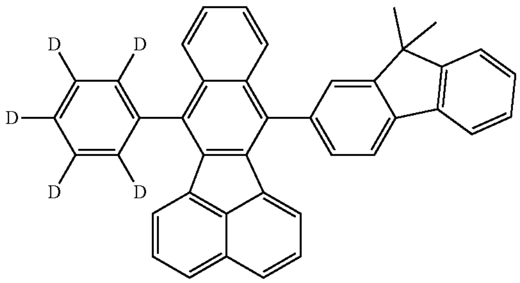
[Formula 283]
1BH-8
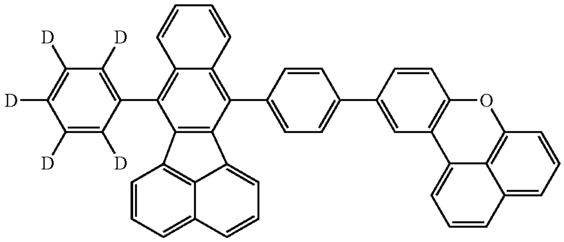
1BH-9
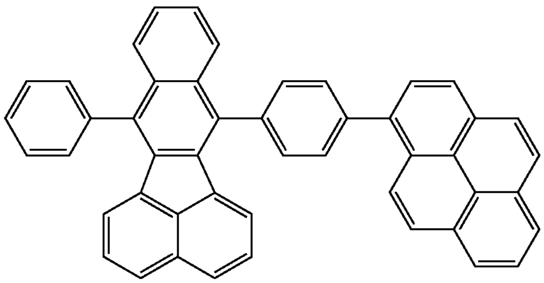
-continued
1BH-10
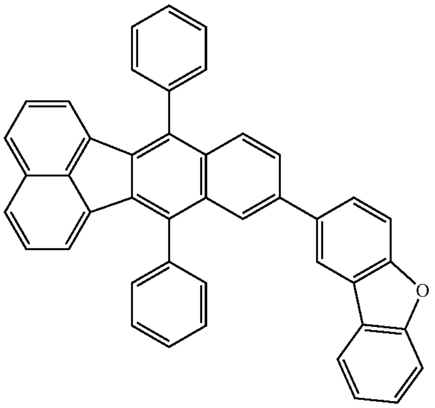
1BH-11
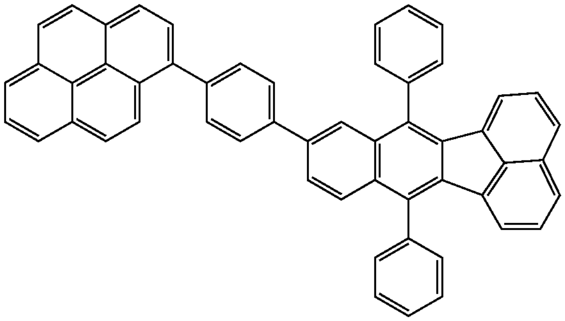
[Formula 284]
FBH1-1
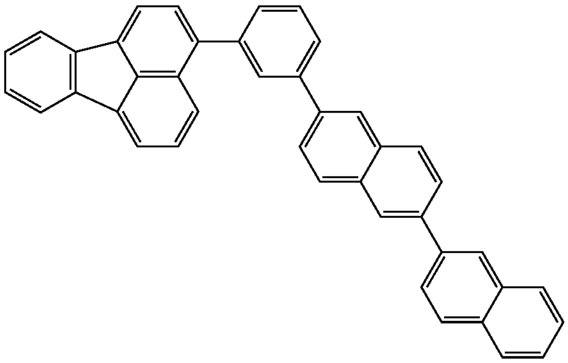
FBH1-2
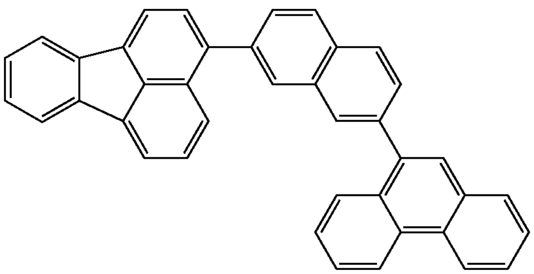
Structures of compounds represented by the formula (2) and used for manufacturing the organic EL devices in Examples are shown below.

[Formula 285]
2BH-1
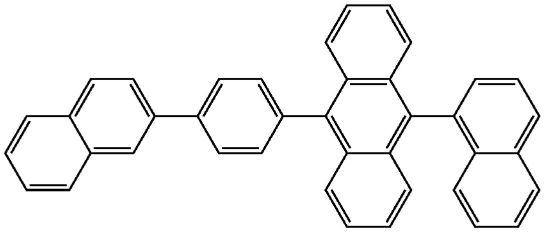
[Formula 286]
2BH-2
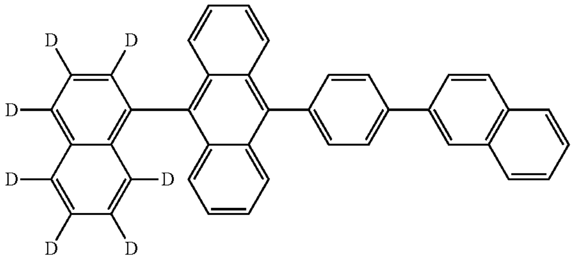
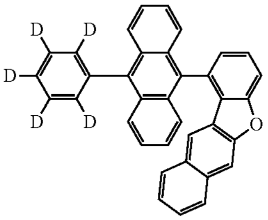
2BH-3a
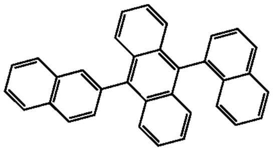
2BH-3b
2BH-3
A mixture of a compound 2BH-3a and a compound 2BH-3b in a mass ratio of 1:1 was used as a compound 2BH-3.
[Formula 287]
2BH-4
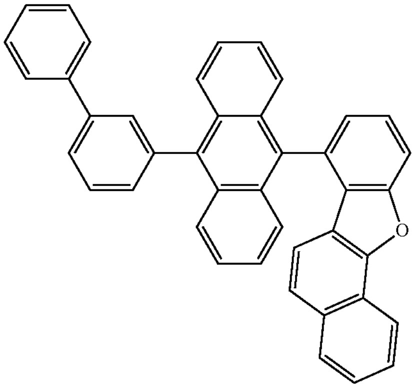
-continued
2BH-5
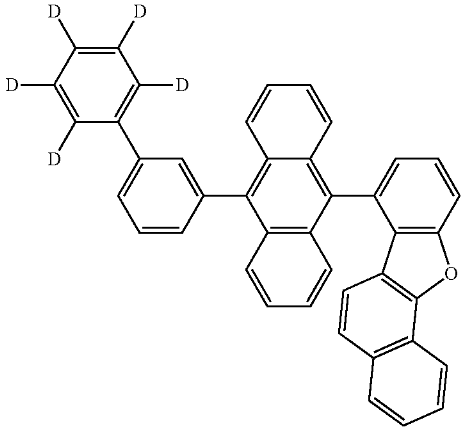
2BH-6
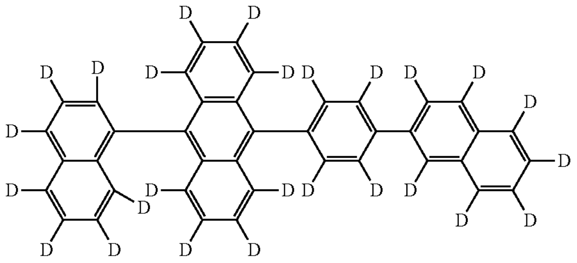
2BH-7
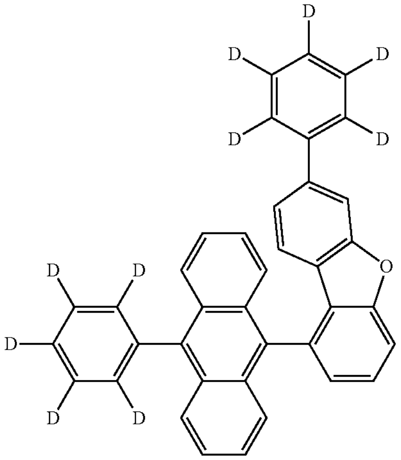
2BH-8
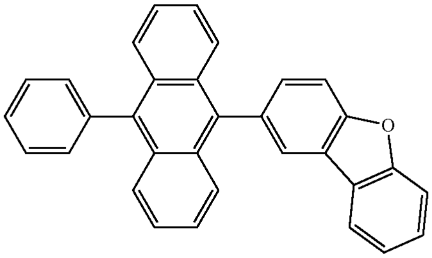

-continued
2BH-9
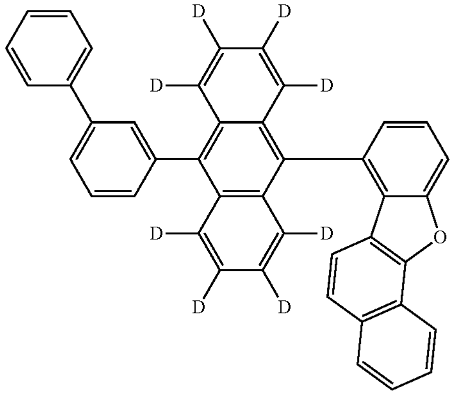
Structures of other compounds used for manufacturing the organic EL devices in Examples and Comparative Examples are shown below.
[Formula 288]
HA1
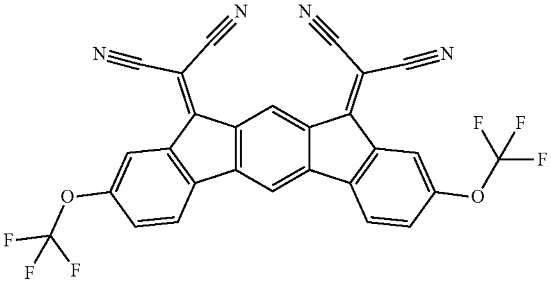
HT1
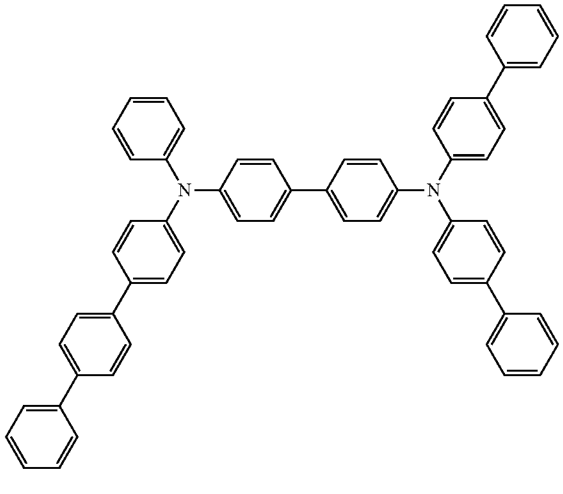
-continued
[Formula 289]
HA2
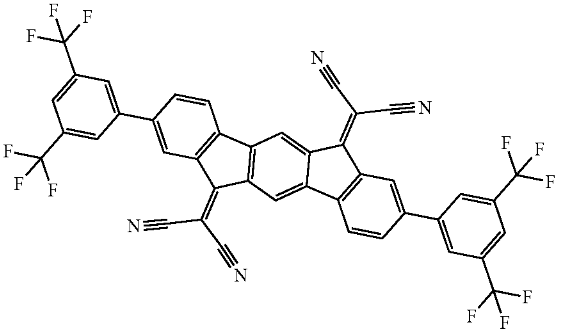
HA3
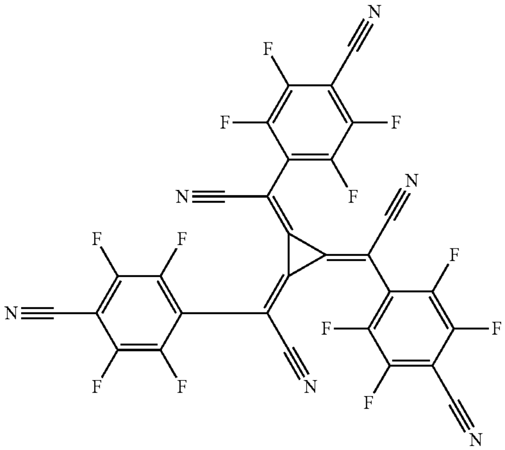
[Formula 290]
HT2
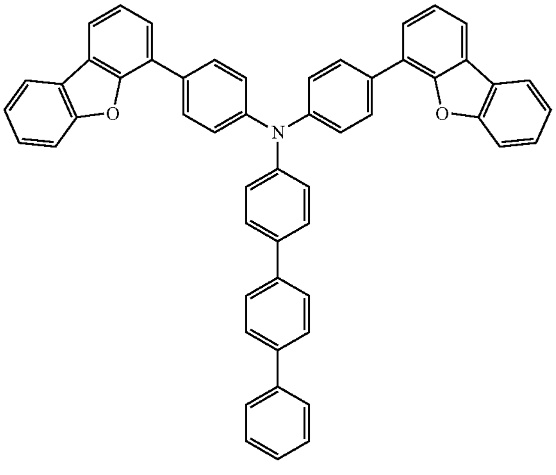

-continued
BD1
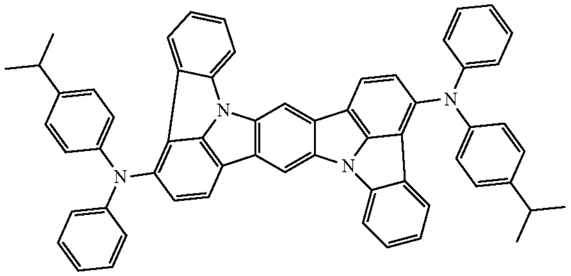
[Formula 291]
HT3
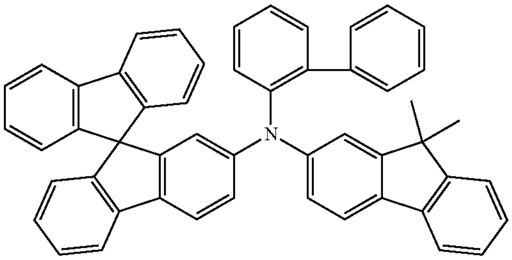
HT4
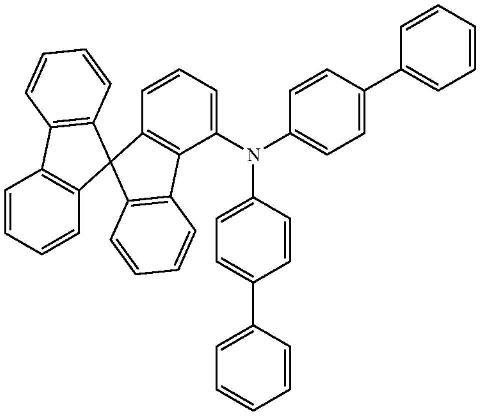
HT5
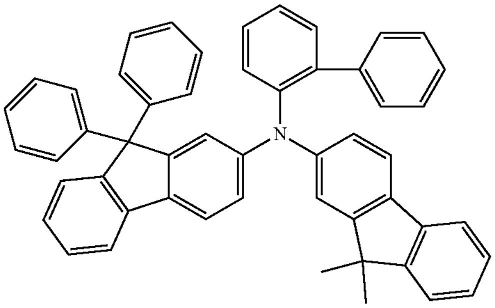
HT6
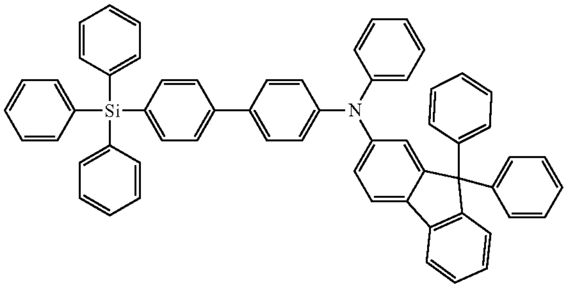
-continued
HT7
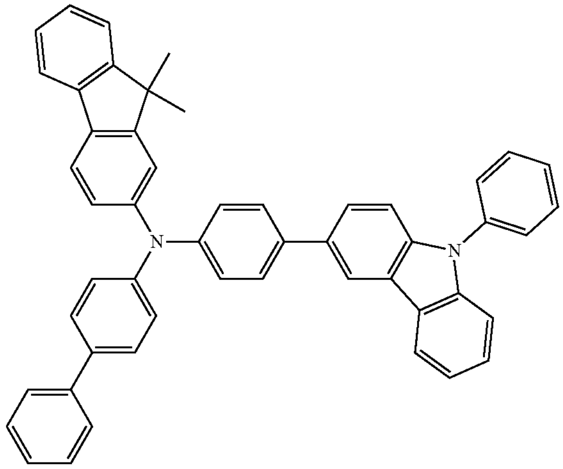
HT8
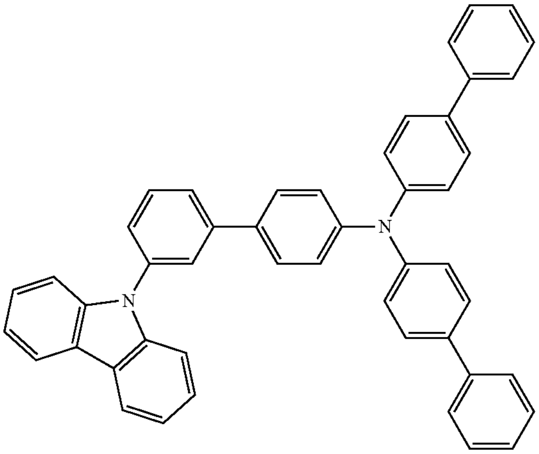
[Formula 292]
BD2
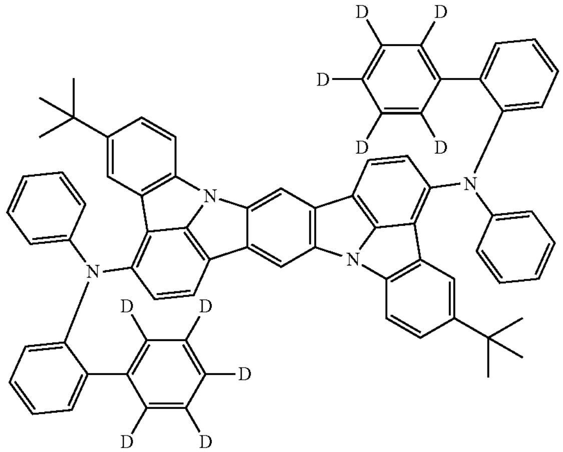

BD3
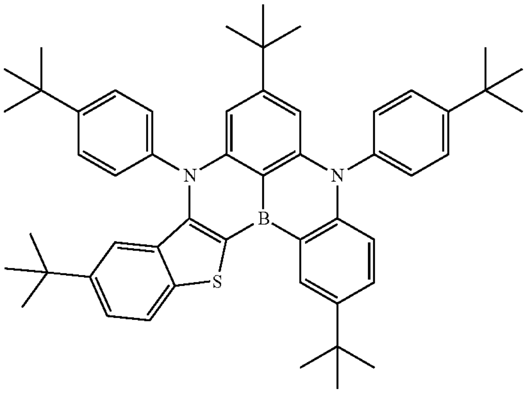
BD4
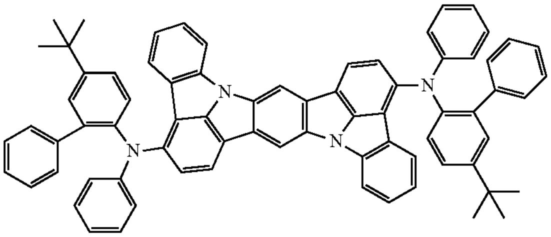
BD5
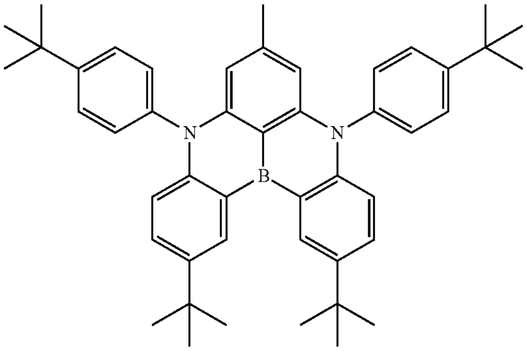
BD6
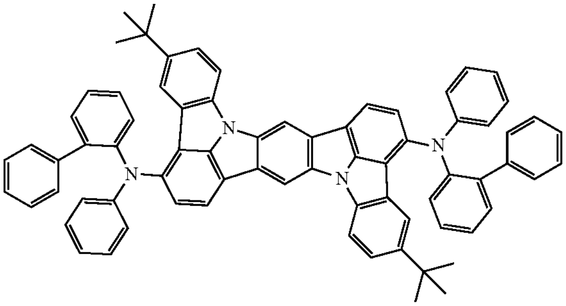
[Formula 293]
ET1
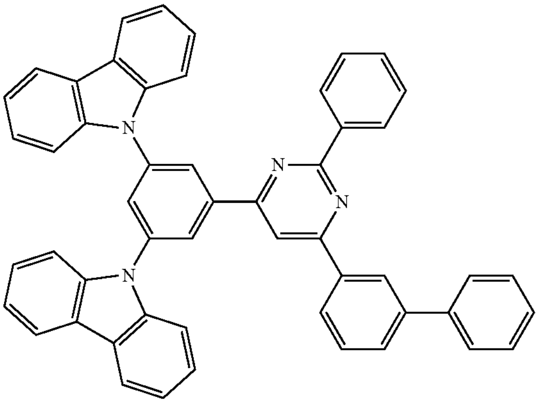
ET2
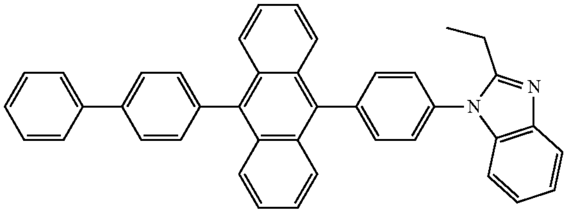
[Fomrula 294]
ET3
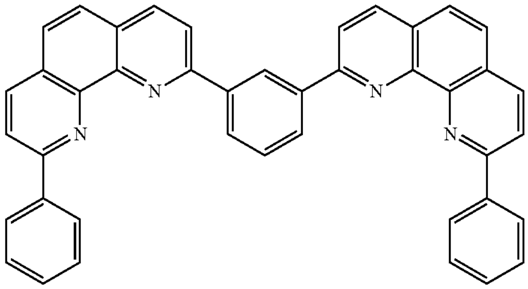
ET4
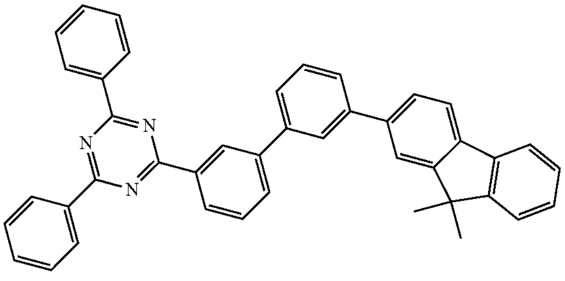

-continued

ET5

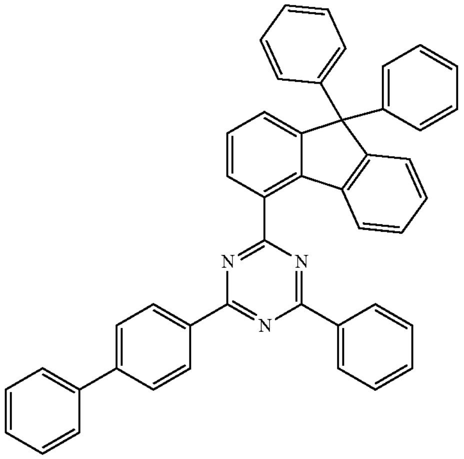

ET6

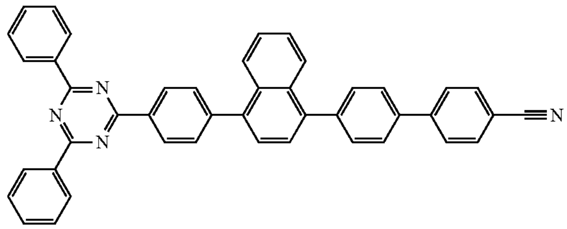

Manufacture of Organic EL Device

Organic EL devices were manufactured and evaluated as follows.

Example 1

A glass substrate (size: 25 mm×75 mm×1.1 mm thick, manufactured by Geomatec Co., Ltd.) having an ITO (Indium Tin Oxide) transparent electrode (anode) was ultrasonic-cleaned in isopropyl alcohol for five minutes, and then UV-ozone-cleaned for 30 minutes. A film thickness of the ITO transparent electrode was 130 nm.

The cleaned glass substrate having the transparent electrode line was attached to a substrate holder of a vacuum deposition apparatus. Initially, a compound HA1 was vapor-deposited on a surface provided with the transparent electrode line to cover the transparent electrode, thereby forming a 5-nm-thick hole injecting layer (HI).

After the formation of the hole injecting layer, a compound HT1 was vapor-deposited to form an 80-nm-thick first hole transporting layer (HT).

After the formation of the first hole transporting layer, a compound HT2 was vapor-deposited to form a 10-nm-thick second hole transporting layer (also referred to as an electron blocking layer (EBL)).

A compound BH1-1 (first host material (BH)) and a compound BD1 (dopant material (BD)) were co-deposited on the second hole transporting layer such that the ratio of the compound BD1 accounted for 2 mass %, thereby forming a 5-nm-thick first emitting layer.

A compound 2BH-1 (second host material (BH)) and the compound BD1 (dopant material (BD)) were co-deposited on the first emitting layer such that the ratio of the compound BD1 accounted for 2 mass %, thereby forming a 20-nm-thick second emitting layer.

A compound ET1 was vapor-deposited on the second emitting layer to form a 10-nm-thick first electron transporting layer (also referred to as a hole blocking layer (HBL)).

A compound ET2 was vapor-deposited on the first electron transporting layer to form a 15-nm-thick second electron transporting layer (ET).

LiF was vapor-deposited on the second electron transporting layer to form a 1-nm-thick electron injecting layer.

Metal Al was vapor-deposited on the electron injecting layer to form an 80-nm-thick cathode.

A device arrangement of the organic EL device in Example 1 is roughly shown as follows.

ITO (130)/HA1 (5)/HT1 (80)/HT2 (10)/BH1-1:BD1 (5, 98%:2%)/2BH-1:BD1 (20, 98%:2%)/ET1 (10)/ET2 (15)/LiF (1)/Al (80)

Numerals in parentheses represent a film thickness (unit: nm).

The numerals (98%:2%) represented by percentage in the same parentheses indicate a ratio (mass %) between the host material (compound BH1-1 or 2BH-1) and the compound BD1 in the first emitting layer or the second emitting layer.

Comparative Example 1

The organic EL device of Comparative Example 1 was manufactured in the same manner as that of Example 1 except that a 25-nm-thick second emitting layer was formed on the second hole transporting layer as the emitting layer without forming the first emitting layer as shown in Table 1.

Evaluation of Organic EL Devices

The organic EL devices manufactured in Examples and Comparative Examples were evaluated as follows. Tables show evaluation results.

External Quantum Efficiency EQE

Voltage was applied on the organic EL devices so that a current density was 10 $mA/cm^2$, where spectral radiance spectrum was measured by a spectroradiometer (CS-2000 manufactured by Konica Minolta, Inc.). The external quantum efficiency EQE (unit: %) was calculated based on the obtained spectral-radiance spectra, assuming that the spectra was provided under a Lambertian radiation.

Drive Voltage

The voltage (unit: V) when electric current was applied between the anode and the cathode so that the current density was 10 $mA/cm^2$ was measured.

Maximum Peak Wavelength λp when Device is Driven

Voltage was applied on the organic EL devices so that a current density of the organic EL device was 10 $mA/cm^2$, where spectral radiance spectrum was measured by a spectroradiometer CS-2000 (manufactured by Konica Minolta, Inc.). The maximum peak wavelength λp (unit: nm) was calculated from the measured spectral radiance spectrum.

Lifetime LT90

Voltage was applied on the resultant organic EL devices so that a current density was 50 $mA/cm^2$, where a time (LT90 (unit: hr)) elapsed before a luminance intensity was reduced to 90% of the initial luminance intensity was measured.

Lifetime LT95

Voltage was applied on the resultant organic EL devices so that a current density was 50 $mA/cm^2$, where a time (LT95 (unit: hr)) elapsed before a luminance intensity was reduced to 95% of the initial luminance intensity was measured.

TABLE 1

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Drive Voltage [V] | λp [nm] | EQE [%] |
| Ex. 1 | BH1-1 | BD1 | 5 | 2BH-1 | BD1 | 20 | 3.48 | 460 | 10.4 |
| Comp. 1 | — | — | — | 2BH-1 | BD1 | 25 | 3.61 | 460 | 9.9 |

As shown in Table 1, the organic EL device of Example 1 that included the first emitting layer containing the first compound as the first host material and the second emitting layer containing the second compound as the second host material had a higher luminous efficiency than the organic EL device of Comparative Example 1 that included only the second emitting layer. Further, the organic EL device of Example 1 was driven at a lower voltage than the organic EL device of Comparative Example 1.

Example 2

A glass substrate (size: 25 mm×75 mm×1.1 mm thick, manufactured by Geomatec Co., Ltd.) having an ITO (Indium Tin Oxide) transparent electrode (anode) was ultrasonic-cleaned in isopropyl alcohol for five minutes, and then UV-ozone-cleaned for 30 minutes. A film thickness of the ITO transparent electrode was 130 nm.

The cleaned glass substrate having the transparent electrode line was attached to a substrate holder of a vacuum deposition apparatus. Initially, a compound HA2 was vapor-deposited on a surface provided with the transparent electrode line to cover the transparent electrode, thereby forming a 5-nm-thick hole injecting layer (HI).

After the formation of the hole injecting layer, a compound HT3 was vapor-deposited to form an 80-nm-thick first hole transporting layer (HT).

After the formation of the first hole transporting layer, a compound HT4 was vapor-deposited to form a 10-nm-thick second hole transporting layer (also referred to as an electron blocking layer (EBL)).

A compound 1BH-2 (first host material (BH)) and a compound BD2 (third compound) were co-deposited on the second hole transporting layer such that the ratio of the compound BD2 accounted for 2 mass %, thereby forming a 12.5-nm-thick first emitting layer.

A compound 2BH-2 (second host material (BH)) and the compound BD2 (fourth compound) were co-deposited on the first emitting layer such that the ratio of the compound BD2 accounted for 2 mass %, thereby forming a 12.5-nm-thick second emitting layer.

The compound ET1 was vapor-deposited on the second emitting layer to form a 10-nm-thick electron transporting layer (also referred to as a hole blocking layer (HBL)).

A compound ET3 and metal Li were co-deposited on the electron transporting layer to form a 15-nm-thick electron injecting layer. The ratios of the compound ET3 and the metal Li in the electron injecting layer were 96 mass % and 4 mass %, respectively.

Metal Al was vapor-deposited on the electron injecting layer to form an 80-nm-thick cathode.

A device arrangement of the organic EL device in Example 2 is roughly shown as follows.

ITO (130)/HA2 (5)/HT3 (80)/HT4 (10)/1BH-2:BD2 (12.5, 98%:2%)/2BH-2:BD2 (12.5, 98%:2%)/ET1 (10)/ET3:Li (15, 96%:4%)/Al (80)

Numerals in parentheses represent a film thickness (unit: nm). The numerals (98%:2%) represented by percentage in the same parentheses indicate a ratio (mass %) between the host material (compound 1BH-2 or 2BH-2) and the compound BD2 in the first emitting layer or the second emitting layer. The numerals (96%:4%) represented by percentage in the same parentheses indicate a ratio (mass %) between the compound ET3 and the metal Li in the electron injecting layer.

Comparative Example 2

The organic EL device of Comparative Example 2 was manufactured in the same manner as that of Example 2 except that a 25-nm-thick second emitting layer was formed on the second hole transporting layer as the emitting layer without forming the first emitting layer as shown in Table 2.

TABLE 2

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Drive Voltage [V] | λp [nm] | EQE [%] |
| Ex. 2 | 1BH-2 | BD2 | 12.5 | 2BH-2 | BD2 | 12.5 | 3.66 | 450 | 10.7 |
| Comp. 2 | — | — | — | 2BH-2 | BD2 | 25 | 3.77 | 450 | 9.9 |

Example 3

The organic EL device of Example 3 was manufactured in the same manner as that of Example 2 except that a 10-nm-thick first emitting layer was formed by changing the first compound and the third compound and a 15-nm-thick second emitting layer was formed by changing the second compound and the fourth compound as shown in Table 3.

Comparative Example 3

The organic EL device of Comparative Example 3 was manufactured in the same manner as that of Example 3 except that a 25-nm-thick second emitting layer was formed on the second hole transporting layer as the emitting layer without forming the first emitting layer as shown in Table 3.

TABLE 3

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Drive Voltage [V] | λp [nm] | EQE [%] |
| Ex. 3 | 1BH-3 | BD3 | 10 | 2BH-3 | BD3 | 15 | 3.25 | 462 | 10.3 |
| Comp. 3 | — | — | — | 2BH-3 | BD3 | 25 | 3.47 | 462 | 9.7 |

Example 4

The organic EL device of Example 4 was manufactured in the same manner as that of Example 2 except that a 5-nm-thick first emitting layer was formed by changing the first compound and a 20-nm-thick second emitting layer was formed by changing the second compound as shown in Table 4.

Comparative Example 4

The organic EL device of Comparative Example 4 was manufactured in the same manner as that of Example 4 except that a 25-nm-thick second emitting layer was formed on the second hole transporting layer as the emitting layer without forming the first emitting layer as shown in Table 4.

TABLE 4

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Drive Voltage [V] | λp [nm] | EQE [%] |
| Ex. 4 | 1BH-4 | BD2 | 5 | 2BH-4 | BD2 | 20 | 3.15 | 450 | 10.4 |
| Comp. 4 | — | — | — | 2BH-4 | BD2 | 25 | 3.29 | 450 | 9.7 |

Example 5

The organic EL device of Example 5 was manufactured in the same manner as that of Example 2 except that the first emitting layer was formed by changing the first compound and the third compound and the second emitting layer was formed by changing the second compound and the fourth compound as shown in Table 5.

Comparative Example 5

The organic EL device of Comparative Example 5 was manufactured in the same manner as that of Example 5 except that a 25-nm-thick second emitting layer was formed on the second hole transporting layer as the emitting layer without forming the first emitting layer as shown in Table 5.

TABLE 5

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Drive Voltage [V] | λp [nm] | EQE [%] |
| Ex. 5 | 1BH-5 | BD4 | 12.5 | 2BH-5 | BD4 | 12.5 | 3.20 | 455 | 9.9 |
| Comp. 5 | — | — | — | 2BH-5 | BD4 | 25 | 3.29 | 455 | 9.7 |

Example 6

The organic EL device of Example 6 was manufactured in the same manner as that of Example 2 except that the first emitting layer was formed by changing the first compound and the second emitting layer was formed by changing the second compound as shown in Table 6.

Comparative Example 4 is shown again in Table 6 for comparison.

TABLE 6

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Drive Voltage [V] | λp [nm] | EQE [%] |
| Ex. 6 | 1BH-6 | BD2 | 12.5 | 2BH-4 | BD2 | 12.5 | 3.06 | 450 | 10.1 |
| Comp. 4 (shown again) | — | — | — | 2BH-4 | BD2 | 25 | 3.29 | 450 | 9.7 |

Example 7

The organic EL device of Example 7 was manufactured in the same manner as that of Example 2 except that the first emitting layer was formed by changing the first compound and the third compound and the second emitting layer was formed by changing the second compound and the fourth compound as shown in Table 7.

Comparative Example 7

The organic EL device of Comparative Example 7 was manufactured in the same manner as that of Example 7 except that a 25-nm-thick second emitting layer was formed on the second hole transporting layer as the emitting layer without forming the first emitting layer as shown in Table 7.

TABLE 7

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Drive Voltage [V] | λp [nm] | EQE [%] |
| Ex. 7 | 1BH-7 | BD4 | 12.5 | 2BH-3 | BD4 | 12.5 | 3.23 | 455 | 9.9 |
| Comp. 7 | — | — | — | 2BH-3 | BD4 | 25 | 3.47 | 455 | 9.3 |

Example 8

The organic EL device of Example 8 was manufactured in the same manner as that of Example 2 except that the first emitting layer was formed by changing the first compound and the third compound and the second emitting layer was formed by changing the fourth compound as shown in Table 8.

Comparative Example 8

The organic EL device of Comparative Example 8 was manufactured in the same manner as that of Example 8 except that a 25-nm-thick second emitting layer was formed on the second hole transporting layer as the emitting layer without forming the first emitting layer as shown in Table 8.

TABLE 8

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Drive Voltage [V] | λp [nm] | EQE [%] |
| Ex. 8 | 1BH-8 | BD4 | 12.5 | 2BH-2 | BD5 | 12.5 | 3.52 | 457 | 10.1 |
| Comp. 8 | — | — | — | 2BH-2 | BD5 | 25 | 3.77 | 461 | 9.3 |

Example 9

The organic EL device of Example 9 was manufactured in the same manner as that of Example 2 except that a 5-nm-thick first emitting layer was formed by changing the first compound and the third compound and a 20-nm-thick second emitting layer was formed by changing the second compound and the fourth compound as shown in Table 9.

Comparative Example 9

The organic EL device of Comparative Example 9 was manufactured in the same manner as that of Example 9 except that a 25-nm-thick second emitting layer was formed on the second hole transporting layer as the emitting layer without forming the first emitting layer as shown in Table 9.

TABLE 9

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Drive Voltage [V] | λp [nm] | EQE [%] |
| Ex. 9 | 1BH-1 | BD3 | 5 | 2BH-6 | BD3 | 20 | 3.48 | 462 | 10.3 |
| Comp. 9 | — | — | — | 2BH-6 | BD3 | 25 | 3.61 | 462 | 9.7 |

Example 10

The organic EL device of Example 10 was manufactured in the same manner as that of Example 2 except that the first emitting layer was formed by changing the first compound and the third compound and the second emitting layer was formed by changing the second compound and the fourth compound as shown in Table 10.

Comparative Example 10

The organic EL device of Comparative Example 10 was manufactured in the same manner as that of Example 10 except that a 25-nm-thick second emitting layer was formed on the second hole transporting layer as the emitting layer by changing the fourth compound without forming the first emitting layer as shown in Table 10.

TABLE 10

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Drive Voltage [V] | λp [nm] | EQE [%] |
| Ex. 10 | 1BH-9 | BD1 | 12.5 | 2BH-1 | BD1 | 12.5 | 3.60 | 460 | 10.2 |
| Comp. 10 | — | — | — | 2BH-1 | BD1 | 25 | 3.61 | 460 | 9.9 |

Example 11

The organic EL device of Example 11 was manufactured in the same manner as that of Example 2 except that a 5-nm-thick first emitting layer was formed by changing the first compound and the third compound and a 20-nm-thick second emitting layer was formed by changing the fourth compound as shown in Table 11.

Comparative Example 11

The organic EL device of Comparative Example 11 was manufactured in the same manner as that of Example 11 except that a 25-nm-thick second emitting layer was formed on the second hole transporting layer as the emitting layer without forming the first emitting layer as shown in Table 11.

TABLE 11

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Drive Voltage [V] | λp [nm] | EQE [%] |
| Ex. 11 | 1BH-10 | BD1 | 5 | 2BH-2 | BD1 | 20 | 3.58 | 460 | 10.1 |
| Comp. 11 | — | — | — | 2BH-2 | BD1 | 25 | 3.62 | 460 | 9.8 |

Example 12

The organic EL device of Example 12 was manufactured in the same manner as that of Example 2 except that a 5-nm-thick first emitting layer was formed by changing the first compound and the third compound and a 20-nm-thick second emitting layer was formed by changing the second compound and the fourth compound as shown in Table 12.

Comparative Example 3 is shown again in Table 12 for comparison.

A compound ET4 was vapor-deposited on the second emitting layer to form a 5-nm-thick first electron transporting layer (also referred to as a hole blocking layer (HBL)).

A compound ET5 and Liq were co-deposited on the first electron transporting layer to form a 25-nm-thick second electron transporting layer (ET). The ratios of the compound ET5 and Liq in the second electron transporting layer (ET) were 50 mass % and 50 mass %, respectively. Liq is an abbreviation for (8-quinolinolato)lithium.

TABLE 12

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Drive Voltage [V] | λp [nm] | EQE [%] |
| Ex. 12 | 1BH-11 | BD3 | 5 | 2BH-3 | BD3 | 20 | 3.45 | 462 | 10.0 |
| Comp. 3 (shown again) | — | — | — | 2BH-3 | BD3 | 25 | 3.47 | 462 | 9.7 |

Example 13

A glass substrate (size: 25 mm×75 mm×1.1 mm thick, manufactured by Geomatec Co., Ltd.) having an ITO (Indium Tin Oxide) transparent electrode (anode) was ultrasonic-cleaned in isopropyl alcohol for five minutes, and then UV-ozone-cleaned for 30 minutes. A film thickness of the ITO transparent electrode was 130 nm.

The cleaned glass substrate having the transparent electrode line was attached to a substrate holder of a vacuum deposition apparatus. Initially, a compound HT5 and a compound HA3 were co-deposited on a surface provided with the transparent electrode line to cover the transparent electrode, thereby forming a 10-nm-thick hole injecting layer (HI). The ratios of the compound HT5 and the compound HA3 in the hole injecting layer were 90 mass % and 10 mass %, respectively.

After the formation of the hole injecting layer, the compound HT5 was vapor-deposited to form an 85-nm-thick first hole transporting layer (HT).

After the formation of the first hole transporting layer, a compound HT6 was vapor-deposited to form a 5-nm-thick second hole transporting layer (also referred to as an electron blocking layer (EBL)).

The compound 1BH-2 (first host material (BH)) and a compound BD4 (third compound) were co-deposited on the second hole transporting layer such that the ratio of the compound BD4 accounted for 2 mass %, thereby forming a 10-nm-thick first emitting layer.

A compound 2BH-7 (second host material (BH)) and the compound BD4 (fourth compound) were co-deposited on the first emitting layer such that the ratio of the compound BD4 accounted for 2 mass %, thereby forming a 10-nm-thick second emitting layer.

Liq was vapor-deposited on the second electron transporting layer to form a 1-nm-thick electron injecting layer.

Metal Al was vapor-deposited on the electron injecting layer to form an 80-nm-thick cathode.

A device arrangement of the organic EL device in Example 13 is roughly shown as follows.

ITO (130)/HT5:HA3 (10, 90%:10%)/HT5 (85)/HT6 (5)/1BH-2:BD4 (10, 98%:2%)/2BH-7:BD4 (10, 98%:2%)/ET4 (5)/ET5:Liq (25, 50%:50%)/Liq (1)/Al (80)

Numerals in parentheses represent a film thickness (unit: nm). The numerals (90%: 10%) represented by percentage in the same parentheses indicate a ratio (mass %) between the compounds HT5 and HA3 in the hole injecting layer. The numerals (98%:2%) represented by percentage in the same parentheses indicate a ratio (mass %) between the host material (compound 1BH-2 or 2BH-7) and the compound BD4 in the first emitting layer or the second emitting layer. The numerals (50%:50%) represented by percentage in the same parentheses indicate a ratio (mass %) between the compound ET5 and Liq in the second electron transporting layer.

Comparative Example 13

The organic EL device of Comparative Example 13 was manufactured in the same manner as that of Example 13 except that a 20-nm-thick second emitting layer was formed on the second hole transporting layer as the emitting layer without forming the first emitting layer as shown in Table 13.

TABLE 13

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Drive Voltage [V] | λp [nm] | EQE [%] |
| Ex. 13 | 1BH-2 | BD4 | 10 | 2BH-7 | BD4 | 10 | 3.20 | 455 | 11.1 |
| Comp. 13 | — | — | — | 2BH-7 | BD4 | 20 | 3.18 | 455 | 9.9 |

Example 14

The organic EL device of Example 14 was manufactured in the same manner as that of Example 13 except that a 5-nm-thick first emitting layer was formed by changing the first compound and the third compound and a 15-nm-thick second emitting layer was formed by changing the second compound and the fourth compound as shown in Table 14.

Comparative Example 14

The organic EL device of Comparative Example 14 was manufactured in the same manner as that of Example 14 except that a 20-nm-thick second emitting layer was formed on the second hole transporting layer as the emitting layer without forming the first emitting layer as shown in Table 14.

TABLE 14

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Drive Voltage [V] | λp [nm] | EQE [%] |
| Ex. 14 | 1BH-3 | BD5 | 5 | 2BH-8 | BD5 | 15 | 3.43 | 461 | 10.1 |
| Comp. 14 | — | — | — | 2BH-8 | BD5 | 20 | 3.55 | 461 | 9.3 |

Example 15

The organic EL device of Example 15 was manufactured in the same manner as that of Example 13 except that the first emitting layer was formed by changing the first compound and the third compound and the second emitting layer was formed by changing the second compound and the fourth compound as shown in Table 15.

Comparative Example 15

The organic EL device of Comparative Example 15 was manufactured in the same manner as that of Example 15 except that a 20-nm-thick second emitting layer was formed on the second hole transporting layer as the emitting layer without forming the first emitting layer as shown in Table 15.

TABLE 15

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Drive Voltage [V] | λp [nm] | EQE [%] |
| Ex. 15 | 1BH-3 | BD6 | 10 | 2BH-3 | BD6 | 10 | 3.14 | 450 | 10.7 |
| Comp. 15 | — | — | — | 2BH-3 | BD6 | 20 | 3.11 | 450 | 8.8 |

Example 16

The organic EL device of Example 16 was manufactured in the same manner as that of Example 13 except that the first emitting layer was formed by changing the first compound and the third compound and the second emitting layer was formed by changing the second compound and the fourth compound as shown in Table 16.

Comparative Example 14 is shown again in Table 16 for comparison.

TABLE 16

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Drive Voltage [V] | λp [nm] | EQE [%] |
| Ex. 16 | 1BH-4 | BD5 | 10 | 2BH-8 | BD5 | 10 | 3.41 | 461 | 10.0 |
| Comp. 14 (shown again) | — | — | — | 2BH-8 | BD5 | 20 | 3.55 | 461 | 9.3 |

Example 17

The organic EL device of Example 17 was manufactured in the same manner as that of Example 13 except that the first emitting layer was formed by changing the first compound and the third compound and the second emitting layer was formed by changing the second compound and the fourth compound as shown in Table 17.

Comparative Example 15 is shown again in Table 17 for comparison.

TABLE 17

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Drive Voltage [V] | λp [nm] | EQE [%] |
| Ex. 17 | 1BH-7 | BD6 | 10 | 2BH-3 | BD6 | 10 | 3.13 | 450 | 10.6 |
| Comp. 15 (shown again) | — | — | — | 2BH-3 | BD6 | 20 | 3.11 | 450 | 8.8 |

Example 18

The organic EL device of Example 18 was manufactured in the same manner as that of Example 13 except that the first emitting layer was formed by changing the first compound and the third compound and the second emitting layer was formed by changing the second compound and the fourth compound as shown in Table 18.

Comparative Example 18

The organic EL device of Comparative Example 18 was manufactured in the same manner as that of Example 18 except that a 20-nm-thick second emitting layer was formed on the second hole transporting layer as the emitting layer without forming the first emitting layer as shown in Table 18.

TABLE 18

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Drive Voltage [V] | λp [nm] | EQE [%] |
| Ex. 18 | 1BH-5 | BD2 | 10 | 2BH-8 | BD2 | 10 | 3.50 | 450 | 10.1 |
| Comp. 18 | — | — | — | 2BH-8 | BD2 | 20 | 3.54 | 450 | 9.9 |

Example 19

The organic EL device of Example 19 was manufactured in the same manner as that of Example 13 except that the first emitting layer was formed by changing the first compound and the third compound and the second emitting layer was formed by changing the fourth compound as shown in Table 19.

Comparative Example 19

The organic EL device of Comparative Example 19 was manufactured in the same manner as that of Example 19 except that a 20-nm-thick second emitting layer was formed on the second hole transporting layer as the emitting layer without forming the first emitting layer as shown in Table 19.

TABLE 19

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Drive Voltage [V] | λp [nm] | EQE [%] |
| Ex. 19 | 1BH-5 | BD6 | 10 | 2BH-7 | BD6 | 10 | 3.13 | 450 | 10.1 |
| Comp. 19 | — | — | — | 2BH-7 | BD6 | 20 | 3.18 | 450 | 9.8 |

Example 20

The organic EL device of Example 20 was manufactured in the same manner as that of Example 13 except that the first emitting layer was formed by changing the first compound and the third compound and the second emitting layer was formed by changing the second compound and the fourth compound as shown in Table 20.

Comparative Example 20

The organic EL device of Comparative Example 20 was manufactured in the same manner as that of Example 20 except that a 20-nm-thick second emitting layer was formed on the second hole transporting layer as the emitting layer without forming the first emitting layer as shown in Table 20.

TABLE 20

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Drive Voltage [V] | λp [nm] | EQE [%] |
| Ex. 20 | 1BH-6 | BD6 | 10 | 2BH-4 | BD6 | 10 | 3.15 | 450 | 10.8 |
| Comp. 20 | — | — | — | 2BH-4 | BD6 | 20 | 3.20 | 450 | 10.4 |

Example 21

The organic EL device of Example 21 was manufactured in the same manner as that of Example 13 except that the first emitting layer was formed by changing the first compound and the third compound and the second emitting layer was formed by changing the second compound and the fourth compound as shown in Table 21.

Comparative Example 21

The organic EL device of Comparative Example 21 was manufactured in the same manner as that of Example 21 except that a 20-nm-thick second emitting layer was formed on the second hole transporting layer as the emitting layer without forming the first emitting layer as shown in Table 21.

TABLE 21

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Drive Voltage [V] | λp [nm] | EQE [%] |
| Ex. 21 | 1BH-6 | BD6 | 10 | 2BH-5 | BD6 | 10 | 3.15 | 450 | 10.8 |
| Comp. 21 | — | — | — | 2BH-5 | BD6 | 20 | 3.20 | 450 | 10.4 |

Example 22

The organic EL device of Example 22 was manufactured in the same manner as that of Example 13 except that the first emitting layer was formed by changing the first compound and the third compound and the second emitting layer was formed by changing the second compound and the fourth compound as shown in Table 22.

Comparative Example 15 is shown again in Table 22 for comparison.

TABLE 22

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Drive Voltage [V] | λp [nm] | EQE [%] |
| Ex. 22 | 1BH-6 | BD6 | 10 | 2BH-3 | BD6 | 10 | 3.11 | 450 | 10.6 |
| Comp. 15 (shown again) | — | — | — | 2BH-3 | BD6 | 20 | 3.11 | 450 | 8.8 |

Example 23

The organic EL device of Example 23 was manufactured in the same manner as that of Example 13 except that the first emitting layer was formed by changing the first compound and the second emitting layer was formed by changing the second compound as shown in Table 23.

Comparative Example 23

The organic EL device of Comparative Example 23 was manufactured in the same manner as that of Example 23 except that a 20-nm-thick second emitting layer was formed on the second hole transporting layer as the emitting layer without forming the first emitting layer as shown in Table 23.

TABLE 23

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Drive Voltage [V] | λp [nm] | EQE [%] |
| Ex. 23 | 1BH-6 | BD4 | 10 | 2BH-8 | BD4 | 10 | 3.40 | 455 | 10.4 |
| Comp. 23 | — | — | — | 2BH-8 | BD4 | 20 | 3.53 | 455 | 9.8 |

Example 24

The organic EL device of Example 24 was manufactured in the same manner as that of Example 13 except that the first emitting layer was formed by changing the first compound and the third compound and the second emitting layer was formed by changing the second compound and the fourth compound as shown in Table 24.

Comparative Example 14 is shown again in Table 24 for comparison.

TABLE 24

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Drive Voltage [V] | λp [nm] | EQE [%] |
| Ex. 24 | 1BH-6 | BD5 | 10 | 2BH-8 | BD5 | 10 | 3.45 | 461 | 9.9 |
| Comp. 14 (shown again) | — | — | — | 2BH-8 | BD5 | 20 | 3.55 | 461 | 9.3 |

Example 25

The organic EL device of Example 25 was manufactured in the same manner as that of Example 13 except that the first emitting layer was formed by changing the first compound and the third compound and the second emitting layer was formed by changing the fourth compound as shown in Table 25.

Comparative Example 19 is shown again in Table 25 for comparison.

TABLE 25

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Drive Voltage [V] | λp [nm] | EQE [%] |
| Ex. 25 | 1BH-8 | BD6 | 10 | 2BH-7 | BD6 | 10 | 3.09 | 450 | 10.4 |
| Comp. 19 (shown again) | — | — | — | 2BH-7 | BD6 | 20 | 3.18 | 450 | 9.8 |

Example 26

The organic EL device of Example 26 was manufactured in the same manner as that of Example 13 except that the first emitting layer was formed by changing the first compound and the third compound and the second emitting layer was formed by changing the second compound and the fourth compound as shown in Table 26.

Comparative Example 20 is shown again in Table 26 for comparison.

TABLE 26

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Drive Voltage [V] | λp [nm] | EQE [%] |
| Ex. 26 | 1BH-8 | BD6 | 10 | 2BH-4 | BD6 | 10 | 3.16 | 450 | 10.8 |
| Comp. 20 (shown again) | — | — | — | 2BH-4 | BD6 | 20 | 3.20 | 450 | 10.4 |

Example 27

The organic EL device of Example 27 was manufactured in the same manner as that of Example 13 except that the first emitting layer was formed by changing the first compound and the third compound and the second emitting layer was formed by changing the second compound and the fourth compound as shown in Table 27.

Comparative Example 27

The organic EL device of Comparative Example 27 was manufactured in the same manner as that of Example 27 except that a 20-nm-thick second emitting layer was formed on the second hole transporting layer as the emitting layer without forming the first emitting layer as shown in Table 27.

TABLE 27

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Drive Voltage [V] | λp [nm] | EQE [%] |
| Ex. 27 | 1BH-8 | BD2 | 10 | 2BH-5 | BD2 | 10 | 3.16 | 450 | 10.7 |
| Comp. 27 | — | — | — | 2BH-5 | BD2 | 20 | 3.21 | 450 | 10.3 |

Example 28

The organic EL device of Example 28 was manufactured in the same manner as that of Example 13 except that a 5-nm-thick first emitting layer was formed by changing the first compound and the third compound and a 15-nm-thick second emitting layer was formed by changing the second compound and the fourth compound as shown in Table 28.

Comparative Example 28

The organic EL device of Comparative Example 28 was manufactured in the same manner as that of Example 28 except that a 20-nm-thick second emitting layer was formed on the second hole transporting layer as the emitting layer without forming the first emitting layer as shown in Table 28.

TABLE 28

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Drive Voltage [V] | λp [nm] | EQE [%] |
| Ex. 28 | 1BH-1 | BD4 | 5 | 2BH-5 | BD4 | 15 | 3.18 | 455 | 10.8 |
| Comp. 28 | — | — | — | 2BH-5 | BD4 | 20 | 3.20 | 455 | 10.8 |

Example 29

A glass substrate (size: 25 mm×75 mm×1.1 mm thick, manufactured by Geomatec Co., Ltd.) having an ITO (Indium Tin Oxide) transparent electrode (anode) was ultrasonic-cleaned in isopropyl alcohol for five minutes, and then UV-ozone-cleaned for 30 minutes. A film thickness of the ITO transparent electrode was 130 nm.

The cleaned glass substrate having the transparent electrode line was attached to a substrate holder of a vacuum deposition apparatus. Initially, a compound HT7 and the compound HA3 were co-deposited on a surface provided with the transparent electrode line to cover the transparent electrode, thereby forming a 10-nm-thick hole injecting layer (HI). The ratios of the compound HT7 and the compound HA3 in the hole injecting layer were 97 mass % and 3 mass %, respectively.

After the formation of the hole injecting layer, the compound HT7 was vapor-deposited to form an 85-nm-thick first hole transporting layer (HT).

After the formation of the first hole transporting layer, a compound HT8 was vapor-deposited to form a 5-nm-thick second hole transporting layer (also referred to as an electron blocking layer (EBL)).

The compound 1BH-2 (first host material (BH)) and a compound BD3 (third compound) were co-deposited on the second hole transporting layer such that the ratio of the compound BD3 accounted for 2 mass %, thereby forming a 5-nm-thick first emitting layer.

The compound 2BH-7 (second host material (BH)) and the compound BD3 (fourth compound) were co-deposited on the first emitting layer such that the ratio of the compound BD3 accounted for 2 mass %, thereby forming a 15-nm-thick second emitting layer.

The compound ET4 was vapor-deposited on the second emitting layer to form a 5-nm-thick first electron transporting layer (also referred to as a hole blocking layer (HBL)).

A compound ET6 and Liq were co-deposited on the first electron transporting layer to form a 25-nm-thick second electron transporting layer (ET). The ratios of the compound ET6 and Liq in the second electron transporting layer (ET) were 50 mass % and 50 mass %, respectively. Liq is an abbreviation for (8-quinolinolato)lithium.

Liq was vapor-deposited on the second electron transporting layer to form a 1-nm-thick electron injecting layer.

Metal Al was vapor-deposited on the electron injecting layer to form an 80-nm-thick cathode.

A device arrangement of the organic EL device in Example 29 is roughly shown as follows.

ITO (130)/HT7:HA3 (10, 97%:3%)/HT7 (85)/HT8 (5)/1BH-2:BD3 (5, 98%:2%)/2BH-7:BD3 (15, 98%:2%)/ET4 (5)/ET6:Liq (25, 50%:50%)/Liq (1)/Al (80)

Numerals in parentheses represent a film thickness (unit: nm). The numerals (97%:3%) represented by percentage in the same parentheses indicate a ratio (mass %) between the compounds HT7 and HA3 in the hole injecting layer. The numerals (98%:2%) represented by percentage in the same parentheses indicate a ratio (mass %) between the host material (compound 1BH-2 or 2BH-7) and the compound BD3 in the first emitting layer or the second emitting layer. The numerals (50%:50%) represented by percentage in the same parentheses indicate a ratio (mass %) between the compound ET6 and Liq in the second electron transporting layer.

Comparative Example 29

The organic EL device of Comparative Example 29 was manufactured in the same manner as that of Example 29 except that a 20-nm-thick second emitting layer was formed on the second hole transporting layer as the emitting layer without forming the first emitting layer as shown in Table 29.

TABLE 29

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Drive Voltage [V] | λp [nm] | EQE [%] |
| Ex. 29 | 1BH-2 | BD3 | 5 | 2BH-7 | BD3 | 15 | 3.52 | 462 | 9.9 |
| Comp. 29 | — | — | — | 2BH-7 | BD3 | 20 | 3.54 | 462 | 9.3 |

Example 30

The organic EL device of Example 30 was manufactured in the same manner as that of Example 29 except that the first emitting layer was formed by changing the first compound and the third compound and the second emitting layer was formed by changing the second compound and the fourth compound as shown in Table 30.

Comparative Example 30

The organic EL device of Comparative Example 30 was manufactured in the same manner as that of Example 30 except that a 20-nm-thick second emitting layer was formed on the second hole transporting layer as the emitting layer without forming the first emitting layer as shown in Table 30.

TABLE 30

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Drive Voltage [V] | λp [nm] | EQE [%] |
| Ex. 30 | 1BH-2 | BD5 | 5 | 2BH-8 | BD5 | 15 | 3.83 | 461 | 9.6 |
| Comp. 30 | — | — | — | 2BH-8 | BD5 | 20 | 3.90 | 461 | 9.2 |

Example 31

The organic EL device of Example 31 was manufactured in the same manner as that of Example 29 except that the first emitting layer was formed by changing the first compound and the second emitting layer was formed by changing the second compound as shown in Table 31.

Comparative Example 31

The organic EL device of Comparative Example 31 was manufactured in the same manner as that of Example 31 except that a 20-nm-thick second emitting layer was formed on the second hole transporting layer as the emitting layer without forming the first emitting layer as shown in Table 31.

TABLE 31

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Drive Voltage [V] | λp [nm] | EQE [%] |
| Ex. 31 | 1BH-6 | BD3 | 5 | 2BH-4 | BD3 | 15 | 3.41 | 462 | 9.7 |
| Comp. 31 | — | — | — | 2BH-4 | BD3 | 20 | 3.51 | 462 | 9.5 |

Example 32

The organic EL device of Example 32 was manufactured in the same manner as that of Example 29 except that the first emitting layer was formed by changing the first compound and the second emitting layer was formed by changing the second compound as shown in Table 32.

Comparative Example 32

The organic EL device of Comparative Example 32 was manufactured in the same manner as that of Example 32 except that a 20-nm-thick second emitting layer was formed on the second hole transporting layer as the emitting layer without forming the first emitting layer as shown in Table 32.

TABLE 32

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Drive Voltage [V] | λp [nm] | EQE [%] |
| Ex. 32 | 1BH-6 | BD3 | 5 | 2BH-5 | BD3 | 15 | 3.42 | 462 | 9.7 |
| Comp. 32 | — | — | — | 2BH-5 | BD3 | 20 | 3.57 | 462 | 9.5 |

Example 33

The organic EL device of Example 33 was manufactured in the same manner as that of Example 29 except that a 10-nm-thick first emitting layer was formed by changing the first compound and the third compound and a 10-nm-thick second emitting layer was formed by changing the second compound and the fourth compound as shown in Table 33.

Comparative Example 33

The organic EL device of Comparative Example 33 was manufactured in the same manner as that of Example 33 except that a 20-nm-thick second emitting layer was formed on the second hole transporting layer as the emitting layer without forming the first emitting layer as shown in Table 33.

TABLE 33

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Drive Voltage [V] | λp [nm] | EQE [%] |
| Ex. 33 | 1BH-6 | BD2 | 10 | 2BH-9 | BD2 | 10 | 3.57 | 450 | 9.9 |
| Comp. 33 | — | — | — | 2BH-9 | BD2 | 20 | 3.59 | 450 | 9.7 |

Example 34

The organic EL device of Example 34 was manufactured in the same manner as that of Example 29 except that a 10-nm-thick first emitting layer was formed by changing the first compound and the third compound and a 10-nm-thick second emitting layer was formed by changing the second compound and the fourth compound as shown in Table 34.

Comparative Example 34

The organic EL device of Comparative Example 34 was manufactured in the same manner as that of Example 34 except that a 20-nm-thick second emitting layer was formed on the second hole transporting layer as the emitting layer without forming the first emitting layer as shown in Table 34.

TABLE 34

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Drive Voltage [V] | λp [nm] | EQE [%] |
| Ex. 34 | 1BH-6 | BD2 | 10 | 2BH-3 | BD2 | 10 | 3.34 | 450 | 9.8 |
| Comp. 34 | — | — | — | 2BH-3 | BD2 | 20 | 3.32 | 450 | 9.6 |

Example 35

The organic EL device of Example 35 was manufactured in the same manner as that of Example 29 except that a 10-nm-thick first emitting layer was formed by changing the first compound and the third compound and a 10-nm-thick second emitting layer was formed as shown in Table 35.

Comparative Example 29 is shown again in Table 35 for comparison.

TABLE 35

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Drive Voltage [V] | λp [nm] | EQE [%] |
| Ex. 35 | 1BH-8 | BD5 | 10 | 2BH-7 | BD3 | 10 | 3.42 | 462 | 9.5 |
| Comp. 29 (shown again) | — | — | — | 2BH-7 | BD3 | 20 | 3.54 | 462 | 9.3 |

Example 36

The organic EL device of Example 36 was manufactured in the same manner as that of Example 29 except that a 10-nm-thick first emitting layer was formed by changing the first compound and a 10-nm-thick second emitting layer was formed by changing the second compound and the fourth compound as shown in Table 36.

Comparative Example 30 is shown again in Table 36 for comparison.

TABLE 36

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Drive Voltage [V] | λp [nm] | EQE [%] |
| Ex. 36 | 1BH-8 | BD3 | 10 | 2BH-8 | BD5 | 10 | 3.72 | 462 | 9.4 |
| Comp. 30 (shown again) | — | — | — | 2BH-8 | BD5 | 20 | 3.90 | 461 | 9.2 |

Example 37

A glass substrate (size: 25 mm×75 mm×1.1 mm thick, manufactured by Geomatec Co., Ltd.) having an ITO (Indium Tin Oxide) transparent electrode (anode) was ultrasonic-cleaned in isopropyl alcohol for five minutes, and then UV-ozone-cleaned for 30 minutes. A film thickness of the ITO transparent electrode was 130 nm.

The cleaned glass substrate having the transparent electrode line was attached to a substrate holder of a vacuum deposition apparatus. Initially, the compound HA1 was vapor-deposited on a surface provided with the transparent electrode line to cover the transparent electrode, thereby forming a 5-nm-thick hole injecting layer (HI).

After the formation of the hole injecting layer, the compound HT1 was vapor-deposited to form an 80-nm-thick first hole transporting layer (HT).

After the formation of the first hole transporting layer, the compound HT2 was vapor-deposited to form a 10-nm-thick second hole transporting layer (also referred to as an electron blocking layer (EBL)).

A compound FBH1-1 (first host material (BH)) and the compound BD1 (dopant material (BD)) were co-deposited on the second hole transporting layer such that the ratio of the compound BD1 accounted for 2 mass %, thereby forming a 5-nm-thick first emitting layer.

The compound 2BH-1 (second host material (BH)) and the compound BD1 (dopant material (BD)) were co-deposited on the first emitting layer such that the ratio of the compound BD1 accounted for 2 mass %, thereby forming a 20-nm-thick second emitting layer.

The compound ET1 was vapor-deposited on the second emitting layer to form a 10-nm-thick first electron transporting layer (also referred to as a hole blocking layer (HBL)).

The compound ET2 was vapor-deposited on the first electron transporting layer to form a 15-nm-thick second electron transporting layer (ET).

LiF was vapor-deposited on the second electron transporting layer to form a 1-nm-thick electron injecting layer.

Metal Al was vapor-deposited on the electron injecting layer to form an 80-nm-thick cathode.

A device arrangement of the organic EL device in Example 37 is roughly shown as follows.

ITO (130)/HA1 (5)/HT1 (80)/HT2 (10)/FBH1-1:BD1 (5, 98%:2%)/2BH-1:BD1 (20, 98%:2%)/ET1 (10)/ET2 (15)/LiF (1)/Al (80)

Numerals in parentheses represent a film thickness (unit: nm). The numerals (98%:2%) represented by percentage in the same parentheses indicate a ratio (mass %) between the host material (compound FBH1-1 or 2BH-1) and the compound BD1 in the first emitting layer or the second emitting layer.

Example 38

The organic EL device of Example 38 was manufactured in the same manner as that of Example 37 except that the compound FBH1-1 (first host material) in the first emitting layer was replaced by the first compound shown in Table 37.

Comparative Example 37

The organic EL device of Comparative Example 37 was manufactured in the same manner as that of Example 37 except that a 25-nm-thick second emitting layer was formed on the second hole transporting layer as the emitting layer without forming the first emitting layer as shown in Table 37.

TABLE 37

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | λp [nm] | LT95 [h] | LT90 [h] |
| Ex. 37 | FBH1-1 | BD1 | 5 | 2BH-1 | BD1 | 20 | 462 | 223 | 475 |
| Ex. 38 | FBH1-2 | BD1 | 5 | 2BH-1 | BD1 | 20 | 462 | 250 | 600 |
| Comp. 37 | — | — | — | 2BH-1 | BD1 | 25 | 460 | 208 | 445 |

As shown in Table 37, the organic EL devices of Examples 37 and 38 that included the first emitting layer containing the first compound as the first host material and the second emitting layer containing the second compound as the second host material emitted light with a longer lifetime than the organic EL device of Comparative Example 37 that included only the second emitting layer.

Evaluation of Compounds

The compounds used for manufacturing the organic EL devices were evaluated as follows. Table 38 shows evaluation results.

Triplet Energy $T_1$

A measurement target compound was dissolved in EPA (diethylether:isopentane:ethanol=5:5:2 in volume ratio) at a concentration of 10 μmol/L, and the obtained solution was put in a quartz cell to provide a measurement sample. A phosphorescence spectrum (ordinate axis: phosphorescent luminous intensity, abscissa axis: wavelength) of the measurement sample was measured at a low temperature (77K). A tangent was drawn to the rise of the phosphorescence spectrum close to the short-wavelength region. An energy amount was calculated by a conversion equation (F1) below on a basis of a wavelength value λedge [nm] at an intersection of the tangent and the abscissa axis. The calculated energy amount was defined as triplet energy $T_1$. It should be noted that the triplet energy $T_1$ has an error of about plus or minus 0.02 eV depending on measurement conditions.

$$T_1[eV]=1239.85/\lambda edge \quad \text{Conversion Equation (F1):}$$

The tangent to the rise of the phosphorescence spectrum close to the short-wavelength region is drawn as follows. While moving on a curve of the phosphorescence spectrum from the short-wavelength region to the local maximum value closest to the short-wavelength region among the local maximum values of the phosphorescence spectrum, a tangent is checked at each point on the curve toward the long-wavelength of the phosphorescence spectrum. An inclination of the tangent is increased along the rise of the curve (i.e., a value of the ordinate axis is increased). A tangent drawn at a point of the local maximum inclination (i.e., a tangent at an inflection point) is defined as the tangent to the rise of the phosphorescence spectrum close to the short-wavelength region.

A local maximum point where a peak intensity is 15% or less of the maximum peak intensity of the spectrum is not counted as the above-mentioned local maximum peak intensity closest to the short-wavelength region. The tangent drawn at a point that is closest to the local maximum peak intensity closest to the short-wavelength region and where the inclination of the curve is the local maximum is defined as a tangent to the rise of the phosphorescence spectrum close to the short-wavelength region.

For phosphorescence measurement, a spectrophotofluorometer body F-4500 (manufactured by Hitachi High-Technologies Corporation) was used.

Measurement of Maximum Fluorescence Peak Wavelength (FL-Peak)

A measurement target compound was dissolved in toluene at a concentration of $4.9\times10^{-6}$ mol/L to prepare a toluene solution thereof. Using a fluorescence spectrometer (spectrophotofluorometer F-7000 manufactured by Hitachi High-Tech Science Corporation), the toluene solution of the measurement target compound was excited at 390 nm, where a maximum fluorescence peak wavelength λ (unit: nm) was measured.

TABLE 38

| Compound | $T_1$ [eV] | Compound | $T_1$ [eV] | Compound | $T_1$ [eV] | λ [nm] |
|---|---|---|---|---|---|---|
| BH1-1 | 2.13 | 2BH-1 | 1.87 | BD1 | 2.29 | 453 |
| 1BH-2 | 2.21 | 2BH-2 | 1.87 | BD2 | 2.32 | 444 |
| 1BH-3 | 2.20 | 2BH-3a | 1.79 | BD3 | 2.45 | 457 |
| 1BH-4 | 2.20 | 2BH-3b | 1.79 | BD4 | 2.30 | 450 |
| 1BH-5 | 2.20 | 2BH-4 | 1.81 | BD5 | 2.64 | 455 |
| 1BH-6 | 2.20 | 2BH-5 | 1.81 | BD6 | 2.32 | 445 |
| 1BH-7 | 2.20 | 2BH-6 | 1.87 | | | |
| 1BH-8 | 2.20 | 2BH-7 | 1.81 | | | |
| 1BH-9 | 2.08 | 2BH-8 | 1.79 | | | |
| 1BH-10 | 2.19 | 2BH-9 | 1.81 | | | |
| 1BH-11 | 2.09 | | | | | |
| FBH1-1 | 2.28 | | | | | |
| FBH1-2 | 2.24 | | | | | |

SYNTHESIS EXAMPLES

Synthesis Example 1

Synthesis of Benzo[k]Fluoranthene Derivative (Compound BH1-1)

The compound BH1-1 was synthesized using the following synthetic pathway.

[Formula 295]

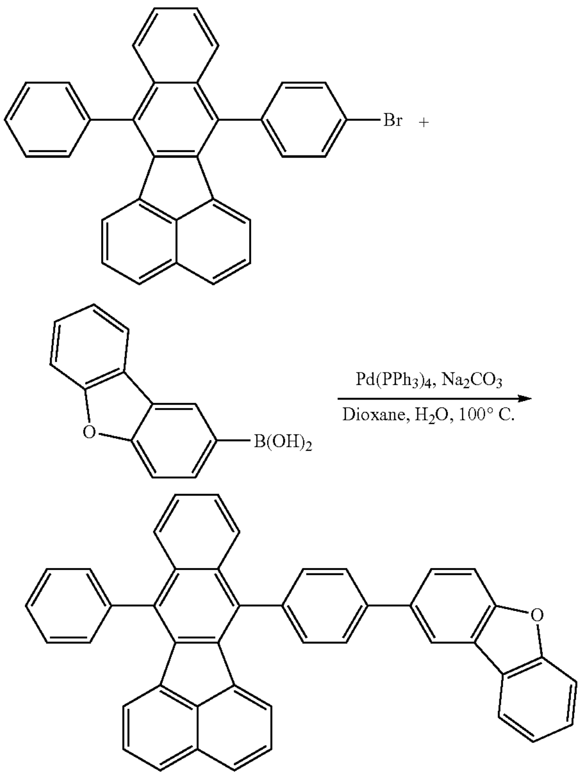

BH1-1

Under argon atmosphere, 1 g of 7-(4-bromophenyl)-12-phenylbenzo[k]fluoranthene synthesized by a known method, 0.78 g of B-2-dibenzofuranylboronic acid, 0.03 g of tetrakistriphenylphosphine palladium(0), 1.35 g of sodium carbonate, 9 mL of 1,4-dioxane and 1.5 mL of ion-exchange water were put into a flask and stirred at reflux for 18 hours. This reaction solution was cooled to room temperature, then thermally dissolved with toluene, and added with anhydrous magnesium sulfate. After an insoluble substance was filtered out through Celite®, the solvent was distilled under reduced pressure. The obtained residue was washed with acetic ether and methanol and then recrystallized with a mixed solvent of toluene and cyclohexane to obtain 0.82 g (a yield: 66%) of a light yellow solid. As a result of mass spectrum analysis, this light yellow solid was the compound BH1-1. m/e was equal to 571 while a molecular weight was 570.69.

Synthesis Example 2
The compound 1BH-2 was synthesized using the following synthetic pathway.
[Formula 296]
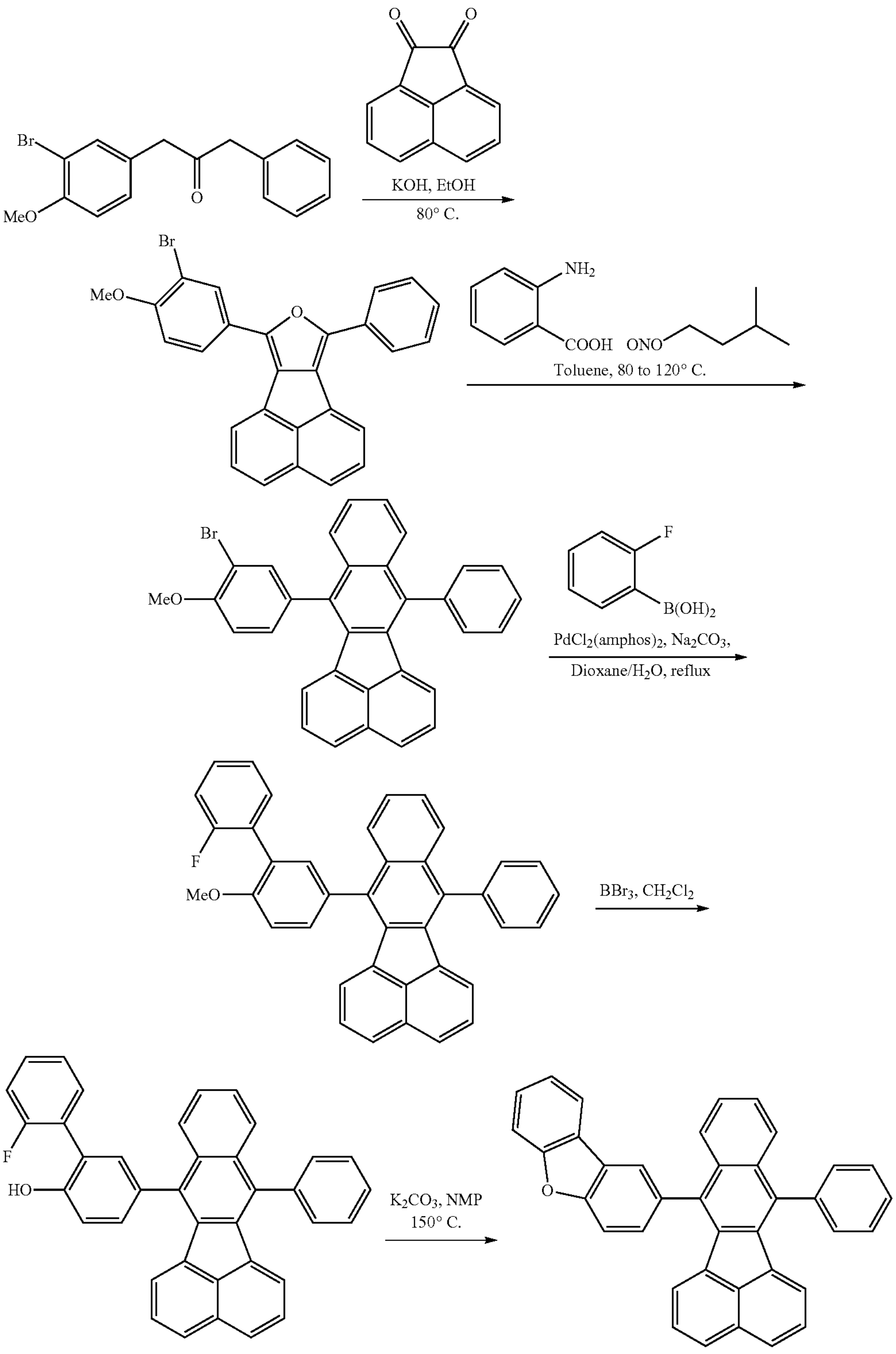
1BH-2

(Step X1) Synthesis of Acenaphthofuran Intermediate (Compound M11a)

[Formula 297]

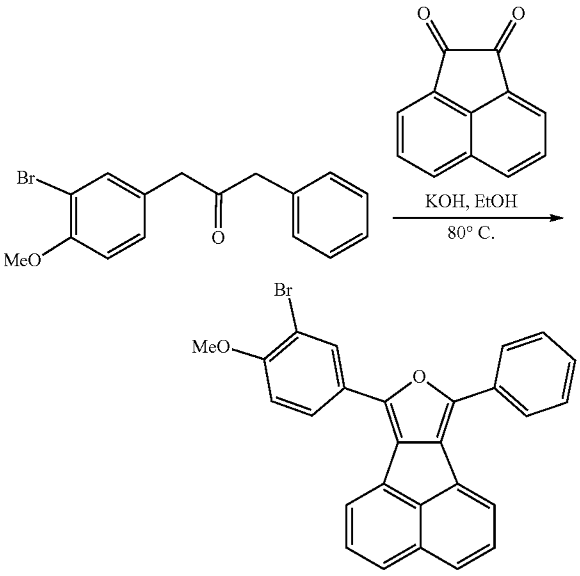

M11a

Under argon atmosphere, 1.28 g of 1-(3-bromo-4-methoxyphenyl)-3-phenyl-2-propanone synthesized by a known method and 0.78 g of acenaphthylene-1,2-dione were mixed in 40 mL of ethanol in a flask. The reaction solution was added with 0.15 g of potassium hydroxide and stirred at reflux for three hours. The reaction solution was cooled to room temperature and then filtered to obtain a deposited solid. The solid was washed with methanol to obtain 1.68 g (a yield: 92%) of a dark green solid. As a result of NMR analysis, this dark green solid was the compound M11a. $^{1}$H NMR (400 MHZ, $CD_2Cl_2$) δ 3.59 (s, 3H), 7.07 (d, J=8.4 Hz, 1H), 7.38-7.42 (m, 1H), 7.49-7.53 (m, 2H), 7.57-7.64 (m, 2H), 7.75-7.80 (m, 3H), 7.88-7.91 (m, 2H), 7.99-8.05 (m, 3H);

(Step X2) Synthesis of Benzo[k]Fluoranthene Intermediate (Compound M11b)

[Formula 298]

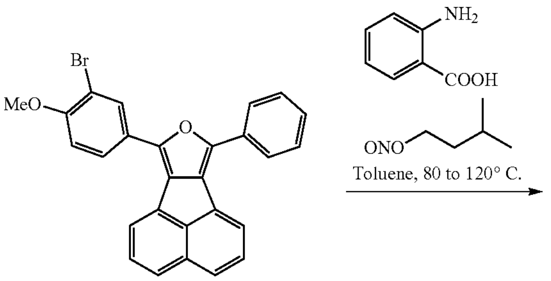

-continued

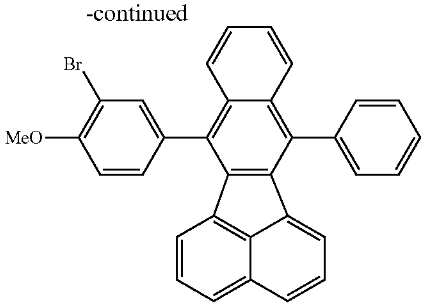

M11b

Under argon atmosphere, 0.31 g of 7-(3-bromo-4-methoxyphenyl)-9-phenyl acenaphtho[1,2-c]furan synthesized in Step X1, 0.10 g of 2-amino benzoic acid and 7 mL of toluene were put into a flask and stirred for ten minutes at a bath temperature of 80 degrees C. The reaction solution was added with 0.1 mL of isopentyl nitrite at the same temperature, heated to 120 degrees C. and stirred at reflux for six hours. The reaction solution was cooled to room temperature, then added with water and extracted with acetic ether. An organic phase was washed twice with water, dried with sodium sulfate. After an insoluble substance was removed by filtration, the solvent was distilled under reduced pressure. The residue was purified by silica gel column chromatography (hexane:acetic ether=95%:5% to 20%:80%) to obtain 0.22 g (a yield of 62%) of a yellow solid. As a result of NMR analysis, this yellow solid was the compound M11b. 1H NMR (400 MHZ, $CD_2Cl_2$) δ 4.06 (s, 3H), 6.59 (d, J=7.2 Hz, 1H), 6.75 (d, J=7.2 Hz, 1H), 7.22 (d, J=8.4 Hz, 1H), 7.29-7.73 (m, 15H);

(Step X3) Synthesis of Benzo[k]Fluoranthene Intermediate (Compound M11c)

[Formula 299]

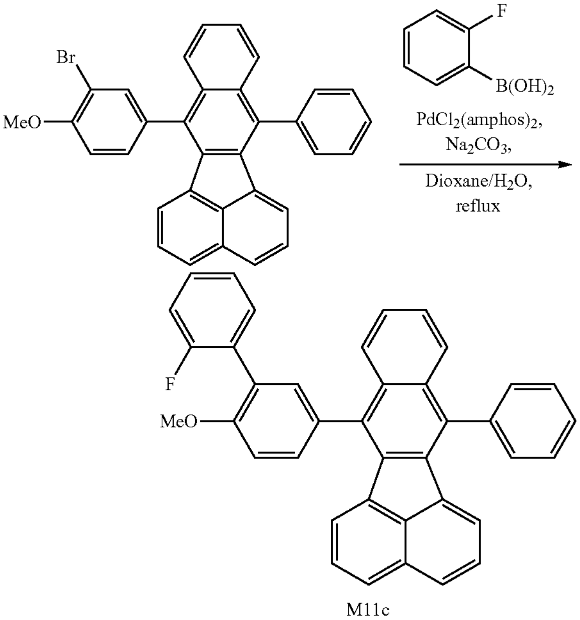

M11c

Under argon atmosphere, 1.42 g of 7-(3-bromo-4-methoxyphenyl)-12-phenylbenzo[k]fluoranthene synthesized in Step X2, 0.80 g of (2-fluorophenyl)boronic acid, 0.16 g of bis(di-tert-butyl(4-dimethylaminophenyl)phosphine)dichloropalladium(II) ($PdCl_2(amphos)_2$), 0.45 g of sodium carbonate, 25 mL of 1,4-dioxane and 3 mL of ion-exchange water were put into a flask and stirred at reflux for 20 hours. The reaction solution was cooled to room temperature, then added with 30 mL of water and extracted with acetic ether. An organic phase was washed with water, dried with sodium sulfate. After an insoluble substance was removed by filtration, the solvent was distilled under reduced pressure. The residue was washed with toluene and hot methanol to obtain 1.38 g (a yield: 95%) of a light yellow solid. As a result of mass spectrum analysis, this light yellow solid was the compound M11c. m/e was equal to 529 while a molecular weight was 528.63.

(Step X4) Synthesis of Benzo[k]Fluoranthene Intermediate (Compound M11d)

[Formula 300]

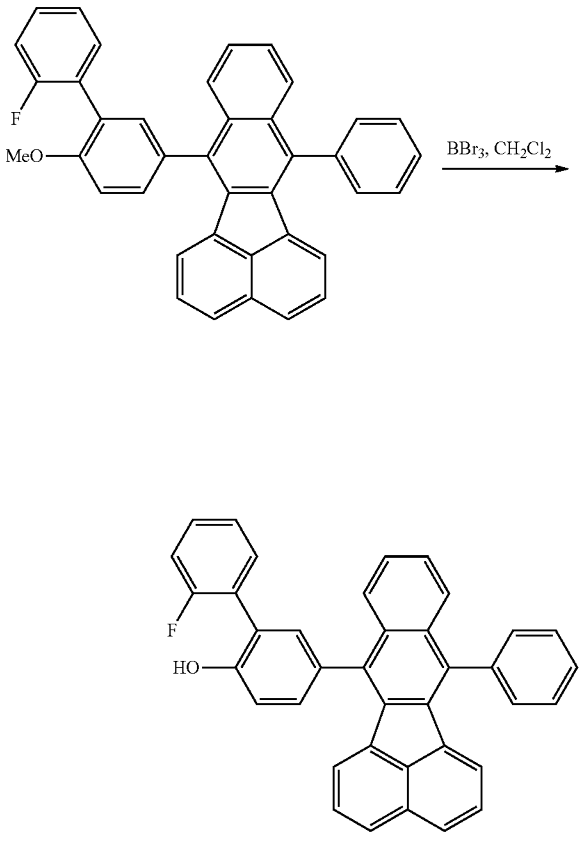

M11d

Under argon atmosphere, 1.62 g of 7-(2'-fluoro-6-methoxy-[1,1'-biphenyl]-3-yl)-12-phenylbenzo[k]fluoranthene synthesized in Step X3 and 25 mL of dichloromethane were put into a flask, added with 4 mL of boron tribromide under ice cooling and stirred for four hours while heated to room temperature. The reaction solution was added with 0.1M hydrochloric acid and extracted with dichloromethane. The solvent was distilled under reduced pressure. The obtained residue was purified by silica gel column chromatography (hexane:acetic ether=90%: 10% to 10%:90%) to obtain 1.50 g (a yield of 100%) of a candy-like yellow solid. As a result of NMR analysis, this yellow solid was the compound M11d. 1H NMR (400 MHZ, CD2C12) δ 5.33 (s, 1H), 6.58 (d, J=6.8 Hz, 1H), 6.90 (d, J=6.8 Hz, 1H), 7.15-7.78 (m, 20H);

(Step X5) Synthesis of Benzo[k]Fluoranthene Derivative (Compound 1BH-2)

[Formula 301]

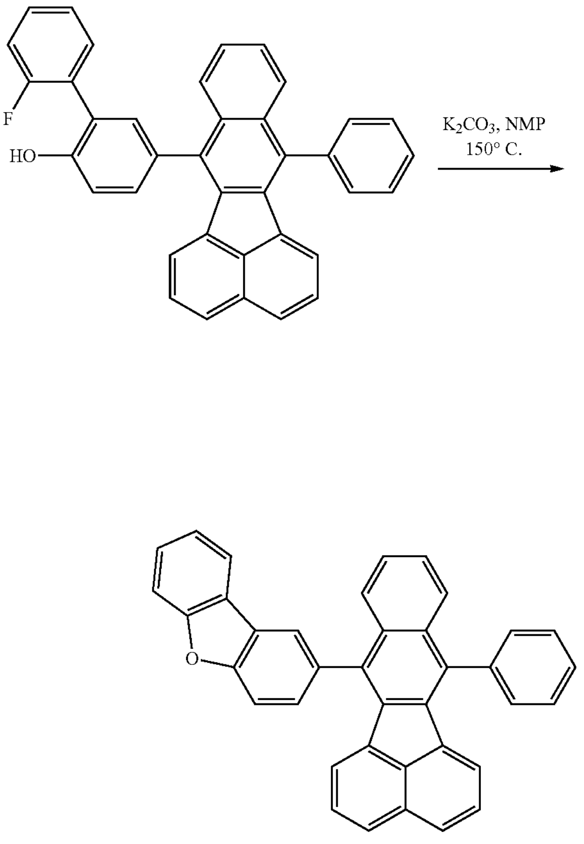

1BH-2

Under argon atmosphere, 0.13 g of 2'-fluoro-5-(12-phenylbenzo[k]fluoranthene-7-yl)-[1,1'-biphenyl]-2-ol synthesized in Step X4, 0.05 g of potassium carbonate and 10 mL of N-methylpyrrolidone were put into a flask and stirred at reflux for three hours at a bath temperature of 150 degrees C. The reaction solution was cooled to room temperature, then added with 10 mL of water and extracted with acetic ether. An organic phase was washed with water, dried with sodium sulfate. After an insoluble substance was removed by filtration, the solvent was distilled under reduced pressure. The residue was purified by silica gel column chromatography (hexane:acetic ether=100%:0% to 30%:70%) to obtain 0.07 g (a yield of 57%) of a light yellow solid. As a result of mass spectrum analysis, this light yellow solid was the compound 1BH-2. m/e was equal to 495 while a molecular weight was 494.59.

Synthesis Example 3

Synthesis of Benzo[k]Fluoranthene Derivative (Compound 1BH-5)

The compound 1BH-5 was synthesized using the following synthetic pathway.

[Formula 302]

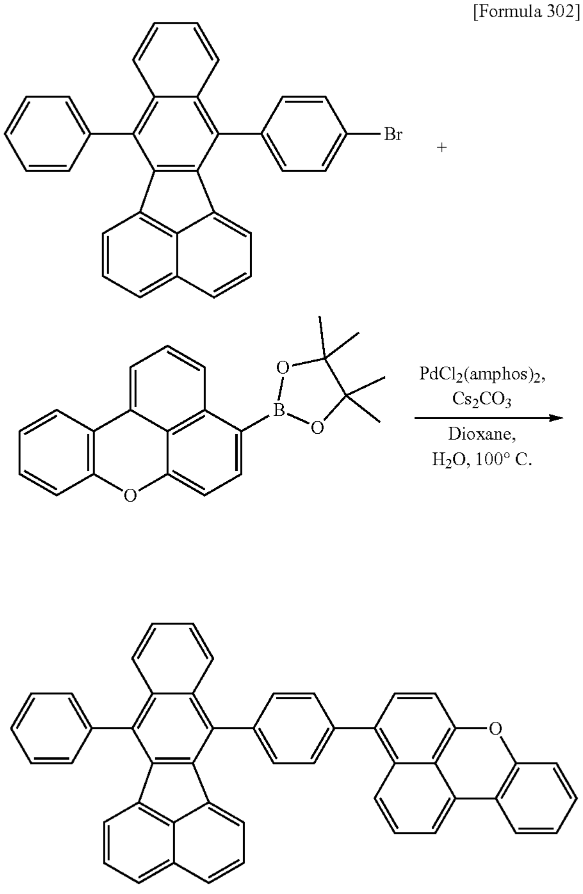

1BH-5

Under argon atmosphere, 1 g of 7-(4-bromophenyl)-12-phenylbenzo[k]fluoranthene synthesized by a known method, 0.78 g of 2-(benzo[kl]xanthene-4-yl)-4,4,5,5-tetramethyl-1,3,2-dioxaborolane, 0.03 g of bis(di-tert-butyl(4-dimethylaminophenyl)phosphine)dichloropalladium(II) ($PdCl_2(amphos)_2$), 1.35 g of cesium carbonate, 9 mL of 1,4-dioxane and 1.5 mL of ion-exchange water were put into a flask and stirred at reflux for four hours. This reaction solution was cooled to room temperature, then thermally dissolved with toluene, and added with anhydrous magnesium sulfate. After an insoluble substance was filtered out through Celite®, the solvent was distilled under reduced pressure. The obtained residue was washed with acetic ether and methanol and then purified by alumina column chromatography (hexane:toluene=75%:25%) to obtain 0.94 g (a yield of 73%) of a light yellow solid. As a result of mass spectrum analysis, this light yellow solid was the compound 1BH-5. m/e was equal to 621 while a molecular weight was 620.75.

Synthesis Example 4

Synthesis of Benzo[k]Fluoranthene Derivative (Compound 1BH-6)

The compound 1BH-6 was synthesized using the following synthetic pathway.

[Formula 303]

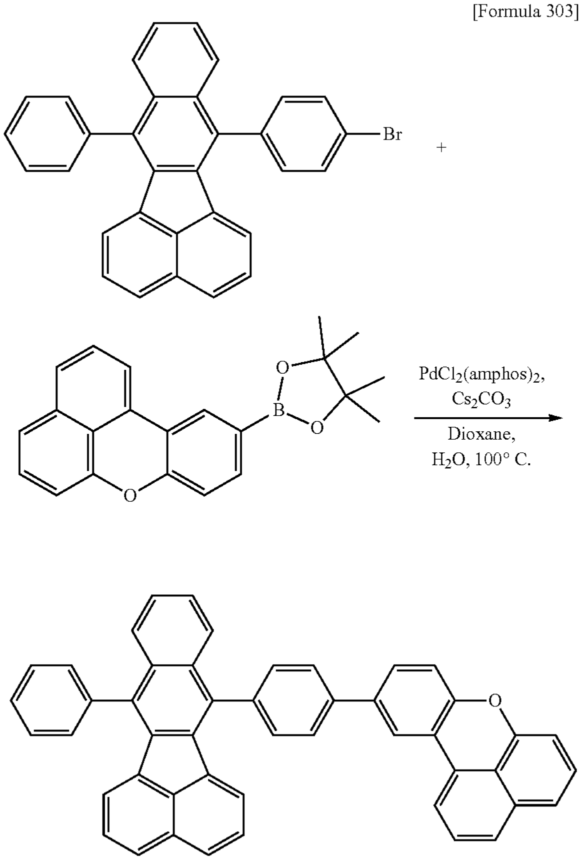

1BH-6

Under argon atmosphere, 5 g of 7-(4-bromophenyl)-12-phenylbenzo[k]fluoranthene synthesized by a known method, 3.92 g of 10-(4,4,5,5-tetramethyl-1,3,2-dioxaborolane-2-yl)-benzo[k]xanthene, 0.15 g of bis(di-tert-butyl(4-dimethylaminophenyl)phosphine)dichloropalladium(II) ($PdCl_2(amphos)_2$), 6.74 g of cesium carbonate, 44 mL of 1,4-dioxane and 7.4 mL of ion-exchange water were put into a flask and stirred at reflux for 25 hours. The reaction solution was cooled to room temperature, then added with water and filtered to obtain a deposited solid. The solid was washed with methanol. The solid was thermally dissolved in 200 mL of toluene and purified through alumina/silica gel at a short column. The solvent was then distilled under reduced pressure. The obtained residue was washed with acetic ether and cyclohexane and then recrystallized with a mixed solvent of acetic ether and tetrahydrofuran to obtain 5.57 g (a yield: 87%) of a light yellow solid. As a result of mass spectrum analysis, this light yellow solid was the compound 1BH-6. m/e was equal to 621 while a molecular weight was 620.75.

Synthesis Example 5

The compound 1BH-8 was synthesized using the following synthetic pathway.

[Formula 304]

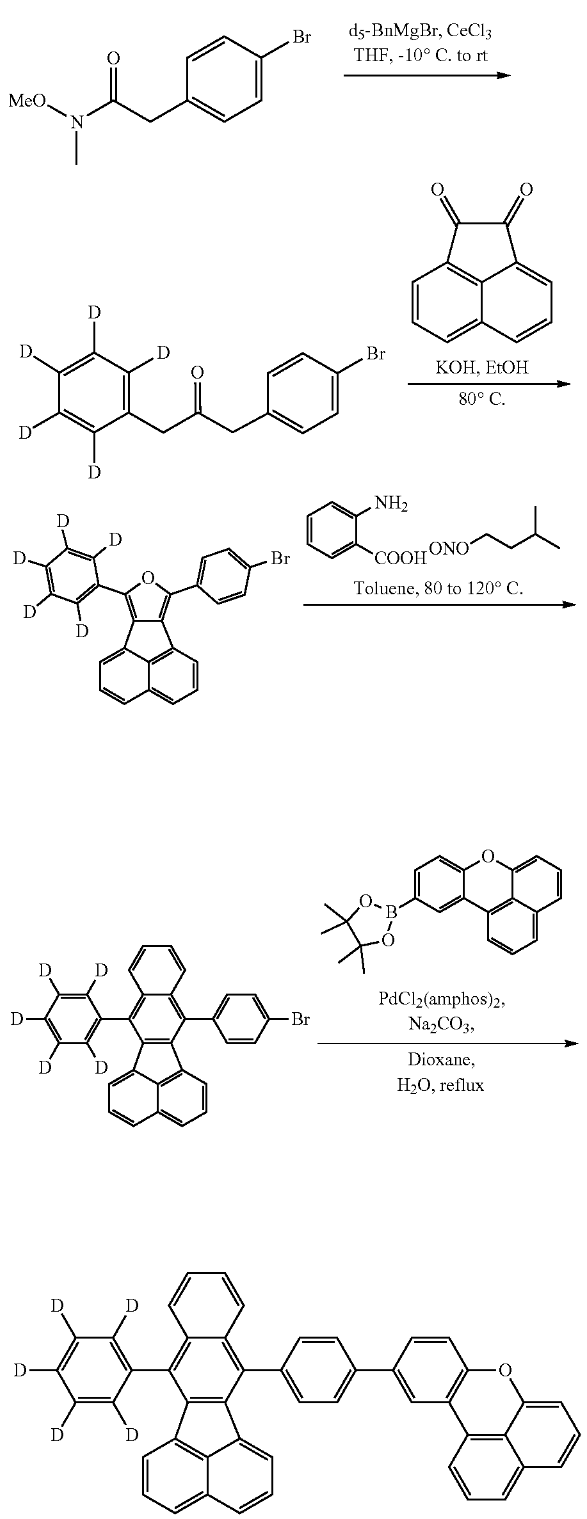

(Step Y1) Synthesis of Dibenzyl Ketone Intermediate (Compound M8a)

[Formula 305]

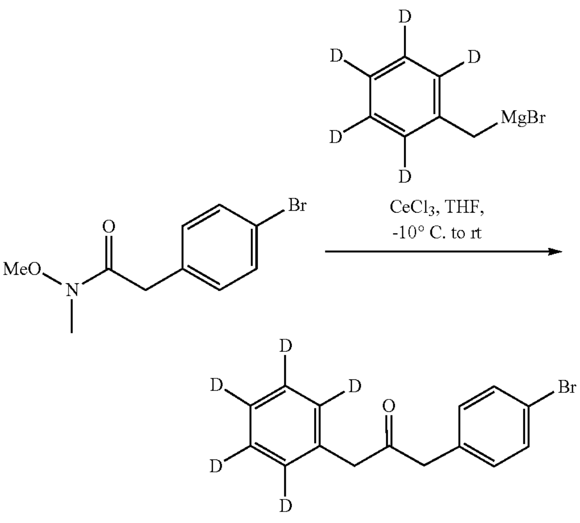

M8a

Under argon atmosphere, 1 g of 4-bromo-N-methoxy-N-methylbenzeneacetamide synthesized by a known synthesis method and 20 mL of tetrahydrofuran were put into a flask, added with 0.10 g of cerium(III) chloride under ice cooling and stirred for ten minutes. The reaction solution was added with 4.30 mL of THF solution of bromo(phenyl-d5-methyl) magnesium (0.9M) at the same temperature and stirred for six hours while heated to room temperature. The reaction solution was added with 0.1M hydrochloric acid and extracted with acetic ether. An organic phase was washed twice with water, dried with sodium sulfate. After an insoluble substance was removed by filtration, the solvent was distilled under reduced pressure. The residue was purified by silica gel column chromatography (hexane:acetic ether=100%:0% to 20%:80%) to obtain 0.30 g (a yield of 26%) of a colorless oily substance. As a result of mass spectrum analysis, this colorless oily substance was the compound M8a. m/e was equal to 295, 297 while a molecular weight was 294.20.

(Step Y2) Synthesis of Acenaphthofuran Intermediate (Compound M8b)

[Formula 306]

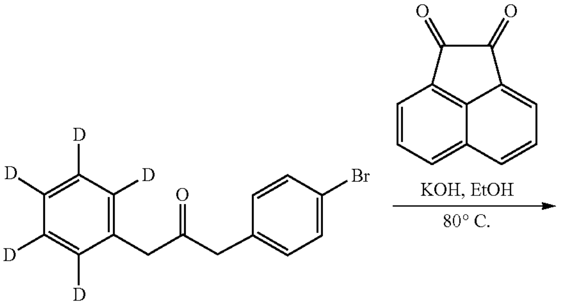

-continued

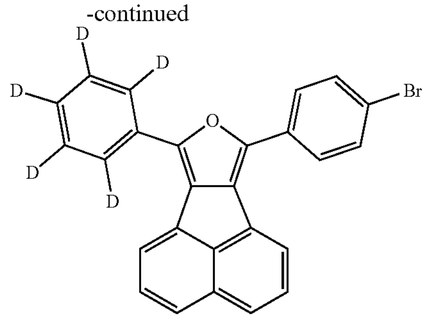

M8b

Under argon atmosphere, 1.23 g of 1-(phenyl-d5)-3-phenyl-2-propanone synthesized by Step Y1 and 0.80 g of acenaphthylene-1,2-dione were mixed in 40 mL of ethanol in a flask. The reaction solution was added with 0.16 g of potassium hydroxide and stirred at reflux for three hours. The reaction solution was cooled to room temperature and then filtered to obtain a deposited solid. The solid was washed with methanol to obtain 1.61 g (a yield: 90%) of a dark green solid. As a result of mass spectrum analysis, this dark green solid was the compound M8b. m/e was equal to 429, 431 while a molecular weight was 428.34.

(Step Y3) Synthesis of Benzo[k]Fluoranthene Intermediate (Compound M8c)

[Formula 307]

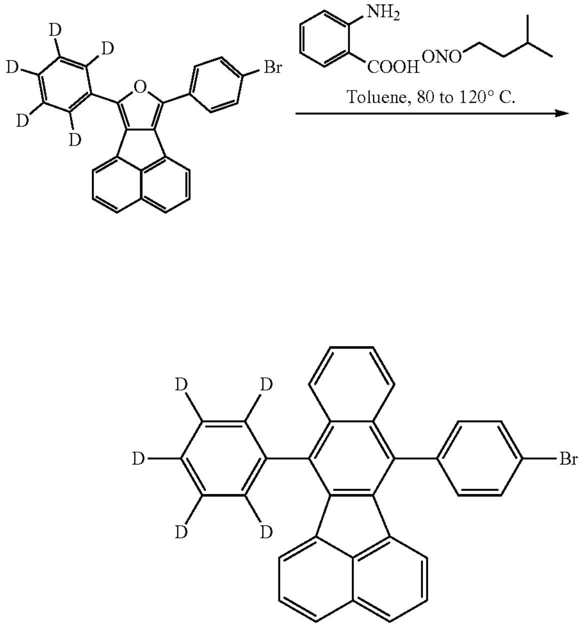

M8c

Under argon atmosphere, 1.60 g of 7-(phenyl-d5)-9-phenyl acenaphtho[1,2-c]furan synthesized in Step Y2, 0.53 g of 2-amino benzoic acid and 20 mL of toluene were put into a flask and stirred for ten minutes at a bath temperature of 80 degrees C. The reaction solution was added with 0.52 mL of isopentyl nitrite at the same temperature, heated to 120 degrees C. and stirred at reflux for six hours. The reaction solution was cooled to room temperature, then added with water and extracted with acetic ether. An organic phase was washed twice with water, dried with sodium sulfate. After an insoluble substance was removed by filtration, the solvent was distilled under reduced pressure. The residue was purified by silica gel column chromatography (hexane:acetic ether=95%:5% to 20%:80%) to obtain 1.72 g (a yield of 94%) of a yellow solid. As a result of mass spectrum analysis, this light yellow solid was the compound M8c. m/e was equal to 489, 491 while a molecular weight was 488.44.

(Step Y4) Synthesis of Benzo[k]Fluoranthene Derivative (Compound 1BH-8)

[Formula 308]

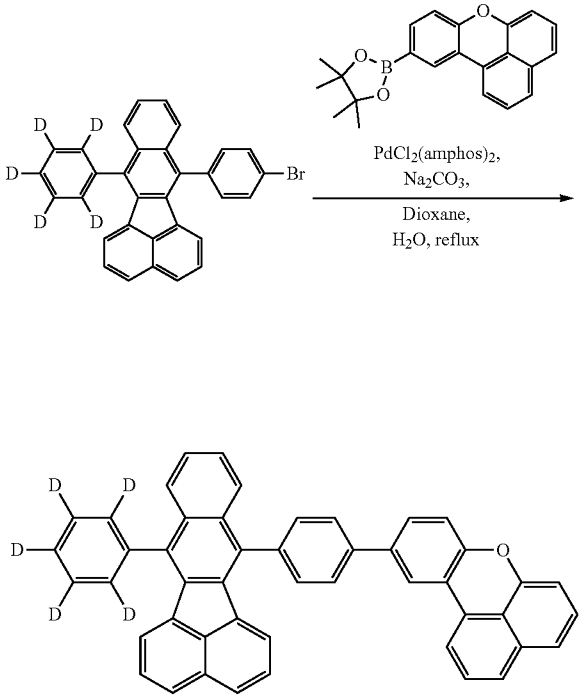

1BH-8

Under argon of 7-(phenyl-d5)-12-atmosphere, 1.70 g phenylbenzo[k]fluoranthene synthesized in Step Y3, 1.20 g of 10-(4,4,5,5-tetramethyl-1,3,2-dioxaborolane-2-yl)-benzo [kl]xanthene, 0.12 g of bis(di-tert-butyl(4-dimethylamino-phenyl)phosphine)dichloropalladium(II) ($PdCl_2(amphos)_2$), 0.60 g of sodium carbonate, 30 mL of 1,4-dioxane and 3 mL of ion-exchange water were put into a flask and stirred at reflux for 20 hours. The reaction solution was cooled to room temperature, then added with 30 mL of water and extracted with acetic ether. An organic phase was washed with water, dried with sodium sulfate. After an insoluble substance was removed by filtration, the solvent was distilled under reduced pressure. The residue was washed with toluene and hot methanol to obtain 1.38 g (a yield: 63%) of a light yellow solid. As a result of mass spectrum analysis, this light yellow solid was the compound 1BH-8. m/e was equal to 626 while a molecular weight was 625.78.

Synthesis Example 6

Synthesis of Benzo[k]Fluoranthene Derivative (Compound 1BH-9)

The compound 1BH-9 was synthesized using the following synthetic pathway.

[Formula 309]

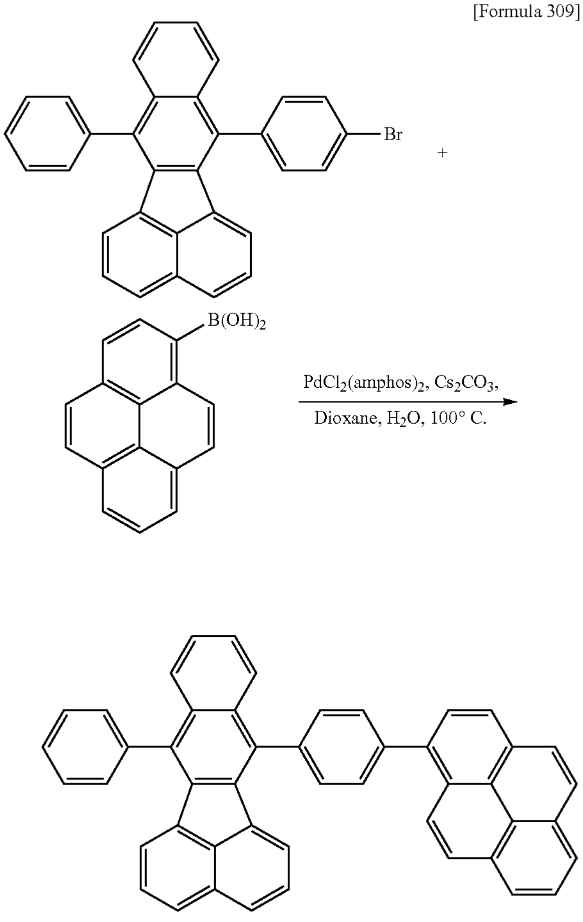

1BH-9

Under argon atmosphere, 2.66 g of 7-(4-bromophenyl)-12-phenylbenzo[k]fluoranthene synthesized by a known method, 1.23 g of pyrene-1-boronic acid, 0.05 g of tris-dibenzyliacetonedipalladium(0), 0.11 g of di-tert-butyl(4-dimethylaminophenyl)phosphine, 6.5 mL of 2M sodium carbonate aqueous solution and 50 mL of 1,4-dioxane were put into a flask and stirred at reflux for five hours. The reaction solution was cooled to room temperature, then added with 50 mL of water and filtered to obtain a deposited solid. The solid was thermally dissolved in 100 ml of toluene and purified through silica gel at a short column. The solvent was then distilled under reduced pressure. The obtained residue was purified by silica gel column chromatography (hexane:toluene=75%:25%) and then recrystallized with a solvent of toluene to obtain 2.11 g (a yield: 70%) of a light yellow solid. As a result of mass spectrum analysis, this light yellow solid was the compound 1BH-9. m/e was equal to 605 while a molecular weight was 604.75.

Synthesis Example 7

Synthesis of Benzo[k]Fluoranthene Derivative (Compound 1BH-10)

The compound 1BH-10 was synthesized using the following synthetic pathway.

[Formula 310]

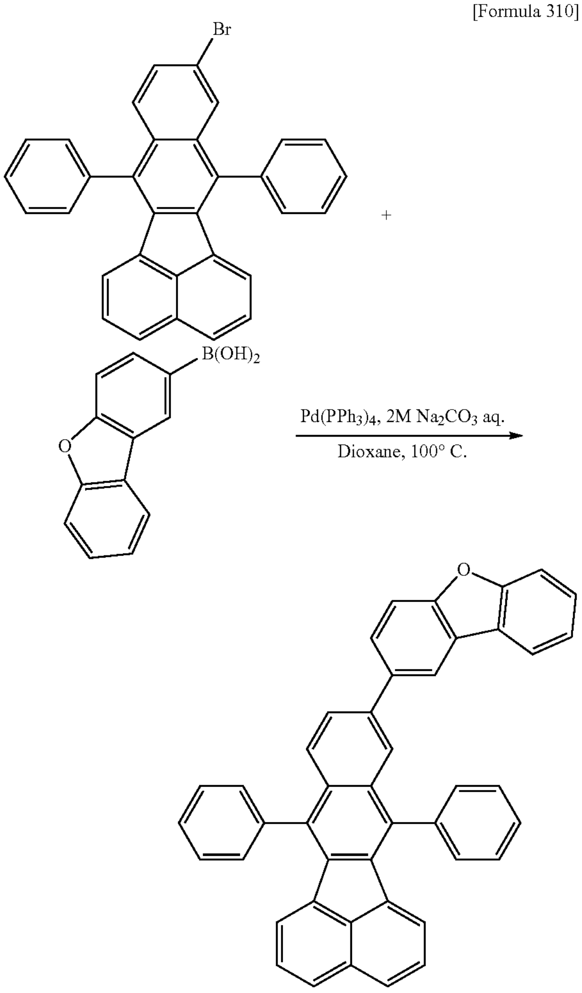

1BH-10

Under argon atmosphere, 1 g of 9-bromo-7,12-diphenylbenzo[k]fluoranthene synthesized by a known method, 0.48 g of B-2-dibenzofuranyl boronic acid, 0.10 g of tetrakistriphenylphosphine palladium(0), 3.1 mL of 2M sodium carbonate aqueous solution and 20 mL of 1,4-dioxane were put into a flask and stirred at reflux for 20 hours. The reaction solution was cooled to room temperature, then added with water and extracted with toluene. An organic phase was washed with saturated saline solution and dried by adding anhydrous magnesium sulfate. After an insoluble substance was removed by filtration, the solvent was distilled under reduced pressure. The obtained residue was purified by silica gel column chromatography (hexane:toluene=80%:20%) to obtain 1.06 g (a yield: 89%) of a light yellow solid. As a result of mass spectrum analysis, this light yellow solid was the compound 1BH-10. m/e was equal to 571 while a molecular weight was 570.69.

Synthesis Example 8

Synthesis of Benzo[k]Fluoranthene Derivative (Compound 1BH-11)

The compound 1BH-11 was synthesized using the following synthetic pathway.

[Formula 311]

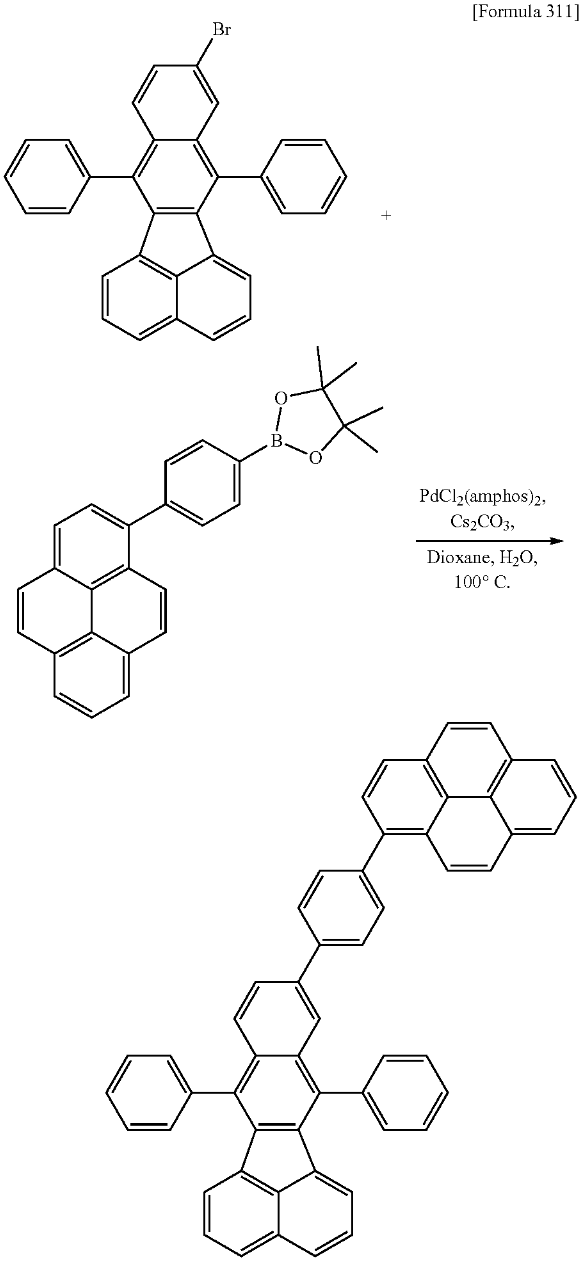

1BH-11

Under argon atmosphere, 1.62 g of 9-bromo-7,12-diphenylbenzo[k]fluoranthene synthesized by a known method, 1.42 g of 4,4,5,5-tetramethyl-2-[4-(1-pyrenyl)phenyl]-1,3,2-dioxaborolane, 0.02 g of bis(di-tert-butyl(4-dimethylaminophenyl)phosphine)dichloropalladium (II) ($PdCl_2$(amphos)$_2$), 2.18 g of cesium carbonate, 14 mL of 1,4-dioxane and 2.3 mL of ion-exchange water were put into a flask and stirred at reflux for seven hours. The reaction solution was cooled to room temperature, then added water and methanol and filtered to obtain a deposited solid. The solid was thermally dissolved in 500 ml of xylene and purified through alumina/silica gel at a short column. The solvent was then distilled under reduced pressure. The obtained residue was purified by alumina column chromatography (toluene elution) and then washed with acetic ether to obtain 1.50 g (a yield: 66%) of a light yellow solid. As a result of mass spectrum analysis, this light yellow solid was the compound 1BH-11. m/e was equal to 681 while a molecular weight was 680.85.

The invention claimed is:

1. An organic electroluminescence device comprising:

an anode;

a cathode;

a first emitting layer provided between the anode and the cathode; and a second emitting layer provided between the anode and the cathode, wherein the first emitting layer comprises, as a first host material, a first compound represented by one of formulae (101) to (104) below and comprising at least one group represented by a formula (11), the second emitting layer comprises a second host material, and the first host material and the second host material are mutually different, (101)

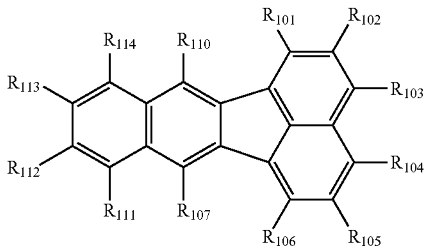

(102)

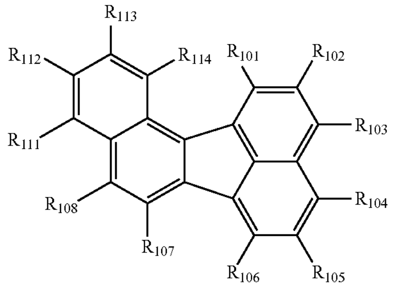

(103)

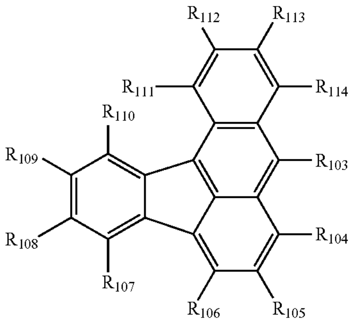

-continued (104)

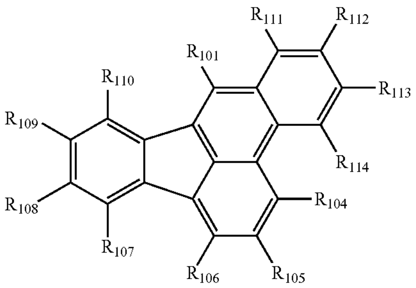

(103)

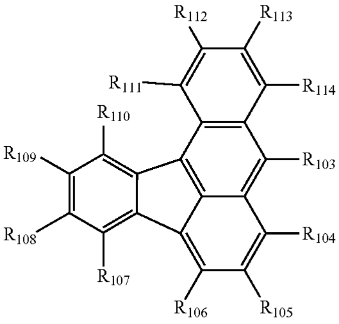

(104)

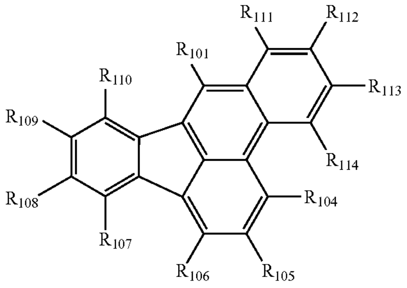

(11)

$$*-\!\left(L_{101}\right)_{mx}\!-Ar_{101},$$

wherein, in the formulae (101) to (104):

$R_{101}$ to $R_{114}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $-Si(R_{901})(R_{902})(R_{903})$, a group represented by $-O-(R_{904})$, a group represented by $-S-(R_{905})$, a substituted or unsubstituted aralkyl group having 7 to 50 carbon atoms, a group represented by $-C(=O)R_{801}$, a group represented by $-COOR_{802}$, a halogen atom, a cyano group, a nitro group, a substituted or unsubstituted aryl group having 6 to 50 ring carbon atoms, a substituted or unsubstituted heterocyclic group having 5 to 50 ring atoms, or a group represented by the formula (11);

at least one of $R_{101}$ to $R_{114}$ is a group represented by the formula (11);

when a plurality of groups represented by the formula (11) are present, the plurality of groups represented by the formula (11) are mutually the same or different;

when a plurality of groups represented by the formula (11) are present, the plurality of groups represented by the formula (11) are mutually the same or different;

$L_{101}$ is a single bond, a substituted or unsubstituted arylene group having 6 to 50 ring carbon atoms, or a substituted or unsubstituted divalent heterocyclic group having 5 to 50 ring atoms;

$Ar_{101}$ is a substituted or unsubstituted aryl group having 6 to 50 ring carbon atoms, or a substituted or unsubstituted heterocyclic group having 5 to 50 ring atoms;

mx is 0, 1, 2, 3, 4, or 5; and when two or more $L_{101}$ are present, the two or more $L_{101}$ are mutually the same or different;

when two or more $Ar_{101}$ are present, the two or more $Ar_{101}$ are mutually the same or different; and

* in the formula (11) represents a bonding position to a ring represented by one of the formulae (101) to (104), $R_{901}$, $R_{902}$, $R_{903}$, $R_{904}$, $R_{905}$, $R_{801}$ and $R_{802}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms, when a plurality of $R_{901}$ are present, the plurality of $R_{901}$ are mutually the same or different;

when a plurality of $R_{902}$ are present, the plurality of $R_{902}$ are mutually the same or different;

when a plurality of $R_{903}$ are present, the plurality of $R_{903}$ are mutually the same or different;

when a plurality of $R_{904}$ are present, the plurality of $R_{904}$ are mutually the same or different;

when a plurality of $R_{905}$ are present, the plurality of $R_{905}$ are mutually the same or different;

when a plurality of $R_{801}$ are present, the plurality of $R_{801}$ are mutually the same or different; and when a plurality of $R_{802}$ are present, the plurality of $R_{802}$ are mutually the same or different.

2. The organic electroluminescence device according to claim 1, wherein the first emitting layer further comprises a third compound that luminesces, and the third compound is a compound that emits light having a maximum peak wavelength in a range from 430 nm to 480 nm.

3. The organic electroluminescence device according to claim 1, wherein the second emitting layer further comprises a fourth compound that luminesces, and the fourth compound is a compound that emits light having a maximum peak wavelength in a range from 430 nm to 480 nm.

4. The organic electroluminescence device according to claim 1, wherein at least one combination of adjacent two or more of $R_{101}$ to $R_{110}$ are mutually bonded to form a substituted or unsubstituted monocyclic ring, or mutually bonded to form a substituted or unsubstituted fused ring.

5. The organic electroluminescence device according to claim 1, wherein the first compound is a compound represented by the formula (101).

6. The organic electroluminescence device according to claim 1, wherein the first compound is a compound represented by a formula (1011) below, (1011)

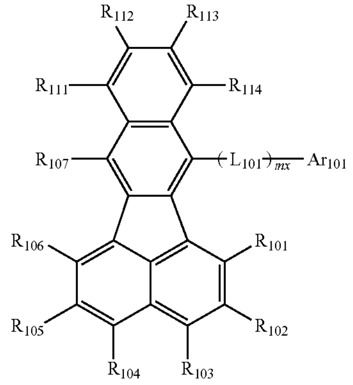

where, in the formula (1011):

$L_{101}$, mx and $Ar_{101}$ respectively represent the same as $L_{101}$, mx and $Ar_{101}$ in the formula (11);

$R_{101}$ to $R_{107}$ and $R_{111}$ to $R_{114}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a substituted or unsubstituted aralkyl group having 7 to 50 carbon atoms, a group represented by —C(═O)$R_{801}$, a group represented by —COO$R_{802}$, a halogen atom, a cyano group, a nitro group, a substituted or unsubstituted aryl group having 6 to 50 ring carbon atoms, a substituted or unsubstituted heterocyclic group having 5 to 50 ring atoms, or a group represented by the formula (11);

when a plurality of groups represented by the formula (11) are present, the plurality of groups represented by the formula (11) are mutually the same or different; and $R_{901}$, $R_{902}$, $R_{903}$, $R_{904}$, $R_{905}$, $R_{801}$ and $R_{802}$ in the formula (1011) each independently represent the same in the formulae (101) to (104).

7. The organic electroluminescence device according to claim 1, wherein $Ar_{101}$ is not a substituted or unsubstituted benzofluoranthenyl group, $L_{101}$ is not a substituted or unsubstituted benzofluoranthene-diyl group, and the substituted or unsubstituted aryl group having 6 to 50 ring carbon atoms not being the group represented by the formula (11) in the first compound is not a substituted or unsubstituted benzofluoranthenyl group.

8. The organic electroluminescence device according to claim 1, wherein $Ar_{101}$ is not a substituted or unsubstituted fluoranthenyl group, $L_{101}$ is not a substituted or unsubstituted fluoranthene-diyl group, and the substituted or unsubstituted aryl group having 6 to 50 ring carbon atoms as $R_{101}$ to $R_{110}$ not being the group represented by the formula (11) is not a substituted or unsubstituted fluoranthenyl group.

9. The organic electroluminescence device according to claim 1, wherein two or more of $R_{101}$ to $R_{110}$ are each a group represented by the formula (11).

10. The organic electroluminescence device according to claim 1, wherein $Ar_{101}$ is a substituted or unsubstituted heterocyclic group having 5 to 50 ring atoms.

11. The organic electroluminescence device according to claim 1, wherein $Ar_{101}$ in the formula (11) is a group represented by the formula (111), (111)

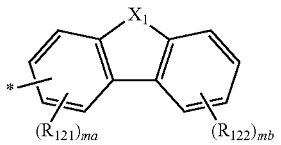

where, in the formula (111):

ma is 3, and three $R_{121}$ are mutually the same or different;

at least one combination of adjacent two or more of the three $R_{121}$ are mutually bonded to form a substituted or unsubstituted monocyclic ring, mutually bonded to form a substituted or unsubstituted fused ring, or not mutually bonded;

mb is 4, and four $R_{122}$ are mutually the same or different;

at least one combination of adjacent two or more of the four $R_{122}$ are mutually bonded to form a substituted or unsubstituted monocyclic ring, mutually bonded to form a substituted or unsubstituted fused ring, or not mutually bonded;

$X_1$ is $CR_{123}R_{124}$, an oxygen atom, a sulfur atom, or $NR_{125}$;

a combination of $R_{123}$ and $R_{124}$ are mutually bonded to form a substituted or unsubstituted monocyclic ring, mutually bonded to form a substituted or unsubstituted fused ring, or not mutually bonded;

$R_{121}$, $R_{122}$, $R_{123}$ and $R_{124}$ not forming the substituted or unsubstituted monocyclic ring and not forming the substituted or unsubstituted fused ring and $R_{125}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a substituted or unsubstituted aralkyl group having 7 to 50 carbon atoms, a group represented by —C(═O)$R_{801}$, a group represented by —COO$R_{802}$, a halogen atom, a cyano group, a nitro group, a substituted or unsubstituted aryl group having 6 to 50 ring carbon atoms, or a substituted or unsubstituted heterocyclic group having 5 to 50 ring atoms;

$R_{901}$, $R_{902}$, $R_{903}$, $R_{904}$, $R_{905}$, $R_{801}$ and $R_{802}$ respectively represent the same as $R_{901}$, $R_{902}$, $R_{903}$, $R_{904}$, $R_{905}$, $R_{801}$ and $R_{802}$ in the formulae (101) to (104); and

* in the formula (111) represents a bonding position.

12. The organic electroluminescence device according to claim 1, wherein $Ar_{101}$ is a substituted or unsubstituted aryl group having 6 to 50 ring carbon atoms.

13. The organic electroluminescence device according to claim 1, wherein $Ar_{101}$ is a substituted or unsubstituted phenyl group, a substituted or unsubstituted naphthyl group, a substituted or unsubstituted biphenyl group, a substituted or unsubstituted terphenyl group, a substituted or unsubstituted pyrenyl group, a substituted or unsubstituted phenanthryl group, or a substituted or unsubstituted fluorenyl group.

14. The organic electroluminescence device according to claim 1, wherein $L_{101}$ is a single bond, or a substituted or unsubstituted arylene group having 6 to 50 ring carbon atoms.

15. The organic electroluminescence device according to claim 1, wherein $R_{101}$ to $R_{110}$ not being the group represented by the formula (11) are each a hydrogen atom or a substituted or unsubstituted aryl group having 6 to 50 ring carbon atoms.

16. The organic electroluminescence device according to claim 1, wherein the second emitting layer comprises a second compound represented by a formula (2) below as the second host material, (2)

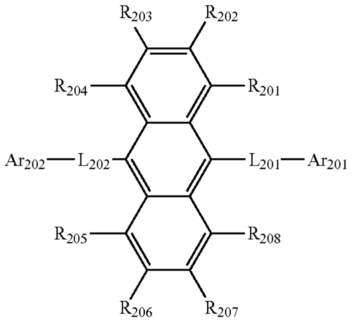

where, in the formula (2):

$R_{201}$ to $R_{208}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $—Si(R_{901})(R_{902})(R_{903})$, a group represented by $—O—(R_{904})$, a group represented by $—S—(R_{905})$, a group represented by $—N(R_{906})(R_{907})$, a substituted or unsubstituted aralkyl group having 7 to 50 carbon atoms, a group represented by $—C(=O)R_{801}$, a group represented by $—COOR_{802}$, a halogen atom, a cyano group, a nitro group, a substituted or unsubstituted aryl group having 6 to 50 ring carbon atoms, or a substituted or unsubstituted heterocyclic group having 5 to 50 ring atoms;

$L_{201}$ and $L_{202}$ are each independently a single bond, a substituted or unsubstituted arylene group having 6 to 50 ring carbon atoms, or a substituted or unsubstituted divalent heterocyclic group having 5 to 50 ring atoms; and $Ar_{201}$ and $Ar_{202}$ are each independently a substituted or unsubstituted aryl group having 6 to 50 ring carbon atoms, or a substituted or unsubstituted heterocyclic group having 5 to 50 ring atoms, in the second compound represented by the formula (2), $R_{901}$, $R_{902}$, $R_{903}$, $R_{904}$, $R_{905}$, $R_{906}$, $R_{907}$, $R_{801}$ and $R_{802}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

when a plurality of $R_{901}$ are present, the plurality of $R_{901}$ are mutually the same or different;

when a plurality of $R_{902}$ are present, the plurality of $R_{902}$ are mutually the same or different;

when a plurality of $R_{903}$ are present, the plurality of $R_{903}$ are mutually the same or different;

when a plurality of $R_{904}$ are present, the plurality of $R_{904}$ are mutually the same or different;

when a plurality of $R_{905}$ are present, the plurality of $R_{905}$ are mutually the same or different;

when a plurality of $R_{906}$ are present, the plurality of $R_{906}$ are mutually the same or different;

when a plurality of $R_{907}$ are present, the plurality of $R_{907}$ are mutually the same or different;

when a plurality of $R_{801}$ are present, the plurality of $R_{801}$ are mutually the same or different; and when a plurality of $R_{802}$ are present, the plurality of $R_{802}$ are mutually the same or different.

17. The organic electroluminescence device according to claim 1, wherein all groups described as "substituted or unsubstituted" groups in the first host material and the second host material are "unsubstituted" groups.

18. The organic electroluminescence device according to claim 1, wherein the first emitting layer and the second emitting layer are in direct contact with each other.

19. An electronic device comprising the organic electroluminescence device according to claim 1.

* * * * *